US006451842B1

(12) United States Patent
Shiota et al.

(10) Patent No.: US 6,451,842 B1
(45) Date of Patent: Sep. 17, 2002

(54) CYCLIC AMINE DERIVATIVES AND THEIR USE AS DRUGS

(75) Inventors: Tatsuki Shiota; Ken-ichiro Kataoka; Minoru Imai; Takaharu Tsutsumi, all of Hino; Masaki Sudoh, Handa; Ryo Sogawa; Takuya Morita, both of Hino; Takahiko Hada, Okayama; Yumiko Muroga, Hino; Osami Takenouchi, Hino; Minoru Furuya, Hino; Noriaki Endo, Hino, all of (JP); Christine M. Tarby, Hockessin, DE (US); Wilna Moree, San Diego; Steven Teig, Sunnyvale, both of CA (US)

(73) Assignees: Dupont Pharmaceuticals Company, San Diego, CA (US); Teijin Limited, Osaka (JP)

( * ) Notice: Subject to any disclaimer, the term of this patent is extended or adjusted under 35 U.S.C. 154(b) by 0 days.

(21) Appl. No.: 09/554,562

(22) PCT Filed: Nov. 17, 1998

(86) PCT No.: PCT/US98/23254

§ 371 (c)(1),
(2), (4) Date: May 16, 2000

(87) PCT Pub. No.: WO99/25686

PCT Pub. Date: May 27, 1999

Related U.S. Application Data

(63) Continuation of application No. 09/133,434, filed on Aug. 13, 1998, now abandoned, which is a continuation of application No. 09/055,285, filed on Apr. 6, 1998, now abandoned, which is a continuation of application No. 08/972,484, filed on Nov. 18, 1997, now abandoned.

(51) Int. Cl.[7] .................. A61K 31/4025; C07D 409/06; C07D 207/04

(52) U.S. Cl. ....................... 514/422; 548/527; 548/525; 548/517; 548/217; 548/557; 514/426

(58) Field of Search ................................ 514/422, 426; 548/557, 527, 525, 517, 217

(56) References Cited

FOREIGN PATENT DOCUMENTS

| | | |
|---|---|---|
| EP | 0 217 286 | 4/1987 |
| EP | 0 417 698 | 3/1991 |
| JP | 9-249566 | 9/1997 |
| JP | 9-249570 | 9/1997 |
| JP | 9-255572 | 9/1997 |
| WO | WO 97/24325 | 7/1997 |
| WO | WO 97/44329 | 11/1997 |
| WO | WO 98/02151 | 1/1998 |
| WO | WO 98/04554 | 2/1998 |
| WO | WO 98/06703 | 2/1998 |
| WO | WO 98/25604 | 6/1998 |
| WO | WO 98/25605 | 6/1998 |
| WO | WO 98/25617 | 6/1998 |
| WO | WO 98/27815 | 7/1998 |
| WO | WO 98/30218 | 7/1998 |
| WO | WO 98/31364 | 7/1998 |
| WO | WO 98/38167 | 9/1998 |
| WO | 98 50534 | 11/1998 |

OTHER PUBLICATIONS

"Identification and Characterization of Small Molecule Functional Antagonists of the CCR1 Chemokine Receptor" by Hesselgessert et al, Journal of Biological Chemistry, 1998.

"Identification of a Non–Peptidic Rantes Antagonist" by Bright et al, vol. 1, No. 1, Bioorganic & Medicinal Chemistry Letters, 1998.

"Inhibition of in Vitro and in Vivo HIV Replication by a Distamycin Analogue that Interferes with Chemokine Receptor Function: A Candidate for Chemotherapeutic and Microbicidal Application" by Howard et al, J. Med. Chem. 1998.

Chemical Abstracts, vol. 107, No. 7, Aug. 17, 1987, Columbus Ohio, US; Abstract No. 51382, Khalid, M. et al: "N,N'–disubstituted L–isoglutamines as novel cancer chemotherapeutic agent" XP002094911, see abstract & Drugs Exp. Clin. Res. (1987), 13(Suppl. 1), 57–60; ISSN; 0378–6501, 1987.

Database WPI, Section Ch, Week 9804, Derwent Publications Ltd., London, GB; Class B03, AN 98–035793, XP002094912 & JP 09 249566 A (Takeda Chem Ind Ltd), Sep. 22, 1997, see abstract.

*Primary Examiner*—Charanjit S. Aulakh
(74) *Attorney, Agent, or Firm*—Sughrue Mion, PLLC

(57) ABSTRACT

(I)

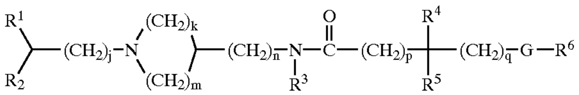

A compound represented by the general formula (I), a pharmaceutically acceptable acid addition salt thereof or a pharmaceutically acceptable $C_1$–$C_6$ alkyl addition salt thereof, and their medical applications. These compounds inhibit the action of chemokines such as MIP-1α and/or MCP-1 on target cells, and are useful as therapeutic and/or preventative drugs in diseases, such as atherosclerosis, rheumatoid arthritis, and the like where blood monocytes and lymphocytes infiltrate into tissues.

37 Claims, No Drawings

CYCLIC AMINE DERIVATIVES AND THEIR USE AS DRUGS

This application is a continuation of Ser. No. 09/133,434 filed Aug. 13, 1998, now abandoned, which is a continuation of Ser. No. 09/055,285 filed Apr. 06, 1998, now abandoned, which is continuation of Ser. No. 08/972,484 filed Nov. 18, 1997, now abandoned.

FIELD OF THE INVENTION

This invention relates to novel cyclic amine derivatives.

This invention also relates to chemokine receptor antagonists that may be effective as a therapeutic agent and/or preventive agent for diseases such as atherosclerosis, rheumatoid arthritis, psoriasis, asthma, ulcerative colitis, nephritis (nephropathy), multiple sclerosis, pulmonary fibrosis, myocarditis, hepatitis, pancreatitis, sarcoidosis, Crohn's disease, endometriosis, congestive heart failure, viral meningitis, cerebral infarction, neuropathy, Kawasaki disease, and sepsis in which tissue infiltration of blood leukocytes, such as monocytes and lymphocytes, play a major role in the initiation, progression or maintenance of the disease.

DESCRIPTION OF RELATED ART

Chemokines are a group of inflammatory/immunomodulatory polypeptide factors which have a molecular weight of 6–15 kD and are produced by a variety of cell types, such as macrophages, monocytes, eosinophils, neutrophiles, fibroblasts, vascular endotherial cells, smooth muscle cells, and mast cells, at inflammatory sites. The chemokines can be classified into two major subfamilies, the CXC chemokines (or α-chemokines) and CC chemokines (or β-chemokines), by the common location of the four conserved cysteine residues and by the differences in the chromosomal locations of the genes encoding them. The first two cysteines of CXC chemokines are separated by one amino acid and those of CC chemokines are adjacent. For example IL-8 (abbreviation for interleukin-8) is a CXC chemokine, while the CC chemokines include MIP-1α/β (abbreviation for macrophage inflammatory protein-1α/β), MCP-1 (abbreviation for monocyte chemoattractant protein-1), and RANTES (abbreviation for regulated upon activation, normal T-cell expressed and secreted). There also exist chemokines which do not fall into either chemokine subfamily. They are lymphotactin, which has only two cysteines and defines the C chemokine, and fractalkine that has a chemokine-like domain in the mucin structure in which the first two cysteines are separated by three amino acids and hence defines $CX_3C$ chemokine. These chemokines promote chemotaxis, cell migration, increase the expression of cellular adhesion molecules such as integrins, and cellular adhesion, and are thought to be the protein factors intimately involved in the adhesion and infiltration of leukocytes into the pathogenic sites in such as inflammatory tissues (for references, see for example, Vaddi, K., et al., The Chemokine Facts Book, Academic Press, 1997; Chemoattractant Ligand and Their Receptors, Horuk, R., Ed., CRC Press, 1996; Ward, G. W., et al, Biochem. J., 1998, 333, 457; Luster, A. D., New Engl. J. Med., 1998, 338, 436; Baggiolini, M., Nature, 1998, 392, 565; Rollins, B. J., Blood, 1997, 90, 909; Alam, R., J. Allergy Clin. Immunol., 1997, 99, 273; Hancock, W. W., Am. J. Pathol., 1996, 148, 681; Taub, D. D. Cytokine & Growth Factor Rev., 1996, 7, 335; Strieter, R. M., et al., J. Immunol., 1996, 156, 3583; Furie, M. B., et al., Am. J. Pathol., 1995, 146, 1287; Schall, T. J., et al., Current Opinion in Immunology, 1994, 6, 865; Edginton, S. M., Biotechnology, 1993, 11, 676).

For example, MIP-1α causes a transient increase in intracellular calcium ion concentration levels and induces migration of T lymphocytes, B lymphocytes (see for example, Taub, D. D., et al., Science, 1993, 260, 355; Schall, T. J., et al., J. Exp. Med., 1993, 177, 1821), and eosinophiles (see for example, Rot, A., et al., J. Exp. Med., 1992, 176, 1489), chemotaxis of natural killer cells (see for example, Maghazachi, A. A., et al., J. Immunol., 1994, 153, 4969), expression of integrins (see for example, Vaddi, K., et al., J. Immunol., 1994, 153, 4721), and osteoclast differentiation (see for example, Kukita, T., et al., Lab. Invest., 1997, 76, 399). MIP-1α also enhances IgE and IgG4 production in B cells (see for example, Kimata, H., et al., J. Exp. Med., 1996, 183, 2397) and inhibits hematopoietic stem cell proliferation (see for example, Mayani, H., et al., Exp. Hematol., 1995, 23, 422; Keller, J. R., et al., Blood, 1994, 84, 2175; Eaves, C. J., et al., Proc. Natl. Acad. Sci. USA, 1993, 90, 12015; Bodine, D. M., et al., Blood, 1991, 78, 914; Broxmeyer, H. E., et al., Blood, 1990, 76, 1110).

With respect to the activity of MIP-1α in vivo and its role in the pathogenesis of disease, it has been reported that it is a pyrogen in rabbits (see for example Davatelis, G., et al., Science, 1989, 243, 1066); that MIP-1α injection into mouse foot pads results in an inflammatory reaction such as infiltration by neutrophils and mononuclear cells (see for example Alam, R., et al., J. Immunol., 1994, 152, 1298); that MIP-1α neutralizing antibody has an inhibitory effect or a therapeutic effect in animal models of granuloma (see for example Lukacs, N. W., et al., J. Exp. Med., 1993, 177, 1551), asthma (see for example Lukacs, N. W., et al., Eur. J. Immunol., 1995, 25, 245; Lukacs, N. W., et al., J. Immunol., 1997, 158, 4398), multiple sclerosis (see for example Karpus, W. J., et al., J. Immunol., 1995, 155, 5003; Karpus, W. J., et al., J. Leukoc. Biol., 1997, 62, 681), idiopathic pulmonary fibrosis (see for example Smith, R. E., et al., J. Immunol., 1994, 153, 4704; Smith, R. E., Biol. Signals, 1996, 5, 223), acute lung injury (see for example Shanley, T. P., et al., J. Immunol., 1995, 154, 4793; Standiford, T. J., et al., J. Immunol., 1995, 155, 1515), and rheumatoid arthritis (see for example Kasama, T., et al., J. Clin. Invest., 1995, 95, 2868); that coxsackie virus induced myocarditis and herpes stromal keratitis are inhibited in mice with a disrupted MIP-1α gene (see for example Cook, D. N. et al., Science, 1995, 269, 1583; Tumpey, T. M., et al., J. Virology, 1998, 72, 3705); and that significant expression of MIP-1α is observed in patients with chronic inflammatory diseases of lung (see for example Standiford, T. J., et al., J. Immunol., 1993, 151, 2852), hypersensitivity pneumonitis (see for example Denis, M., Am,. J. Respir. Crit. Care Med., 1995, 151, 164), rheumatoid arthritis (see for example Koch, A.E., et al., J. Clin. Invest., 1994, 93, 921), infectious meningitis (see for example Lahrtz, F., et al., J. Neuroimmunol., 1998, 85, 33), and chronic inflammation of muscle (see for example Adams, E. M., et al., Proc. Assoc. Am. Physicians, 1997, 109, 275). These studies indicate that MIP-1α is deeply involved in the local attraction of various subtypes of leukocytes and the initiation, progression and maintenance of resulting inflammatory response.

MCP-1 (also known as MCAF (abbreviation for macrophage chemotactic and activating factor) or JE) is a CC chemokine produced by monocytes/macrophages, smooth muscle cells, fibroblasts, and vascular endothelial cells and causes cell migration and cell adhesion of monocytes (see for example Valente, A. J., et al., Biochemistry, 1988, 27, 4162; Matsushima, K., et al., J. Exp. Med., 1989, 169, 1485;

Yoshimura, T., et al., J. Immunol., 1989, 142, 1956; Rollins, B. J., et al., Proc. Natl. Acad. Sci. USA, 1988, 85, 3738; Rollins, B. J., et al., Blood, 1991, 78, 1112; Jiang, Y., et al., J. Immunol., 1992, 148, 2423; Vaddi, K., et al., J. Immunol., 1994, 153, 4721), memory T lymphocytes (see for example Carr, M. W., et al., Proc. Natl. Acad. Sci. USA, 1994, 91, 3652), T lymphocytes (see for example Loetscher, P., et al., FASEB J., 1994, 8, 1055) and natural killer cells (see for example Loetscher, P., et al., J. Immunol., 1996, 156, 322; Allavena, P., et al., Eur. J. Immunol. , 1994, 24, 3233), as well as mediating histamine release by basophils (see for example Alam, R., et al., J. Clin. Invest., 1992, 89, 723; Bischoff, S. C., et al., J. Exp. Med., 1992, 175, 1271; Kuna, P., et al., J. Exp. Med., 1992, 175, 489).

In addition, high expression of MCP-1 has been reported in diseases where accumulation of monocyte/macrophage and/or T cells is thought to be important in the initiation or progression of diseases, such as atherosclerosis (see for example Hayes, I. M., et al., Arterioscler. Thromb. Vasc. Biol., 1998, 18, 397; Takeya, M.. et al., Hum. Pathol., 1993, 24, 534; Yla-Herttuala, S., et al., Proc. Natl. Acad. Sci. USA, 1991, 88, 5252; Nelken, N. A., J. Clin. Invest., 1991, 88, 1121), rheumatoid arthritis (see for example Koch, A. E., et al., J. Clin. Invest., 1992, 90, 772; Akahoshi, T., et al., Arthritis Rheum., 1993, 36, 762; Robinson, E., et al., Clin. Exp. Immunol., 101, 398), nephritis (see for example Noris, M., et al., Lab. Invest., 1995, 73, 804; Wada, T., at al., Kidney Int., 1996, 49, 761; Gesualdo, L., et al., Kidney Int., 1997, 51, 155), nephropathy (see for example Saitoh, A., et al., J. Clin. Lab. Anal., 1998, 12, 1; Yokoyama, H., et al., J. Leukoc. Biol., 1998, 63, 493), pulmonary fibrosis, pulmonary sarcoidosis (see for example Sugiyama, Y., et al., Internal Medicine, 1997, 36, 856), asthma (see for example Karina, M., et al., J. Invest. Allergol. Clin. Immunol., 1997, 7, 254; Stephene, T. H., Am. J. Respir. Crit. Care Med., 1997, 156, 1377; Sousa, A. R., et al., Am. J. Respir. Cell Mol. Biol., 1994, 10, 142), multiple sclerosis (see for example McManus, C., et al., J. Neuroimmunol., 1998, 86, 20), psoriasis (see for example Gillitzer, R., et al., J. Invest. Dermatol., 1993, 101, 127), inflammatory bowel disease (see for example Grimm, M. C., et al., J. Leukoc. Biol., 1996, 59, 804; Reinecker, H. C., et al., Gastroenterology, 1995, 106, 40), myocarditis (see for example Seino, Y., et al., Cytokine, 1995, 7, 301), endometriosis (see for example Jolicoeur, C., et al., Am. J. Pathol., 1998, 152, 125), intraperitoneal adhesion (see for example Zeyneloglu, H. B., et al., Human Reproduction, 1998, 13, 1194), congestive heart failure (see for example Aurust, P., et al., Circulation, 1998, 97, 1136), chronic liver disease (see for example Marra, F., et al., Am. J. Pathol., 1998, 152, 423), viral meningitis (see for example Lahrtz, F., et al., Eur. J. Immunol., 1997, 27, 2484), Kawasaki disease (see for example Wong, M.; et al., J. Rheumatol., 1997, 24,1179) and sepsis (see for example Salkowski, C. A.; et al., Infect. Immun., 1998, 66, 3569). Furthermore, anti-MCP-1 antibody has been reported to show an inhibitory effect or a therapeutic effect in animal models of rheumatoid arthritis (see for example Schimmer, R. C., et al., J. Immunol., 1998, 160, 1466; Schrier, D. J., J. Leukoc. Biol., 1998, 63, 359; Ogata, H., et al., J. Pathol., 1997, 182, 106), multiple sclerosis (see for example Karpus, W. J., et al., J. Leukoc. Biol., 1997, 62, 681), nephritis (see for example Lloyd, C. M., et al., J. Exp. Med., 1997, 185, 1371; Wada, T., et al., FASEB J., 1996, 10, 1418), Asthma (see for example Gonzalo, J.-A., et al., J. Exp. Med., 1998, 188, 157; Lukacs, N. W., J. Immunol., 1997, 158, 4398), atherosclerosis (see for example Guzman, L. A., et al., Circulation, 1993, 88 (suppl.), I-371), delayed type hypersensitivity (see for example Rand, M. L., et al., Am. J. Pathol., 1996, 148, 855), pulmonary hypertension (see for example Kimura, H., et al., Lab. Invest., 1998, 78, 571), and intraperitoneal adhesion (see for example Zeyneloglu, H. B., et al., Am. J. Obstet. Gynecol., 1998, 179, 438). A peptide antagonist of MCP-1, MCP-1(9–76), has been also reported to inhibit arthritis in the mouse model (see Gong, J.-H., J. Exp. ,4ed. , 1997, 186, 131), as well as studies in MCP-1-deficient mice have shown that MCP-1 is essential for monocyte recruitment in vivo (see Lu, B., et al., J. Exp. Med., 1998, 187, 601; Gu, L., et al., Moll. Cell, 1998, 2, 275).

These data indicate that chemokines such as MIP-1α and MCP-1 attract monocytes and lymphocytes to disease sites and mediate their activation and thus are thought to be intimately involved in the initiation, progression and maintenance of diseases deeply involving monocytes and lymphocytes, such as atherosclerosis, rheumatoid arthritis, psoriasis, asthma, ulcerative colitis, nephritis (nephropathy), multiple sclerosis, pulmonary fibrosis, myocarditis, hepatitis, pancreatitis, sarcoidosis, Crohn's disease, endometriosis, congestive heart failure, viral meningitis, cerebral infarction, neuropathy, Kawasaki disease, and sepsis (see for example Rovin, B. H., et al., Am. J. Kidney. Dis., 1998, 31, 1065; Lloyd, C., et al., Curr. Opin. Nephrol. Hypertens., 1998, 7, 281; Conti, P., et al., Allergy and Asthma Proc., 1998, 19, 121; Ransohoff, R. M., et al., Trends Neurosci., 1998, 21, 154; MacDermott, R. P., et al., Inflammatory Bowel Diseases, 1998, 4, 54). Therefore, drugs which inhibit the action of chemokines on target cells may be effective as a therapeutic and/or preventive drug in the diseases.

Genes encoding receptors of specific chemokines have been cloned, and it is now known that these receptors are G protein-coupled seven-transmembrane receptors present on various leukocyte populations. So far, at least five CXC chemokine receptors (CXCR1–CXCR5) and eight CC chemokine receptors (CCR1–CCR8) have been identified. For example IL-8 is a ligand for CXCR1 and CXCR2, MIP-1α is that for CCR1 and CCR5, and MCP-1 is that for CCR2A and CCR2B (for reference, see for example, Holmes, W. E., et al., Science 1991, 253, 1278–1280; Murphy P. M., et al., Science, 253, 1280–1283; Neote, K. et al, Cell, 1993, 72, 415–425; Charo, I. F., et al., Proc. Natl. Acad. Sci. USA, 1994, 91, 2752–2756; Yamagami, S., et al., Biochem. Biophys. Res. Commun., 1994, 202, 1156–1162; Combadier, C., et al., The Journal of Biological Chemistry, 1995, 270, 16491–16494, Power, C. A., et al., J. Biol. Chem., 1995, 270, 19495–19500; Samson, M., et al., Biochemistry, 1996, 35, 3362–3367; Murphy, P. M., Annual Review of Immunology, 1994, 12, 592–633). It has been reported that lung inflammation and granuroma formation are suppressed in CCR1-deficient mice (see Gao, J.-L., et al., J. Exp. Med., 1997, 185, 1959; Gerard, C., et al., J. Clin. Invest., 1997, 100, 2022), and that recruitment of macrophages and formation of atherosclerotic lesion decreased in CCR2-deficient mice (see Boring, L., et al., Nature, 1998, 394, 894; Kuziel, W. A., et al., Proc. Natl. Acad. Sci., USA, 1997, 94, 12053; Kurihara, T., et al., J. Exp. Med., 1997, 186, 1757; Boring, L., et al., J. Clin. Invest., 1997, 100, 2552). Therefore, compound which inhibit the binding of chemokines such as MIP-1α and/or MCP-1 to these receptors, that is, chemokine receptor antagonist, may be useful as drugs which inhibit the action of chemokines such as MIP-1α and/or MCP-1 on the target cells, but there are no drugs known to have such effects.

The cyclic amine derivatives provided by the present invention is quite novel. Recently, it has been reported that the diphenylmethane derivatives (WO9724325; Hesselgesser, J., et al., J. Biol. Chem., 1998, 273, 15687), piperidine derivatives (JP9-249566), imidazobenzodiazepine derivatives (JP9-249570), benzazocine derivatives (JP9-255572), tricyclic compounds with cyclic amino group (WO9804554), phenothiazine derivatives (Bright, C., et al., Bioorg. Med. Chem. Lett., 1998, 8, 771), pieprazine derivatives (WO9744329), benzimidazole derivatives (WO9806703), distamycin analogues (Howard, O. M. Z., et al., J. Med. Chem., 1998, 41, 2184), bis-acridine derivatives (WO9830218), spiro-substituted azacycles (WO9825604; WO9825605), substituted aryl piperazines (WO9825617), aminoquinoline derivatives (WO9827815) 3-arylpiperidine derivatives (WO9831364), hexanoicamide derivatives (WO9838167), and other small molecules (WO9744329; WO9802151; WO9804554) have antagonistic activity of chemokine receptor, such as CXCR1, CXCR4, CCR1, CCR2, CCR3, and CCR5. However, these compounds differ from the compound of the present invention.

SUMMARY OF THE INVENTION

Therefore, it is an object of the present invention to provide small molecule compound which inhibits the binding of chemokines such as MIP-1α and/or MCP-1 to their receptors on the target cells.

It is another object of the present invention to establish a method to inhibit the binding to the receptors on the target cells and/or effects on target cells of chemokines such as MIP-1α and/or MCP-1.

It is an additional object of the present invention to propose a method for the treatment of diseases for which the binding of chemokines such as MIP-1α and/or MCP-1 to the receptor on the target cell is one of the causes.

As a result of intensive studies, the present inventors discovered that a cyclic amine derivative having a arylalkyl group, its pharmaceutically acceptable $C_1$–$C_6$ alkyl addition salt or its pharmaceutically acceptable acid addition salt has an excellent activity to inhibit the binding of chemokines such as MIP-1α and/or MCP-1 and the like to the receptor of a target cell, which has led to the completion of this invention.

That is, the present invention is a compound of the formula (I) below:

(I)

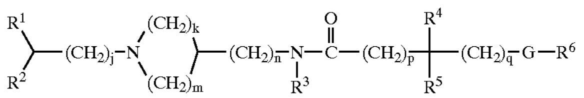

a pharmaceutically acceptable acid addition salt thereof or a pharmaceutically acceptable $C_1$–$C_6$ alkyl addition salt thereof (Invention 1), wherein $R^1$ is a phenyl group, a $C_3$–$C_8$ cycloalkyl group, or an aromatic heterocyclic group having 1–3 heteroatoms selected from the group consisting of an oxygen atom, a sulfur atom, a nitrogen atom, or a combination thereof, in which the phenyl or aromatic heterocyclic group may be condensed with a benzene ring or an aromatic heterocyclic group having 1–3 heteroatoms selected from the group consisting of an oxygen atom, a sulfur atom, a nitrogen atom, or a combination thereof, to form a condensed ring, and the phenyl group, $C_3$–$C_8$ cycloalkyl group, aromatic heterocyclic group, or condensed ring may be substituted with one or more of a halogen atom, a hydroxy group, a cyano group, a nitro group, a carboxy group, a carbamoyl group, a $C_1$–$C_6$ alkyl group, a $C_3$–$C_8$ cycloalkyl group, a $C_2$–$C_6$ alkenyl group, a $C_1$–$C_6$ alkoxy group, a $C_1$–$C_6$ alkylthio group, a $C_3$–$C_5$ alkylene group, a $C_2$–$C_4$ alkylenoxy group, a $C_1$–$C_3$ alkylenedioxy group, a phenyl group, a phenoxy group, a phenylthio group, a benzyl group, a benzyloxy group, a benzoylamino group, a $C_2$–$C_7$ alkanoyl group, a $C_2$–$C_7$ alkoxycarbonyl group, a $C_2$–$C_7$ alkanoyloxy group, a $C_2$–$C_7$ alkanoylamino group, a $C_2$–$C_7$ N-alkylcarbamoyl group, a $C_4$–$C_9$ N-cycloalkylcarbamoyl group, a $C_1$–$C_6$ alkylsulfonyl group, a $C_3$–$C_8$ (alkoxycarbonyl)methyl group, a N-phenylcarbamoyl group, a piperidinocarbonyl group, a morpholinocarbonyl group, a 1-pyrrolidinylcarbonyl group, a divalent group represented by the formula: —NH(C═O)O—, a divalent group represented by the formula: —NH(C═S)O—, an amino group, a mono($c_1$–$C_6$ alkyl)amino group, or a di($C_1$–$C_6$ alkyl)amino group, wherein the substituent for the phenyl group, $C_3$–$C_8$cycloalkyl group, aromatic heterocyclic group, or condensed ring is optionally substituted with one or more of a halogen atom, a hydroxy group, an amino group, a trifluoromethyl group, a $C_1$–$C_6$ alkyl group, or a $C_1$–$C_6$ alkoxy group;

$R^2$ is a hydrogen atom, a $C_1$–$C_6$ alkyl group, a $C_2$–$C_7$ alkoxycarbonyl group, a hydroxy group, or a phenyl group, in which the $C_1$–$C_6$ alkyl or phenyl group may be substituted with one or more of a halogen atom, a hydroxy group, a $C_1$–$C_6$ alkyl group, or a $C_1$–$C_6$ alkoxy group, and when j=0, $R^2$ is not a hydroxy group;

j represents an integer of 0–2;

k represents an integer of 0–2;

m represents an integer of 2–4;

n represents 0 or 1;

$R^3$ is a hydrogen atom or a $C_1$–$C_6$ alkyl group optionally substituted with one or two phenyl groups each of which may be substituted with one or more of a halogen atom, a hydroxy group, a $C_1$–$C_6$ alkyl group, or a $C_1$–$C_6$ alkoxy group;

$R^4$ and $R^5$ are the same or different from each other and are a hydrogen atom, a hydroxy group, a phenyl group, or a $C_1$–$C_6$ alkyl group, in which the $C_1$–$C_6$ alkyl group is optionally substituted with one or more of a halogen atom, a hydroxy group, a cyano group, a nitro group, a carboxy group, a carbamoyl group, a mercapto group, a guanidino group, a $C_3$–$C_8$ cycloalkyl group, a $C_1$–$C_6$ alkoxy group, a $C_1$–$C_6$ alkylthio group, a phenyl group optionally substituted with one or more of a halogen atom, a hydroxy group, a $C_1$–$C_6$ alkyl group, a $C_1$–$C_6$ alkoxy group, or a benzyloxy group, a phenoxy group, a benzyloxy group, a benzyloxycarbonyl group, a $C_2$–$C_7$ alkanoyl group, a $C_2$–$C_7$ alkoxycarbonyl group, a $C_2$–$C_7$ alkanoyloxy group, a $C_2$–$C_7$ alkanoylamino group, a $C_2$–$C_7$ N-alkylcarbamoyl group, a $C_1$–$C_6$ alkylsulfonyl group, an amino group, a mono($C_1$–$C_6$ alkyl)amino group, a di($C_2$–$C_6$ alkyl)amino group, or an aromatic heterocyclic group having 1–3 of heteroatoms selected from the group consisting of an oxygen atom, a sulfur atom, a nitrogen atom, or a combination thereof and optionally condensed with benzene ring, or $R^4$ and $R^5$ taken together form a 3 to 6 membered cyclic hydrocarbon;

p represents 0 or 1;

q represents 0 or 1;

G is a group represented by —CO—, —$SO_2$—, —CO—O—, —$NR_7$—CO—, —CO—$NR^7$——NH—CO—

NH—, —NH—CS—NH—, —$NR_7$—$SO_2$—, —$SO_2$—$NR_7$—, —NH—CO—O—, or —O—CO—NH—, wherein $R^7$ is a hydrogen atom or a $C_1$–$C_6$ alkyl group, or $R^3$ taken together with $R_5$ represents $C_2$–$C_5$ alkylene group;

$R^6$ is a phenyl group, a $C_3$–$C_8$ cycloalkyl group, a $C_3$–$C_8$ cycloalkenyl group, a benzyl group, or an aromatic heterocyclic group having 1–3 heteroatoms selected from the group consisting of an oxygen atom, a sulfur atom, a nitrogen atom, or a combination thereof, in which the phenyl, benzyl, or aromatic heterocyclic group may be condensed with a benzene ring or an aromatic heterocyclic group having 1–3 heteroatoms selected from the group consisting of an oxygen atom, a sulfur atom, a nitrogen atom, or a combination thereof, to form a condensed ring, and the phenyl group, $C_3$–$C_8$ cycloalkyl group, $C_3$–$C_8$ cycloalkenyl group, benzyl group, aromatic heterocyclic group, or condensed ring may be substituted with one or more of a halogen atom, a hydroxy group, a mercapto group, a cyano group, a nitro group, a thiocyanato group, a carboxy group, a carbamoyl group, a trifluoromethyl group, a $C_1$–$C_6$ alkyl group, a $C_3$–$C_6$ cycloalkyl group, a $C_2$–$C_6$ alkenyl group, a $C_1$–$C_6$ alkoxy group, a $C_3$–$C_8$ cycloalkyloxy group, a $C_1$–$C_6$ alkylthio group, a $C_1$–$C_3$ alkylenedioxy group, a phenyl group, a phenoxy group, a phenylamino group, a benzyl group, a benzoyl group, a phenylsulfinyl group, a phenylsulfonyl group, a 3-phenylureido group, a $C_2$–$C_7$ alkanoyl group, a $C_2$–$C_7$ alkoxycarbonyl group, a $C_2$–$C_7$ alkanoyloxy group, a $C_2$–$C_7$ alkanoylamino group, a $C_2$–$C_7$ N-alkylcarbamoyl group, a $C_1$–$C_6$ alkylsulfonyl group, a phenylcarbamoyl group, a N,N-di($C_1$–$C_6$ alkyl)sulfamoyl group, an amino group, a mono($C_1$–$C_6$ alkyl)amino group, a di($C_1$–$C_6$ alkyl)amino group, a benzylamino group, a $C_2$–$C_7$ (alkoxycarbonyl)amino group, a $C_1$–$C_6$ (alkylsulfonyl)amino group, or a bis($C_1$–$C_6$ alkylsulfonyl) amino group, wherein the substituent for the phenyl group, $C_3$–$C_8$ cycloalkyl group, $C_3$–$C_8$ cycloalkenyl group, benzyl group, aromatic heterocyclic group, or condensed ring is optionally substituted with one or more of a halogen atom, a cyano group, a hydroxy group, an amino group, trifluoromethyl group, a $C_1$–$C_6$ alkyl group, a $C_1$–$C_6$ alkoxy group, a $C_1$–$C_6$ alkylthio group, a mono($C_1$–$C_6$ alkyl)amino group, or a di($C_1$–$C_6$ alkyl)amino group.

Also the present invention is a method of inhibiting the binding of a chemokine to the receptor of a target cell and/or its action on a target cell using a pharmaceutical preparation containing a therapeutically effective amount of a compound represented by the above formula (I), a pharmaceutically acceptable acid addition salt thereof, or a pharmaceutically acceptable $C_1$–$C_6$ alkyl addition salt thereof (Invention 2).

Here, the compound represented by the above formula (I) have activities to inhibit the binding of chemokines such as MIP-1α and/or MCP-1 and the like to the receptor of a target cell and activities to inhibit physiological activities of cells caused by chemokines such as MIP-1α and/or MCP-1 and the like.

DESCRIPTION OF THE PREFERRED EMBODIMENTS (1) On Invention 1

In the above formula (I), $R^1$ is a phenyl group, a $C_3$–$C_8$ cycloalkyl group, or an aromatic heterocyclic group having 1–3 heteroatoms selected from the group consisting of an oxygen atom, a sulfur atom, a nitrogen atom, or a combination thereof, in which the phenyl or aromatic heterocyclic group may be condensed with a benzene ring or an aromatic heterocyclic group having 1–3 heteroatoms selected from the group consisting of an oxygen atom, a sulfur atom, a nitrogen atom, or a combination thereof, to form a condensed ring, and the phenyl group, $C_3$–$C_8$ cycloalkyl group, aromatic heterocyclic group, or condensed ring may be substituted with one or more of a halogen atom, a hydroxy group, a cyano group, a nitro group, a carboxy group, a carbamoyl group, a $C_1$–$C_6$ alkyl group, a $C_3$–$C_8$ cycloalkyl group, a $C_2$–$C_6$ alkenyl group, a $C_1$–$C_6$ alkoxy group, a $C_1$–$C_6$ alkylthio group, a $C_3$–$C_5$ alkylene group, a $C_2$–$C_4$ alkylenoxy group, a $C_1$–$C_3$ alkylenedioxy group, a phenyl group, a phenoxy group, a phenylthio group, a benzyl group, a benzyloxy group, a benzoylamino group, a $C_2$–$C_7$ alkanoyl group, a $C_2$–$C_7$ alkoxycarbonyl group, a $C_2$–$C_7$ alkanoyloxy group, a $C_2$–$C_7$ alkanoylamino group, a $C_2$–$C_7$ N-alkylcarbamoyl group, a $C_4$–$C_9$ N-cycloalkylcarbamoyl group, a $C_1$–$C_6$ alkylsulfonyl group, a $C_3$–$C_8$ (alkoxycarbonyl)methyl group, a N-phenylcarbamoyl group, a piperidinocarbonyl group, a morpholinocarbonyl group, a 1-pyrrolidinylcarbonyl group, a divalent group represented by the formula: —NH(C═O)O—, a divalent group represented by the formula: —NH(C═S)O—, an amino group, a mono($C_1$–$C_6$ alkyl)amino group, or a di($C_1$–$C_6$ alkyl)amino group.

The "$C_3$–$C_8$ cycloalkyl group" for $R^1$ means a cyclic alkyl group such as a cyclopropyl, cyclobutyl, cyclopentyl, cyclohexyl, cycloheptyl, and cyclooctyl group, specifically including a cyclopropyl, cyclopentyl, and cyclohexyl group.

The "aromatic heterocyclic group having 1–3 heteroatoms selected from the group consisting of an oxygen atom, a sulfur atom, a nitrogen atom, or a combination thereof" for $R^1$ is specifically, for example, thienyl, furyl, pyrrolyl, imidazolyl, pyrazolyl, oxazolyl, isoxazolyl, thiazolyl, isothiazolyl, pyridyl, pyrimidinyl, triazinyl, triazolyl, oxadiazolyl (furazanyl), thiadiazolyl group and the like, preferably including a thienyl, furyl, pyrrolyl, isoxazolyl, and pyridyl group.

The "condensed ring" for $R^1$ means a ring obtained by the condensation with a benzene ring or an aromatic heterocyclic group having 1–3 heteroatoms selected from the group consisting of an oxygen atom, a sulfur atom, a nitrogen atom of a phenyl group or an aromatic heterocyclic group having 1–3 heteroatoms selected from the group consisting of an oxygen atom, a sulfur atom and/or a nitrogen atom, at any possible sites, suitably and specifically for example, naphthyl, indolyl, benzofuranyl, benzothienyl, quinolyl, benzimidazolyl, benzoxazolyl, benzotriazolyl, benzoxadiazolyl (benzofurazanyl), and benzothiadiazolyl group.

Among them, a phenyl group and an isoxazolyl group can be listed as a preferred specific example for $R^1$.

The "halogen atom" as a substituent for the phenyl group, $C_3$–$C_8$ cycloalkyl group, aromatic heterocyclic group, or condensed ring in $R^1$ includes a fluorine atom, chlorine atom, bromine atom, and iodine atom, suitably including a fluorine atom, chlorine atom, and bromine atom.

The "$C_1$–$C_6$ alkyl group" as a substituent for $R^1$ means a $C_1$–$C_6$ straight-chain or a branched alkyl group such as a methyl, ethyl, n-propyl, n-butyl, n-pentyl, n-hexyl, n-heptyl, n-octyl, isopropyl, isobutyl, sec-butyl, tert-butyl, isopentyl, neopentyl, tert-pentyl, isohexyl, 2-methylpentyl, 1-ethylbutyl group, and the like, suitably specifically including a methyl, ethyl, propyl, and isopropyl group.

The "$C_3$–$C_8$ cycloalkyl group" as a substituent for $R^1$ is the same as defined for the aforementioned "$C_3$–$C_8$ cycloalkyl group" for $R^1$, where the same examples can be given for the preferred specific examples.

The "$C_2$–$C_6$ alkenyl group" as a substituent for $R^1$ means a $C_2$–$C_6$ straight-chain or a branched alkenyl group such as a vinyl, allyl, 1-propenyl, 2-butenyl, 3-butenyl, 2-methyl-1- propenyl, 4-pentenyl, 5-hexenyl, 4-methyl-3-pentenyl group, and the like, suitably specifically including a vinyl and 2-methyl-1-propenyl group.

The "$C_1$–$C_6$ alkoxy group" as a substituent for $R^1$ means group consisting of the aforementioned $C_1$–$C_6$ alkyl group and oxy group, specifically, for example, a methoxy and ethoxy group.

The "$C_1$–$C_6$ alkylthio group" as a substituent for $R^1$ means group consisting of the aforementioned $C_1$–$C_6$ alkyl group and thio group, specifically, for example, a methylthio and ethylthio group.

The "$C_3$–$C_5$ alkylene group" as a substituent for $R^1$ means the $C_3$–$C_9$ divalent alkylene group such as a trimethylene, tetramethylene, pentamethylene, and 1-methyltrimethylene group, specifically, for example, a trimethylene and a tetramethylene group.

The "$C_2$–$C_4$ alkylenoxy group" as a substituent for $R^1$ means group consisting of the aforementioned $C_2$–$C_4$ divalent alkylene group and oxy group such as a ethylenoxy ($—CH_2CH_2O—$), trimethylenoxy ($—CH_2CH_2CH_2O—$), tetramethylenoxy ($—CH_2CH_2CH_2CH_2O—$), and 1,1-dimethylethylenoxy ($—CH_2C(CH_3)_2O—$) group, specifically, for example, a ethylenoxy and trimethylenoxy group.

The "$C_1$–$C_3$ alkylenedioxy group" as a substituent for $R^1$ means group consisting of $C_1$–$C_3$ divalent alkylene group and two oxy groups such as a methylenedioxy ($—OCH_2O—$), ethylenedioxy ($—OCH_2CH_2O—$), trimethylenedioxy ($—OCH_2CH_2CH_2O—$, and propylenedioxy ($—OCH_2CH(CH_3)O—$) group, specifically, for example, a methylenedioxy and ethylenedioxy group.

The "$C_2$–$C_7$ alkanoyl group" as a substituent for $R^1$ means $C_2$–$C_7$ straight-chain or branched alkanoyl group such as an acetyl, propanoyl, butanoyl, pentanoyl, hexanoyl, heptanoyl, isobutyryl, 3-methylbutanoyl, 2-methylbutanoyl, pivaloyl, 4-methylpentanoyl, 3,3-dimethylbutanoyl, 5-methylhexanoyl group, and the like, where the preferred and specific example includes an acetyl group.

The "$C_2$–$C_7$ alkoxycarbonyl group" as a substituent for $R^1$ means group consisting of the aforementioned $C_1$–$C_6$ alkoxy group and carbonyl group, preferably and specifically for example, a methoxycarbonyl and ethoxycarbonyl group.

The "$C_2$–$C_7$ alkanoyloxy group" as a substituent for $R^1$ means group consisting of the aforementioned $C_2$–$C_7$ alkanoyl group and oxy group, specifically, for example, an acetyloxy group.

The "$C_2$–$C_7$ alkanoylamino group" as a substituent for $R^1$ means group consisting of the aforementioned $C_2$–$C_7$ alkanoyl group and amino group, specifically, for example, an acetylamino group.

The "$C_2$–$C_7$ N-alkylcarbamoyl group" as a substituent for $R^1$ means group consisting of the aforementioned $C_1$–$C_6$ alkyl group and carbamoyl group, specifically, for example, a N-methylcarbamoyl and N-ethylcarbamoyl group.

The "$C_4$–$C_9$ N-cycloalkylcarbamoyl group" as a substituent for $R^1$ means group consisting of the aforementioned $C_3$–$C_8$ cycloalkyl group and carbamoyl group, specifically, for example, a N-cyclopentylcarbamoyl and N-cyclohexylcarbamoyl group.

The "$C_1$–$C_6$ alkylsulfonyl group" as a substituent for $R^1$ means group consisting of the aforementioned $C_1$–$C_6$ alkyl group and sulfonyl group, preferably and specifically, for example, a methylsulfonyl group.

The "$C_3$–$C_8$ (alkoxycarbonyl)methyl group" as a substituent for $R^1$ means group consisting of the aforementioned $C_2$–$C_7$ alkoxycarbonyl group and methyl group, preferably and specifically for example, a (methoxycarbonyl)methyl and (ethoxycarbonyl)methyl group.

The "mono($C_1$–$C_6$ alkyl)amino group" as a substituent for $R^1$ means amino group substituted with one of the aforementioned $C_1$–$C_6$ alkyl group, preferably and specifically, for example, a methylamino and ethyl amino group.

The "di($C_1$–$C_6$ alkyl)amino group" as a substituent for $R^1$ means amino group substituted with the same or different two $C_1$–$C_6$ alkyl group aforementioned, preferably and specifically, for example, a dimethylamino, diethylamino, and N-ethyl-N-methylamino group.

Among them, a halogen atom, a hydroxy group, a $C_1$–$C_6$ alkyl group, a $C_2$–$C_6$ alkenyl group, a $C_1$–$C_6$ alkoxy group, a $C_1$–$C_6$ alkylthio group, a $C_2$–$C_4$ alkylenoxy group, a methylenedioxy group, a N-phenylcarbamoyl group, an amino group, a mono($C_1$–$C_6$ alkyl)amino group, and a di($C_1$–$C_6$ alkyl)amino group can be listed as a preferred specific example for substituent for the phenyl group, $C_3$–$C_8$ cycloalkyl group, aromatic heterocyclic group, or condensed ring in $R^1$.

Furthermore above substituent for the phenyl group, $C_3$–$C_8$ cycloalkyl group, aromatic heterocyclic group, or condensed ring in $R^1$ are optionally substituted with one or more of a halogen atom, a hydroxy group, an amino group, a trifluoromethyl group, a $C_1$–$C_6$ alkyl group, or a $C_1$–$C_6$ alkoxy group. The halogen atom, $C_1$–$C_6$ alkyl group, and $C_1$–$C_6$ alkoxy group are the same as defined for the aforementioned substituents for the phenyl group, $C_3$–$C_8$ cycloalkyl group, aromatic heterocyclic group, or condensed ring in $R^1$, and the same examples can be listed as preferred specific examples.

In the above formula (I), $R^2$ represents a hydrogen atom, a $C_1$–$C_6$ alkyl group, a $C_2$–$C_7$ alkoxycarbonyl group, a hydroxy group, or a phenyl group, in which the $C_1$–$C_6$ alkyl or phenyl group may be substituted with one or more of a halogen atom, a hydroxy group, a $C_1$–$C_6$ alkyl group, or a $C_1$–$C_6$ alkoxy group, and when j=0, $R^2$ is not a hydroxy group.

The $C_1$–$C_6$ alkyl group and $C_2$–$C_7$ alkoxycarbonyl group for $R^2$ are the same as defined for the aforementioned substituent for the phenyl group, $C_3$–$C_8$ cycloalkyl group, aromatic heterocyclic group, or condensed ring in $R^1$, and the same examples can be listed as preferred specific examples.

The halogen atom, $C_1$–$C_6$ alkyl group, and $C_1$–$C_6$ alkoxy group as substituents for the $C_1$–$C_6$ alkyl or phenyl group in $R^2$ are the same as defined for the aforementioned substituent for the phenyl group, $C_3$–$C_8$ cycloalkyl group, aromatic heterocyclic group, or condensed ring in $R^1$, and the same examples can be listed as preferred specific examples.

Among them, a hydrogen atom is a preferred specific example for $R^2$.

In the above formula (I), j represents an integer of 0–2. It is particularly preferred for j to be 0.

In the above formula (I), k represents an integer of 0–2 and m represents an integer of 2–4. It is preferred to use a 2-substituted pyrrolidine in which k is 0 and m is 3, a 3-substituted pyrrolidine in which k is 1 and m is 2, a 3-substituted piperidine in which k is 1 and m is 3, a 4-substituted piperidine in which k is 2 and m is 2, or 3-substituted hexahydroazepine in which k is 1 and m is 4.

n in the above formula (I) represents 0 or 1.

Especially, 3-amidopyrrolidines in which k is 1, m is 2, and n is 0 and 4-(amidomethyl)piperidines in which k is 2, m is 2, and n is 1 can be listed as a particularly preferred example.

$R^1$ in the above formula (I) represents a hydrogen atom or a $C_1$–$C_6$ alkyl group optionally substituted with one or two phenyl groups each of which may be substituted with one or more of a halogen atom, a hydroxy group, a $C_1$–$C_6$ alkyl group, or a $C_1$–$C_6$ alkoxy group.

The $C_1$–$C_6$ alkyl group for $R^2$ is the same as defined for the aforementioned substituents for the phenyl group, $C_3$–$C_8$ cycloalkyl group, aromatic heterocyclic group, or condensed ring in $R^1$, specifically, for example, a methyl, ethyl and propyl group.

The halogen atom, $C_1$–$C_6$ alkyl group, and $C_1$–$C_6$ alkoxy group as substituents for the phenyl group, which is a substituent for $C_1$–$C_6$ alkyl group in $R^3$, are the same as defined for the aforementioned substituents for the phenyl group, $C_3$–$C_8$ cycloalkyl group, aromatic heterocyclic group, or condensed ring in $R^1$, and the same examples can be listed as preferred specific examples.

Among them, a hydrogen atom is a preferred specific example for $R^3$.

In the above formula (I), $R^4$ and $R^5$ are the same or different from each other and are a hydrogen atom, a hydroxy group, a phenyl group, or a $C_1$–$C_6$ alkyl group, in which the $C_1$–$C_6$ alkyl group is optionally substituted with one or more of a halogen atom, a hydroxy group, a cyano group, a nitro group, a carboxy group, a carbamoyl group, a mercapto group, a guanidino group, a $C_3$–$C_8$ cycloalkyl group, a $C_1$–$C_6$ alkoxy group, a $C_1$–$C_6$ alkylthio group, a phenyl group optionally substituted with one or more of a halogen atom, a hydroxy group, a $C_1$–$C_6$ alkyl group, a $C_1$–$C_6$ alkoxy group, or a benzyloxy group, a phenoxy group, a benzyloxy group, a benzyloxycarbonyl group, a $C_2$–$C_7$ alkanoyl group, a $C_2$–$C_7$ alkoxycarbonyl group, a $C_2$–$C_7$ alkanoyloxy group, a $C_2$–$C_7$ alkanoylamino group, a $C_2C_7$ N-alkylcarbamoyl group, a $C_1$–$C_6$ alkylsulfonyl group, an amino group, a mono($C_1$–$C_6$alkyl)amino group, a di($C_1$–$C_6$ alkyl)amino group, or an aromatic heterocyclic group having 1–3 of heteroatoms selected from the group consisting of an oxygen atom, a sulfur atom, a nitrogen atom, or a combination thereof and optionally condensed with benzene ring, or $R^4$ and $R^5$ taken together form a 3 to 6 membered cyclic hydrocarbon.

The $C_1$–$C_6$ alkyl group for $R^4$ and $R^5$ is the same as defined for the aforementioned substituent for the phenyl group, $C_3$–$C_8$ cycloalkyl group, aromatic heterocyclic group, or condensed ring in $R^1$, and the same examples can be listed as preferred specific examples.

The halogen atom, $C_1$–$C_6$ alkoxy group, $C_1$–$C_6$ alkylthio group, $C_2$–$C_7$ alkanoyl group, $C_2$–$C_7$ alkoxycarbonyl group, $C_2$–$C_7$ alkanoyloxy group, $C_2$–$C_7$ alkanoylamino group, $C_2$–$C_7$ N-alkylcarbamoyl group, $C_1$–$C_6$ alkylsulfonyl group, mono($C_1$–$C_6$ alkyl)amino group, and di($C_1$–$C_6$ alkyl)amino group as a substituent for the $C_1$–$C_6$ alkyl group in $R^4$ and $R^5$ are the same as defined for the aforementioned substituent for the phenyl group, $C_3$–$C_8$ cycloalkyl group, aromatic heterocyclic group, or condensed ring in $R^1$, and the same examples can be listed as preferred specific examples.

The $C_3$–$C_8$ cycloalkyl group and aromatic heterocyclic group having 1–3 heteroatoms selected from the group consisting of an oxygen atom, a sulfur atom, a nitrogen atom, or a combination thereof as substituent for the $C_1$–$C_6$ alkyl group in $R^4$ and $R^5$ are the same as defined for the aforementioned group for $R^1$, and the same examples can be listed as preferred specific examples.

The halogen atom, $C_1$–$C_6$ alkyl group, and $C_1$–$C_6$ alkoxy group for the substituent for the phenyl group which is substituent for the $C_1$–$C_6$ alkyl group in $R^4$ and $R^5$ are the same as defined for the aforementioned substituent for the phenyl group, $C_3$–$C_8$ cycloalkyl group, aromatic heterocyclic group, or condensed ring in $R^1$, and the same examples can be listed as preferred specific examples.

The "3 to 6 membered cyclic hydrocarbon" consisting of $R^4$, $R^5$, and the adjacent carbon atom includes a cyclopropane, cyclobutane, cyclopentane, and cyclohexane.

Among them, a hydrogen atom and a $C_1$–$C_6$ alkyl group can be listed as a preferred specific example for $R^4$ and $R^5$.

In the above formula (I), p represents 0 or 1, and q represents 0 or 1. It is particularly preferred for both p and q to be 0.

In the above formula (I), G is a group represented by —CO—, —$SO_2$—, —CO—O—, —$NR^7$—CO—, —CO—$NR^7$—, —NH—CO—NH—, —NH—CS—NH—, —$NR^7$—$SO_2$—, —$SO_2NR^7$—, —NH—CO—O—, or —O—CO—NH—, wherein $R^7$ is a hydrogen atom or a $C_1$–$C_6$ alkyl group, or $R^7$ taken together with $R^5$ represents a $C_2$–$C_5$ alkylene group.

In the above formula, —CO— means a carbonyl group, —$SO_2$— means a sulfonyl group, and —CS— means a thiocarbonyl group Preferred G group is specifically, for example, those represented by the formula —$NR^7$—CO— and —NH—CO—NH—.

The $C_1$–$C_6$ alkyl group for $R^7$ are the same as defined for the aforementioned substituent for the phenyl group, $C_3$–$C_8$ cycloalkyl group, aromatic heterocyclic group, or condensed ring in $R^1$, and the same examples can be listed as preferred specific examples.

The "$C_2$–$C_5$ alkylene group" consisting of $R^5$ and $R^7$ means $C_2$–$C_5$ straight-chain or branched alkylene group such as a methylene, ethylene, propylene, trimethylene, tetramethylene, 1-methyltrimethylene, pentamethylene group, and the like, suitably and specifically including a ethylene, trimethylene and tetramethylene group.

A hydrogen atom is a preferred specific example for $R^7$.

In the above formula (I), $R^6$ is a phenyl group, a $C_3$–$C_8$ cycloalkyl group, a $C_3$–$C_8$ cycloalkenyl group, a benzyl group, or an aromatic heterocyclic group having 1–3 heteroatoms selected from the group consisting of an oxygen atom, a sulfur atom, a nitrogen atom, or a combination thereof, in which the phenyl, benzyl, or aromatic heterocyclic group may be condensed with a benzene ring or an aromatic heterocyclic group having 1–3 heteroatoms selected from the group consisting of an oxygen atom, a sulfur atom, a nitrogen atom, or a combination thereof, to form a condensed ring, and the phenyl group, $C_3$–$C_8$ cycloalkyl group, $C_3$–$C_8$ cycloalkenyl group, benzyl group, aromatic heterocyclic group, or condensed ring may be substituted with one or more of a halogen atom, a hydroxy group, a mercapto group, a cyano group, a nitro group, a thiocyanato group, a carboxy group, a carbamoyl group, a trifluoromethyl group, a $C_1$–$C_6$ alkyl group, a $C_3$–$C_6$ cycloalkyl group, a $C_2$–$C_6$ alkenyl group, a $C_1$–$C_6$ alkoxy group, a $C_3$–$C_8$ cycloalkyloxy group, a $C_1$–$C_6$ alkylthio group, a $C_1$–$C_6$ alkylenedioxy group, a phenyl group, a phenoxy group, a phenylamino group, a benzyl group, a benzoyl group, a phenylsulfinyl group, a phenylsulfonyl group, a 3-phenylureido group, a $C_2$–$C_7$ alkanoyl group, a $C_2$–$C_7$ alkoxycarbonyl group, a $C_2$–$C_7$ alkanoyloxy group, a $C_2$–$C_7$ alkanoylamino group, a $C_2$–$C_7$ N-alkylcarbamoyl group, a $C_1$–$C_6$ alkylsulfonyl group, a phenylcarbamoyl group, a N,N-di($C_1$–$C_6$ alkyl)sulfamoyl group, an amino group, a mono($C_1$–$C_6$alkyl)amino group, a di($C_1$–$C_6$alkyl) amino group, a benzylamino group, a $C_2$–$C_7$ (alkoxycarbonyl)amino group, a $C_1$–$C_6$ (alkylsulfonyl) amino group, or a bis($C_1$–$C_6$ alkylsulfonyl)amino group.

The $C_3$–$C_8$ cycloalkyl group, aromatic heterocyclic group having 1–3 heteroatoms selected from the group consisting of an oxygen atom, a sulfur atom, a nitrogen atom, or a combination thereof, and the condensed ring for $R^6$ are the same as defined for the aforementioned $R^1$, and the same examples can be listed as preferred specific examples.

The "$C_3$–$C_8$ cycloalkenyl group" for $R^6$ means a cyclic alkenyl group such as a cyclobutenyl, cyclopentenyl, cyclohexenyl, cycloheptenyl, and cyclooctenyl group, specifically including a 1-cyclopentenyl and 1-cyclohexenyl group.

Among them, a phenyl group, a furyl group, and a thienyl group can be listed as a preferred specific example for $R^6$.

The halogen atom, $C_1$–$C_6$ alkyl group, $C_2$–$C_6$ alkenyl group, $C_1$–$C_6$ alkoxy group, $C_1$–$C_6$ alkylthio group, $C_1$–$C_6$ alkylenedioxy group, $C_2$–$C_7$ alkanoyl group, $C_2$–$C_7$ alkoxycarbonyl group, $C_2$–$C_7$ alkanoyloxy group, $C_2$–$C_7$ alkanoylamino group, $C_2$–$C_7$ N-alkylcarbamoyl group, $C_1$–$C_6$ alkylsulfonyl group, mono($C_1$–$C_6$ alkyl)amino group, and di($C_1$–$C_6$ alkyl)amino group as a substituent for the phenyl group, $C_3$–$C_8$ cycloalkyl group, $C_3$–$C_8$ cycloalkenyl group, benzyl group, aromatic heterocyclic group, or condensed ring in $R^6$ are the same as defined for the aforementioned substituent for the phenyl group, $C_3$–$C_8$ cycloalkyl group, aromatic heterocyclic group, or condensed ring in $R^1$, and the same examples can be listed as preferred specific examples.

The $C_3$–$C_8$ cycloalkyl group as a substituent for $R^6$ is the same as defined for the aforementioned $C_3$–$C_8$ cycloalkyl group for $R^1$, where the same examples can be given for the preferred specific examples.

The "$C_3$–$C_8$ cycloalkyloxy group" as a substituent for $R^6$ means group consisting of the aforementioned $C_3$–$C_8$ cycloalkyl group and oxy group, specifically, for example, a cyclopropyloxy, cyclopentyloxy, and cyclohexyloxy group.

The "N,N-di($C_1$–$C_6$ alkyl)sulfamoyl group" as a substituent for $R^6$ means sulfamoyl group substituted with the same or different two $C_1$–$C_6$ alkyl group aforementioned, preferably and specifically, for example, a N,N-dimethylsulfamoyl, N,N-diethylsulfamoyl, and N-ethyl-N-methylsulfamoyl group.

The "$C_2$–$C_7$ (alkoxycarbonyl)amino group" as a substituent for $R^6$ means group consisting of the aforementioned $C_2$–$C_7$ alkoxycarbonyl group and amino group, specifically, for example, a (methoxycarbonyl)amino and (ethoxycarbonyl)amino group.

The "$C_1$–$C_6$ (alkylsulfonyl)amino" group as a substituent for $R^6$ means group consisting of the aforementioned $C_1$–$C_6$ alkylsulfonyl group and amino group, specifically, for example, a (methylsulfonyl)amino group.

The "bis($C_1$–$C_6$ alkylsulfonyl)amino" group as a substituent for $R^6$ means amino group substituted with the same or different two $C_1$–$C_6$ alkylsulfonyl group aforementioned, preferably and specifically, for example, a bis (methylsulfonyl)amino group.

Among them, a halogen atom, a mercapto group, a nitro group, a thiocyanato group, a trifluoromethyl group, a $C_1$–$C_6$ alkyl group, a $C_1$–$C_6$ alkoxy group, a phenyl group, a phenylsulfonyl group, a $C_2$–$C_7$ alkanoylamino group or an amino group can be listed as preferred specific example for substituent for the phenyl group, $C_3$–$C_8$ cycloalkyl group, $C_3$–$C_8$ cycloalkenyl group, benzyl group, aromatic heterocyclic group, or condensed ring in $R^6$.

Furthermore above substituents for the phenyl group, $C_3$–$C_8$ cycloalkyl group, $C_3$–$C_8$ cycloalkenyl group, benzyl group, aromatic heterocyclic group, or condensed ring in $R^6$ are optionally substituted with one or more of a halogen atom, a cyano group, a hydroxy group, an amino group, trifluoromethyl group, a $C_1$–$C_6$ alkyl group, a $C_1$–$C_6$ alkoxy group, a $C_1$–$C_6$ alkylthio group, a mono($C_1$–$C_6$ alkyl)amino group, or a di($C_1$–$C_6$ alkyl)amino group.

The halogen atom, $C_1$–$C_6$ alkyl group, $C_1$–$C_6$ alkoxy group, a $C_1$–$C_6$ alkylthio group, mono($C_1$–$C_6$ alkyl)amino group, and di($C_1$–$C_6$ alkyl)amino group are the same as defined for the aforementioned substituents for the phenyl group, $C_3$–$C_8$ cycloalkyl group, aromatic heterocyclic group, or condensed ring in $R^1$, and the same examples can be listed as preferred specific examples.

(2) On Invention 2

The compound represented by the formula (I) above, a pharmaceutically acceptable acid addition salt thereof or a pharmaceutically acceptable $C_1$–$C_6$ alkyl addition salt can be used to prepare a chemokine receptor antagonist preparation of the present invention by formulating the therapeutically effected amount and a carrier and/or diluent into a pharmaceutical composition. Thus, the cyclic amine derivatives shown by the above formula (I), a pharmaceutically acceptable acid addition salt thereof or a pharmaceutically acceptable $C_1$–$C_6$ alkyl addition salt can be administered orally or by parenterally, for example, intravenously, subcutaneously, intramuscularly, percutaneously or intrarectally.

The oral administration can be accomplished in the form of tablets, pills, granules, powder, solution, suspension, capsules, etc.

The tablets for example can be prepared using a vehicle such as lactose, starch and crystallized cellulose; binder such as carboxymethylcellulose, methylcellulose, and polyvinylpyrrolidone; disintegrator such as sodium alginate, sodium bicarbonate and sodium lauryl sulfate, etc.

Pills, powder and granule preparations can be prepared by a standard method using the vehicles mentioned above. Solution or suspension can be prepared by a standard method using glycerin ester such as tricaprylin and triacetin or alcohols such as ethanol. Capsules can be made by charging granules, powder or solution in gelatin, etc.

Subcutaneous, intramuscular or intravenous preparations can be prepared as an injection using aqueous or nonaqueous solution. Aqueous solution for example may include isotonic sodium chloride solution. Nonaqueous solutions may include for example, propyleneglycol, polyethyleneglycol, olive oil, ethyl oleate, etc., and optionally, one can add antiseptics and stabilizers. For injection, one can be sterilized by filtration through a bacterial filter or combination of disinfectant.

Percutaneous administration may be in the form of an ointment or cream, and ointment can be prepared in the standard manner using fatty oils such as castor oil and olive oil, or Vaseline, while creams can be made using fatty oils or emulsifying agent such as diethyleneglycol and sorbitan esters of fatty acid.

For intrarectal administration, one can use standard suppositories using gelatin soft capsules, etc.

The cyclic amine derivatives of the present invention, a pharmaceutically acceptable acid addition salt thereof or a pharmaceutically acceptable $C_1$–$C_6$ alkyl addition salt is administered at a dose that varies depending on the type of disease, route of administration, age and sex of patient, and severity of disease, but is likely to be 1–500 mg/day in an average adult.

(3) Matter Common Throughout Invention 1 and Invention 2

Preferred specific examples for the cyclic amine compound in the above formula (I) include compound having each substituent as shown in the following Tables 1.1–1.201.

In the Tables 1.1–1.201, "chirality" means configuration of the asymmetric carbon atom on the cyclic amine. "R"

shows that the asymmetric carbon atom has a R configuration, "S" shows that the asymmetric carbon atom has a S configuration, and "–" means racemate or that the compound do not have a asymmetric carbon atom on the nitrogen containing ring.
[Table 1.1–Table 1.201]
TABLE 1.1
| Compd. No. | 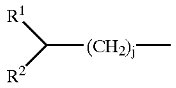 | k | m | n | chirality | $R^3$ | 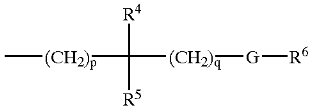 |
|---|---|---|---|---|---|---|---|
| 1 | 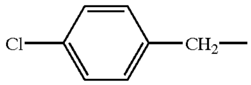 | 1 | 2 | 0 | — | H | 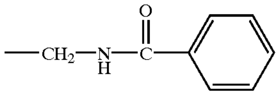 |
| 2 | 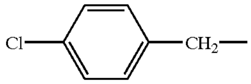 | 1 | 2 | 0 | — | H | 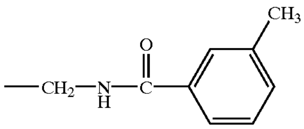 |
| 3 | 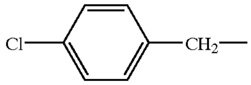 | 1 | 2 | 0 | — | H | 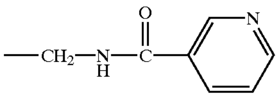 |
| 4 | 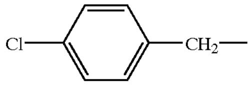 | 1 | 2 | 0 | — | H | 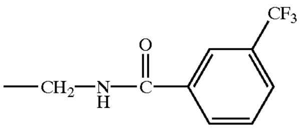 |
| 5 | 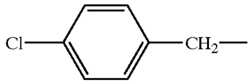 | 1 | 2 | 0 | S | H | 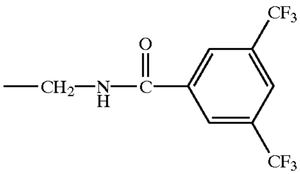 |
| 6 | 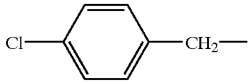 | 1 | 2 | 0 | S | H | 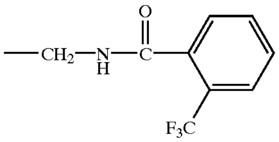 |
| 7 | 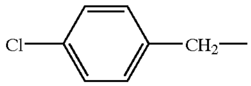 | 1 | 2 | 0 | S | H | 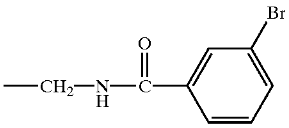 |
| 8 | 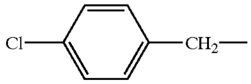 | 1 | 2 | 0 | S | H | 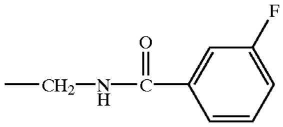 |
| 9 | 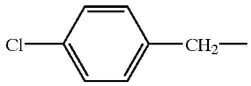 | 1 | 2 | 0 | S | H | 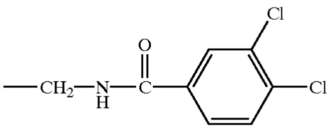 |

TABLE 1.1-continued
| Compd. No. | 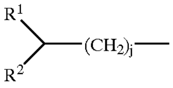 | k | m | n | chirality | $R^3$ | 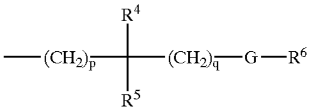 |
|---|---|---|---|---|---|---|---|
| 10 | 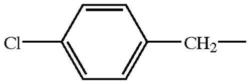 | 1 | 2 | 0 | S | H | 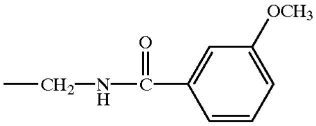 |
| 11 | 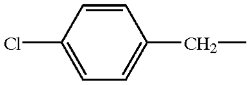 | 1 | 2 | 0 | S | H | 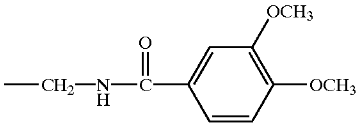 |
TABLE 1.2
| Compd. No. | 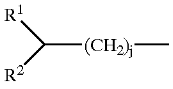 | k | m | n | chirality | $R^3$ | 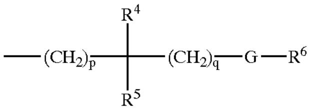 |
|---|---|---|---|---|---|---|---|
| 12 | 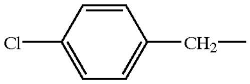 | 1 | 2 | 0 | S | H | 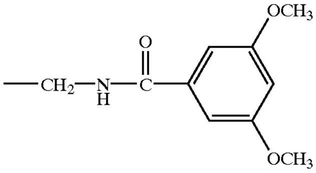 |
| 13 | 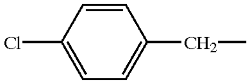 | 1 | 2 | 0 | S | H | 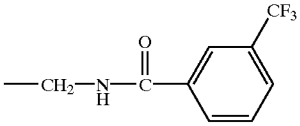 |
| 14 | 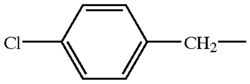 | 1 | 2 | 0 | S | H | 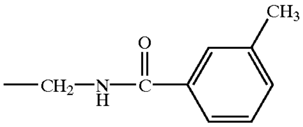 |
| 15 | 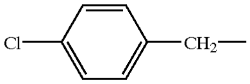 | 1 | 2 | 0 | S | H | 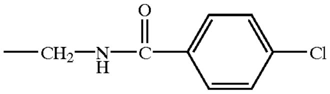 |
| 16 | 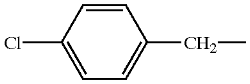 | 1 | 2 | 0 | S | H | 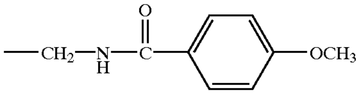 |
| 17 | 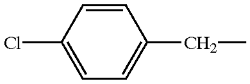 | 1 | 2 | 0 | S | H | 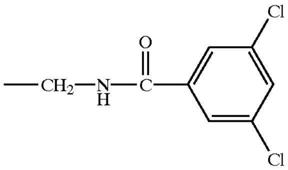 |

TABLE 1.2-continued
| Compd. No. | 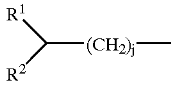 | k | m | n | chirality | $R^3$ | 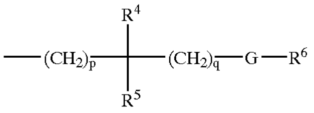 |
|---|---|---|---|---|---|---|---|
| 18 | 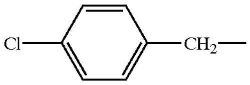 | 1 | 2 | 0 | S | H | 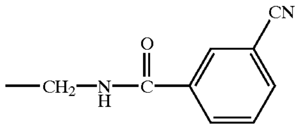 |
| 19 | 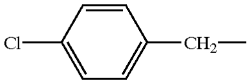 | 1 | 2 | 0 | S | H | 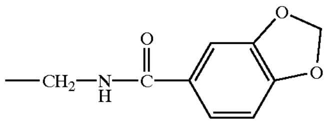 |
| 20 | 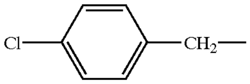 | 1 | 2 | 0 | S | H | 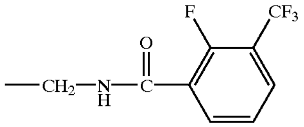 |
| 21 | 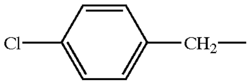 | 1 | 2 | 0 | S | H | 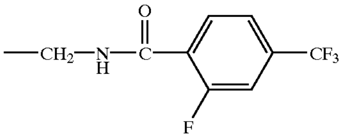 |
| 22 | 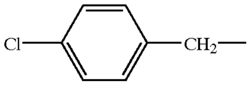 | 1 | 2 | 0 | S | H | 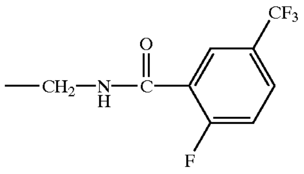 |
TABLE 1.3
| Compd. No. | 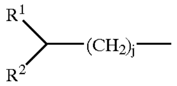 | k | m | n | chirality | $R^3$ | 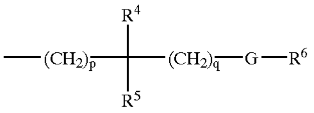 |
|---|---|---|---|---|---|---|---|
| 23 | 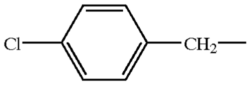 | 1 | 2 | 0 | S | H | 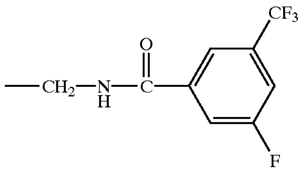 |
| 24 | 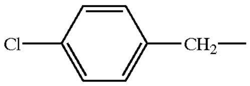 | 1 | 2 | 0 | S | H | 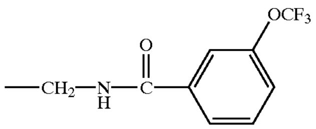 |
| 25 | 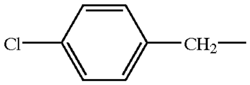 | 1 | 2 | 0 | S | H | 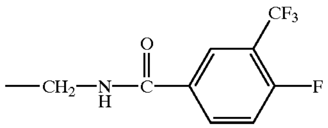 |

TABLE 1.3-continued
| Compd. No. | 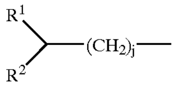 | k | m | n | chirality | $R^3$ | 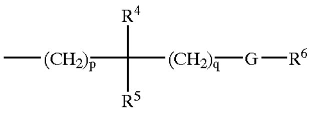 |
|---|---|---|---|---|---|---|---|
| 26 | 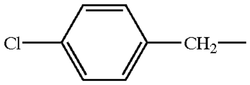 | 1 | 2 | 0 | S | H | 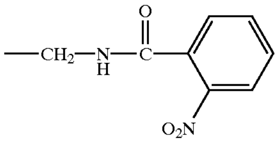 |
| 27 | 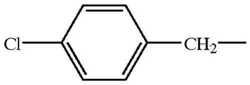 | 1 | 2 | 0 | S | H | 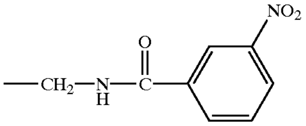 |
| 28 | 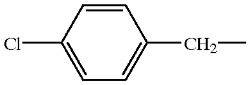 | 1 | 2 | 0 | S | H | 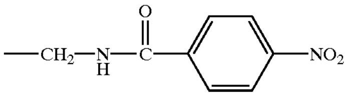 |
| 29 | 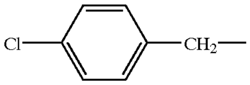 | 1 | 2 | 0 | R | H | 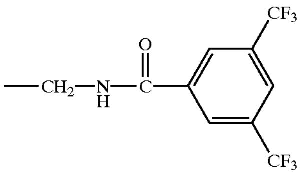 |
| 30 | 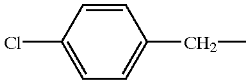 | 1 | 2 | 0 | R | H | 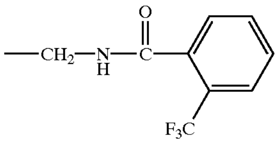 |
| 31 | 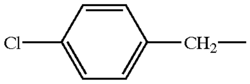 | 1 | 2 | 0 | R | H | 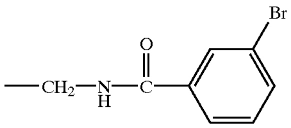 |
| 32 | 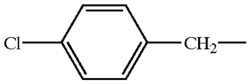 | 1 | 2 | 0 | R | H | 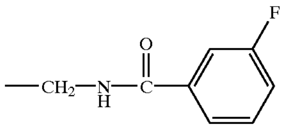 |
| 33 | 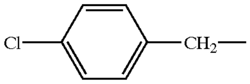 | 1 | 2 | 0 | R | H | 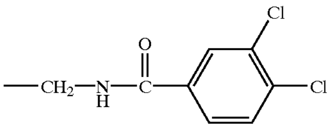 |

TABLE 1.4
| Compd. No. | 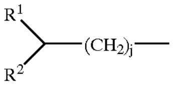 | k | m | n | chirality | $R^3$ | 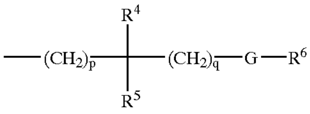 |
|---|---|---|---|---|---|---|---|
| 34 | 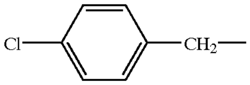 | 1 | 2 | 0 | R | H | 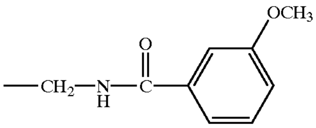 |
| 35 | 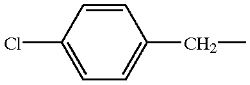 | 1 | 2 | 0 | R | H | 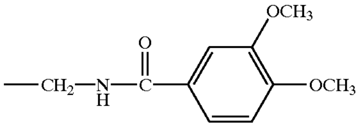 |
| 36 | 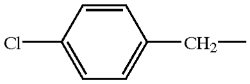 | 1 | 2 | 0 | R | H | 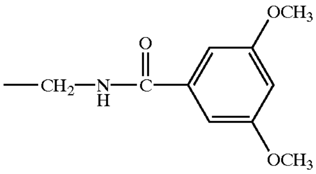 |
| 37 | 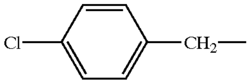 | 1 | 2 | 0 | R | H | 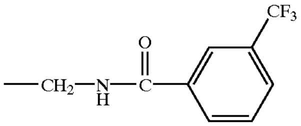 |
| 38 | 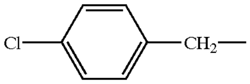 | 1 | 2 | 0 | R | H | 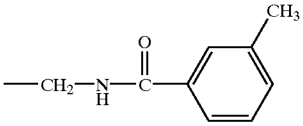 |
| 39 | 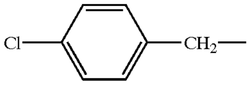 | 1 | 2 | 0 | R | H | 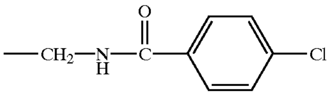 |
| 40 | 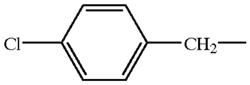 | 1 | 2 | 0 | R | H | 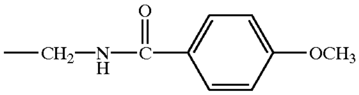 |
| 41 | 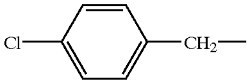 | 1 | 2 | 0 | R | H | 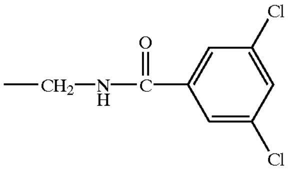 |
| 42 | 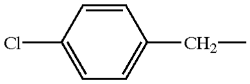 | 1 | 2 | 0 | R | H | 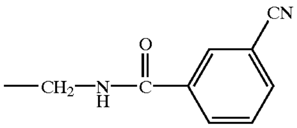 |
| 43 | 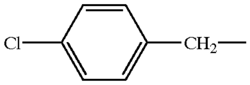 | 1 | 2 | 0 | R | H | 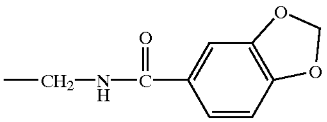 |

TABLE 1.4-continued
| Compd. No. | 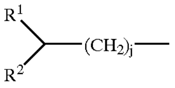 | k | m | n | chirality | $R^3$ | 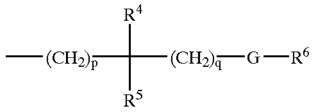 |
|---|---|---|---|---|---|---|---|
| 44 | 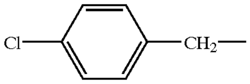 | 1 | 2 | 0 | R | H | 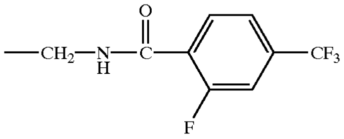 |
TABLE 1.5
| Compd. No. | 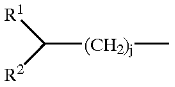 | k | m | n | chirality | $R^3$ | 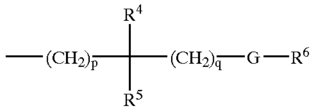 |
|---|---|---|---|---|---|---|---|
| 45 | 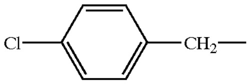 | 1 | 2 | 0 | R | H | 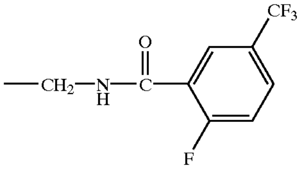 |
| 46 | 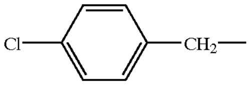 | 1 | 2 | 0 | R | H | 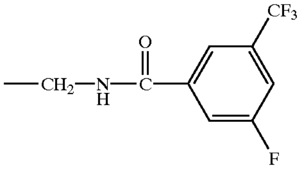 |
| 47 | 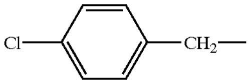 | 1 | 2 | 0 | R | H | 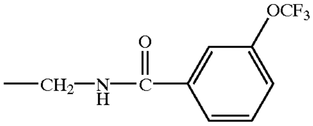 |
| 48 | 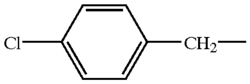 | 1 | 2 | 0 | R | H | 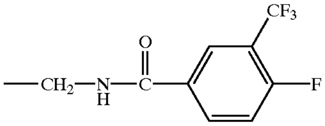 |
| 49 | 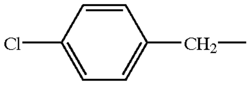 | 1 | 2 | 0 | R | H | 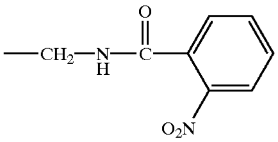 |
| 50 | 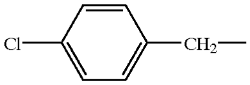 | 1 | 2 | 0 | R | H | 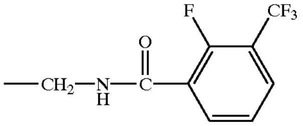 |

TABLE 1.5-continued
| Compd. No. | 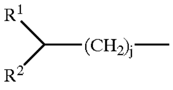 | k | m | n | chirality | $R^3$ | 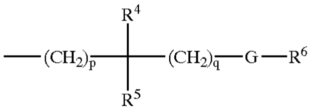 |
|---|---|---|---|---|---|---|---|
| 51 | 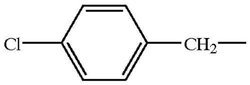 | 1 | 2 | 0 | R | H | 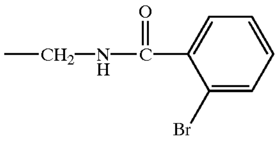 |
| 52 | 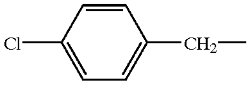 | 1 | 2 | 0 | R | H | 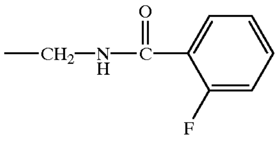 |
| 53 | 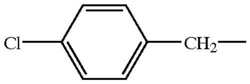 | 1 | 2 | 0 | R | H | 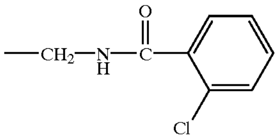 |
| 54 | 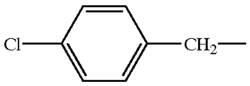 | 1 | 2 | 0 | R | H | 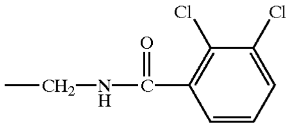 |
| 55 | 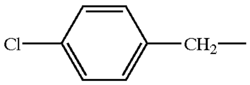 | 1 | 2 | 0 | R | H | 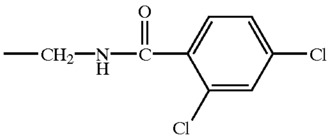 |
TABLE 1.6
| Compd. No. | 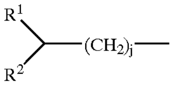 | k | m | n | chirality | $R^3$ | 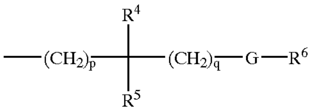 |
|---|---|---|---|---|---|---|---|
| 56 | 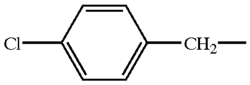 | 1 | 2 | 0 | R | H | 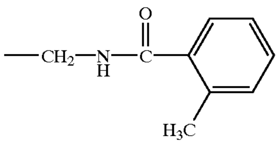 |
| 57 | 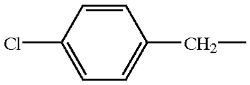 | 1 | 2 | 0 | R | H | 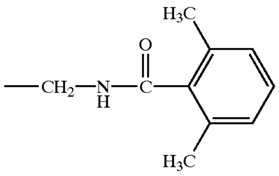 |

TABLE 1.6-continued
| Compd. No. | 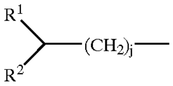 | k | m | n | chirality | $R^3$ | 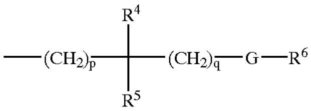 |
|---|---|---|---|---|---|---|---|
| 58 | 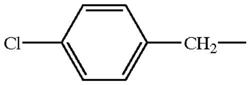 | 1 | 2 | 0 | R | H | 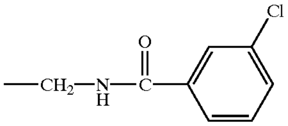 |
| 59 | 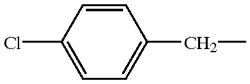 | 1 | 2 | 0 | R | H | 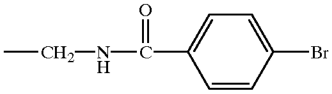 |
| 60 | 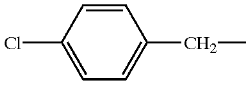 | 1 | 2 | 0 | R | H | 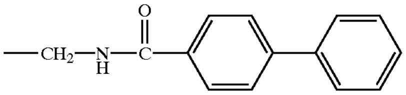 |
| 61 | 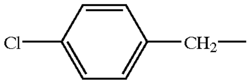 | 1 | 2 | 0 | R | H | 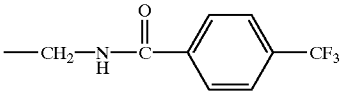 |
| 62 | 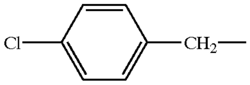 | 1 | 2 | 0 | R | H | 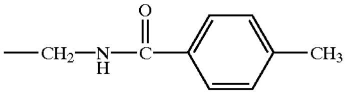 |
| 63 | 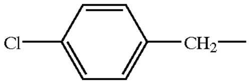 | 1 | 2 | 0 | R | H | 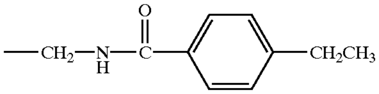 |
| 64 | 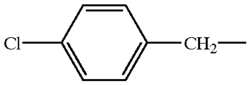 | 1 | 2 | 0 | R | H | 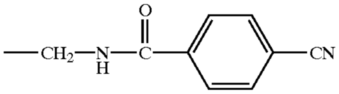 |
| 65 | 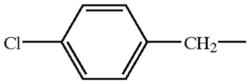 | 1 | 2 | 0 | R | H | 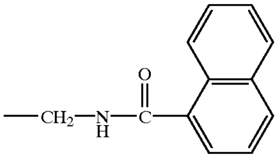 |
| 66 | 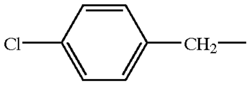 | 1 | 2 | 0 | R | H | 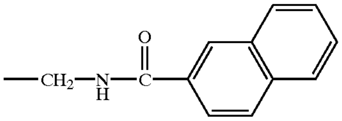 |

TABLE 1.7
| Compd. No. | 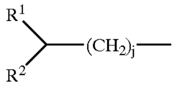 | k | m | n | chirality | $R^3$ | 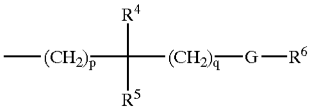 |
|---|---|---|---|---|---|---|---|
| 67 | 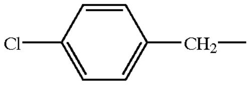 | 1 | 2 | 0 | R | H | 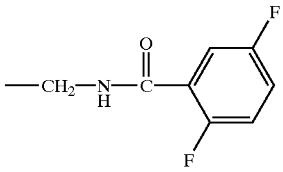 |
| 68 | 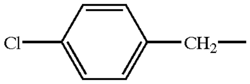 | 1 | 2 | 0 | R | H | 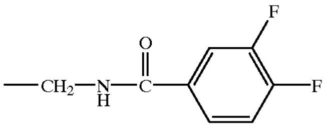 |
| 69 | 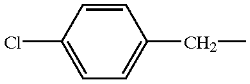 | 1 | 2 | 0 | R | H | 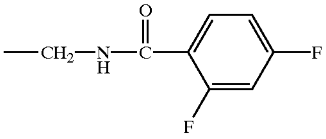 |
| 70 | 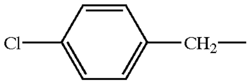 | 1 | 2 | 0 | R | H | 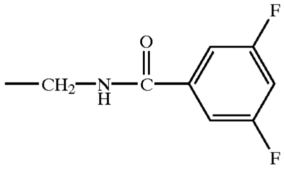 |
| 71 | 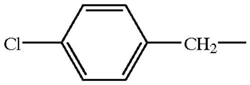 | 1 | 2 | 0 | R | H | 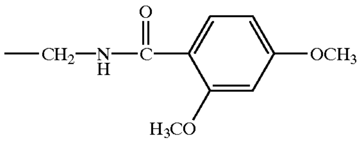 |
| 72 | 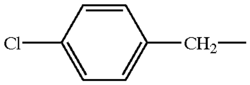 | 1 | 2 | 0 | R | H | 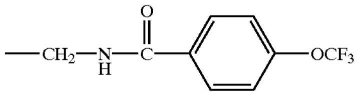 |
| 73 | 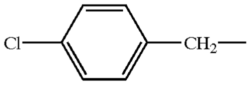 | 1 | 2 | 0 | R | H | 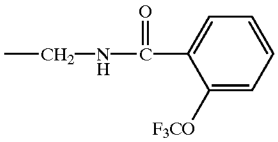 |
| 74 | 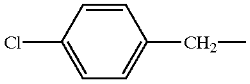 | 1 | 2 | 0 | R | H | 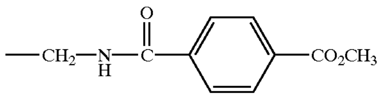 |
| 75 | 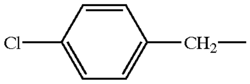 | 1 | 2 | 0 | R | H | 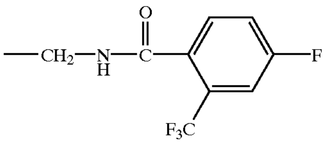 |

TABLE 1.7-continued
| Compd. No. | 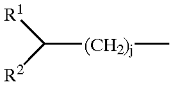 | k | m | n | chirality | $R^3$ | 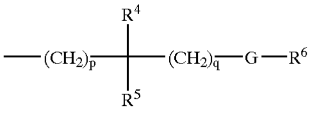 |
|---|---|---|---|---|---|---|---|
| 76 | 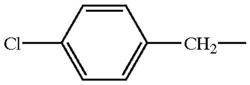 | 1 | 2 | 0 | R | H | 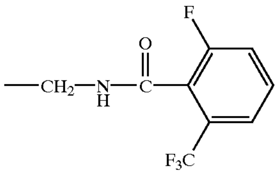 |
| 77 | 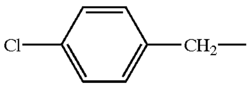 | 1 | 2 | 0 | R | H | 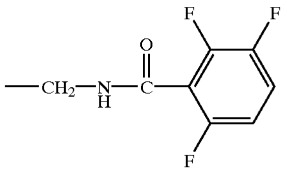 |
TABLE 1.8
| Compd. No. | 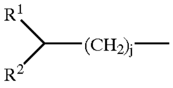 | k | m | n | chirality | $R^3$ | 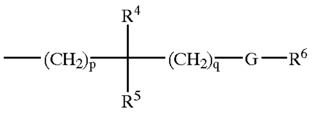 |
|---|---|---|---|---|---|---|---|
| 78 | 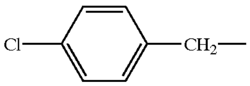 | 1 | 2 | 0 | R | H | 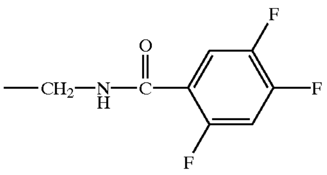 |
| 79 | 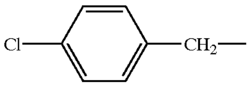 | 1 | 2 | 0 | R | H | 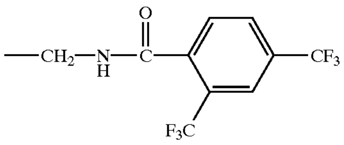 |
| 80 | 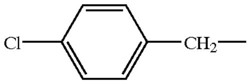 | 1 | 2 | 0 | R | H | 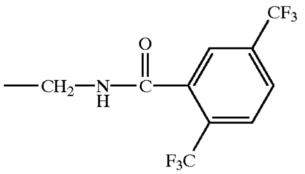 |
| 81 | 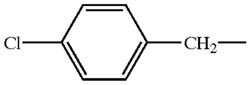 | 1 | 2 | 0 | R | H | 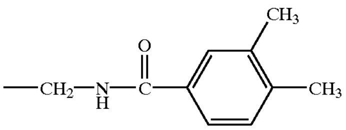 |
| 82 | 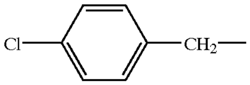 | 1 | 2 | 0 | — | $-CH_3$ | 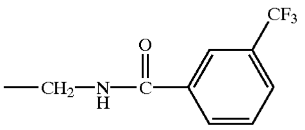 |

TABLE 1.8-continued
| Compd. No. | 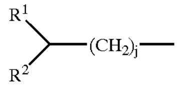 | k | m | n | chirality | $R^3$ | 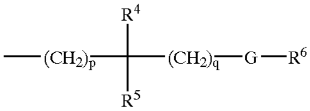 |
|---|---|---|---|---|---|---|---|
| 83 | 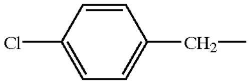 | 1 | 2 | 0 | R | H | 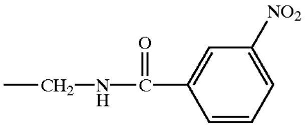 |
| 84 | 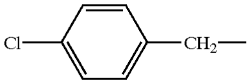 | 1 | 2 | 0 | R | H | 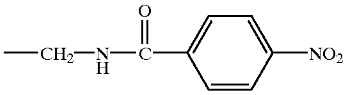 |
| 85 | 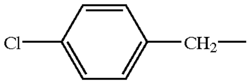 | 1 | 2 | 0 | — | H | 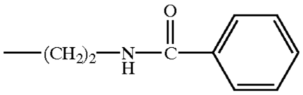 |
| 86 | 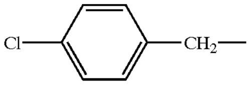 | 1 | 2 | 0 | — | H | 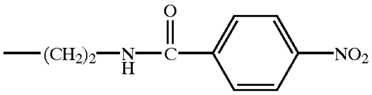 |
| 87 | 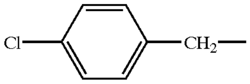 | 1 | 2 | 0 | S | H | 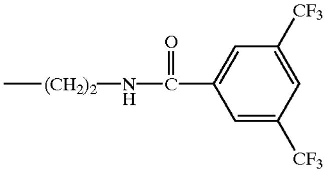 |
| 88 | 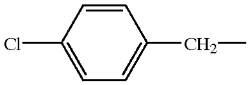 | 1 | 2 | 0 | S | H | 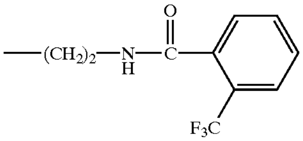 |
TABLE 1.9
| Compd. No. | 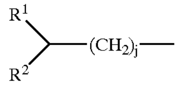 | k | m | n | chirality | $R^3$ | 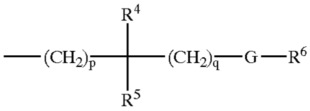 |
|---|---|---|---|---|---|---|---|
| 89 | 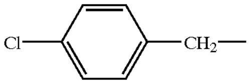 | 1 | 2 | 0 | S | H | 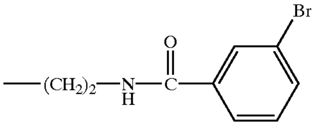 |
| 90 | 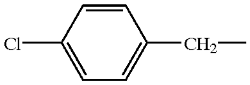 | 1 | 2 | 0 | S | H | 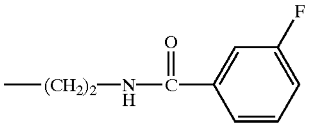 |

TABLE 1.9-continued
| Compd. No. | 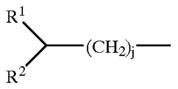 | k | m | n | chirality | $R^3$ | 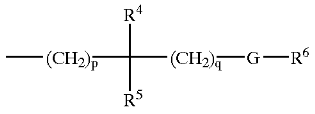 |
|---|---|---|---|---|---|---|---|
| 91 | 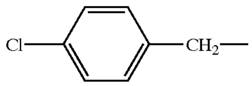 | 1 | 2 | 0 | S | H | 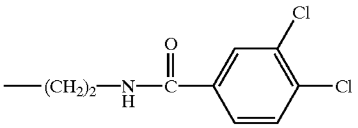 |
| 92 | 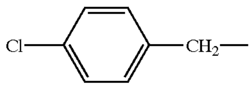 | 1 | 2 | 0 | S | H | 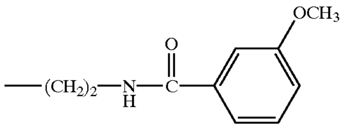 |
| 93 | 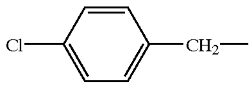 | 1 | 2 | 0 | S | H | 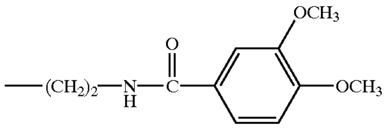 |
| 94 | 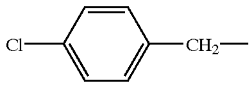 | 1 | 2 | 0 | S | H | 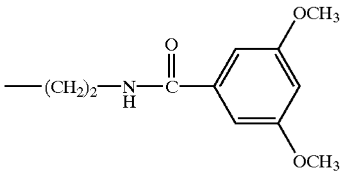 |
| 95 | 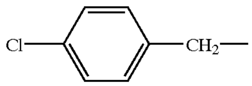 | 1 | 2 | 0 | S | H | 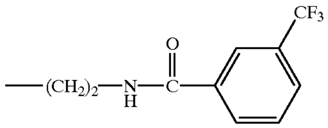 |
| 96 | 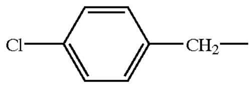 | 1 | 2 | 0 | S | H | 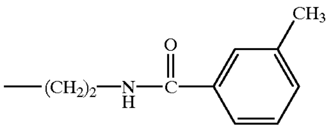 |
| 97 | 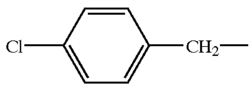 | 1 | 2 | 0 | S | H | 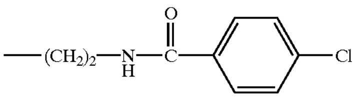 |
| 98 | 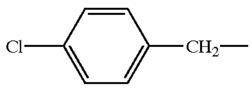 | 1 | 2 | 0 | S | H | 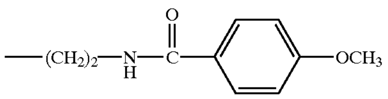 |
| 99 | 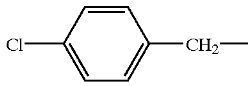 | 1 | 2 | 0 | S | H | 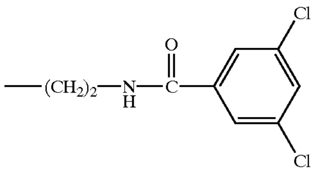 |

TABLE 1.10
| Compd. No. | 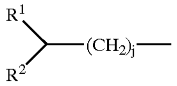 | k | m | n | chirality | $R^3$ | 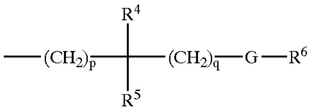 |
|---|---|---|---|---|---|---|---|
| 100 | 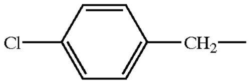 | 1 | 2 | 0 | S | H | 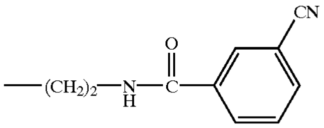 |
| 101 | 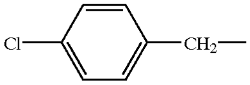 | 1 | 2 | 0 | S | H | 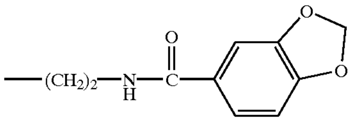 |
| 102 | 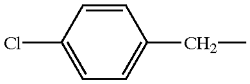 | 1 | 2 | 0 | S | H | 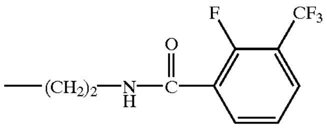 |
| 103 | 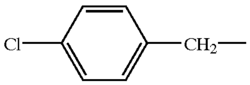 | 1 | 2 | 0 | S | H | 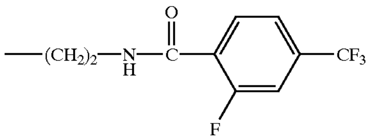 |
| 104 | 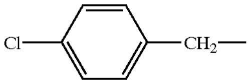 | 1 | 2 | 0 | S | H | 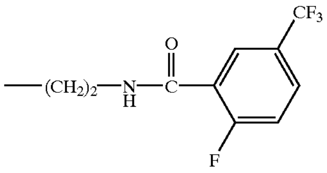 |
| 105 | 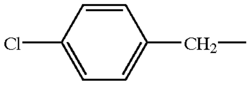 | 1 | 2 | 0 | S | H | 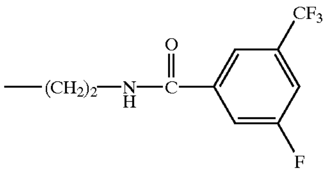 |
| 106 | 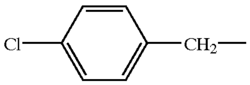 | 1 | 2 | 0 | S | H | 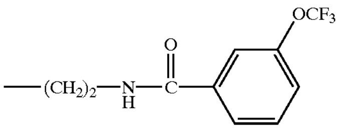 |
| 107 | 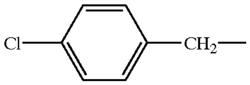 | 1 | 2 | 0 | S | H | 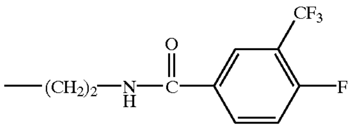 |
| 108 | 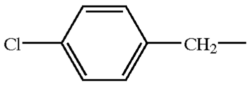 | 1 | 2 | 0 | S | H | 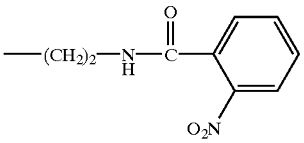 |

TABLE 1.10-continued
| Compd. No. | 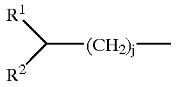 | k | m | n | chirality | $R^3$ | 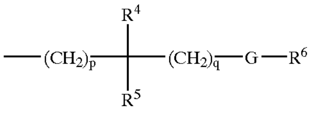 |
|---|---|---|---|---|---|---|---|
| 109 | 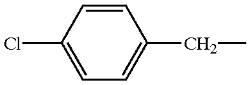 | 1 | 2 | 0 | S | H | 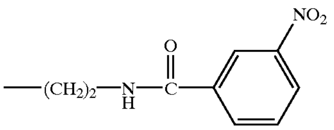 |
| 110 | 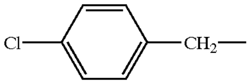 | 1 | 2 | 0 | S | H | 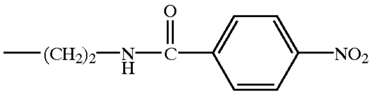 |
TABLE 1.11
| Compd. No. | 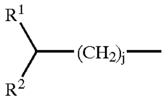 | k | m | n | chirality | $R^3$ | 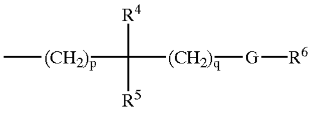 |
|---|---|---|---|---|---|---|---|
| 111 | 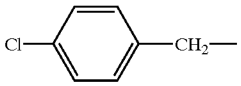 | 1 | 2 | 0 | R | H | 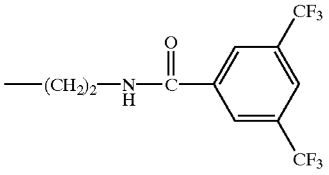 |
| 112 | 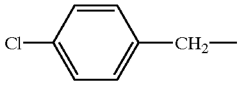 | 1 | 2 | 0 | R | H | 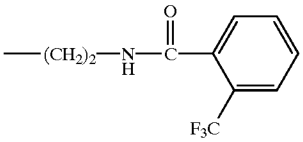 |
| 113 | 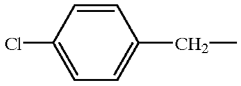 | 1 | 2 | 0 | R | H | 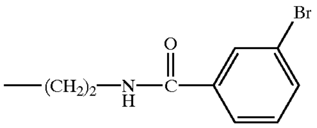 |
| 114 | 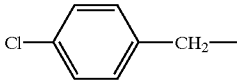 | 1 | 2 | 0 | R | H | 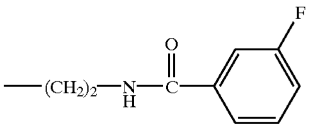 |
| 115 | 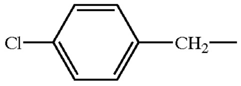 | 1 | 2 | 0 | R | H | 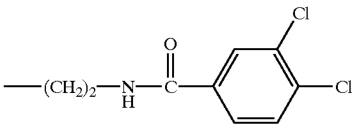 |
| 116 | 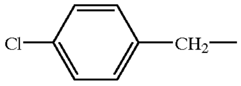 | 1 | 2 | 0 | R | H | 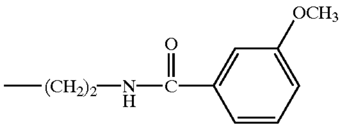 |

TABLE 1.11-continued
| Compd. No. | 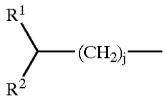 | k | m | n | chirality | $R^3$ | 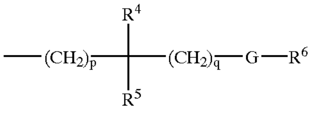 |
|---|---|---|---|---|---|---|---|
| 117 | 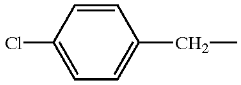 | 1 | 2 | 0 | R | H | 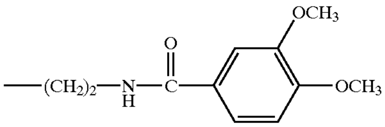 |
| 118 | 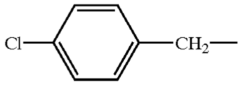 | 1 | 2 | 0 | R | H | 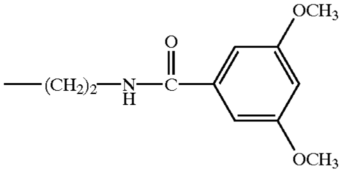 |
| 119 | 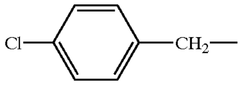 | 1 | 2 | 0 | R | H | 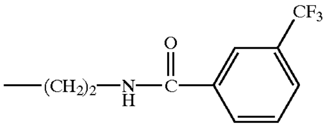 |
| 120 | 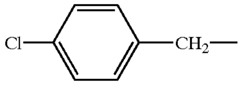 | 1 | 2 | 0 | R | H | 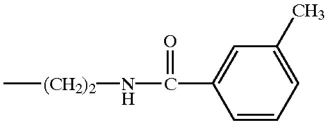 |
| 121 | 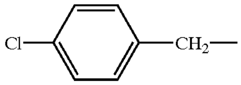 | 1 | 2 | 0 | R | H | 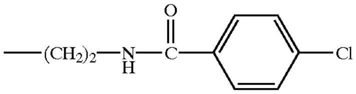 |
TABLE 1.12
| Compd. No. | 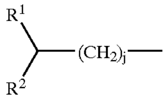 | k | m | n | chirality | $R^3$ | 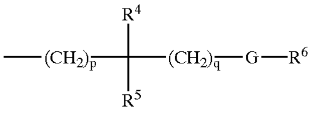 |
|---|---|---|---|---|---|---|---|
| 122 | 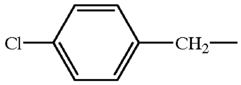 | 1 | 2 | 0 | R | H | 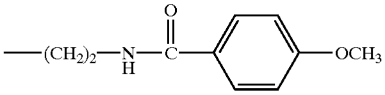 |
| 123 | 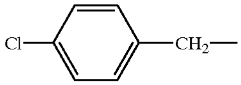 | 1 | 2 | 0 | R | H | 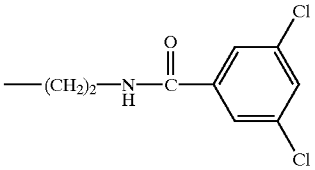 |
| 124 | 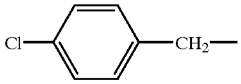 | 1 | 2 | 0 | R | H | 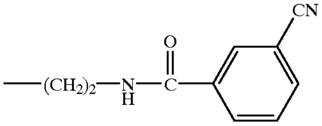 |

TABLE 1.12-continued
| Compd. No. | 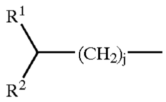 | k | m | n | chirality | $R^3$ | 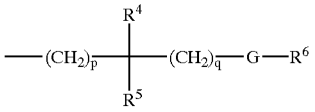 |
|---|---|---|---|---|---|---|---|
| 125 | 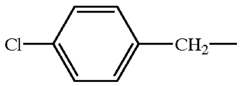 | 1 | 2 | 0 | R | H | 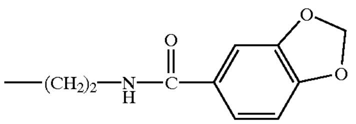 |
| 126 | 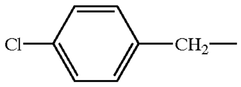 | 1 | 2 | 0 | R | H | 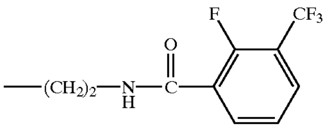 |
| 127 | 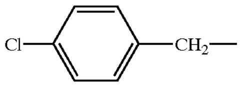 | 1 | 2 | 0 | R | H | 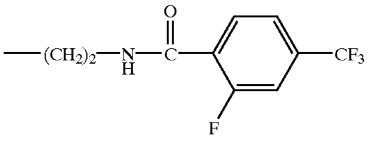 |
| 128 | 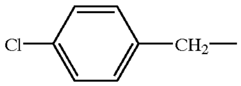 | 1 | 2 | 0 | R | H | 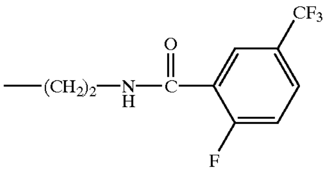 |
| 129 | 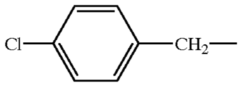 | 1 | 2 | 0 | R | H | 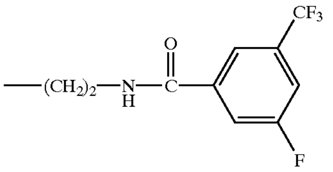 |
| 130 | 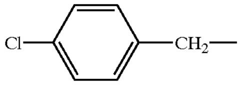 | 1 | 2 | 0 | R | H | 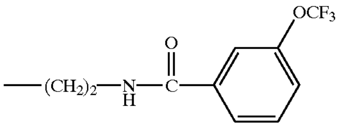 |
| 131 | 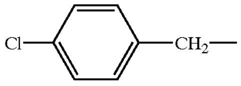 | 1 | 2 | 0 | R | H | 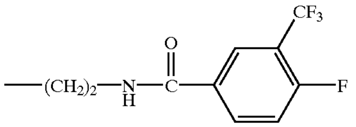 |
| 132 | 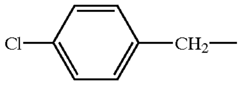 | 1 | 2 | 0 | R | H | 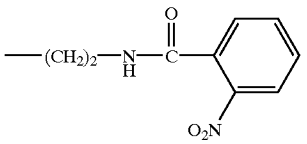 |

TABLE 1.13
| Compd. No. | 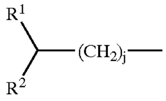 | k | m | n | chirality | $R^3$ | 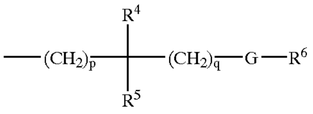 |
|---|---|---|---|---|---|---|---|
| 133 | 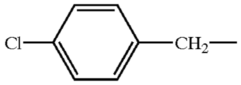 | 1 | 2 | 0 | R | H | 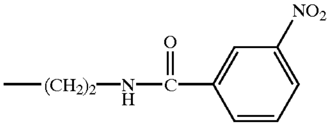 |
| 134 | 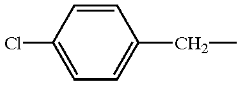 | 1 | 2 | 0 | R | H | 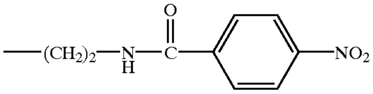 |
| 135 | 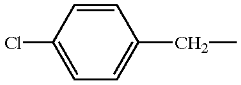 | 1 | 2 | 0 | R | H | 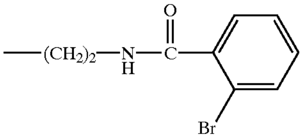 |
| 136 | 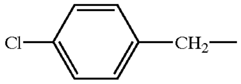 | 1 | 2 | 0 | R | H | 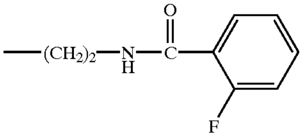 |
| 137 | 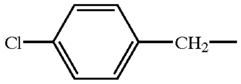 | 1 | 2 | 0 | R | H | 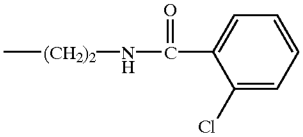 |
| 138 | 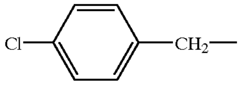 | 1 | 2 | 0 | R | H | 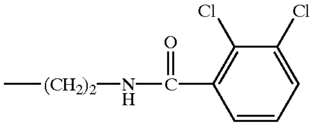 |
| 139 | 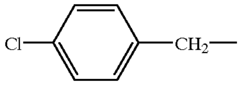 | 1 | 2 | 0 | R | H | 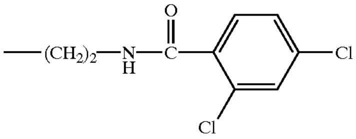 |
| 140 | 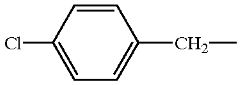 | 1 | 2 | 0 | R | H | 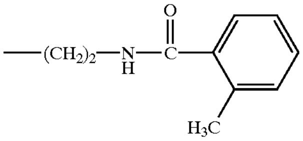 |
| 141 | 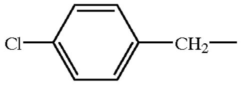 | 1 | 2 | 0 | R | H | 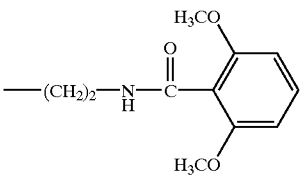 |
| 142 | 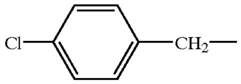 | 1 | 2 | 0 | R | H | 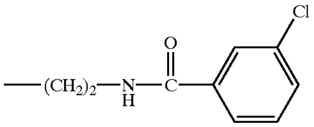 |

TABLE 1.13-continued
| Compd. No. | 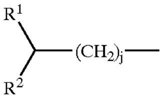 | k | m | n | chirality | $R^3$ | 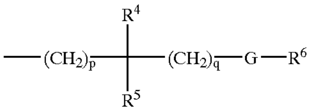 |
|---|---|---|---|---|---|---|---|
| 143 | 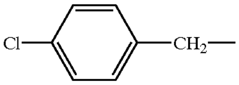 | 1 | 2 | 0 | R | H | 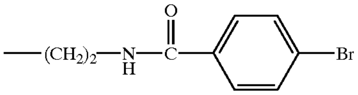 |
TABLE 1.14
| Compd. No. | 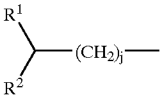 | k | m | n | chirality | $R^3$ | 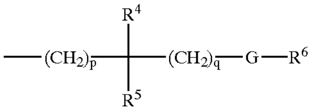 |
|---|---|---|---|---|---|---|---|
| 144 | 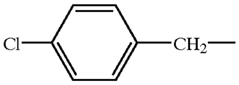 | 1 | 2 | 0 | R | H | 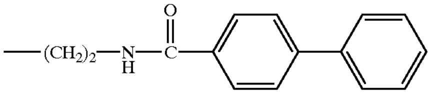 |
| 145 | 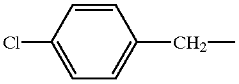 | 1 | 2 | 0 | R | H | 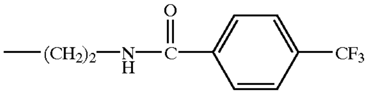 |
| 146 | 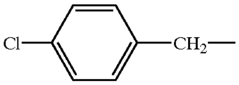 | 1 | 2 | 0 | R | H | 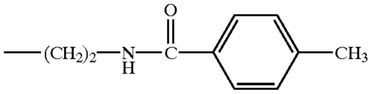 |
| 147 | 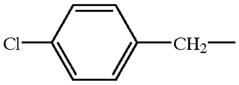 | 1 | 2 | 0 | R | H | 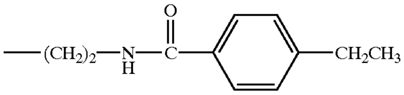 |
| 148 | 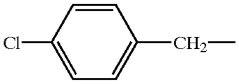 | 1 | 2 | 0 | R | H | 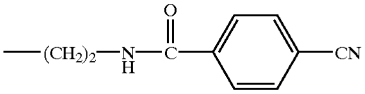 |
| 149 | 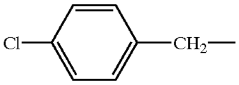 | 1 | 2 | 0 | R | H | 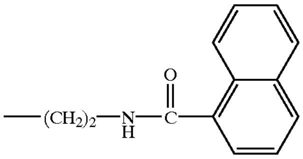 |
| 150 | 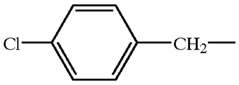 | 1 | 2 | 0 | R | H | 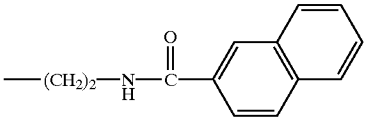 |
| 151 | 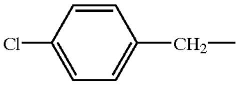 | 1 | 2 | 0 | R | H | 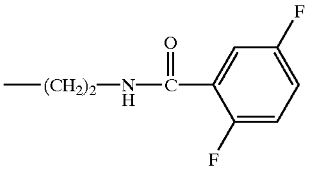 |

TABLE 1.14-continued
| Compd. No. | 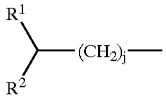 | k | m | n | chirality | $R^3$ | 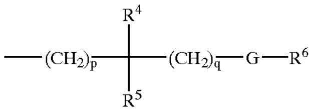 |
|---|---|---|---|---|---|---|---|
| 152 | 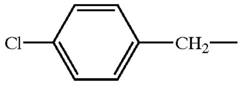 | 1 | 2 | 0 | R | H | 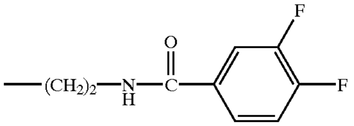 |
| 153 | 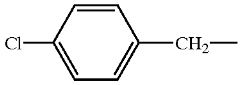 | 1 | 2 | 0 | R | H | 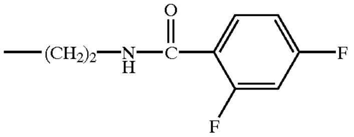 |
| 154 | 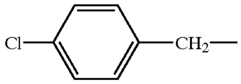 | 1 | 2 | 0 | R | H | 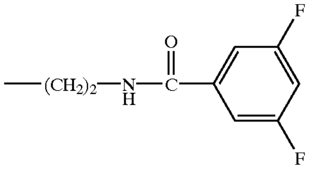 |
TABLE 1.15
| Compd. No. | 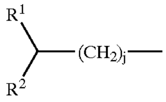 | k | m | n | chirality | $R^3$ | 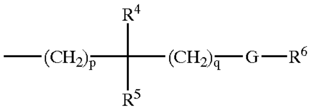 |
|---|---|---|---|---|---|---|---|
| 155 | 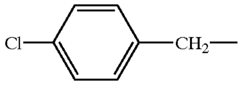 | 1 | 2 | 0 | R | H | 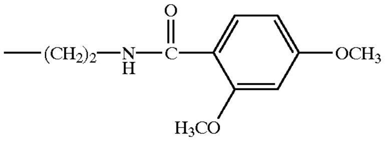 |
| 156 | 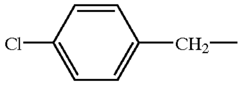 | 1 | 2 | 0 | R | H | 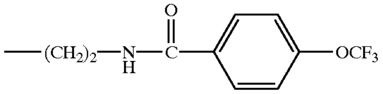 |
| 157 | 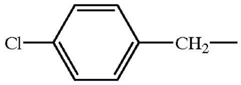 | 1 | 2 | 0 | R | H | 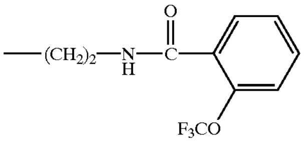 |
| 158 | 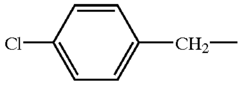 | 1 | 2 | 0 | R | H | 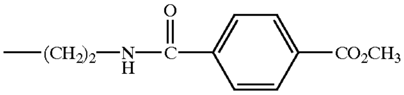 |
| 159 | 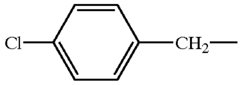 | 1 | 2 | 0 | R | H | 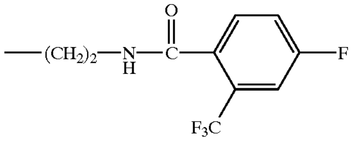 |

TABLE 1.15-continued
| Compd. No. | 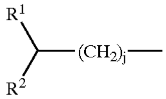 | k | m | n | chirality | $R^3$ | 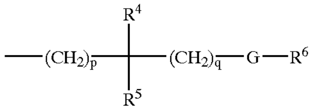 |
|---|---|---|---|---|---|---|---|
| 160 | 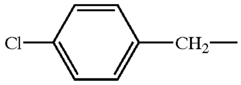 | 1 | 2 | 0 | R | H | 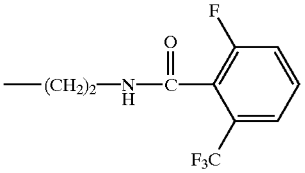 |
| 161 | 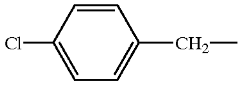 | 1 | 2 | 0 | R | H | 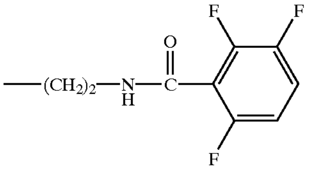 |
| 162 | 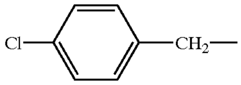 | 1 | 2 | 0 | R | H | 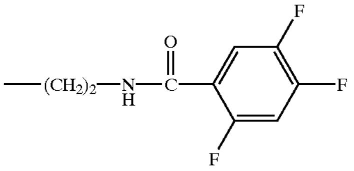 |
| 163 | 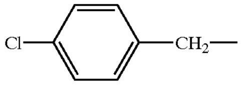 | 1 | 2 | 0 | R | H | 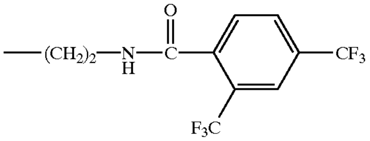 |
| 164 | 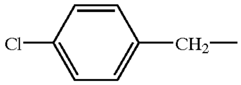 | 1 | 2 | 0 | R | H | 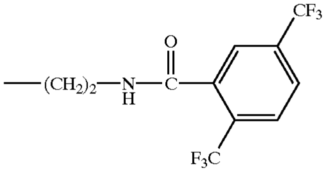 |
| 165 | 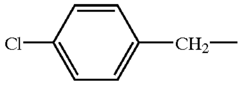 | 1 | 2 | 0 | R | H | 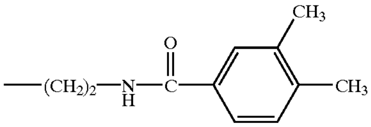 |
TABLE 1.16
| Compd. No. | 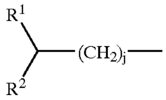 | k | m | n | chirality | $R^3$ | 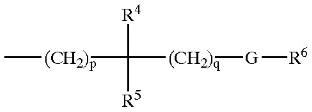 |
|---|---|---|---|---|---|---|---|
| 166 | 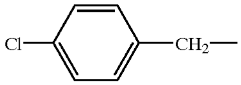 | 1 | 2 | 0 | R | H | 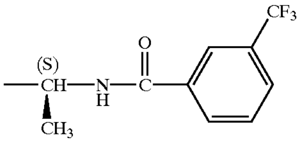 |

TABLE 1.16-continued
| Compd. No. | 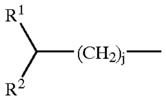 | k | m | n | chirality | $R^3$ | 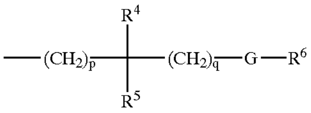 |
|---|---|---|---|---|---|---|---|
| 167 | 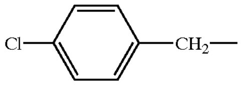 | 1 | 2 | 0 | R | H | 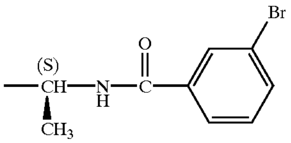 |
| 168 | 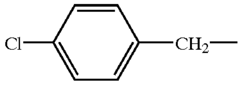 | 1 | 2 | 0 | R | H | 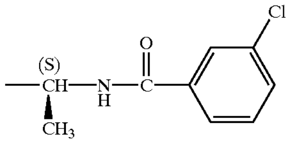 |
| 169 | 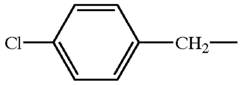 | 1 | 2 | 0 | R | H | 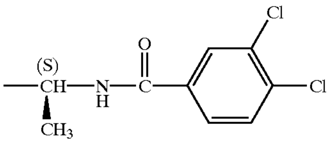 |
| 170 | 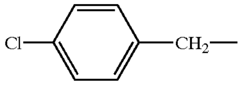 | 1 | 2 | 0 | R | H | 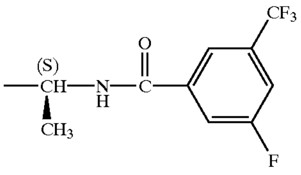 |
| 171 | 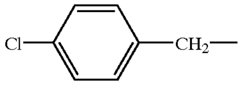 | 1 | 2 | 0 | R | H | 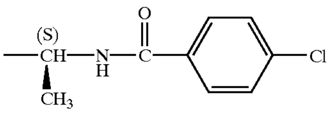 |
| 172 | 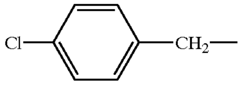 | 1 | 2 | 0 | R | H | 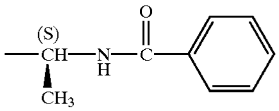 |
| 173 | 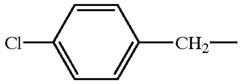 | 1 | 2 | 0 | R | H | 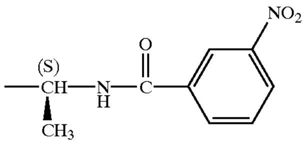 |
| 174 | 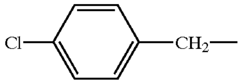 | 1 | 2 | 0 | R | H | 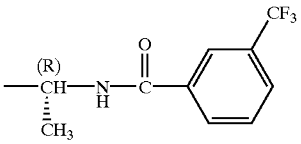 |
| 175 | 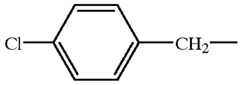 | 1 | 2 | 0 | R | H | 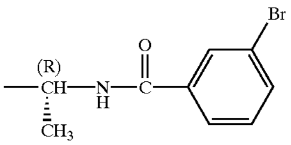 |

TABLE 1.16-continued
| Compd. No. | 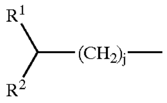 | k | m | n | chirality | $R^3$ | 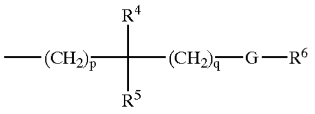 |
|---|---|---|---|---|---|---|---|
| 176 | 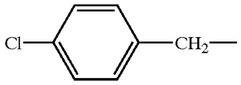 | 1 | 2 | 0 | R | H | 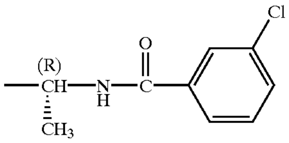 |
TABLE 1.17
| Compd. No. | 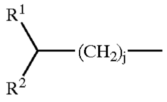 | k | m | n | chirality | $R^3$ | 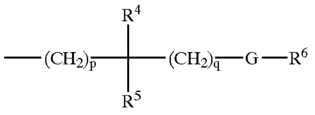 |
|---|---|---|---|---|---|---|---|
| 177 | 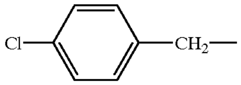 | 1 | 2 | 0 | R | H | 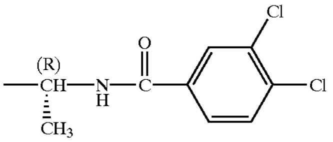 |
| 178 | 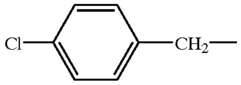 | 1 | 2 | 0 | R | H | 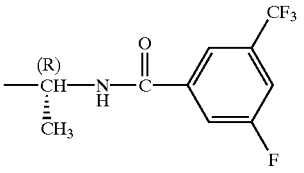 |
| 179 | 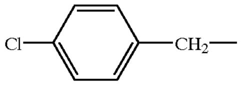 | 1 | 2 | 0 | R | H | 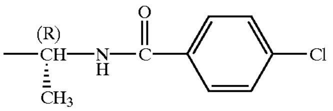 |
| 180 | 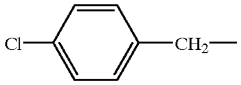 | 1 | 2 | 0 | R | H | 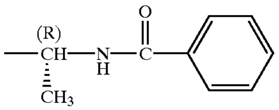 |
| 181 | 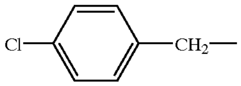 | 1 | 2 | 0 | R | H | 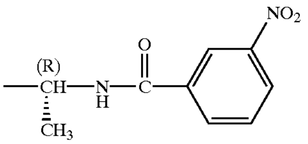 |
| 182 | 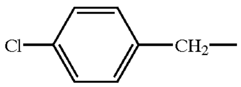 | 1 | 2 | 0 | R | H | 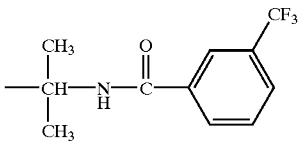 |
| 183 | 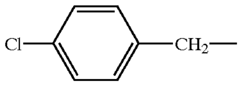 | 1 | 2 | 0 | R | H | 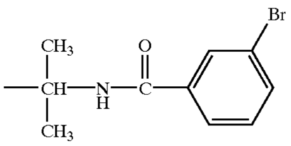 |

TABLE 1.17-continued
| Compd. No. | 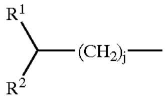 | k | m | n | chirality | $R^3$ | 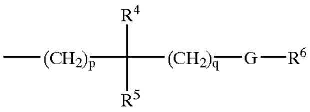 |
|---|---|---|---|---|---|---|---|
| 184 | 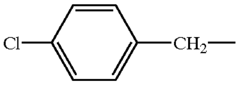 | 1 | 2 | 0 | R | H | 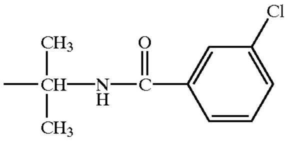 |
| 185 | 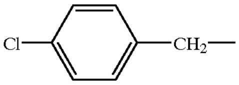 | 1 | 2 | 0 | R | H | 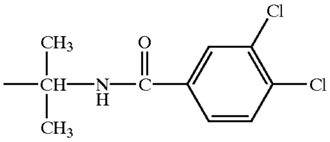 |
| 186 | 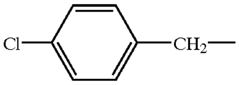 | 1 | 2 | 0 | R | H | 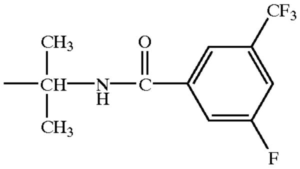 |
| 187 | 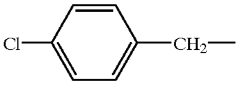 | 1 | 2 | 0 | R | H | 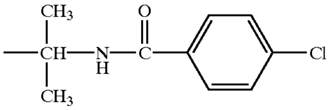 |
TABLE 1.18
| Compd. No. | 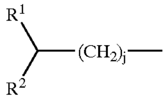 | k | m | n | chirality | $R^3$ | 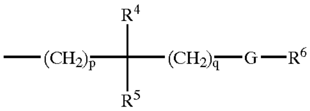 |
|---|---|---|---|---|---|---|---|
| 188 | 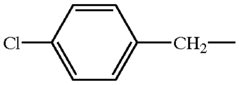 | 1 | 2 | 0 | R | H | 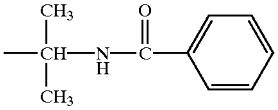 |
| 189 | 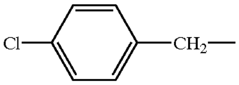 | 1 | 2 | 0 | R | H | 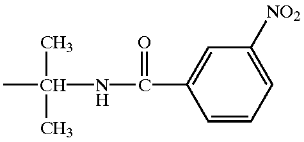 |
| 190 | 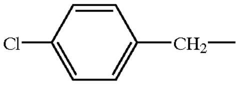 | 1 | 2 | 0 | R | H | 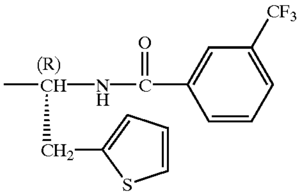 |

TABLE 1.18-continued
| Compd. No. | 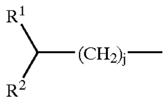 | k | m | n | chirality | $R^3$ | 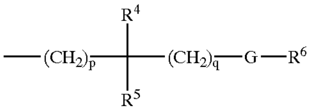 |
|---|---|---|---|---|---|---|---|
| 191 | 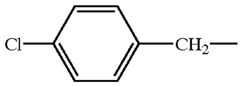 | 1 | 2 | 0 | R | H | 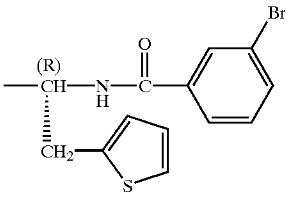 |
| 192 | 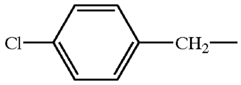 | 1 | 2 | 0 | R | H | 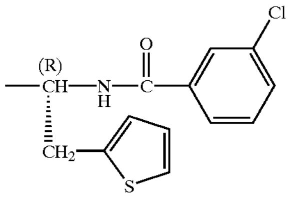 |
| 193 | 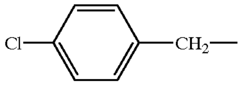 | 1 | 2 | 0 | R | H | 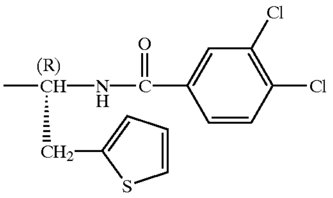 |
| 194 | 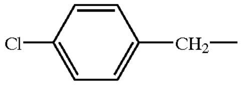 | 1 | 2 | 0 | R | H | 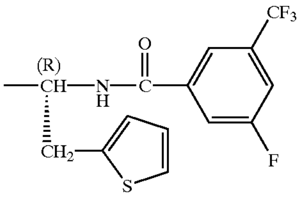 |
| 195 | 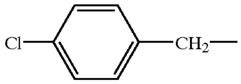 | 1 | 2 | 0 | R | H | 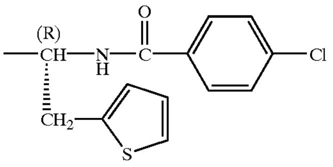 |
| 196 | 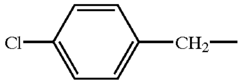 | 1 | 2 | 0 | R | H | 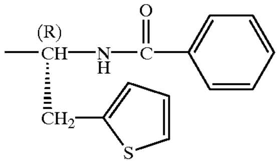 |
| 197 | 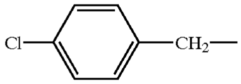 | 1 | 2 | 0 | R | H | 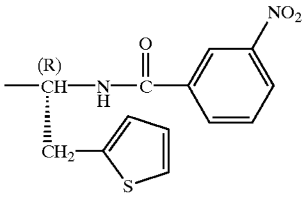 |

TABLE 1.18-continued
| Compd. No. | 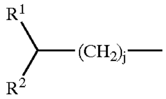 | k | m | n | chirality | $R^3$ | 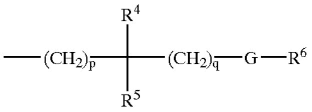 |
|---|---|---|---|---|---|---|---|
| 198 | 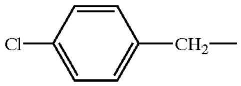 | 1 | 2 | 0 | R | H | 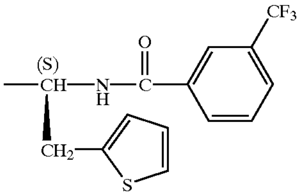 |
TABLE 1.19
| Compd. No. | 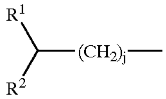 | k | m | n | chirality | $R^3$ | 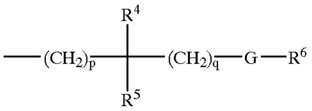 |
|---|---|---|---|---|---|---|---|
| 199 | 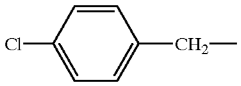 | 1 | 2 | 0 | R | H | 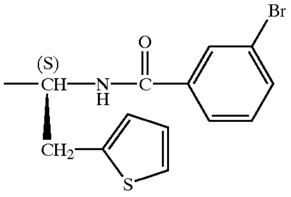 |
| 200 | 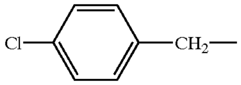 | 1 | 2 | 0 | R | H | 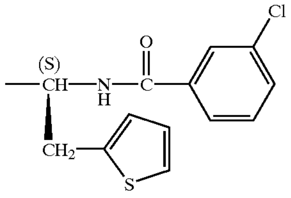 |
| 201 | 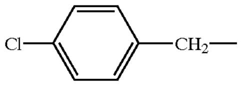 | 1 | 2 | 0 | R | H | 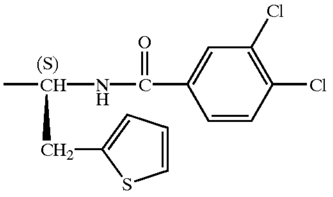 |
| 202 | 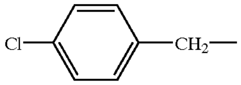 | 1 | 2 | 0 | R | H | 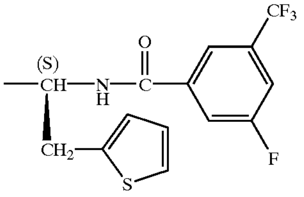 |
| 203 | 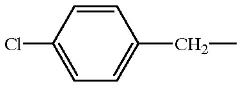 | 1 | 2 | 0 | R | H | 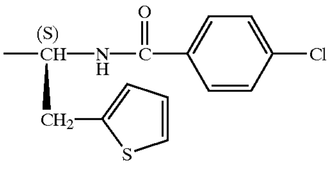 |

TABLE 1.19-continued
| Compd. No. | 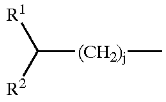 | k | m | n | chirality | $R^3$ | 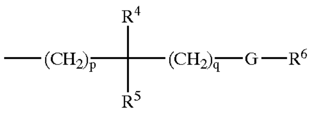 |
|---|---|---|---|---|---|---|---|
| 204 | 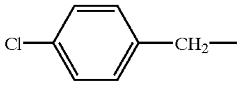 | 1 | 2 | 0 | R | H | 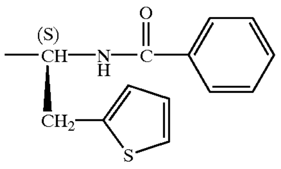 |
| 205 | 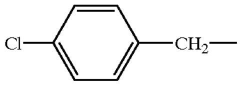 | 1 | 2 | 0 | R | H | 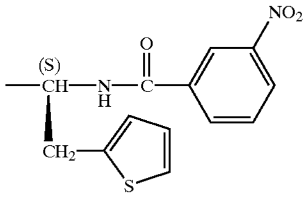 |
| 206 | 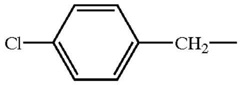 | 1 | 2 | 0 | R | H | 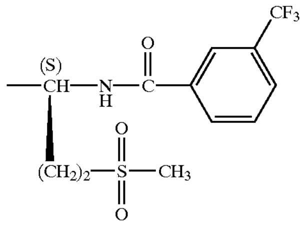 |
| 207 | 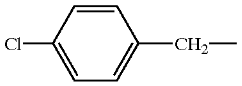 | 1 | 2 | 0 | R | H | 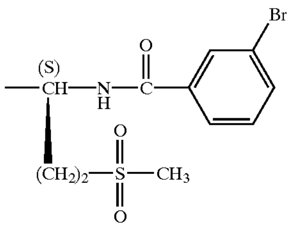 |
| 208 | 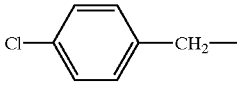 | 1 | 2 | 0 | R | H | 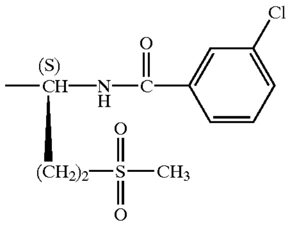 |
| 209 | 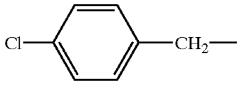 | 1 | 2 | 0 | R | H | 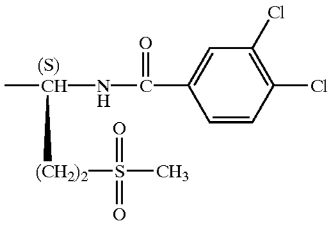 |

TABLE 1.20
| Compd. No. | 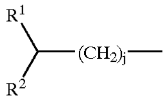 | k | m | n | chirality | $R^3$ | 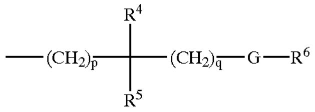 |
|---|---|---|---|---|---|---|---|
| 210 | 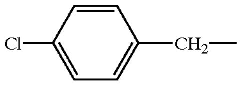 | 1 | 2 | 0 | R | H | 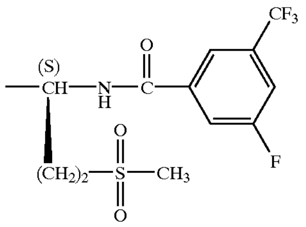 |
| 211 | 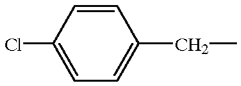 | 1 | 2 | 0 | R | H | 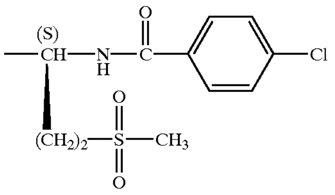 |
| 212 | 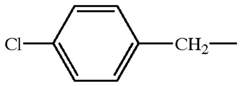 | 1 | 2 | 0 | R | H | 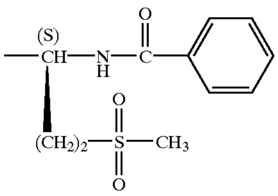 |
| 213 | 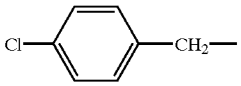 | 1 | 2 | 0 | R | H | 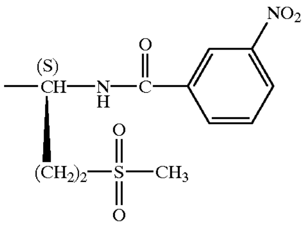 |
| 214 | 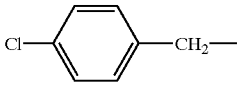 | 1 | 2 | 0 | — | H | 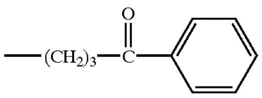 |
| 215 | 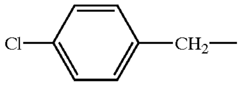 | 1 | 2 | 0 | — | H | 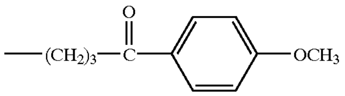 |
| 216 | 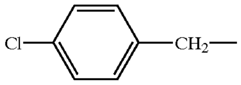 | 1 | 2 | 0 | — | H | 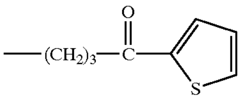 |
| 217 | 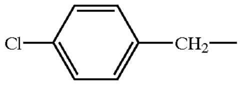 | 1 | 2 | 0 | — | H | 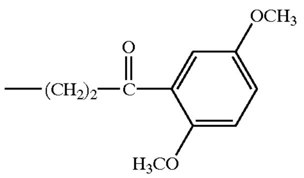 |

TABLE 1.20-continued
| Compd. No. | 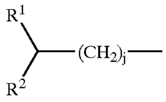 | k | m | n | chirality | $R^3$ | 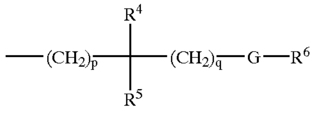 |
|---|---|---|---|---|---|---|---|
| 218 | 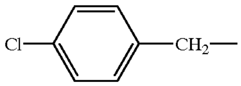 | 1 | 2 | 0 | — | H | 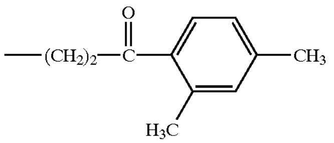 |
| 219 | 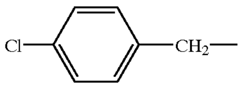 | 1 | 2 | 0 | — | H | 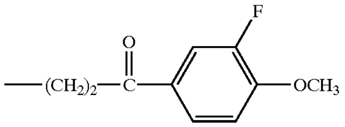 |
| 220 | 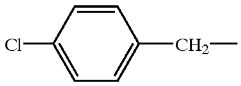 | 1 | 2 | 0 | — | H | 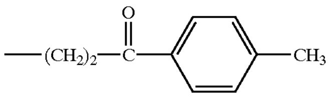 |
TABLE 1.21
| Compd. No. | 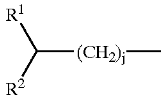 | k | m | n | chirality | $R^3$ | 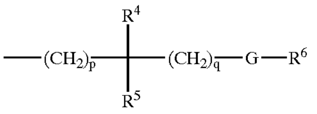 |
|---|---|---|---|---|---|---|---|
| 221 | 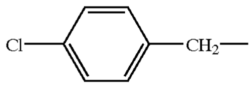 | 1 | 2 | 0 | — | H | 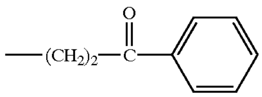 |
| 222 | 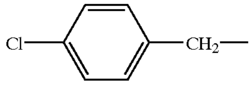 | 1 | 2 | 0 | — | H | 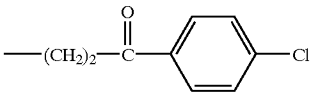 |
| 223 | 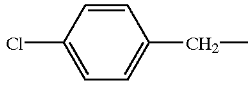 | 1 | 2 | 0 | — | H | 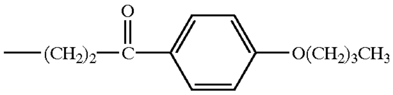 |
| 224 | 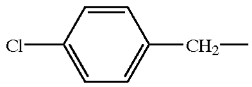 | 1 | 2 | 0 | — | H | 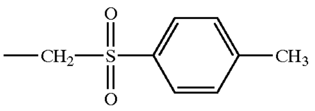 |
| 225 | 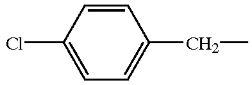 | 1 | 2 | 0 | — | H | 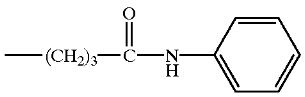 |
| 226 | 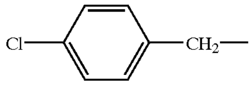 | 1 | 2 | 0 | — | H | 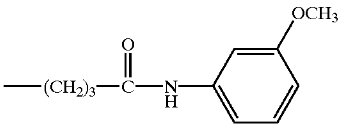 |

TABLE 1.21-continued
| Compd. No. | 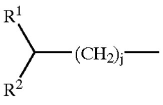 | k | m | n | chirality | $R^3$ | 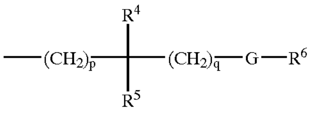 |
|---|---|---|---|---|---|---|---|
| 227 | 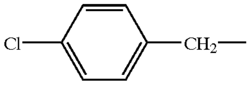 | 1 | 2 | 0 | — | H | 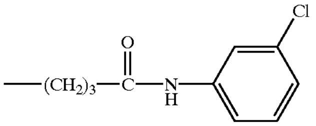 |
| 228 | 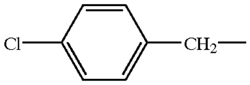 | 1 | 2 | 0 | — | H | 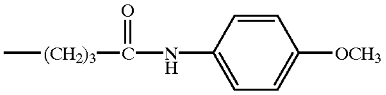 |
| 229 | 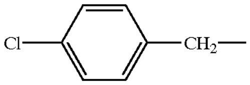 | 1 | 2 | 0 | — | H | 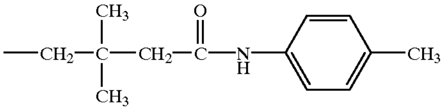 |
| 230 | 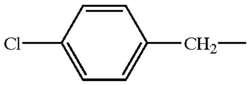 | 1 | 2 | 0 | — | H | 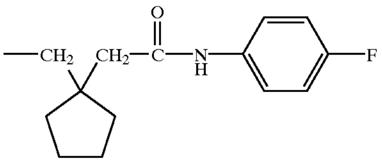 |
| 231 | 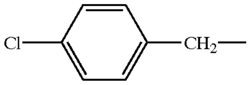 | 1 | 2 | 0 | — | H | 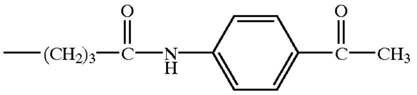 |
TABLE 1.22
| Compd. No. | 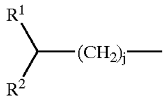 | k | m | n | chirality | $R^3$ | 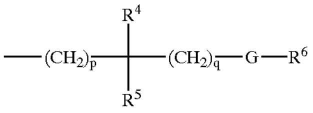 |
|---|---|---|---|---|---|---|---|
| 232 | 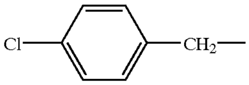 | 1 | 2 | 0 | — | H | 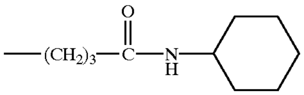 |
| 233 | 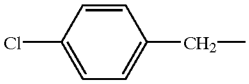 | 1 | 2 | 0 | — | H | 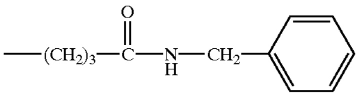 |
| 234 | 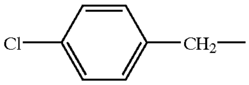 | 1 | 2 | 0 | — | H | 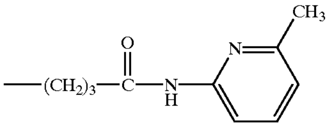 |
| 235 | 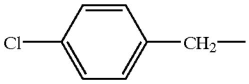 | 1 | 2 | 0 | — | H | 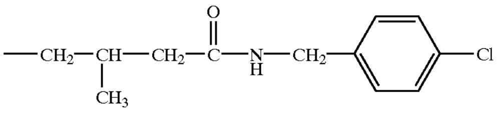 |

TABLE 1.22-continued
| Compd. No. | 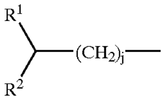 | k | m | n | chirality | $R^3$ | 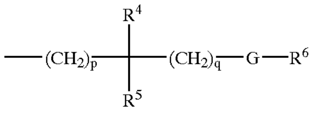 |
|---|---|---|---|---|---|---|---|
| 236 | 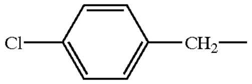 | 1 | 2 | 0 | — | H | 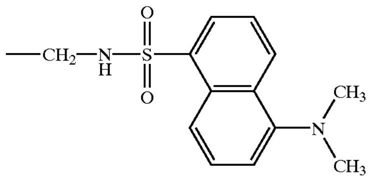 |
| 237 | 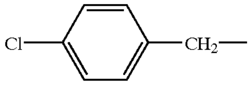 | 1 | 2 | 0 | — | H | 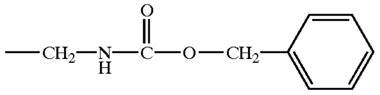 |
| 238 | 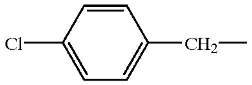 | 1 | 2 | 0 | — | H | 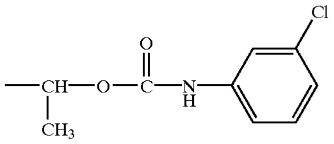 |
| 239 | 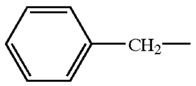 | 1 | 2 | 0 | S | H | 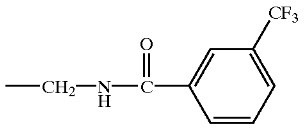 |
| 240 | 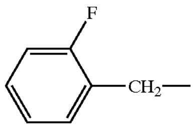 | 1 | 2 | 0 | S | H | 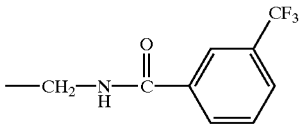 |
| 241 | 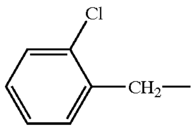 | 1 | 2 | 0 | S | H | 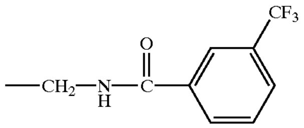 |
| 242 | 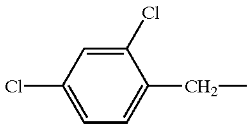 | 1 | 2 | 0 | S | H | 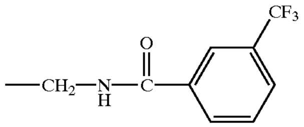 |
TABLE 1.23
| Compd. No. | 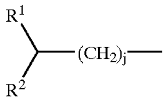 | k | m | n | chirality | $R^3$ | 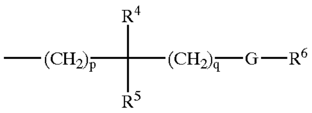 |
|---|---|---|---|---|---|---|---|
| 243 | 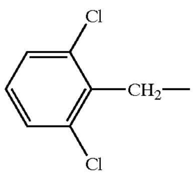 | 1 | 2 | 0 | S | H | 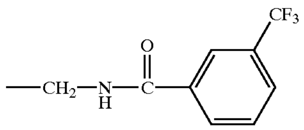 |

TABLE 1.23-continued
| Compd. No. | 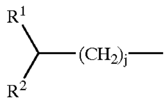 | k | m | n | chirality | $R^3$ | 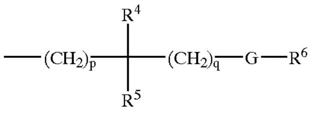 |
|---|---|---|---|---|---|---|---|
| 244 | 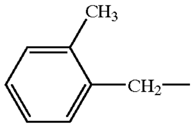 | 1 | 2 | 0 | S | H | 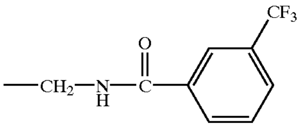 |
| 245 | 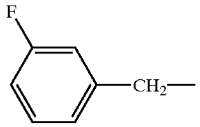 | 1 | 2 | 0 | S | H | 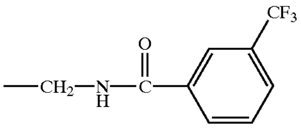 |
| 246 | 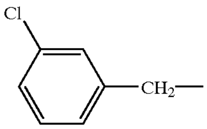 | 1 | 2 | 0 | S | H | 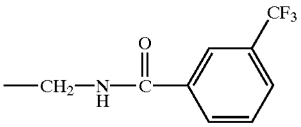 |
| 247 | 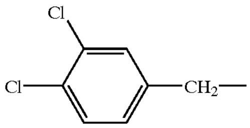 | 1 | 2 | 0 | S | H | 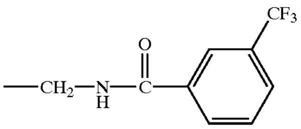 |
| 248 | 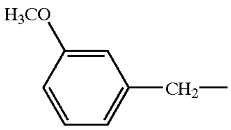 | 1 | 2 | 0 | S | H | 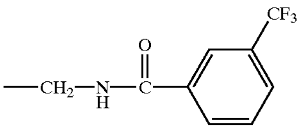 |
| 249 | 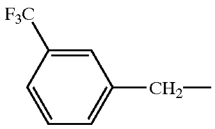 | 1 | 2 | 0 | S | H | 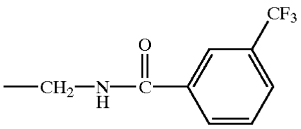 |
| 250 | 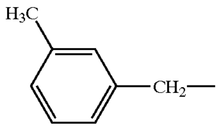 | 1 | 2 | 0 | S | H | 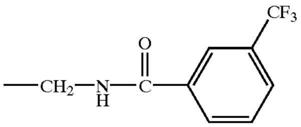 |
| 251 | 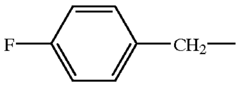 | 1 | 2 | 0 | S | H | 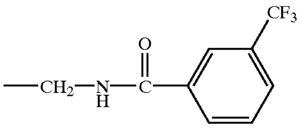 |
| 252 | 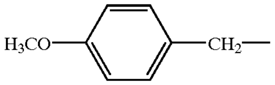 | 1 | 2 | 0 | S | H | 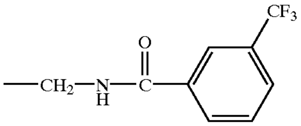 |
| 253 | 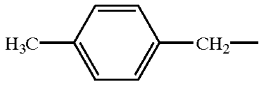 | 1 | 2 | 0 | S | H | 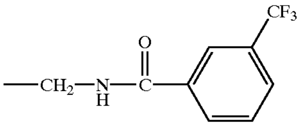 |

TABLE 1.24
| Compd. No. | 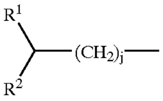 | k | m | n | chirality | $R^3$ | 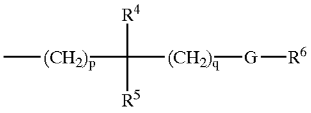 |
|---|---|---|---|---|---|---|---|
| 254 | 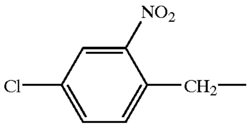 | 1 | 2 | 0 | S | H | 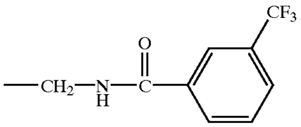 |
| 255 | 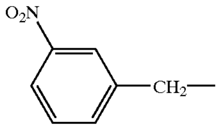 | 1 | 2 | 0 | S | H | 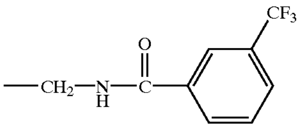 |
| 256 | 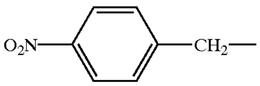 | 1 | 2 | 0 | S | H | 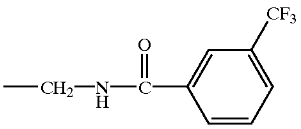 |
| 257 | 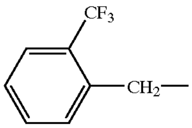 | 1 | 2 | 0 | S | H | 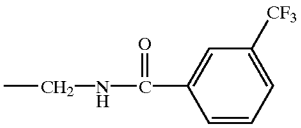 |
| 258 | 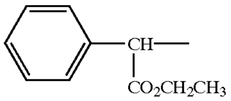 | 1 | 2 | 0 | S | H | 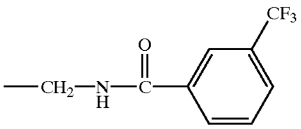 |
| 259 | 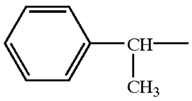 | 1 | 2 | 0 | S | H | 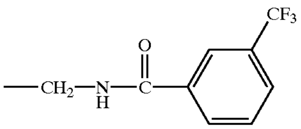 |
| 260 | 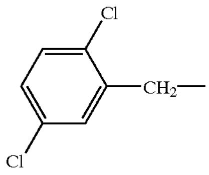 | 1 | 2 | 0 | S | H | 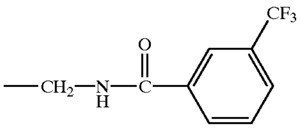 |
| 261 | 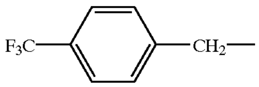 | 1 | 2 | 0 | S | H | 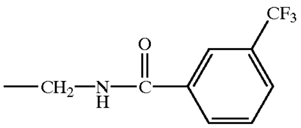 |
| 262 | 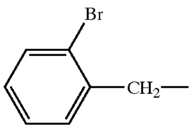 | 1 | 2 | 0 | S | H | 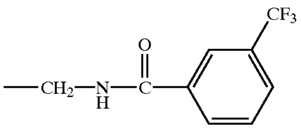 |

TABLE 1.24-continued
| Compd. No. | 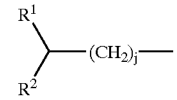 | k | m | n | chirality | $R^3$ | 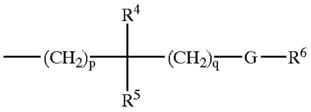 |
|---|---|---|---|---|---|---|---|
| 263 | 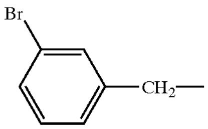 | 1 | 2 | 0 | S | H | 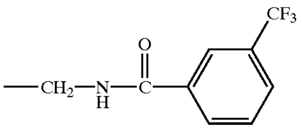 |
| 264 | 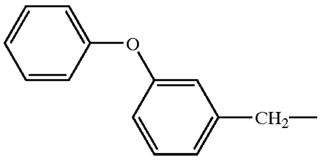 | 1 | 2 | 0 | S | H | 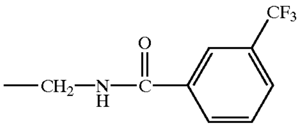 |
TABLE 1.25
| Compd. No. | 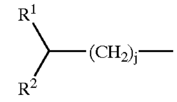 | k | m | n | chirality | $R^3$ | 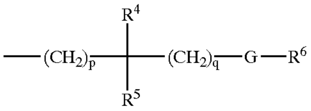 |
|---|---|---|---|---|---|---|---|
| 265 | 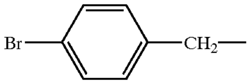 | 1 | 2 | 0 | S | H | 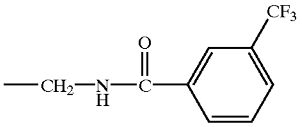 |
| 266 | 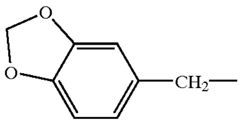 | 1 | 2 | 0 | S | H | 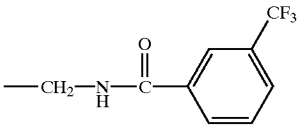 |
| 267 | 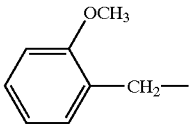 | 1 | 2 | 0 | S | H | 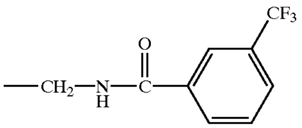 |
| 268 | 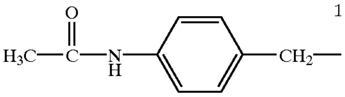 | 1 | 2 | 0 | S | H | 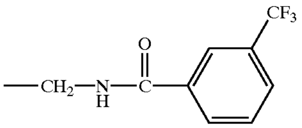 |
| 269 | 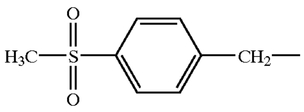 | 1 | 2 | 0 | S | H | 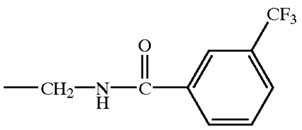 |
| 270 | 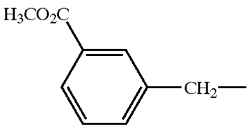 | 1 | 2 | 0 | S | H | 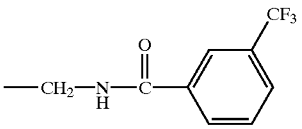 |

TABLE 1.25-continued
| Compd. No. | 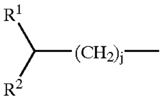 | k | m | n | chirality | $R^3$ | 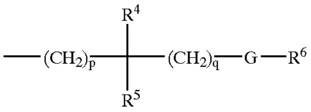 |
|---|---|---|---|---|---|---|---|
| 271 | 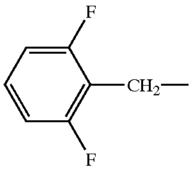 | 1 | 2 | 0 | S | H | 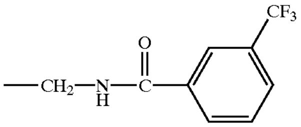 |
| 272 | 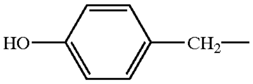 | 1 | 2 | 0 | S | H | 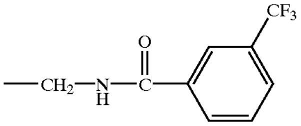 |
| 273 | 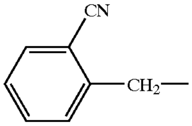 | 1 | 2 | 0 | S | H | 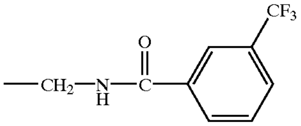 |
| 274 | 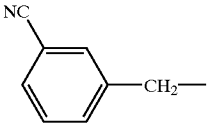 | 1 | 2 | 0 | S | H | 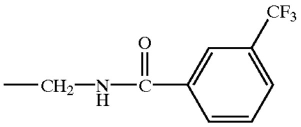 |
| 275 | 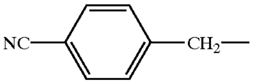 | 1 | 2 | 0 | S | H | 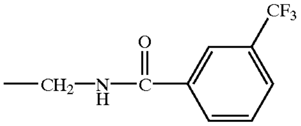 |
TABLE 1.26
| Compd. No. | 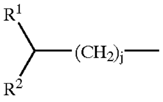 | k | m | n | chirality | $R^3$ | 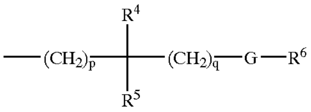 |
|---|---|---|---|---|---|---|---|
| 276 | 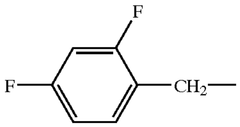 | 1 | 2 | 0 | S | H | 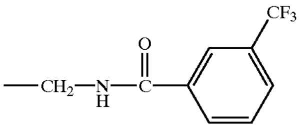 |
| 277 | 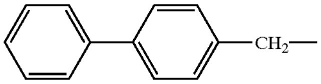 | 1 | 2 | 0 | S | H | 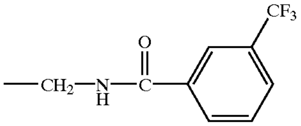 |
| 278 | 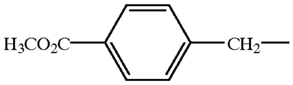 | 1 | 2 | 0 | S | H | 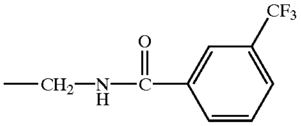 |

TABLE 1.26-continued
| Compd. No. | 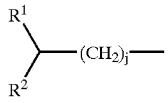 | k | m | n | chirality | $R^3$ | 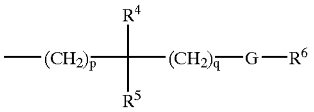 |
|---|---|---|---|---|---|---|---|
| 279 | 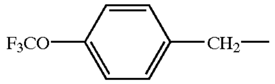 | 1 | 2 | 0 | S | H | 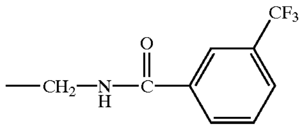 |
| 280 | 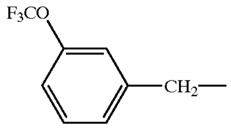 | 1 | 2 | 0 | S | H | 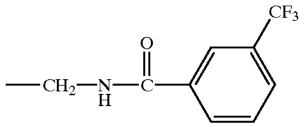 |
| 281 | 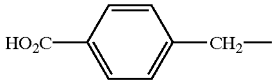 | 1 | 2 | 0 | S | H | 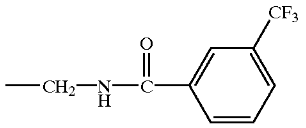 |
| 282 | 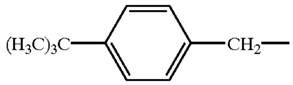 | 1 | 2 | 0 | S | H | 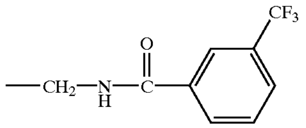 |
| 283 | 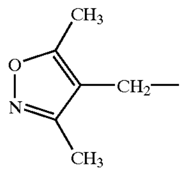 | 1 | 2 | 0 | S | H | 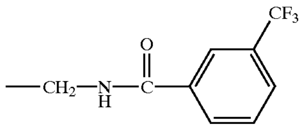 |
| 284 | 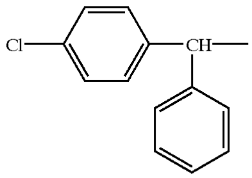 | 1 | 2 | 0 | S | H | 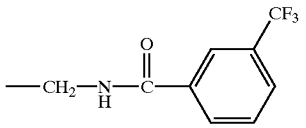 |
| 285 | 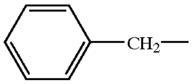 | 1 | 2 | 0 | R | H | 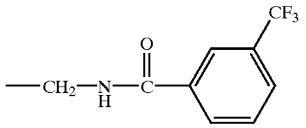 |
| 286 | 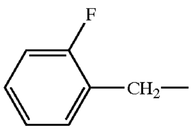 | 1 | 2 | 0 | R | H | 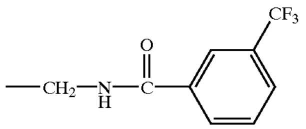 |

TABLE 1.27
| Compd. No. | 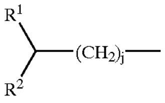 | k | m | n | chirality | $R^3$ | 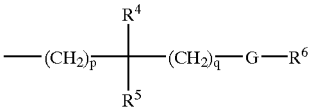 |
|---|---|---|---|---|---|---|---|
| 287 | 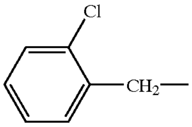 | 1 | 2 | 0 | R | H | 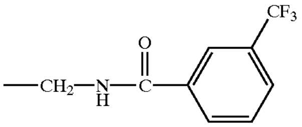 |
| 288 | 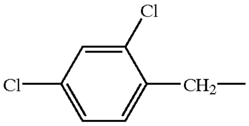 | 1 | 2 | 0 | R | H | 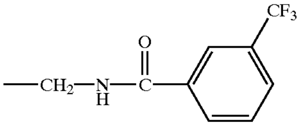 |
| 289 | 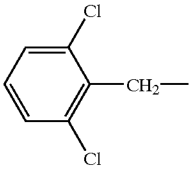 | 1 | 2 | 0 | R | H | 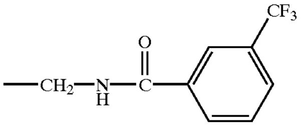 |
| 290 | 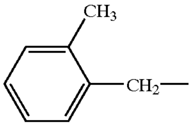 | 1 | 2 | 0 | R | H | 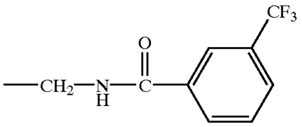 |
| 291 | 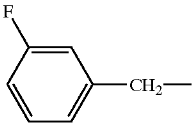 | 1 | 2 | 0 | R | H | 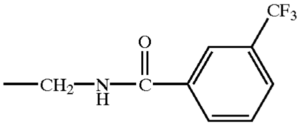 |
| 292 | 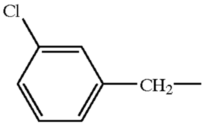 | 1 | 2 | 0 | R | H | 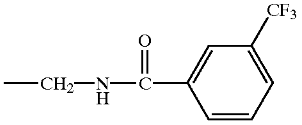 |
| 293 | 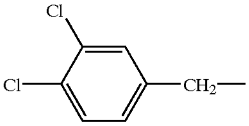 | 1 | 2 | 0 | R | H | 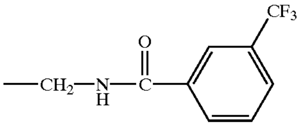 |
| 294 | 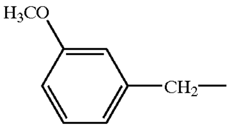 | 1 | 2 | 0 | R | H | 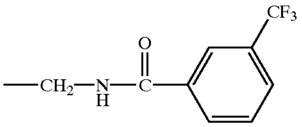 |
| 295 | 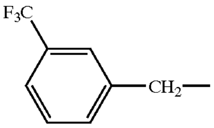 | 1 | 2 | 0 | R | H | 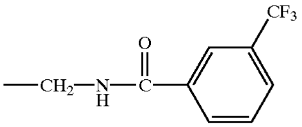 |
| 296 | 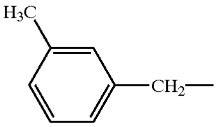 | 1 | 2 | 0 | R | H | 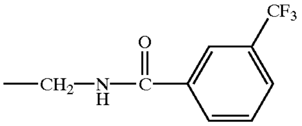 |

TABLE 1.27-continued
| Compd. No. | 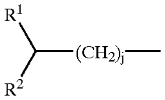 | k | m | n | chirality | $R^3$ | 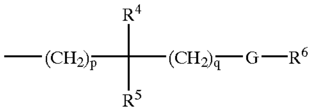 |
|---|---|---|---|---|---|---|---|
| 297 | 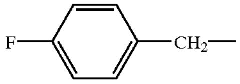 | 1 | 2 | 0 | R | H | 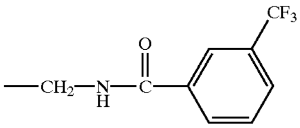 |
TABLE 1.28
| Compd. No. | 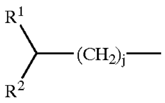 | k | m | n | chirality | $R^3$ | 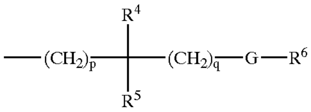 |
|---|---|---|---|---|---|---|---|
| 298 | 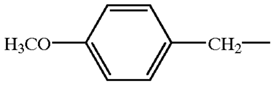 | 1 | 2 | 0 | R | H | 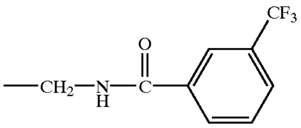 |
| 299 | 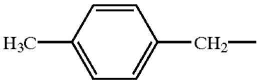 | 1 | 2 | 0 | R | H | 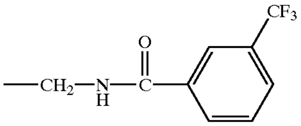 |
| 300 | 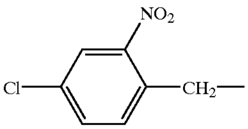 | 1 | 2 | 0 | R | H | 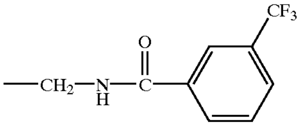 |
| 301 | 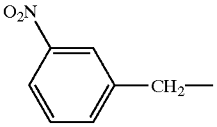 | 1 | 2 | 0 | R | H | 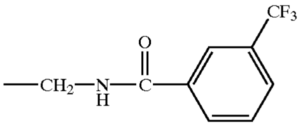 |
| 302 | 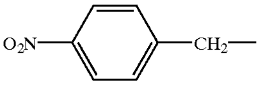 | 1 | 2 | 0 | R | H | 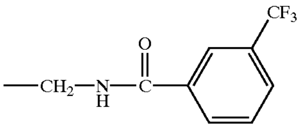 |
| 303 | 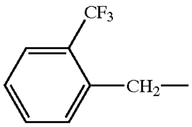 | 1 | 2 | 0 | R | H | 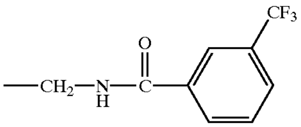 |
| 304 | 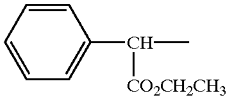 | 1 | 2 | 0 | R | H | 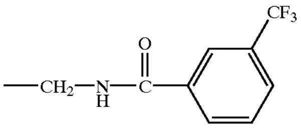 |

TABLE 1.28-continued
| Compd. No. | 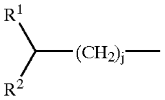 | k | m | n | chirality | $R^3$ | 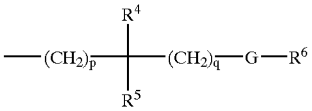 |
|---|---|---|---|---|---|---|---|
| 305 | 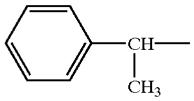 | 1 | 2 | 0 | R | H | 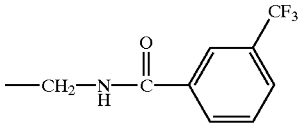 |
| 306 | 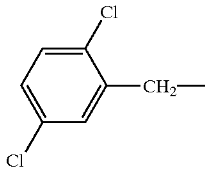 | 1 | 2 | 0 | R | H | 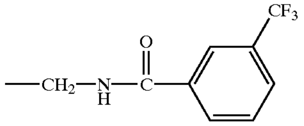 |
| 307 | 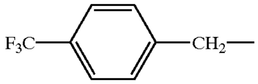 | 1 | 2 | 0 | R | H | 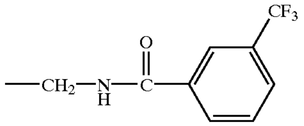 |
| 308 | 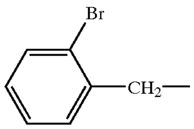 | 1 | 2 | 0 | R | H | 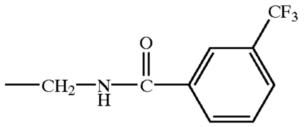 |
TABLE 1.29
| Compd. No. | 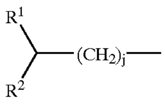 | k | m | n | chirality | $R^3$ | 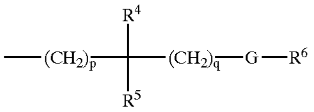 |
|---|---|---|---|---|---|---|---|
| 309 | 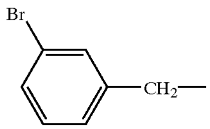 | 1 | 2 | 0 | R | H | 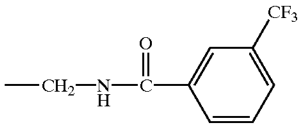 |
| 310 | 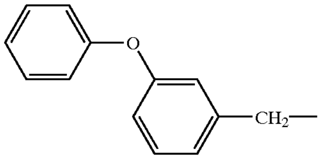 | 1 | 2 | 0 | R | H | 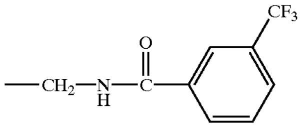 |
| 311 | 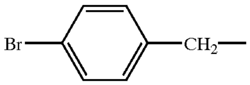 | 1 | 2 | 0 | R | H | 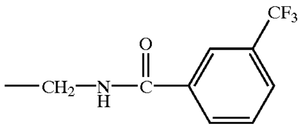 |
| 312 | 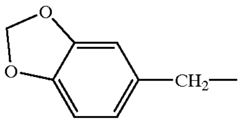 | 1 | 2 | 0 | R | H | 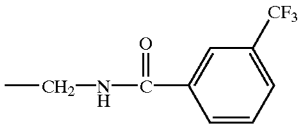 |

TABLE 1.29-continued
| Compd. No. | 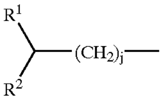 | k | m | n | chirality | $R^3$ | 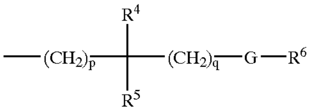 |
|---|---|---|---|---|---|---|---|
| 313 | 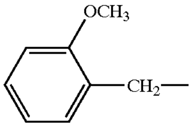 | 1 | 2 | 0 | R | H | 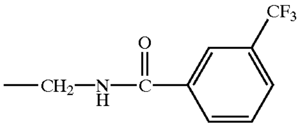 |
| 314 | 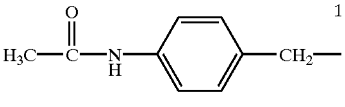 | 1 | 2 | 0 | R | H | 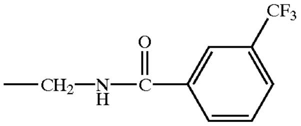 |
| 315 | 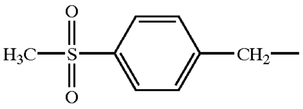 | 1 | 2 | 0 | R | H | 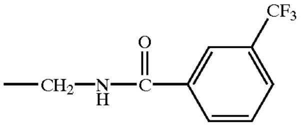 |
| 316 | 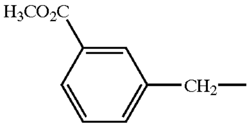 | 1 | 2 | 0 | R | H | 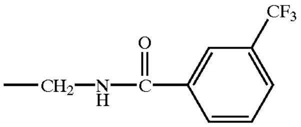 |
| 317 | 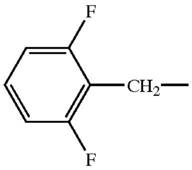 | 1 | 2 | 0 | R | H | 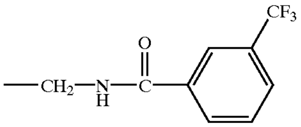 |
| 318 | 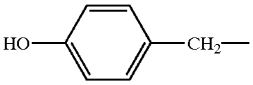 | 1 | 2 | 0 | R | H | 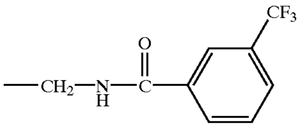 |
| 319 | 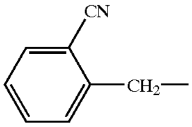 | 1 | 2 | 0 | R | H | 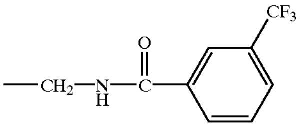 |
TABLE 1.30
| Compd. No. | 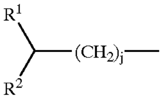 | k | m | n | chirality | $R^3$ | 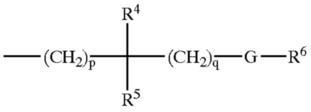 |
|---|---|---|---|---|---|---|---|
| 320 | 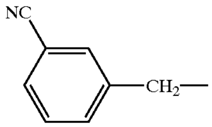 | 1 | 2 | 0 | R | H | 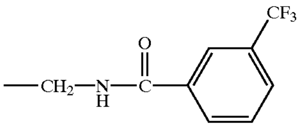 |

TABLE 1.30-continued
| Compd. No. | 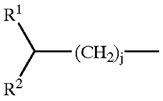 | k | m | n | chirality | $R^3$ | 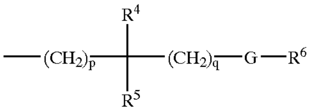 |
|---|---|---|---|---|---|---|---|
| 321 | 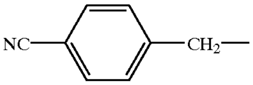 | 1 | 2 | 0 | R | H | 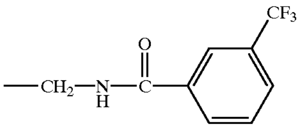 |
| 322 | 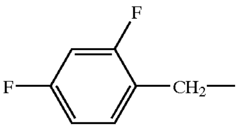 | 1 | 2 | 0 | R | H | 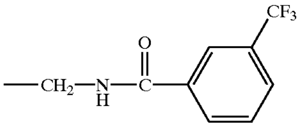 |
| 323 | 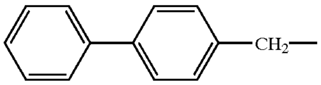 | 1 | 2 | 0 | R | H | 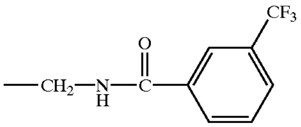 |
| 324 | 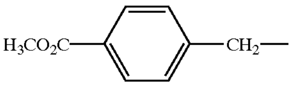 | 1 | 2 | 0 | R | H | 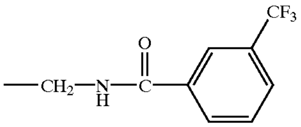 |
| 325 | 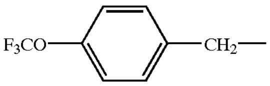 | 1 | 2 | 0 | R | H | 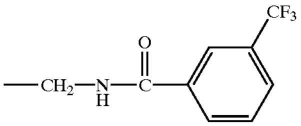 |
| 326 | 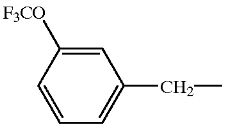 | 1 | 2 | 0 | R | H | 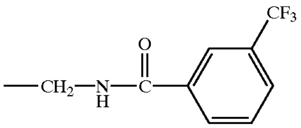 |
| 327 | 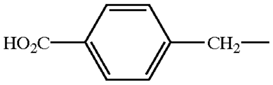 | 1 | 2 | 0 | R | H | 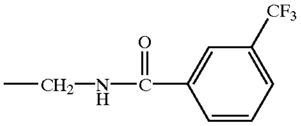 |
| 328 | 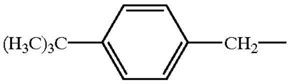 | 1 | 2 | 0 | R | H | 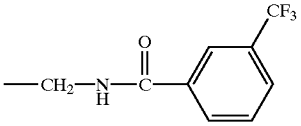 |
| 329 | 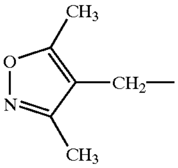 | 1 | 2 | 0 | R | H | 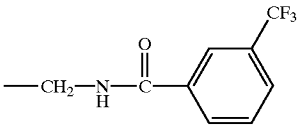 |
| 330 | 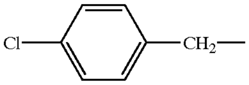 | 0 | 3 | 1 | — | H | 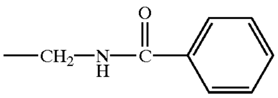 |

TABLE 1.31
| Compd. No. | 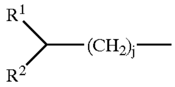 | k | m | n | chirality | $R^3$ | 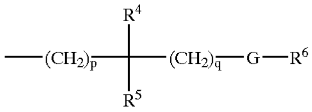 |
|---|---|---|---|---|---|---|---|
| 331 | 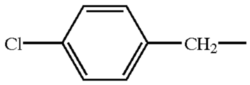 | 0 | 3 | 1 | — | H | 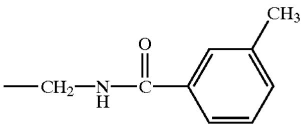 |
| 332 | 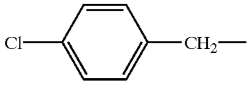 | 0 | 3 | 1 | — | H | 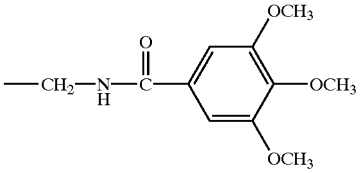 |
| 333 | 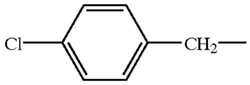 | 0 | 3 | 1 | — | H | 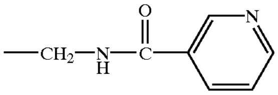 |
| 334 | 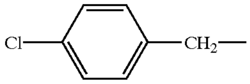 | 0 | 3 | 1 | — | H | 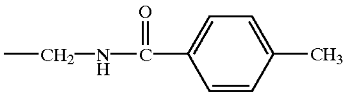 |
| 335 | 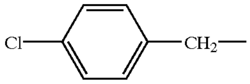 | 0 | 3 | 1 | — | H | 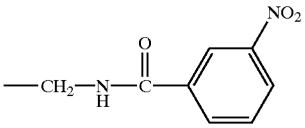 |
| 336 | 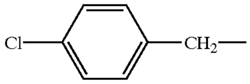 | 0 | 3 | 1 | — | H | 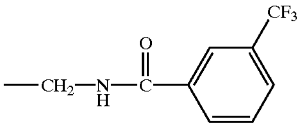 |
| 337 | 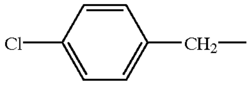 | 0 | 3 | 1 | — | H | 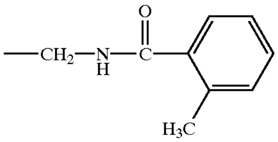 |
| 338 | 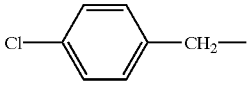 | 0 | 3 | 1 | — | H | 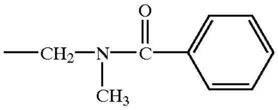 |
| 339 | 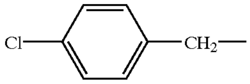 | 0 | 3 | 1 | R | H | 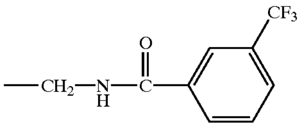 |
| 340 | 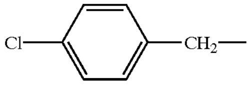 | 0 | 3 | 1 | S | H | 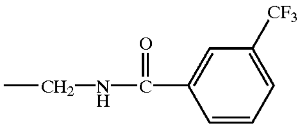 |

TABLE 1.31-continued
| Compd. No. | 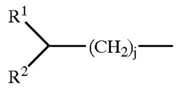 | k | m | n | chirality | $R^3$ | 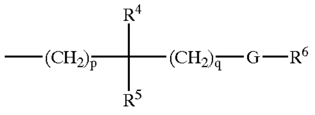 |
|---|---|---|---|---|---|---|---|
| 341 | 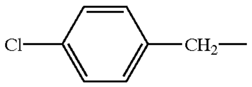 | 0 | 3 | 1 | — | H | 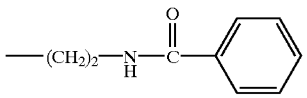 |
TABLE 1.32
| Compd. No. | 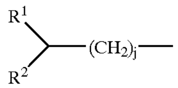 | k | m | n | chirality | $R^3$ | 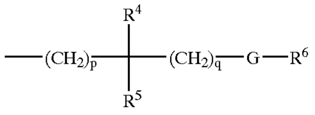 |
|---|---|---|---|---|---|---|---|
| 342 | 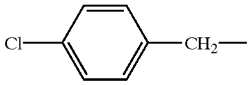 | 0 | 3 | 1 | — | H | 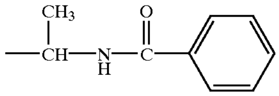 |
| 343 | 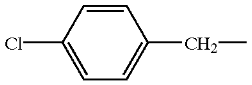 | 0 | 3 | 1 | — | H | 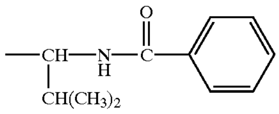 |
| 344 | 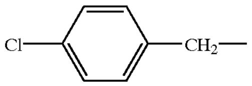 | 0 | 3 | 1 | — | H | 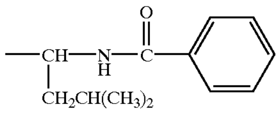 |
| 345 | 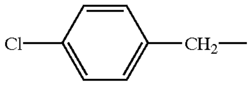 | 0 | 3 | 1 | — | H | 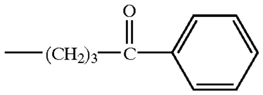 |
| 346 | 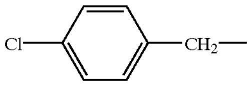 | 0 | 3 | 1 | — | H | 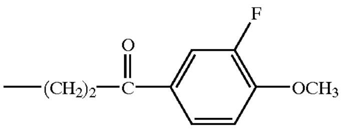 |
| 347 | 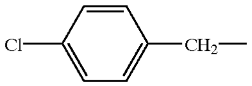 | 0 | 3 | 1 | — | H | 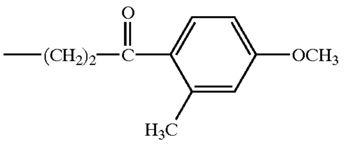 |
| 348 | 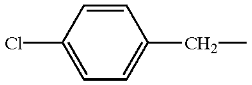 | 0 | 3 | 1 | — | H | 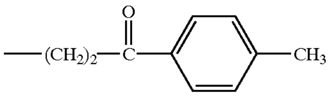 |
| 349 | 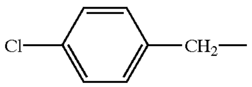 | 0 | 3 | 1 | — | H | 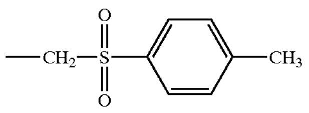 |

TABLE 1.32-continued
| Compd. No. | 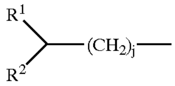 | k | m | n | chirality | R3 | 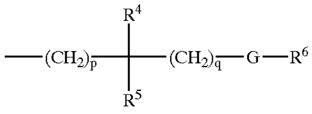 |
|---|---|---|---|---|---|---|---|
| 350 | 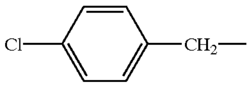 | 0 | 3 | 1 | — | H | 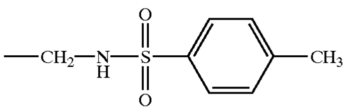 |
| 351 | 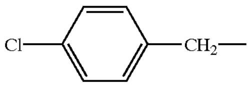 | 0 | 3 | 1 | — | H | 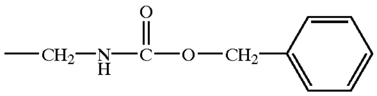 |
| 352 | 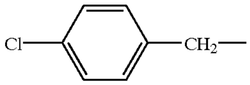 | 0 | 3 | 1 | — | H | 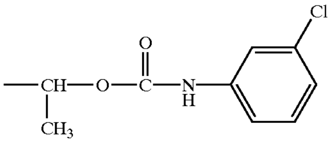 |
TABLE 1.33
| Compd. No. | 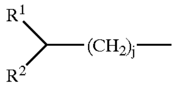 | k | m | n | chirality | R3 | 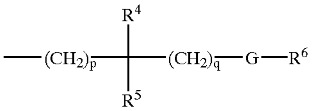 |
|---|---|---|---|---|---|---|---|
| 353 | 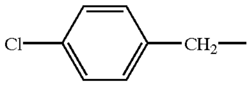 | 1 | 2 | 1 | — | H | 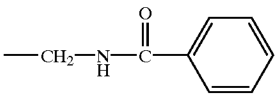 |
| 354 | 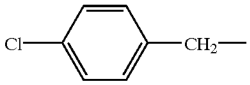 | 1 | 3 | 0 | — | H | 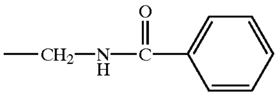 |
| 355 | 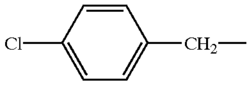 | 1 | 3 | 0 | — | H | 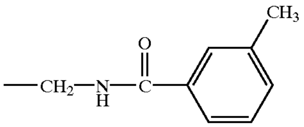 |
| 356 | 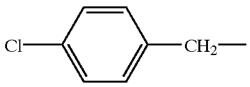 | 1 | 3 | 0 | — | H | 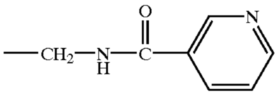 |
| 357 | 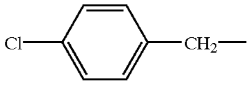 | 1 | 3 | 0 | — | H | 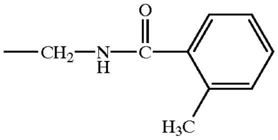 |
| 358 | 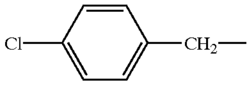 | 1 | 3 | 0 | — | H | 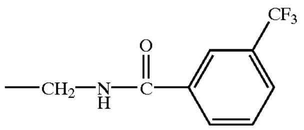 |

TABLE 1.33-continued
| Compd. No. | 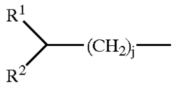 | k | m | n | chirality | $R^3$ | 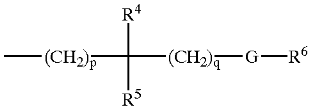 |
|---|---|---|---|---|---|---|---|
| 359 | 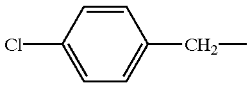 | 1 | 3 | 0 | — | H | 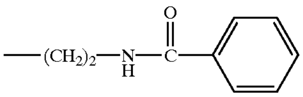 |
| 360 | 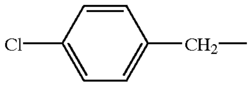 | 1 | 3 | 0 | — | H | 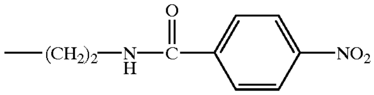 |
| 361 | 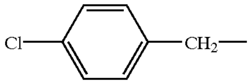 | 1 | 3 | 0 | — | H | 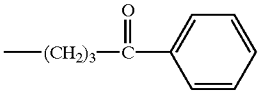 |
| 362 | 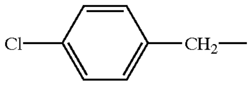 | 1 | 3 | 0 | — | H | 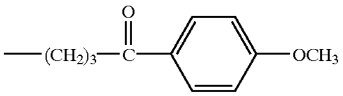 |
| 363 | 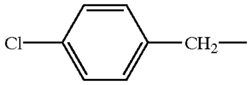 | 1 | 3 | 0 | — | H | 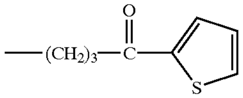 |
TABLE 1.34
| Compd. No. | 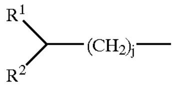 | k | m | n | chirality | $R^3$ | 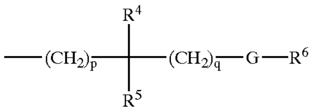 |
|---|---|---|---|---|---|---|---|
| 364 | 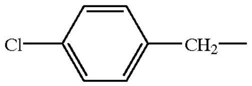 | 1 | 3 | 0 | — | H | 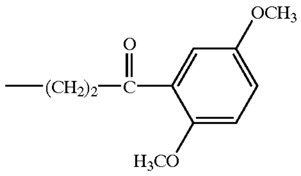 |
| 365 | 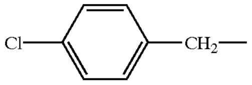 | 1 | 3 | 0 | — | H | 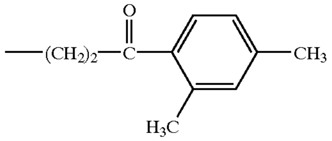 |
| 366 | 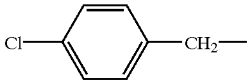 | 1 | 3 | 0 | — | H | 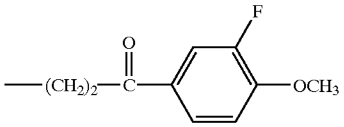 |
| 367 | 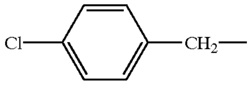 | 1 | 3 | 0 | — | H | 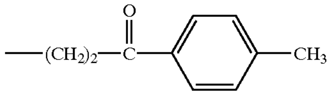 |

TABLE 1.34-continued
| Compd. No. | 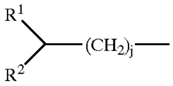 | k | m | n | chirality | $R^3$ | 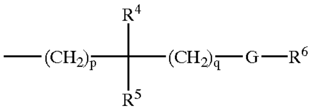 |
|---|---|---|---|---|---|---|---|
| 368 | 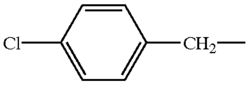 | 1 | 3 | 0 | — | H | 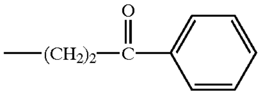 |
| 369 | 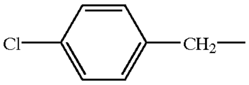 | 1 | 3 | 0 | — | H | 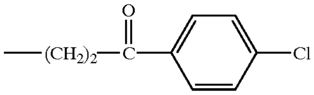 |
| 370 | 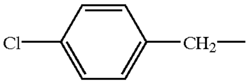 | 1 | 3 | 0 | — | H | 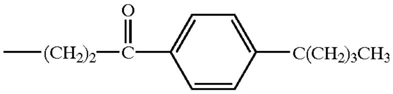 |
| 371 | 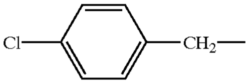 | 1 | 3 | 0 | — | H | 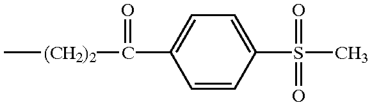 |
| 372 | 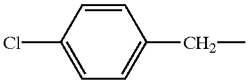 | 1 | 3 | 0 | — | H | 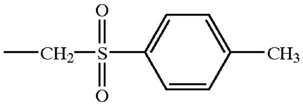 |
| 373 | 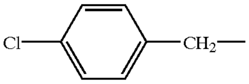 | 1 | 3 | 0 | — | H | 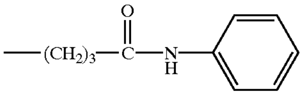 |
| 374 | 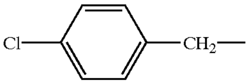 | 1 | 3 | 0 | — | H | 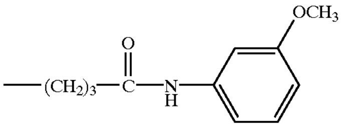 |
TABLE 1.35
| Compd. No. | 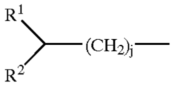 | k | m | n | chirality | $R^3$ | 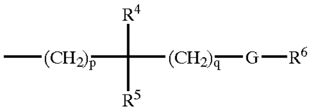 |
|---|---|---|---|---|---|---|---|
| 375 | 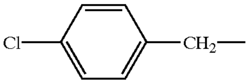 | 1 | 3 | 0 | — | H | 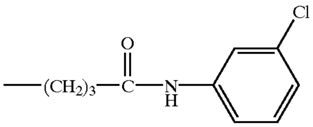 |
| 376 | 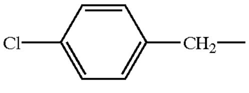 | 1 | 3 | 0 | — | H | 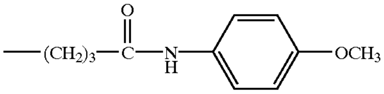 |
| 377 | 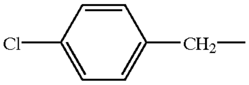 | 1 | 3 | 0 | — | H | 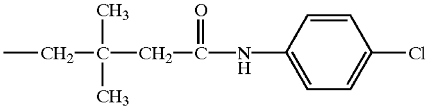 |

TABLE 1.35-continued
| Compd. No. | 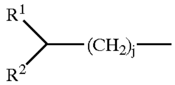 | k | m | n | chirality | $R^3$ | 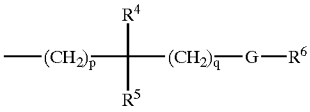 |
|---|---|---|---|---|---|---|---|
| 378 | 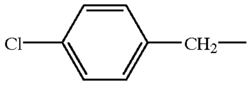 | 1 | 3 | 0 | — | H | 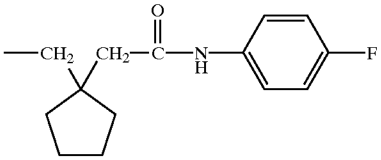 |
| 379 | 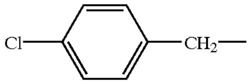 | 1 | 3 | 0 | — | H | 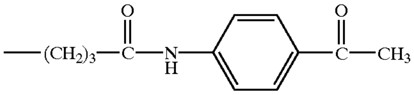 |
| 380 | 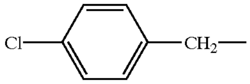 | 1 | 3 | 0 | — | H | 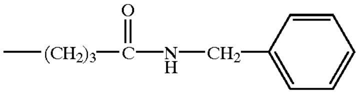 |
| 381 | 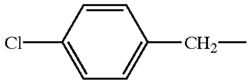 | 1 | 3 | 0 | — | H | 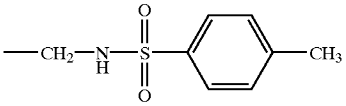 |
| 382 | 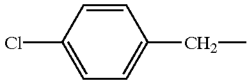 | 1 | 3 | 0 | — | H | 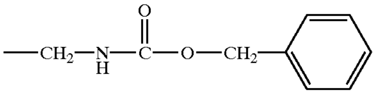 |
| 383 | 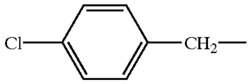 | 1 | 3 | 0 | — | H | 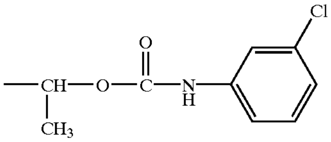 |
| 384 | 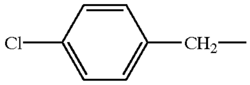 | 2 | 2 | 0 | — | H | 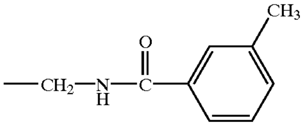 |
| 385 | 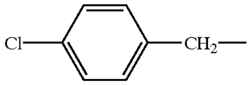 | 2 | 2 | 0 | — | H | 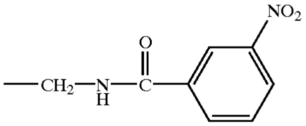 |
TABLE 13.6
| Compd. No. | 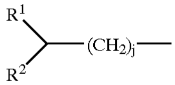 | k | m | n | chirality | $R^3$ | 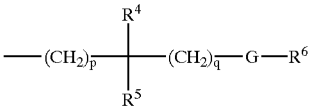 |
|---|---|---|---|---|---|---|---|
| 386 | 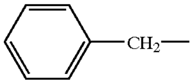 | 2 | 2 | 0 | — | H | 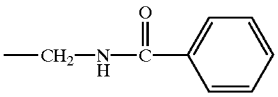 |

TABLE 13.6-continued
| Compd. No. | 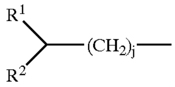 | k | m | n | chirality | $R^3$ | 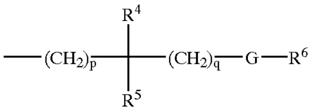 |
|---|---|---|---|---|---|---|---|
| 387 | 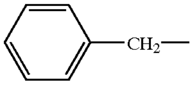 | 2 | 2 | 0 | — | H | 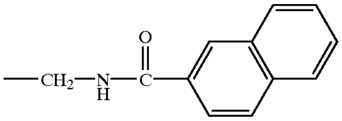 |
| 388 | 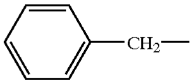 | 2 | 2 | 0 | — | H | 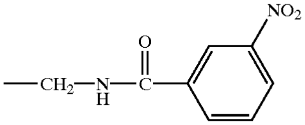 |
| 389 | 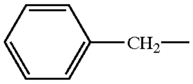 | 2 | 2 | 0 | — | H | 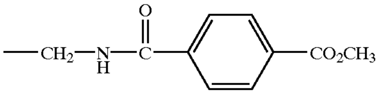 |
| 390 | 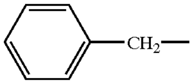 | 2 | 2 | 0 | — | H | 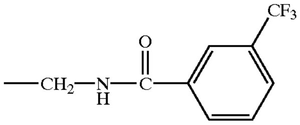 |
| 391 | 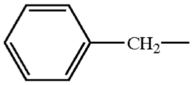 | 2 | 2 | 0 | — | H | 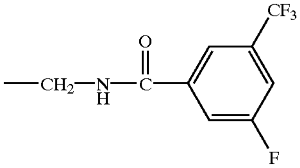 |
| 392 | 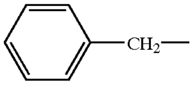 | 2 | 2 | 0 | — | H | 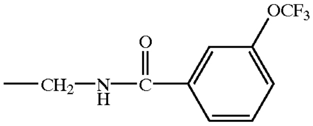 |
| 393 | 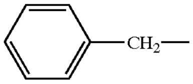 | 2 | 2 | 0 | — | H | 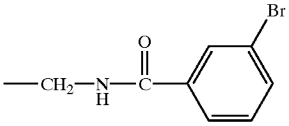 |
| 394 | 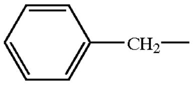 | 2 | 2 | 0 | — | H | 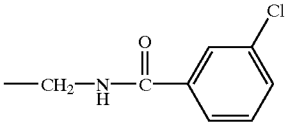 |
| 395 | 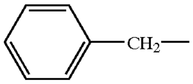 | 2 | 2 | 0 | — | H | 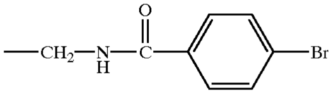 |
| 396 | 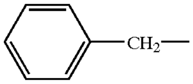 | 2 | 2 | 0 | — | H | 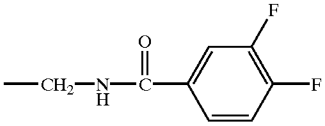 |

TABLE 1.37
| Compd. No. | 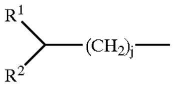 | k | m | n | chirality | $R^3$ | 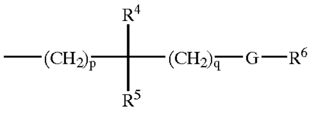 |
|---|---|---|---|---|---|---|---|
| 397 | 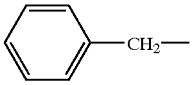 | 2 | 2 | 0 | — | H | 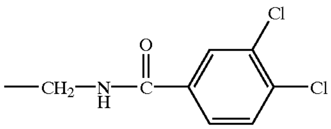 |
| 398 | 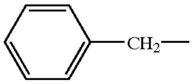 | 2 | 2 | 0 | — | H | 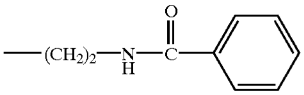 |
| 399 | 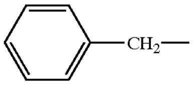 | 2 | 2 | 0 | — | H | 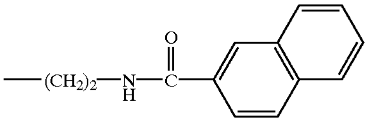 |
| 400 | 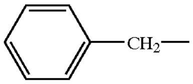 | 2 | 2 | 0 | — | H | 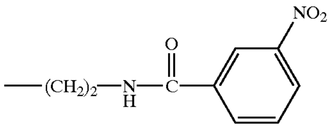 |
| 401 | 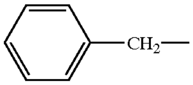 | 2 | 2 | 0 | — | H | 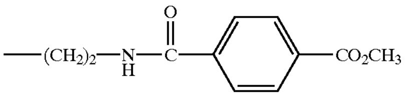 |
| 402 | 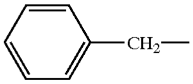 | 2 | 2 | 0 | — | H | 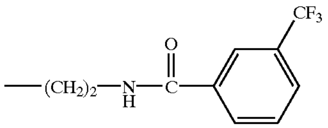 |
| 403 | 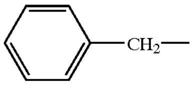 | 2 | 2 | 0 | — | H | 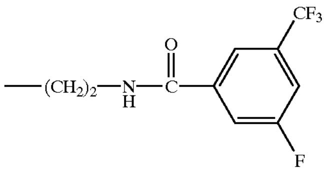 |
| 404 | 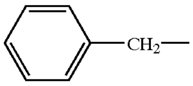 | 2 | 2 | 0 | — | H | 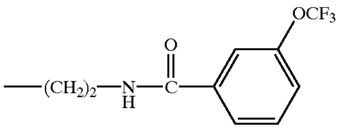 |
| 405 | 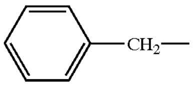 | 2 | 2 | 0 | — | H | 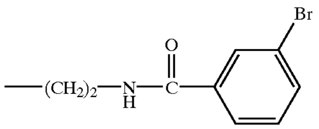 |
| 406 | 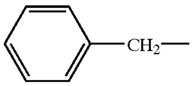 | 2 | 2 | 0 | — | H | 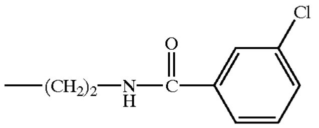 |

TABLE 1.37-continued
| Compd. No. | 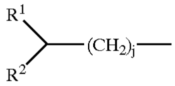 | k | m | n | chirality | $R^3$ | 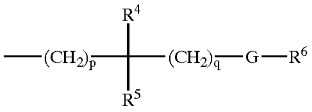 |
|---|---|---|---|---|---|---|---|
| 407 | 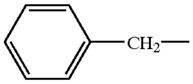 | 2 | 2 | 0 | — | H | 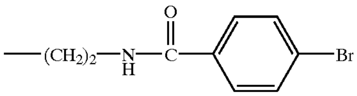 |
TABLE 1.38
| Compd. No. | 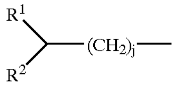 | k | m | n | chirality | $R^3$ | 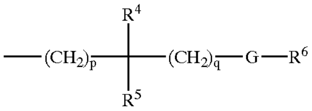 |
|---|---|---|---|---|---|---|---|
| 408 | 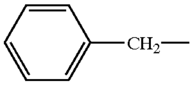 | 2 | 2 | 0 | — | H | 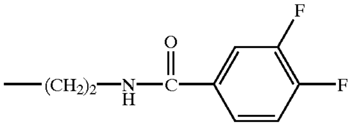 |
| 409 | 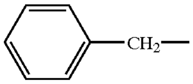 | 2 | 2 | 0 | — | H | 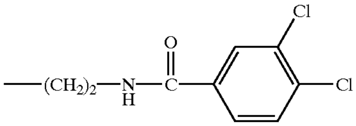 |
| 410 | 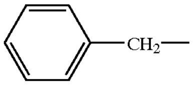 | 2 | 2 | 0 | — | H | 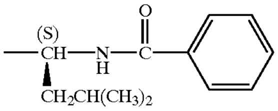 |
| 411 | 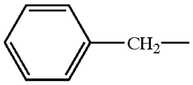 | 2 | 2 | 0 | — | H | 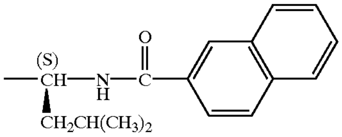 |
| 412 | 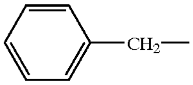 | 2 | 2 | 0 | — | H | 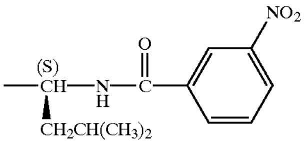 |
| 413 | 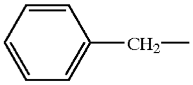 | 2 | 2 | 0 | — | H | 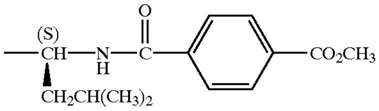 |
| 414 | 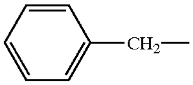 | 2 | 2 | 0 | — | H | 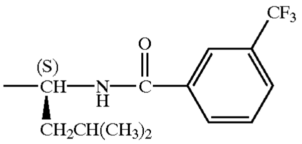 |

TABLE 1.38-continued
| Compd. No. | 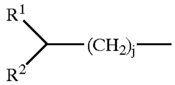 | k | m | n | chirality | $R^3$ | 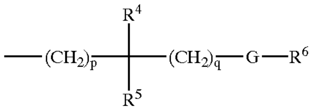 |
|---|---|---|---|---|---|---|---|
| 415 | 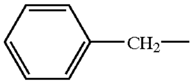 | 2 | 2 | 0 | — | H | 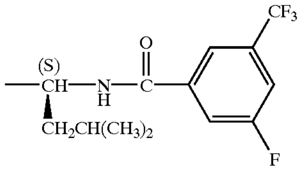 |
| 416 | 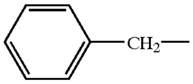 | 2 | 2 | 0 | — | H | 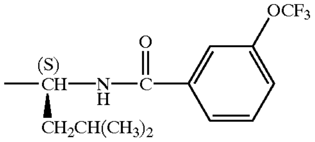 |
| 417 | 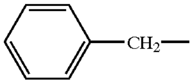 | 2 | 2 | 0 | — | H | 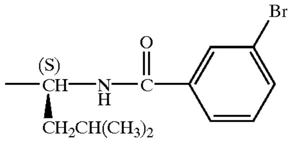 |
| 418 | 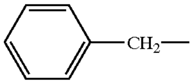 | 2 | 2 | 0 | — | H | 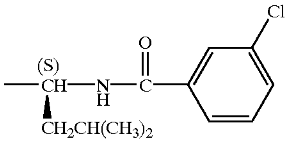 |
TABLE 1.39
| Compd. No. | 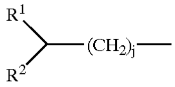 | k | m | n | chirality | $R^3$ | 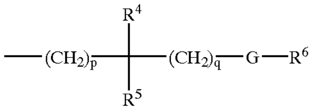 |
|---|---|---|---|---|---|---|---|
| 419 | 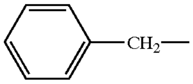 | 2 | 2 | 0 | — | H | 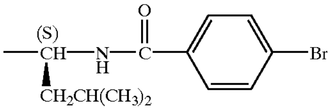 |
| 420 | 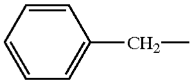 | 2 | 2 | 0 | — | H | 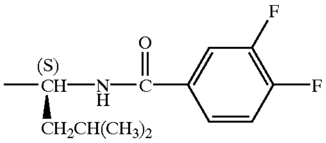 |
| 421 | 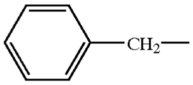 | 2 | 2 | 0 | — | H | 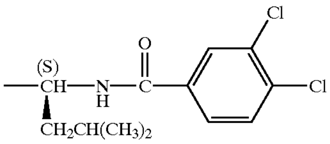 |
| 422 | 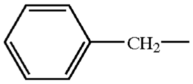 | 2 | 2 | 0 | — | H | 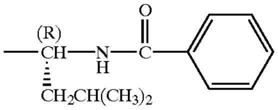 |

TABLE 1.39-continued
| Compd. No. | 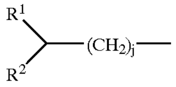 | k | m | n | chirality | $R^3$ | 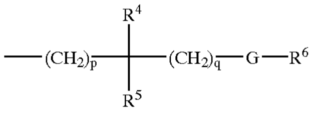 |
|---|---|---|---|---|---|---|---|
| 423 | 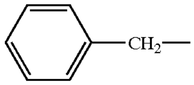 | 2 | 2 | 0 | — | H | 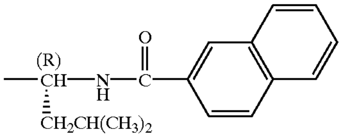 |
| 424 | 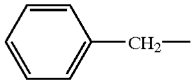 | 2 | 2 | 0 | — | H | 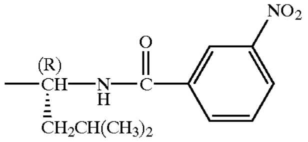 |
| 425 | 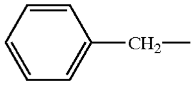 | 2 | 2 | 0 | — | H | 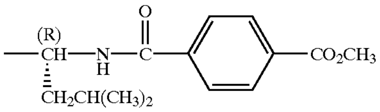 |
| 426 | 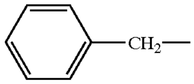 | 2 | 2 | 0 | — | H | 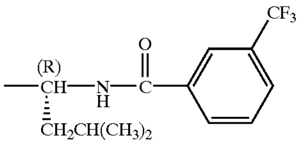 |
| 427 | 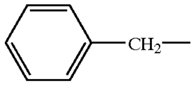 | 2 | 2 | 0 | — | H | 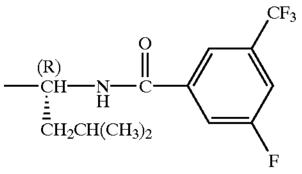 |
| 428 | 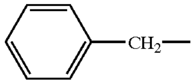 | 2 | 2 | 0 | — | H | 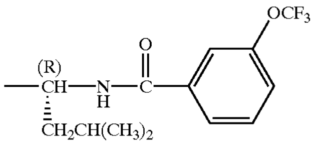 |
| 429 | 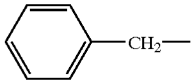 | 2 | 2 | 0 | — | H | 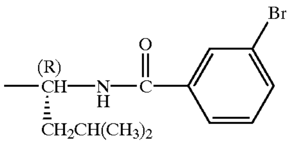 |

TABLE 1.40
| Compd. No. | 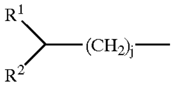 | k | m | n | chirality | $R^3$ | 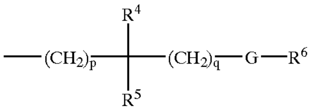 |
|---|---|---|---|---|---|---|---|
| 430 | 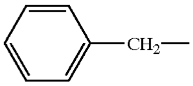 | 2 | 2 | 0 | — | H | 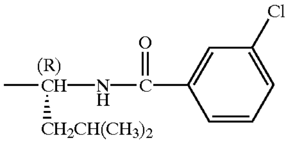 |
| 431 | 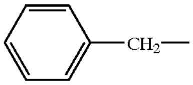 | 2 | 2 | 0 | — | H | 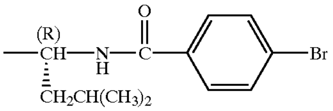 |
| 432 | 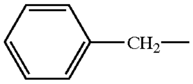 | 2 | 2 | 0 | — | H | 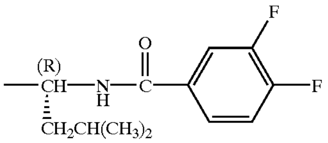 |
| 433 | 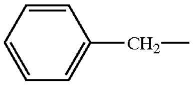 | 2 | 2 | 0 | — | H | 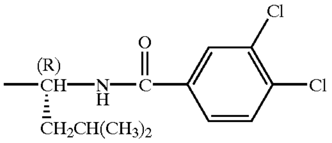 |
| 434 | 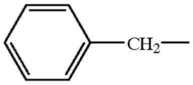 | 1 | 3 | 1 | — | H | 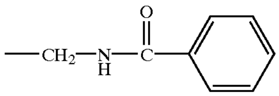 |
| 435 | 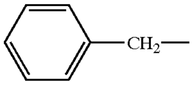 | 1 | 3 | 1 | — | H | 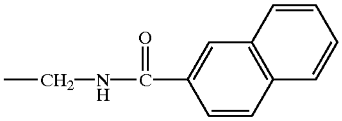 |
| 436 | 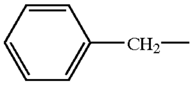 | 1 | 3 | 1 | — | H | 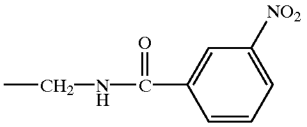 |
| 437 | 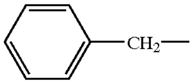 | 1 | 3 | 1 | — | H | 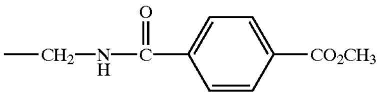 |
| 438 | 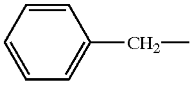 | 1 | 3 | 1 | — | H | 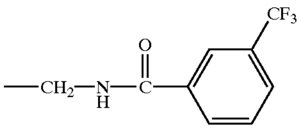 |
| 439 | 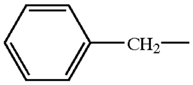 | 1 | 3 | 1 | — | H | 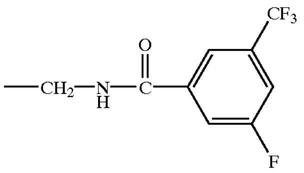 |

TABLE 1.40-continued
| Compd. No. | 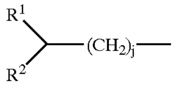 | k | m | n | chirality | $R^3$ | 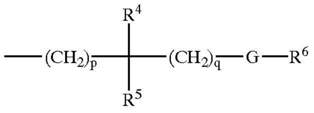 |
|---|---|---|---|---|---|---|---|
| 440 | 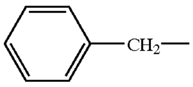 | 1 | 3 | 1 | — | H | 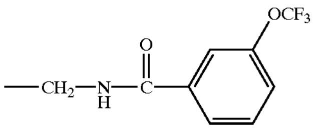 |
TABLE 1.41
| Compd. No. | 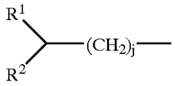 | k | m | n | chirality | $R^3$ | 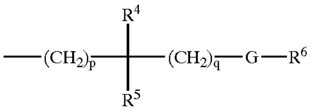 |
|---|---|---|---|---|---|---|---|
| 441 | 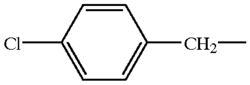 | 1 | 3 | 1 | — | H | 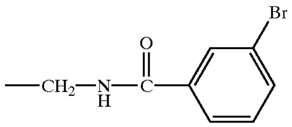 |
| 442 | 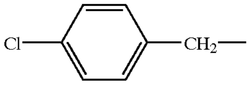 | 1 | 3 | 1 | — | H | 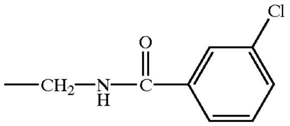 |
| 443 | 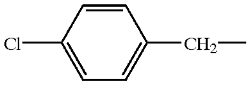 | 1 | 3 | 1 | — | H | 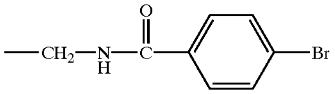 |
| 444 | 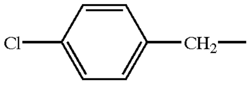 | 1 | 3 | 1 | — | H | 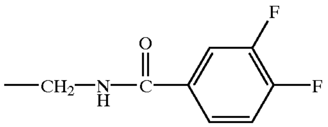 |
| 445 | 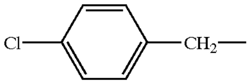 | 1 | 3 | 1 | — | H | 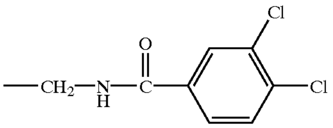 |
| 446 | 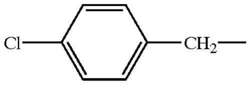 | 1 | 3 | 1 | — | H | 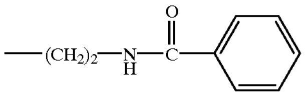 |
| 447 | 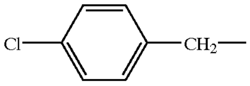 | 1 | 3 | 1 | — | H | 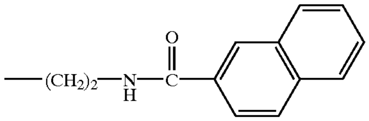 |
| 448 | 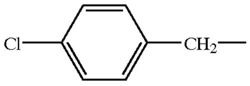 | 1 | 3 | 1 | — | H | 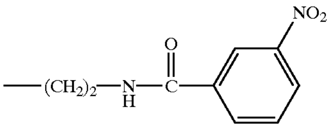 |

TABLE 1.41-continued
| Compd. No. | 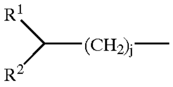 | k | m | n | chirality | $R^3$ | 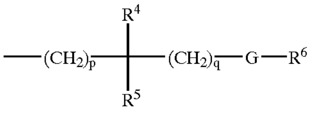 |
|---|---|---|---|---|---|---|---|
| 449 | 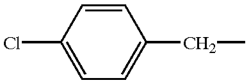 | 1 | 3 | 1 | — | H | 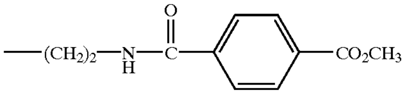 |
| 450 | 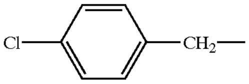 | 1 | 3 | 1 | — | H | 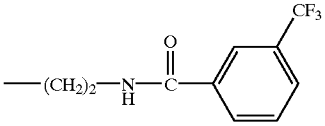 |
| 451 | 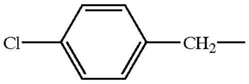 | 1 | 3 | 1 | — | H | 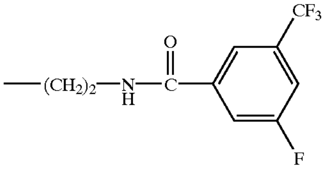 |
TABLE 1.42
| Compd. No. | 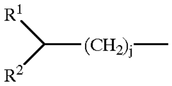 | k | m | n | chirality | $R^3$ | 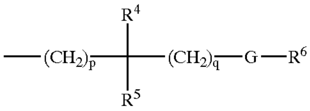 |
|---|---|---|---|---|---|---|---|
| 452 | 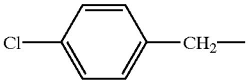 | 1 | 3 | 1 | — | H | 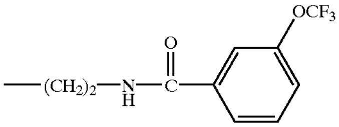 |
| 453 | 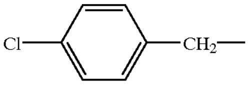 | 1 | 3 | 1 | — | H | 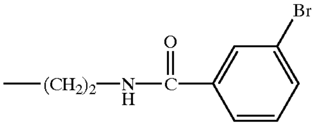 |
| 454 | 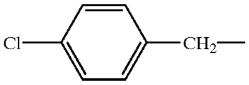 | 1 | 3 | 1 | — | H | 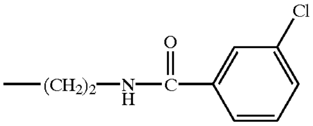 |
| 455 | 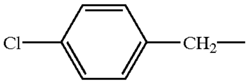 | 1 | 3 | 1 | — | H | 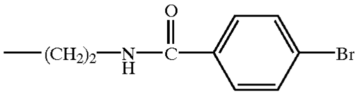 |
| 456 | 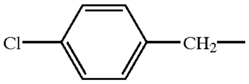 | 1 | 3 | 1 | — | H | 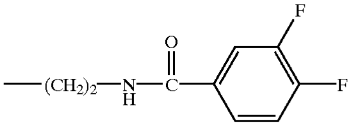 |

TABLE 1.42-continued
| Compd. No. | 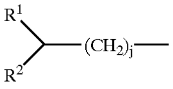 | k | m | n | chirality | $R^3$ | 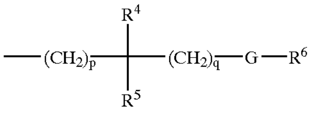 |
|---|---|---|---|---|---|---|---|
| 457 | 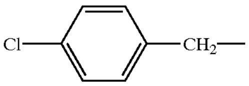 | 1 | 3 | 1 | — | H | 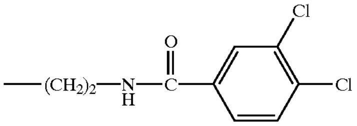 |
| 458 | 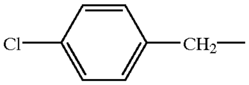 | 2 | 2 | 1 | — | H | 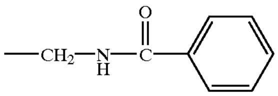 |
| 459 | 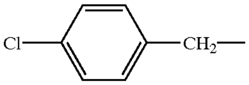 | 2 | 2 | 1 | — | H | 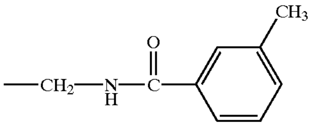 |
| 460 | 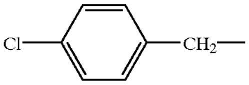 | 2 | 2 | 1 | — | H | 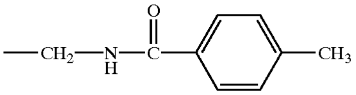 |
| 461 | 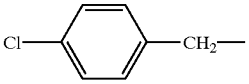 | 2 | 2 | 1 | — | H | 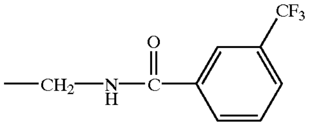 |
| 462 | 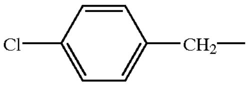 | 2 | 2 | 1 | — | H | 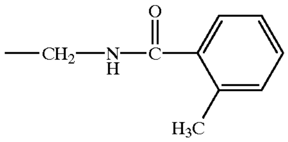 |
TABLE 1.43
| Compd. No. | 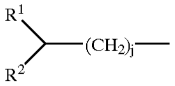 | k | m | n | chirality | $R^3$ | 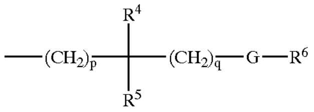 |
|---|---|---|---|---|---|---|---|
| 463 | 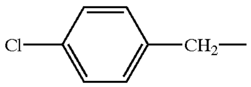 | 2 | 2 | 1 | — | H | 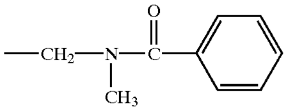 |
| 464 | 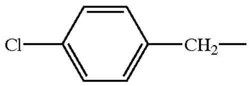 | 2 | 2 | 1 | — | H | 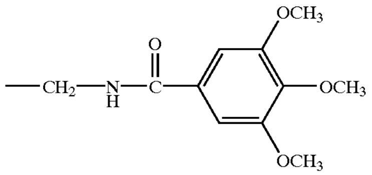 |

TABLE 1.43-continued
| Compd. No. | 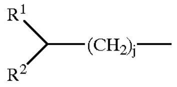 | k | m | n | chirality | $R^3$ | 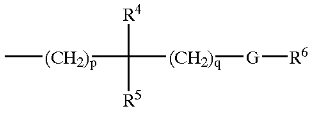 |
|---|---|---|---|---|---|---|---|
| 465 | 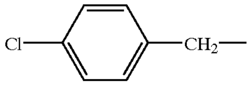 | 2 | 2 | 1 | — | H | 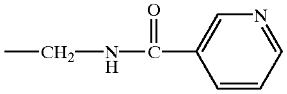 |
| 466 | 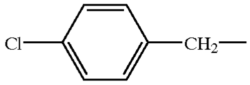 | 2 | 2 | 1 | — | H | 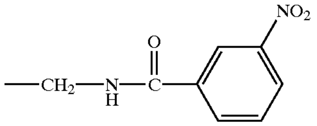 |
| 467 | 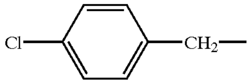 | 2 | 2 | 1 | — | H | 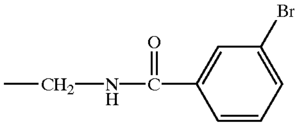 |
| 468 | 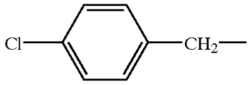 | 2 | 2 | 1 | — | H | 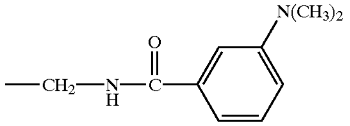 |
| 469 | 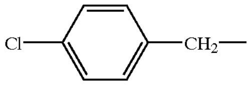 | 2 | 2 | 1 | — | H | 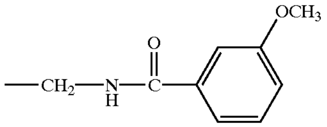 |
| 470 | 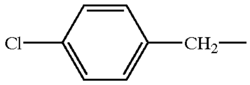 | 2 | 2 | 1 | — | H | 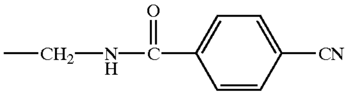 |
| 471 | 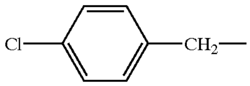 | 2 | 2 | 1 | — | H | 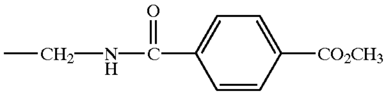 |
| 472 | 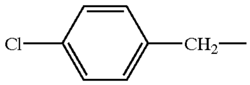 | 2 | 2 | 1 | — | H | 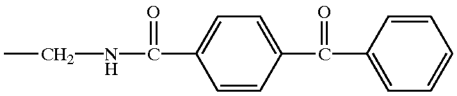 |
| 473 | 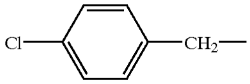 | 2 | 2 | 1 | — | H | 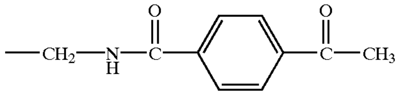 |

TABLE 1.44
| Compd. No. | 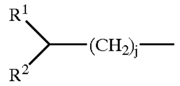 | k | m | n | chirality | $R^3$ | 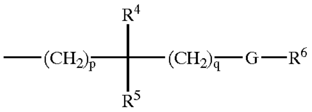 |
|---|---|---|---|---|---|---|---|
| 474 | 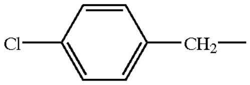 | 2 | 2 | 1 | — | H | 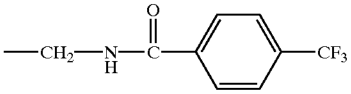 |
| 475 | 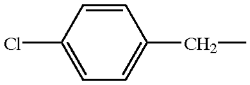 | 2 | 2 | 1 | — | H | 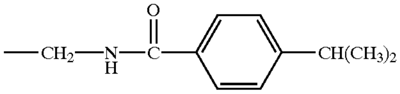 |
| 476 | 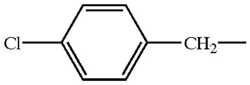 | 2 | 2 | 1 | — | H | 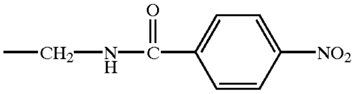 |
| 477 | 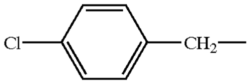 | 2 | 2 | 1 | — | H | 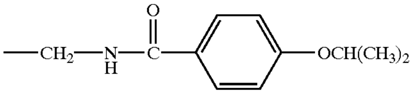 |
| 478 | 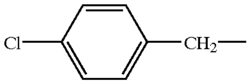 | 2 | 2 | 1 | — | H | 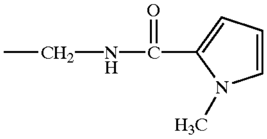 |
| 479 | 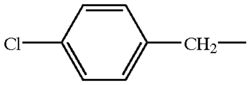 | 2 | 2 | 1 | — | H | 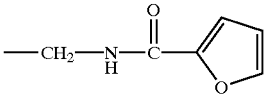 |
| 480 | 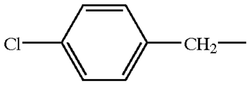 | 2 | 2 | 1 | — | H | 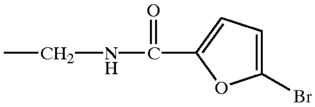 |
| 481 | 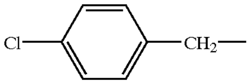 | 2 | 2 | 1 | — | H | 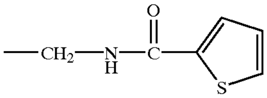 |
| 482 | 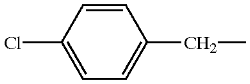 | 2 | 2 | 1 | — | H | 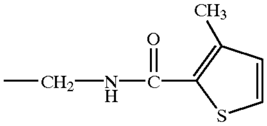 |
| 483 | 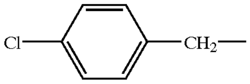 | 2 | 2 | 1 | — | H | 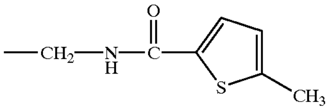 |
| 484 | 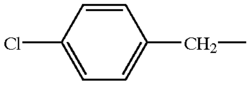 | 2 | 2 | 1 | — | H | 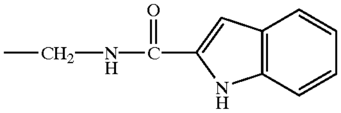 |

TABLE 1.45
| Compd. No. | 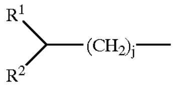 | k | m | n | chirality | $R^3$ | 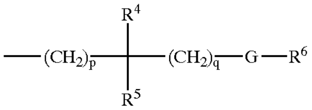 |
|---|---|---|---|---|---|---|---|
| 485 | 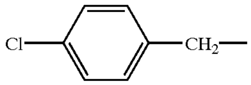 | 2 | 2 | 1 | — | H | 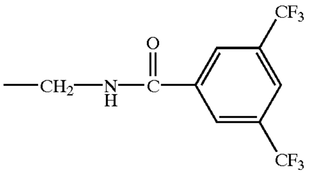 |
| 486 | 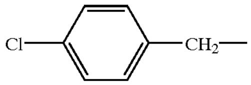 | 2 | 2 | 1 | — | H | 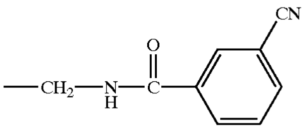 |
| 487 | 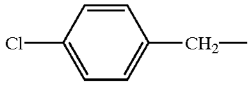 | 2 | 2 | 1 | — | H | 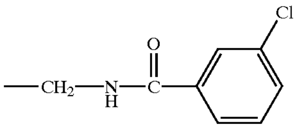 |
| 488 | 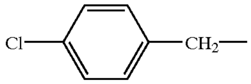 | 2 | 2 | 1 | — | H | 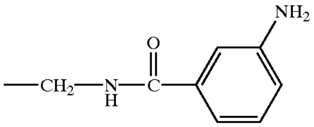 |
| 489 | 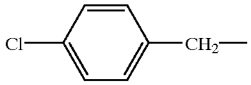 | 2 | 2 | 1 | — | H | 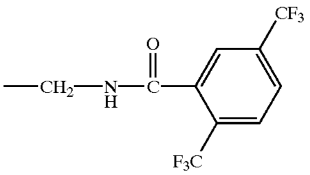 |
| 490 | 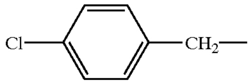 | 2 | 2 | 1 | — | H | 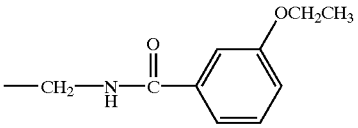 |
| 491 | 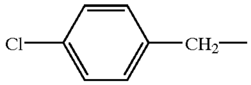 | 2 | 2 | 1 | — | H | 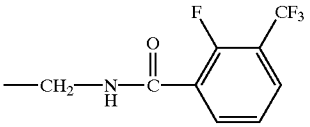 |
| 492 | 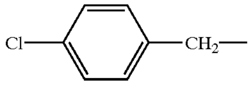 | 2 | 2 | 1 | — | H | 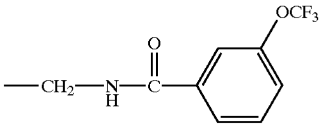 |
| 493 | 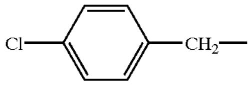 | 2 | 2 | 1 | — | H | 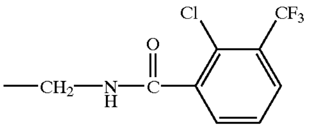 |

TABLE 1.45-continued
| Compd. No. | 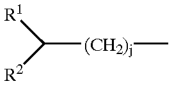 | k | m | n | chirality | $R^3$ | 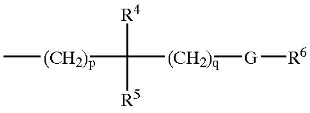 |
|---|---|---|---|---|---|---|---|
| 494 | 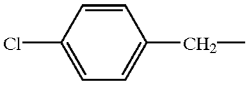 | 2 | 2 | 1 | — | H | 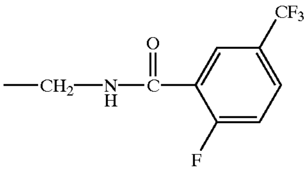 |
| 495 | 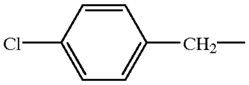 | 2 | 2 | 1 | — | H | 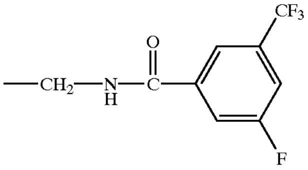 |
TABLE 1.46
| Compd. No. | 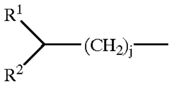 | k | m | n | chirality | $R^3$ | 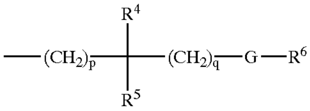 |
|---|---|---|---|---|---|---|---|
| 496 | 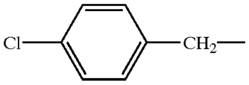 | 2 | 2 | 1 | — | H | 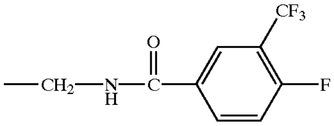 |
| 497 | 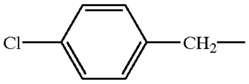 | 2 | 2 | 1 | — | H | 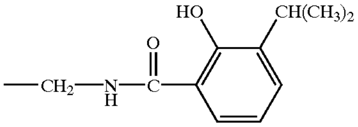 |
| 498 | 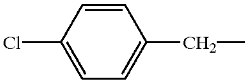 | 2 | 2 | 1 | — | H | 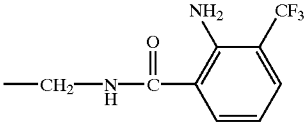 |
| 499 | 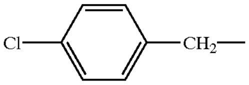 | 2 | 2 | 1 | — | H | 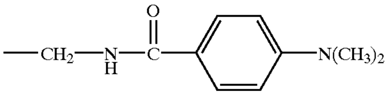 |
| 500 | 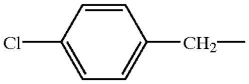 | 2 | 2 | 1 | — | H | 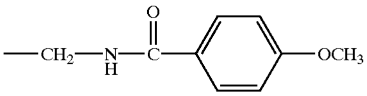 |
| 501 | 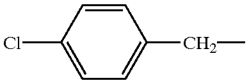 | 2 | 2 | 1 | — | H | 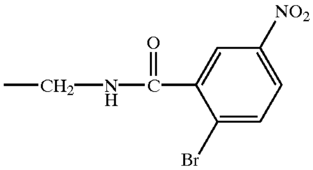 |

TABLE 1.46-continued
| Compd. No. | 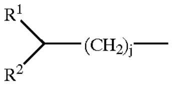 | k | m | n | chirality | $R^3$ | 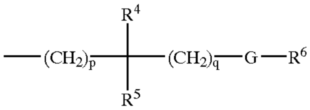 |
|---|---|---|---|---|---|---|---|
| 502 | 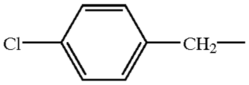 | 2 | 2 | 1 | — | H | 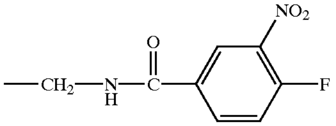 |
| 503 | 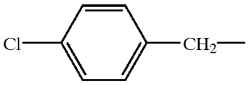 | 2 | 2 | 1 | — | H | 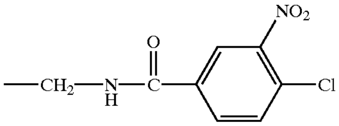 |
| 504 | 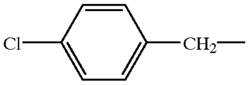 | 2 | 2 | 1 | — | H | 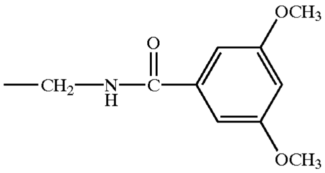 |
| 505 | 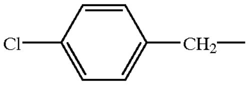 | 2 | 2 | 1 | — | H | 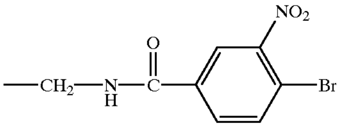 |
| 506 | 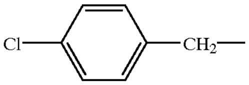 | 2 | 2 | 1 | — | H | 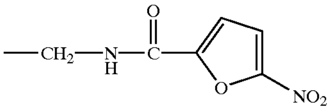 |
TABLE 1.47
| Compd. No. | 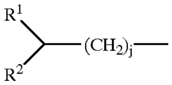 | k | m | n | chirality | $R^3$ | 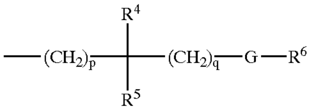 |
|---|---|---|---|---|---|---|---|
| 507 | 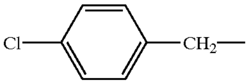 | 2 | 2 | 1 | — | H | 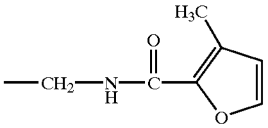 |
| 508 | 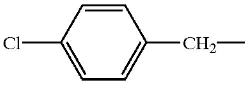 | 2 | 2 | 1 | — | H | 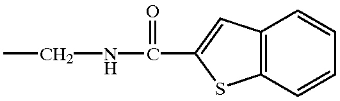 |
| 509 | 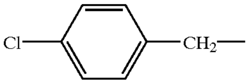 | 2 | 2 | 1 | — | H | 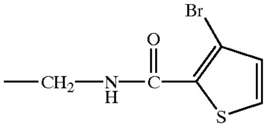 |

TABLE 1.47-continued
| Compd. No. | 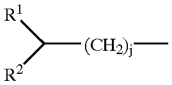 | k | m | n | chirality | $R^3$ | 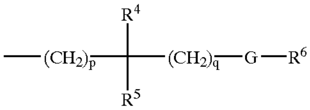 |
|---|---|---|---|---|---|---|---|
| 510 | 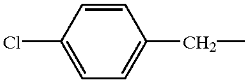 | 2 | 2 | 1 | — | H | 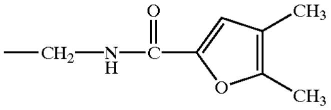 |
| 511 | 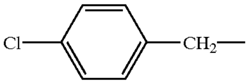 | 2 | 2 | 1 | — | H | 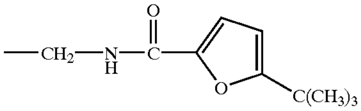 |
| 512 | 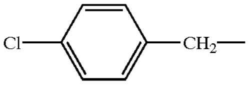 | 2 | 2 | 1 | — | H | 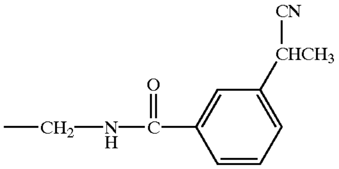 |
| 513 | 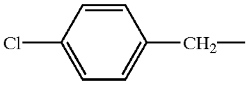 | 2 | 2 | 1 | — | H | 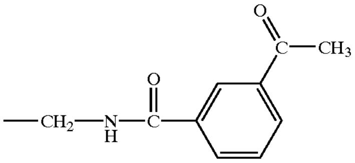 |
| 514 | 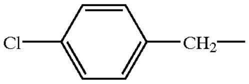 | 2 | 2 | 1 | — | H | 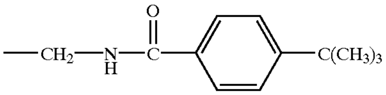 |
| 515 | 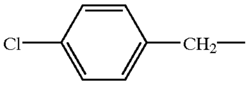 | 2 | 2 | 1 | — | H | 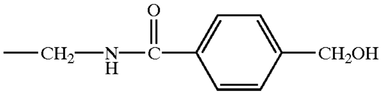 |
| 516 | 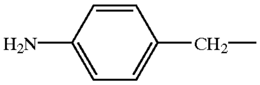 | 2 | 2 | 1 | — | H | 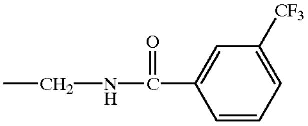 |
| 517 | 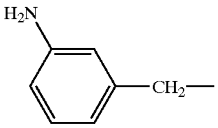 | 2 | 2 | 1 | — | H | 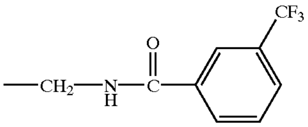 |
TABLE 1.48
| Compd. No. | 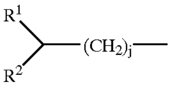 | k | m | n | chirality |
|---|---|---|---|---|---|
| 518 | 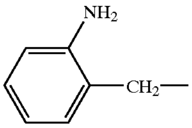 | 2 | 2 | 1 | — |

TABLE 1.48-continued
| | | | | | |
|---|---|---|---|---|---|
| 519 | 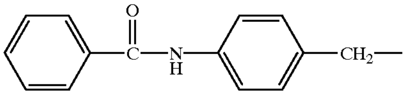 | 2 | 2 | 1 | — |
| 520 | 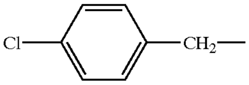 | 2 | 2 | 1 | — |
| 521 | 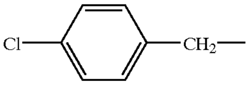 | 2 | 2 | 1 | — |
| 522 | 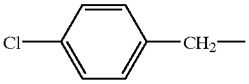 | 2 | 2 | 1 | — |
| 523 | 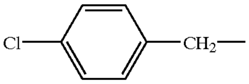 | 2 | 2 | 1 | — |
| 524 | 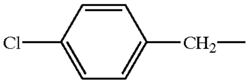 | 2 | 2 | 1 | — |
| 525 | 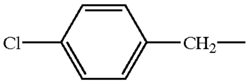 | 2 | 2 | 1 | — |
| 526 | 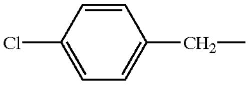 | 2 | 2 | 1 | — |
| 527 | 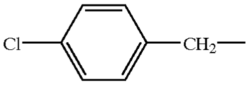 | 2 | 2 | 1 | — |
| 528 | 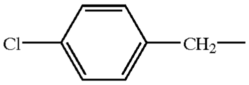 | 2 | 2 | 1 | — |
| Compd. No. | $R^3$ | 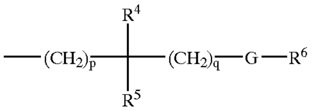 |
|---|---|---|
| 518 | H | 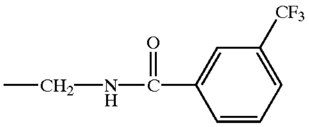 |
| 519 | H | 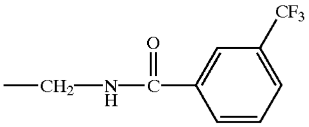 |

TABLE 1.48-continued
| | | |
|---|---|---|
| 520 | $-CH_3$ | 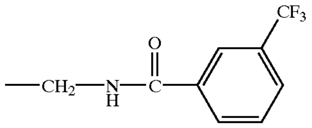 |
| 521 | 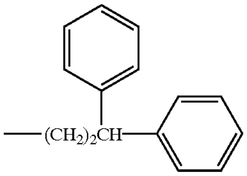 | 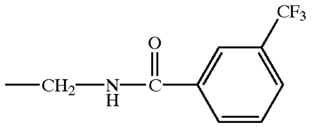 |
| 522 | 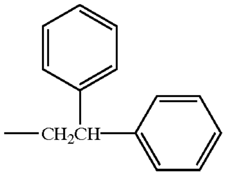 | 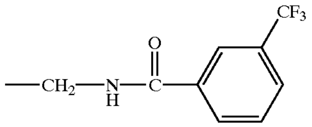 |
| 523 | 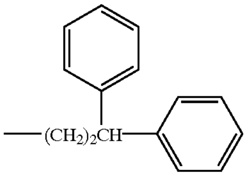 | 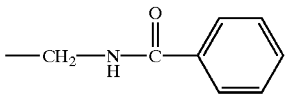 |
| 524 | 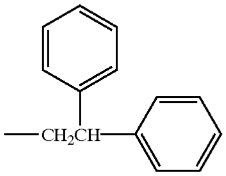 | 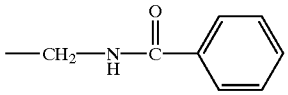 |
| 525 | H | 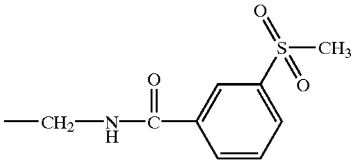 |
| 526 | H | 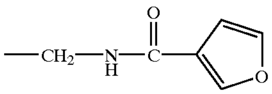 |
| 527 | H | 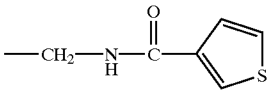 |
| 528 | H | 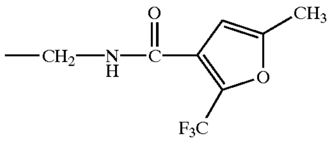 |

TABLE 1.49
| Compd. No. | 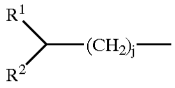 | k | m | n | chirality | $R^3$ | 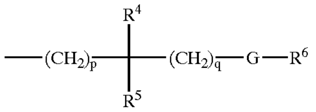 |
|---|---|---|---|---|---|---|---|
| 529 | 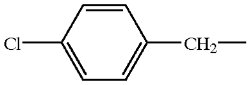 | 2 | 2 | 1 | — | H | 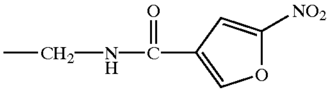 |
| 530 | 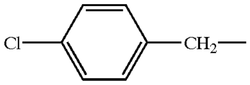 | 2 | 2 | 1 | — | H | 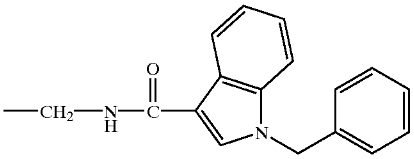 |
| 531 | 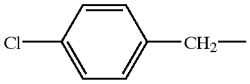 | 2 | 2 | 1 | — | H | 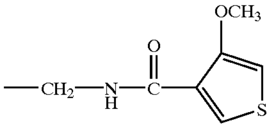 |
| 532 | 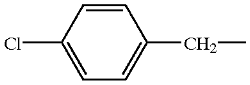 | 2 | 2 | 1 | — | H | 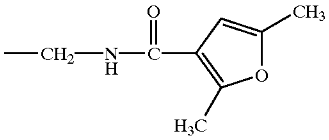 |
| 533 | 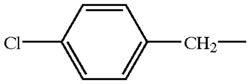 | 2 | 2 | 1 | — | H | 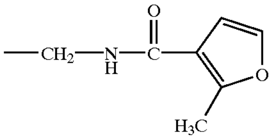 |
| 534 | 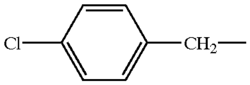 | 2 | 2 | 1 | — | H | 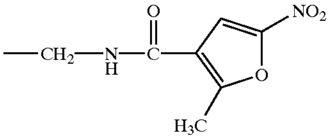 |
| 535 | 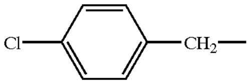 | 2 | 2 | 1 | — | H | 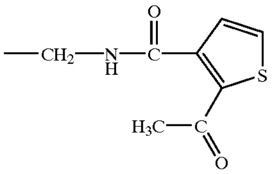 |
| 536 | 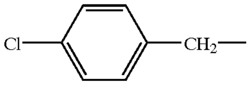 | 2 | 2 | 1 | — | H | 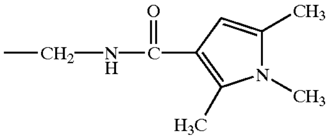 |
| 537 | 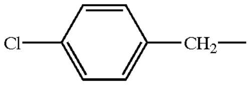 | 2 | 2 | 1 | — | H | 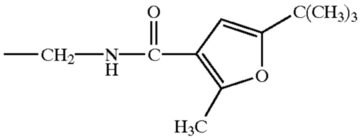 |

TABLE 1.49-continued
| Compd. No. | 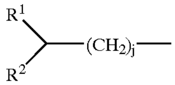 | k | m | n | chirality | $R^3$ | 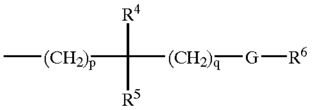 |
|---|---|---|---|---|---|---|---|
| 538 | 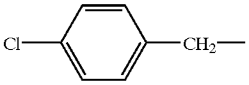 | 2 | 2 | 1 | — | H | 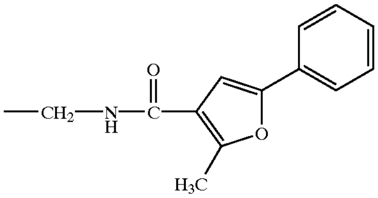 |
| 539 | 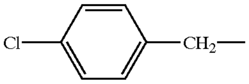 | 2 | 2 | 1 | — | H | 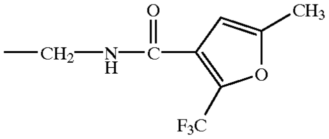 |
TABLE 1.50
| Compd. No. | 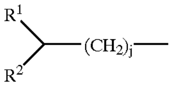 | k | m | n | chirality | $R^3$ | 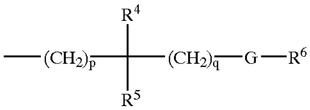 |
|---|---|---|---|---|---|---|---|
| 540 | 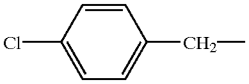 | 2 | 2 | 1 | — | H | 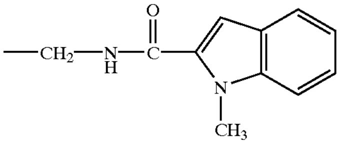 |
| 541 | 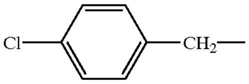 | 2 | 2 | 1 | — | H | 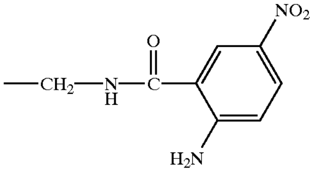 |
| 542 | 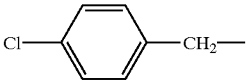 | 2 | 2 | 1 | — | H | 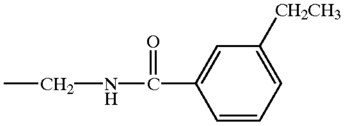 |
| 543 | 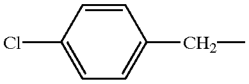 | 2 | 2 | 1 | — | H | 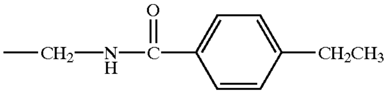 |
| 544 | 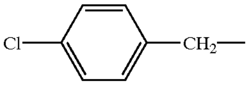 | 2 | 2 | 1 | — | H | 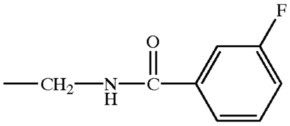 |

TABLE 1.50-continued
| Compd. No. | 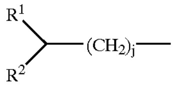 | k | m | n | chirality | $R^3$ | 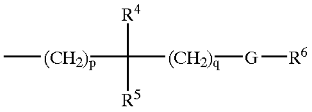 |
|---|---|---|---|---|---|---|---|
| 545 | 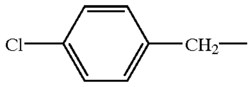 | 2 | 2 | 1 | — | H | 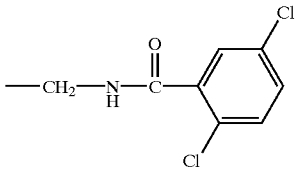 |
| 546 | 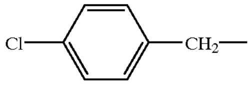 | 2 | 2 | 1 | — | H | 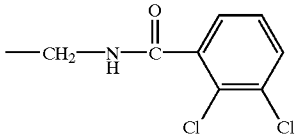 |
| 547 | 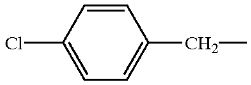 | 2 | 2 | 1 | — | H | 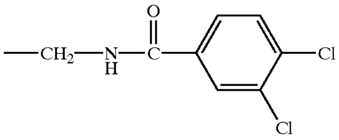 |
| 548 | 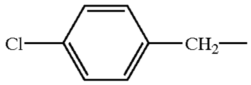 | 2 | 2 | 1 | — | H | 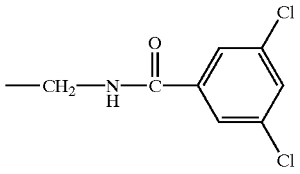 |
| 549 | 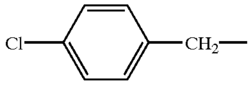 | 2 | 2 | 1 | — | H | 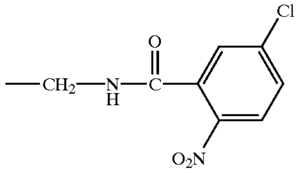 |
| 550 | 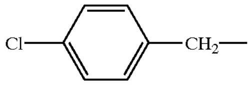 | 2 | 2 | 1 | — | H | 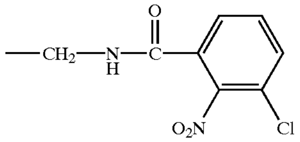 |
TABLE 1.51
| Compd. No. | 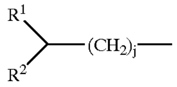 | k | m | n | chirality | $R^3$ | 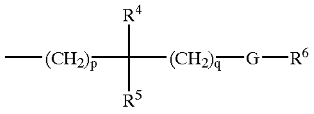 |
|---|---|---|---|---|---|---|---|
| 551 | 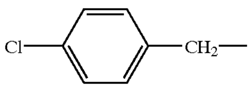 | 2 | 2 | 1 | — | H | 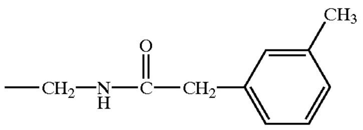 |

TABLE 1.51-continued
| Compd. No. | 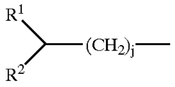 | k | m | n | chirality | $R^3$ | 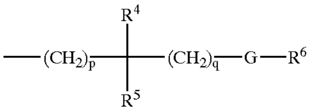 |
|---|---|---|---|---|---|---|---|
| 552 | 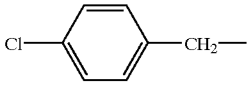 | 2 | 2 | 1 | — | H | 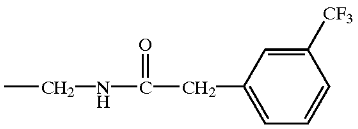 |
| 553 | 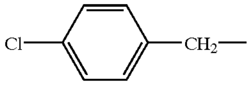 | 2 | 2 | 1 | — | H | 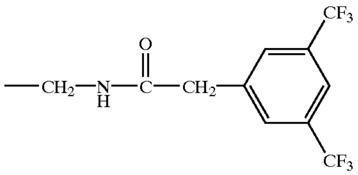 |
| 554 | 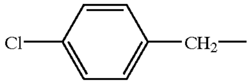 | 2 | 2 | 1 | — | H | 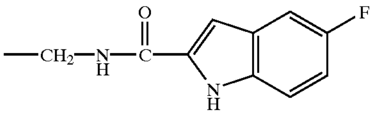 |
| 555 | 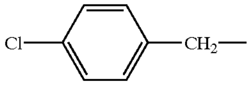 | 2 | 2 | 1 | — | H | 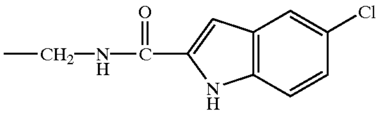 |
| 556 | 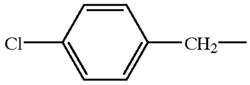 | 2 | 2 | 1 | — | H | 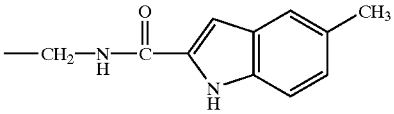 |
| 557 | 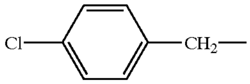 | 2 | 2 | 1 | — | H | 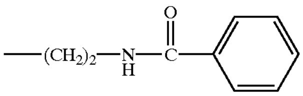 |
| 558 | 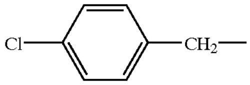 | 2 | 2 | 1 | — | H | 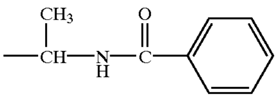 |
| 559 | 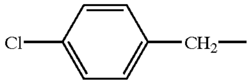 | 2 | 2 | 1 | — | H | 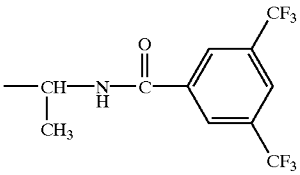 |
| 560 | 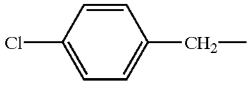 | 2 | 2 | 1 | — | H | 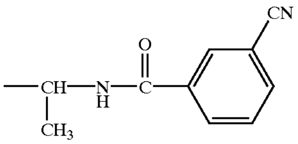 |
| 561 | 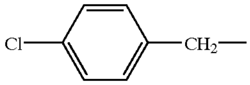 | 2 | 2 | 1 | — | H | 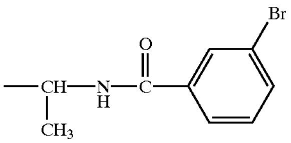 |

TABLE 1.52
| Compd. No. | 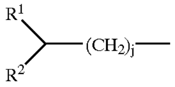 | k | m | n | chirality | $R^3$ | 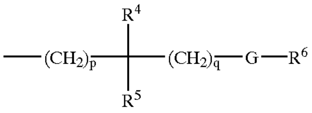 |
|---|---|---|---|---|---|---|---|
| 562 | 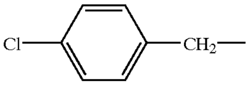 | 2 | 2 | 1 | — | H | 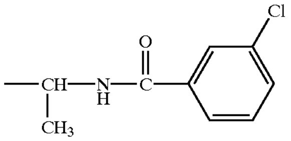 |
| 563 | 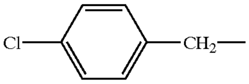 | 2 | 2 | 1 | — | H | 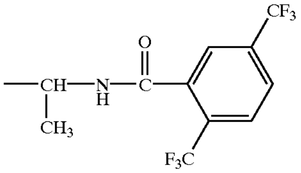 |
| 564 | 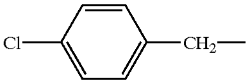 | 2 | 2 | 1 | — | H | 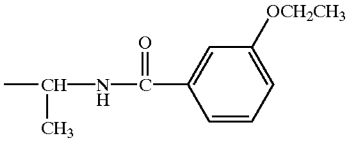 |
| 565 | 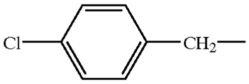 | 2 | 2 | 1 | — | H | 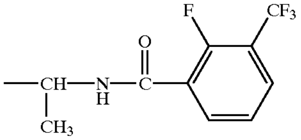 |
| 566 | 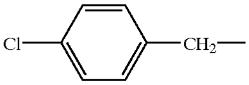 | 2 | 2 | 1 | — | H | 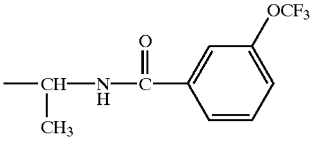 |
| 567 | 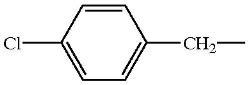 | 2 | 2 | 1 | — | H | 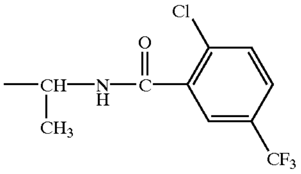 |
| 568 | 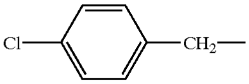 | 2 | 2 | 1 | — | H | 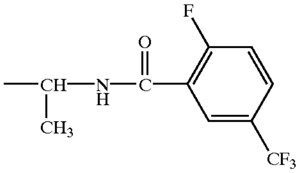 |
| 569 | 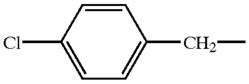 | 2 | 2 | 1 | — | H | 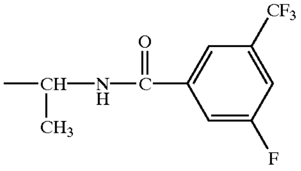 |

TABLE 1.52-continued
| Compd. No. | 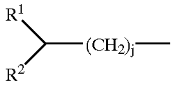 | k | m | n | chirality | $R^3$ | 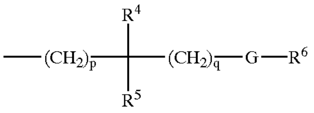 |
|---|---|---|---|---|---|---|---|
| 570 | 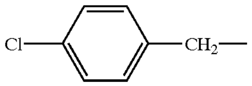 | 2 | 2 | 1 | — | H | 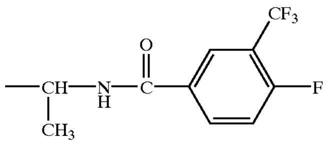 |
| 571 | 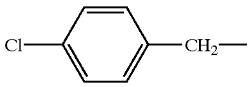 | 2 | 2 | 1 | — | H | 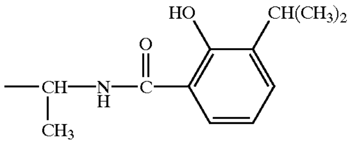 |
| 572 | 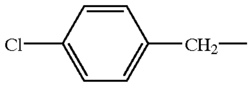 | 2 | 2 | 1 | — | H | 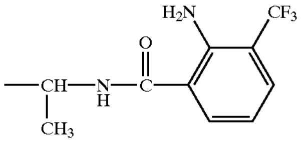 |
TABLE 1.53
| Compd. No. | 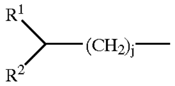 | k | m | n | chirality | $R^3$ | 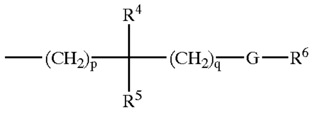 |
|---|---|---|---|---|---|---|---|
| 573 | 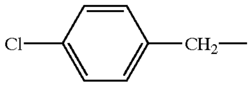 | 2 | 2 | 1 | — | H | 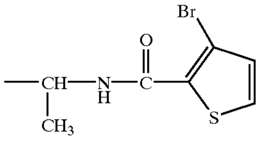 |
| 574 | 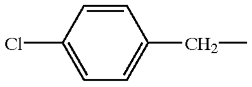 | 2 | 2 | 1 | — | H | 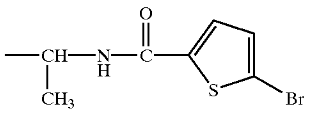 |
| 575 | 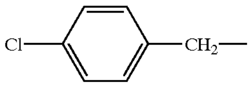 | 2 | 2 | 1 | — | H | 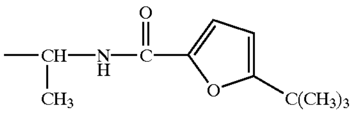 |
| 576 | 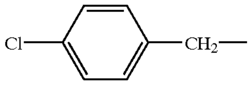 | 2 | 2 | 1 | — | H | 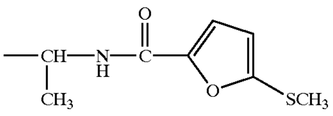 |
| 577 | 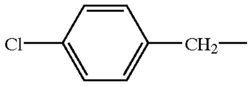 | 2 | 2 | 1 | — | H | 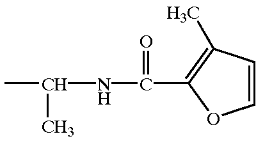 |

TABLE 1.53-continued
| Compd. No. | 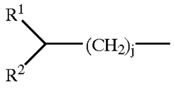 | k | m | n | chirality | $R^3$ | 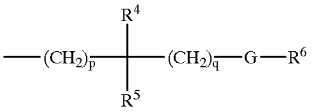 |
|---|---|---|---|---|---|---|---|
| 578 | 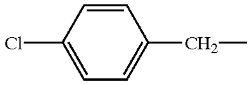 | 2 | 2 | 1 | — | H | 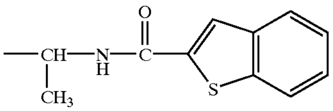 |
| 579 | 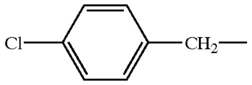 | 2 | 2 | 1 | — | H | 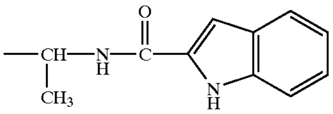 |
| 580 | 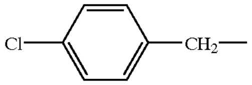 | 2 | 2 | 1 | — | H | 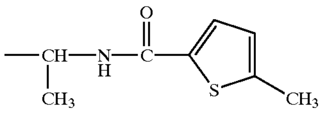 |
| 581 | 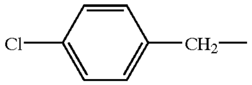 | 2 | 2 | 1 | — | H | 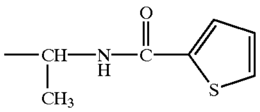 |
| 582 | 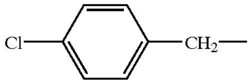 | 2 | 2 | 1 | — | H | 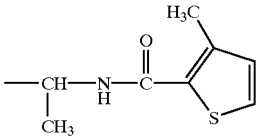 |
| 583 | 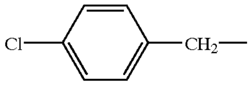 | 2 | 2 | 1 | — | H | 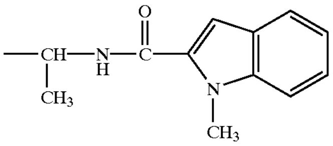 |
TABLE 1.54
| Compd. No. | 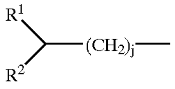 | k | m | n | chirality | $R^3$ | 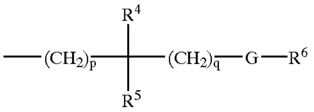 |
|---|---|---|---|---|---|---|---|
| 584 | 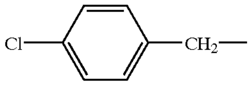 | 2 | 2 | 1 | — | H | 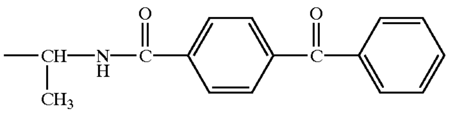 |
| 585 | 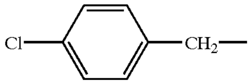 | 2 | 2 | 1 | — | H | 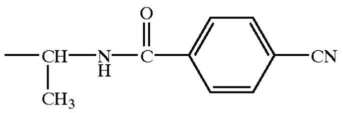 |
| 586 | 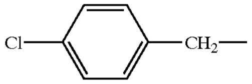 | 2 | 2 | 1 | — | H | 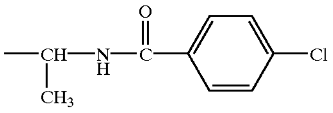 |

TABLE 1.54-continued
| Compd. No. | 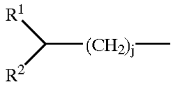 | k | m | n | chirality | $R^3$ | 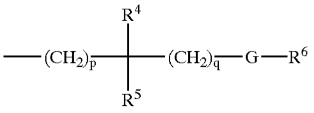 |
|---|---|---|---|---|---|---|---|
| 587 | 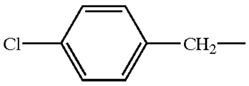 | 2 | 2 | 1 | — | H | 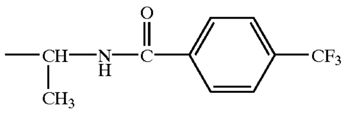 |
| 588 | 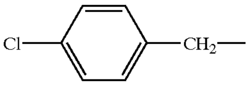 | 2 | 2 | 1 | — | H | 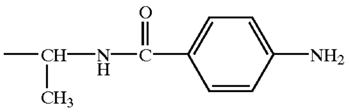 |
| 589 | 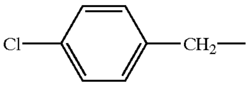 | 2 | 2 | 1 | — | H | 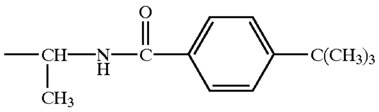 |
| 590 | 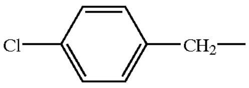 | 2 | 2 | 1 | — | H | 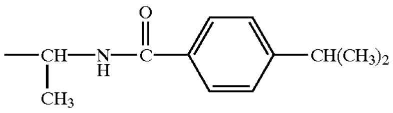 |
| 591 | 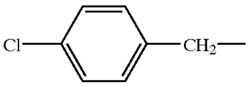 | 2 | 2 | 1 | — | H | 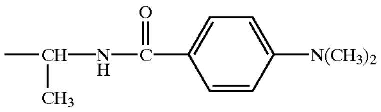 |
| 592 | 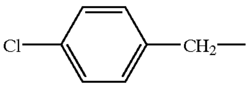 | 2 | 2 | 1 | — | H | 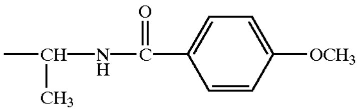 |
| 593 | 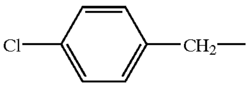 | 2 | 2 | 1 | — | H | 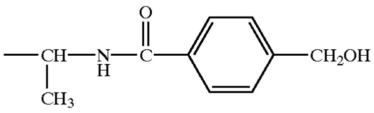 |
| 594 | 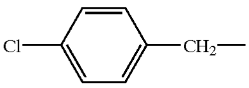 | 2 | 2 | 1 | — | H | 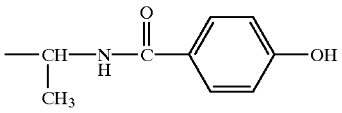 |
TABLE 1.55
| Compd. No. | 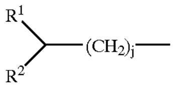 | k | m | n | chirality | $R^3$ | 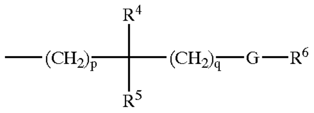 |
|---|---|---|---|---|---|---|---|
| 595 | 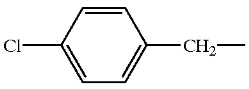 | 2 | 2 | 1 | — | H | 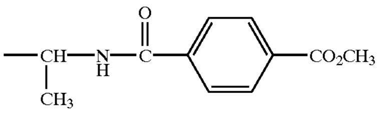 |

TABLE 1.55-continued
| Compd. No. | 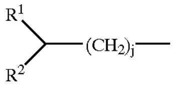 | k | m | n | chirality | $R^3$ | 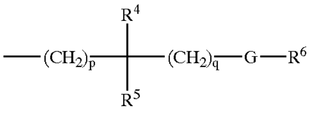 |
|---|---|---|---|---|---|---|---|
| 596 | 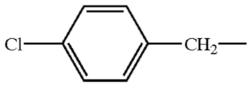 | 2 | 2 | 1 | — | H | 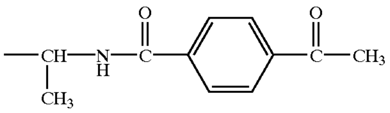 |
| 597 | 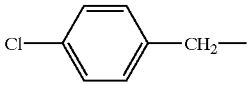 | 2 | 2 | 1 | — | H | 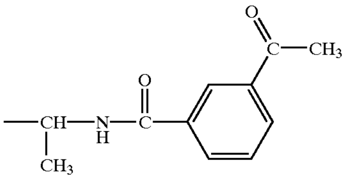 |
| 598 | 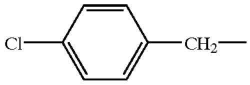 | 2 | 2 | 1 | — | H | 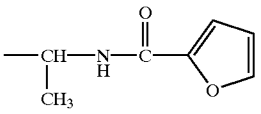 |
| 599 | 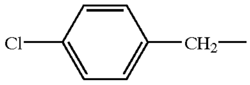 | 2 | 2 | 1 | — | H | 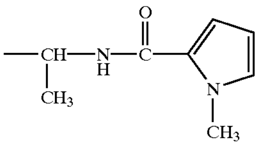 |
| 600 | 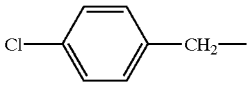 | 2 | 2 | 1 | — | H | 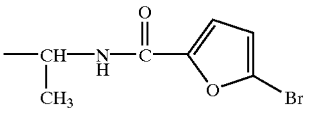 |
| 601 | 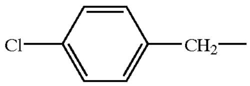 | 2 | 2 | 1 | — | H | 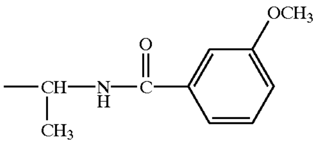 |
| 602 | 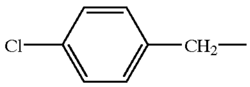 | 2 | 2 | 1 | — | H | 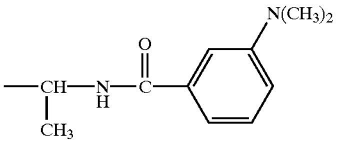 |
| 603 | 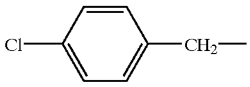 | 2 | 2 | 1 | — | H | 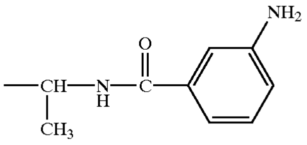 |
| 604 | 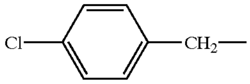 | 2 | 2 | 1 | — | H | 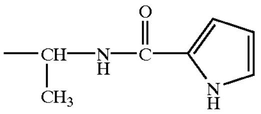 |
| 605 | 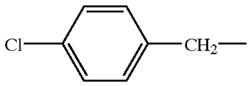 | 2 | 2 | 1 | — | H | 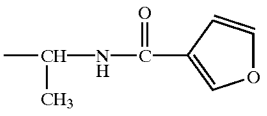 |

TABLE 1.56
| Compd. No. | 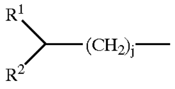 | k | m | n | chirality | $R^3$ | 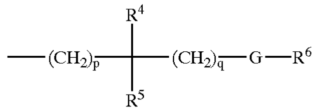 |
|---|---|---|---|---|---|---|---|
| 606 | 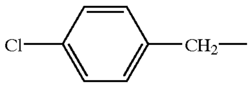 | 2 | 2 | 1 | — | H | 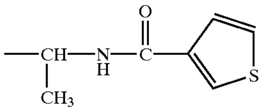 |
| 607 | 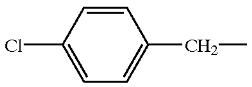 | 2 | 2 | 1 | — | H | 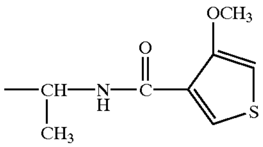 |
| 608 | 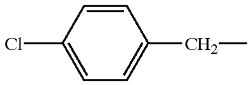 | 2 | 2 | 1 | — | H | 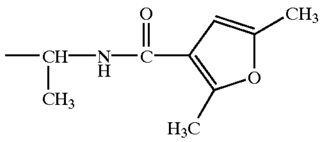 |
| 609 | 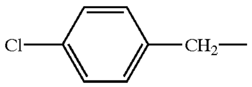 | 2 | 2 | 1 | — | H | 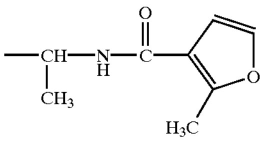 |
| 610 | 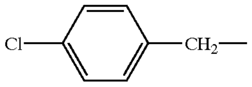 | 2 | 2 | 1 | — | H | 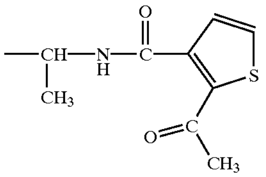 |
| 611 | 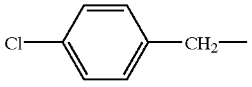 | 2 | 2 | 1 | — | H | 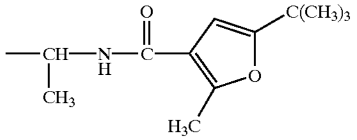 |
| 612 | 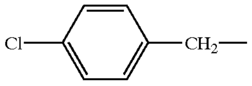 | 2 | 2 | 1 | — | H | 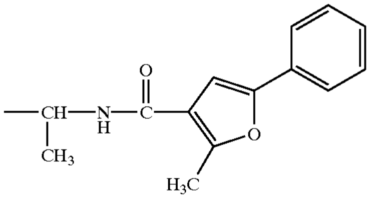 |
| 613 | 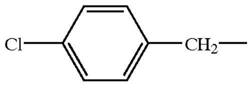 | 2 | 2 | 1 | — | H | 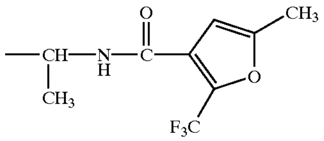 |
| 614 | 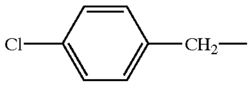 | 2 | 2 | 1 | — | H | 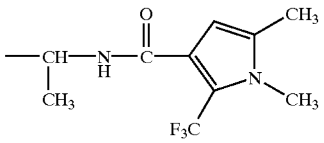 |

TABLE 1.56-continued
| Compd. No. | 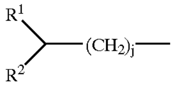 | k | m | n | chirality | $R^3$ | 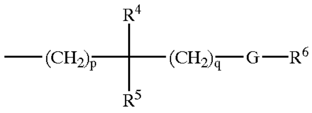 |
|---|---|---|---|---|---|---|---|
| 615 | 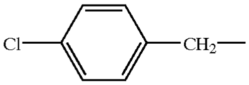 | 2 | 2 | 1 | — | H | 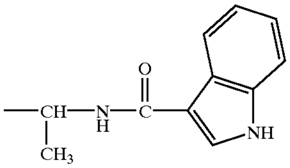 |
| 616 | 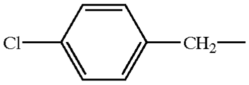 | 2 | 2 | 1 | — | H | 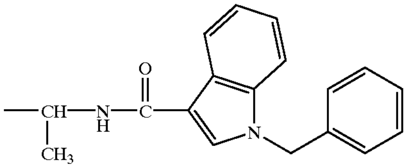 |
TABLE 1.57
| Compd. No. | 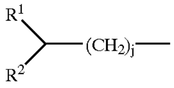 | k | m | n | chirality | $R^3$ | 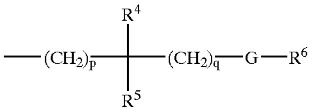 |
|---|---|---|---|---|---|---|---|
| 617 | 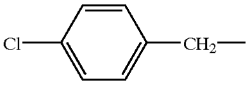 | 2 | 2 | 1 | — | H | 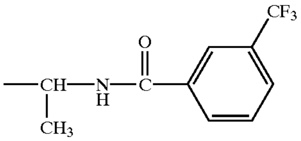 |
| 618 | 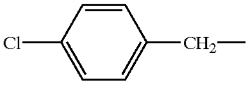 | 2 | 2 | 1 | — | H | 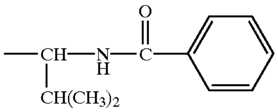 |
| 619 | 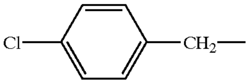 | 2 | 2 | 1 | — | H | 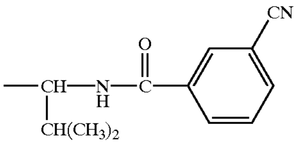 |
| 620 | 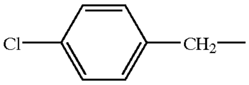 | 2 | 2 | 1 | — | H | 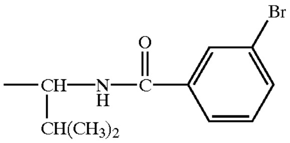 |
| 621 | 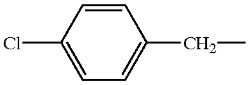 | 2 | 2 | 1 | — | H | 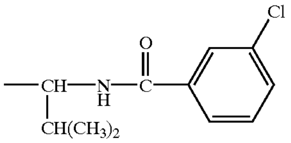 |

TABLE 1.57-continued
| Compd. No. | 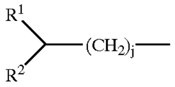 | k | m | n | chirality | $R^3$ | 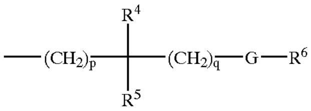 |
|---|---|---|---|---|---|---|---|
| 622 | 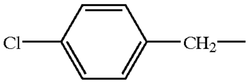 | 2 | 2 | 1 | — | H | 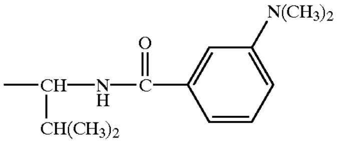 |
| 623 | 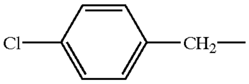 | 2 | 2 | 1 | — | H | 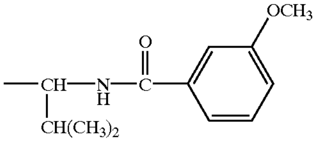 |
| 624 | 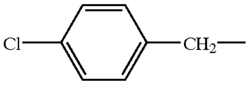 | 2 | 2 | 1 | — | H | 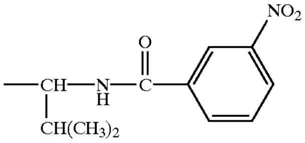 |
| 625 | 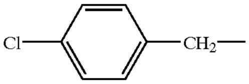 | 2 | 2 | 1 | — | H | 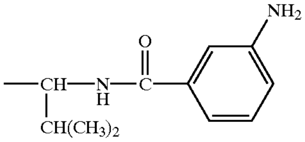 |
| 626 | 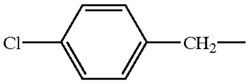 | 2 | 2 | 1 | — | H | 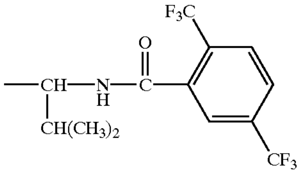 |
| 627 | 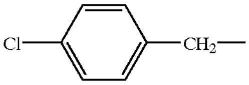 | 2 | 2 | 1 | — | H | 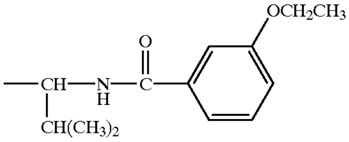 |
TABLE 1.58
| Compd. No. | 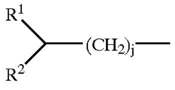 | k | m | n | chirality | $R^3$ | 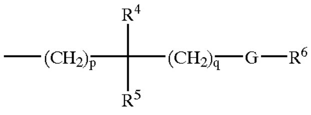 |
|---|---|---|---|---|---|---|---|
| 628 | 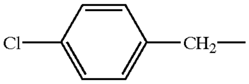 | 2 | 2 | 1 | — | H | 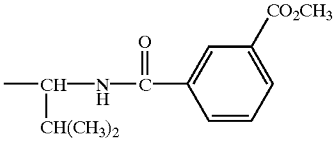 |

TABLE 1.58-continued
| Compd. No. | 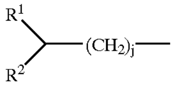 | k | m | n | chirality | $R^3$ | 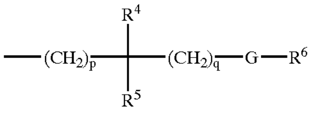 |
|---|---|---|---|---|---|---|---|
| 629 | 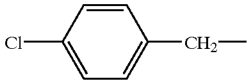 | 2 | 2 | 1 | — | H | 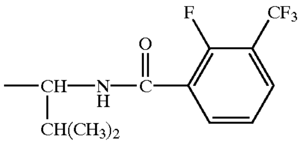 |
| 630 | 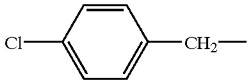 | 2 | 2 | 1 | — | H | 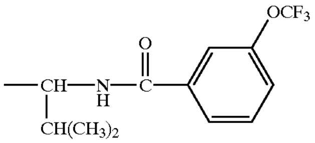 |
| 631 | 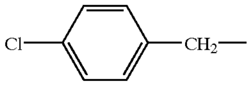 | 2 | 2 | 1 | — | H | 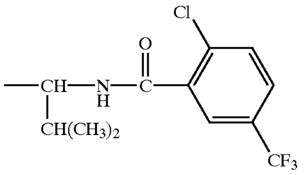 |
| 632 | 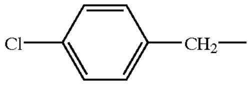 | 2 | 2 | 1 | — | H | 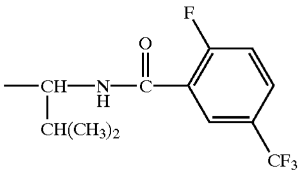 |
| 633 | 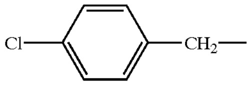 | 2 | 2 | 1 | — | H | 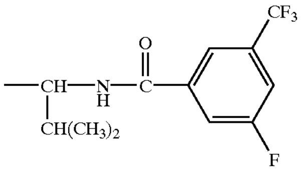 |
| 634 | 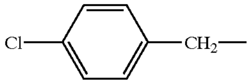 | 2 | 2 | 1 | — | H | 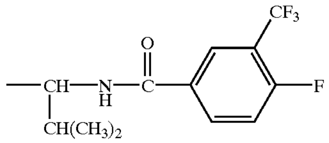 |
| 635 | 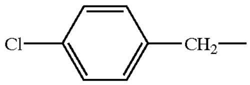 | 2 | 2 | 1 | — | H | 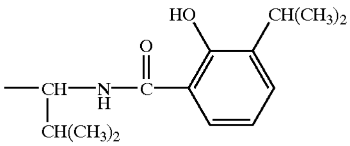 |
| 636 | 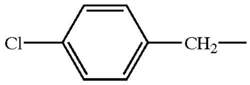 | 2 | 2 | 1 | — | H | 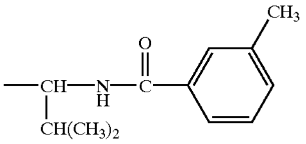 |

TABLE 1.58-continued
| Compd. No. | 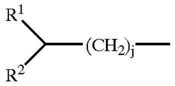 | k | m | n | chirality | $R^3$ | 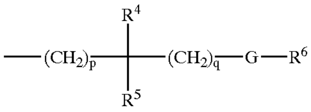 |
|---|---|---|---|---|---|---|---|
| 637 | 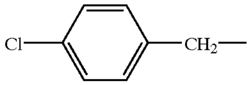 | 2 | 2 | 1 | — | H | 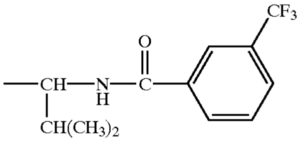 |
| 638 | 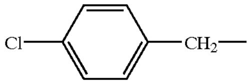 | 2 | 2 | 1 | — | H | 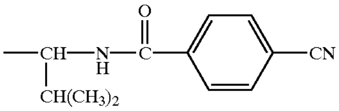 |
TABLE 1.59
| Compd. No. | 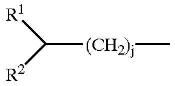 | k | m | n | chirality | $R^3$ | 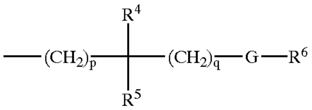 |
|---|---|---|---|---|---|---|---|
| 639 | 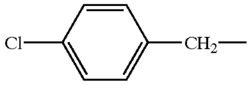 | 2 | 2 | 1 | — | H | 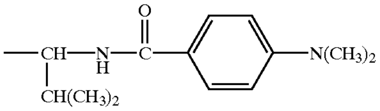 |
| 640 | 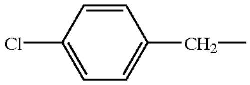 | 2 | 2 | 1 | — | H | 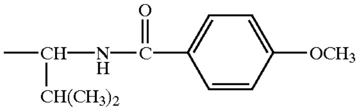 |
| 641 | 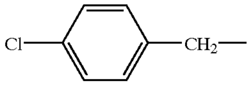 | 2 | 2 | 1 | — | H | 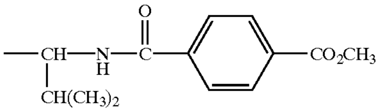 |
| 642 | 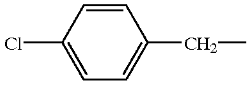 | 2 | 2 | 1 | — | H | 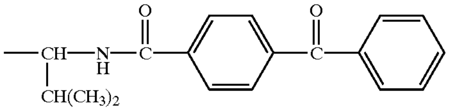 |
| 643 | 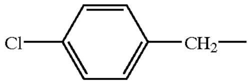 | 2 | 2 | 1 | — | H | 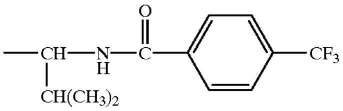 |
| 644 | 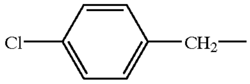 | 2 | 2 | 1 | — | H | 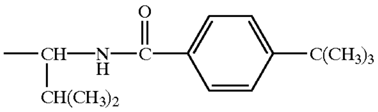 |
| 645 | 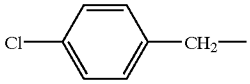 | 2 | 2 | 1 | — | H | 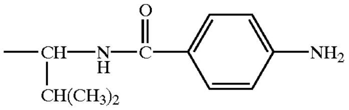 |

TABLE 1.59-continued
| Compd. No. | 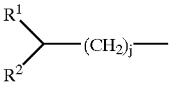 | k | m | n | chirality | $R^3$ | 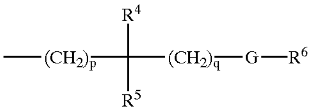 |
|---|---|---|---|---|---|---|---|
| 646 | 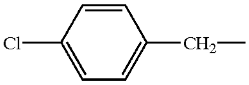 | 2 | 2 | 1 | — | H | 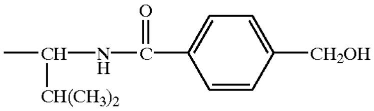 |
| 647 | 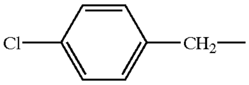 | 2 | 2 | 1 | — | H | 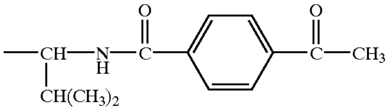 |
| 648 | 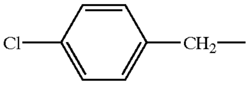 | 2 | 2 | 1 | — | H | 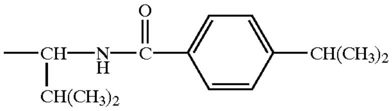 |
| 649 | 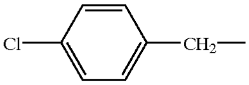 | 2 | 2 | 1 | — | H | 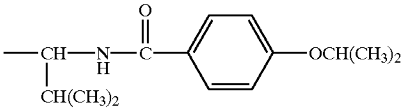 |
TABLE 1.60
| Compd. No. | 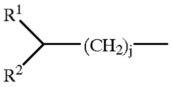 | k | m | n | chirality | $R^3$ | 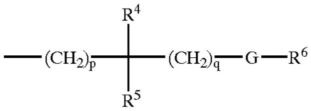 |
|---|---|---|---|---|---|---|---|
| 650 | 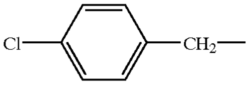 | 2 | 2 | 1 | — | H | 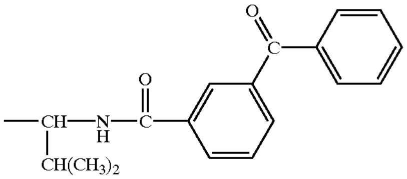 |
| 651 | 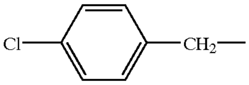 | 2 | 2 | 1 | — | H | 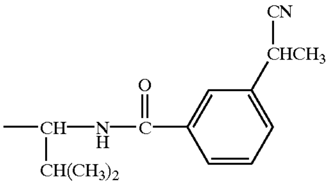 |
| 652 | 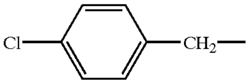 | 2 | 2 | 1 | — | H | 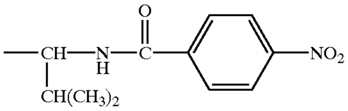 |
| 653 | 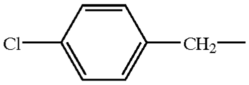 | 2 | 2 | 1 | — | H | 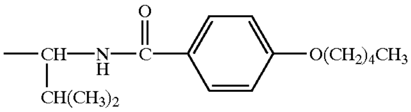 |

TABLE 1.60-continued
| Compd. No. | 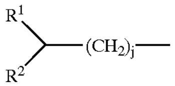 | k | m | n | chirality | $R^3$ | 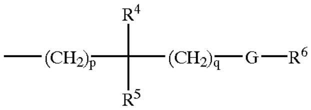 |
|---|---|---|---|---|---|---|---|
| 654 | 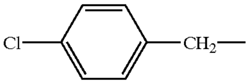 | 2 | 2 | 1 | — | H | 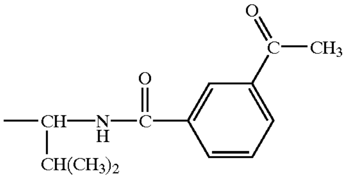 |
| 655 | 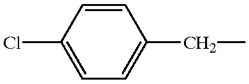 | 2 | 2 | 1 | — | H | 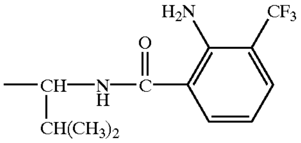 |
| 656 | 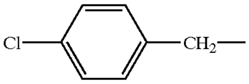 | 2 | 2 | 1 | — | H | 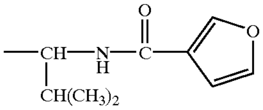 |
| 657 | 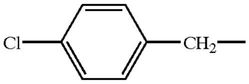 | 2 | 2 | 1 | — | H | 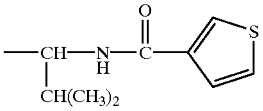 |
| 658 | 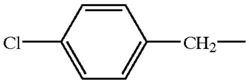 | 2 | 2 | 1 | — | H | 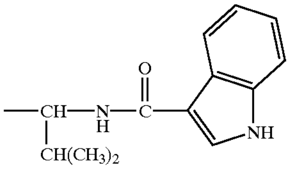 |
| 659 | 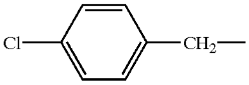 | 2 | 2 | 1 | — | H | 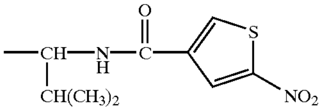 |
| 660 | 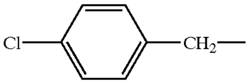 | 2 | 2 | 1 | — | H | 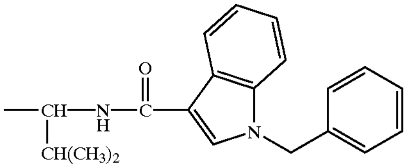 |

TABLE 1.61
| Compd. No. | 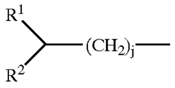 | k | m | n | chirality | $R^3$ | 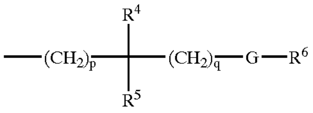 |
|---|---|---|---|---|---|---|---|
| 661 | 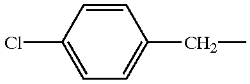 | 2 | 2 | 1 | — | H | 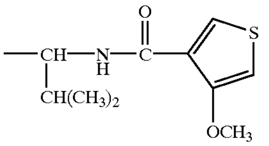 |
| 662 | 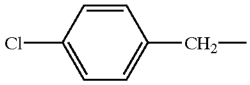 | 2 | 2 | 1 | — | H | 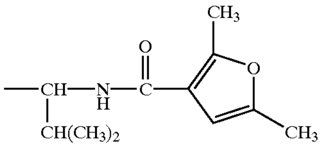 |
| 663 | 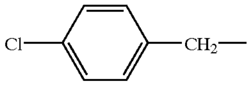 | 2 | 2 | 1 | — | H | 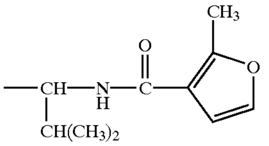 |
| 664 | 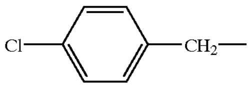 | 2 | 2 | 1 | — | H | 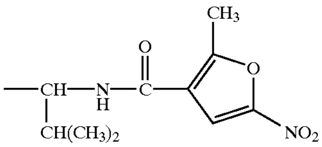 |
| 665 | 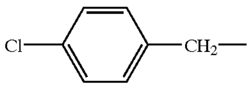 | 2 | 2 | 1 | — | H | 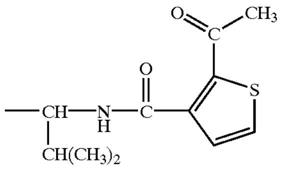 |
| 666 | 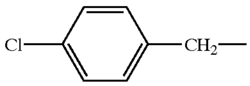 | 2 | 2 | 1 | — | H | 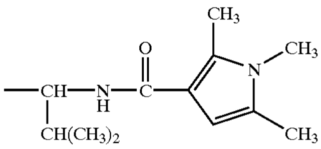 |
| 667 | 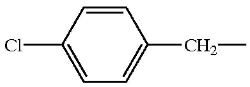 | 2 | 2 | 1 | — | H | 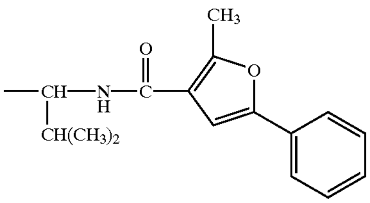 |
| 668 | 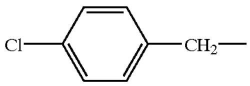 | 2 | 2 | 1 | — | H | 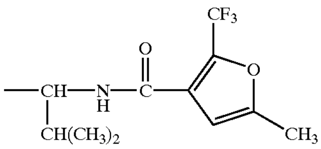 |

TABLE 1.61-continued
| Compd. No. | 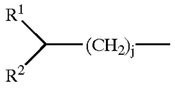 | k | m | n | chirality | $R^3$ | 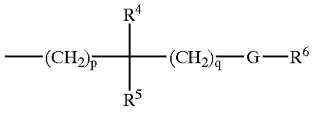 |
|---|---|---|---|---|---|---|---|
| 669 | 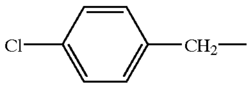 | 2 | 2 | 1 | — | H | 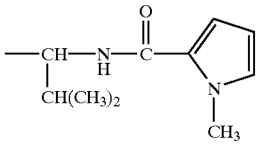 |
| 670 | 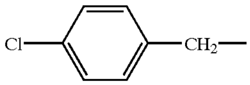 | 2 | 2 | 1 | — | H | 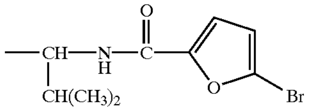 |
| 671 | 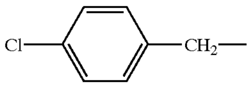 | 2 | 2 | 1 | — | H | 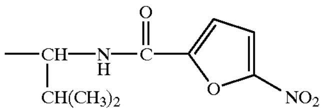 |
TABLE 1.62
| Compd. No. | 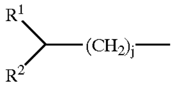 | k | m | n | chirality | $R^3$ | 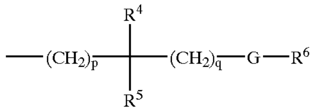 |
|---|---|---|---|---|---|---|---|
| 672 | 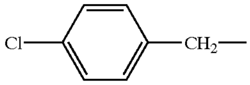 | 2 | 2 | 1 | — | H | 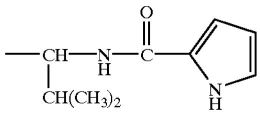 |
| 673 | 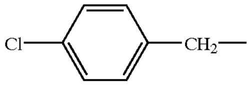 | 2 | 2 | 1 | — | H | 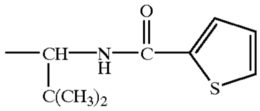 |
| 674 | 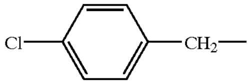 | 2 | 2 | 1 | — | H | 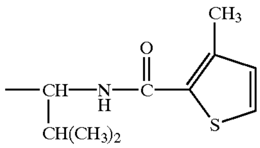 |
| 675 | 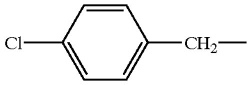 | 2 | 2 | 1 | — | H | 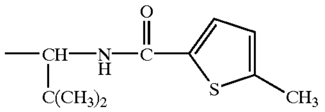 |
| 676 | 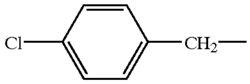 | 2 | 2 | 1 | — | H | 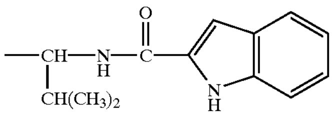 |

TABLE 1.62-continued
| Compd. No. | 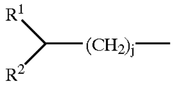 | k | m | n | chirality | $R^3$ | 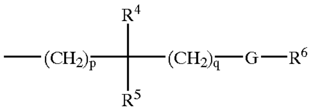 |
|---|---|---|---|---|---|---|---|
| 677 | 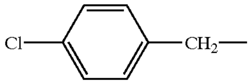 | 2 | 2 | 1 | — | H | 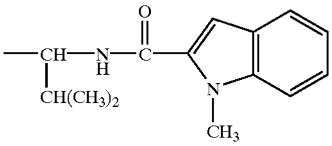 |
| 678 | 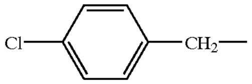 | 2 | 2 | 1 | — | H | 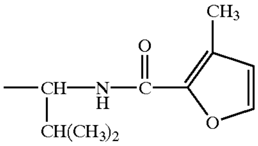 |
| 679 | 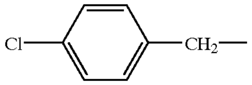 | 2 | 2 | 1 | — | H | 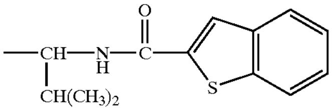 |
| 680 | 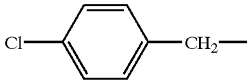 | 2 | 2 | 1 | — | H | 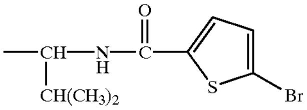 |
| 681 | 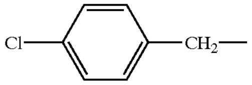 | 2 | 2 | 1 | — | H | 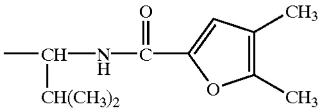 |
| 682 | 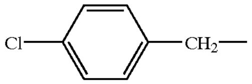 | 2 | 2 | 1 | — | H | 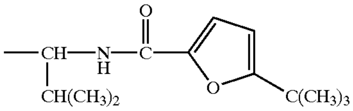 |
TABLE 1.63
| Compd. No. | 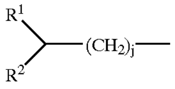 | k | m | n | chirality | $R^3$ | 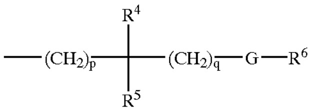 |
|---|---|---|---|---|---|---|---|
| 683 | 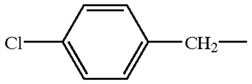 | 2 | 2 | 1 | — | H | 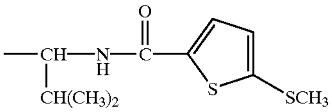 |
| 684 | 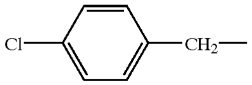 | 2 | 2 | 1 | — | H | 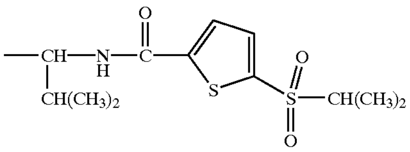 |

TABLE 1.63-continued
| Compd. No. | 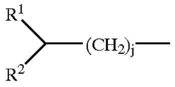 | k | m | n | chirality | $R^3$ | 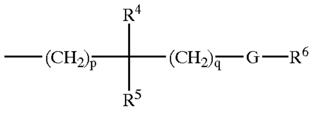 |
|---|---|---|---|---|---|---|---|
| 685 | 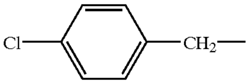 | 2 | 2 | 1 | — | H | 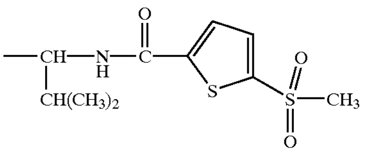 |
| 686 | 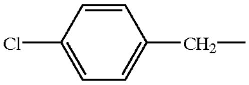 | 2 | 2 | 1 | — | H | 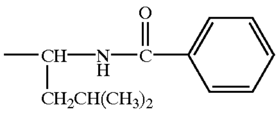 |
| 687 | 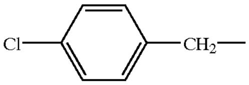 | 2 | 2 | 1 | — | H | 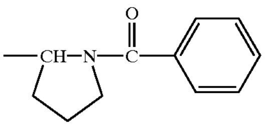 |
| 688 | 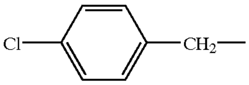 | 2 | 2 | 1 | — | H | 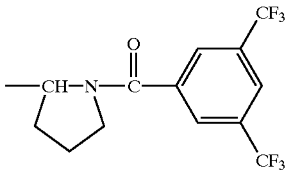 |
| 689 | 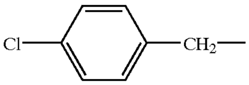 | 2 | 2 | 1 | — | H | 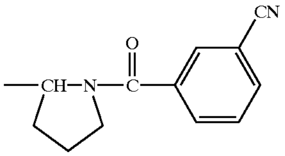 |
| 690 | 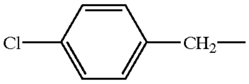 | 2 | 2 | 1 | — | H | 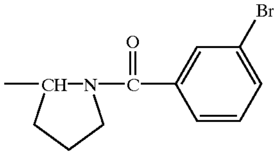 |
| 691 | 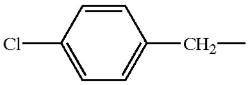 | 2 | 2 | 1 | — | H | 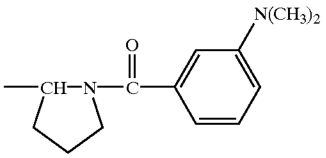 |
| 692 | 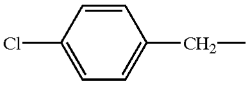 | 2 | 2 | 1 | — | H | 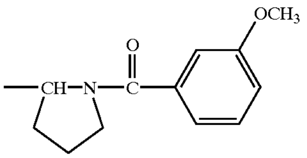 |

TABLE 1.63-continued
| Compd. No. | 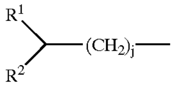 | k | m | n | chirality | $R^3$ | 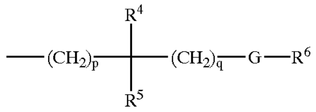 |
|---|---|---|---|---|---|---|---|
| 693 | 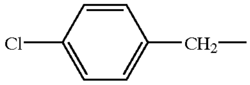 | 2 | 2 | 1 | — | H | 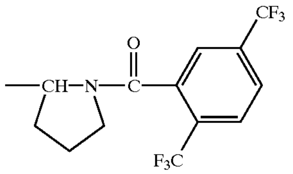 |
TABLE 1.64
| Compd. No. | 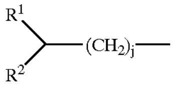 | k | m | n | chirality | $R^3$ | 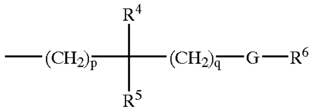 |
|---|---|---|---|---|---|---|---|
| 694 | 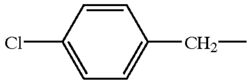 | 2 | 2 | 1 | — | H | 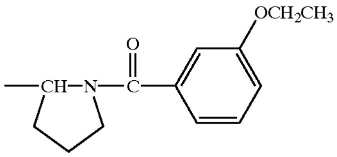 |
| 695 | 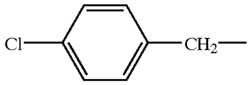 | 2 | 2 | 1 | — | H | 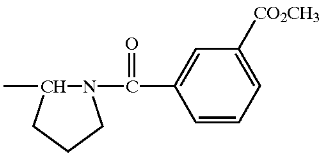 |
| 696 | 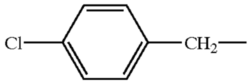 | 2 | 2 | 1 | — | H | 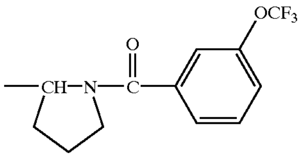 |
| 697 | 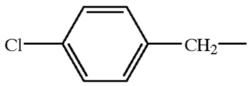 | 2 | 2 | 1 | — | H | 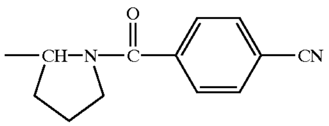 |
| 698 | 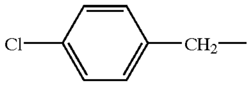 | 2 | 2 | 1 | — | H | 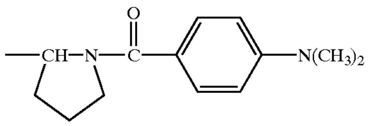 |
| 699 | 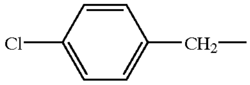 | 2 | 2 | 1 | — | H | 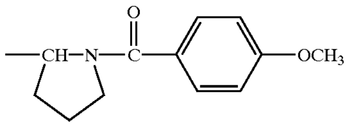 |

TABLE 1.64-continued
| Compd. No. | 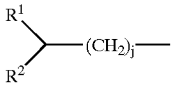 | k | m | n | chirality | $R^3$ | 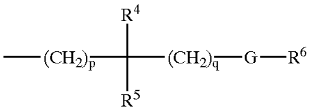 |
|---|---|---|---|---|---|---|---|
| 700 | 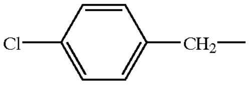 | 2 | 2 | 1 | — | H | 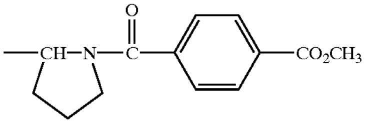 |
| 701 | 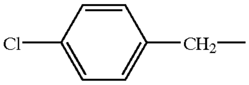 | 2 | 2 | 1 | — | H | 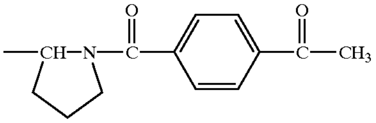 |
| 702 | 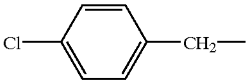 | 2 | 2 | 1 | — | H | 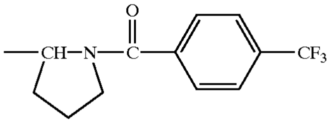 |
| 703 | 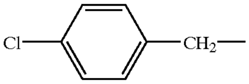 | 2 | 2 | 1 | — | H | 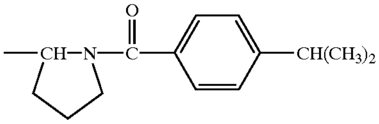 |
| 704 | 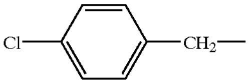 | 2 | 2 | 1 | — | H | 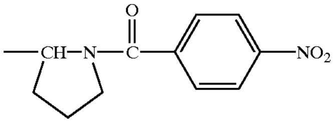 |
TABLE 1.65
| Compd. No. | 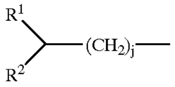 | k | m | n | chirality | $R^3$ | 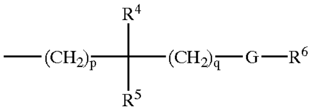 |
|---|---|---|---|---|---|---|---|
| 705 | 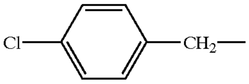 | 2 | 2 | 1 | — | H | 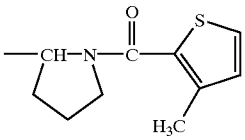 |
| 706 | 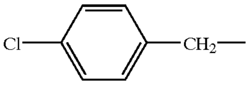 | 2 | 2 | 1 | — | H | 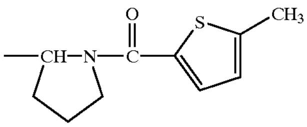 |
| 707 | 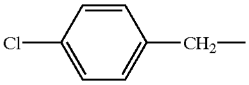 | 2 | 2 | 1 | — | H | 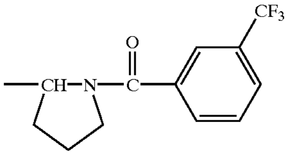 |

TABLE 1.65-continued
| Compd. No. | 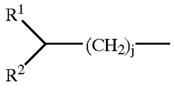 | k | m | n | chirality | $R^3$ | 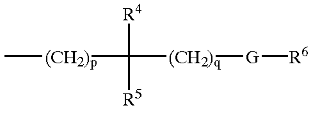 |
| --- | --- | --- | --- | --- | --- | --- | --- |
| 708 | 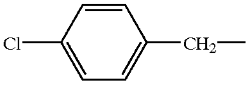 | 2 | 2 | 1 | — | H | 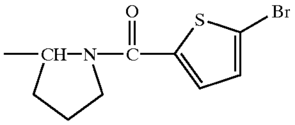 |
| 709 | 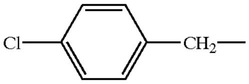 | 2 | 2 | 1 | — | H | 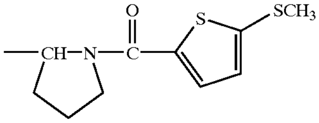 |
| 710 | 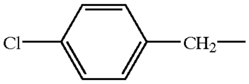 | 2 | 2 | 1 | — | H | 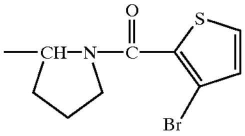 |
| 711 | 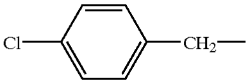 | 2 | 2 | 1 | — | H | 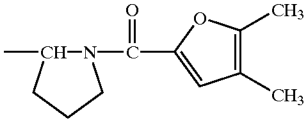 |
| 712 | 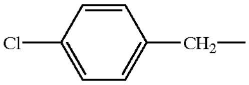 | 2 | 2 | 1 | — | H | 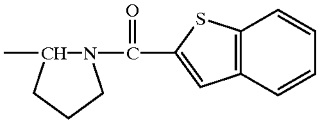 |
| 713 | 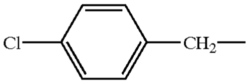 | 2 | 2 | 1 | — | H | 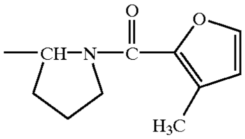 |
| 714 | 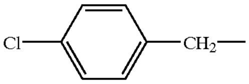 | 2 | 2 | 1 | — | H | 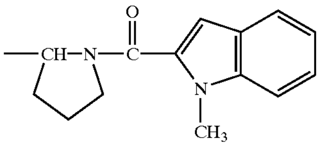 |
| 715 | 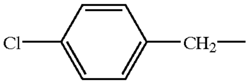 | 2 | 2 | 1 | — | H | 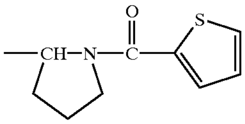 |

TABLE 1.66
| Compd. No. | 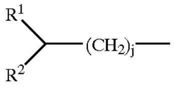 | k | m | n | chirality | $R^3$ | 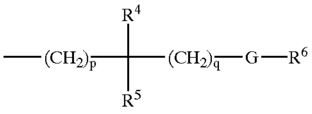 |
|---|---|---|---|---|---|---|---|
| 716 | 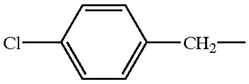 | 2 | 2 | 1 | — | H | 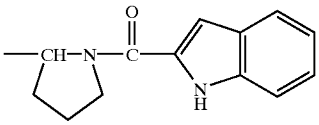 |
| 717 | 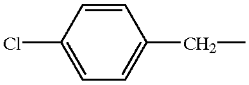 | 2 | 2 | 1 | — | H | 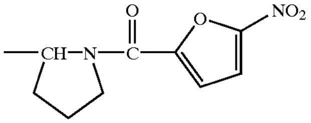 |
| 718 | 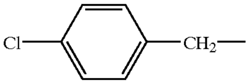 | 2 | 2 | 1 | — | H | 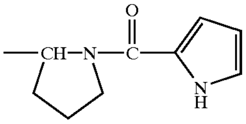 |
| 719 | 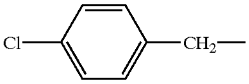 | 2 | 2 | 1 | — | H | 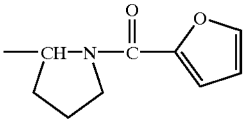 |
| 720 | 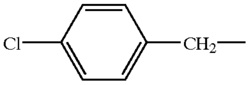 | 2 | 2 | 1 | — | H | 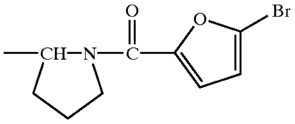 |
| 721 | 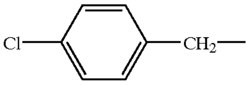 | 2 | 2 | 1 | — | H | 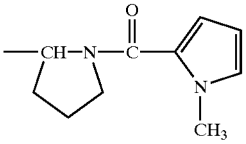 |
| 722 | 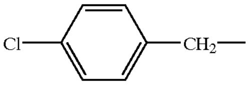 | 2 | 2 | 1 | — | H | 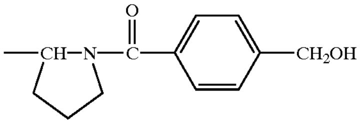 |
| 723 | 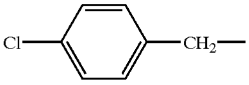 | 2 | 2 | 1 | — | H | 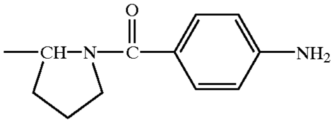 |
| 724 | 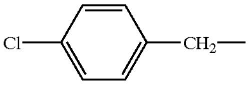 | 2 | 2 | 1 | — | H | 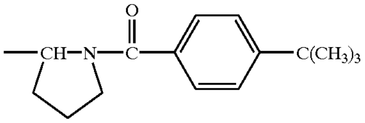 |
| 725 | 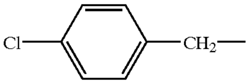 | 2 | 2 | 1 | — | H | 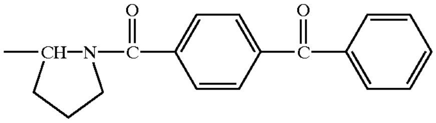 |

TABLE 1.66-continued
| Compd. No. | 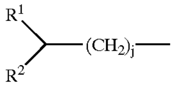 | k | m | n | chirality | $R^3$ | 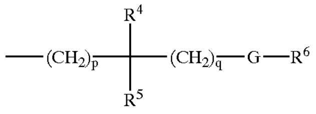 |
|---|---|---|---|---|---|---|---|
| 726 | 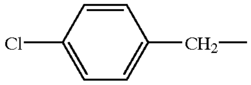 | 2 | 2 | 1 | — | H | 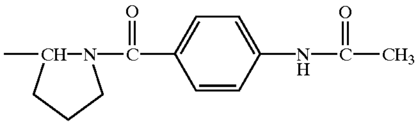 |
TABLE 1.67
| Compd. No. | 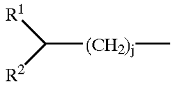 | k | m | n | chirality | $R^3$ | 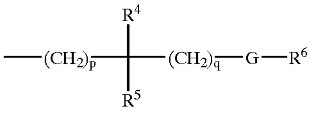 |
|---|---|---|---|---|---|---|---|
| 727 | 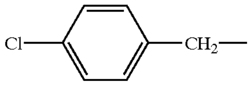 | 2 | 2 | 1 | — | H | 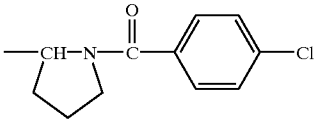 |
| 728 | 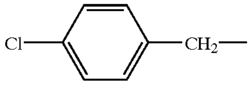 | 2 | 2 | 1 | — | H | 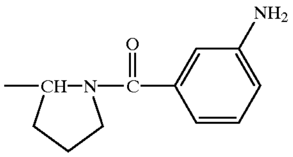 |
| 729 | 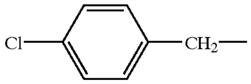 | 2 | 2 | 1 | — | H | 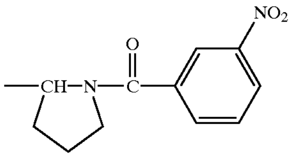 |
| 730 | 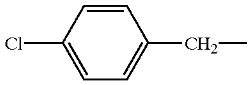 | 2 | 2 | 1 | — | H | 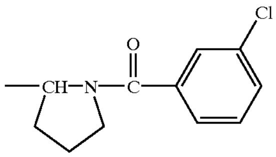 |
| 731 | 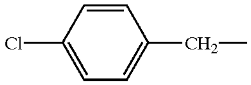 | 2 | 2 | 1 | — | H | 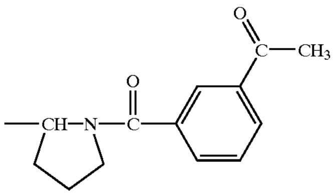 |
| 732 | 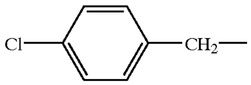 | 2 | 2 | 1 | — | H | 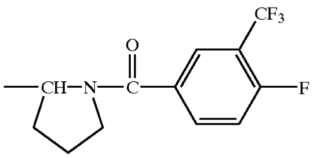 |

TABLE 1.67-continued
| Compd. No. | 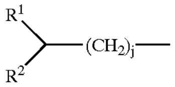 | k | m | n | chirality | $R^3$ | 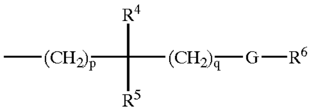 |
|---|---|---|---|---|---|---|---|
| 733 | 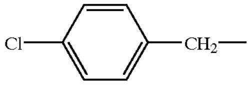 | 2 | 2 | 1 | — | H | 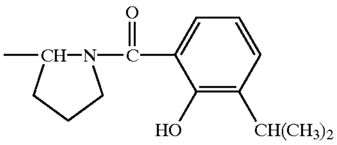 |
| 734 | 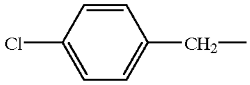 | 2 | 2 | 1 | — | H | 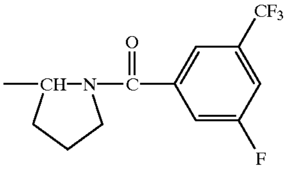 |
| 735 | 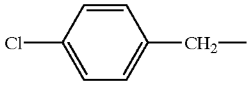 | 2 | 2 | 1 | — | H | 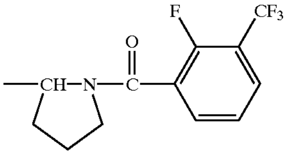 |
| 736 | 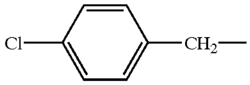 | 2 | 2 | 1 | — | H | 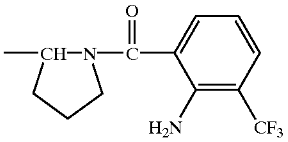 |
| 737 | 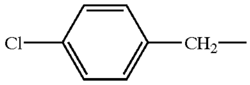 | 2 | 2 | 1 | — | H | 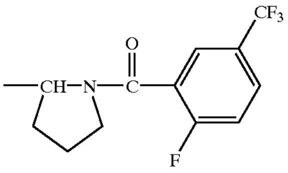 |
TABLE 1.68
| Compd. No. | 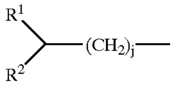 | k | m | n | chirality | $R^3$ | 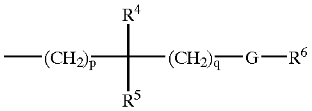 |
|---|---|---|---|---|---|---|---|
| 738 | 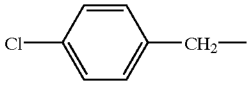 | 2 | 2 | 1 | — | H | 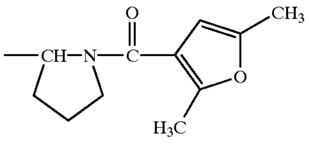 |
| 739 | 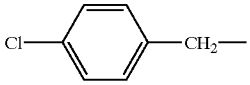 | 2 | 2 | 1 | — | H | 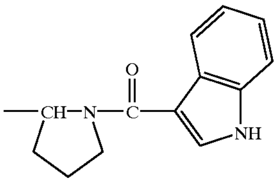 |

TABLE 1.68-continued
| Compd. No. | 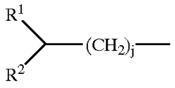 | k | m | n | chirality | $R^3$ | 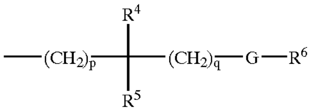 |
|---|---|---|---|---|---|---|---|
| 740 | 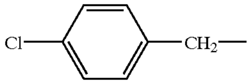 | 2 | 2 | 1 | — | H | 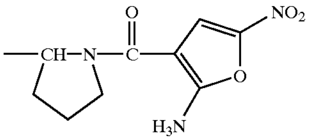 |
| 741 | 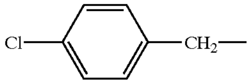 | 2 | 2 | 1 | — | H | 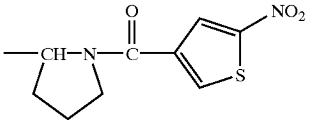 |
| 742 | 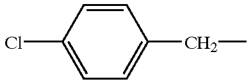 | 2 | 2 | 1 | — | H | 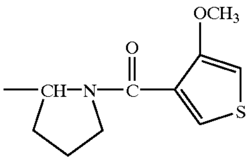 |
| 743 | 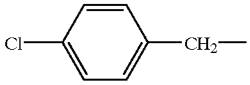 | 2 | 2 | 1 | — | H | 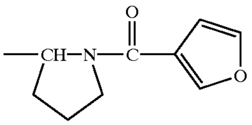 |
| 744 | 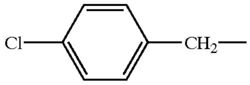 | 2 | 2 | 1 | — | H | 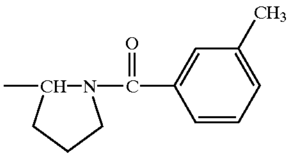 |
| 745 | 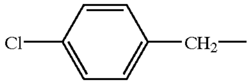 | 2 | 2 | 1 | — | H | 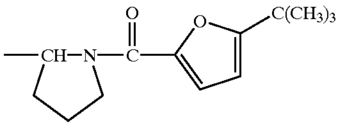 |
| 746 | 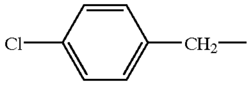 | 2 | 2 | 1 | — | H | 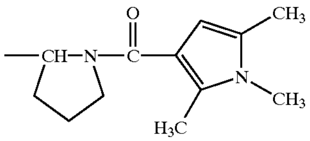 |
| 747 | 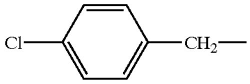 | 2 | 2 | 1 | — | H | 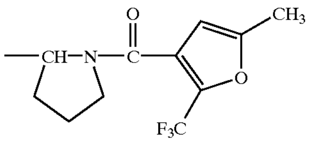 |
| 748 | 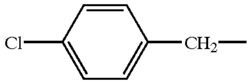 | 2 | 2 | 1 | — | H | 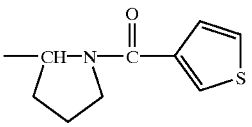 |

TABLE 1.69
| Compd. No. | 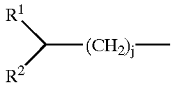 | k | m | n | chirality | $R^3$ | 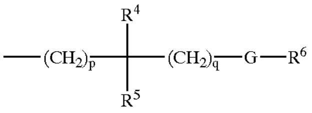 |
|---|---|---|---|---|---|---|---|
| 749 | 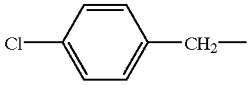 | 2 | 2 | 1 | — | H | 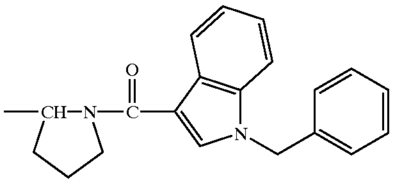 |
| 750 | 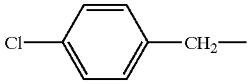 | 2 | 2 | 1 | — | H | 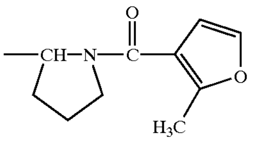 |
| 751 | 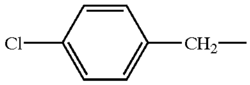 | 2 | 2 | 1 | — | H | 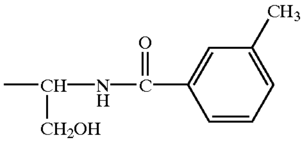 |
| 752 | 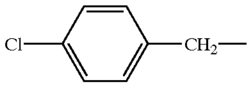 | 2 | 2 | 1 | — | H | 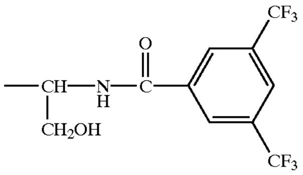 |
| 753 | 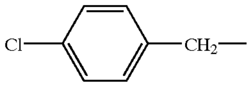 | 2 | 2 | 1 | — | H | 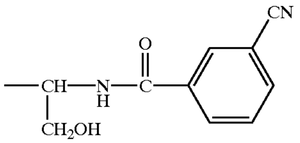 |
| 754 | 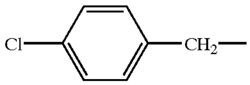 | 2 | 2 | 1 | — | H | 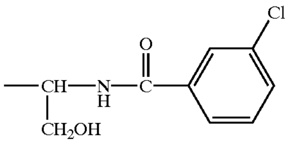 |
| 755 | 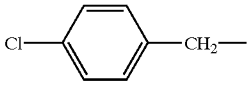 | 2 | 2 | 1 | — | H | 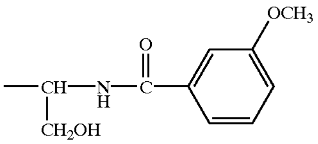 |
| 756 | 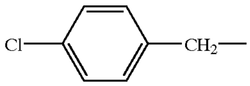 | 2 | 2 | 1 | — | H | 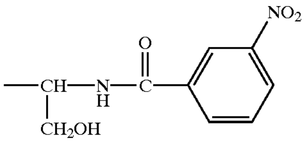 |
| 757 | 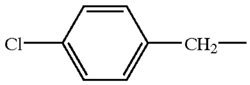 | 2 | 2 | 1 | — | H | 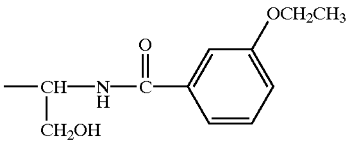 |

TABLE 1.69-continued
| Compd. No. | 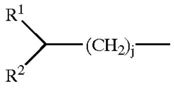 | k | m | n | chirality | $R^3$ | 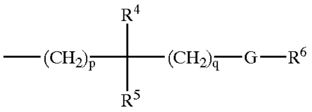 |
|---|---|---|---|---|---|---|---|
| 758 | 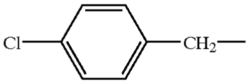 | 2 | 2 | 1 | — | H | 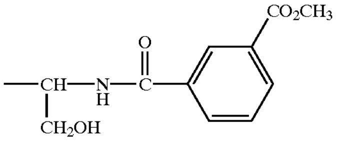 |
| 759 | 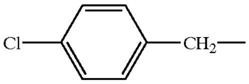 | 2 | 2 | 1 | — | H | 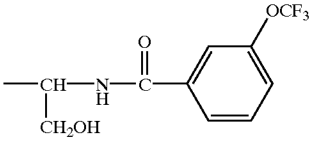 |
TABLE 1.70
| Compd. No. | 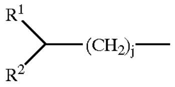 | k | m | n | chirality | $R^3$ | 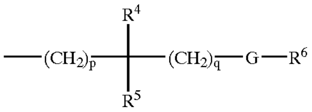 |
|---|---|---|---|---|---|---|---|
| 760 | 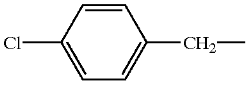 | 2 | 2 | 1 | — | H | 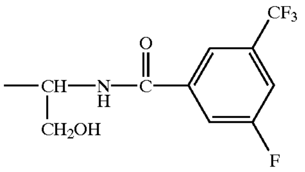 |
| 761 | 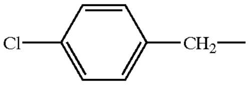 | 2 | 2 | 1 | — | H | 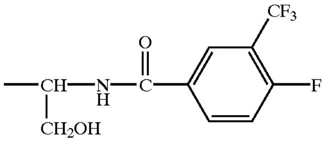 |
| 762 | 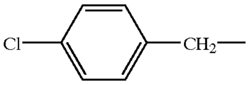 | 2 | 2 | 1 | — | H | 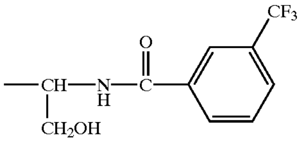 |
| 763 | 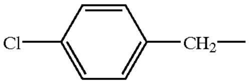 | 2 | 2 | 1 | — | H | 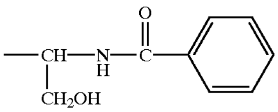 |
| 764 | 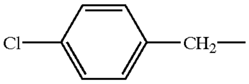 | 2 | 2 | 1 | — | H | 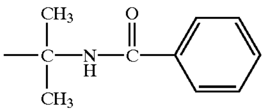 |

TABLE 1.70-continued
| Compd. No. | 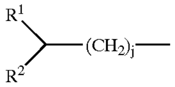 | k | m | n | chirality | $R^3$ | 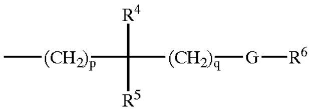 |
|---|---|---|---|---|---|---|---|
| 765 | 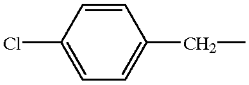 | 2 | 2 | 1 | — | H | 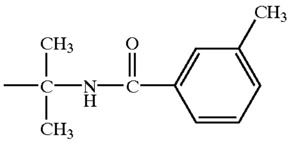 |
| 766 | 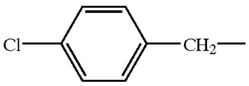 | 2 | 2 | 1 | — | H | 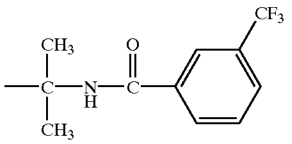 |
| 767 | 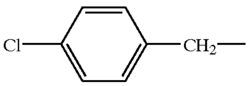 | 2 | 2 | 1 | — | H | 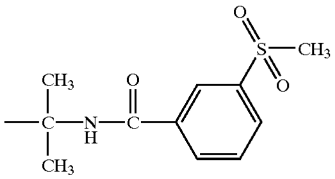 |
| 768 | 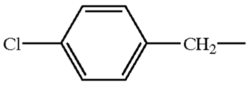 | 2 | 2 | 1 | — | H | 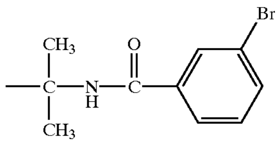 |
| 769 | 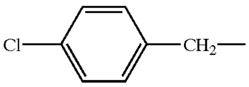 | 2 | 2 | 1 | — | H | 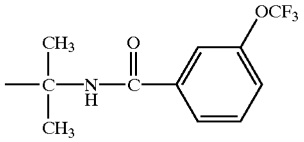 |
| 770 | 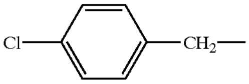 | 2 | 2 | 1 | — | H | 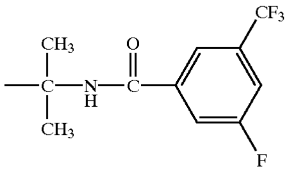 |
TABLE 1.71
| Compd. No. | 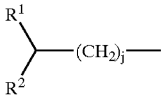 | k | m | n | chirality | $R^3$ | 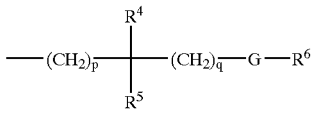 |
|---|---|---|---|---|---|---|---|
| 771 | 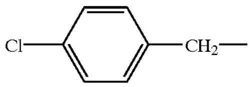 | 2 | 2 | 1 | — | H | 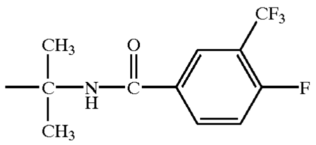 |

TABLE 1.71-continued
| Compd. No. 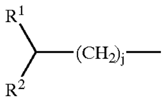 | | k | m | n | chirality | $R^3$ | 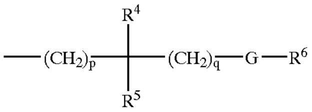 |
|---|---|---|---|---|---|---|---|
| 772 | 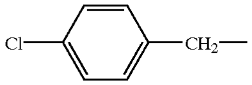 | 2 | 2 | 1 | — | H | 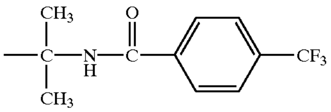 |
| 773 | 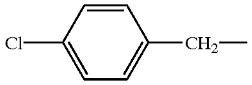 | 2 | 2 | 1 | — | H | 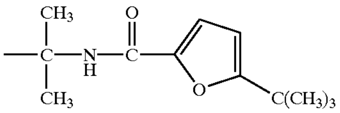 |
| 774 | 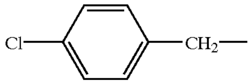 | 2 | 2 | 1 | — | H | 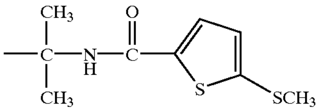 |
| 775 | 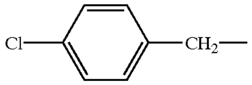 | 2 | 2 | 1 | — | H | 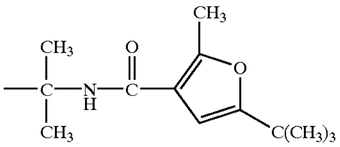 |
| 776 | 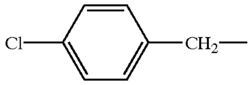 | 2 | 2 | 1 | — | H | 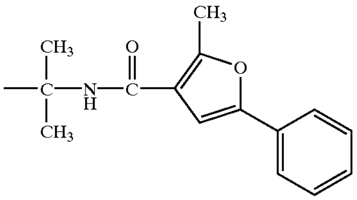 |
| 777 | 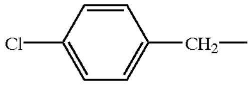 | 2 | 2 | 1 | — | H | 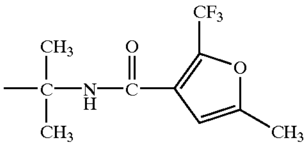 |
| 778 | 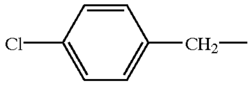 | 2 | 2 | 1 | — | H | 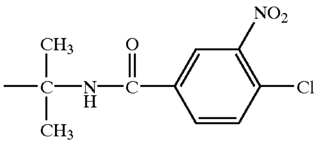 |
| 779 | 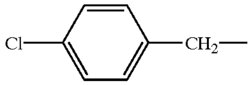 | 2 | 2 | 1 | — | H | 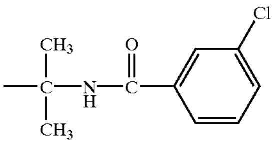 |
| 780 | 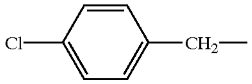 | 2 | 2 | 1 | — | H | 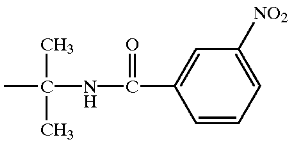 |

TABLE 1.71-continued
| Compd. No. | 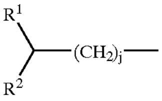 | k | m | n | chirality | $R^3$ | 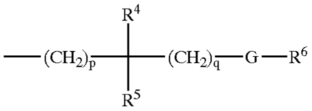 |
|---|---|---|---|---|---|---|---|
| 781 | 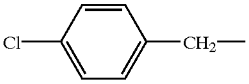 | 2 | 2 | 1 | — | H | 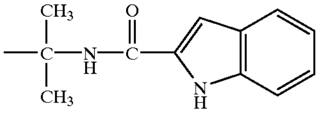 |
TABLE 1.72
| Compd. No. | 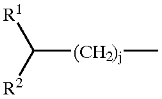 | k | m | n | chirality | $R^3$ | 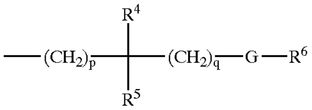 |
|---|---|---|---|---|---|---|---|
| 782 | 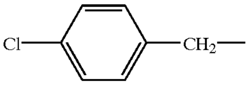 | 2 | 2 | 1 | — | H | 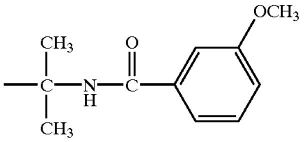 |
| 783 | 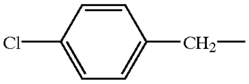 | 2 | 2 | 1 | — | H | 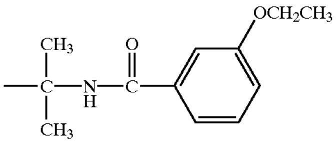 |
| 784 | 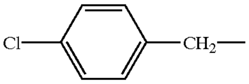 | 2 | 2 | 1 | — | H | 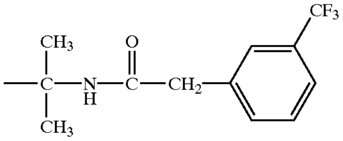 |
| 785 | 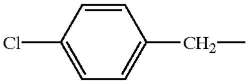 | 2 | 2 | 1 | — | H | 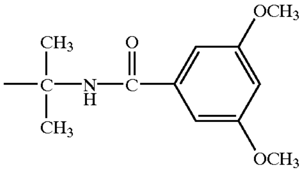 |
| 786 | 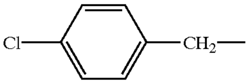 | 2 | 2 | 1 | — | H | 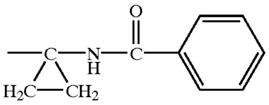 |
| 787 | 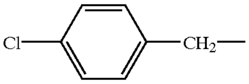 | 2 | 2 | 1 | — | H | 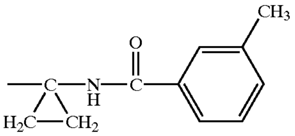 |
| 788 | 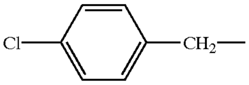 | 2 | 2 | 1 | — | H | 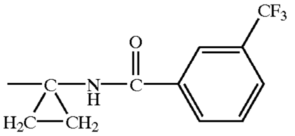 |

TABLE 1.72-continued
| Compd. No. | 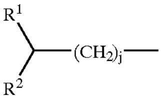 | k | m | n | chirality | $R^3$ | 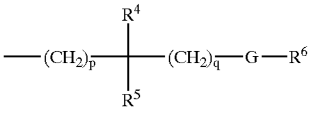 |
|---|---|---|---|---|---|---|---|
| 789 | 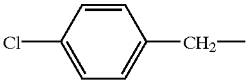 | 2 | 2 | 1 | — | H | 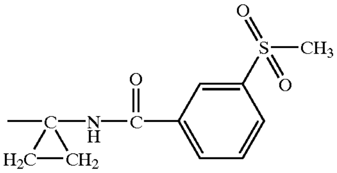 |
| 790 | 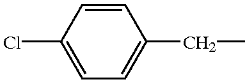 | 2 | 2 | 1 | — | H | 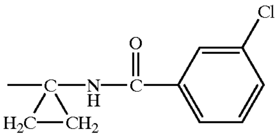 |
| 791 | 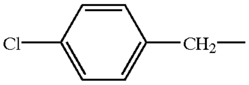 | 2 | 2 | 1 | — | H | 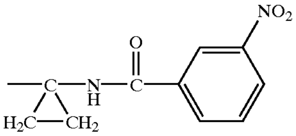 |
| 792 | 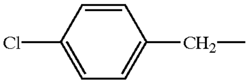 | 2 | 2 | 1 | — | H | 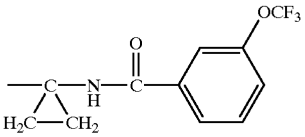 |
TABLE 1.73
| Compd. No. | 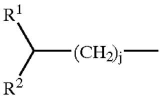 | k | m | n | chirality | $R^3$ | 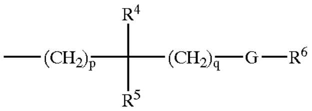 |
|---|---|---|---|---|---|---|---|
| 793 | 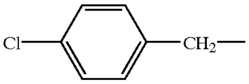 | 2 | 2 | 1 | — | H | 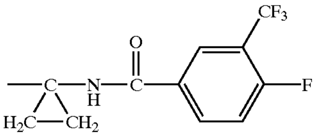 |
| 794 | 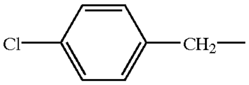 | 2 | 2 | 1 | — | H | 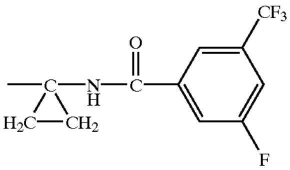 |
| 795 | 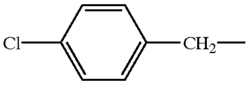 | 2 | 2 | 1 | — | H | 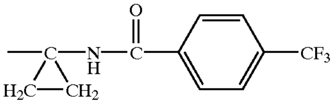 |
| 796 | 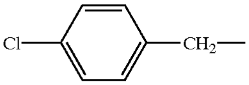 | 2 | 2 | 1 | — | H | 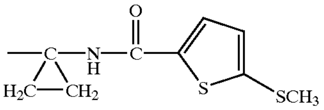 |

TABLE 1.73-continued
| Compd. No. | 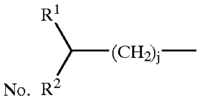 | k | m | n | chirality | $R^3$ | 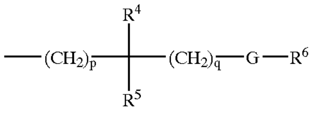 |
|---|---|---|---|---|---|---|---|
| 797 | 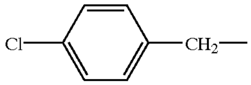 | 2 | 2 | 1 | — | H | 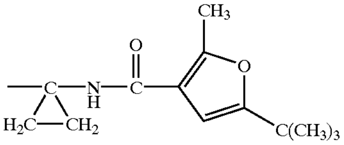 |
| 798 | 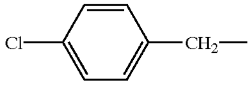 | 2 | 2 | 1 | — | H | 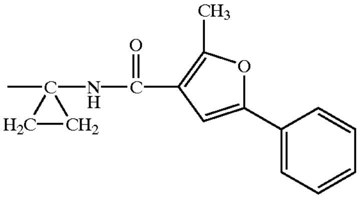 |
| 799 | 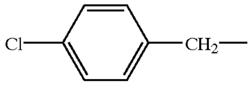 | 2 | 2 | 1 | — | H | 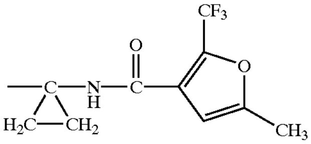 |
| 800 | 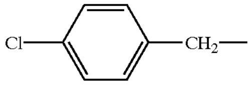 | 2 | 2 | 1 | — | H | 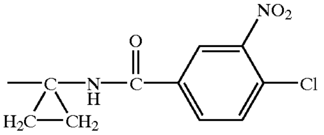 |
| 801 | 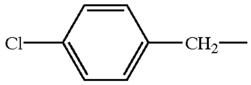 | 2 | 2 | 1 | — | H | 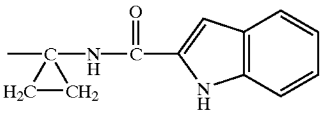 |
| 802 | 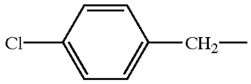 | 2 | 2 | 1 | — | H | 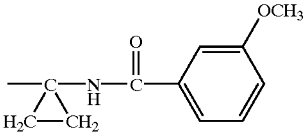 |
| 803 | 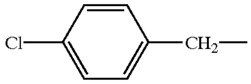 | 2 | 2 | 1 | — | H | 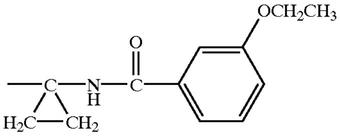 |

TABLE 1.74
| Compd. No. 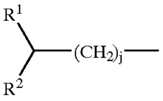 | | k | m | n | chirality | $R^3$ | 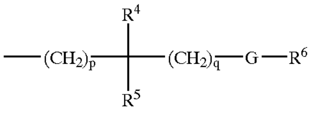 |
|---|---|---|---|---|---|---|---|
| 804 | 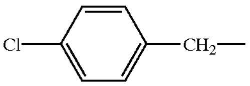 | 2 | 2 | 1 | — | H | 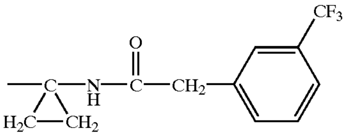 |
| 805 | 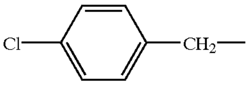 | 2 | 2 | 1 | — | H | 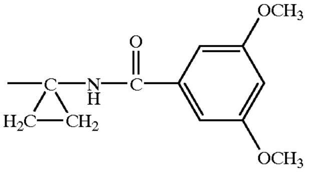 |
| 806 | 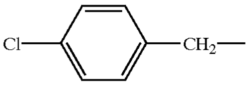 | 2 | 2 | 1 | — | H | 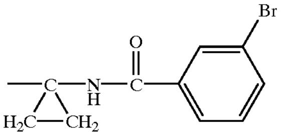 |
| 807 | 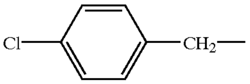 | 2 | 2 | 1 | — | H | 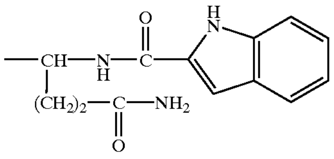 |
| 808 | 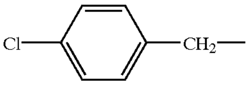 | 2 | 2 | 1 | — | H | 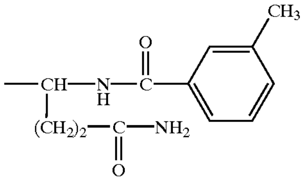 |
| 809 | 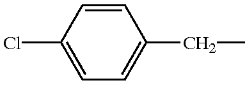 | 2 | 2 | 1 | — | H | 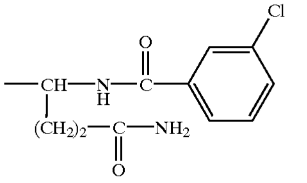 |
| 810 | 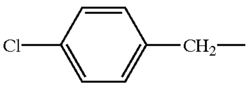 | 2 | 2 | 1 | — | H | 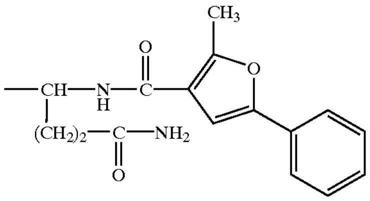 |
| 811 | 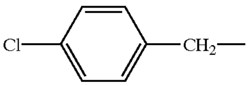 | 2 | 2 | 1 | — | H | 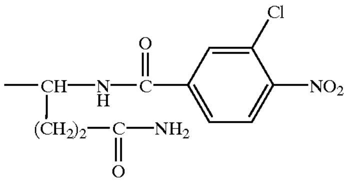 |

TABLE 1.74-continued
| Compd. No. | 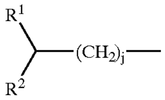 | k | m | n | chirality | $R^3$ | 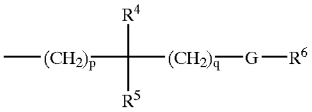 |
|---|---|---|---|---|---|---|---|
| 812 | 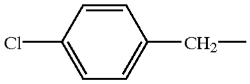 | 2 | 2 | 1 | — | H | 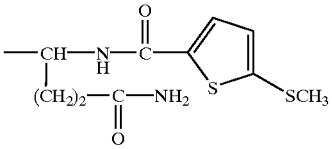 |
| 813 | 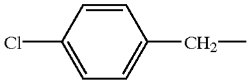 | 2 | 2 | 1 | — | H | 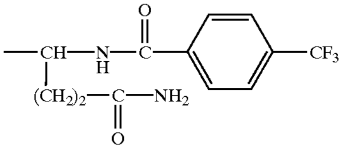 |
| 814 | 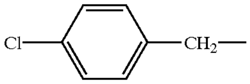 | 2 | 2 | 1 | — | H | 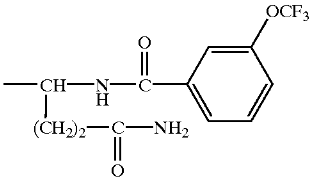 |
TABLE 1.75
| Compd. No. | 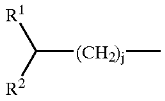 | k | m | n | chirality | $R^3$ | 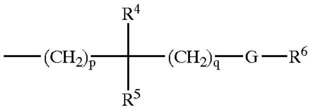 |
|---|---|---|---|---|---|---|---|
| 815 | 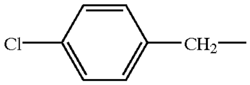 | 2 | 2 | 1 | — | H | 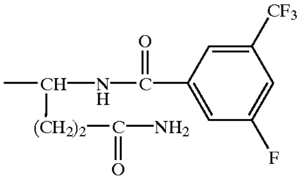 |
| 816 | 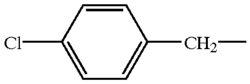 | 2 | 2 | 1 | — | H | 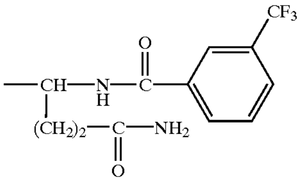 |
| 817 | 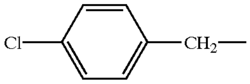 | 2 | 2 | 1 | — | H | 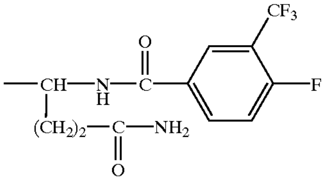 |

TABLE 1.75-continued
| Compd. No. | 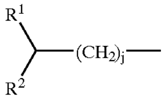 | k | m | n | chirality | $R^3$ | 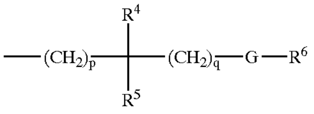 |
|---|---|---|---|---|---|---|---|
| 818 | 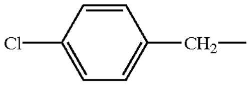 | 2 | 2 | 1 | — | H | 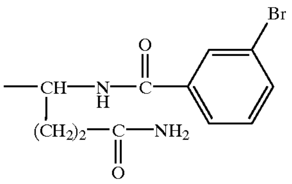 |
| 819 | 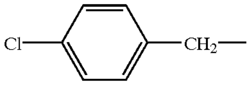 | 2 | 2 | 1 | — | H | 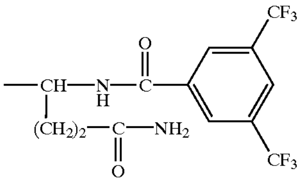 |
| 820 | 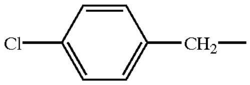 | 2 | 2 | 1 | — | H | 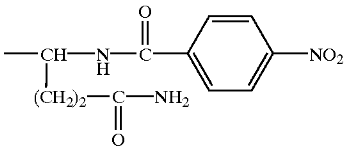 |
| 821 | 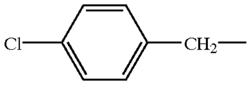 | 2 | 2 | 1 | — | H | 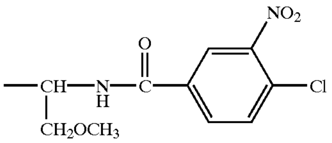 |
| 822 | 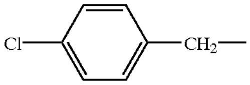 | 2 | 2 | 1 | — | H | 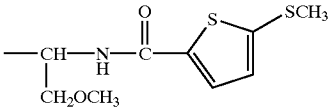 |
| 823 | 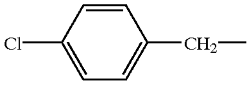 | 2 | 2 | 1 | — | H | 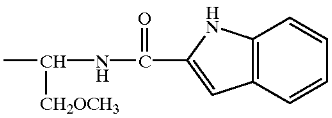 |
| 824 | 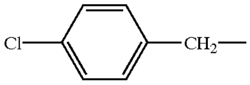 | 2 | 2 | 1 | — | H | 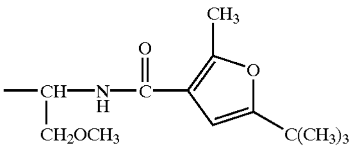 |
| 825 | 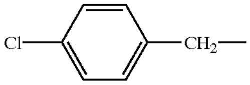 | 2 | 2 | 1 | — | H | 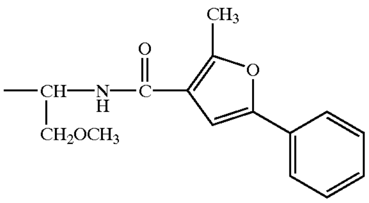 |

TABLE 1.76
| Compd. No. | 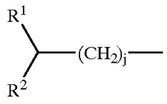 | k | m | n | chirality | $R^3$ | 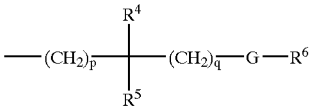 |
|---|---|---|---|---|---|---|---|
| 826 | 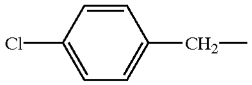 | 2 | 2 | 1 | — | H | 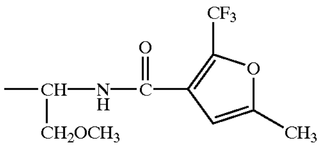 |
| 827 | 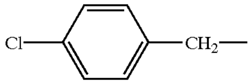 | 2 | 2 | 1 | — | H | 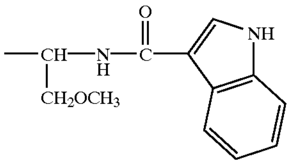 |
| 828 | 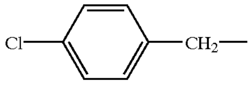 | 2 | 2 | 1 | — | H | 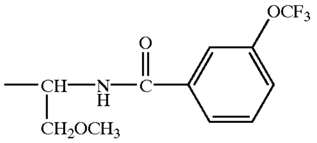 |
| 829 | 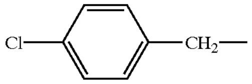 | 2 | 2 | 1 | — | H | 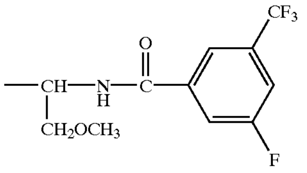 |
| 830 | 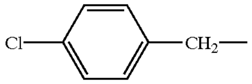 | 2 | 2 | 1 | — | H | 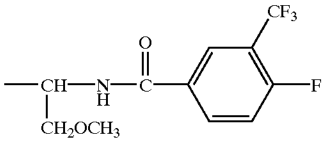 |
| 831 | 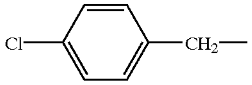 | 2 | 2 | 1 | — | H | 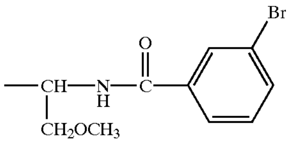 |
| 832 | 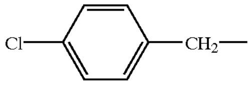 | 2 | 2 | 1 | — | H | 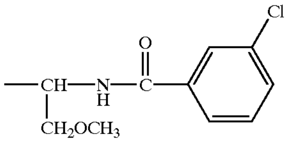 |
| 833 | 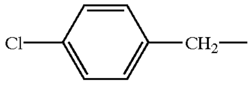 | 2 | 2 | 1 | — | H | 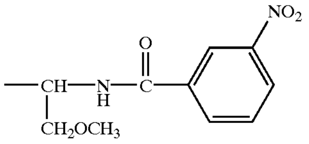 |
| 834 | 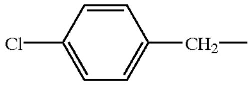 | 2 | 2 | 1 | — | H | 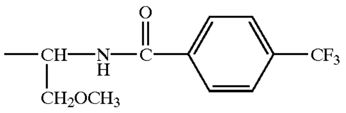 |

TABLE 1.76-continued
| Compd. No. | 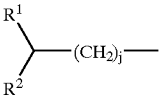 | k | m | n | chirality | $R^3$ | 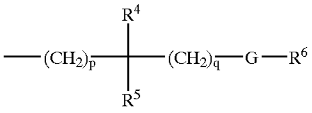 |
|---|---|---|---|---|---|---|---|
| 835 | 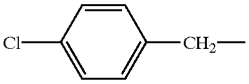 | 2 | 2 | 1 | — | H | 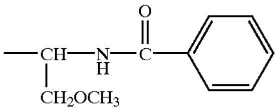 |
| 836 | 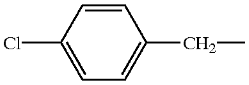 | 2 | 2 | 1 | — | H | 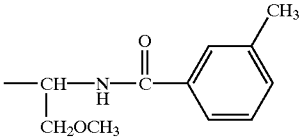 |
TABLE 1.77
| Compd. No. | 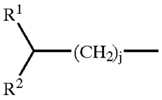 | k | m | n | chirality | $R^3$ | 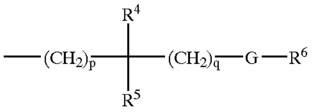 |
|---|---|---|---|---|---|---|---|
| 837 | 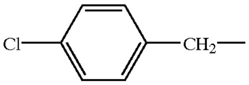 | 2 | 2 | 1 | — | H | 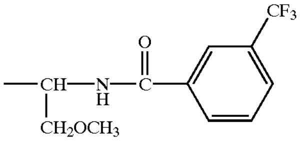 |
| 838 | 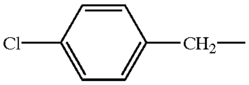 | 2 | 2 | 1 | — | H | 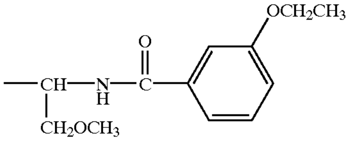 |
| 839 | 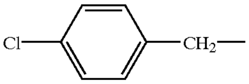 | 2 | 2 | 1 | — | H | 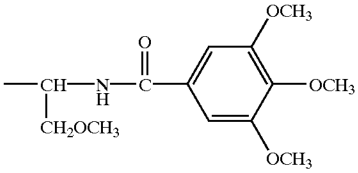 |
| 840 | 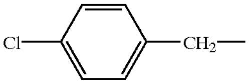 | 2 | 2 | 1 | — | H | 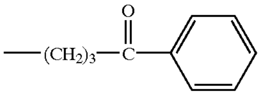 |
| 841 | 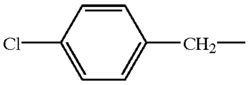 | 2 | 2 | 1 | — | H | 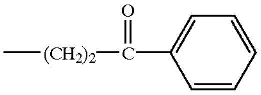 |
| 842 | 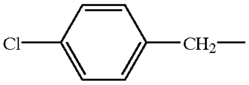 | 2 | 2 | 1 | — | H | 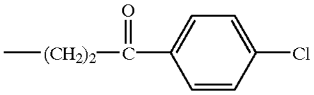 |

TABLE 1.77-continued
| Compd. No. | 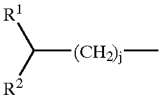 | k | m | n | chirality | $R^3$ | 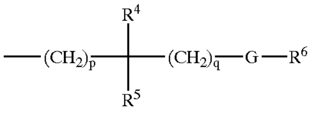 |
|---|---|---|---|---|---|---|---|
| 843 | 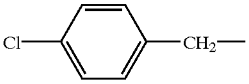 | 2 | 2 | 1 | — | H | 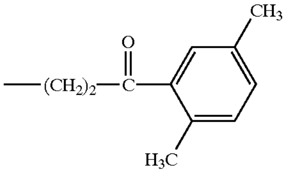 |
| 844 | 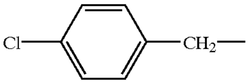 | 2 | 2 | 1 | — | H | 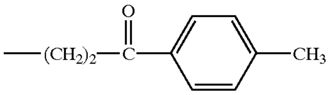 |
| 845 | 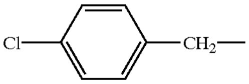 | 2 | 2 | 1 | — | H | 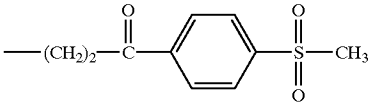 |
| 846 | 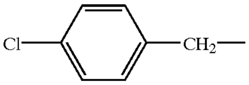 | 2 | 2 | 1 | — | H | 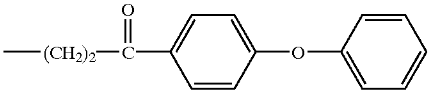 |
| 847 | 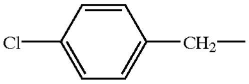 | 2 | 2 | 1 | — | H | 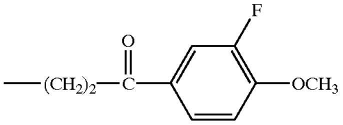 |
TABLE 1.78
| Compd. No. | 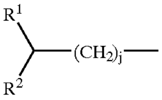 | k | m | n | chirality | $R^3$ | 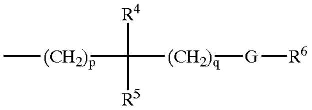 |
|---|---|---|---|---|---|---|---|
| 848 | 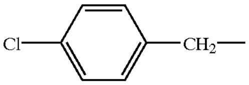 | 2 | 2 | 1 | — | H | 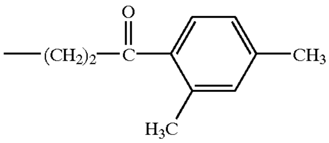 |
| 849 | 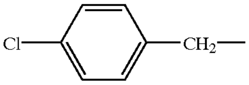 | 2 | 2 | 1 | — | H | 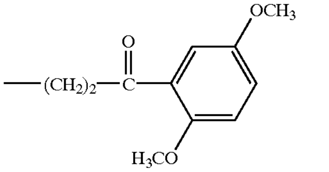 |
| 850 | 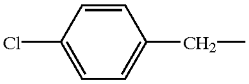 | 2 | 2 | 1 | — | H | 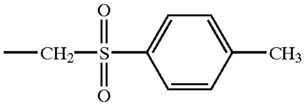 |

TABLE 1.78-continued
| Compd. No. | 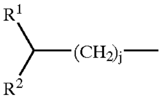 | k | m | n | chirality | $R^3$ | 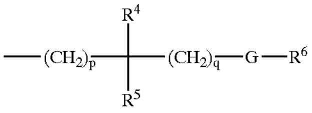 |
|---|---|---|---|---|---|---|---|
| 851 | 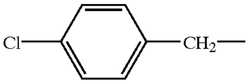 | 2 | 2 | 1 | — | H | 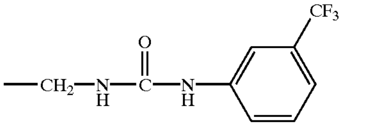 |
| 852 | 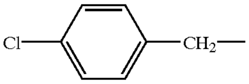 | 2 | 2 | 1 | — | H | 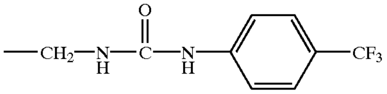 |
| 853 | 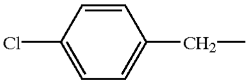 | 2 | 2 | 1 | — | H | 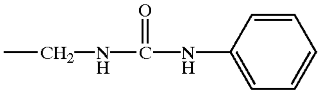 |
| 854 | 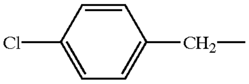 | 2 | 2 | 1 | — | H | 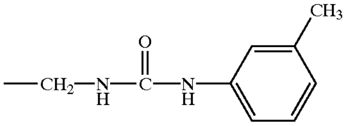 |
| 855 | 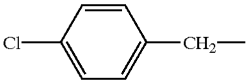 | 2 | 2 | 1 | — | H | 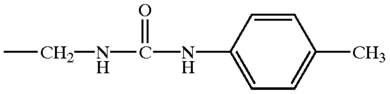 |
| 856 | 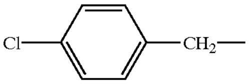 | 2 | 2 | 1 | — | H | 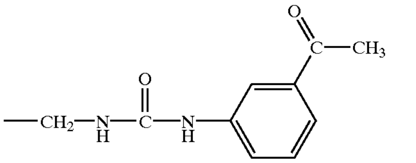 |
| 857 | 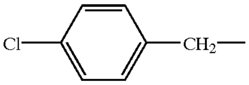 | 2 | 2 | 1 | — | H | 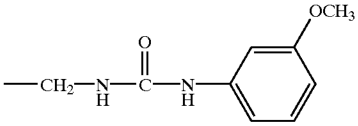 |
| 858 | 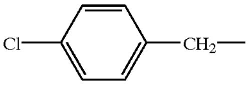 | 2 | 2 | 1 | — | H | 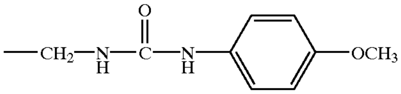 |
TABLE 1.79
| Compd. No. | 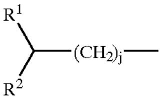 | k | m | n | chirality | $R^3$ | 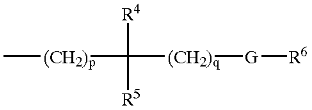 |
|---|---|---|---|---|---|---|---|
| 859 | 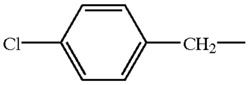 | 2 | 2 | 1 | — | H | 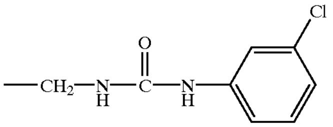 |

TABLE 1.79-continued
| Compd. No. | 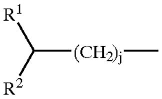 | k | m | n | chirality | $R^3$ | 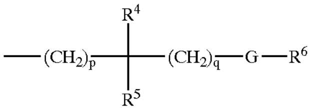 |
|---|---|---|---|---|---|---|---|
| 860 | 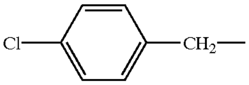 | 2 | 2 | 1 | — | H | 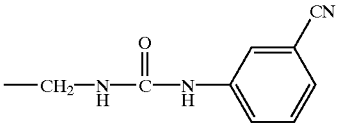 |
| 861 | 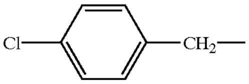 | 2 | 2 | 1 | — | H | 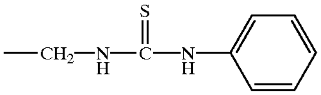 |
| 862 | 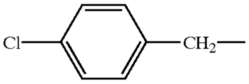 | 2 | 2 | 1 | — | H | 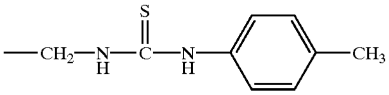 |
| 863 | 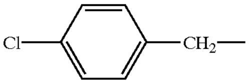 | 2 | 2 | 1 | — | H | 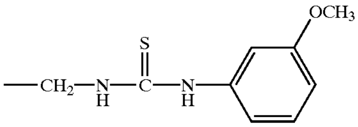 |
| 864 | 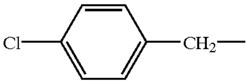 | 2 | 2 | 1 | — | H | 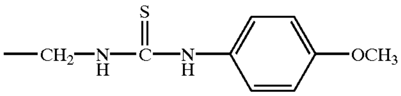 |
| 865 | 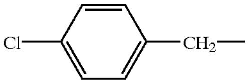 | 2 | 2 | 1 | — | H | 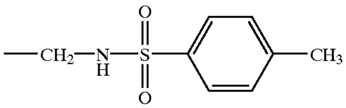 |
| 866 | 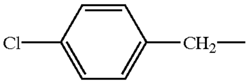 | 2 | 2 | 1 | — | H | 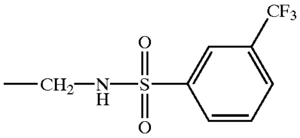 |
| 867 | 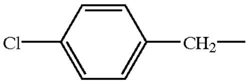 | 2 | 2 | 1 | — | H | 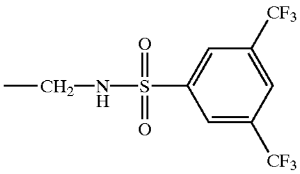 |
| 868 | 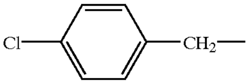 | 2 | 2 | 1 | — | H | 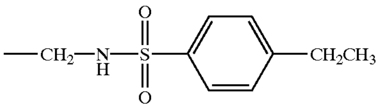 |
| 869 | 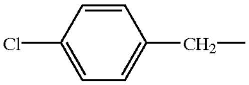 | 2 | 2 | 1 | — | H | 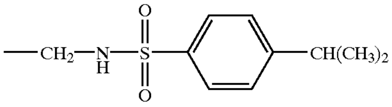 |

TABLE 1.80
| Compd. No. | 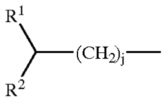 | k | m | n | chirality | $R^3$ | 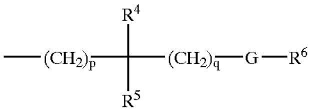 |
|---|---|---|---|---|---|---|---|
| 870 | 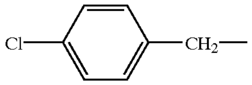 | 2 | 2 | 1 | — | H | 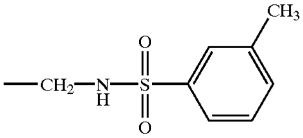 |
| 871 | 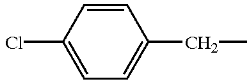 | 2 | 2 | 1 | — | H | 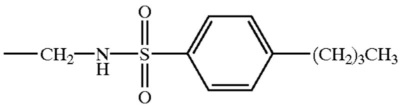 |
| 872 | 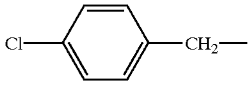 | 2 | 2 | 1 | — | H | 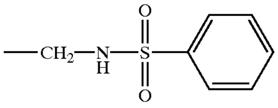 |
| 873 | 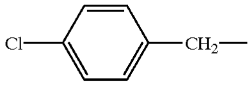 | 2 | 2 | 1 | — | H | 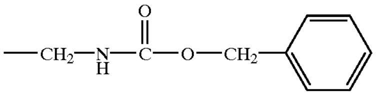 |
| 874 | 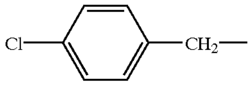 | 2 | 2 | 1 | — | H | 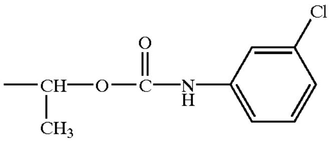 |
| 875 | 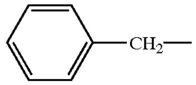 | 2 | 2 | 1 | — | H | 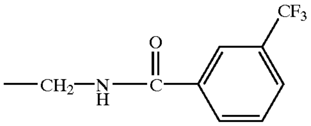 |
| 876 | 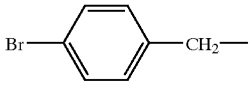 | 2 | 2 | 1 | — | H | 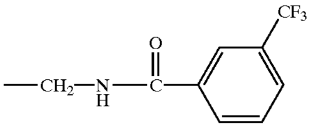 |
| 877 | 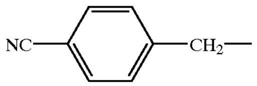 | 2 | 2 | 1 | — | H | 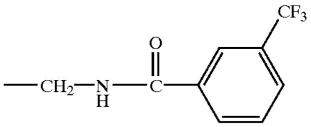 |
| 878 | 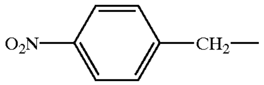 | 2 | 2 | 1 | — | H | 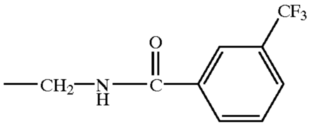 |
| 879 | 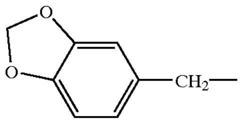 | 2 | 2 | 1 | — | H | 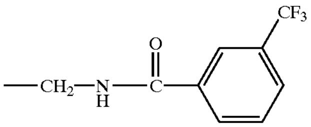 |

TABLE 1.80-continued
| Compd. No. 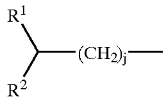 | k | m | n | chirality | $R^3$ | 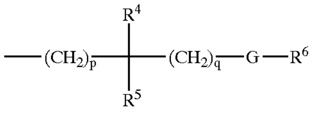 |
|---|---|---|---|---|---|---|
| 880 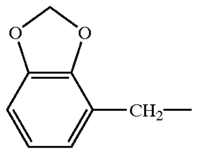 | 2 | 2 | 1 | — | H | 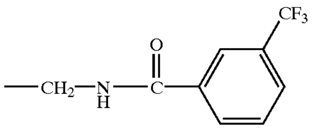 |
TABLE 1.81
| Compd. No. | 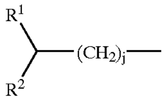 | k | m | n | chirality | $R^3$ | 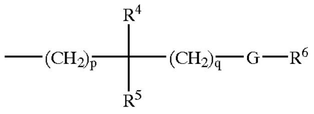 |
|---|---|---|---|---|---|---|---|
| 881 | 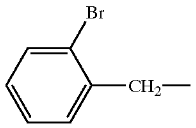 | 2 | 2 | 1 | — | H | 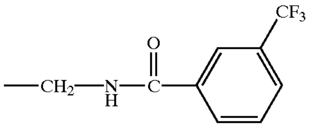 |
| 882 | 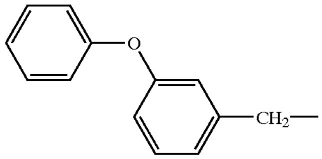 | 2 | 2 | 1 | — | H | 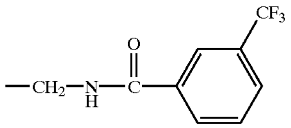 |
| 883 | 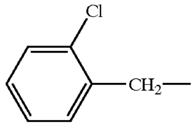 | 2 | 2 | 1 | — | H | 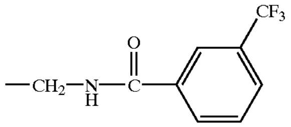 |
| 884 | 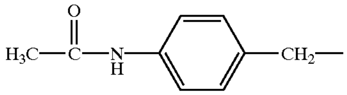 | 2 | 2 | 1 | — | H | 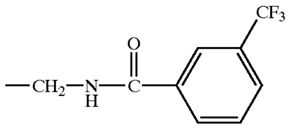 |
| 885 | 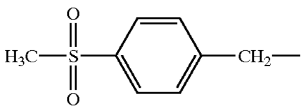 | 2 | 2 | 1 | — | H | 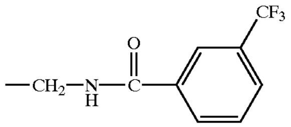 |
| 886 | 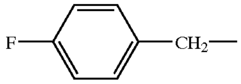 | 2 | 2 | 1 | — | H | 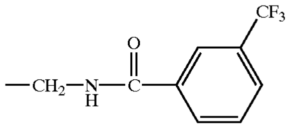 |
| 887 | 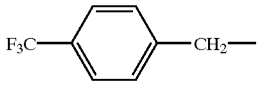 | 2 | 2 | 1 | — | H | 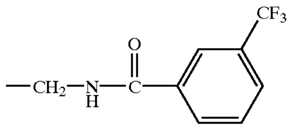 |

TABLE 1.81-continued
| Compd. No. | 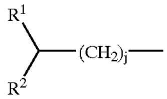 | k | m | n | chirality | $R^3$ | 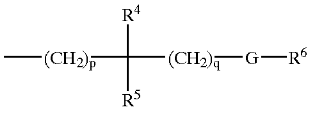 |
|---|---|---|---|---|---|---|---|
| 888 | 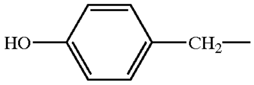 | 2 | 2 | 1 | — | H | 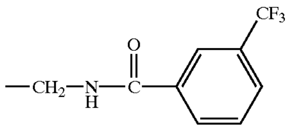 |
| 889 | 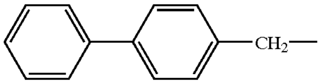 | 2 | 2 | 1 | — | H | 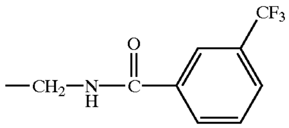 |
| 890 | 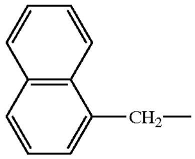 | 2 | 2 | 1 | — | H | 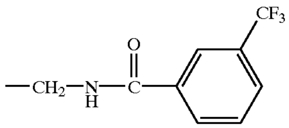 |
| 891 | 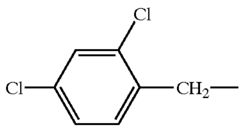 | 2 | 2 | 1 | — | H | 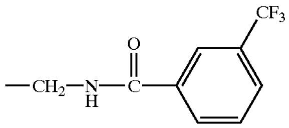 |
TABLE 1.82
| Compd. No. | 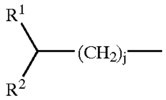 | k | m | n | chirality | $R^3$ | 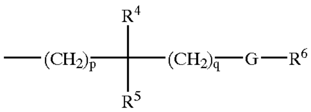 |
|---|---|---|---|---|---|---|---|
| 892 | 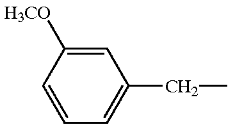 | 2 | 2 | 1 | — | H | 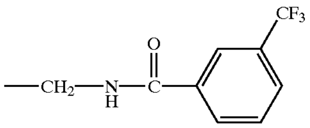 |
| 893 | 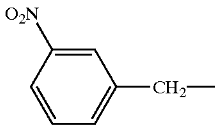 | 2 | 2 | 1 | — | H | 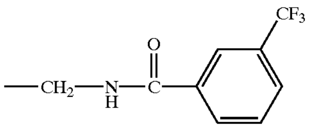 |
| 894 | 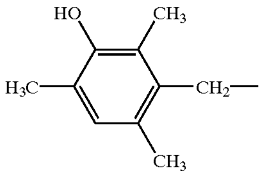 | 2 | 2 | 1 | — | H | 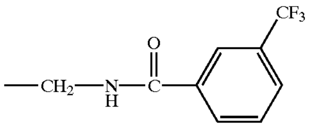 |
| 895 | 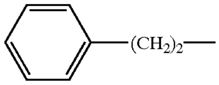 | 2 | 2 | 1 | — | H | 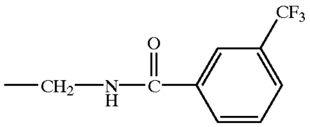 |

TABLE 1.82-continued
| Compd. No. | 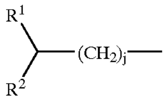 | k | m | n | chirality | $R^3$ | 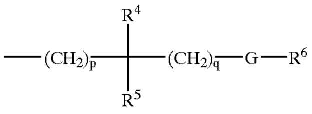 |
|---|---|---|---|---|---|---|---|
| 896 | 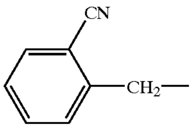 | 2 | 2 | 1 | — | H | 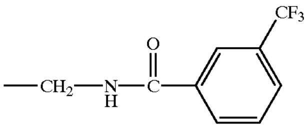 |
| 897 | 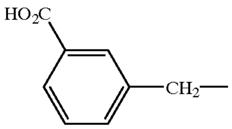 | 2 | 2 | 1 | — | H | 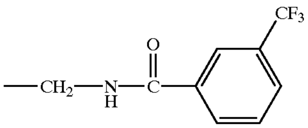 |
| 898 | 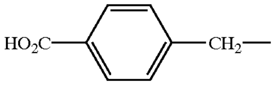 | 2 | 2 | 1 | — | H | 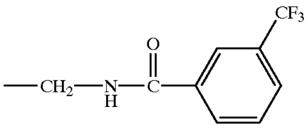 |
| 899 | 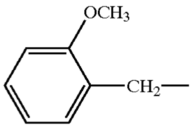 | 2 | 2 | 1 | — | H | 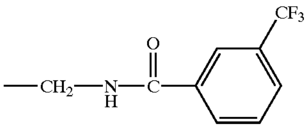 |
| 900 | 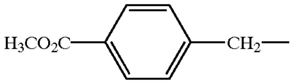 | 2 | 2 | 1 | — | H | 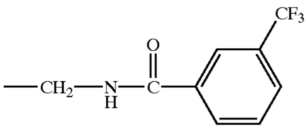 |
| 901 | 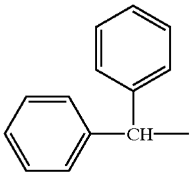 | 2 | 2 | 1 | — | H | 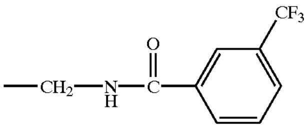 |
| 902 | 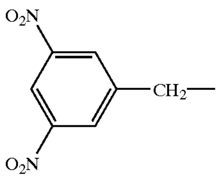 | 2 | 2 | 1 | — | H | 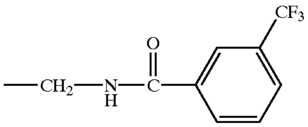 |

TABLE 1.83
| Compd. No. | 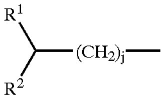 | k | m | n | chirality | $R^3$ | 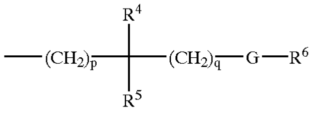 |
|---|---|---|---|---|---|---|---|
| 903 | 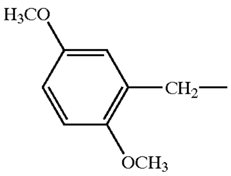 | 2 | 2 | 1 | — | H | 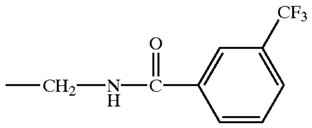 |
| 904 | 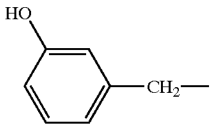 | 2 | 2 | 1 | — | H | 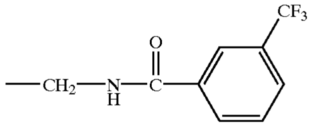 |
| 905 | 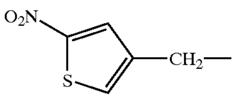 | 2 | 2 | 1 | — | H | 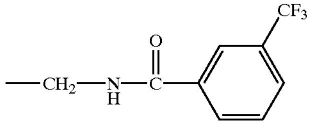 |
| 906 | 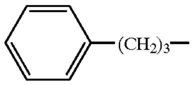 | 2 | 2 | 1 | — | H | 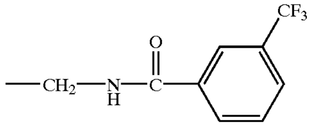 |
| 907 | 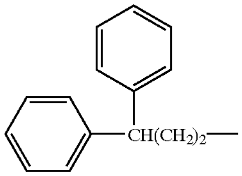 | 2 | 2 | 1 | — | H | 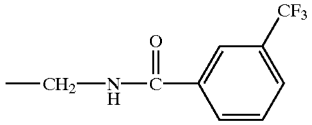 |
| 908 | 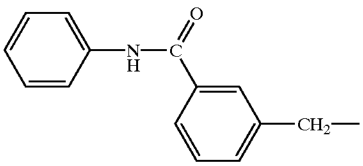 | 2 | 2 | 1 | — | H | 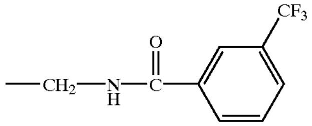 |
| 909 | 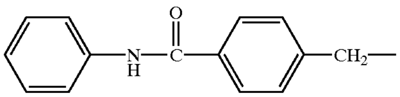 | 2 | 2 | 1 | — | H | 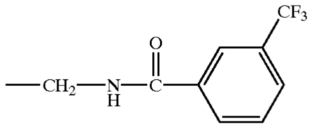 |
| 910 | 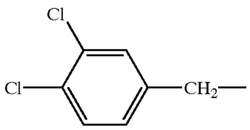 | 2 | 2 | 1 | — | H | 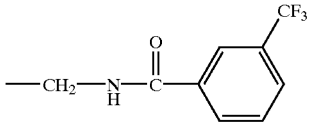 |
| 911 | 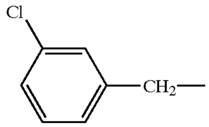 | 2 | 2 | 1 | — | H | 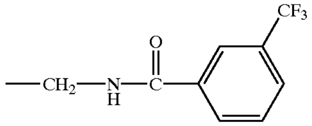 |

TABLE 1.83-continued
| Compd. No. | 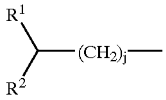 | k | m | n | chirality | $R^3$ | 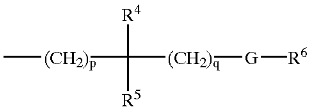 |
|---|---|---|---|---|---|---|---|
| 912 | 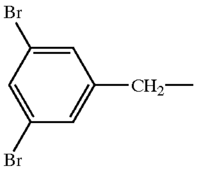 | 2 | 2 | 1 | — | H | 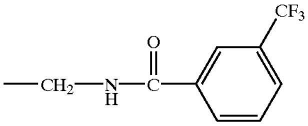 |
| 913 | 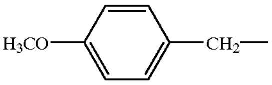 | 2 | 2 | 1 | — | H | 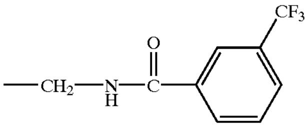 |
TABLE 1.84
| Compd. No. | 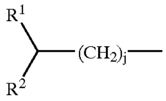 | k | m | n | chirality | $R^3$ | 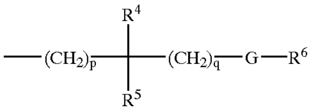 |
|---|---|---|---|---|---|---|---|
| 914 | 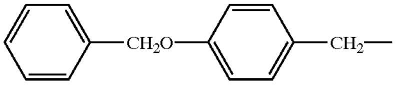 | 2 | 2 | 1 | — | H | 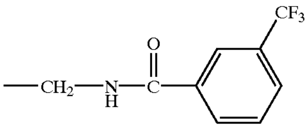 |
| 915 | 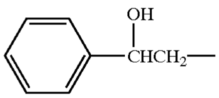 | 2 | 2 | 1 | — | H | 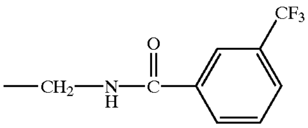 |
| 916 | 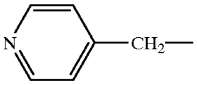 | 2 | 2 | 1 | — | H | 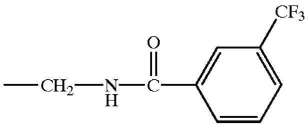 |
| 917 | 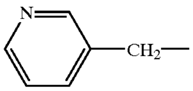 | 2 | 2 | 1 | — | H | 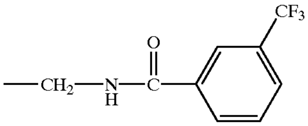 |
| 918 | 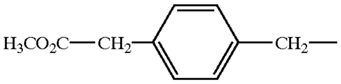 | 2 | 2 | 1 | — | H | 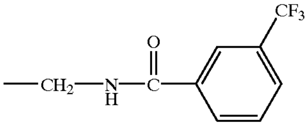 |
| 919 | 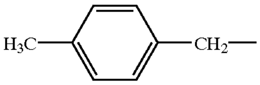 | 2 | 2 | 1 | — | H | 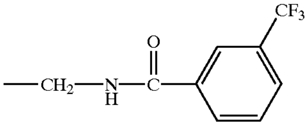 |

TABLE 1.84-continued
| Compd. No. | 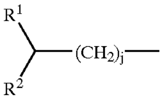 | k | m | n | chirality | $R^3$ | 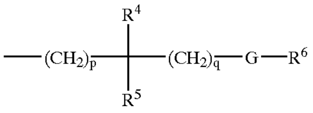 |
|---|---|---|---|---|---|---|---|
| 920 | 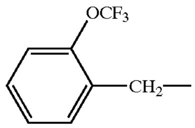 | 2 | 2 | 1 | — | H | 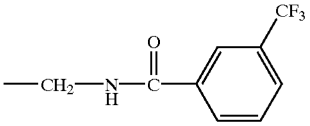 |
| 921 | 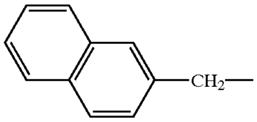 | 2 | 2 | 1 | — | H | 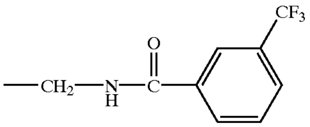 |
| 922 | 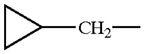 | 2 | 2 | 1 | — | H | 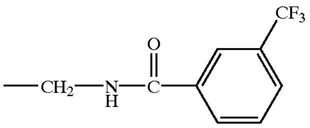 |
| 923 | 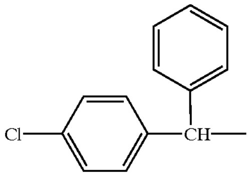 | 2 | 2 | 1 | — | H | 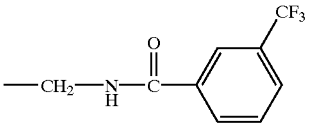 |
| 924 | 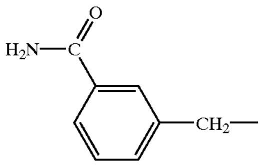 | 2 | 2 | 1 | — | H | 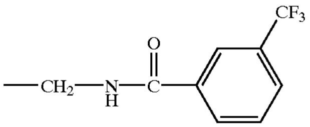 |
TABLE 1.85
| Compd. No. | 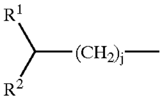 | k | m | n | chirality | $R^3$ | 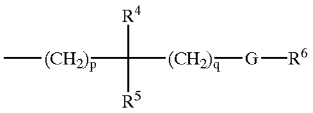 |
|---|---|---|---|---|---|---|---|
| 925 | 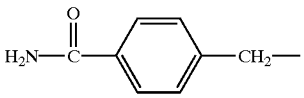 | 2 | 2 | 1 | — | H | 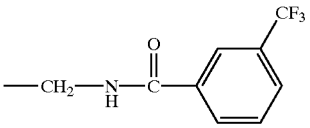 |
| 926 | 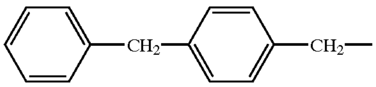 | 2 | 2 | 1 | — | H | 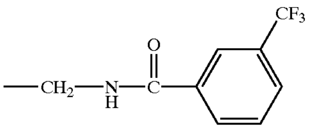 |
| 927 | 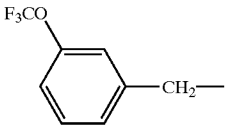 | 2 | 2 | 1 | — | H | 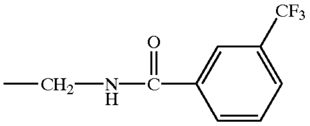 |

TABLE 1.85-continued
| Compd. No. | 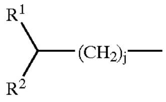 | k | m | n | chirality | $R^3$ | 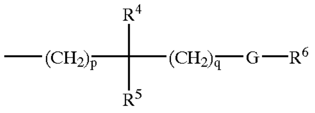 |
|---|---|---|---|---|---|---|---|
| 928 | 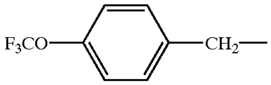 | 2 | 2 | 1 | — | H | 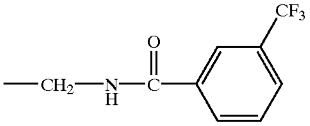 |
| 929 | 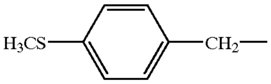 | 2 | 2 | 1 | — | H | 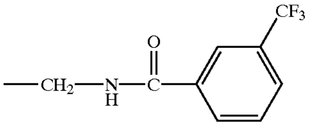 |
| 930 | 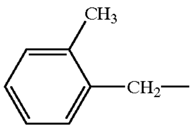 | 2 | 2 | 1 | — | H | 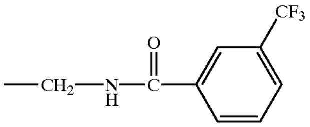 |
| 931 | 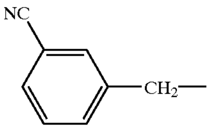 | 2 | 2 | 1 | — | H | 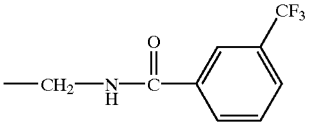 |
| 932 | 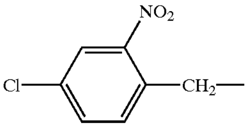 | 2 | 2 | 1 | — | H | 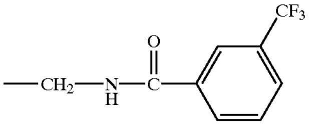 |
| 933 | 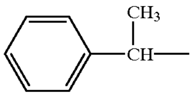 | 2 | 2 | 1 | — | H | 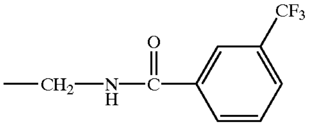 |
| 934 | 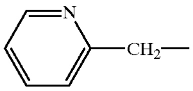 | 2 | 2 | 1 | — | H | 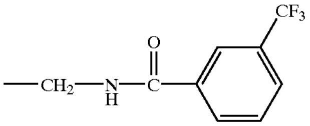 |
| 935 | 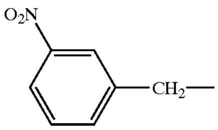 | 2 | 2 | 1 | — | H | 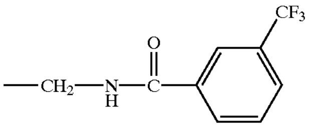 |

TABLE 1.86
| Compd. No. | 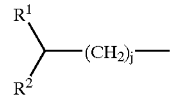 | k | m | n | chirality | $R^3$ | 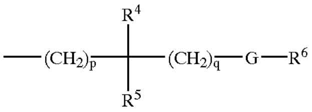 |
|---|---|---|---|---|---|---|---|
| 936 | 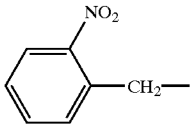 | 2 | 2 | 1 | — | H | 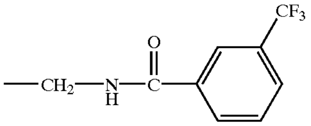 |
| 937 | 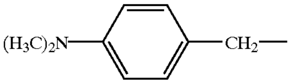 | 2 | 2 | 1 | — | H | 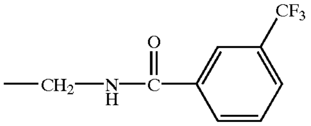 |
| 938 | 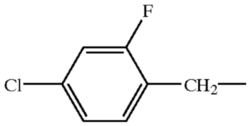 | 2 | 2 | 1 | — | H | 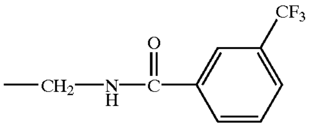 |
| 939 | 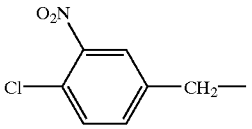 | 2 | 2 | 1 | — | H | 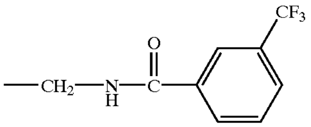 |
| 940 | 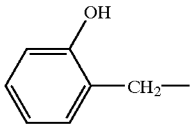 | 2 | 2 | 1 | — | H | 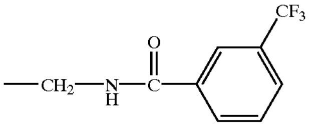 |
| 941 | 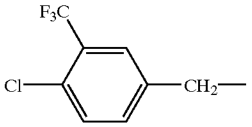 | 2 | 2 | 1 | — | H | 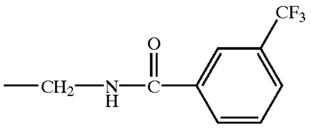 |
| 942 | 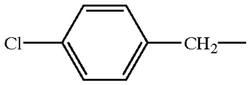 | 2 | 2 | 1 | — | H | 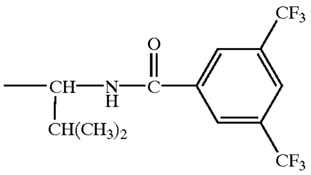 |
| 943 | 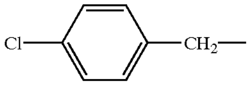 | 1 | 4 | 0 | — | H | 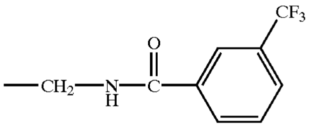 |
| 944 | 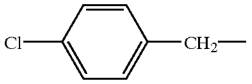 | 1 | 4 | 0 | — | H | 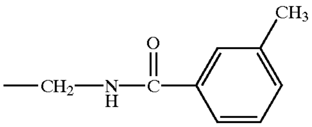 |
| 945 | 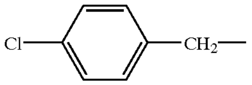 | 1 | 4 | 0 | — | H | 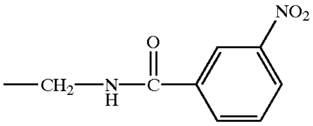 |

TABLE 1.86-continued
| Compd. No. | 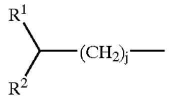 | k | m | n | chirality | $R^3$ | 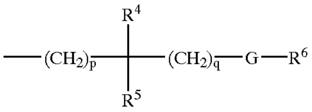 |
|---|---|---|---|---|---|---|---|
| 946 | 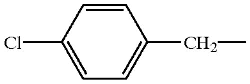 | 1 | 4 | 0 | — | H | 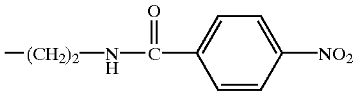 |
TABLE 1.87
| Compd. No. | 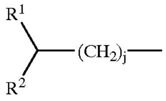 | k | m | n | chirality | $R^3$ | 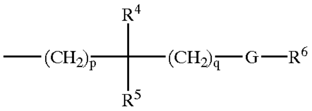 |
|---|---|---|---|---|---|---|---|
| 947 | 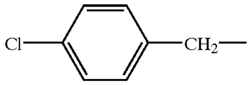 | 1 | 4 | 0 | — | H | 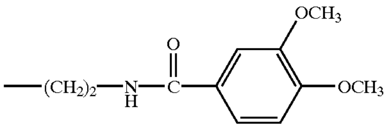 |
| 948 | 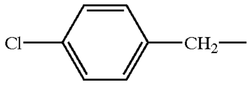 | 1 | 4 | 0 | — | H | 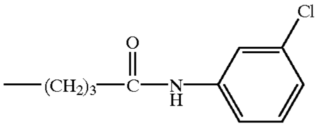 |
| 949 | 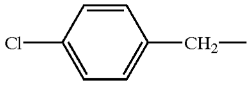 | 1 | 4 | 0 | — | H | 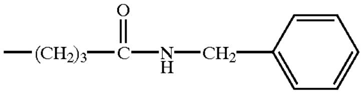 |
| 950 | 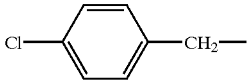 | 0 | 4 | 1 | — | H | 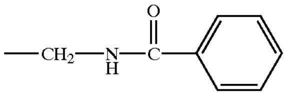 |
| 951 | 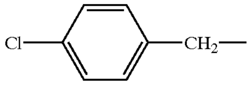 | 1 | 2 | 0 | R | H | 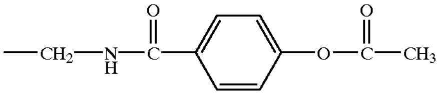 |
| 952 | 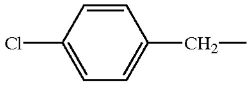 | 1 | 2 | 0 | R | H | 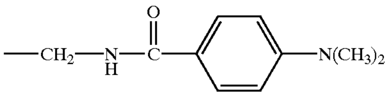 |
| 953 | 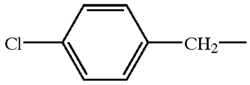 | 1 | 2 | 0 | R | H | 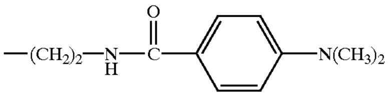 |
| 954 | 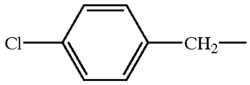 | 1 | 2 | 0 | R | H | 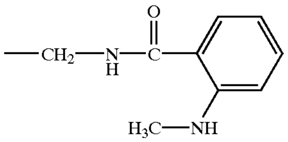 |

TABLE 1.87-continued
| Compd. No. | 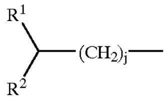 | k | m | n | chirality | $R^3$ | 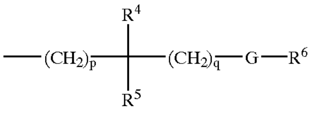 |
|---|---|---|---|---|---|---|---|
| 955 | 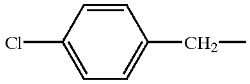 | 1 | 2 | 0 | R | H | 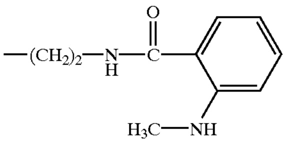 |
| 956 | 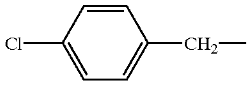 | 1 | 2 | 0 | R | H | 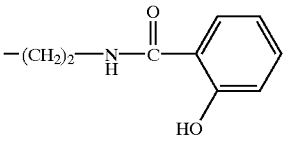 |
| 957 | 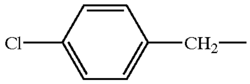 | 1 | 2 | 0 | R | H | 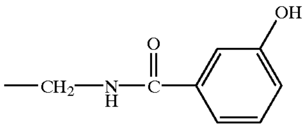 |
TABLE 1.88
| Compd. No. | 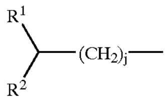 | k | m | n | chirality | $R^3$ | 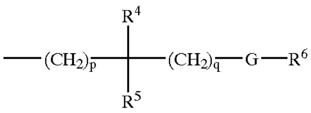 |
|---|---|---|---|---|---|---|---|
| 958 | 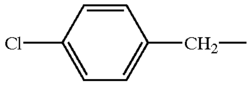 | 1 | 2 | 0 | R | H | 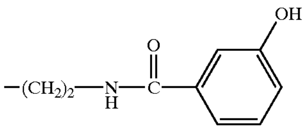 |
| 959 | 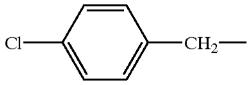 | 1 | 2 | 0 | R | H | 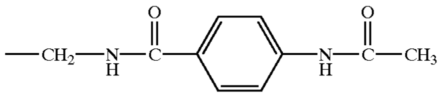 |
| 960 | 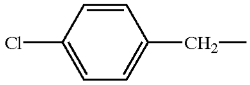 | 1 | 2 | 0 | R | H | 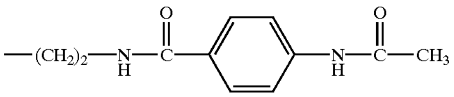 |
| 961 | 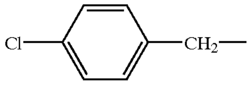 | 1 | 2 | 0 | R | H | 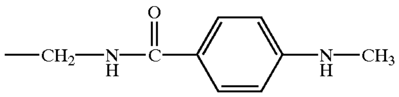 |
| 962 | 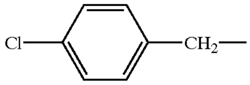 | 1 | 2 | 0 | R | H | 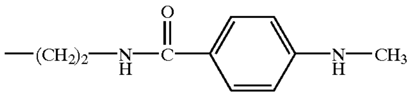 |
| 963 | 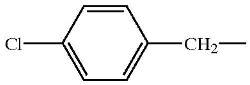 | 1 | 2 | 0 | R | H | 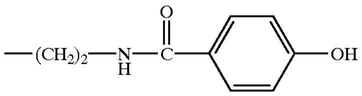 |

TABLE 1.88-continued
| Compd. No. | 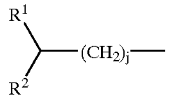 | k | m | n | chirality | $R^3$ | 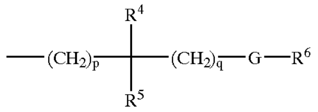 |
|---|---|---|---|---|---|---|---|
| 964 | 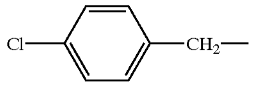 | 1 | 2 | 0 | R | H | 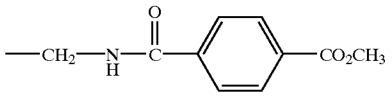 |
| 965 | 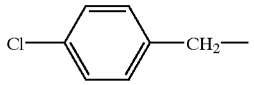 | 1 | 2 | 0 | R | H | 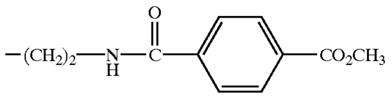 |
| 966 | 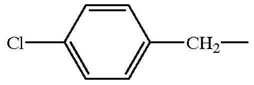 | 1 | 2 | 0 | R | H | 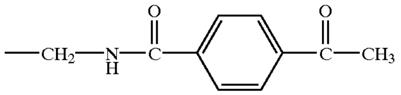 |
| 967 | 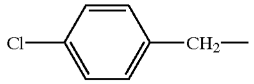 | 1 | 2 | 0 | R | H | 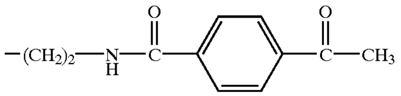 |
| 968 | 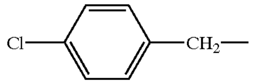 | 1 | 2 | 0 | R | H | 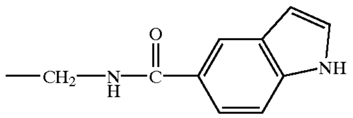 |
TABLE 1.89
| Compd. No. | 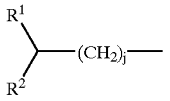 | k | m | n | chirality | $R^3$ | 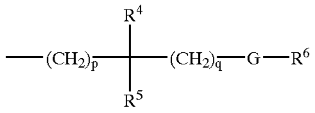 |
|---|---|---|---|---|---|---|---|
| 969 | 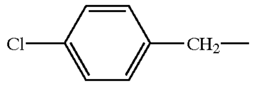 | 1 | 2 | 0 | R | H | 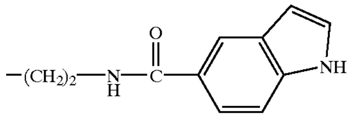 |
| 970 | 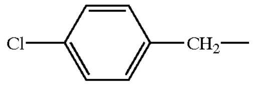 | 1 | 2 | 0 | R | H | 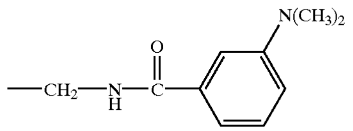 |
| 971 | 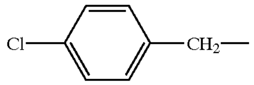 | 1 | 2 | 0 | R | H | 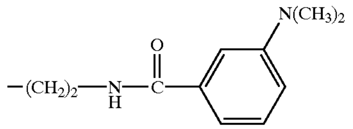 |
| 972 | 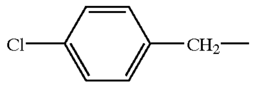 | 1 | 2 | 0 | R | H | 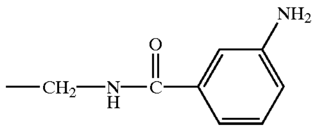 |

TABLE 1.89-continued
| Compd. No. | 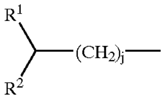 | k | m | n | chirality | $R^3$ | 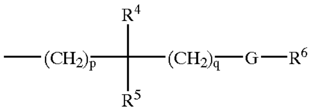 |
|---|---|---|---|---|---|---|---|
| 973 | 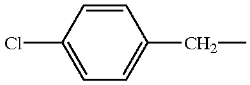 | 1 | 2 | 0 | R | H | 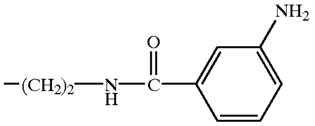 |
| 974 | 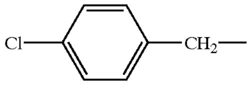 | 1 | 2 | 0 | R | H | 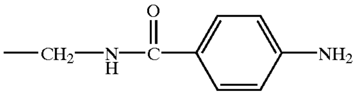 |
| 975 | 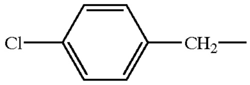 | 1 | 2 | 0 | R | H | 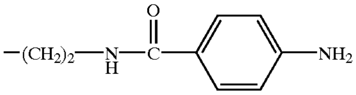 |
| 976 | 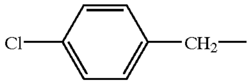 | 1 | 2 | 0 | R | H | 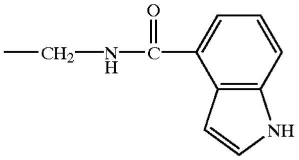 |
| 977 | 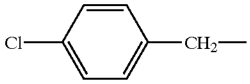 | 1 | 2 | 0 | R | H | 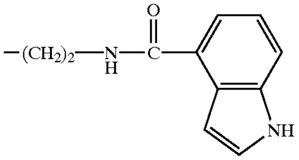 |
| 978 | 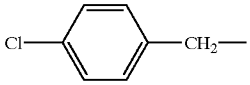 | 1 | 2 | 0 | R | H | 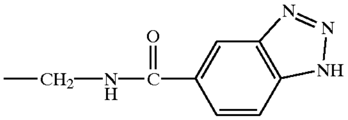 |
| 979 | 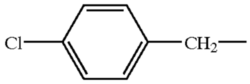 | 1 | 2 | 0 | R | H | 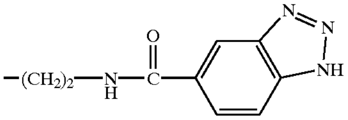 |
TABLE 1.90
| Compd. No. | 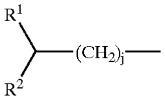 | k | m | n | chirality | $R^3$ | 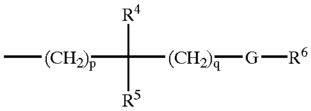 |
|---|---|---|---|---|---|---|---|
| 980 | 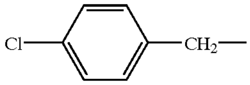 | 1 | 2 | 0 | R | H | 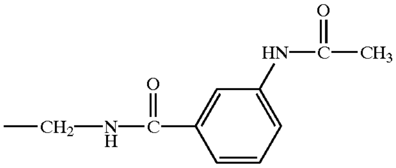 |

TABLE 1.90-continued
| Compd. No. | 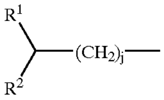 | k | m | n | chirality | $R^3$ | 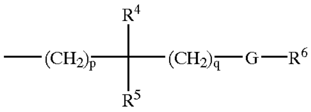 |
|---|---|---|---|---|---|---|---|
| 981 | 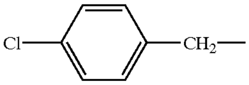 | 1 | 2 | 0 | R | H | 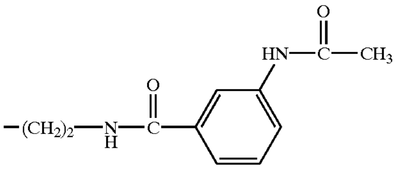 |
| 982 | 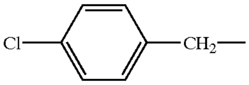 | 1 | 2 | 0 | R | H | 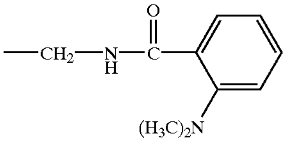 |
| 983 | 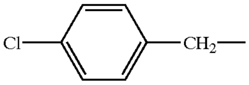 | 1 | 2 | 0 | R | H | 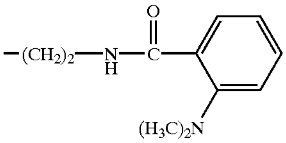 |
| 984 | 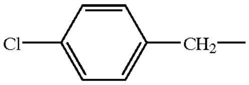 | 1 | 2 | 0 | R | H | 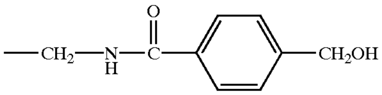 |
| 985 | 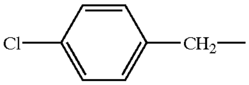 | 1 | 2 | 0 | R | H | 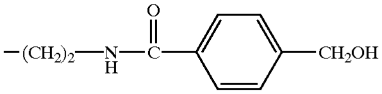 |
| 986 | 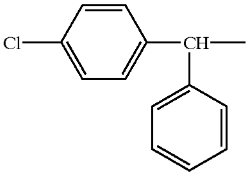 | 1 | 2 | 0 | R | H | 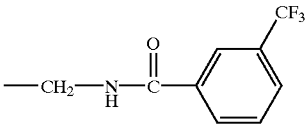 |
| 987 | 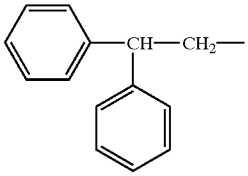 | 2 | 2 | 1 | — | H | 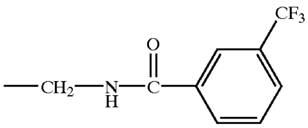 |
| 988 | 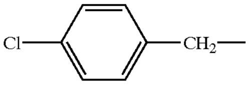 | 1 | 4 | 0 | — | H | 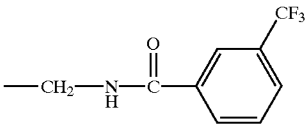 |
| 989 | 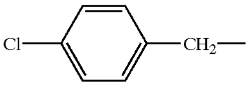 | 1 | 4 | 0 | — | H | 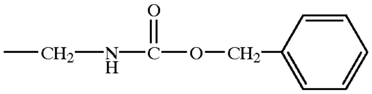 |
| 990 | 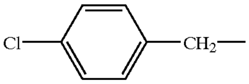 | 1 | 4 | 0 | — | H | 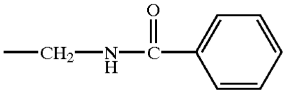 |

TABLE 1.91
| Compd. No. | 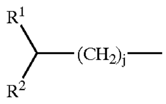 | k | m | n | chirality | $R^3$ | 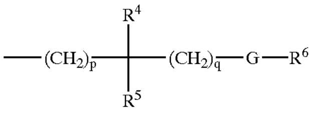 |
|---|---|---|---|---|---|---|---|
| 991 | 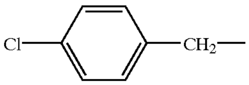 | 1 | 4 | 0 | — | H | 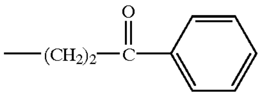 |
| 992 | 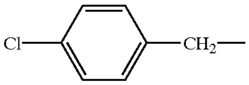 | 1 | 4 | 0 | — | H | 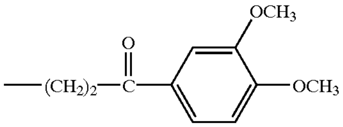 |
| 993 | 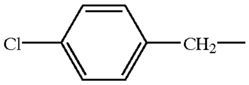 | 1 | 4 | 0 | — | H | 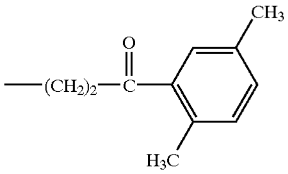 |
| 994 | 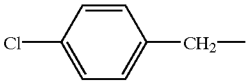 | 1 | 4 | 0 | — | H | 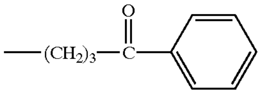 |
| 995 | 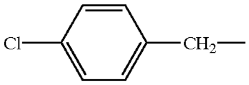 | 1 | 4 | 0 | — | H | 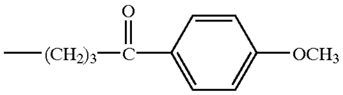 |
| 996 | 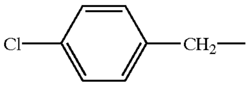 | 1 | 4 | 0 | — | H | 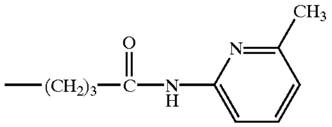 |
| 997 | 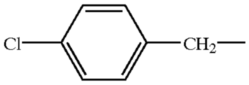 | 2 | 2 | 1 | — | H | 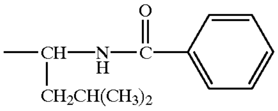 |
| 998 | 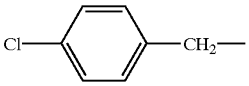 | 2 | 2 | 1 | — | H | 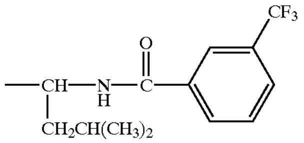 |
| 999 | 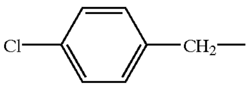 | 2 | 2 | 1 | — | H | 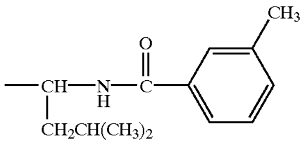 |
| 1000 | 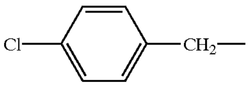 | 2 | 2 | 1 | — | H | 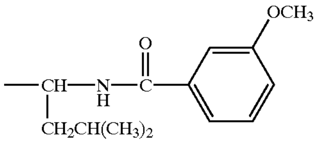 |

TABLE 1.91-continued
| Compd. No. | 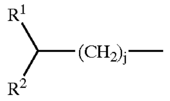 | k | m | n | chirality | $R^3$ | 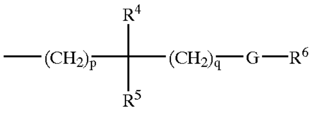 |
|---|---|---|---|---|---|---|---|
| 1001 | 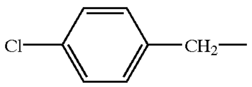 | 2 | 2 | 1 | — | H | 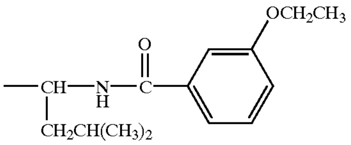 |
TABLE 1.92
| Compd. No. | 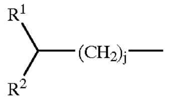 | k | m | n | chirality | $R^3$ | 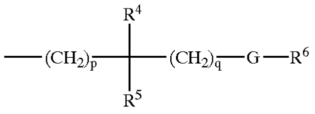 |
|---|---|---|---|---|---|---|---|
| 1002 | 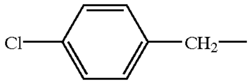 | 2 | 2 | 1 | — | H | 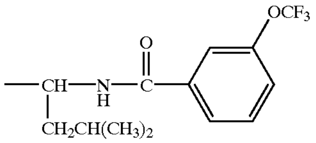 |
| 1003 | 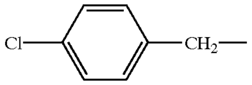 | 2 | 2 | 1 | — | H | 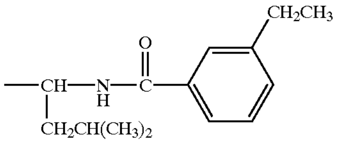 |
| 1004 | 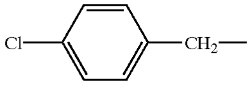 | 2 | 2 | 1 | — | H | 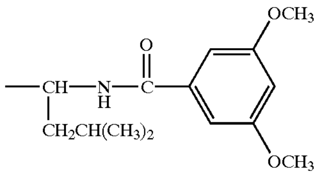 |
| 1005 | 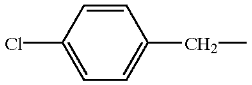 | 2 | 2 | 1 | — | H | 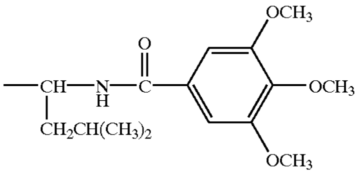 |
| 1006 | 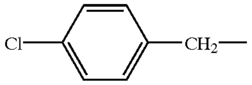 | 2 | 2 | 1 | — | H | 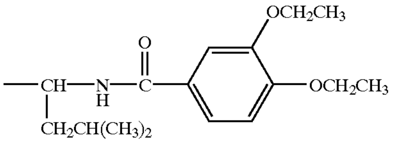 |
| 1007 | 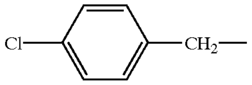 | 2 | 2 | 1 | — | H | 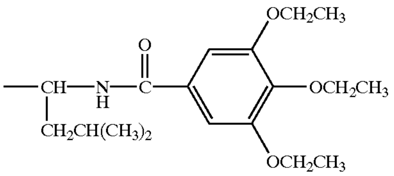 |

TABLE 1.92-continued
| Compd. No. | 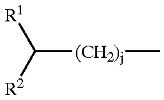 | k | m | n | chirality | $R^3$ | 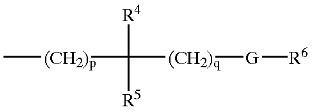 |
|---|---|---|---|---|---|---|---|
| 1008 | 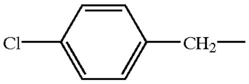 | 2 | 2 | 1 | — | H | 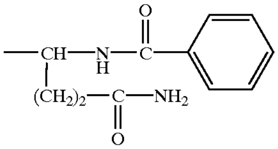 |
| 1009 | 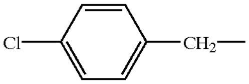 | 2 | 2 | 1 | — | H | 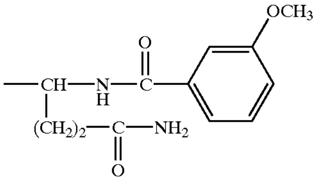 |
| 1010 | 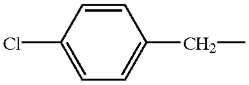 | 2 | 2 | 1 | — | H | 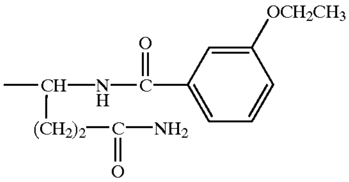 |
| 1011 | 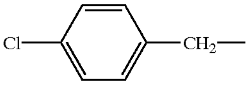 | 2 | 2 | 1 | — | H | 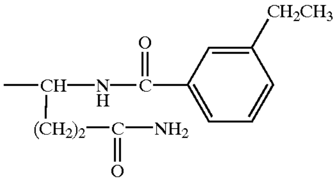 |
| 1012 | 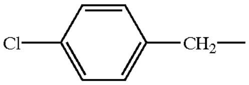 | 2 | 2 | 1 | — | H | 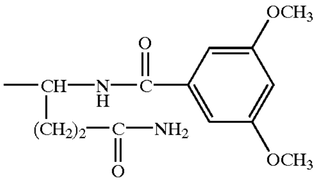 |
TABLE 1.93
| Compd. No. | 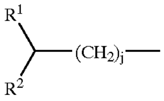 | k | m | n | chirality | $R^3$ | 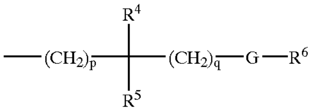 |
|---|---|---|---|---|---|---|---|
| 1013 | 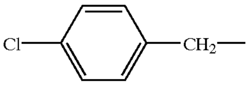 | 2 | 2 | 1 | — | H | 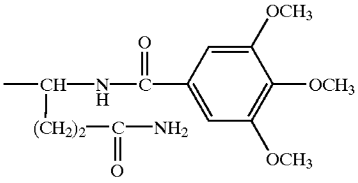 |

TABLE 1.93-continued
| Compd. No. | 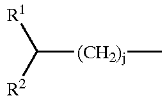 | k | m | n | chirality | $R^3$ | 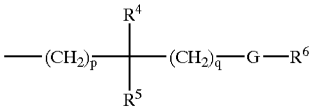 |
|---|---|---|---|---|---|---|---|
| 1014 | 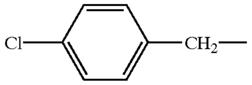 | 2 | 2 | 1 | — | H | 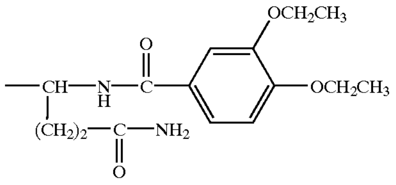 |
| 1015 | 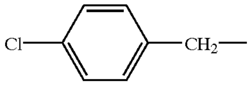 | 2 | 2 | 1 | — | H | 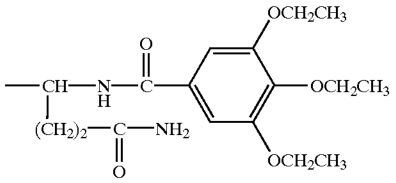 |
| 1016 | 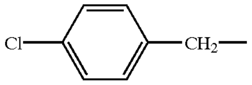 | 2 | 2 | 0 | — | H | 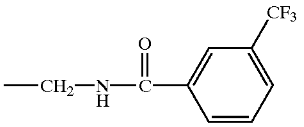 |
| 1017 | 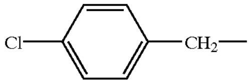 | 2 | 2 | 0 | — | H | 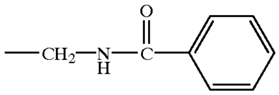 |
| 1018 | 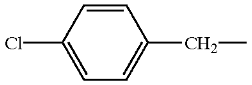 | 2 | 2 | 1 | — | H | 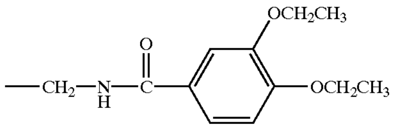 |
| 1019 | 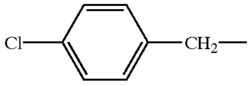 | 2 | 2 | 1 | — | H | 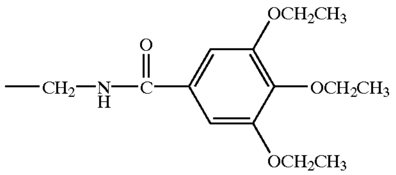 |
| 1020 | 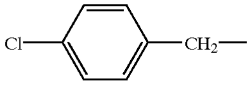 | 2 | 2 | 1 | — | H | 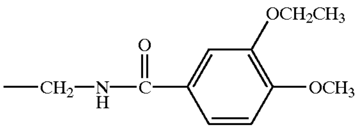 |
| 1021 | 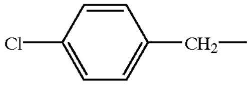 | 2 | 2 | 1 | — | H | 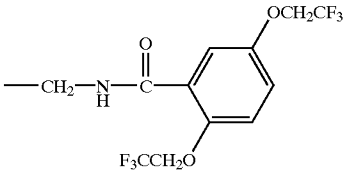 |
| 1022 | 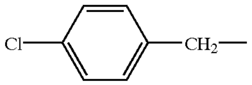 | 2 | 2 | 1 | — | H | 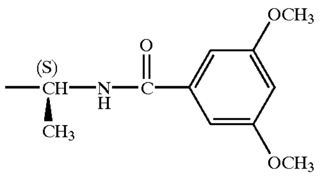 |

TABLE 1.93-continued
| Compd. No. | 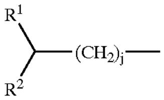 | k | m | n | chirality | $R^3$ | 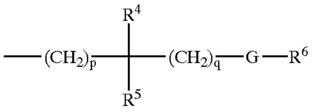 |
|---|---|---|---|---|---|---|---|
| 1023 | 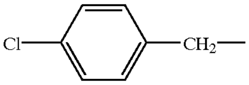 | 2 | 2 | 1 | — | H | 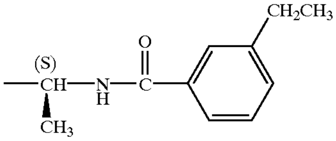 |
TABLE 1.94
| Compd. No. | 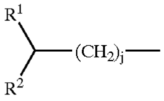 | k | m | n | chirality | $R^3$ | 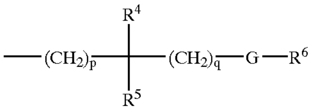 |
|---|---|---|---|---|---|---|---|
| 1024 | 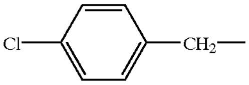 | 2 | 2 | 1 | — | H | 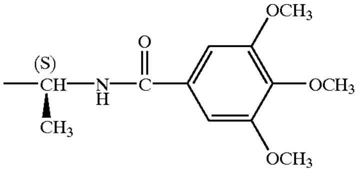 |
| 1025 | 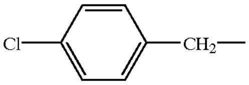 | 2 | 2 | 1 | — | H | 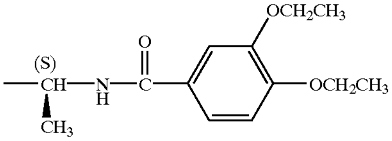 |
| 1026 | 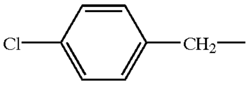 | 2 | 2 | 1 | — | H | 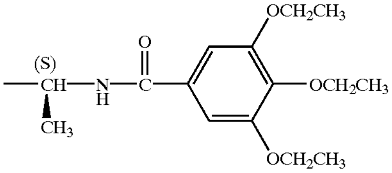 |
| 1027 | 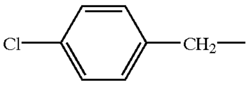 | 2 | 2 | 1 | — | H | 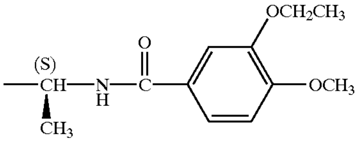 |
| 1028 | 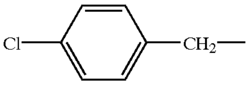 | 2 | 2 | 1 | — | H | 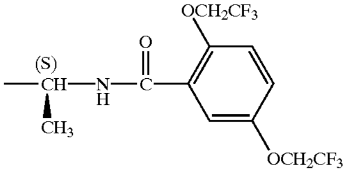 |
| 1029 | 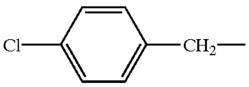 | 2 | 2 | 1 | — | H | 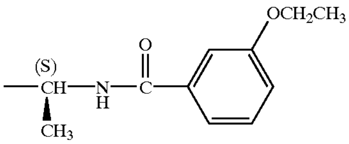 |

TABLE 1.94-continued
| Compd. No. | 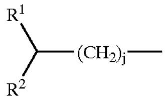 | k | m | n | chirality | $R^3$ | 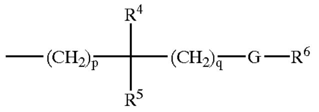 |
|---|---|---|---|---|---|---|---|
| 1030 | 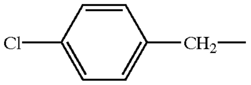 | 2 | 2 | 1 | — | H | 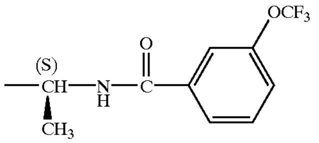 |
| 1031 | 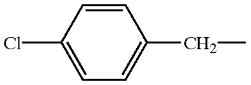 | 2 | 2 | 1 | — | H | 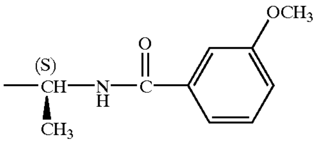 |
| 1032 | 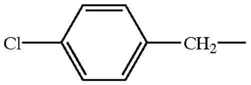 | 2 | 2 | 1 | — | H | 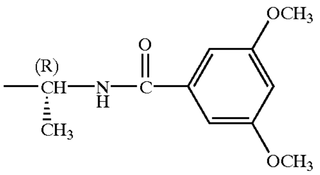 |
| 1033 | 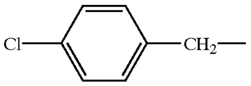 | 2 | 2 | 1 | — | H | 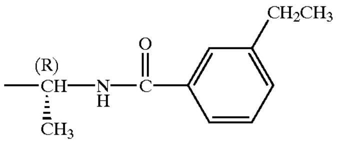 |
| 1034 | 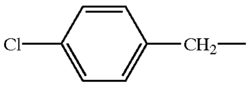 | 2 | 2 | 1 | — | H | 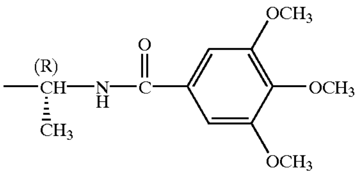 |
TABLE 1.95
| Compd. No. | 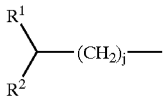 | k | m | n | chirality | $R^3$ | 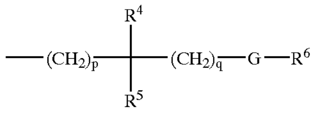 |
|---|---|---|---|---|---|---|---|
| 1035 | 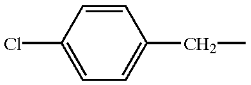 | 2 | 2 | 1 | — | H | 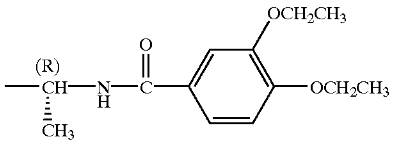 |
| 1036 | 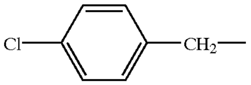 | 2 | 2 | 1 | — | H | 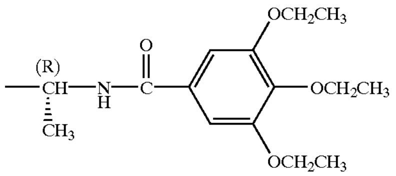 |

TABLE 1.95-continued
| Compd. No. | 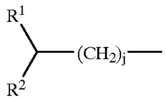 | k | m | n | chirality | $R^3$ | 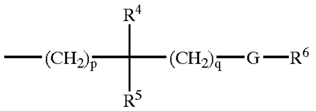 |
|---|---|---|---|---|---|---|---|
| 1037 | 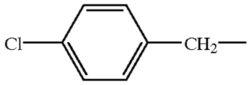 | 2 | 2 | 1 | — | H | 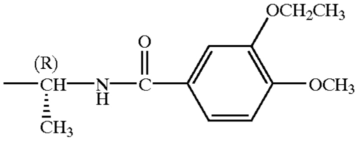 |
| 1038 | 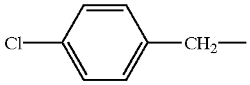 | 2 | 2 | 1 | — | H | 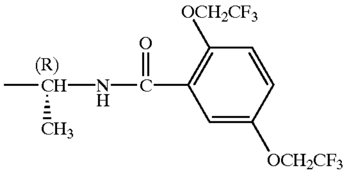 |
| 1039 | 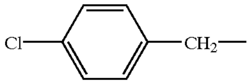 | 2 | 2 | 1 | — | H | 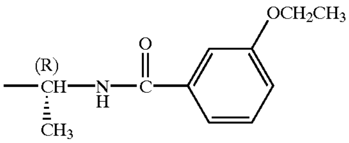 |
| 1040 | 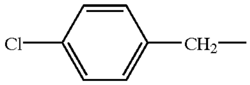 | 2 | 2 | 1 | — | H | 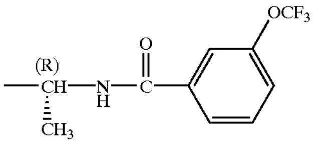 |
| 1041 | 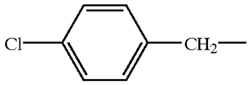 | 2 | 2 | 1 | — | H | 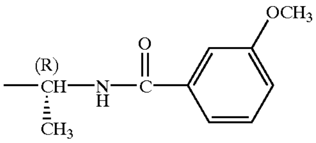 |
| 1042 | 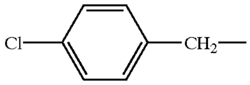 | 2 | 2 | 1 | — | H | 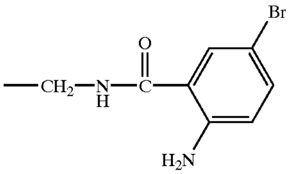 |
| 1043 | 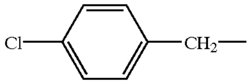 | 2 | 2 | 1 | — | H | 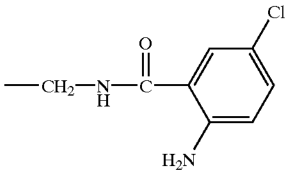 |
| 1044 | 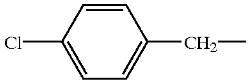 | 2 | 2 | 1 | — | H | 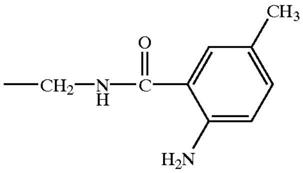 |

TABLE 1.95-continued
| Compd. No. | 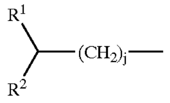 | k | m | n | chirality | $R^3$ | 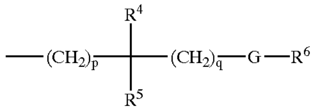 |
|---|---|---|---|---|---|---|---|
| 1045 | 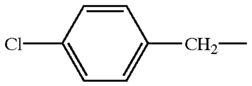 | 2 | 2 | 1 | — | H | 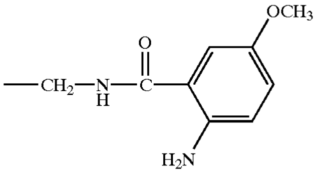 |
TABLE 1.96
| Compd. No. | 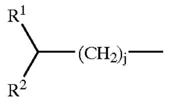 | k | m | n | chirality | $R^3$ | 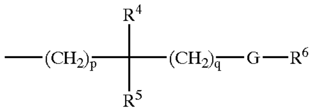 |
|---|---|---|---|---|---|---|---|
| 1046 | 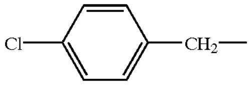 | 2 | 2 | 1 | — | H | 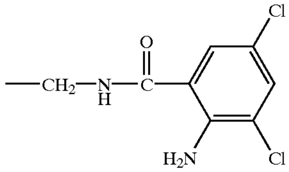 |
| 1047 | 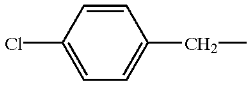 | 2 | 2 | 1 | — | H | 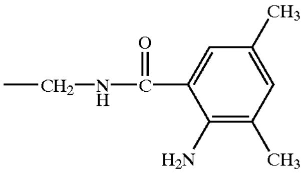 |
| 1048 | 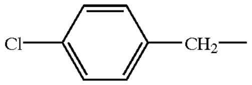 | 2 | 2 | 1 | — | H | 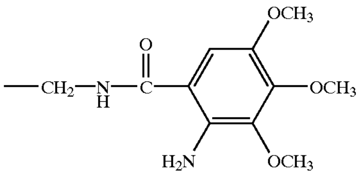 |
| 1049 | 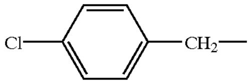 | 2 | 2 | 1 | — | H | 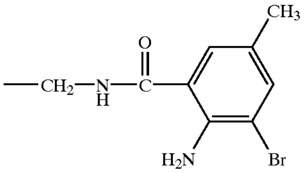 |
| 1050 | 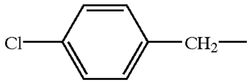 | 2 | 2 | 1 | — | H | 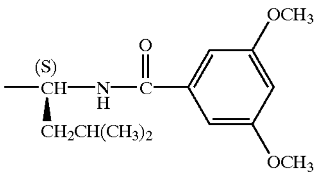 |

TABLE 1.96-continued
| Compd. No. | 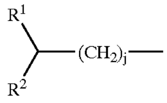 | k | m | n | chirality | $R^3$ | 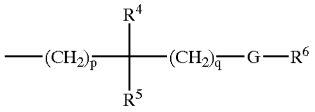 |
|---|---|---|---|---|---|---|---|
| 1051 | 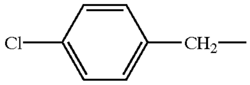 | 2 | 2 | 1 | — | H | 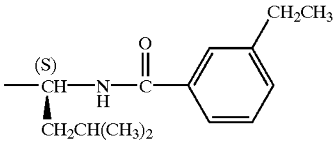 |
| 1052 | 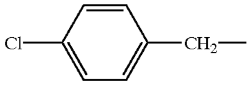 | 2 | 2 | 1 | — | H | 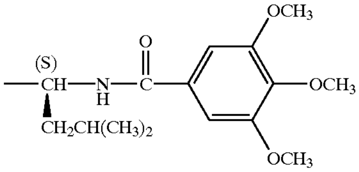 |
| 1053 | 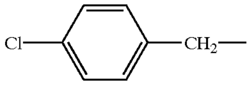 | 2 | 2 | 1 | — | H | 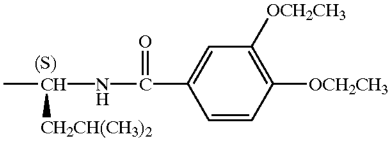 |
| 1054 | 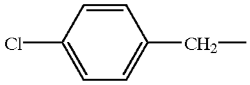 | 2 | 2 | 1 | — | H | 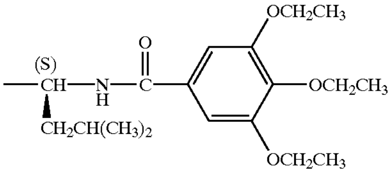 |
| 1055 | 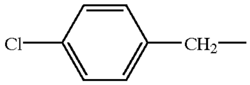 | 2 | 2 | 1 | — | H | 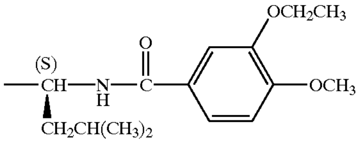 |
| 1056 | 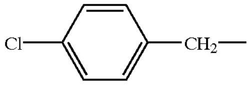 | 2 | 2 | 1 | — | H | 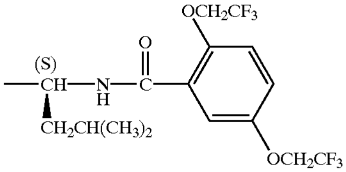 |
TABLE 1.97
| Compd. No. | 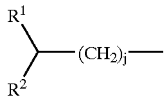 | k | m | n | chirality | $R^3$ | 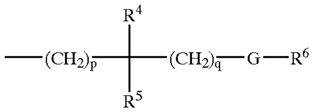 |
|---|---|---|---|---|---|---|---|
| 1057 | 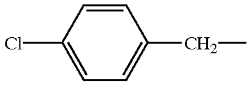 | 2 | 2 | 1 | — | H | 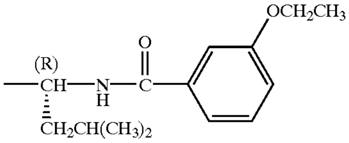 |

TABLE 1.97-continued
| Compd. No. | 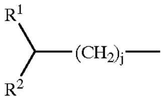 | k | m | n | chirality | $R^3$ | 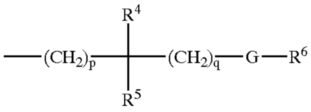 |
|---|---|---|---|---|---|---|---|
| 1058 | 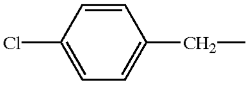 | 2 | 2 | 1 | — | H | 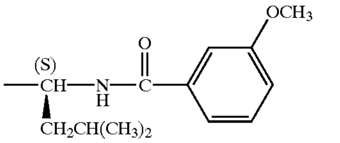 |
| 1059 | 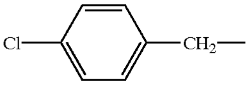 | 2 | 2 | 1 | — | H | 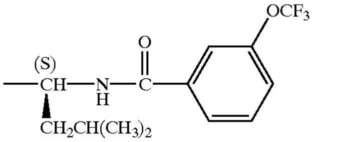 |
| 1060 | 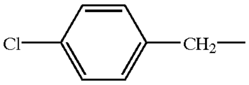 | 2 | 2 | 1 | — | H | 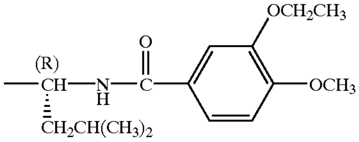 |
| 1061 | 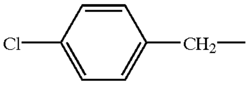 | 2 | 2 | 1 | — | H | 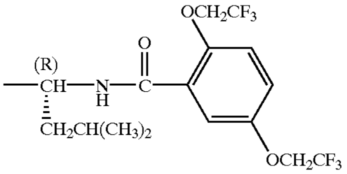 |
| 1062 | 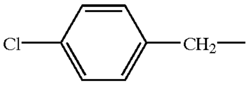 | 2 | 2 | 1 | — | H | 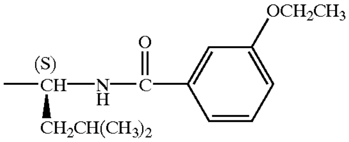 |
| 1063 | 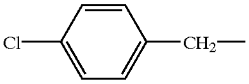 | 2 | 2 | 1 | — | H | 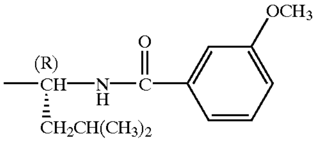 |
| 1064 | 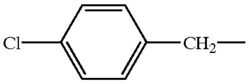 | 2 | 2 | 1 | — | H | 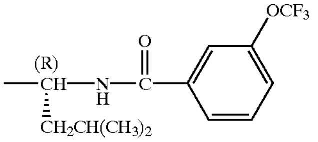 |
| 1065 | 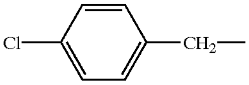 | 2 | 2 | 1 | — | H | 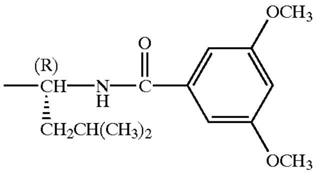 |
| 1066 | 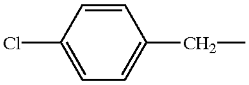 | 2 | 2 | 1 | — | H | 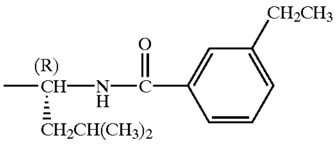 |

TABLE 1.97-continued
| Compd. No. | 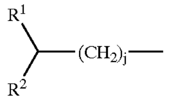 | k | m | n | chirality | $R^3$ | 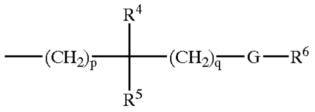 |
|---|---|---|---|---|---|---|---|
| 1067 | 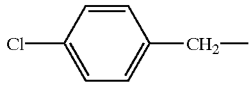 | 2 | 2 | 1 | — | H | 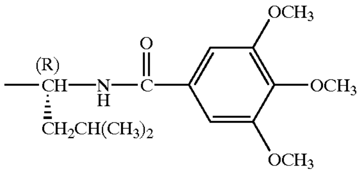 |
TABLE 1.98
| Compd. No. | 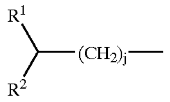 | k | m | n | chirality | $R^3$ | 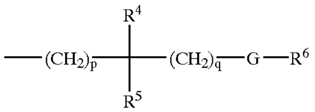 |
|---|---|---|---|---|---|---|---|
| 1068 | 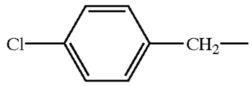 | 2 | 2 | 1 | — | H | 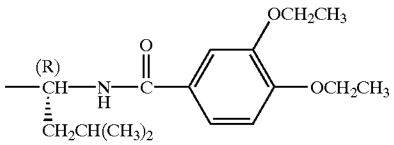 |
| 1069 | 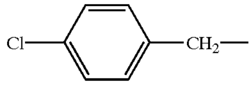 | 2 | 2 | 1 | — | H | 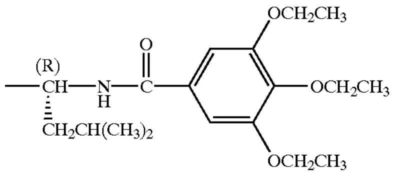 |
| 1070 | 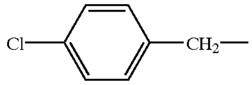 | 2 | 2 | 1 | — | H | 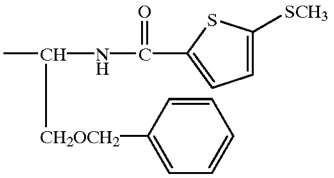 |
| 1071 | 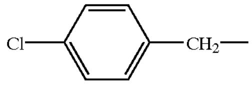 | 2 | 2 | 1 | — | H | 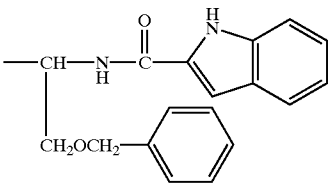 |
| 1072 | 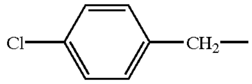 | 2 | 2 | 1 | — | H | 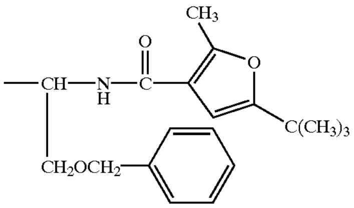 |

TABLE 1.98-continued
| Compd. No. | 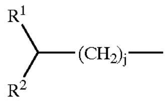 | k | m | n | chirality | $R^3$ | 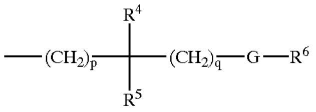 |
|---|---|---|---|---|---|---|---|
| 1073 | 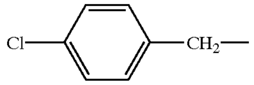 | 2 | 2 | 1 | — | H | 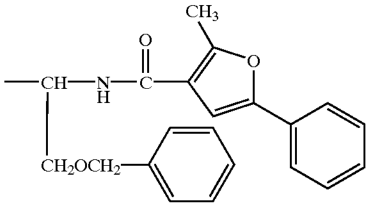 |
| 1074 | 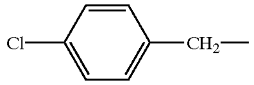 | 2 | 2 | 1 | — | H | 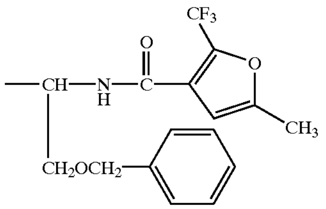 |
| 1075 | 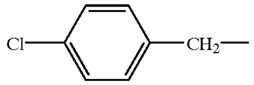 | 2 | 2 | 1 | — | H | 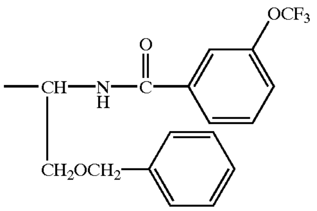 |
| 1076 | 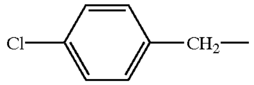 | 2 | 2 | 1 | — | H | 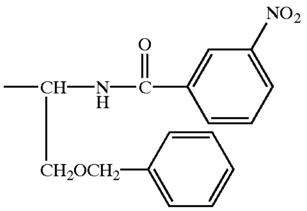 |
| 1077 | 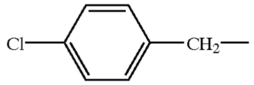 | 2 | 2 | 1 | — | H | 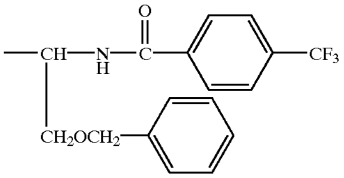 |
| 1078 | 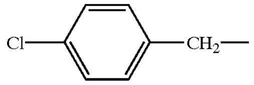 | 2 | 2 | 1 | — | H | 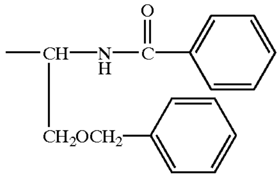 |

TABLE 1.99
| Compd. No. | 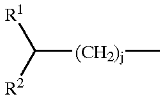 | k | m | n | chirality | $R^3$ | 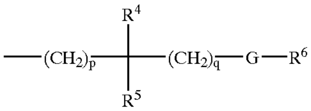 |
|---|---|---|---|---|---|---|---|
| 1079 | 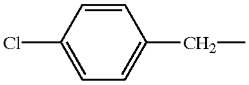 | 2 | 2 | 1 | — | H | 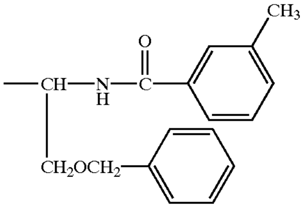 |
| 1080 | 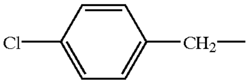 | 2 | 2 | 1 | — | H | 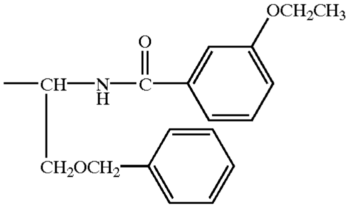 |
| 1081 | 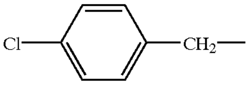 | 2 | 2 | 1 | — | H | 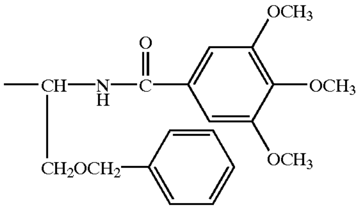 |
| 1082 | 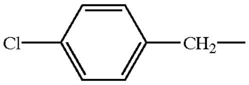 | 2 | 2 | 1 | — | H | 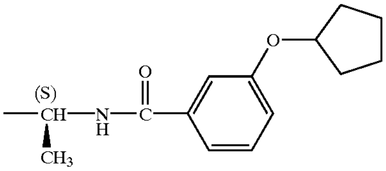 |
| 1083 | 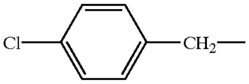 | 2 | 2 | 1 | — | H | 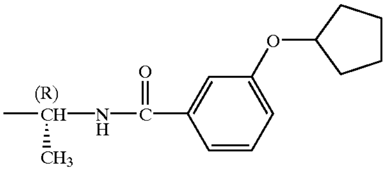 |
| 1084 | 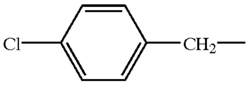 | 1 | 2 | 0 | R | H | 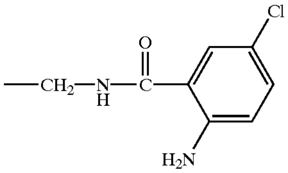 |
| 1085 | 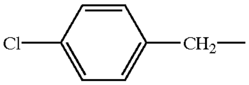 | 1 | 2 | 0 | R | H | 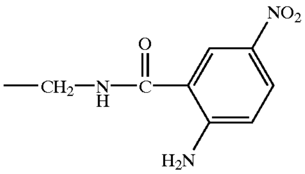 |

TABLE 1.99-continued
| Compd. No. | 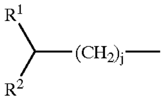 | k | m | n | chirality | $R^3$ | 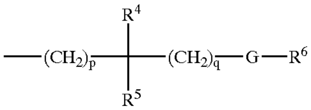 |
|---|---|---|---|---|---|---|---|
| 1086 | 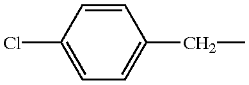 | 1 | 2 | 0 | R | H | 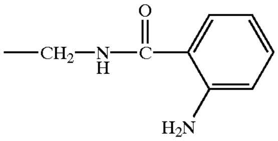 |
| 1087 | 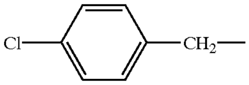 | 1 | 2 | 0 | R | H | 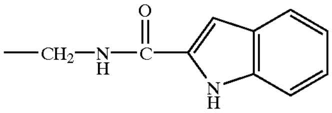 |
| 1088 | 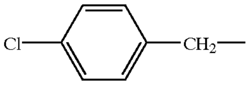 | 1 | 2 | 0 | R | H | 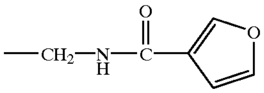 |
| 1089 | 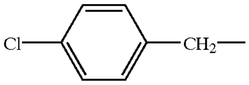 | 1 | 2 | 0 | R | H | 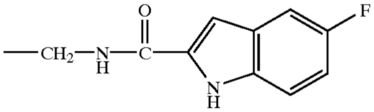 |
TABLE 1.100
| Compd. No. | 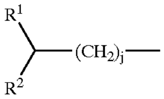 | k | m | n | chirality | $R^3$ | 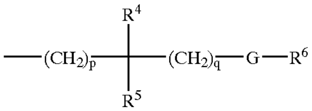 |
|---|---|---|---|---|---|---|---|
| 1090 | 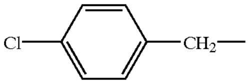 | 1 | 2 | 0 | R | H | 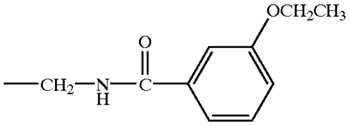 |
| 1091 | 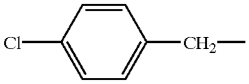 | 1 | 2 | 0 | R | H | 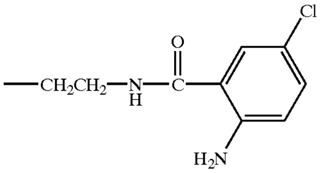 |
| 1092 | 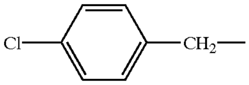 | 1 | 2 | 0 | R | H | 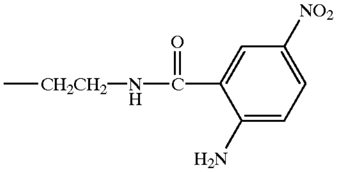 |
| 1093 | 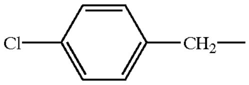 | 1 | 2 | 0 | R | H | 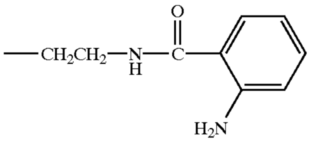 |

TABLE 1.100-continued
| Compd. No. | 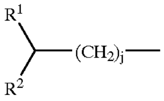 | k | m | n | chirality | $R^3$ | 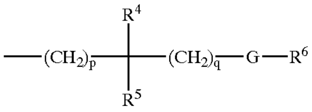 |
|---|---|---|---|---|---|---|---|
| 1094 | 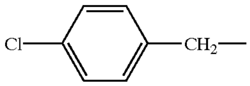 | 1 | 2 | 0 | R | H | 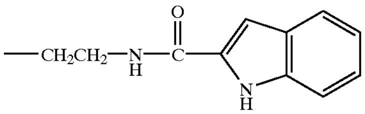 |
| 1095 | 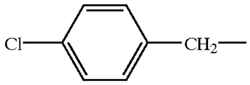 | 1 | 2 | 0 | R | H | 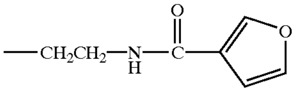 |
| 1096 | 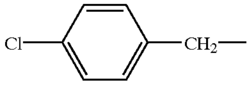 | 1 | 2 | 0 | R | H | 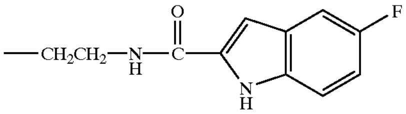 |
| 1097 | 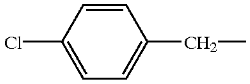 | 1 | 2 | 0 | R | H | 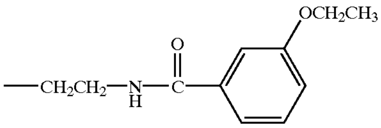 |
| 1098 | 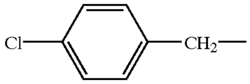 | 1 | 2 | 0 | R | H | 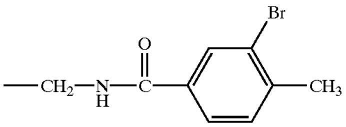 |
| 1099 | 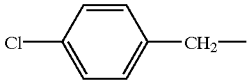 | 1 | 2 | 0 | R | H | 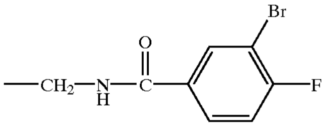 |
| 1100 | 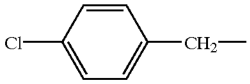 | 1 | 2 | 0 | R | H | 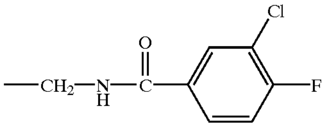 |
TABLE 1.101
| Compd. No. | 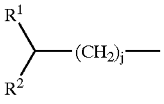 | k | m | n | chirality | $R^3$ | 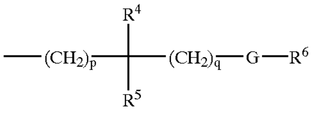 |
|---|---|---|---|---|---|---|---|
| 1101 | 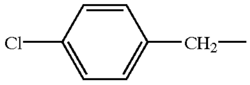 | 1 | 2 | 0 | R | H | 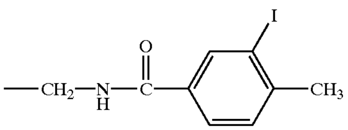 |
| 1102 | 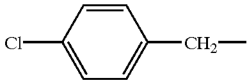 | 1 | 2 | 0 | R | H | 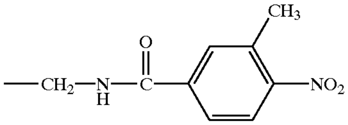 |

TABLE 1.101-continued
| Compd. No. | 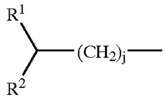 | k | m | n | chirality | $R^3$ | 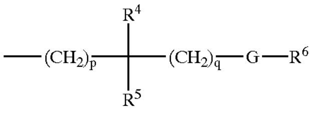 |
|---|---|---|---|---|---|---|---|
| 1103 | 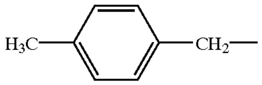 | 1 | 2 | 0 | R | H | 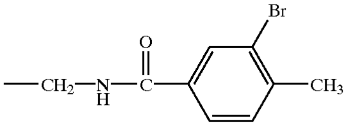 |
| 1104 | 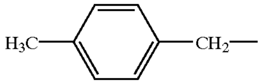 | 1 | 2 | 0 | R | H | 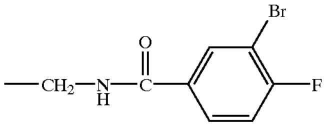 |
| 1105 | 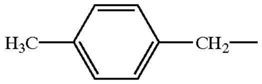 | 1 | 2 | 0 | R | H | 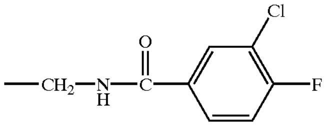 |
| 1106 | 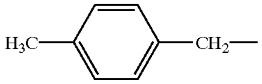 | 1 | 2 | 0 | R | H | 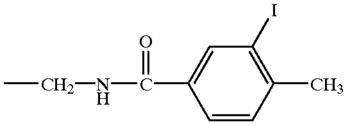 |
| 1107 | 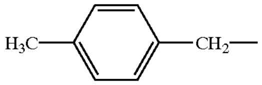 | 1 | 2 | 0 | R | H | 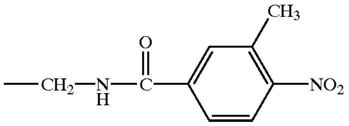 |
| 1108 | 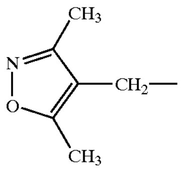 | 1 | 2 | 0 | R | H | 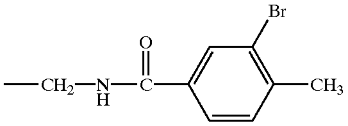 |
| 1109 | 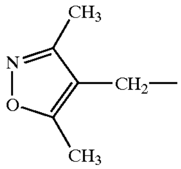 | 1 | 2 | 0 | R | H | 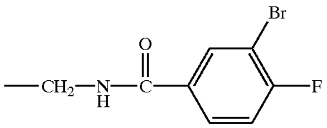 |
| 1110 | 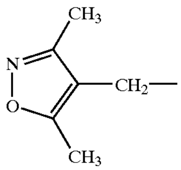 | 1 | 2 | 0 | R | H | 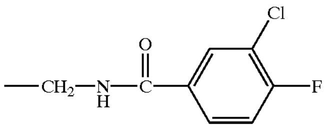 |
| 1111 | 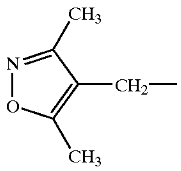 | 1 | 2 | 0 | R | H | 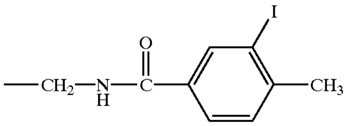 |

TABLE 1.102
| Compd. No. | 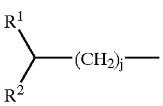 | k | m | n | chirality | $R^3$ | 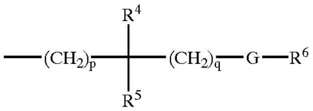 |
|---|---|---|---|---|---|---|---|
| 1112 | 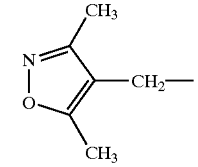 | 1 | 2 | 0 | R | H | 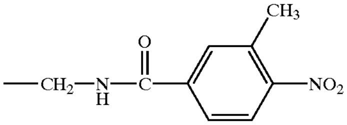 |
| 1113 | 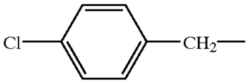 | 2 | 2 | 1 | — | H | 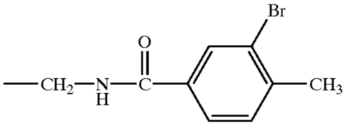 |
| 1114 | 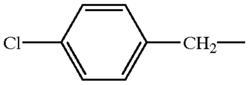 | 2 | 2 | 1 | — | H | 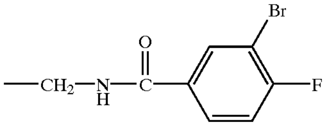 |
| 1115 | 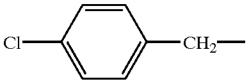 | 2 | 2 | 1 | — | H | 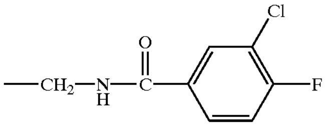 |
| 1116 | 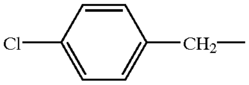 | 2 | 2 | 1 | — | H | 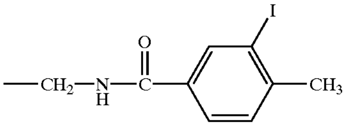 |
| 1117 | 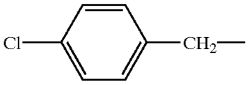 | 2 | 2 | 1 | — | H | 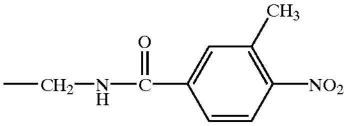 |
| 1118 | 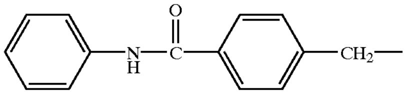 | 1 | 2 | 0 | R | H | 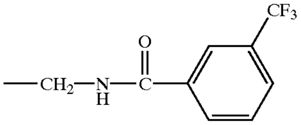 |
| 1119 | 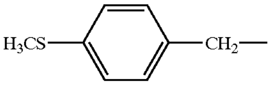 | 1 | 2 | 0 | R | H | 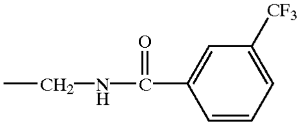 |
| 1120 | 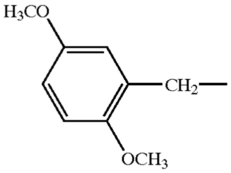 | 1 | 2 | 0 | R | H | 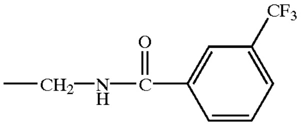 |

TABLE 1.102-continued
| Compd. No. | 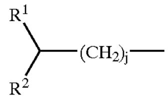 | k | m | n | chirality | $R^3$ | 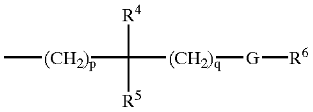 |
|---|---|---|---|---|---|---|---|
| 1121 | 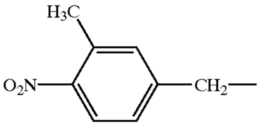 | 1 | 2 | 0 | R | H | 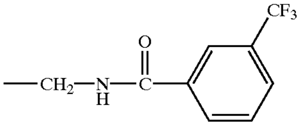 |
| 1122 | 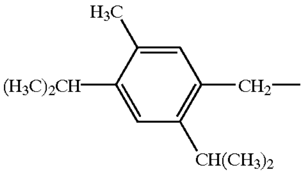 | 1 | 2 | 0 | R | H | 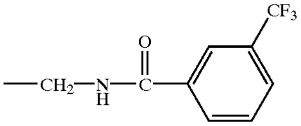 |
TABLE 1.103
| Compd. No. | 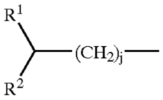 | k | m | n | chirality | $R^3$ | 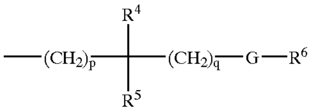 |
|---|---|---|---|---|---|---|---|
| 1123 | 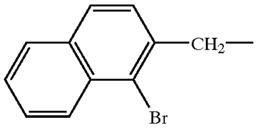 | 1 | 2 | 0 | R | H | 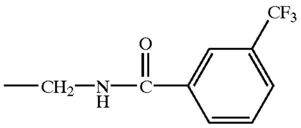 |
| 1124 | 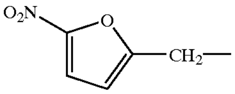 | 1 | 2 | 0 | R | H | 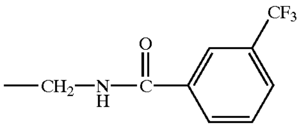 |
| 1125 | 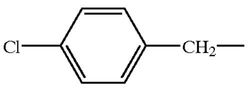 | 2 | 2 | 1 | — | H | 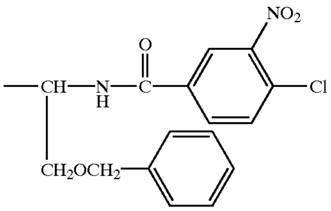 |
| 1126 | 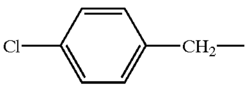 | 2 | 2 | 1 | — | H | 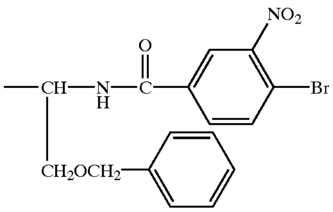 |

TABLE 1.103-continued
| Compd. No. | 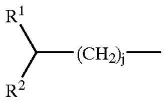 | k | m | n | chirality | R3 | 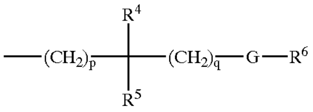 |
|---|---|---|---|---|---|---|---|
| 1127 | 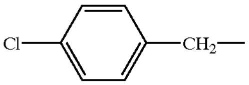 | 2 | 2 | 1 | — | H | 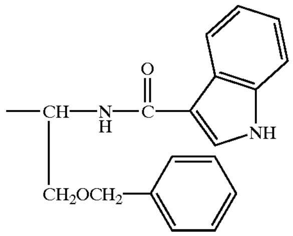 |
| 1128 | 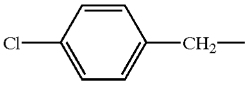 | 2 | 2 | 1 | — | H | 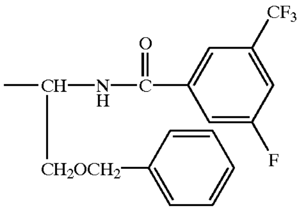 |
| 1129 | 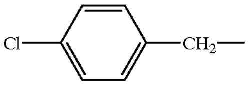 | 2 | 2 | 1 | — | H | 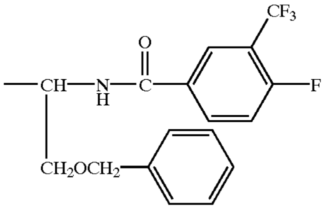 |
| 1130 | 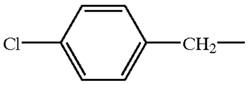 | 2 | 2 | 1 | — | H | 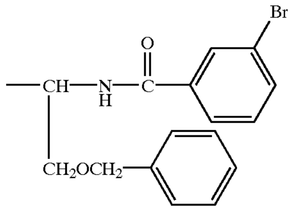 |
| 1131 | 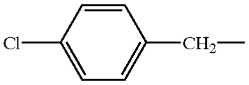 | 2 | 2 | 1 | — | H | 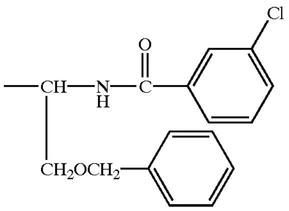 |
| 1132 | 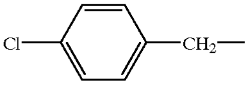 | 2 | 2 | 1 | — | H | 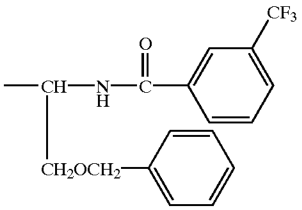 |

TABLE 1.103-continued
| Compd. No. | 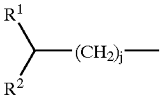 | k | m | n | chirality | $R^3$ | 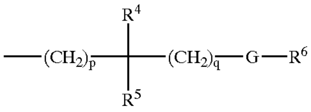 |
|---|---|---|---|---|---|---|---|
| 1133 | 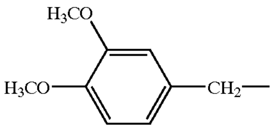 | 1 | 2 | 0 | R | H | 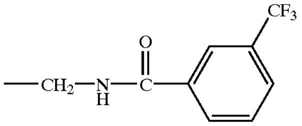 |
TABLE 1.104
| Compd. No. | 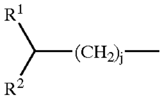 | k | m | n | chirality | $R^3$ | 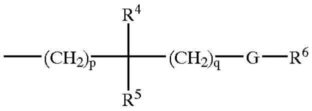 |
|---|---|---|---|---|---|---|---|
| 1134 | 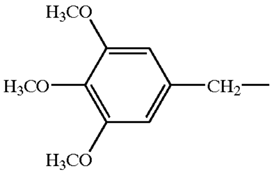 | 1 | 2 | 0 | R | H | 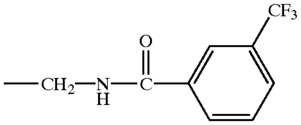 |
| 1135 | 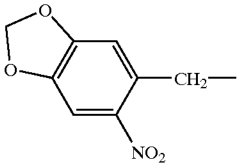 | 1 | 2 | 0 | R | H | 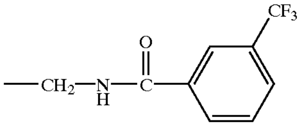 |
| 1136 | 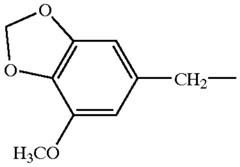 | 1 | 2 | 0 | R | H | 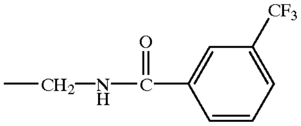 |
| 1137 | 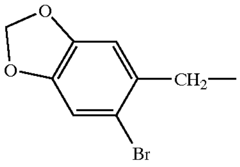 | 1 | 2 | 0 | R | H | 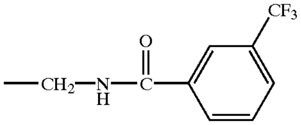 |
| 1138 | 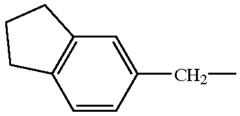 | 1 | 2 | 0 | R | H | 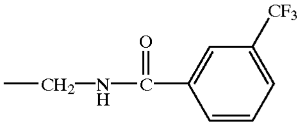 |
| 1139 | 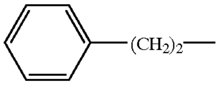 | 1 | 2 | 0 | R | H | 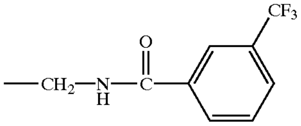 |

TABLE 1.104-continued
| Compd. No. | 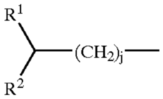 | k | m | n | chirality | $R^3$ | 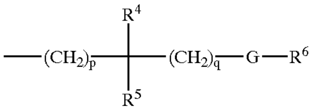 |
|---|---|---|---|---|---|---|---|
| 1140 | 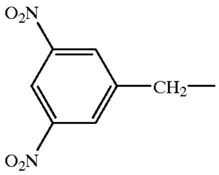 | 1 | 2 | 0 | R | H | 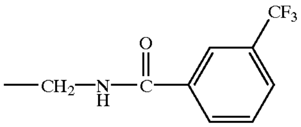 |
| 1141 | 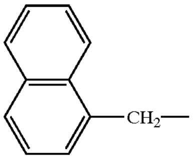 | 1 | 2 | 0 | R | H | 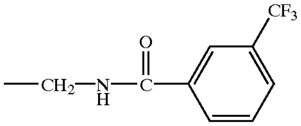 |
| 1142 | 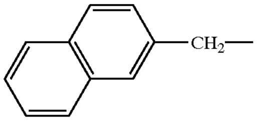 | 1 | 2 | 0 | R | H | 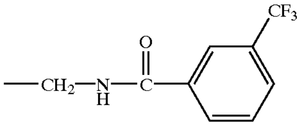 |
| 1143 | 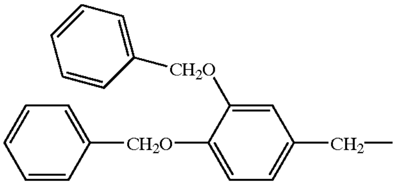 | 1 | 2 | 0 | R | H | 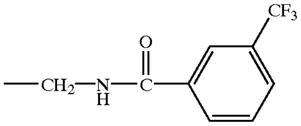 |
| 1144 | 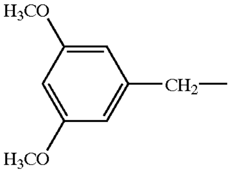 | 1 | 2 | 0 | R | H | 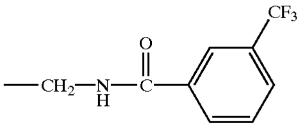 |
TABLE 1.105
| Compd. No. | 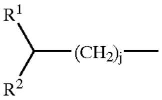 | k | m | n | chirality | $R^3$ | 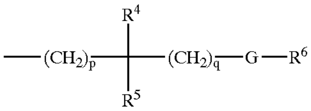 |
|---|---|---|---|---|---|---|---|
| 1145 | 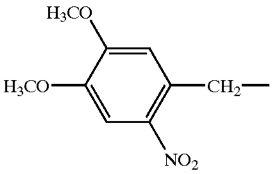 | 1 | 2 | 0 | R | H | 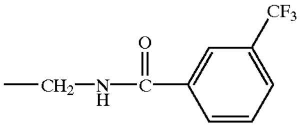 |
| 1146 | 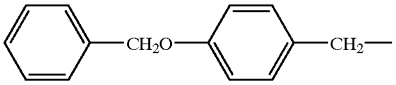 | 1 | 2 | 0 | R | H | 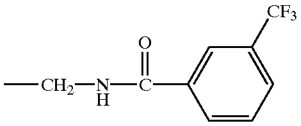 |

TABLE 1.105-continued
| Compd. No. | 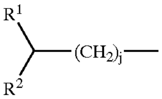 | k | m | n | chirality | $R^3$ | 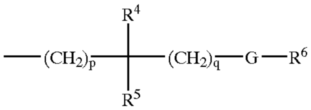 |
|---|---|---|---|---|---|---|---|
| 1147 | 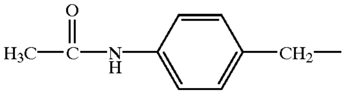 | 1 | 2 | 0 | R | H | 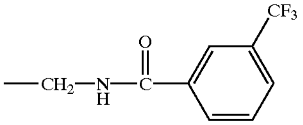 |
| 1148 | 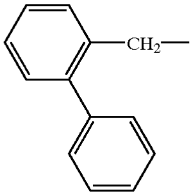 | 1 | 2 | 0 | R | H | 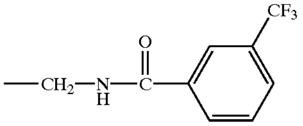 |
| 1149 | 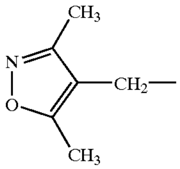 | 1 | 2 | 0 | R | H | 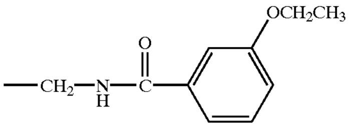 |
| 1150 | 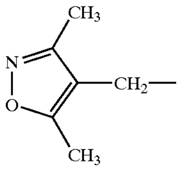 | 1 | 2 | 0 | R | H | 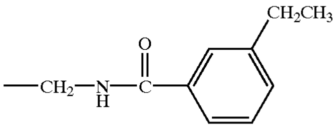 |
| 1151 | 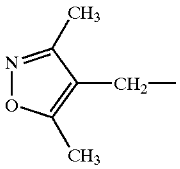 | 1 | 2 | 0 | R | H | 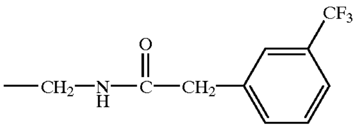 |
| 1152 | 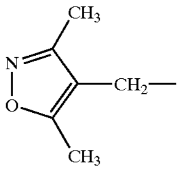 | 1 | 2 | 0 | R | H | 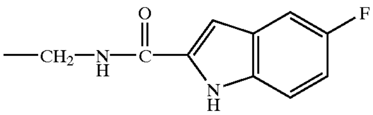 |
| 1153 | 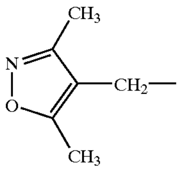 | 1 | 2 | 0 | R | H | 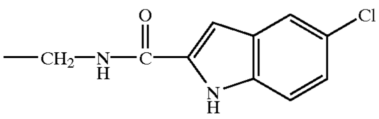 |
| 1154 | 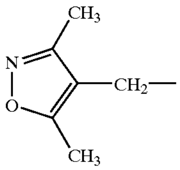 | 1 | 2 | 0 | R | H | 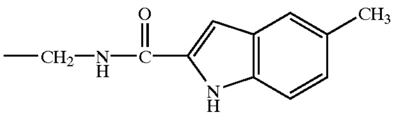 |

TABLE 1.105-continued
| Compd. No. | 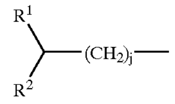 | k | m | n | chirality | $R^3$ | 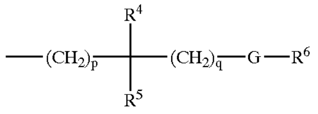 |
|---|---|---|---|---|---|---|---|
| 1155 | 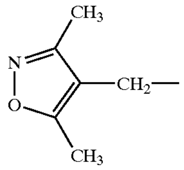 | 1 | 2 | 0 | R | H | 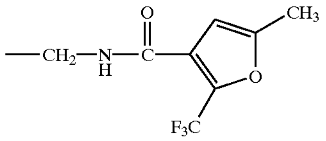 |
TABLE 1.106
| Compd. No. | 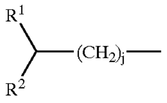 | k | m | n | chirality | $R^3$ | 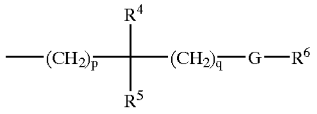 |
|---|---|---|---|---|---|---|---|
| 1156 | 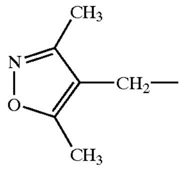 | 1 | 2 | 0 | R | H | 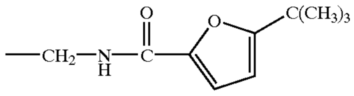 |
| 1157 | 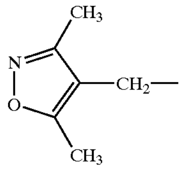 | 1 | 2 | 0 | R | H | 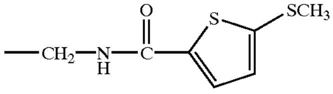 |
| 1158 | 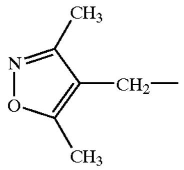 | 1 | 2 | 0 | R | H | 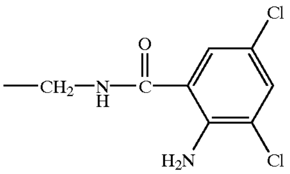 |
| 1159 | 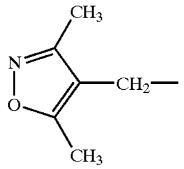 | 1 | 2 | 0 | R | H | 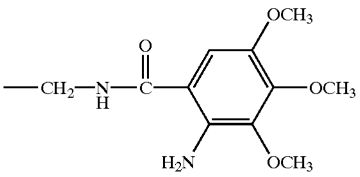 |
| 1160 | 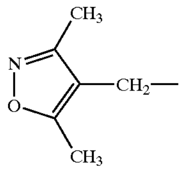 | 1 | 2 | 0 | R | H | 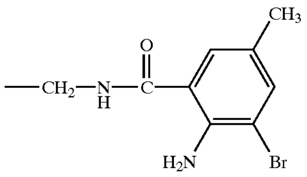 |

TABLE 1.106-continued
| Compd. No. | 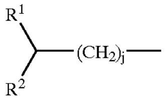 | k | m | n | chirality | $R^3$ | 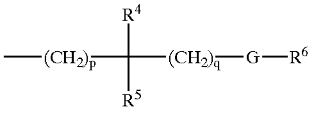 |
|---|---|---|---|---|---|---|---|
| 1161 | 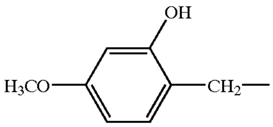 | 1 | 2 | 0 | R | H | 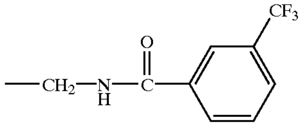 |
| 1162 | 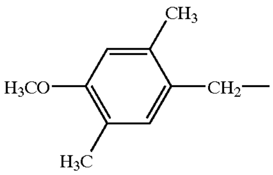 | 1 | 2 | 0 | R | H | 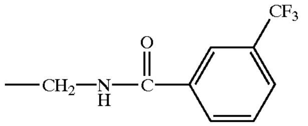 |
| 1163 | 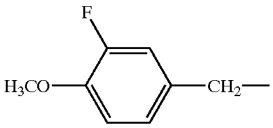 | 1 | 2 | 0 | R | H | 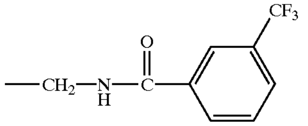 |
| 1164 | 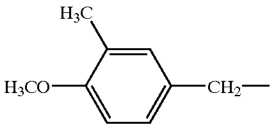 | 1 | 2 | 0 | R | H | 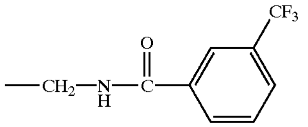 |
| 1165 | 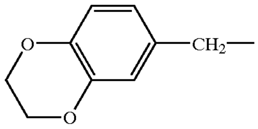 | 1 | 2 | 0 | R | H | 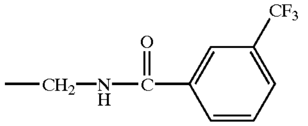 |
| 1166 | 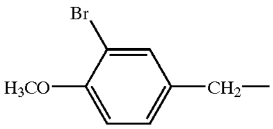 | 1 | 2 | 0 | R | H | 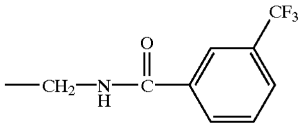 |
TABLE 1.107
| Compd. No. | 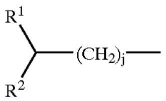 | k | m | n | chirality | $R^3$ | 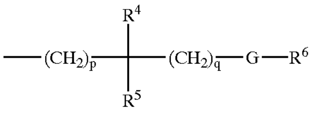 |
|---|---|---|---|---|---|---|---|
| 1167 | 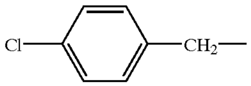 | 2 | 2 | 1 | — | H | 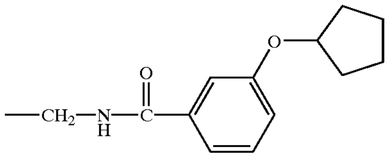 |
| 1168 | 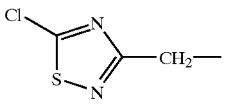 | 1 | 2 | 0 | R | H | 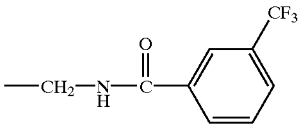 |

TABLE 1.107-continued
| Compd. No. | 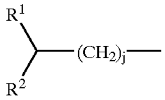 | k | m | n | chirality | $R^3$ | 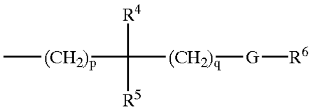 |
|---|---|---|---|---|---|---|---|
| 1169 | 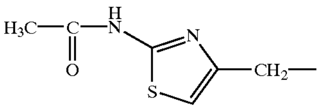 | 1 | 2 | 0 | R | H | 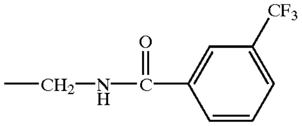 |
| 1170 | 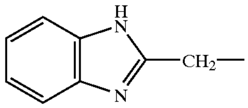 | 1 | 2 | 0 | R | H | 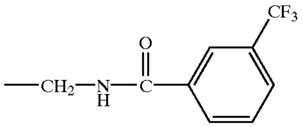 |
| 1171 | 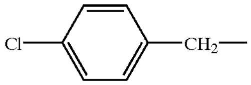 | 1 | 2 | 0 | R | H | 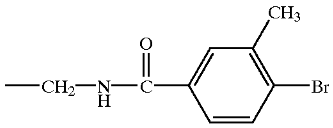 |
| 1172 | 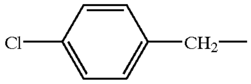 | 1 | 2 | 0 | R | H | 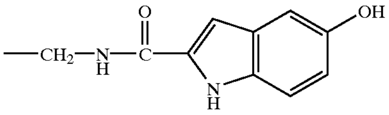 |
| 1173 | 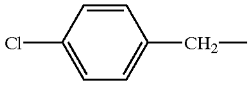 | 1 | 2 | 0 | R | H | 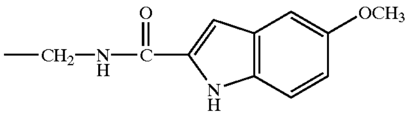 |
| 1174 | 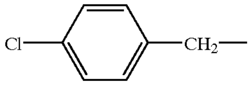 | 1 | 2 | 0 | R | H | 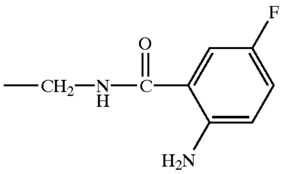 |
| 1175 | 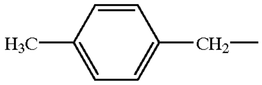 | 1 | 2 | 0 | R | H | 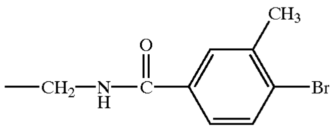 |
| 1176 | 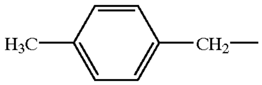 | 1 | 2 | 0 | R | H | 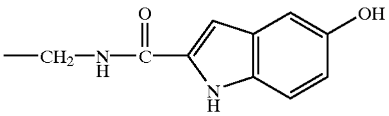 |
| 1177 | 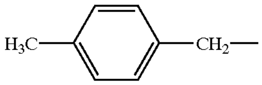 | 1 | 2 | 0 | R | H | 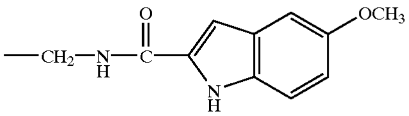 |

TABLE 1.108
| Compd. No. | 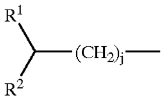 | k | m | n | chirality | $R^3$ | 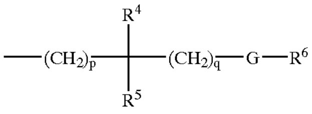 |
|---|---|---|---|---|---|---|---|
| 1178 | 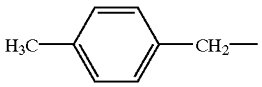 | 1 | 2 | 0 | R | H | 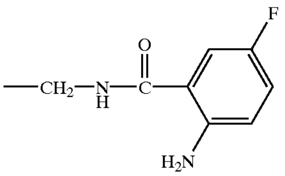 |
| 1179 | 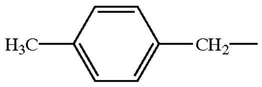 | 1 | 2 | 0 | R | H | 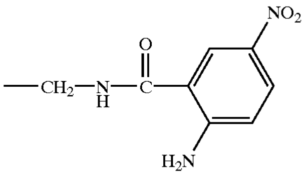 |
| 1180 | 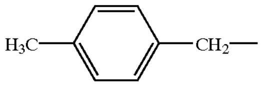 | 1 | 2 | 0 | R | H | 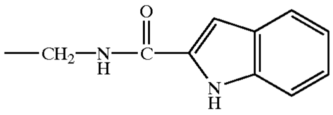 |
| 1181 | 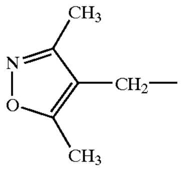 | 1 | 2 | 0 | R | H | 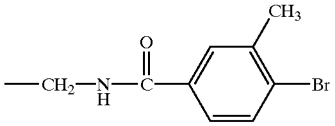 |
| 1182 | 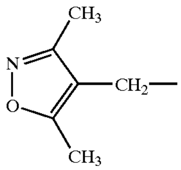 | 1 | 2 | 0 | R | H | 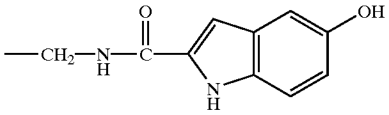 |
| 1183 | 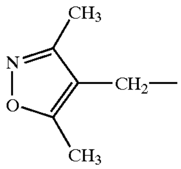 | 1 | 2 | 0 | R | H | 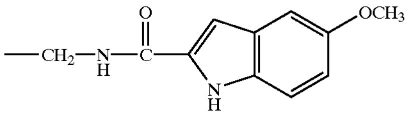 |
| 1184 | 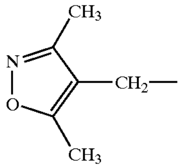 | 1 | 2 | 0 | R | H | 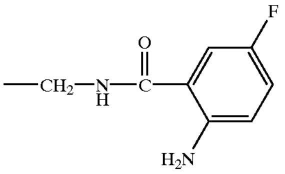 |
| 1185 | 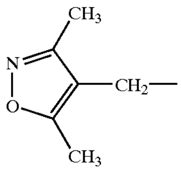 | 1 | 2 | 0 | R | H | 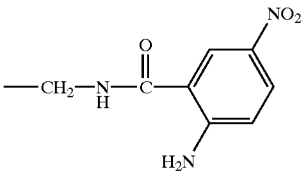 |

TABLE 1.108-continued
| Compd. No. | 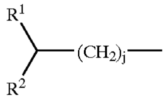 | k | m | n | chirality | $R^3$ | 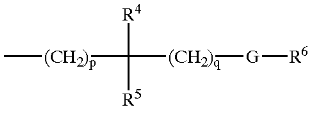 |
|---|---|---|---|---|---|---|---|
| 1186 | 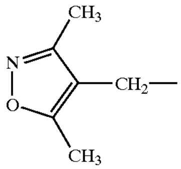 | 1 | 2 | 0 | R | H | 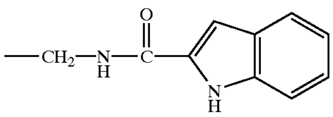 |
| 1187 | 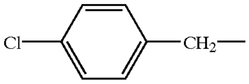 | 2 | 2 | 1 | — | H | 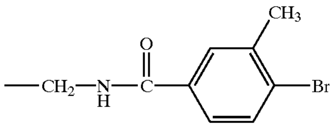 |
| 1188 | 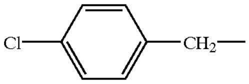 | 2 | 2 | 1 | — | H | 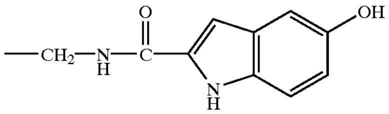 |
TABLE 1.109
| Compd. No. | 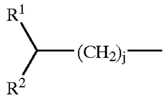 | k | m | n | chirality | $R^3$ | 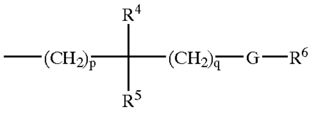 |
|---|---|---|---|---|---|---|---|
| 1189 | 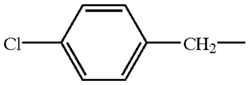 | 2 | 2 | 1 | — | H | 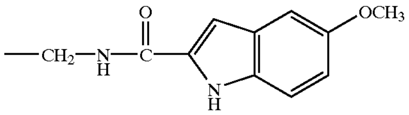 |
| 1190 | 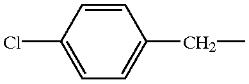 | 2 | 2 | 1 | — | H | 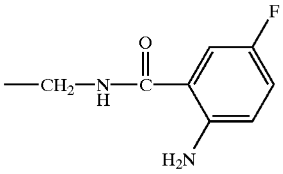 |
| 1191 | 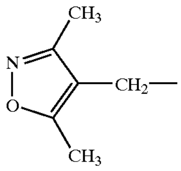 | 1 | 2 | 0 | R | H | 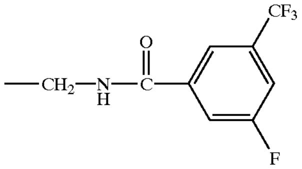 |
| 1192 | 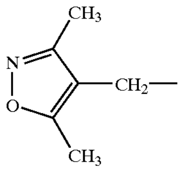 | 1 | 2 | 0 | R | H | 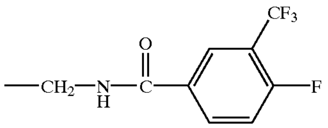 |

TABLE 1.109-continued
| Compd. No. | 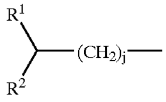 | k | m | n | chirality | $R^3$ | 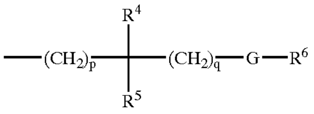 |
|---|---|---|---|---|---|---|---|
| 1193 | 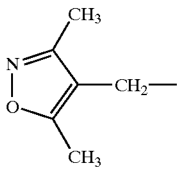 | 1 | 2 | 0 | R | H | 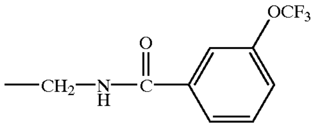 |
| 1194 | 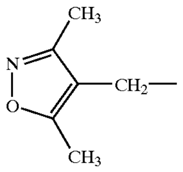 | 1 | 2 | 0 | R | H | 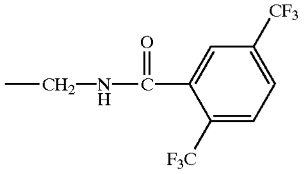 |
| 1195 | 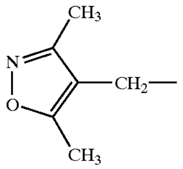 | 1 | 2 | 0 | R | H | 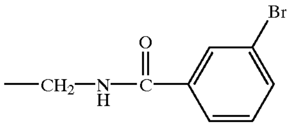 |
| 1196 | 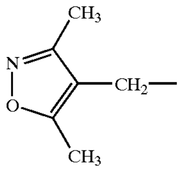 | 1 | 2 | 0 | R | H | 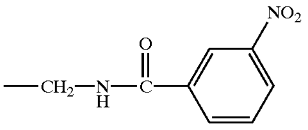 |
| 1197 | 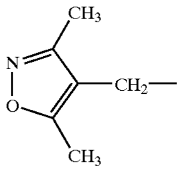 | 1 | 2 | 0 | R | H | 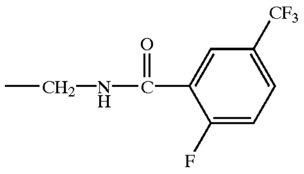 |
| 1198 | 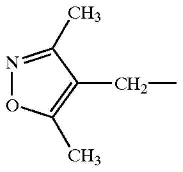 | 1 | 2 | 0 | R | H | 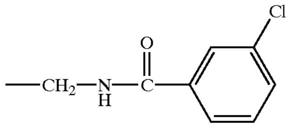 |
| 1199 | 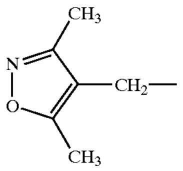 | 1 | 2 | 0 | R | H | 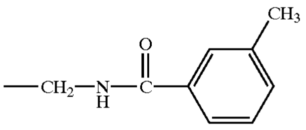 |

TABLE 1.110
| Compd. No. | 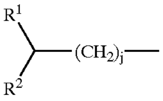 | k | m | n | chirality | $R^3$ | 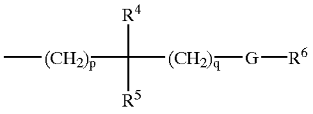 |
|---|---|---|---|---|---|---|---|
| 1200 | 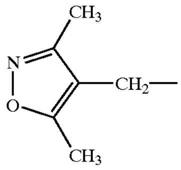 | 1 | 2 | 0 | R | H | 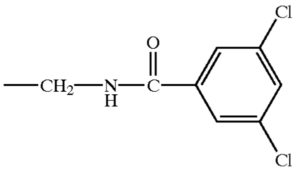 |
| 1201 | 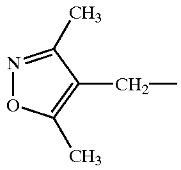 | 1 | 2 | 0 | R | H | 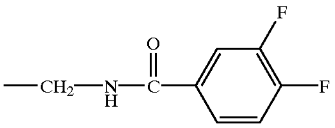 |
| 1202 | 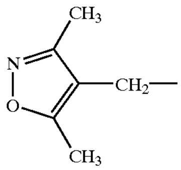 | 1 | 2 | 0 | R | H | 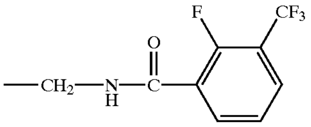 |
| 1203 | 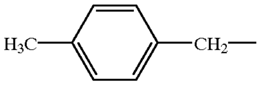 | 1 | 2 | 0 | R | H | 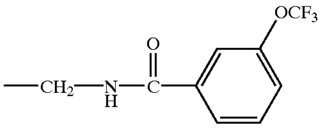 |
| 1204 | 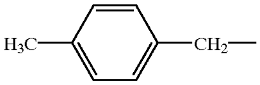 | 1 | 2 | 0 | R | H | 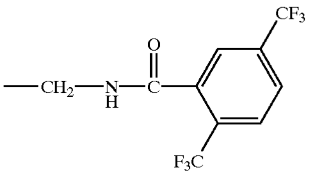 |
| 1205 | 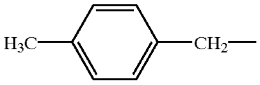 | 1 | 2 | 0 | R | H | 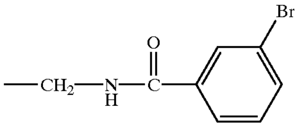 |
| 1206 | 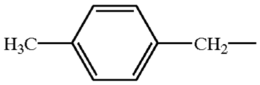 | 1 | 2 | 0 | R | H | 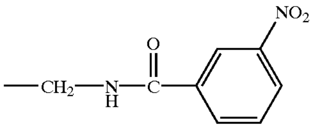 |
| 1207 | 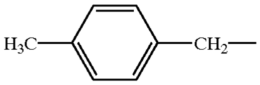 | 1 | 2 | 0 | R | H | 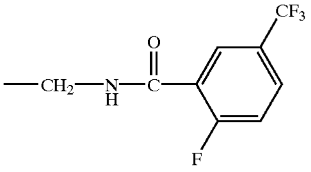 |
| 1208 | 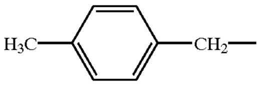 | 1 | 2 | 0 | R | H | 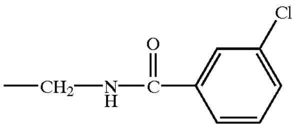 |

TABLE 1.110-continued
| Compd. No. | 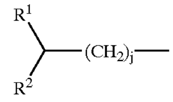 | k | m | n | chirality | $R^3$ | 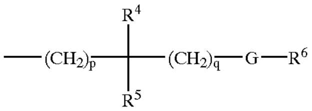 |
|---|---|---|---|---|---|---|---|
| 1209 | 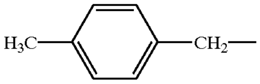 | 1 | 2 | 0 | R | H | 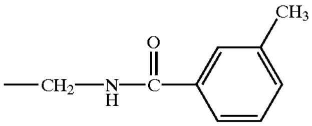 |
| 1210 | 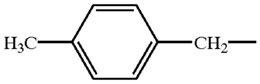 | 1 | 2 | 0 | R | H | 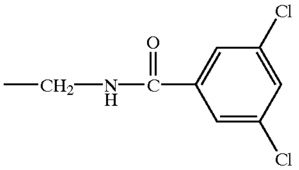 |
TABLE 1.111
| Compd. No. | 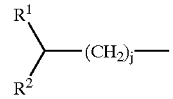 | k | m | n | chirality | $R^3$ | 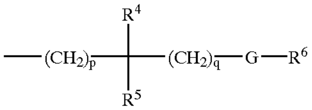 |
|---|---|---|---|---|---|---|---|
| 1211 | 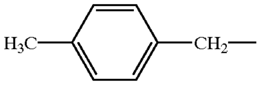 | 1 | 2 | 0 | R | H | 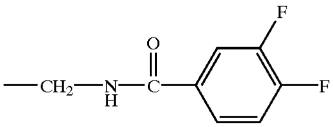 |
| 1212 | 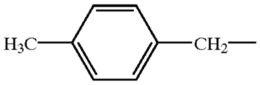 | 1 | 2 | 0 | R | H | 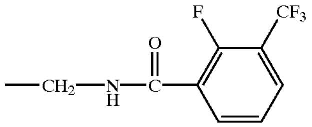 |
| 1213 | 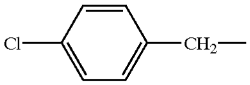 | 2 | 2 | 1 | — | H | 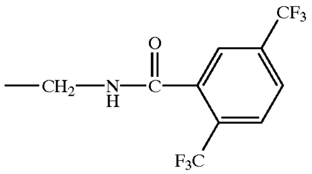 |
| 1214 | 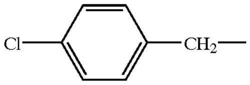 | 2 | 2 | 1 | — | H | 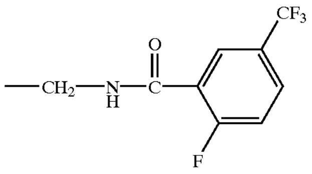 |
| 1215 | 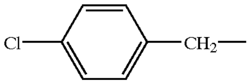 | 2 | 2 | 1 | — | H | 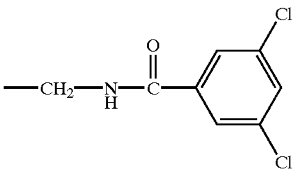 |

TABLE 1.111-continued
| Compd. No. | 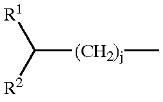 | k | m | n | chirality | $R^3$ | 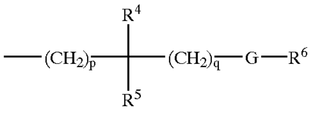 |
|---|---|---|---|---|---|---|---|
| 1216 | 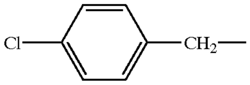 | 2 | 2 | 1 | — | H | 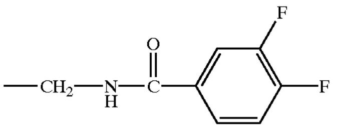 |
| 1217 | 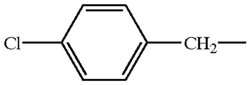 | 1 | 2 | 0 | R | H | 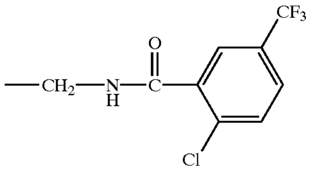 |
| 1218 | 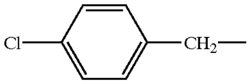 | 1 | 2 | 0 | R | H | 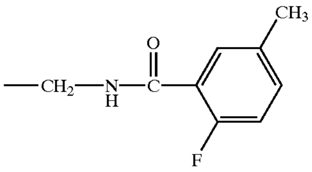 |
| 1219 | 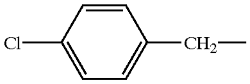 | 1 | 2 | 0 | R | H | 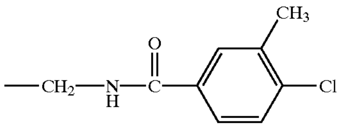 |
| 1220 | 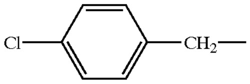 | 1 | 2 | 0 | R | H | 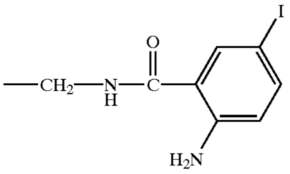 |
| 1221 | 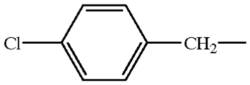 | 1 | 2 | 0 | R | H | 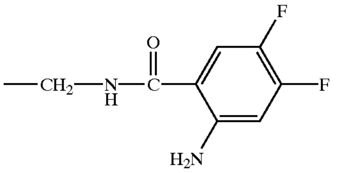 |
TABLE 1.112
| Compd. No. | 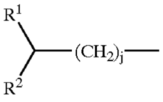 | k | m | n | chirality | $R^3$ | 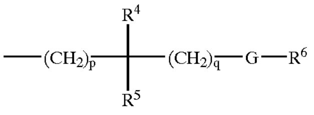 |
|---|---|---|---|---|---|---|---|
| 1222 | 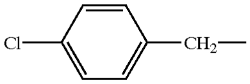 | 1 | 2 | 0 | R | H | 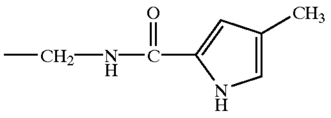 |

TABLE 1.112-continued
| Compd. No. | 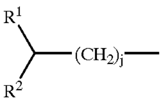 | k | m | n | chirality | $R^3$ | 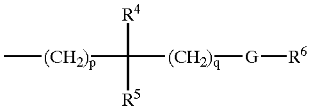 |
|---|---|---|---|---|---|---|---|
| 1223 | 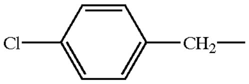 | 1 | 2 | 0 | R | H | 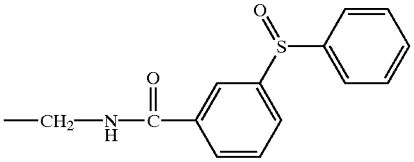 |
| 1224 | 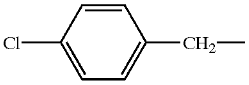 | 1 | 2 | 0 | R | H | 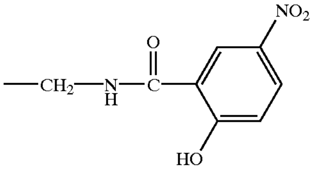 |
| 1225 | 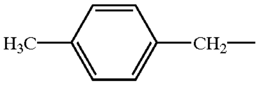 | 1 | 2 | 0 | R | H | 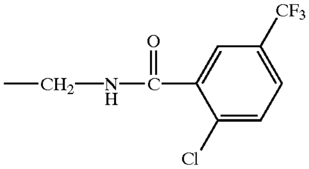 |
| 1226 | 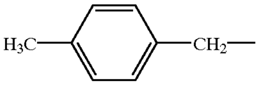 | 1 | 2 | 0 | R | H | 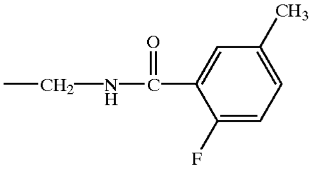 |
| 1227 | 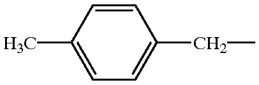 | 1 | 2 | 0 | R | H | 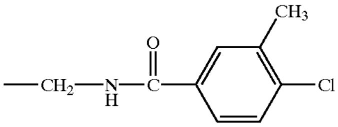 |
| 1228 | 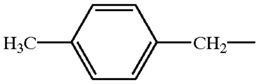 | 1 | 2 | 0 | R | H | 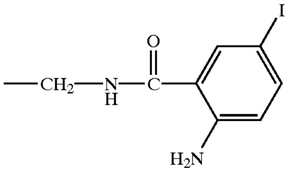 |
| 1229 | 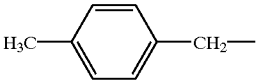 | 1 | 2 | 0 | R | H | 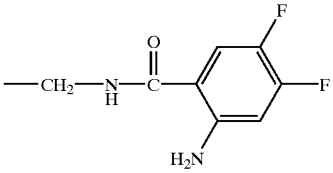 |
| 1230 | 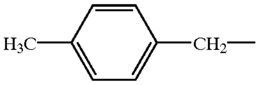 | 1 | 2 | 0 | R | H | 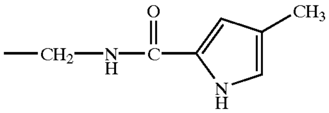 |

TABLE 1.112-continued
| Compd. No. | 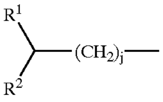 | k | m | n | chirality | $R^3$ | 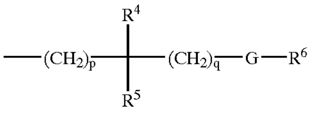 |
|---|---|---|---|---|---|---|---|
| 1231 | 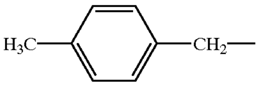 | 1 | 2 | 0 | R | H | 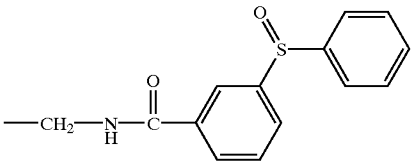 |
| 1232 | 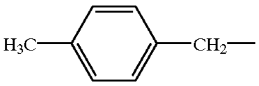 | 1 | 2 | 0 | R | H | 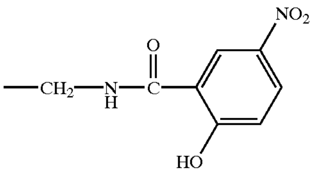 |
TABLE 1.113
| Compd. No. | 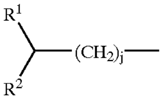 | k | m | n | chirality | $R^3$ | 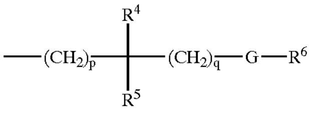 |
|---|---|---|---|---|---|---|---|
| 1233 | 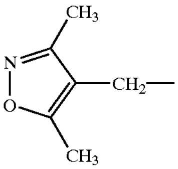 | 1 | 2 | 0 | R | H | 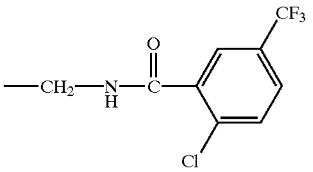 |
| 1234 | 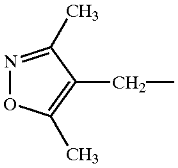 | 1 | 2 | 0 | R | H | 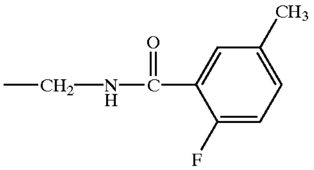 |
| 1235 | 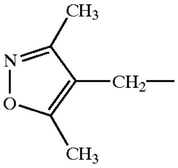 | 1 | 2 | 0 | R | H | 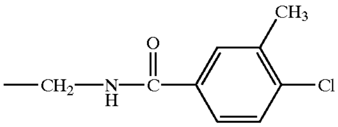 |
| 1236 | 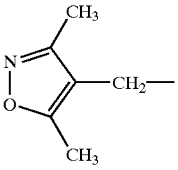 | 1 | 2 | 0 | R | H | 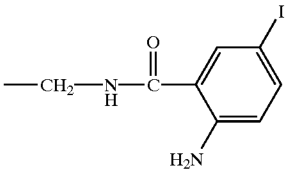 |

TABLE 1.113-continued
| Compd. No. | 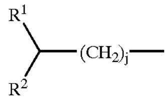 | k | m | n | chirality | $R^3$ | 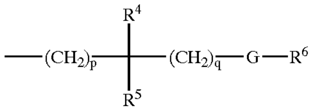 |
|---|---|---|---|---|---|---|---|
| 1237 | 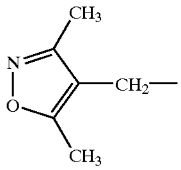 | 1 | 2 | 0 | R | H | 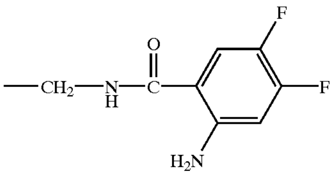 |
| 1238 | 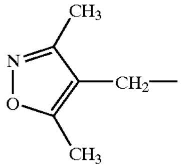 | 1 | 2 | 0 | R | H | 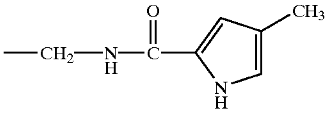 |
| 1239 | 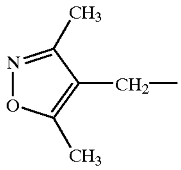 | 1 | 2 | 0 | R | H | 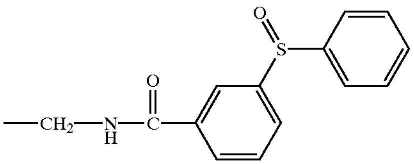 |
| 1240 | 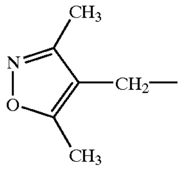 | 1 | 2 | 0 | R | H | 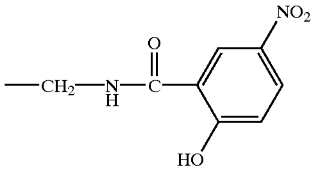 |
| 1241 | 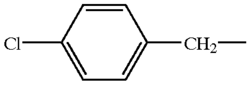 | 2 | 2 | 1 | — | H | 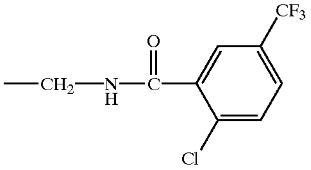 |
| 1242 | 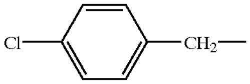 | 2 | 2 | 1 | — | H | 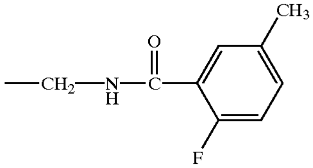 |
| 1243 | 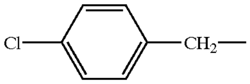 | 2 | 2 | 1 | — | H | 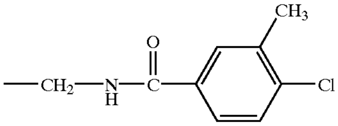 |

TABLE 1.114
| Compd. No. | 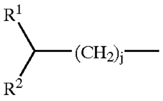 | k | m | n | chirality | $R^3$ | 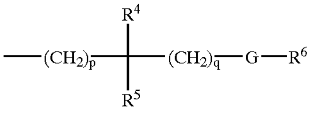 |
|---|---|---|---|---|---|---|---|
| 1244 | 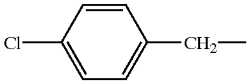 | 2 | 2 | 1 | — | H | 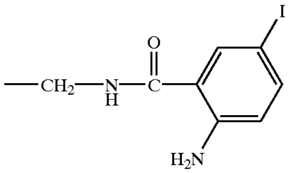 |
| 1245 | 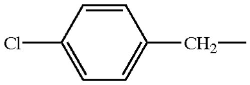 | 2 | 2 | 1 | — | H | 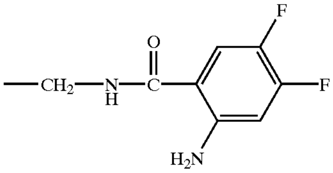 |
| 1246 | 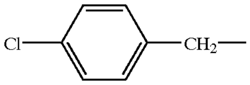 | 2 | 2 | 1 | — | H | 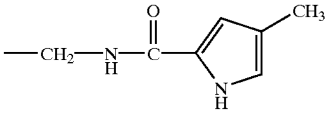 |
| 1247 | 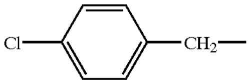 | 2 | 2 | 1 | — | H | 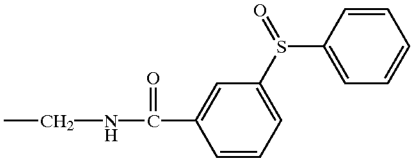 |
| 1248 | 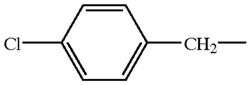 | 2 | 2 | 1 | — | H | 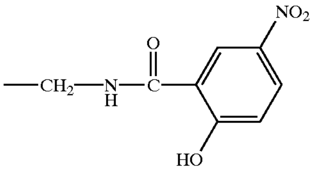 |
| 1249 | 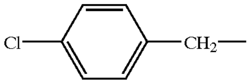 | 1 | 2 | 0 | R | H | 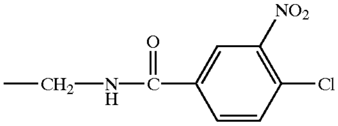 |
| 1250 | 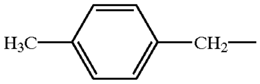 | 1 | 2 | 0 | R | H | 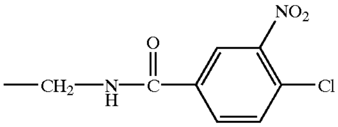 |
| 1251 | 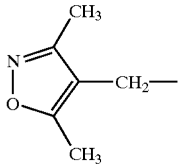 | 1 | 2 | 0 | R | H | 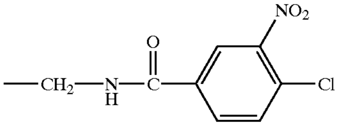 |
| 1252 | 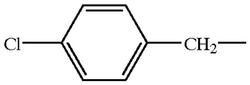 | 1 | 2 | 0 | R | H | 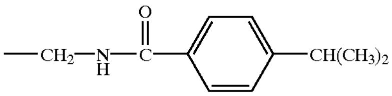 |

TABLE 1.114-continued
| Compd. No. | 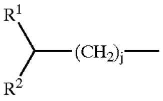 | k | m | n | chirality | $R^3$ | 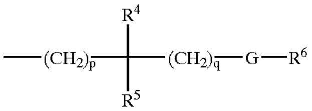 |
|---|---|---|---|---|---|---|---|
| 1253 | 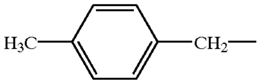 | 1 | 2 | 0 | R | H | 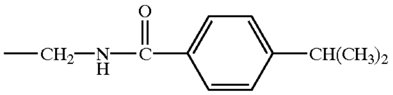 |
| 1254 | 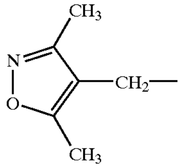 | 1 | 2 | 0 | R | H | 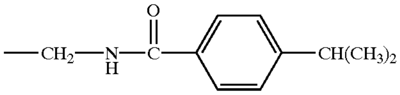 |
TABLE 1.115
| Compd. No. | 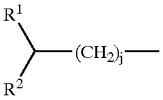 | k | m | n | chirality | $R^3$ | 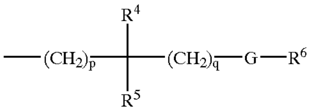 |
|---|---|---|---|---|---|---|---|
| 1255 | 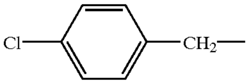 | 1 | 2 | 0 | R | H | 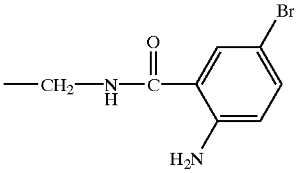 |
| 1256 | 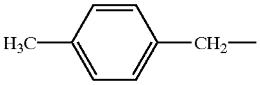 | 1 | 2 | 0 | R | H | 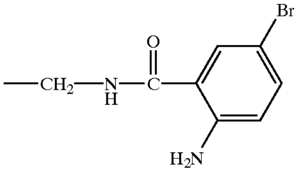 |
| 1257 | 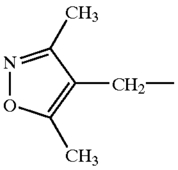 | 1 | 2 | 0 | R | H | 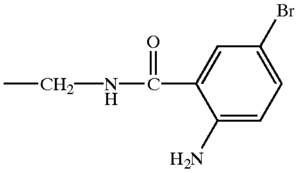 |
| 1258 | 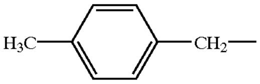 | 1 | 2 | 0 | R | H | 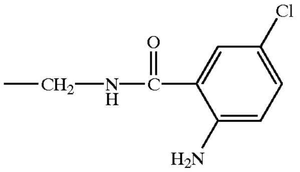 |
| 1259 | 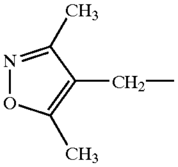 | 1 | 2 | 0 | R | H | 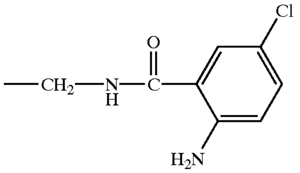 |

TABLE 1.115-continued
| Compd. No. | 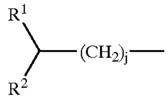 | k | m | n | chirality | $R^3$ | 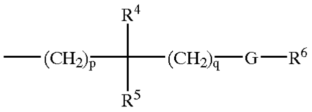 |
|---|---|---|---|---|---|---|---|
| 1260 | 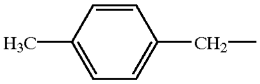 | 1 | 2 | 0 | R | H | 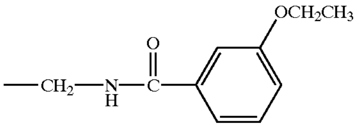 |
| 1261 | 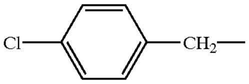 | 1 | 2 | 0 | R | H | 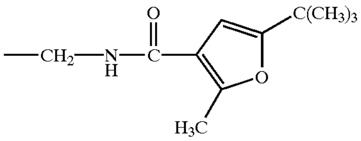 |
| 1262 | 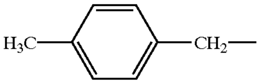 | 1 | 2 | 0 | R | H | 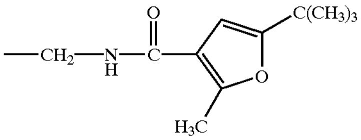 |
| 1263 | 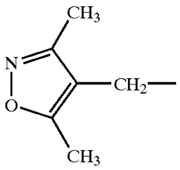 | 1 | 2 | 0 | R | H | 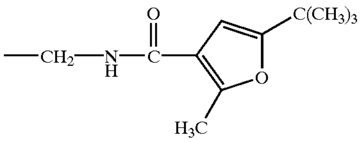 |
| 1264 | 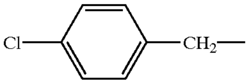 | 1 | 2 | 0 | R | H | 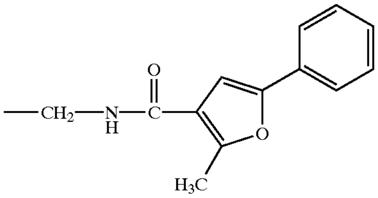 |
| 1265 | 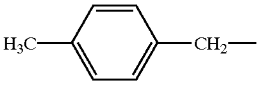 | 1 | 2 | 0 | R | H | 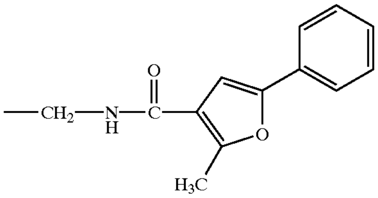 |

TABLE 1.116
| Compd. No. | 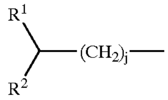 | k | m | n | chirality | $R^3$ | 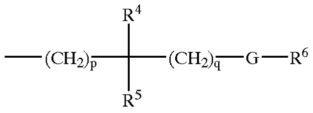 |
| --- | --- | --- | --- | --- | --- | --- | --- |
| 1266 | 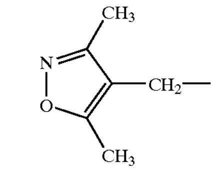 | 1 | 2 | 0 | R | H | 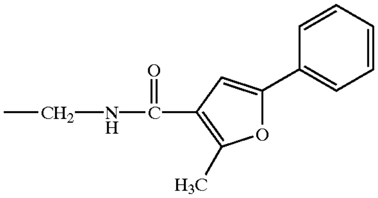 |
| 1267 | 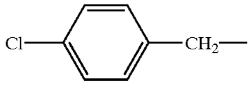 | 1 | 2 | 0 | R | H | 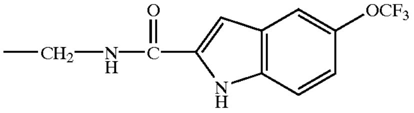 |
| 1268 | 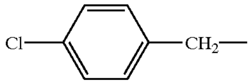 | 1 | 2 | 0 | R | H | 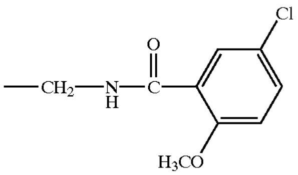 |
| 1269 | 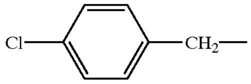 | 1 | 2 | 0 | R | H | 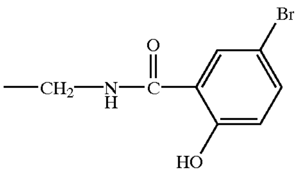 |
| 1270 | 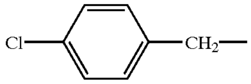 | 1 | 2 | 0 | R | H | 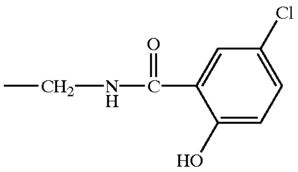 |
| 1271 | 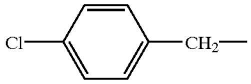 | 1 | 2 | 0 | R | H | 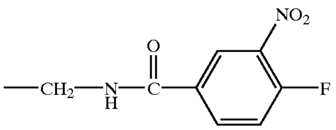 |
| 1272 | 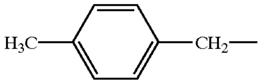 | 1 | 2 | 0 | R | H | 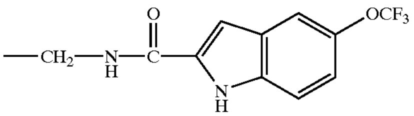 |
| 1273 | 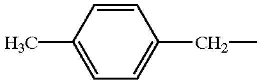 | 1 | 2 | 0 | R | H | 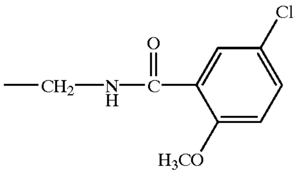 |

TABLE 1.116-continued
| Compd. No. | 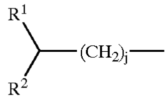 | k | m | n | chirality | $R^3$ | 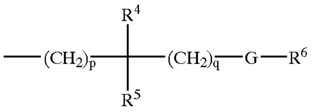 |
|---|---|---|---|---|---|---|---|
| 1274 | 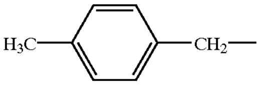 | 1 | 2 | 0 | R | H | 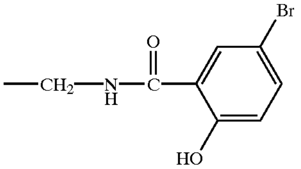 |
| 1275 | 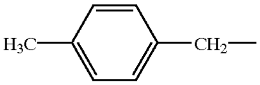 | 1 | 2 | 0 | R | H | 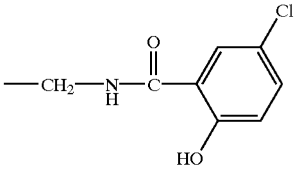 |
| 1276 | 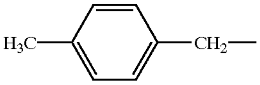 | 1 | 2 | 0 | R | H | 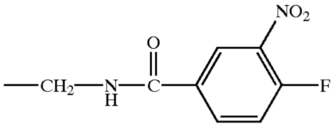 |
TABLE 1.117
| Compd. No. | 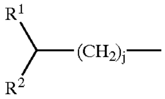 | k | m | n | chirality | $R^3$ | 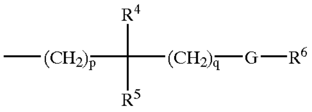 |
|---|---|---|---|---|---|---|---|
| 1277 | 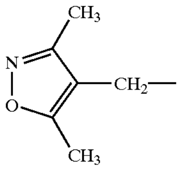 | 1 | 2 | 0 | R | H | 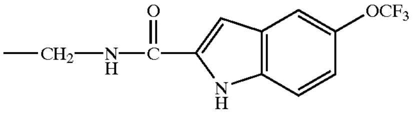 |
| 1278 | 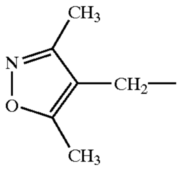 | 1 | 2 | 0 | R | H | 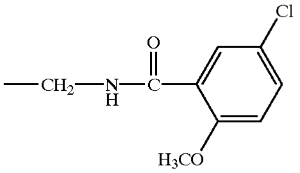 |
| 1279 | 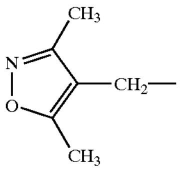 | 1 | 2 | 0 | R | H | 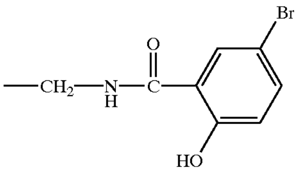 |

TABLE 1.117-continued
| Compd. No. | 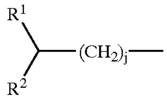 | k | m | n | chirality | $R^3$ | 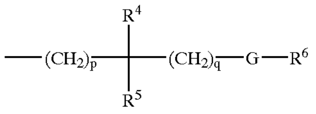 |
|---|---|---|---|---|---|---|---|
| 1280 | 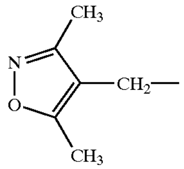 | 1 | 2 | 0 | R | H | 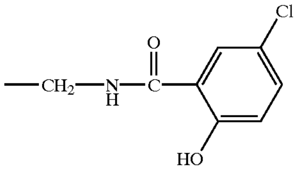 |
| 1281 | 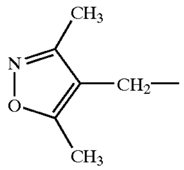 | 1 | 2 | 0 | R | H | 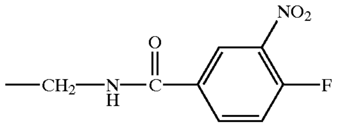 |
| 1282 | 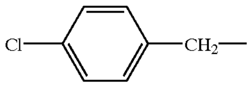 | 2 | 2 | 1 | — | H | 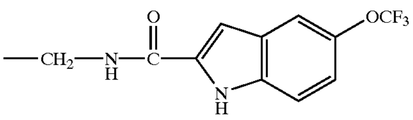 |
| 1283 | 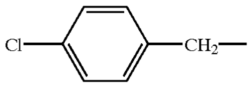 | 2 | 2 | 1 | — | H | 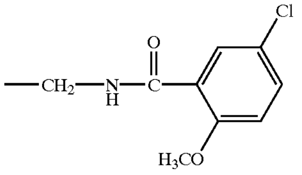 |
| 1284 | 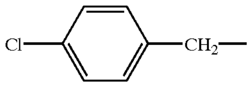 | 2 | 2 | 1 | — | H | 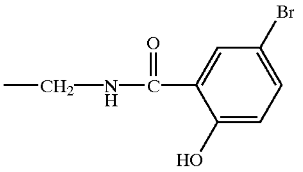 |
| 1285 | 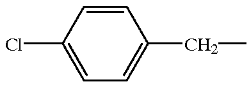 | 2 | 2 | 1 | — | H | 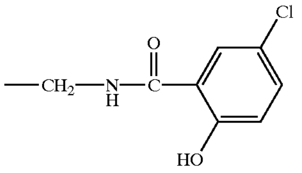 |
| 1286 | 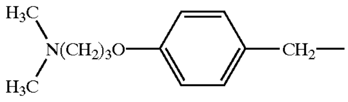 | 1 | 2 | 0 | R | H | 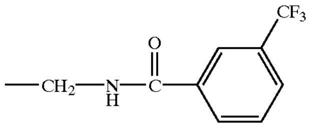 |
| 1287 | 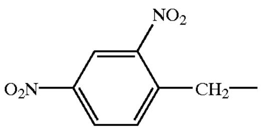 | 1 | 2 | 0 | R | H | 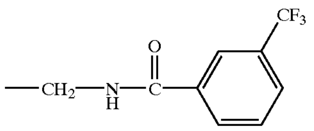 |

TABLE 1.118
| Compd. No. | 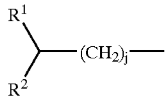 | k | m | n | chirality | $R^3$ | 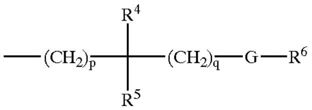 |
|---|---|---|---|---|---|---|---|
| 1288 | 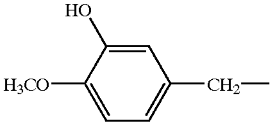 | 1 | 2 | 0 | R | H | 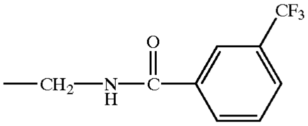 |
| 1289 | 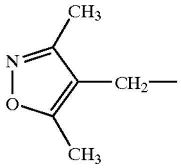 | 1 | 2 | 0 | R | H | 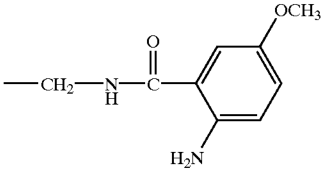 |
| 1290 | 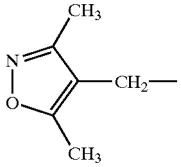 | 1 | 2 | 0 | R | H | 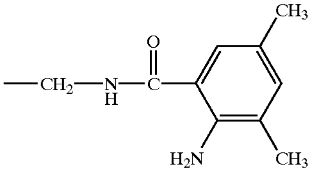 |
| 1291 | 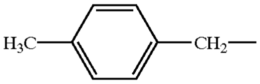 | 1 | 2 | 0 | R | H | 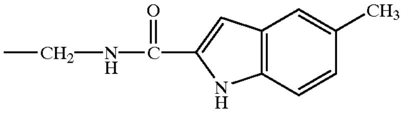 |
| 1292 | 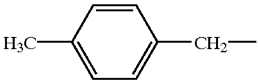 | 1 | 2 | 0 | R | H | 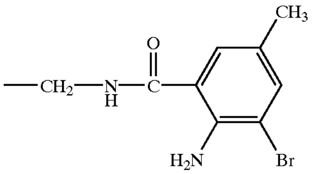 |
| 1293 | 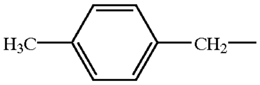 | 1 | 2 | 0 | R | H | 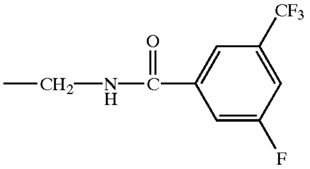 |
| 1294 | 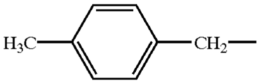 | 1 | 2 | 0 | R | H | 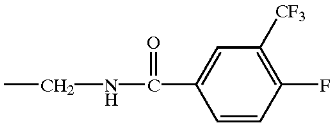 |
| 1295 | 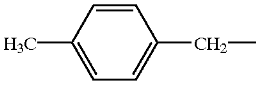 | 1 | 2 | 0 | R | H | 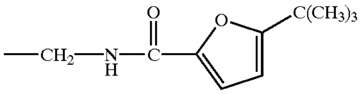 |
| 1296 | 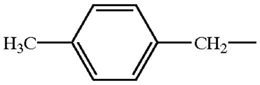 | 1 | 2 | 0 | R | H | 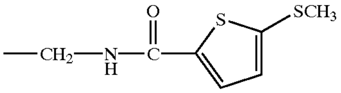 |

TABLE 1.118-continued
| Compd. No. | 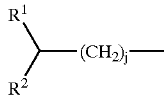 | k | m | n | chirality | $R^3$ | 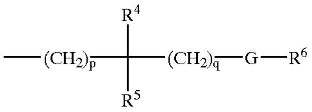 |
|---|---|---|---|---|---|---|---|
| 1297 | 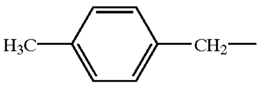 | 1 | 2 | 0 | R | H | 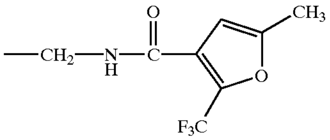 |
| 1298 | 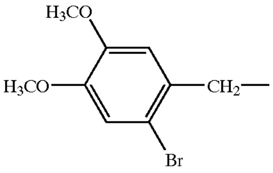 | 1 | 2 | 0 | R | H | 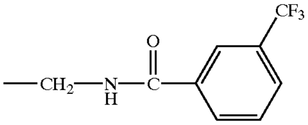 |
TABLE 1.119
| Compd. No. | 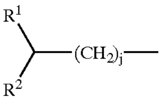 | k | m | n | chirality | $R^3$ | 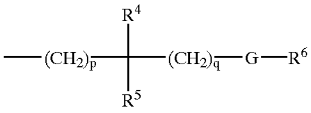 |
|---|---|---|---|---|---|---|---|
| 1299 | 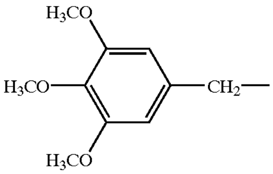 | 1 | 2 | 0 | R | H | 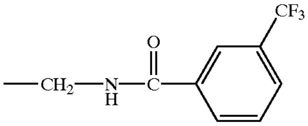 |
| 1300 | 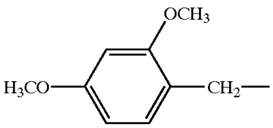 | 1 | 2 | 0 | R | H | 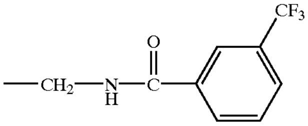 |
| 1301 | 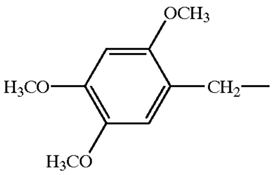 | 1 | 2 | 0 | R | H | 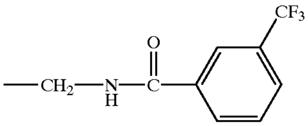 |
| 1302 | 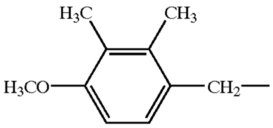 | 1 | 2 | 0 | R | H | 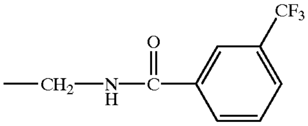 |
| 1303 | 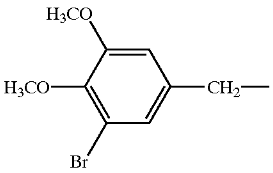 | 1 | 2 | 0 | R | H | 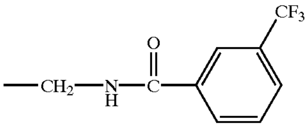 |

TABLE 1.119-continued
| Compd. No. | 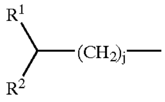 | k | m | n | chirality | $R^3$ | 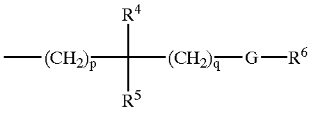 |
|---|---|---|---|---|---|---|---|
| 1304 | 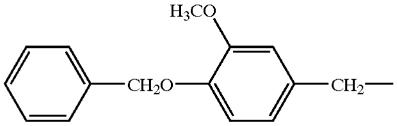 | 1 | 2 | 0 | R | H | 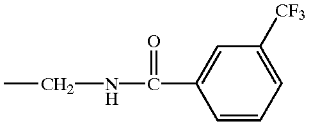 |
| 1305 | 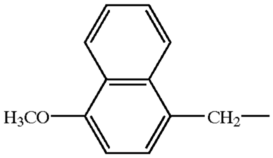 | 1 | 2 | 0 | R | H | 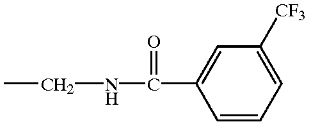 |
| 1306 | 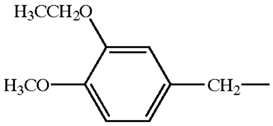 | 1 | 2 | 0 | R | H | 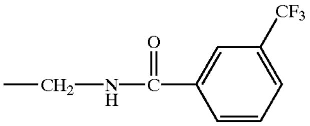 |
| 1307 | 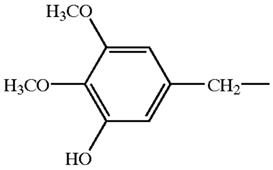 | 1 | 2 | 0 | R | H | 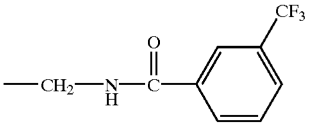 |
| 1308 | 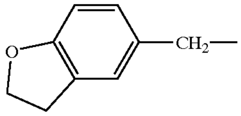 | 1 | 2 | 0 | R | H | 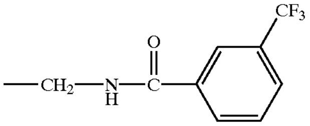 |
| 1309 | 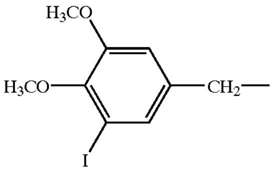 | 1 | 2 | 0 | R | H | 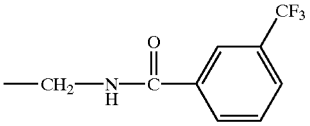 |
TABLE 1.120
| Compd. No. | 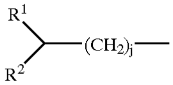 | k | m | n | chirality | $R^3$ | 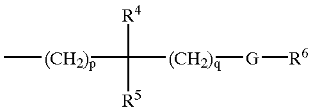 |
|---|---|---|---|---|---|---|---|
| 1310 | 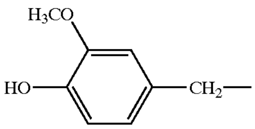 | 1 | 2 | 0 | R | H | 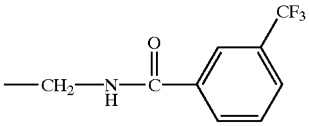 |

TABLE 1.120-continued
| Compd. No. | 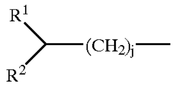 | k | m | n | chirality | $R^3$ | 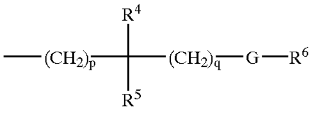 |
|---|---|---|---|---|---|---|---|
| 1311 | 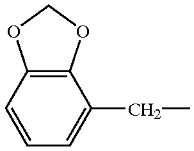 | 1 | 2 | 0 | R | H | 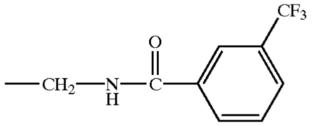 |
| 1312 | 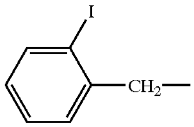 | 1 | 2 | 0 | R | H | 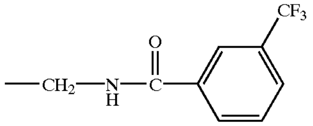 |
| 1313 | 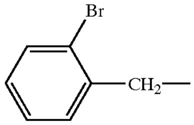 | 1 | 2 | 0 | R | H | 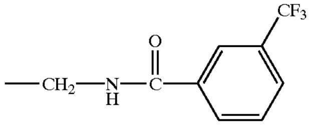 |
| 1314 | 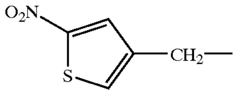 | 1 | 2 | 0 | R | H | 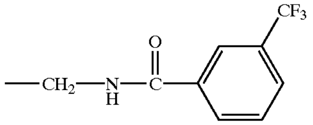 |
| 1315 | 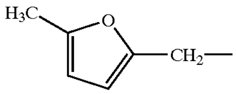 | 1 | 2 | 0 | R | H | 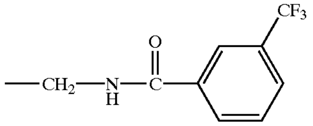 |
| 1316 | 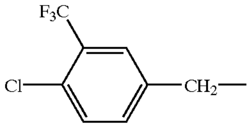 | 1 | 2 | 0 | R | H | 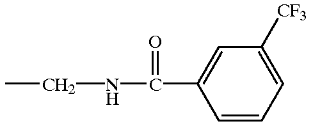 |
| 1317 | 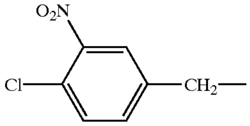 | 1 | 2 | 0 | R | H | 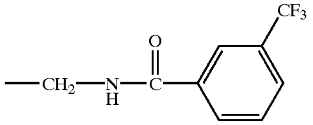 |
| 1318 | 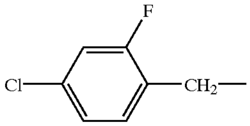 | 1 | 2 | 0 | R | H | 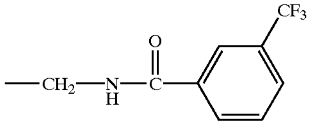 |
| 1319 | 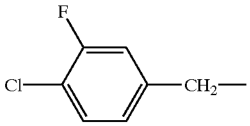 | 1 | 2 | 0 | R | H | 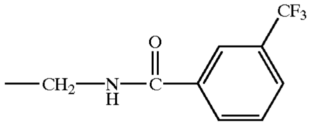 |
| 1320 | 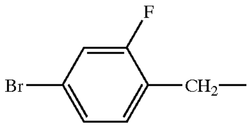 | 1 | 2 | 0 | R | H | 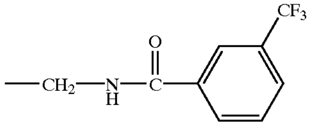 |

TABLE 1.121
| Compd. No. | 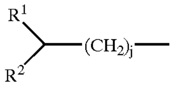 | k | m | n | chirality | R³ | 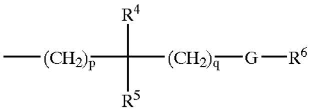 |
|---|---|---|---|---|---|---|---|
| 1321 | 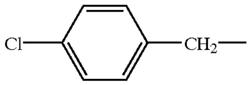 | 1 | 2 | 0 | R | H | 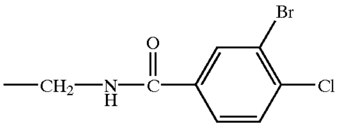 |
| 1322 | 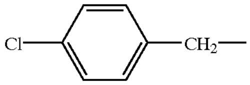 | 1 | 2 | 0 | R | H | 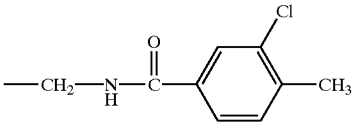 |
| 1323 | 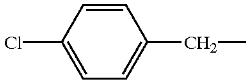 | 1 | 2 | 0 | R | H | 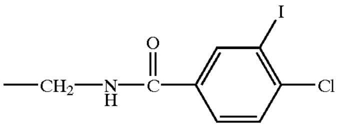 |
| 1324 | 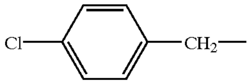 | 1 | 2 | 0 | R | H | 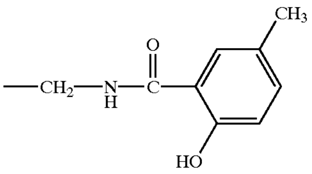 |
| 1325 | 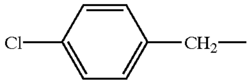 | 1 | 2 | 0 | R | H | 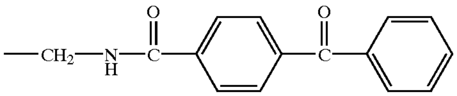 |
| 1326 | 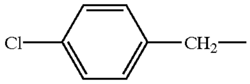 | 1 | 2 | 0 | R | H | 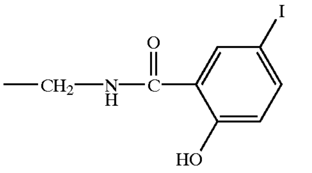 |
| 1327 | 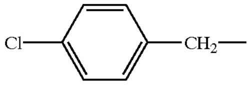 | 1 | 2 | 0 | R | H | 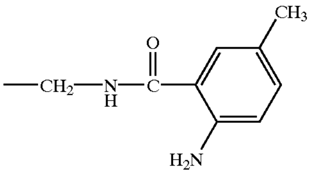 |
| 1328 | 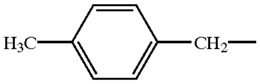 | 1 | 2 | 0 | R | H | 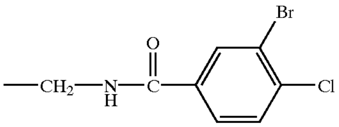 |
| 1329 | 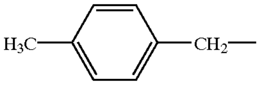 | 1 | 2 | 0 | R | H | 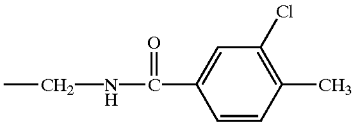 |

TABLE 1.121-continued
| Compd. No. | 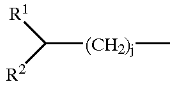 | k | m | n | chirality | $R^3$ | 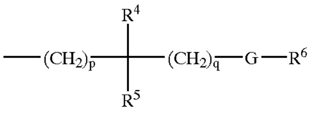 |
|---|---|---|---|---|---|---|---|
| 1330 | 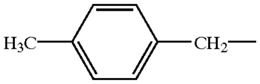 | 1 | 2 | 0 | R | H | 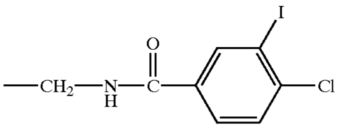 |
| 1331 | 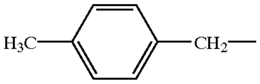 | 1 | 2 | 0 | R | H | 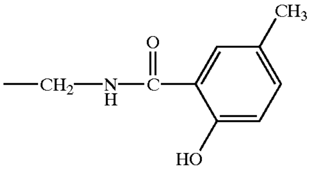 |
TABLE 1.122
| Compd. No. | 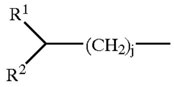 | k | m | n | chirality | $R^3$ | 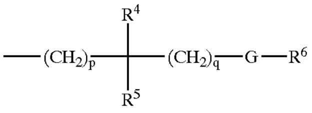 |
|---|---|---|---|---|---|---|---|
| 1332 | 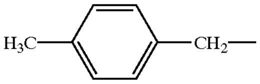 | 1 | 2 | 0 | R | H | 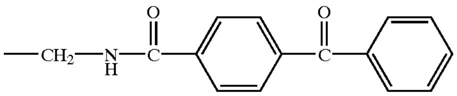 |
| 1333 | 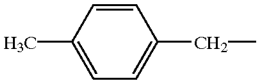 | 1 | 2 | 0 | R | H | 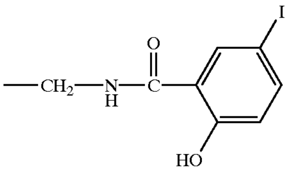 |
| 1334 | 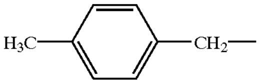 | 1 | 2 | 0 | R | H | 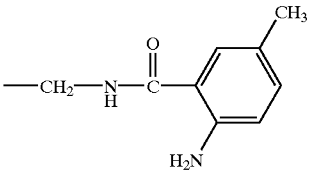 |
| 1335 | 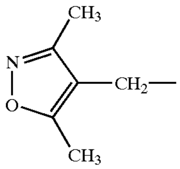 | 1 | 2 | 0 | R | H | 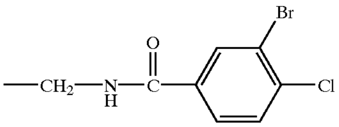 |
| 1336 | 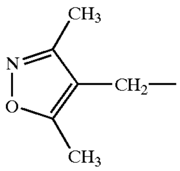 | 1 | 2 | 0 | R | H | 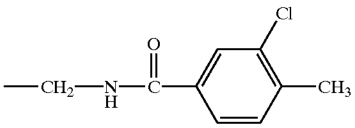 |

TABLE 1.122-continued
| Compd. No. | 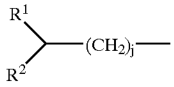 | k | m | n | chirality | $R^3$ | 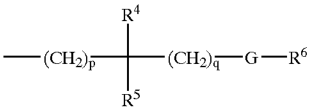 |
|---|---|---|---|---|---|---|---|
| 1337 | 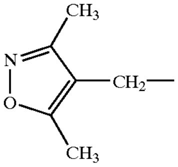 | 1 | 2 | 0 | R | H | 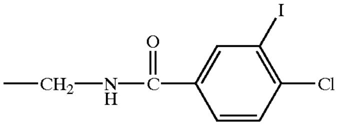 |
| 1338 | 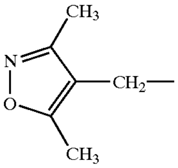 | 1 | 2 | 0 | R | H | 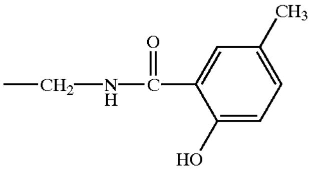 |
| 1339 | 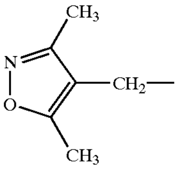 | 1 | 2 | 0 | R | H | 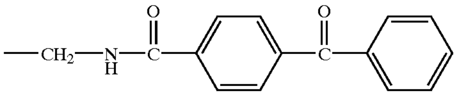 |
| 1340 | 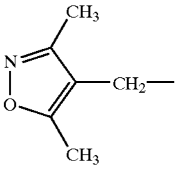 | 1 | 2 | 0 | R | H | 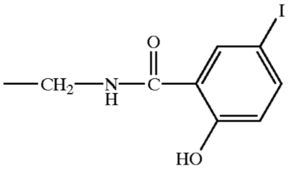 |
| 1341 | 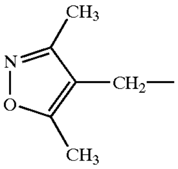 | 1 | 2 | 0 | R | H | 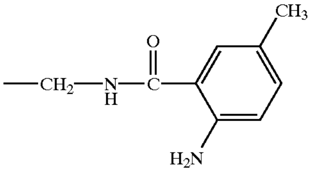 |
| 1342 | 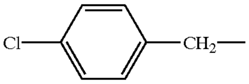 | 2 | 2 | 1 | — | H | 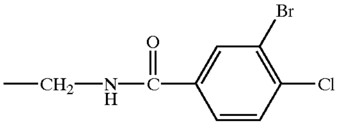 |
TABLE 1.123
| Compd. No. | 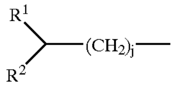 | k | m | n | chirality | $R^3$ | 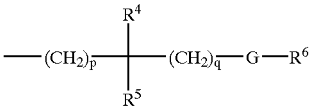 |
|---|---|---|---|---|---|---|---|
| 1343 | 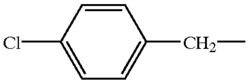 | 2 | 2 | 1 | — | H | 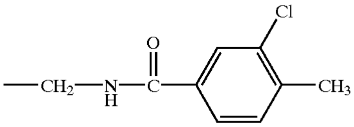 |

TABLE 1.123-continued
| Compd. No. | 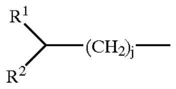 | k | m | n | chirality | $R^3$ | 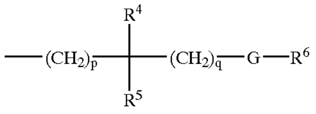 |
|---|---|---|---|---|---|---|---|
| 1344 | 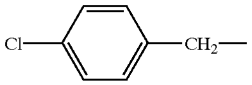 | 2 | 2 | 1 | — | H | 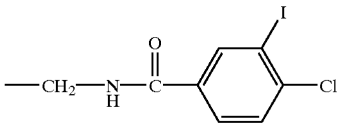 |
| 1345 | 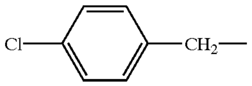 | 2 | 2 | 1 | — | H | 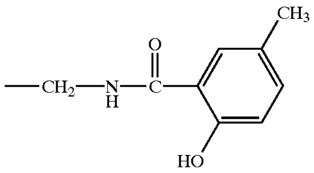 |
| 1346 | 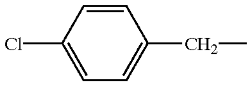 | 2 | 2 | 1 | — | H | 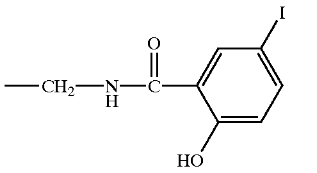 |
| 1347 | 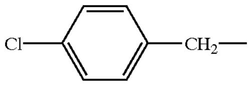 | 1 | 2 | 0 | R | H | 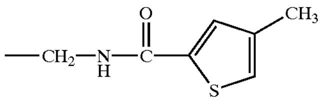 |
| 1348 | 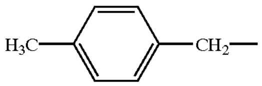 | 1 | 2 | 0 | R | H | 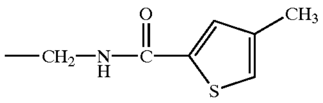 |
| 1349 | 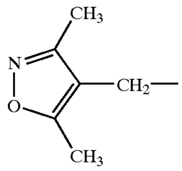 | 1 | 2 | 0 | R | H | 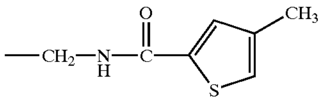 |
| 1350 | 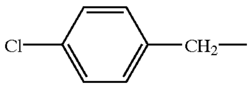 | 2 | 2 | 1 | — | H | 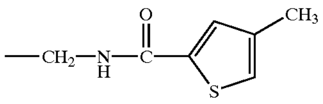 |
| 1351 | 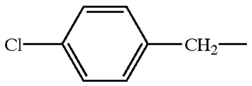 | 1 | 2 | 0 | R | H | 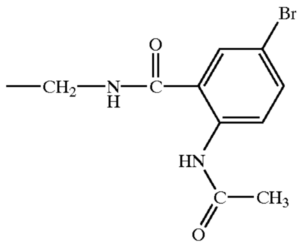 |

TABLE 1.123-continued
| Compd. No. | 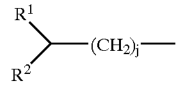 | k | m | n | chirality | $R^3$ | 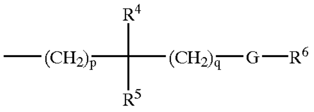 |
|---|---|---|---|---|---|---|---|
| 1352 | 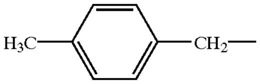 | 1 | 2 | 0 | R | H | 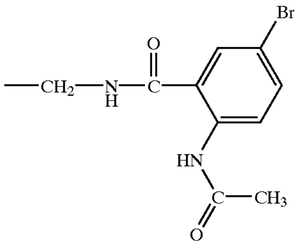 |
| 1353 | 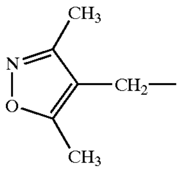 | 1 | 2 | 0 | R | H | 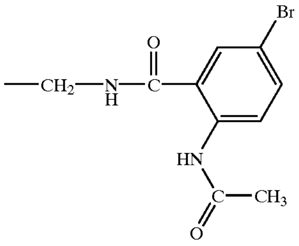 |
TABLE 1.124
| Compd. No. | 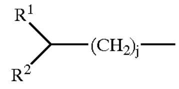 | k | m | n | chirality | $R^3$ | 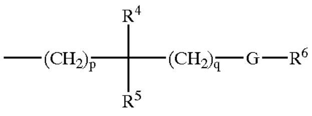 |
|---|---|---|---|---|---|---|---|
| 1354 | 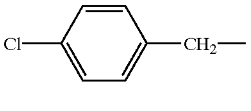 | 2 | 2 | 1 | — | H | 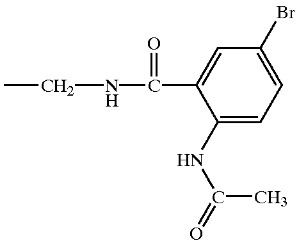 |
| 1355 | 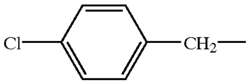 | 1 | 2 | 0 | R | H | 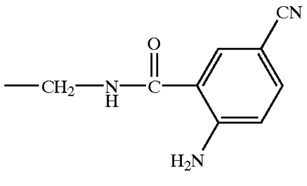 |
| 1356 | 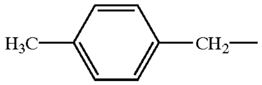 | 1 | 2 | 0 | R | H | 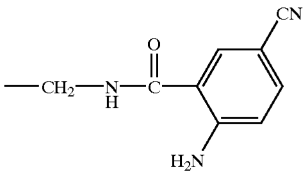 |

TABLE 1.124-continued
| Compd. No. | 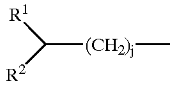 | k | m | n | chirality | R³ | 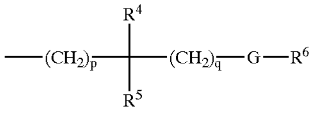 |
|---|---|---|---|---|---|---|---|
| 1357 | 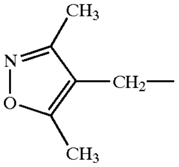 | 1 | 2 | 0 | R | H | 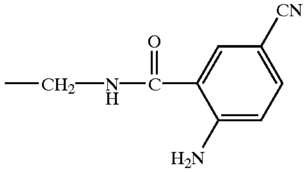 |
| 1358 | 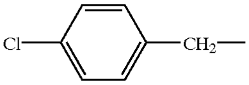 | 2 | 2 | 1 | — | H | 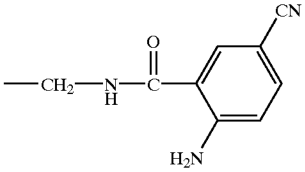 |
| 1359 | 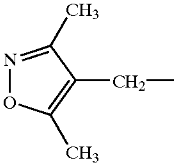 | 1 | 2 | 0 | R | H | 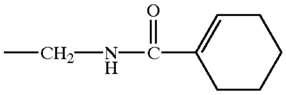 |
| 1360 | 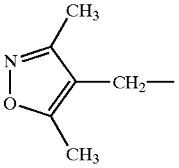 | 1 | 2 | 0 | R | H | 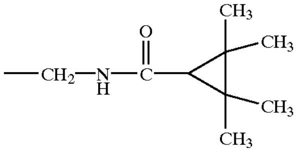 |
| 1361 | 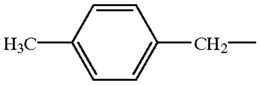 | 1 | 2 | 0 | R | H | 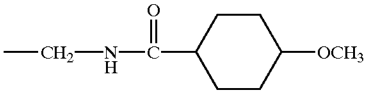 |
| 1362 | 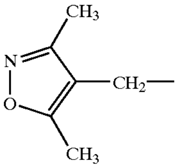 | 1 | 2 | 0 | R | H | 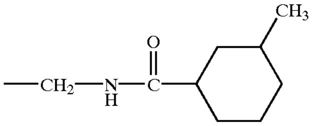 |
| 1363 | 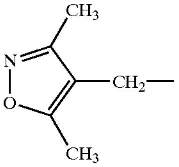 | 1 | 2 | 0 | R | H | 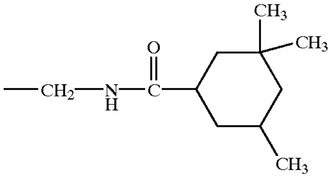 |
| 1364 | 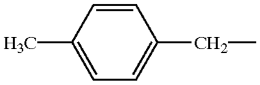 | 1 | 2 | 0 | R | H | 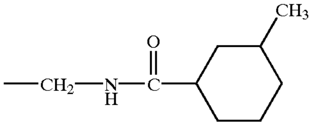 |

TABLE 1.125
| Compd. No. | 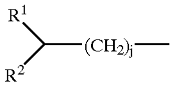 | k | m | n | chirality | R3 | 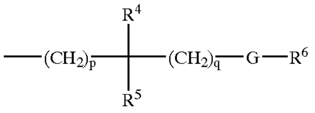 |
|---|---|---|---|---|---|---|---|
| 1365 | 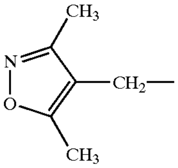 | 1 | 2 | 0 | R | H | 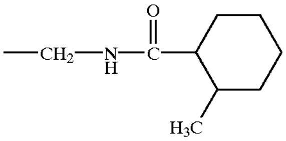 |
| 1366 | 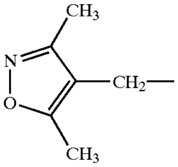 | 1 | 2 | 0 | R | H | 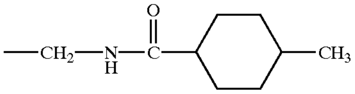 |
| 1367 | 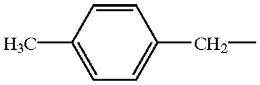 | 1 | 2 | 0 | R | H | 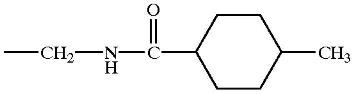 |
| 1368 | 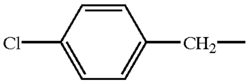 | 1 | 2 | 0 | R | H | 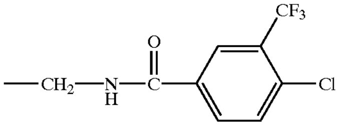 |
| 1369 | 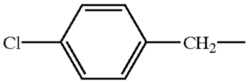 | 1 | 2 | 0 | R | H | 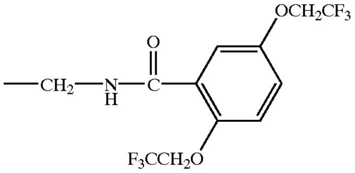 |
| 1370 | 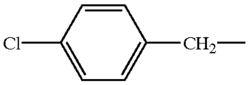 | 1 | 2 | 0 | R | H | 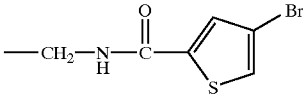 |
| 1371 | 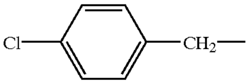 | 1 | 2 | 0 | R | H | 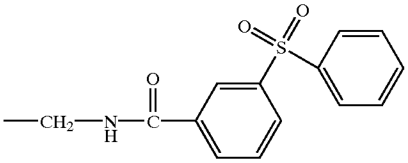 |
| 1372 | 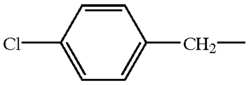 | 1 | 2 | 0 | R | H | 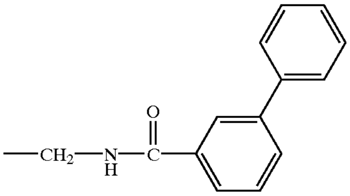 |
| 1373 | 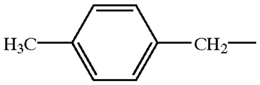 | 1 | 2 | 0 | R | H | 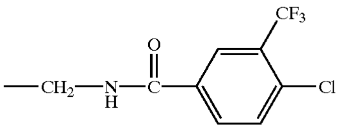 |

TABLE 1.125-continued
| Compd. No. | 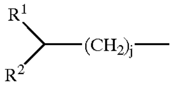 | k | m | n | chirality | $R^3$ | 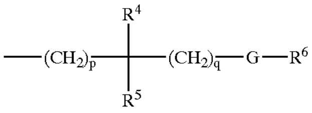 |
|---|---|---|---|---|---|---|---|
| 1374 | 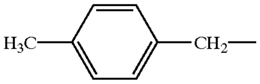 | 1 | 2 | 0 | R | H | 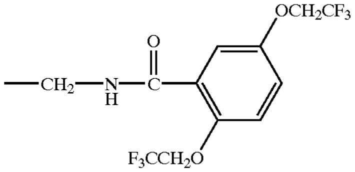 |
| 1375 | 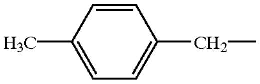 | 1 | 2 | 0 | R | H | 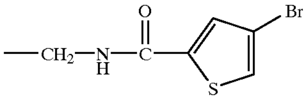 |
TABLE 1.126
| Compd. No. | 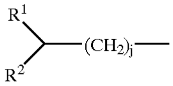 | k | m | n | chirality | $R^3$ | 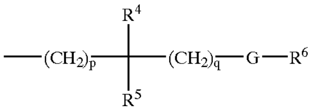 |
|---|---|---|---|---|---|---|---|
| 1376 | 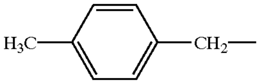 | 1 | 2 | 0 | R | H | 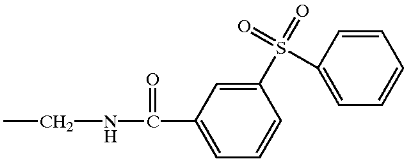 |
| 1377 | 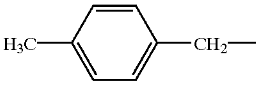 | 1 | 2 | 0 | R | H | 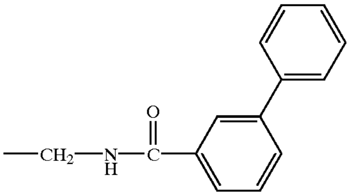 |
| 1378 | 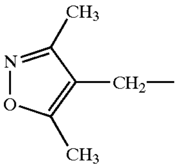 | 1 | 2 | 0 | R | H | 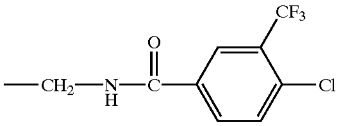 |
| 1379 | 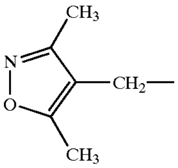 | 1 | 2 | 0 | R | H | 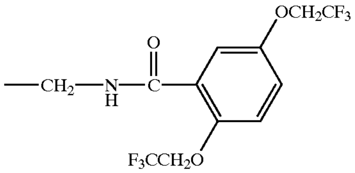 |

TABLE 1.126-continued
| Compd. No. | 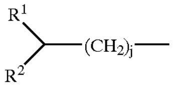 | k | m | n | chirality | $R^3$ | 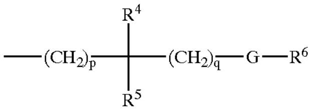 |
|---|---|---|---|---|---|---|---|
| 1380 | 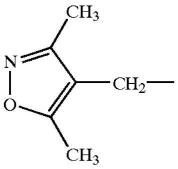 | 1 | 2 | 0 | R | H | 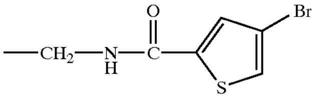 |
| 1381 | 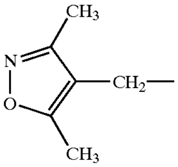 | 1 | 2 | 0 | R | H | 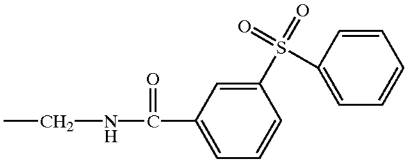 |
| 1382 | 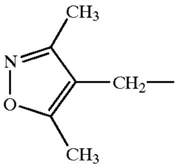 | 1 | 2 | 0 | R | H | 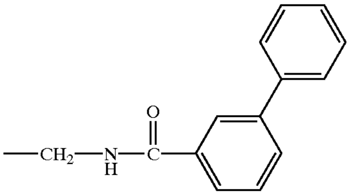 |
| 1383 | 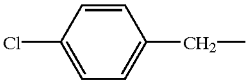 | 2 | 2 | 1 | — | H | 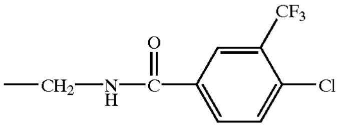 |
| 1384 | 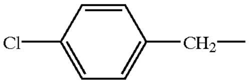 | 2 | 2 | 1 | — | H | 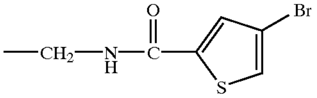 |
| 1385 | 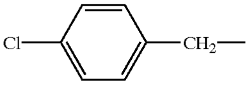 | 2 | 2 | 1 | — | H | 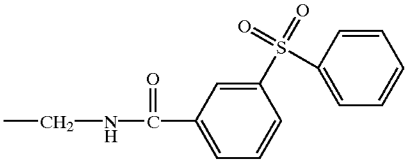 |
| 1386 | 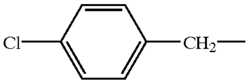 | 2 | 2 | 1 | — | H | 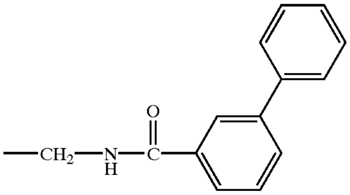 |

TABLE 1.127
| Compd. No. | 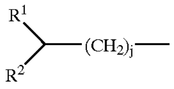 | k | m | n | chirality | $R^3$ | 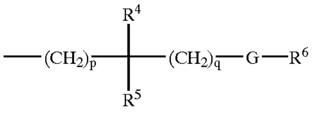 |
|---|---|---|---|---|---|---|---|
| 1387 | 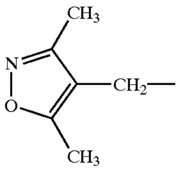 | 1 | 2 | 0 | R | H | 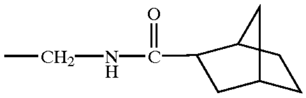 |
| 1388 | 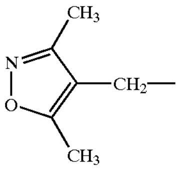 | 1 | 2 | 0 | R | H | 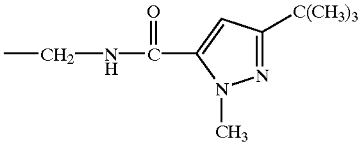 |
| 1389 | 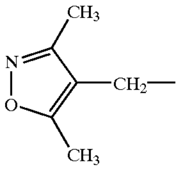 | 1 | 2 | 0 | R | H | 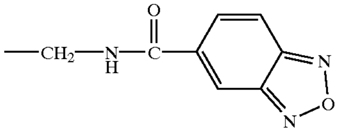 |
| 1390 | 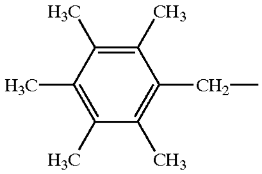 | 1 | 2 | 0 | R | H | 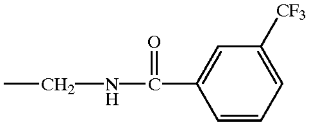 |
| 1391 | 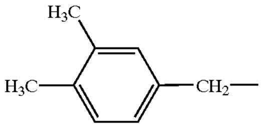 | 1 | 2 | 0 | R | H | 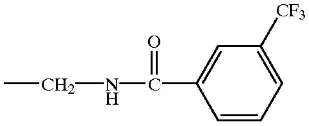 |
| 1392 | 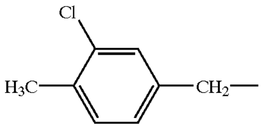 | 1 | 2 | 0 | R | H | 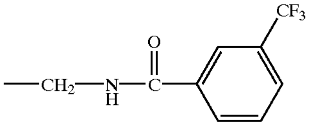 |
| 1393 | 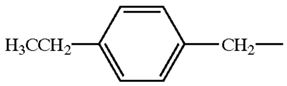 | 1 | 2 | 0 | R | H | 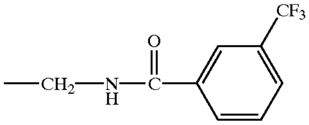 |
| 1394 | 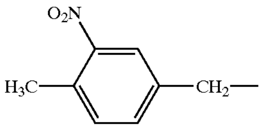 | 1 | 2 | 0 | R | H | 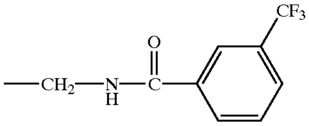 |
| 1395 | 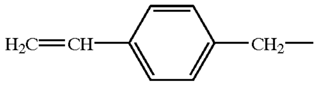 | 1 | 2 | 0 | R | H | 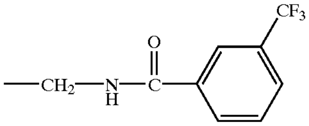 |

TABLE 1.127-continued
| Compd. No. | 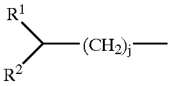 | k | m | n | chirality | $R^3$ | 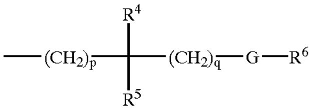 |
|---|---|---|---|---|---|---|---|
| 1396 | 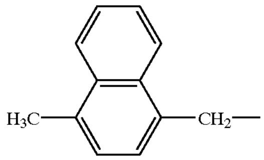 | 1 | 2 | 0 | R | H | 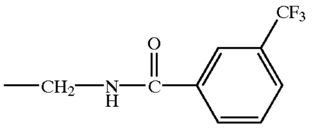 |
| 1397 | 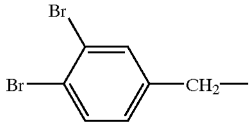 | 1 | 2 | 0 | R | H | 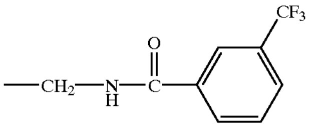 |
TABLE 1.128
| Compd. No. | 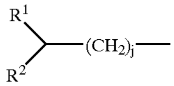 | k | m | n | chirality | $R^3$ | 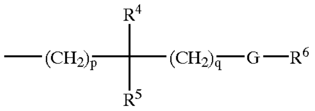 |
|---|---|---|---|---|---|---|---|
| 1398 | 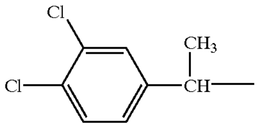 | 1 | 2 | 0 | R | H | 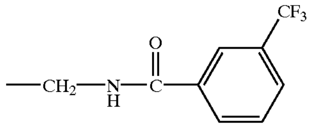 |
| 1399 | 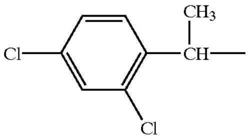 | 1 | 2 | 0 | R | H | 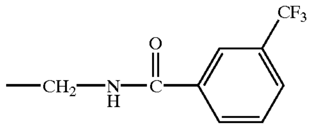 |
| 1400 | 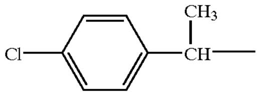 | 1 | 2 | 0 | R | H | 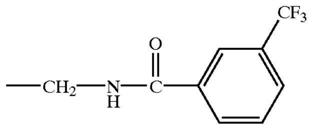 |
| 1401 | 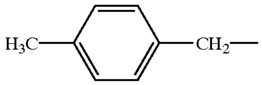 | 1 | 2 | 0 | R | H | 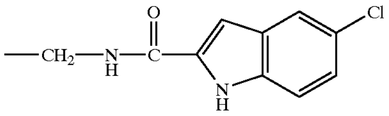 |
| 1402 | 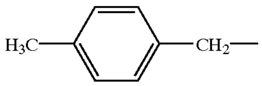 | 1 | 2 | 0 | R | H | 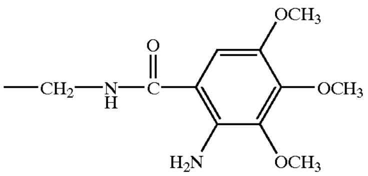 |
| 1403 | 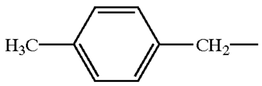 | 1 | 2 | 0 | R | H | 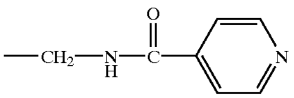 |

TABLE 1.128-continued
| Compd. No. | 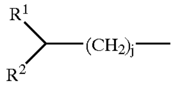 | k | m | n | chirality | $R^3$ | 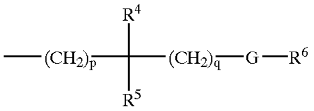 |
|---|---|---|---|---|---|---|---|
| 1404 | 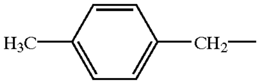 | 1 | 2 | 0 | R | H | 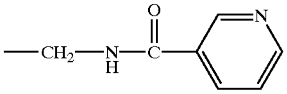 |
| 1405 | 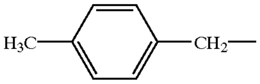 | 1 | 2 | 0 | R | H | 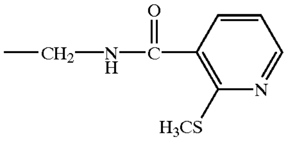 |
| 1406 | 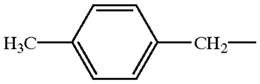 | 1 | 2 | 0 | R | H | 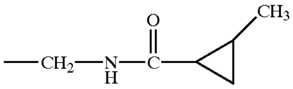 |
| 1407 | 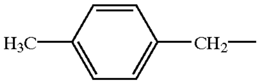 | 1 | 2 | 0 | R | H | 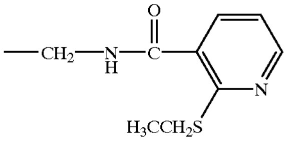 |
| 1408 | 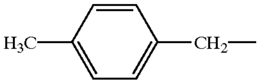 | 1 | 2 | 0 | R | H | 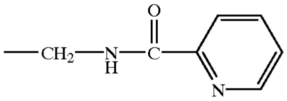 |
TABLE 1.129
| Compd. No. | 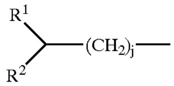 | k | m | n | chirality | $R^3$ | 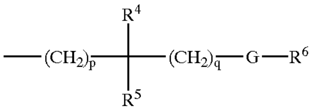 |
|---|---|---|---|---|---|---|---|
| 1409 | 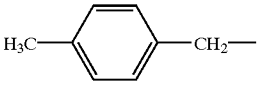 | 1 | 2 | 0 | R | H | 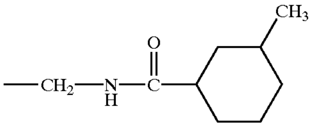 |
| 1410 | 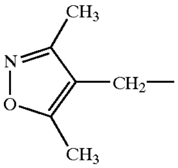 | 1 | 2 | 0 | R | H | 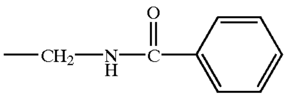 |
| 1411 | 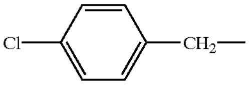 | 1 | 2 | 0 | R | H | 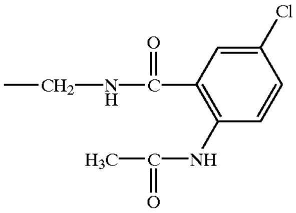 |

TABLE 1.129-continued
| Compd. No. | 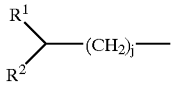 | k | m | n | chirality | $R^3$ | 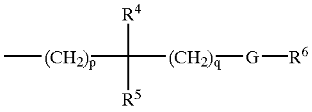 |
|---|---|---|---|---|---|---|---|
| 1412 | 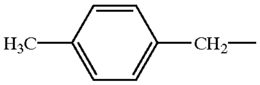 | 1 | 2 | 0 | R | H | 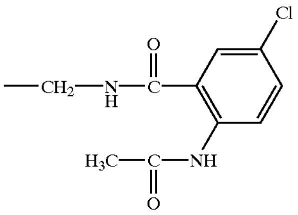 |
| 1413 | 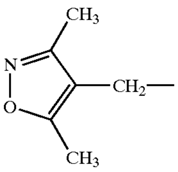 | 1 | 2 | 0 | R | H | 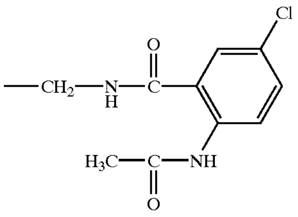 |
| 1414 | 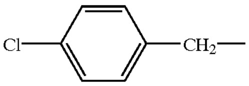 | 2 | 2 | 1 | — | H | 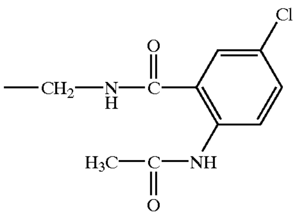 |
| 1415 | 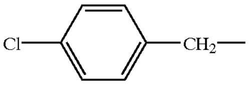 | 1 | 2 | 0 | R | H | 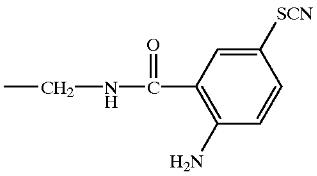 |
| 1416 | 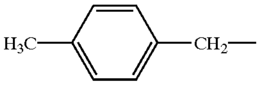 | 1 | 2 | 0 | R | H | 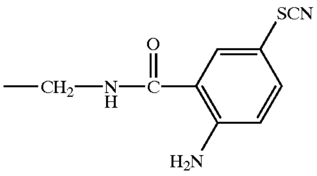 |
| 1417 | 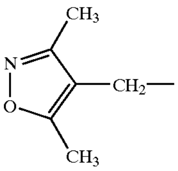 | 1 | 2 | 0 | R | H | 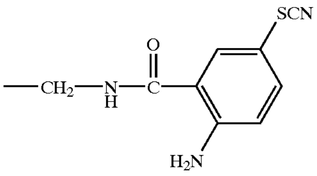 |
| 1418 | 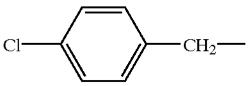 | 2 | 2 | 1 | — | H | 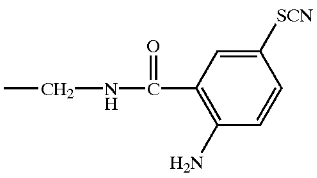 |

TABLE 1.129-continued
| Compd. No. | 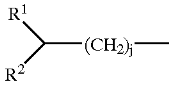 | k | m | n | chirality | $R^3$ | 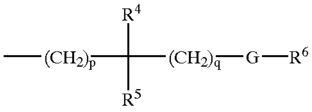 |
|---|---|---|---|---|---|---|---|
| 1419 | 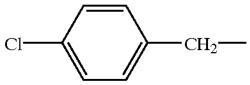 | 1 | 2 | 0 | R | H | 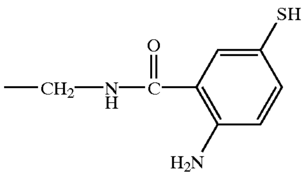 |
TABLE 1.130
| Compd. No. | 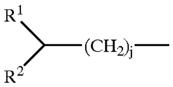 | k | m | n | chirality | $R^3$ | 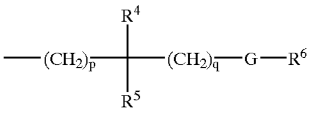 |
|---|---|---|---|---|---|---|---|
| 1420 | 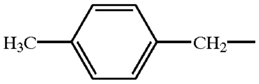 | 1 | 2 | 0 | R | H | 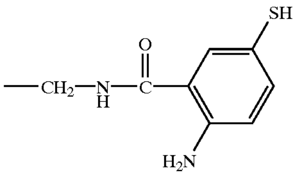 |
| 1421 | 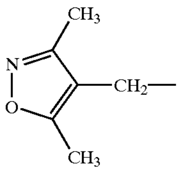 | 1 | 2 | 0 | R | H | 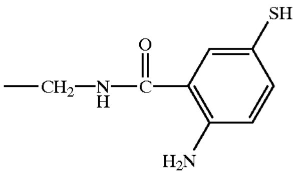 |
| 1422 | 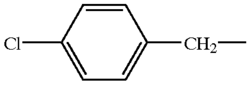 | 2 | 2 | 1 | — | H | 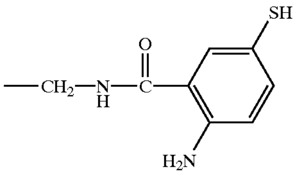 |
| 1423 | 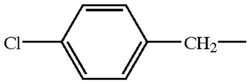 | 1 | 2 | 0 | R | H | 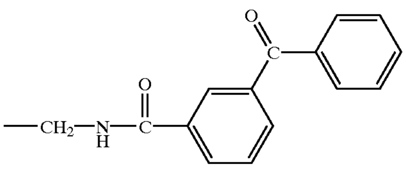 |
| 1424 | 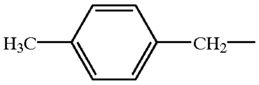 | 1 | 2 | 0 | R | H | 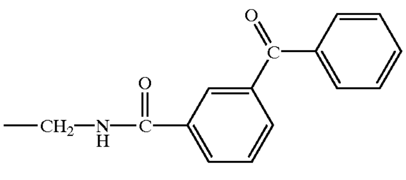 |

TABLE 1.130-continued
| Compd. No. | 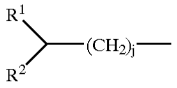 | k | m | n | chirality | $R^3$ | 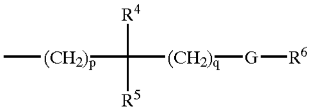 |
|---|---|---|---|---|---|---|---|
| 1425 | 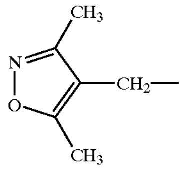 | 1 | 2 | 0 | R | H | 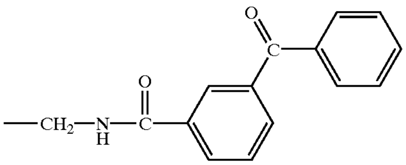 |
| 1426 | 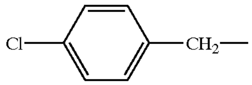 | 2 | 2 | 1 | — | H | 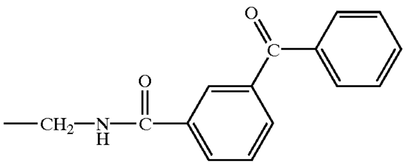 |
| 1427 | 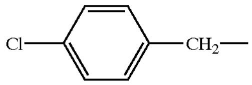 | 2 | 2 | 1 | — | H | 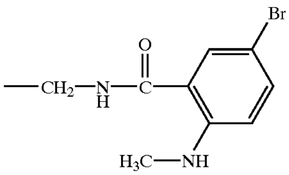 |
| 1428 | 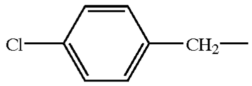 | 2 | 2 | 1 | — | H | 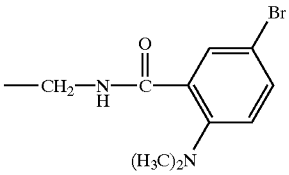 |
| 1429 | 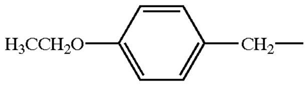 | 2 | 2 | 1 | — | H | 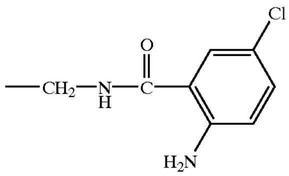 |
| 1430 | 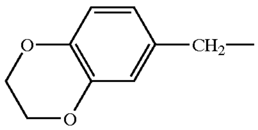 | 2 | 2 | 1 | — | H | 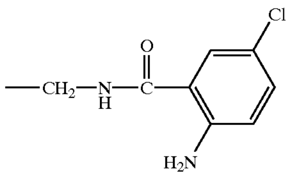 |

TABLE 1.131
| Compd. No. | 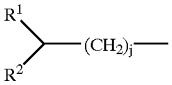 | k | m | n | chirality | $R^3$ | 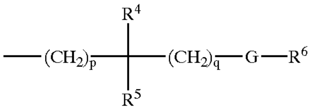 |
|---|---|---|---|---|---|---|---|
| 1431 | 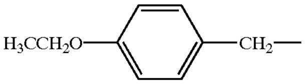 | 2 | 2 | 1 | — | H | 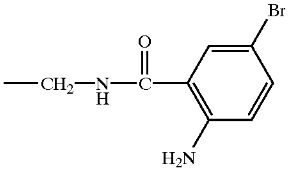 |
| 1432 | 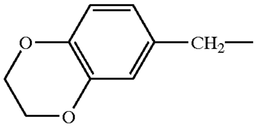 | 2 | 2 | 1 | — | H | 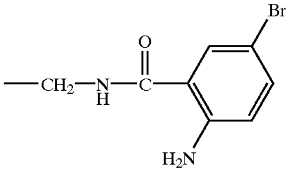 |
| 1433 | 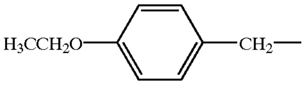 | 2 | 2 | 1 | — | H | 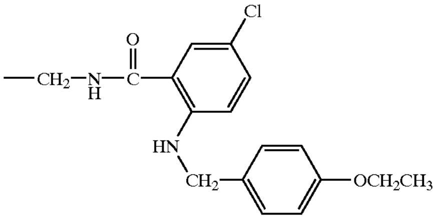 |
| 1434 | 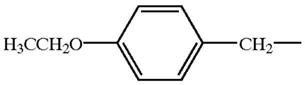 | 2 | 2 | 1 | — | H | 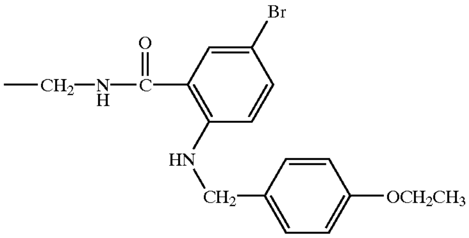 |
| 1435 | 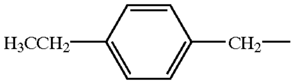 | 2 | 2 | 1 | — | H | 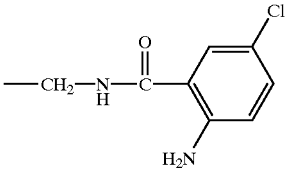 |
| 1436 | 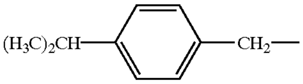 | 2 | 2 | 1 | — | H | 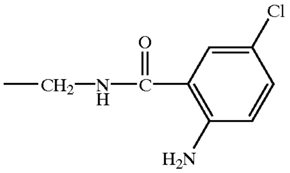 |
| 1437 | 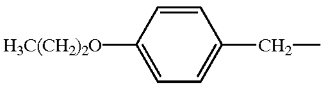 | 2 | 2 | 1 | — | H | 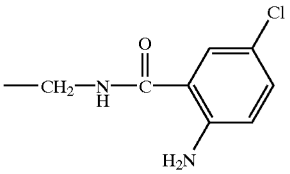 |

TABLE 1.131-continued
| Compd. No. | 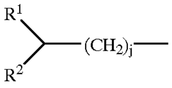 | k | m | n | chirality | $R^3$ | 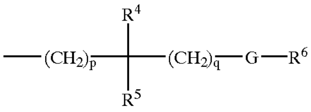 |
|---|---|---|---|---|---|---|---|
| 1438 | 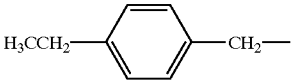 | 2 | 2 | 1 | — | H | 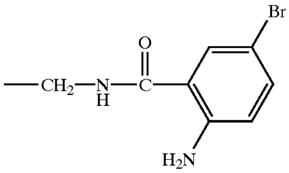 |
| 1439 | 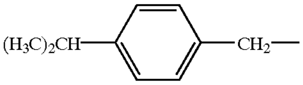 | 2 | 2 | 1 | — | H | 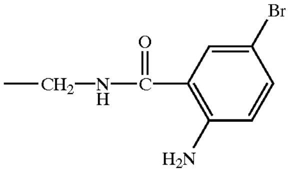 |
| 1440 | 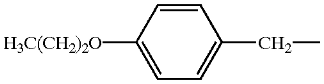 | 2 | 2 | 1 | — | H | 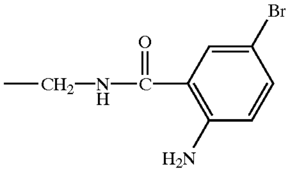 |
| 1441 | 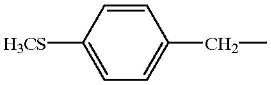 | 2 | 2 | 1 | — | H | 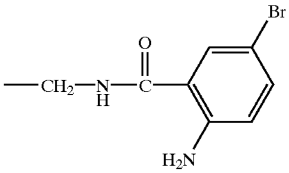 |
TABLE 1.132
| Compd. No. | 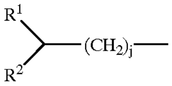 | k | m | n | chirality | $R^3$ | 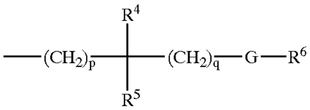 |
|---|---|---|---|---|---|---|---|
| 1442 | 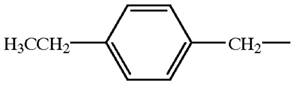 | 2 | 2 | 1 | — | H | 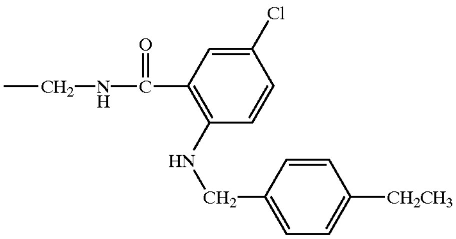 |

TABLE 1.132-continued
| Compd. No. | 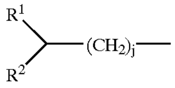 | k | m | n | chirality | $R^3$ | 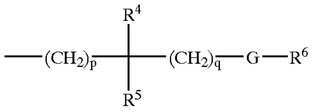 |
|---|---|---|---|---|---|---|---|
| 1443 | 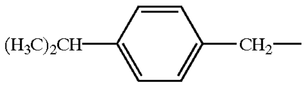 | 2 | 2 | 1 | — | H | 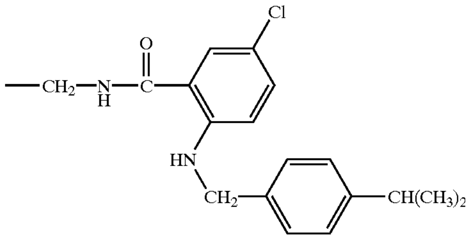 |
| 1444 | 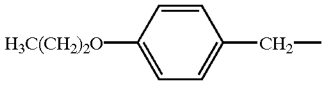 | 2 | 2 | 1 | — | H | 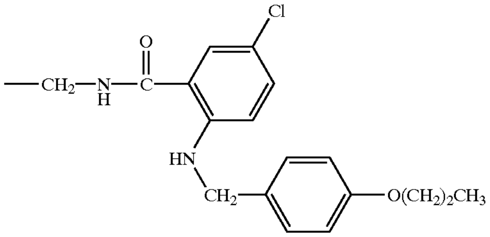 |
| 1445 | 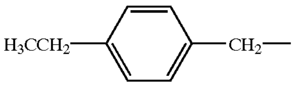 | 2 | 2 | 1 | — | H | 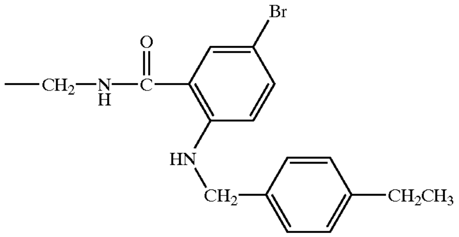 |
| 1446 | 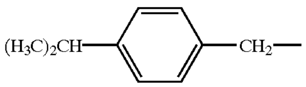 | 2 | 2 | 1 | — | H | 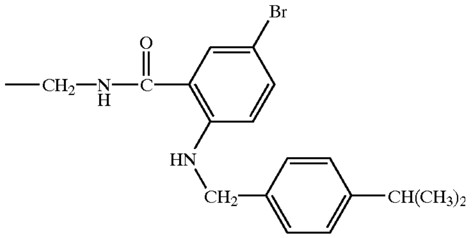 |
| 1447 | 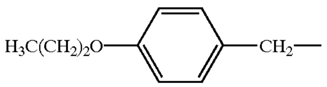 | 2 | 2 | 1 | — | H | 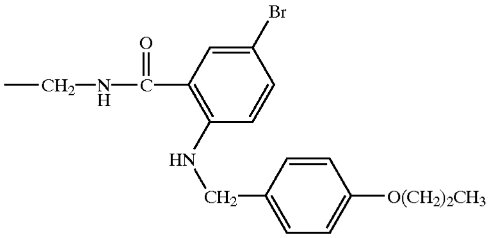 |
| 1448 | 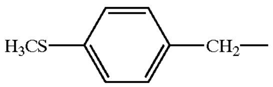 | 2 | 2 | 1 | — | H | 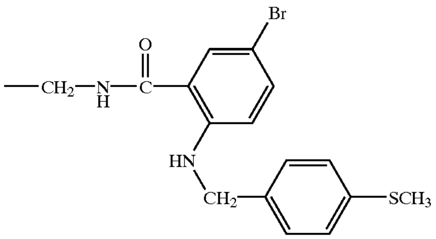 |

TABLE 1.132-continued
| Compd. No. | 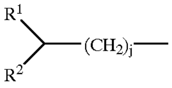 | k | m | n | chirality | $R^3$ | 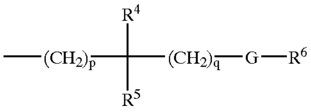 |
|---|---|---|---|---|---|---|---|
| 1449 | 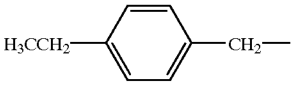 | 2 | 2 | 1 | — | H | 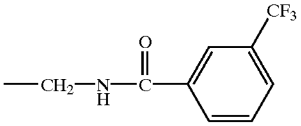 |
| 1450 | 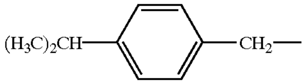 | 2 | 2 | 1 | — | H | 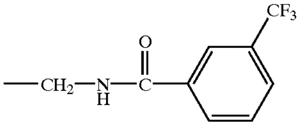 |
| 1451 | 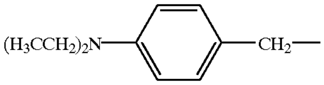 | 2 | 2 | 1 | — | H | 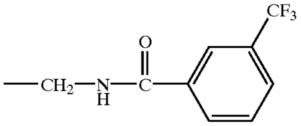 |
| 1452 | 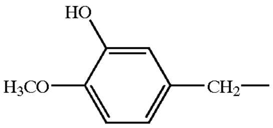 | 2 | 2 | 1 | — | H | 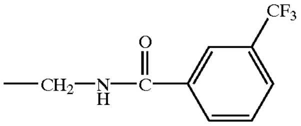 |
TABLE 1.133
| Compd. No. | 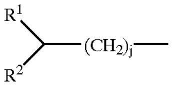 | k | m | n | chirality | $R^3$ | 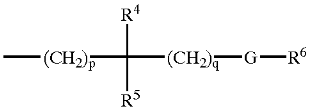 |
|---|---|---|---|---|---|---|---|
| 1453 | 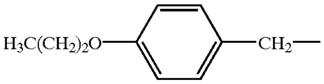 | 2 | 2 | 1 | — | H | 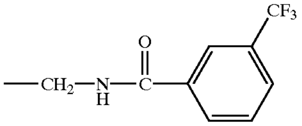 |
| 1454 | 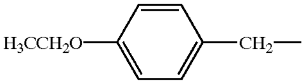 | 2 | 2 | 1 | — | H | 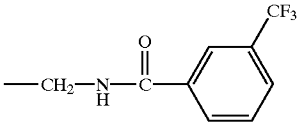 |
| 1455 | 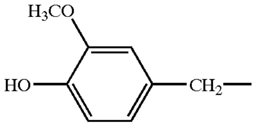 | 2 | 2 | 1 | — | H | 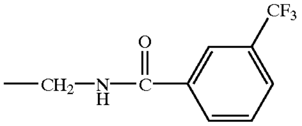 |
| 1456 | 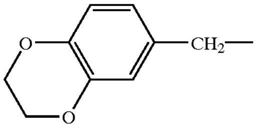 | 2 | 2 | 1 | — | H | 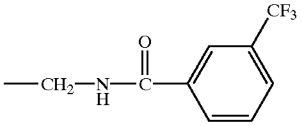 |

TABLE 1.133-continued
| Compd. No. | 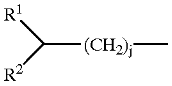 | k | m | n | chirality | $R^3$ | 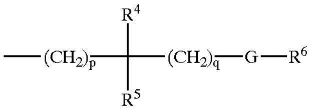 |
|---|---|---|---|---|---|---|---|
| 1457 | 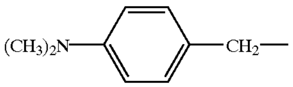 | 2 | 2 | 1 | — | H | 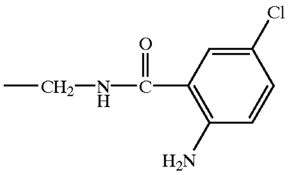 |
| 1458 | 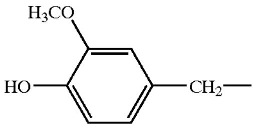 | 2 | 2 | 1 | — | H | 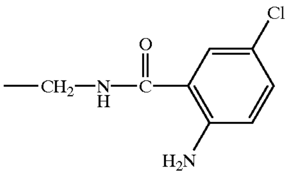 |
| 1459 | 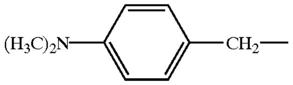 | 2 | 2 | 1 | — | H | 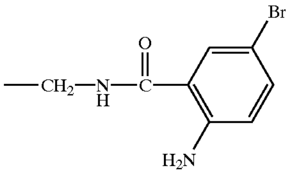 |
| 1460 | 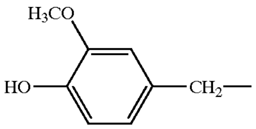 | 2 | 2 | 1 | — | H | 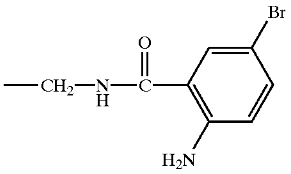 |
| 1461 | 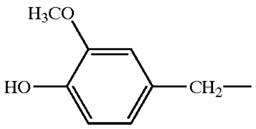 | 2 | 2 | 1 | — | H | 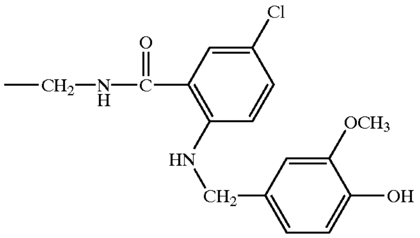 |
| 1462 | 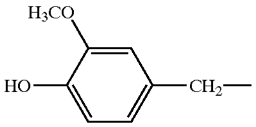 | 2 | 2 | 1 | — | H | 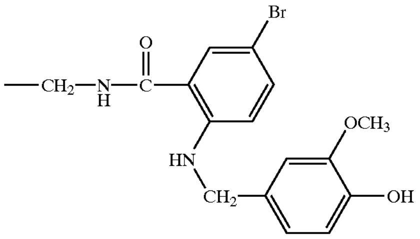 |
| 1463 | 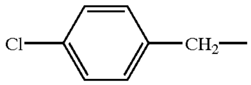 | 2 | 1 | 1 | — | H | 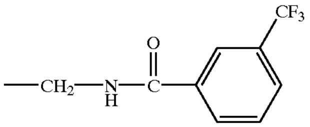 |

TABLE 1.134
| Compd. No. | 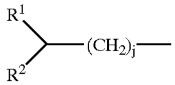 | k | m | n | chirality | $R^3$ | 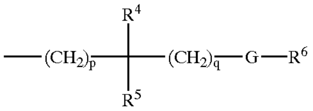 |
|---|---|---|---|---|---|---|---|
| 1464 | 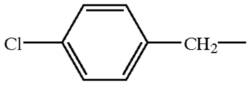 | 2 | 1 | 1 | — | H | 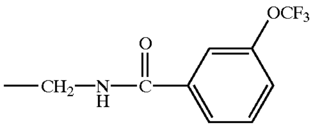 |
| 1465 | 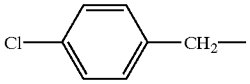 | 2 | 1 | 1 | — | H | 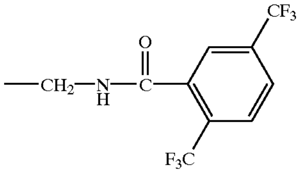 |
| 1466 | 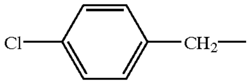 | 2 | 1 | 1 | — | H | 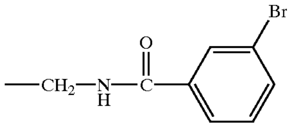 |
| 1467 | 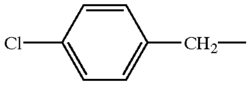 | 2 | 1 | 1 | — | H | 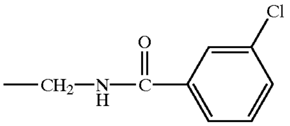 |
| 1468 | 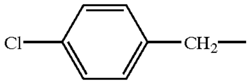 | 2 | 1 | 1 | — | H | 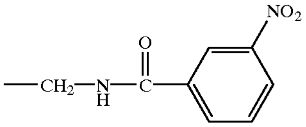 |
| 1469 | 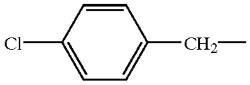 | 2 | 1 | 1 | — | H | 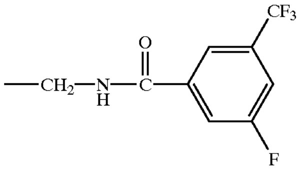 |
| 1470 | 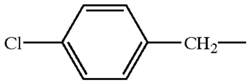 | 2 | 1 | 1 | — | H | 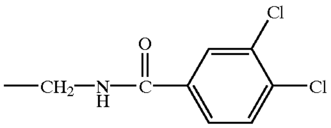 |
| 1471 | 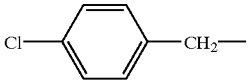 | 2 | 1 | 1 | — | H | 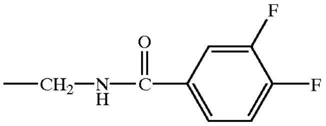 |
| 1472 | 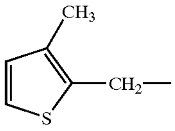 | 1 | 2 | 0 | R | H | 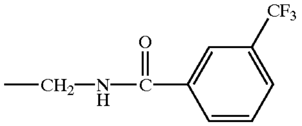 |

TABLE 1.134-continued
| Compd. No. | 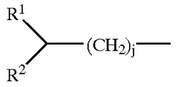 | k | m | n | chirality | $R^3$ | 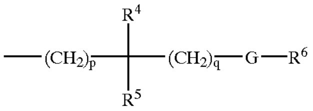 |
| --- | --- | --- | --- | --- | --- | --- | --- |
| 1473 | 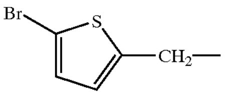 | 1 | 2 | 0 | R | H | 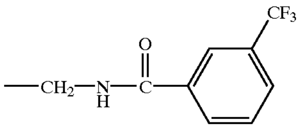 |
| 1474 | 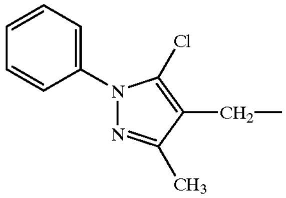 | 1 | 2 | 0 | R | H | 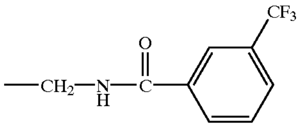 |
TABLE 1.135
| Compd. No. | 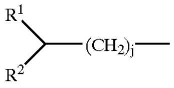 | k | m | n | chirality | $R^3$ | 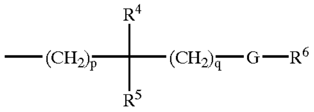 |
| --- | --- | --- | --- | --- | --- | --- | --- |
| 1475 | 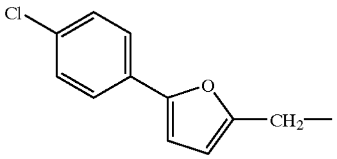 | 1 | 2 | 0 | R | H | 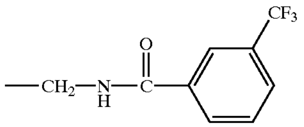 |
| 1476 | 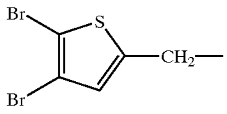 | 1 | 2 | 0 | R | H | 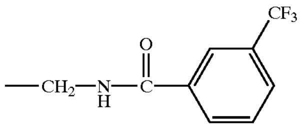 |
| 1477 | 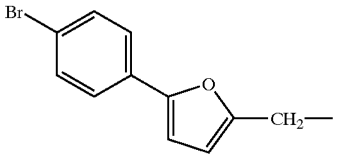 | 1 | 2 | 0 | R | H | 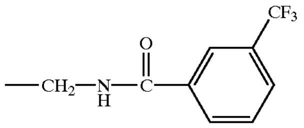 |
| 1478 | 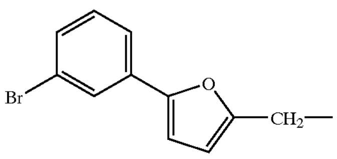 | 1 | 2 | 0 | R | H | 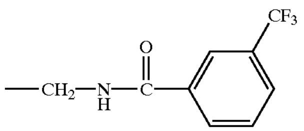 |
| 1479 | 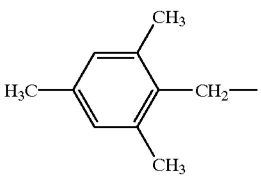 | 1 | 2 | 0 | R | H | 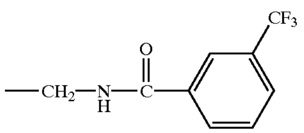 |

TABLE 1.135-continued
| Compd. No. | 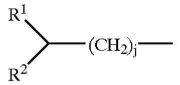 | k | m | n | chirality | $R^3$ | 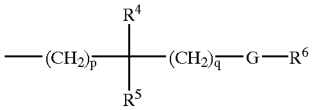 |
|---|---|---|---|---|---|---|---|
| 1480 | 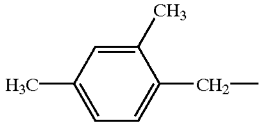 | 1 | 2 | 0 | R | H | 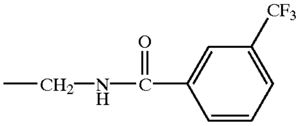 |
| 1481 | 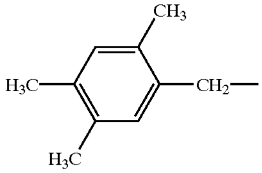 | 1 | 2 | 0 | R | H | 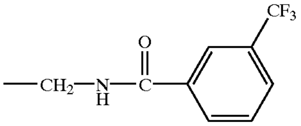 |
| 1482 | 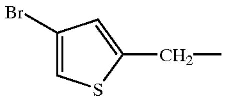 | 1 | 2 | 0 | R | H | 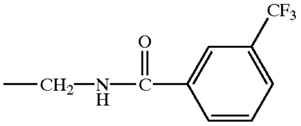 |
| 1483 | 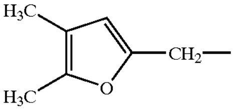 | 1 | 2 | 0 | R | H | 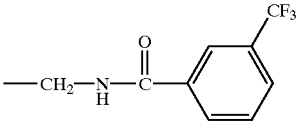 |
| 1484 | 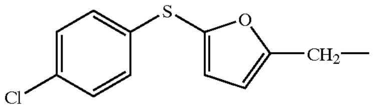 | 1 | 2 | 0 | R | H | 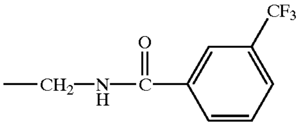 |
| 1485 | 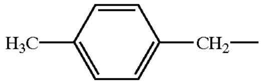 | 1 | 2 | 0 | R | H | 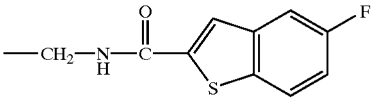 |
TABLE 1.136
| Compd. No. | 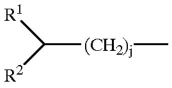 | k | m | n | chirality | $R^3$ | 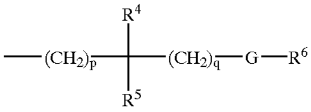 |
|---|---|---|---|---|---|---|---|
| 1486 | 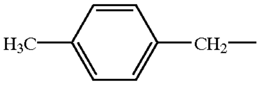 | 1 | 2 | 0 | R | H | 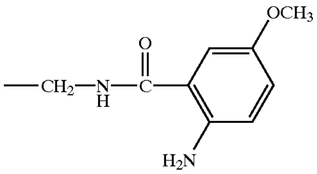 |

TABLE 1.136-continued
| Compd. No. | 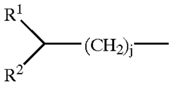 | k | m | n | chirality | $R^3$ | 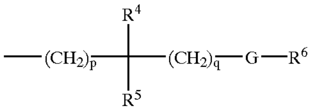 |
|---|---|---|---|---|---|---|---|
| 1487 | 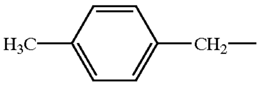 | 1 | 2 | 0 | R | H | 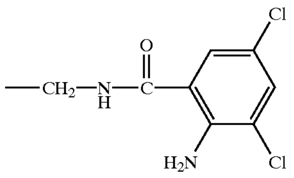 |
| 1488 | 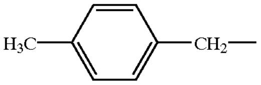 | 1 | 2 | 0 | R | H | 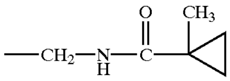 |
| 1489 | 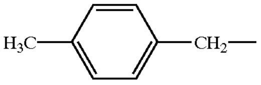 | 1 | 2 | 0 | R | H | 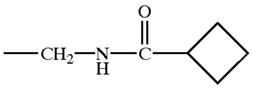 |
| 1490 | 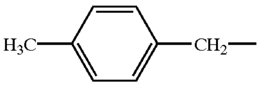 | 1 | 2 | 0 | R | H | 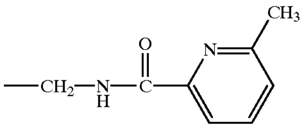 |
| 1491 | 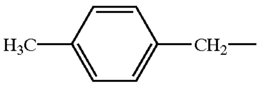 | 1 | 2 | 0 | R | H | 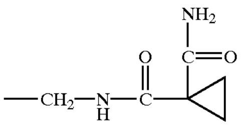 |
| 1492 | 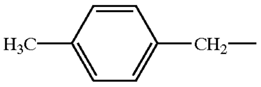 | 1 | 2 | 0 | R | H | 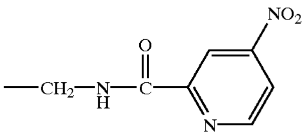 |
| 1493 | 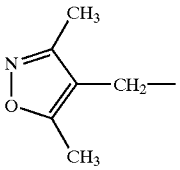 | 1 | 2 | 0 | R | H | 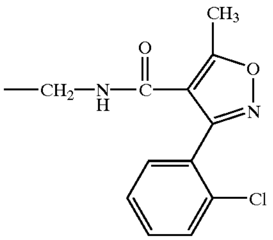 |
| 1494 | 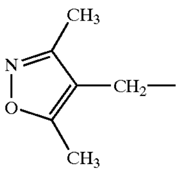 | 1 | 2 | 0 | R | H | 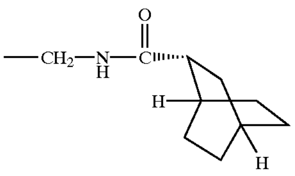 |
| 1495 | 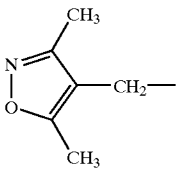 | 1 | 2 | 0 | R | H | 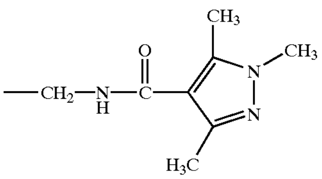 |

TABLE 1.136-continued
| Compd. No. | 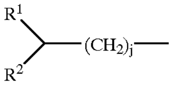 | k | m | n | chirality | $R^3$ | 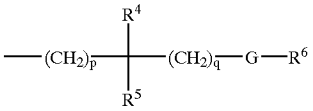 |
|---|---|---|---|---|---|---|---|
| 1496 | 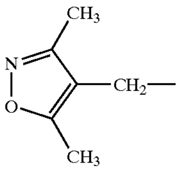 | 1 | 2 | 0 | R | H | 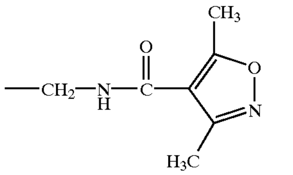 |
TABLE 1.137
| Compd. No. | 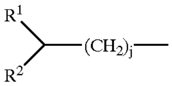 | k | m | n | chirality | $R^3$ | 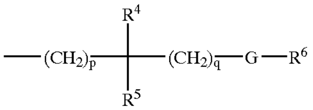 |
|---|---|---|---|---|---|---|---|
| 1497 | 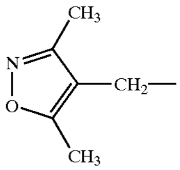 | 1 | 2 | 0 | R | H | 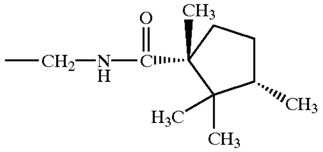 |
| 1498 | 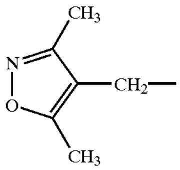 | 1 | 2 | 0 | R | H | 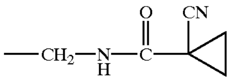 |
| 1499 | 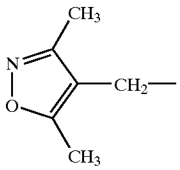 | 1 | 2 | 0 | R | H | 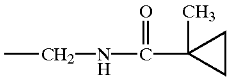 |
| 1500 | 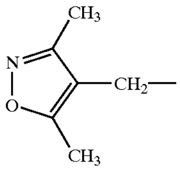 | 1 | 2 | 0 | R | H | 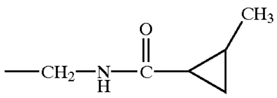 |
| 1501 | 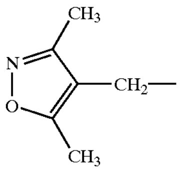 | 1 | 2 | 0 | R | H | 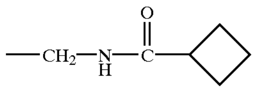 |

TABLE 1.137-continued
| Compd. No. | 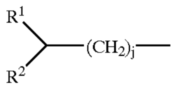 | k | m | n | chirality | $R^3$ | 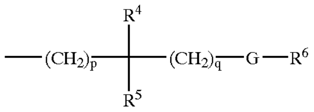 |
|---|---|---|---|---|---|---|---|
| 1502 | 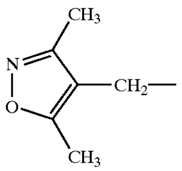 | 1 | 2 | 0 | R | H | 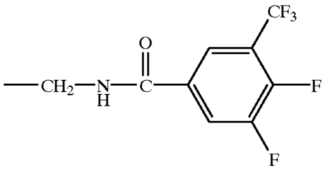 |
| 1503 | 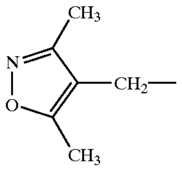 | 1 | 2 | 0 | R | H | 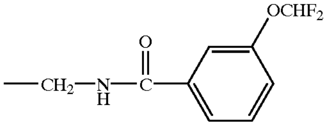 |
| 1504 | 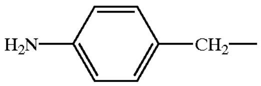 | 1 | 2 | 0 | R | H | 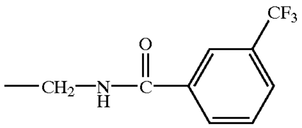 |
| 1505 | 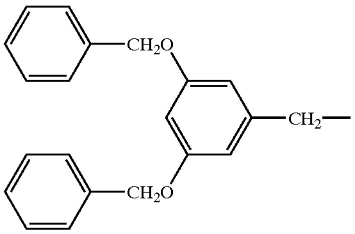 | 1 | 2 | 0 | R | H | 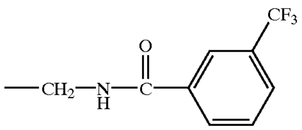 |
| 1506 | 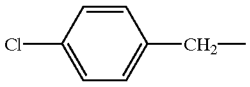 | 2 | 1 | 1 | — | H | 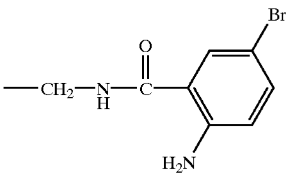 |
| 1507 | 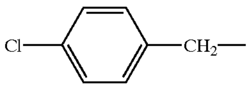 | 2 | 1 | 1 | — | H | 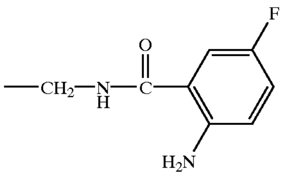 |

TABLE 1.138
| Compd. No. | 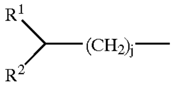 | k | m | n | chirality | $R^3$ | 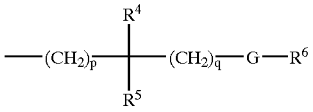 |
|---|---|---|---|---|---|---|---|
| 1508 | 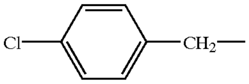 | 2 | 1 | 1 | — | H | 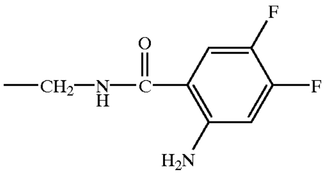 |
| 1509 | 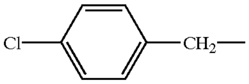 | 2 | 1 | 1 | — | H | 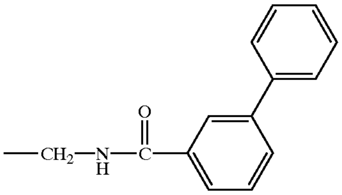 |
| 1510 | 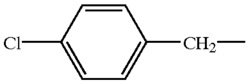 | 2 | 1 | 1 | — | H | 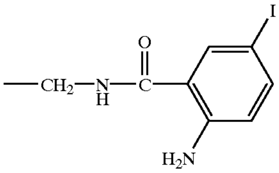 |
| 1511 | 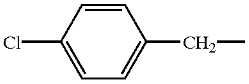 | 2 | 1 | 1 | — | H | 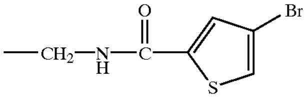 |
| 1512 | 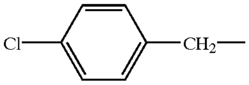 | 2 | 1 | 1 | — | H | 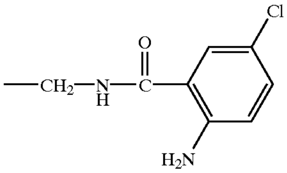 |
| 1513 | 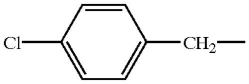 | 2 | 1 | 1 | — | H | 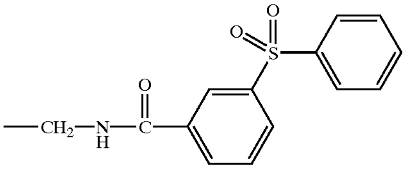 |
| 1514 | 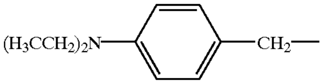 | 2 | 2 | 1 | — | H | 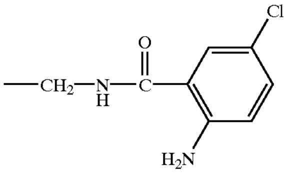 |
| 1515 | 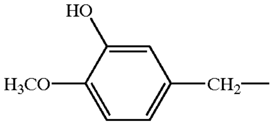 | 2 | 2 | 1 | — | H | 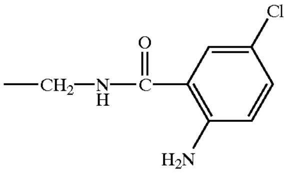 |

TABLE 1.138-continued
| Compd. No. | 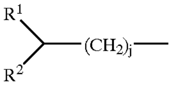 | k | m | n | chirality | R³ | 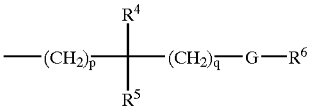 |
|---|---|---|---|---|---|---|---|
| 1516 | 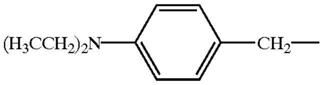 | 2 | 2 | 1 | — | H | 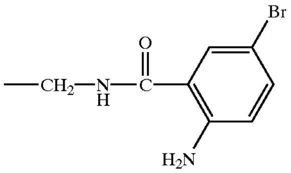 |
| 1517 | 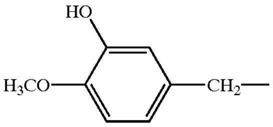 | 2 | 2 | 1 | — | H | 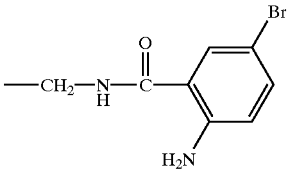 |
| 1518 | 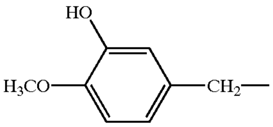 | 2 | 2 | 1 | — | H | 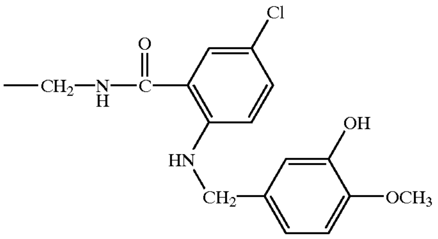 |
TABLE 1.139
| Compd. No. | 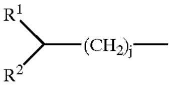 | k | m | n | chirality | R³ | 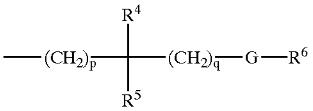 |
|---|---|---|---|---|---|---|---|
| 1519 | 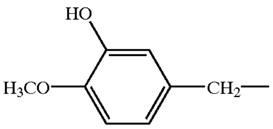 | 2 | 2 | 1 | — | H | 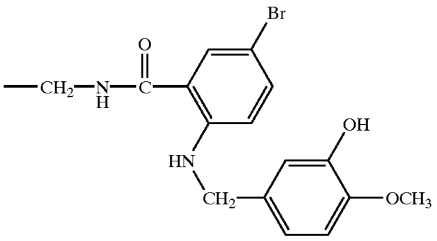 |
| 1520 | 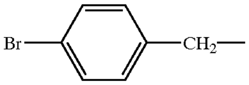 | 1 | 2 | 0 | R | H | 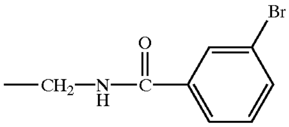 |
| 1521 | 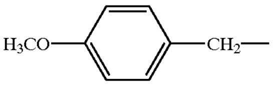 | 1 | 2 | 0 | R | H | 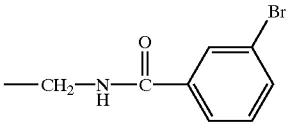 |

TABLE 1.139-continued
| Compd. No. | 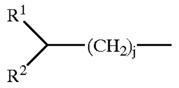 | k | m | n | chirality | $R^3$ | 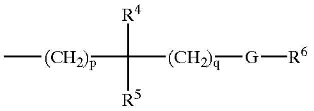 |
|---|---|---|---|---|---|---|---|
| 1522 | 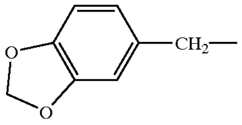 | 1 | 2 | 0 | R | H | 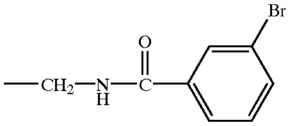 |
| 1523 | 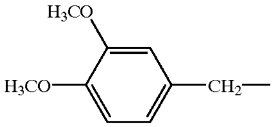 | 1 | 2 | 0 | R | H | 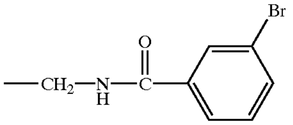 |
| 1524 | 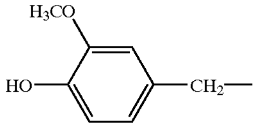 | 1 | 2 | 0 | R | H | 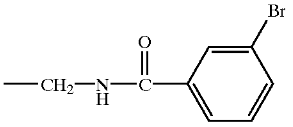 |
| 1525 | 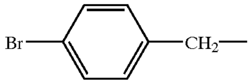 | 1 | 2 | 0 | R | H | 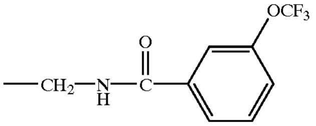 |
| 1526 | 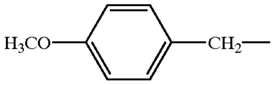 | 1 | 2 | 0 | R | H | 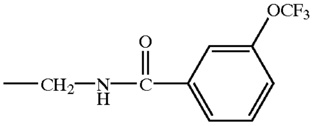 |
| 1527 | 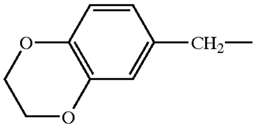 | 1 | 2 | 0 | R | H | 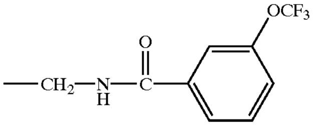 |
| 1528 | 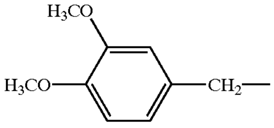 | 1 | 2 | 0 | R | H | 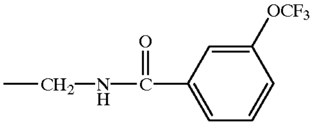 |
| 1529 | 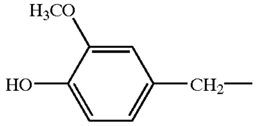 | 1 | 2 | 0 | R | H | 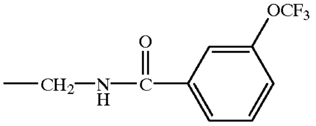 |

TABLE 1.140
| Compd. No. | 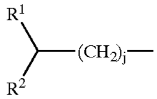 | k | m | n | chirality | $R^3$ | 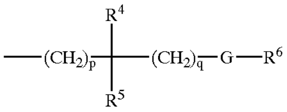 |
|---|---|---|---|---|---|---|---|
| 1530 | 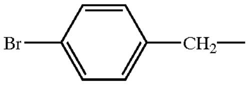 | 1 | 2 | 0 | R | H | 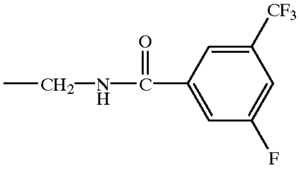 |
| 1531 | 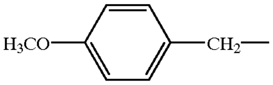 | 1 | 2 | 0 | R | H | 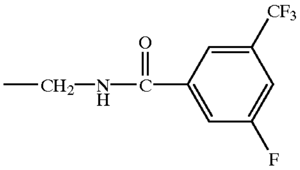 |
| 1532 | 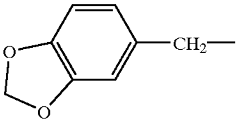 | 1 | 2 | 0 | R | H | 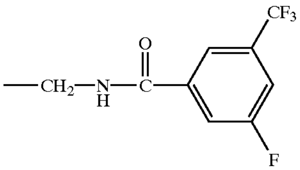 |
| 1533 | 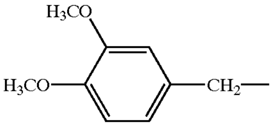 | 1 | 2 | 0 | R | H | 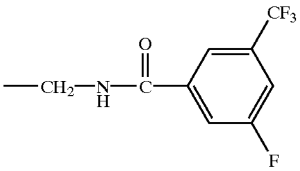 |
| 1534 | 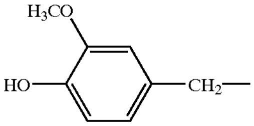 | 1 | 2 | 0 | R | H | 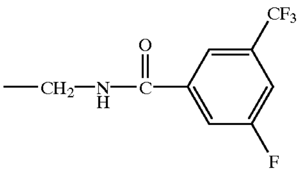 |
| 1535 | 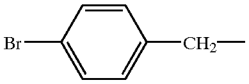 | 1 | 2 | 0 | R | H | 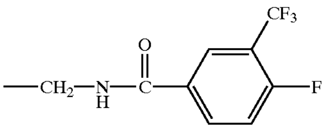 |
| 1536 | 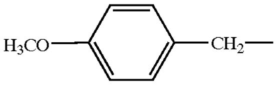 | 1 | 2 | 0 | R | H | 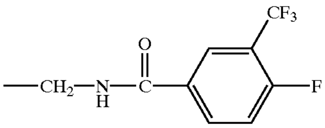 |
| 1537 | 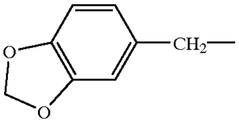 | 1 | 2 | 0 | R | H | 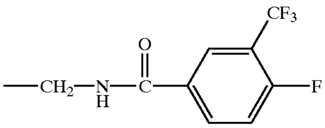 |
| 1538 | 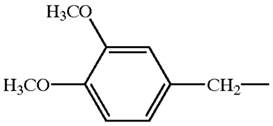 | 1 | 2 | 0 | R | H | 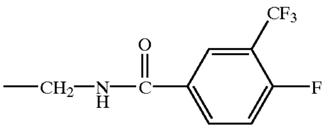 |

TABLE 1.140-continued
| Compd. No. | 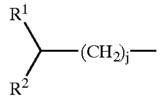 | k | m | n | chirality | $R^3$ | 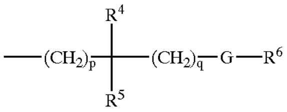 |
|---|---|---|---|---|---|---|---|
| 1539 | 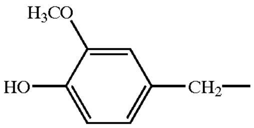 | 1 | 2 | 0 | R | H | 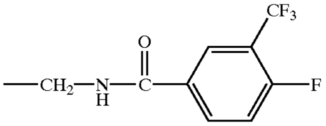 |
| 1540 | 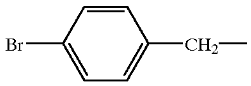 | 1 | 2 | 0 | R | H | 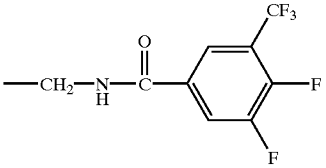 |
TABLE 1.141
| Compd. No. | 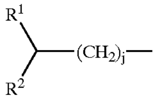 | k | m | n | chirality | $R^3$ | 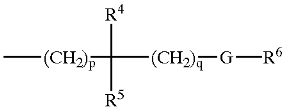 |
|---|---|---|---|---|---|---|---|
| 1541 | 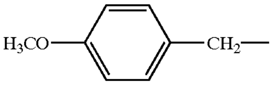 | 1 | 2 | 0 | R | H | 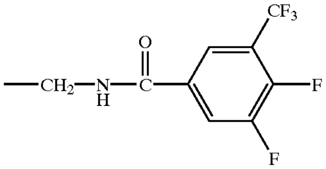 |
| 1542 | 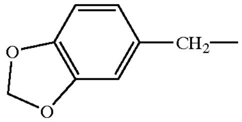 | 1 | 2 | 0 | R | H | 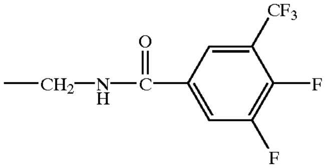 |
| 1543 | 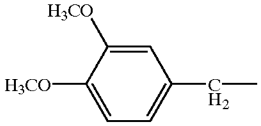 | 1 | 2 | 0 | R | H | 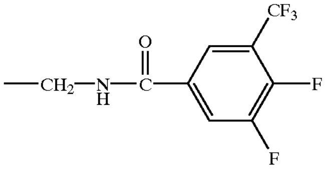 |
| 1544 | 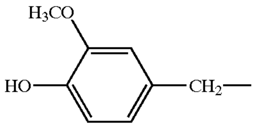 | 1 | 2 | 0 | R | H | 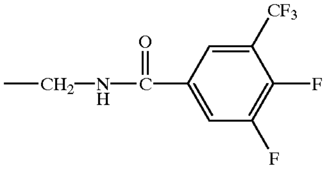 |
| 1545 | 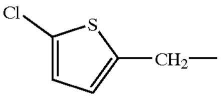 | 1 | 2 | 0 | R | H | 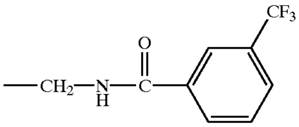 |

TABLE 1.141-continued
| Compd. No. | 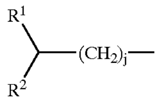 | k | m | n | chirality | $R^3$ | 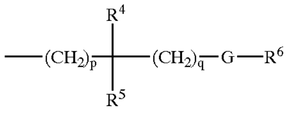 |
|---|---|---|---|---|---|---|---|
| 1546 | 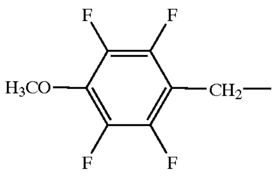 | 1 | 2 | 0 | R | H | 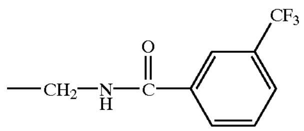 |
| 1547 | 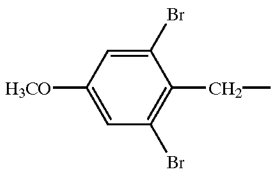 | 1 | 2 | 0 | R | H | 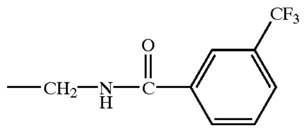 |
| 1548 | 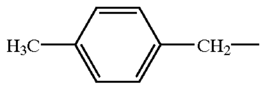 | 1 | 2 | 0 | R | H | 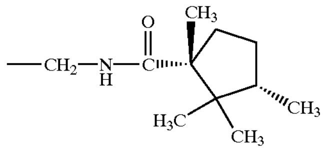 |
| 1549 | 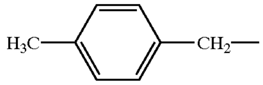 | 1 | 2 | 0 | R | H | 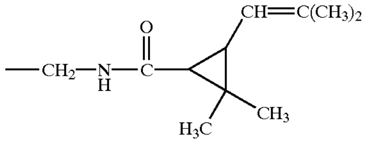 |
| 1550 | 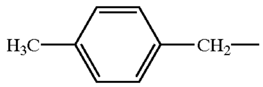 | 1 | 2 | 0 | R | H | 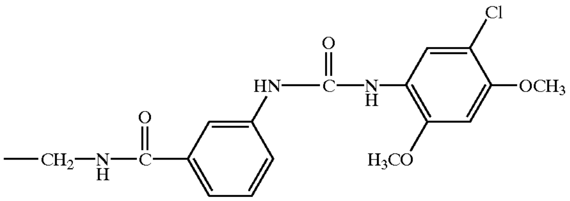 |
| 1551 | 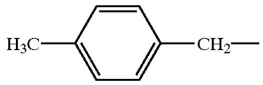 | 1 | 2 | 0 | R | H | 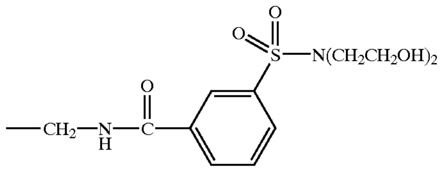 |
TABLE 1.142
| Compd. No. | 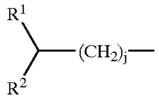 | k | m | n | chirality | $R^3$ | 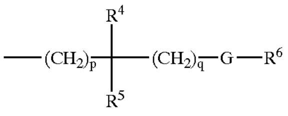 |
|---|---|---|---|---|---|---|---|
| 1552 | 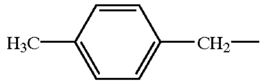 | 1 | 2 | 0 | R | H | 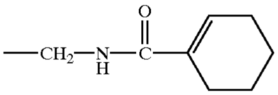 |

TABLE 1.142-continued
| Compd. No. | 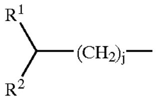 | k | m | n | chirality | $R^3$ | 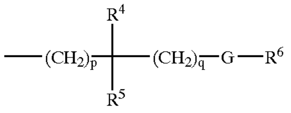 |
|---|---|---|---|---|---|---|---|
| 1553 | 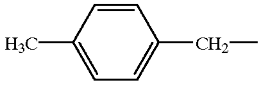 | 1 | 2 | 0 | R | H | 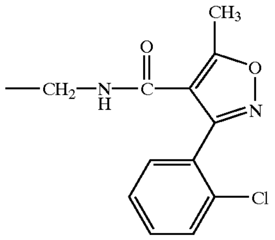 |
| 1554 | 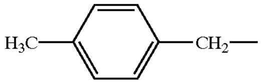 | 1 | 2 | 0 | R | H | 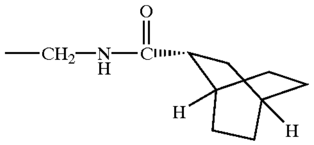 |
| 1555 | 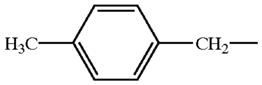 | 1 | 2 | 0 | R | H | 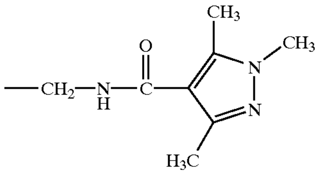 |
| 1556 | 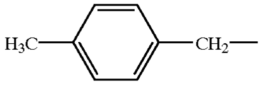 | 1 | 2 | 0 | R | H | 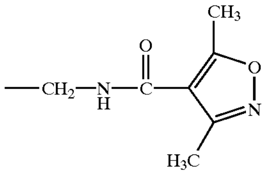 |
| 1557 | 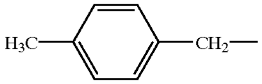 | 1 | 2 | 0 | R | H | 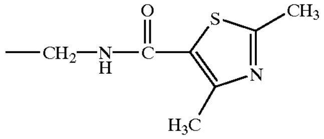 |
| 1558 | 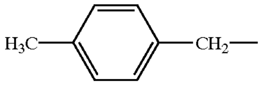 | 1 | 2 | 0 | R | H | 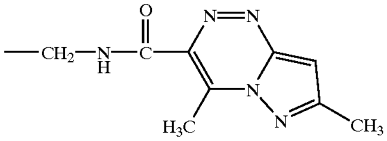 |
| 1559 | 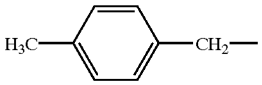 | 1 | 2 | 0 | R | H | 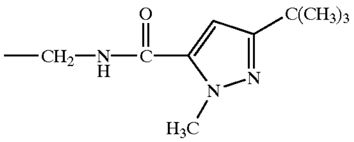 |
| 1560 | 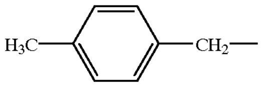 | 1 | 2 | 0 | R | H | 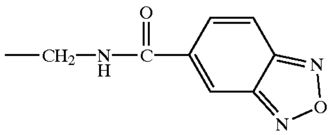 |

TABLE 1.142-continued
| Compd. No. | 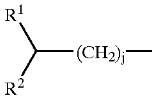 | k | m | n | chirality | $R^3$ | 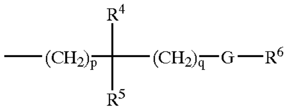 |
|---|---|---|---|---|---|---|---|
| 1561 | 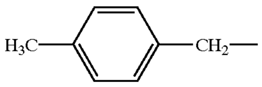 | 1 | 2 | 0 | R | H | 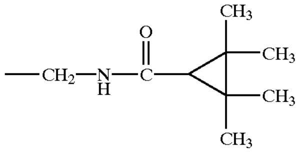 |
| 1562 | 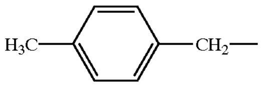 | 1 | 2 | 0 | R | H | 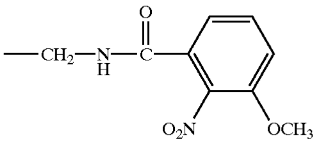 |
TABLE 1.143
| Compd. No. | 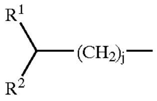 | k | m | n | chirality | $R^3$ | 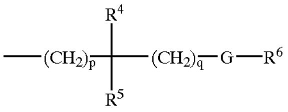 |
|---|---|---|---|---|---|---|---|
| 1563 | 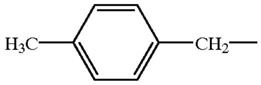 | 1 | 2 | 0 | R | H | 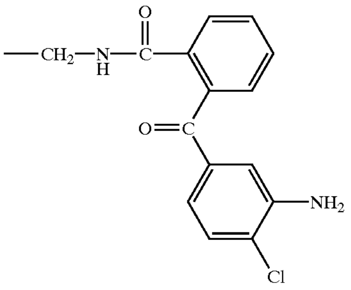 |
| 1564 | 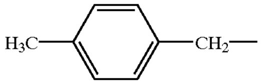 | 1 | 2 | 0 | R | H | 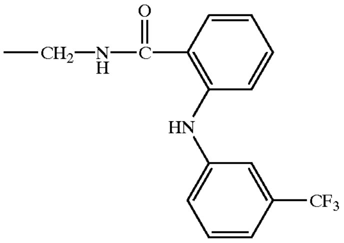 |
| 1565 | 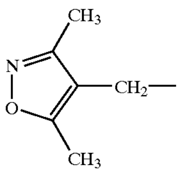 | 1 | 2 | 0 | R | H | 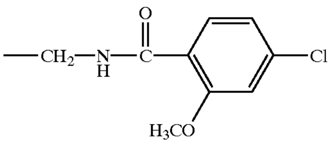 |

TABLE 1.143-continued
| Compd. No. | 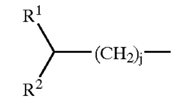 | k | m | n | chirality | $R^3$ | 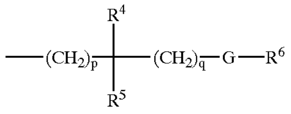 |
|---|---|---|---|---|---|---|---|
| 1566 | 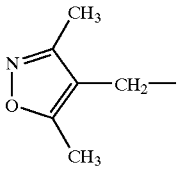 | 1 | 2 | 0 | R | H | 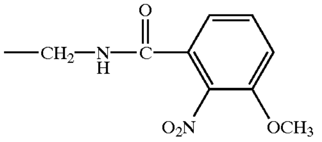 |
| 1567 | 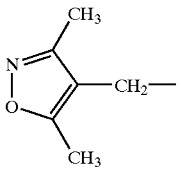 | 1 | 2 | 0 | R | H | 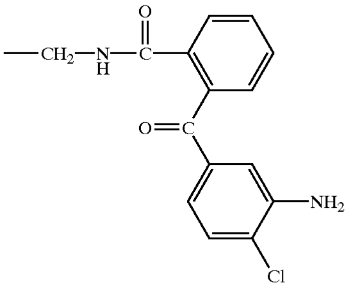 |
| 1568 | 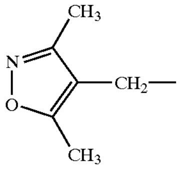 | 1 | 2 | 0 | R | H | 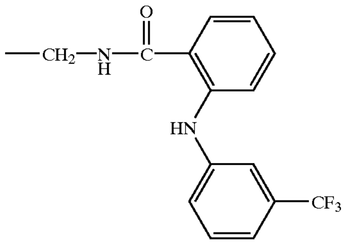 |
| 1569 | 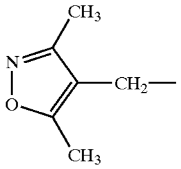 | 1 | 2 | 0 | R | H | 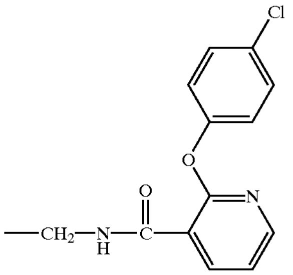 |
| 1570 | 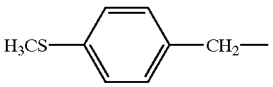 | 2 | 2 | 1 | — | H | 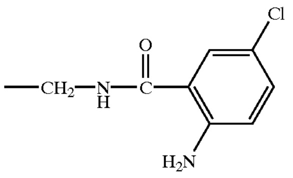 |
| 1571 | 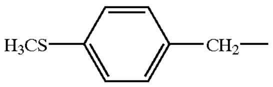 | 2 | 2 | 1 | — | H | 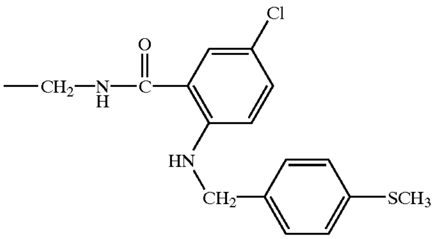 |

TABLE 1.143-continued
| Compd. No. | 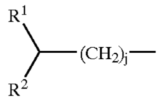 | k | m | n | chirality | $R^3$ | 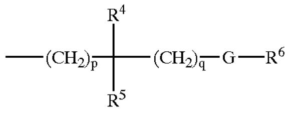 |
|---|---|---|---|---|---|---|---|
| 1572 | 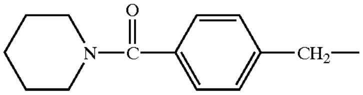 | 2 | 2 | 1 | — | H | 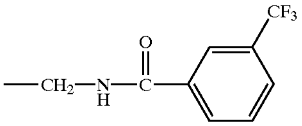 |
| 1573 | 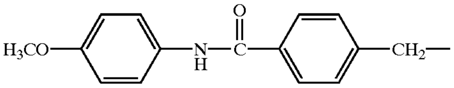 | 2 | 2 | 1 | — | H | 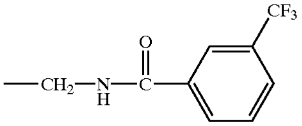 |
TABLE 1.144
| Compd. No. | 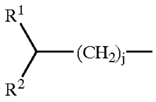 | k | m | n | chirality | $R^3$ | 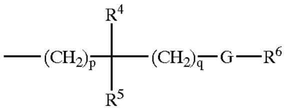 |
|---|---|---|---|---|---|---|---|
| 1574 | 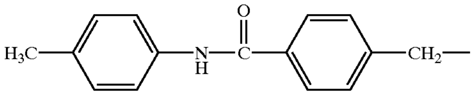 | 2 | 2 | 1 | — | H | 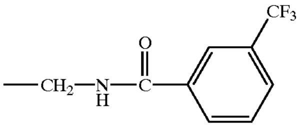 |
| 1575 | 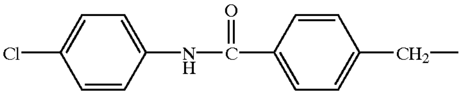 | 2 | 2 | 1 | — | H | 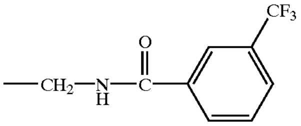 |
| 1576 | 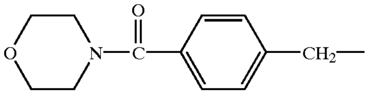 | 2 | 2 | 1 | — | H | 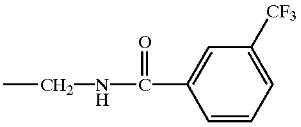 |
| 1577 | 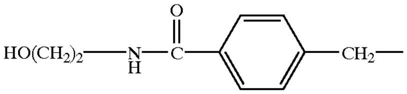 | 2 | 2 | 1 | — | H | 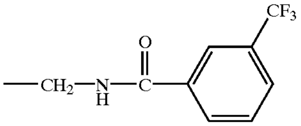 |
| 1578 | 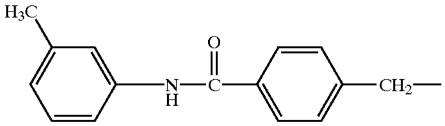 | 2 | 2 | 1 | — | H | 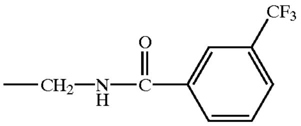 |
| 1579 | 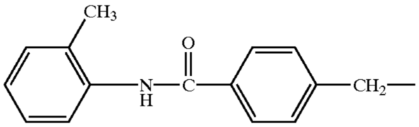 | 2 | 2 | 1 | — | H | 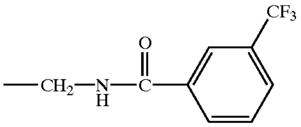 |

TABLE 1.144-continued
| Compd. No. | 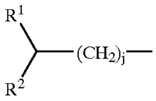 | k | m | n | chirality | $R^3$ | 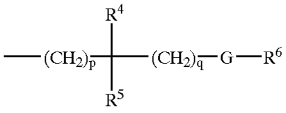 |
|---|---|---|---|---|---|---|---|
| 1580 | 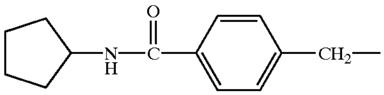 | 2 | 2 | 1 | — | H | 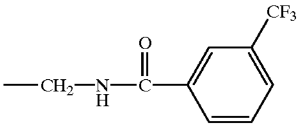 |
| 1581 | 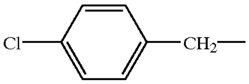 | 2 | 2 | 1 | — | H | 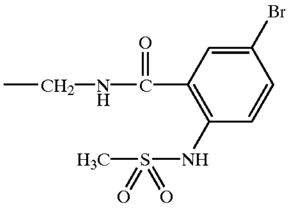 |
| 1582 | 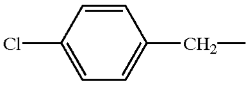 | 2 | 2 | 1 | — | H | 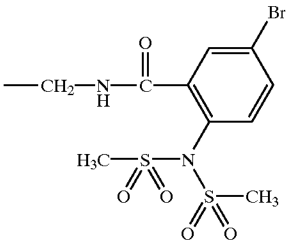 |
| 1583 | 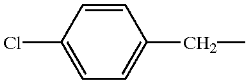 | 1 | 2 | 0 | R | H | 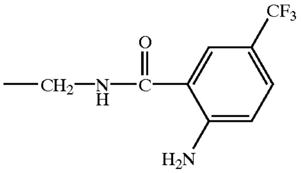 |
| 1584 | 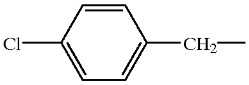 | 1 | 2 | 0 | R | H | 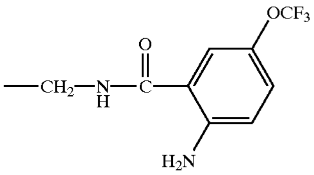 |
TABLE 1.145
| Compd. No. | 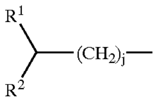 | k | m | n | chirality | $R^3$ | 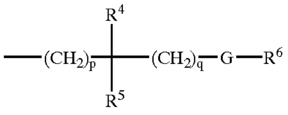 |
|---|---|---|---|---|---|---|---|
| 1585 | 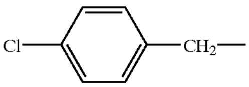 | 1 | 2 | 0 | R | H | 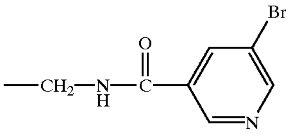 |

TABLE 1.145-continued
| Compd. No. | 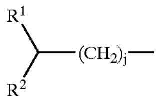 | k | m | n | chirality | $R^3$ | 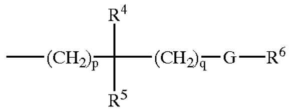 |
|---|---|---|---|---|---|---|---|
| 1586 | 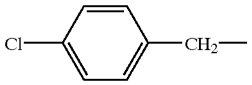 | 1 | 2 | 0 | R | H | 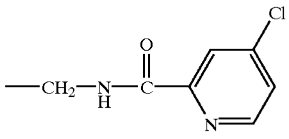 |
| 1587 | 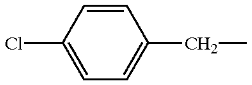 | 1 | 2 | 0 | R | H | 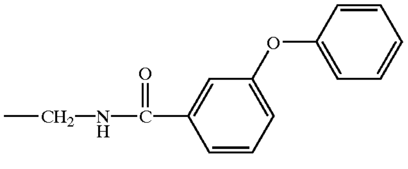 |
| 1588 | 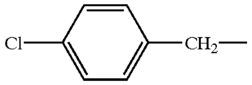 | 1 | 2 | 0 | R | H | 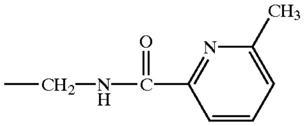 |
| 1589 | 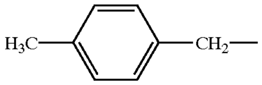 | 1 | 2 | 0 | R | H | 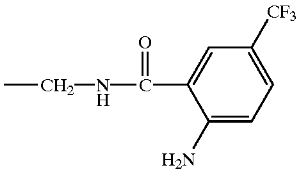 |
| 1590 | 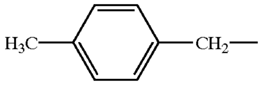 | 1 | 2 | 0 | R | H | 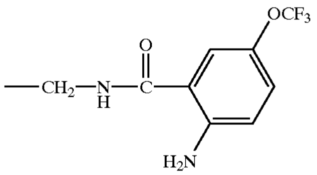 |
| 1591 | 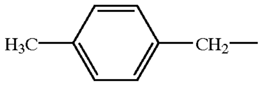 | 1 | 2 | 0 | R | H | 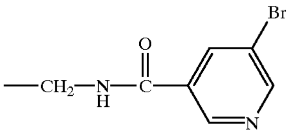 |
| 1592 | 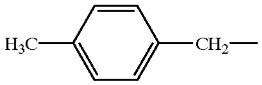 | 1 | 2 | 0 | R | H | 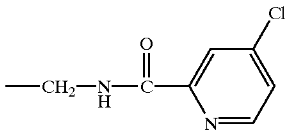 |
| 1593 | 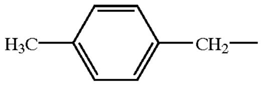 | 1 | 2 | 0 | R | H | 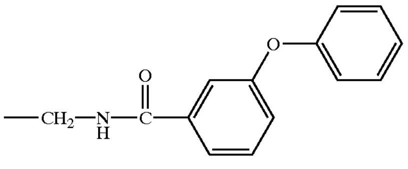 |
| 1594 | 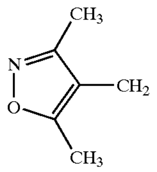 | 1 | 2 | 0 | R | H | 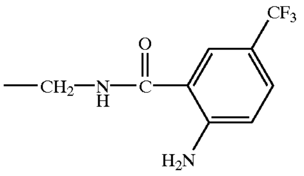 |

TABLE 1.145-continued
| Compd. No. | 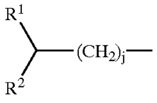 | k | m | n | chirality | $R^3$ | 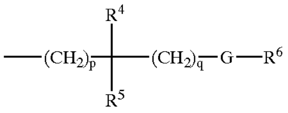 |
|---|---|---|---|---|---|---|---|
| 1595 | 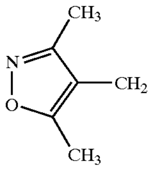 | 1 | 2 | 0 | R | H | 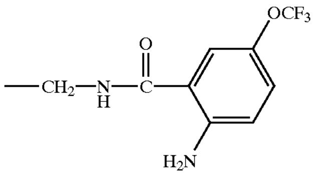 |
TABLE 1.146
| Compd. No. | 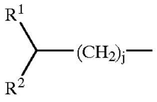 | k | m | n | chirality | $R^3$ | 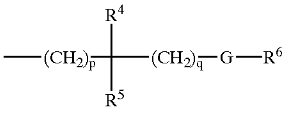 |
|---|---|---|---|---|---|---|---|
| 1596 | 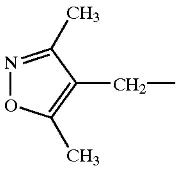 | 1 | 2 | 0 | R | H | 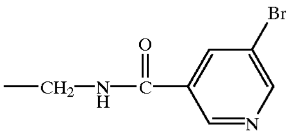 |
| 1597 | 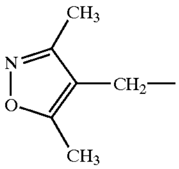 | 1 | 2 | 0 | R | H | 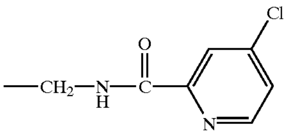 |
| 1598 | 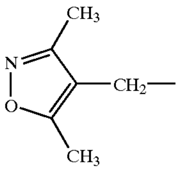 | 1 | 2 | 0 | R | H | 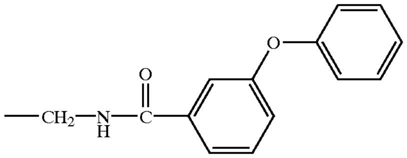 |
| 1599 | 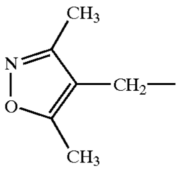 | 1 | 2 | 0 | R | H | 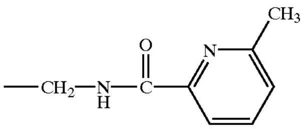 |
| 1600 | 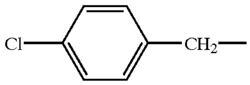 | 2 | 2 | 1 | — | H | 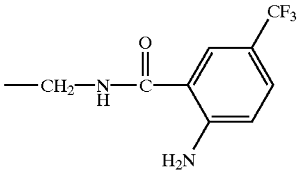 |

TABLE 1.146-continued
| Compd. No. | 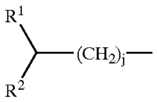 | k | m | n | chirality | $R^3$ | 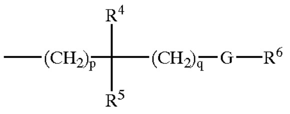 |
|---|---|---|---|---|---|---|---|
| 1601 | 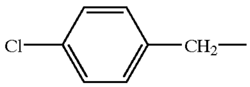 | 2 | 2 | 1 | — | H | 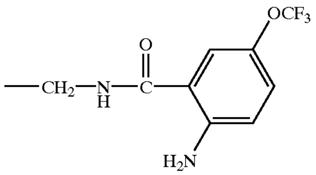 |
| 1602 | 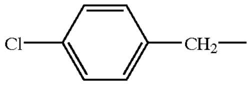 | 2 | 2 | 1 | — | H | 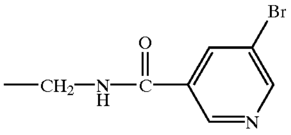 |
| 1603 | 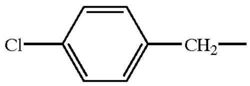 | 2 | 2 | 1 | — | H | 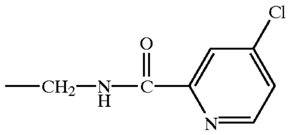 |
| 1604 | 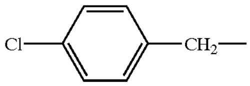 | 2 | 2 | 1 | — | H | 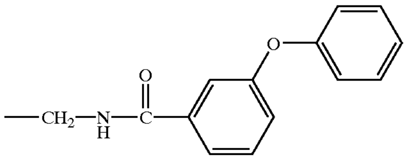 |
| 1605 | 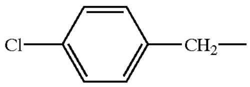 | 2 | 2 | 1 | — | H | 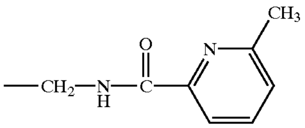 |
| 1606 | 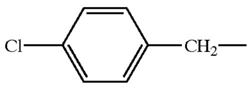 | 1 | 2 | 0 | R | H | 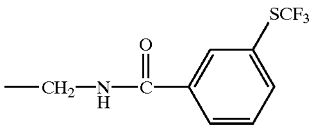 |
TABLE 1.147
| Compd. No. | 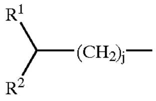 | k | m | n | chirality | $R^3$ | 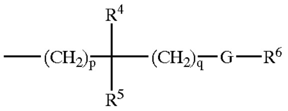 |
|---|---|---|---|---|---|---|---|
| 1607 | 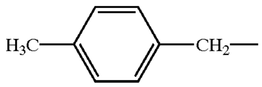 | 1 | 2 | 0 | R | H | 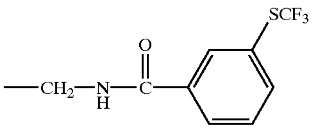 |

TABLE 1.147-continued
| Compd. No. | 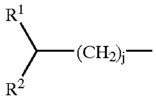 | k | m | n | chirality | $R^3$ | 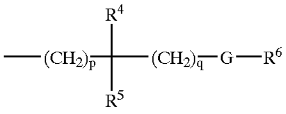 |
|---|---|---|---|---|---|---|---|
| 1608 | 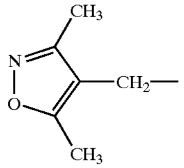 | 1 | 2 | 0 | R | H | 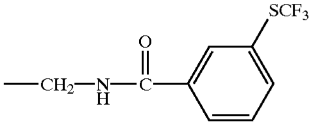 |
| 1609 | 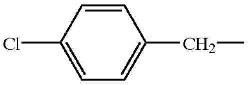 | 2 | 2 | 1 | — | H | 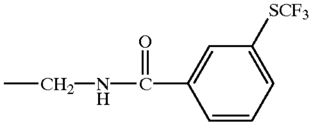 |
| 1610 | 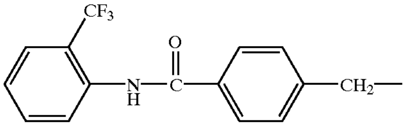 | 2 | 2 | 1 | — | H | 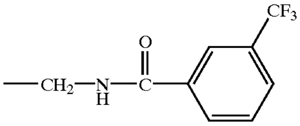 |
| 1611 | 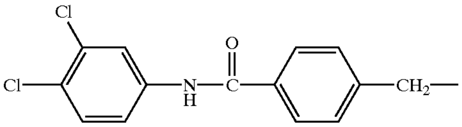 | 2 | 2 | 1 | — | H | 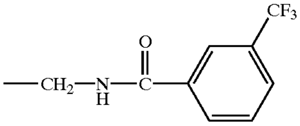 |
| 1612 | 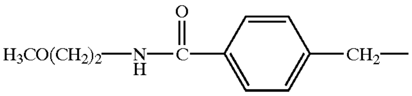 | 2 | 2 | 1 | — | H | 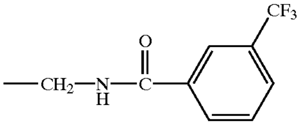 |
| 1613 | 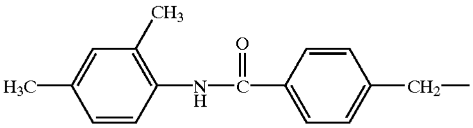 | 2 | 2 | 1 | — | H | 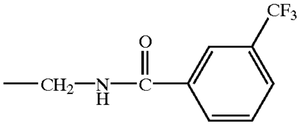 |
| 1614 | 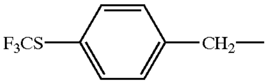 | 1 | 2 | 0 | R | H | 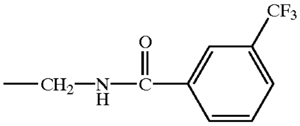 |
| 1615 | 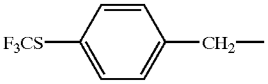 | 2 | 2 | 1 | — | H | 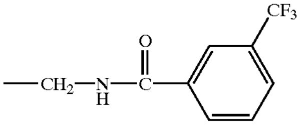 |
| 1616 | 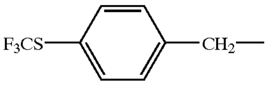 | 2 | 2 | 1 | — | H | 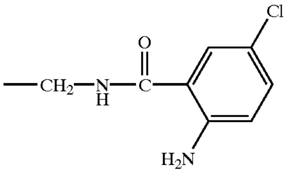 |

TABLE 1.147-continued
| Compd. No. | 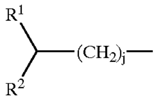 | k | m | n | chirality | $R^3$ | 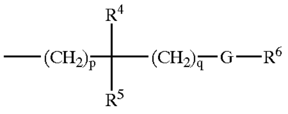 |
|---|---|---|---|---|---|---|---|
| 1617 | 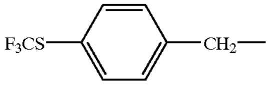 | 2 | 2 | 1 | — | H | 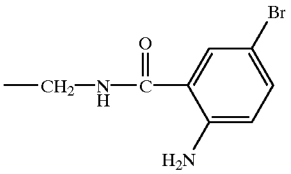 |
TABLE 1.148
| Compd. No. | 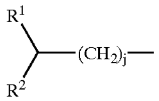 | k | m | n | chirality | $R^3$ | 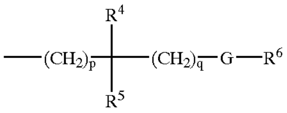 |
|---|---|---|---|---|---|---|---|
| 1618 | 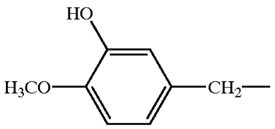 | 1 | 2 | 0 | R | H | 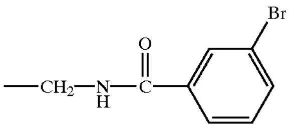 |
| 1619 | 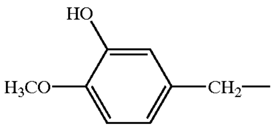 | 1 | 2 | 0 | R | H | 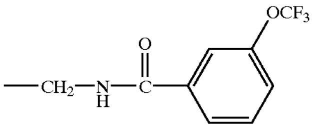 |
| 1620 | 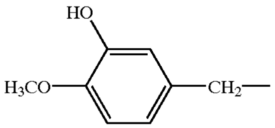 | 1 | 2 | 0 | R | H | 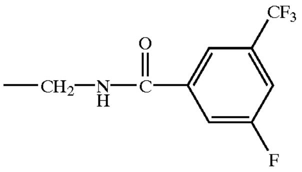 |
| 1621 | 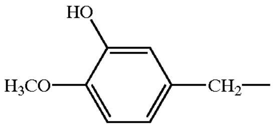 | 1 | 2 | 0 | R | H | 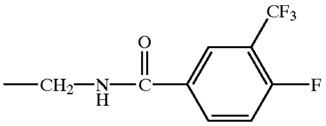 |
| 1622 | 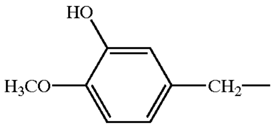 | 1 | 2 | 0 | R | H | 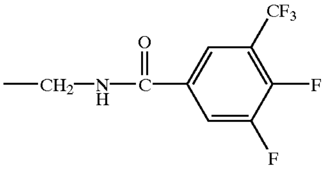 |
| 1623 | 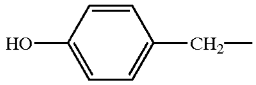 | 1 | 2 | 0 | R | H | 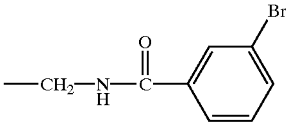 |

TABLE 1.148-continued
| Compd. No. | 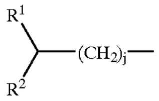 | k | m | n | chirality | $R^3$ | 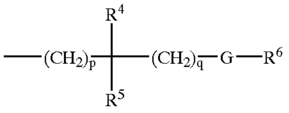 |
|---|---|---|---|---|---|---|---|
| 1624 | 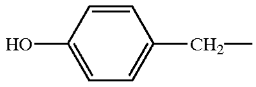 | 1 | 2 | 0 | R | H | 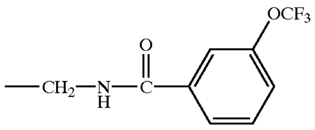 |
| 1625 | 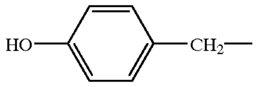 | 1 | 2 | 0 | R | H | 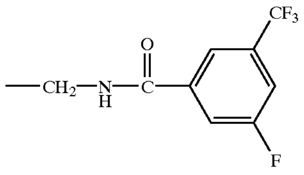 |
| 1626 | 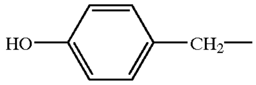 | 1 | 2 | 0 | R | H | 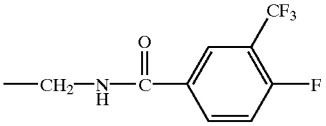 |
| 1627 | 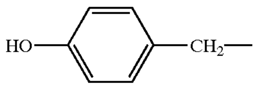 | 1 | 2 | 0 | R | H | 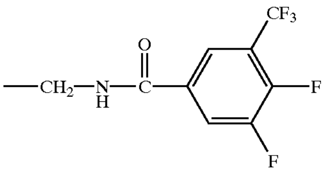 |
| 1628 | 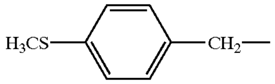 | 1 | 2 | 0 | R | H | 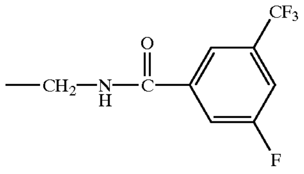 |
TABLE 1.149
| Compd. No. | 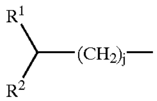 | k | m | n | chirality | $R^3$ | 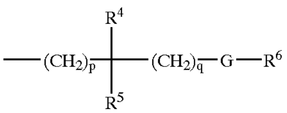 |
|---|---|---|---|---|---|---|---|
| 1629 | 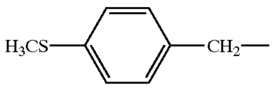 | 1 | 2 | 0 | R | H | 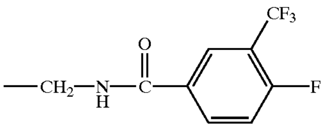 |
| 1630 | 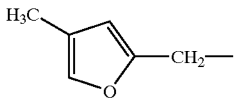 | 1 | 2 | 0 | R | H | 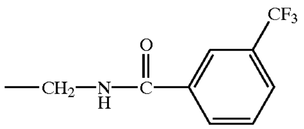 |

TABLE 1.149-continued
| Compd. No. | 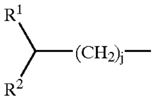 | k | m | n | chirality | $R^3$ | 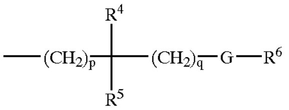 |
|---|---|---|---|---|---|---|---|
| 1631 | 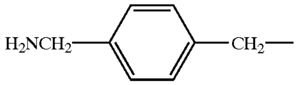 | 1 | 2 | 0 | R | H | 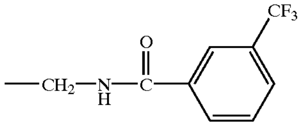 |
| 1632 | 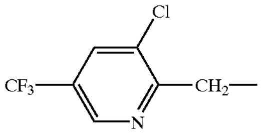 | 1 | 2 | 0 | R | H | 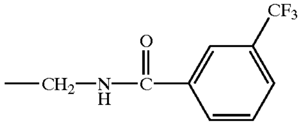 |
| 1633 | 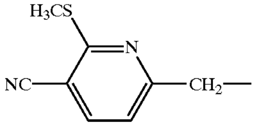 | 1 | 2 | 0 | R | H | 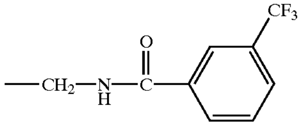 |
| 1634 | 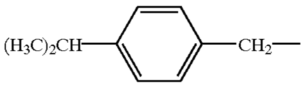 | 1 | 2 | 0 | R | H | 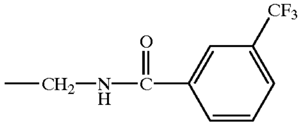 |
| 1635 | 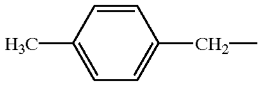 | 1 | 2 | 0 | R | H | 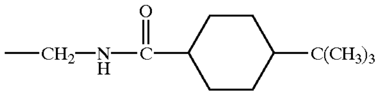 |
| 1636 | 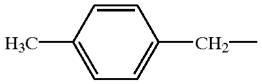 | 1 | 2 | 0 | R | H | 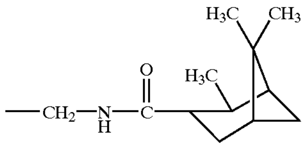 |
| 1637 | 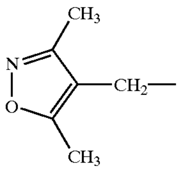 | 1 | 2 | 0 | R | H | 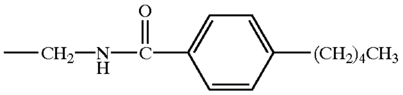 |
| 1638 | 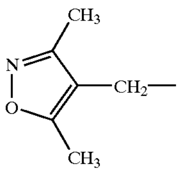 | 1 | 2 | 0 | R | H | 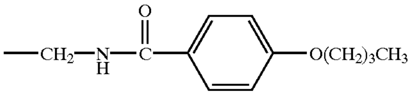 |
| 1639 | 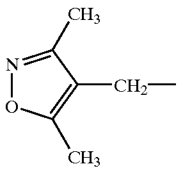 | 1 | 2 | 0 | R | H | 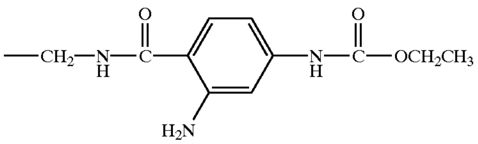 |

TABLE 1.150
| Compd. No. | 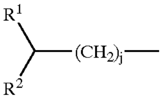 | k | m | n | chirality | $R^3$ | 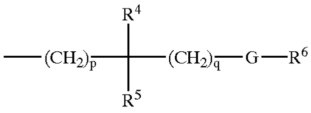 |
|---|---|---|---|---|---|---|---|
| 1640 | 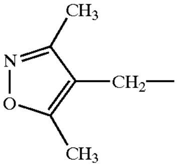 | 1 | 2 | 0 | R | H | 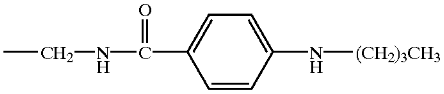 |
| 1641 | 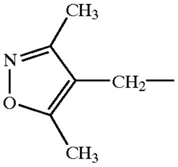 | 1 | 2 | 0 | R | H | 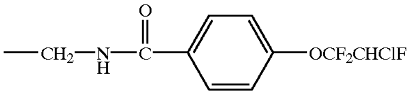 |
| 1642 | 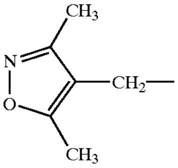 | 1 | 2 | 0 | R | H | 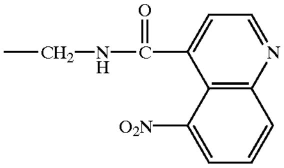 |
| 1643 | 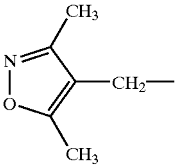 | 1 | 2 | 0 | R | H | 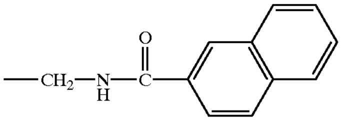 |
| 1644 | 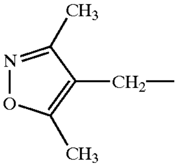 | 1 | 2 | 0 | R | H | 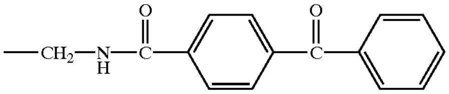 |
| 1645 | 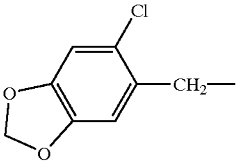 | 1 | 2 | 0 | R | H | 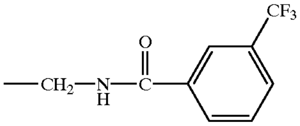 |
| 1646 | 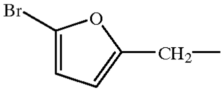 | 1 | 2 | 0 | R | H | 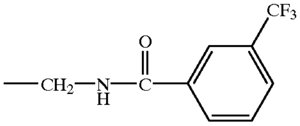 |
| 1647 | 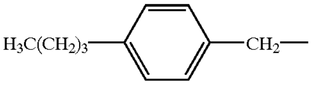 | 2 | 2 | 1 | — | H | 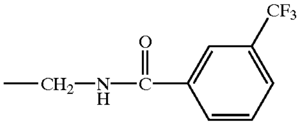 |

TABLE 1.150-continued
| Compd. No. 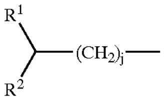 | | k | m | n | chirality | $R^3$ | 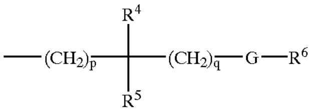 |
|---|---|---|---|---|---|---|---|
| 1648 | 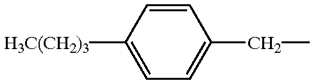 | 1 | 2 | 0 | R | H | 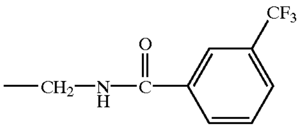 |
| 1649 | 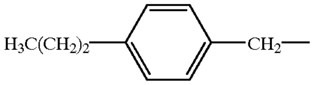 | 2 | 2 | 1 | — | H | 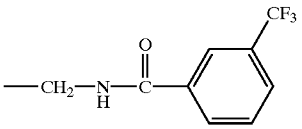 |
| 1650 | 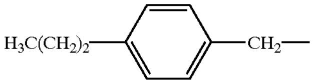 | 1 | 2 | 0 | R | H | 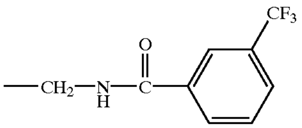 |
TABLE 1.151
| Compd. No. 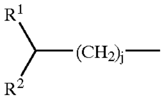 | | k | m | n | chirality | $R^3$ | 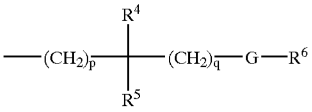 |
|---|---|---|---|---|---|---|---|
| 1651 | 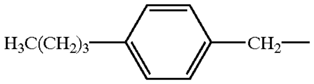 | 2 | 2 | 1 | — | H | 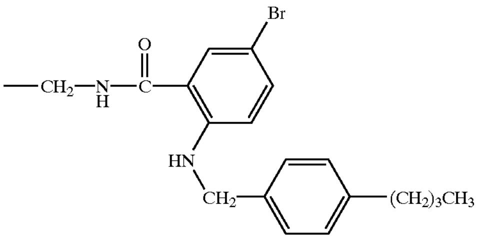 |
| 1652 | 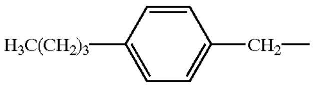 | 2 | 2 | 1 | — | H | 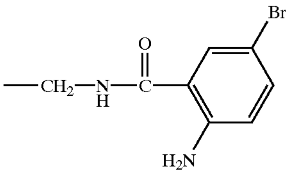 |
| 1653 | 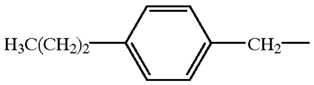 | 2 | 2 | 1 | — | H | 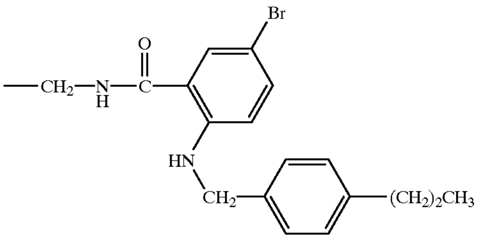 |

TABLE 1.151-continued
| Compd. No. | 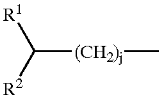 | k | m | n | chirality | $R^3$ | 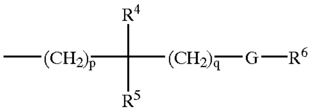 |
|---|---|---|---|---|---|---|---|
| 1654 | 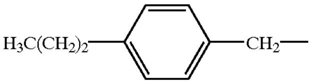 | 2 | 2 | 1 | — | H | 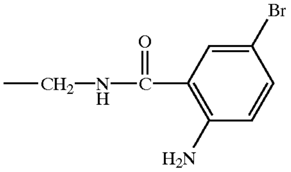 |
| 1655 | 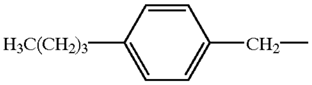 | 2 | 2 | 1 | — | H | 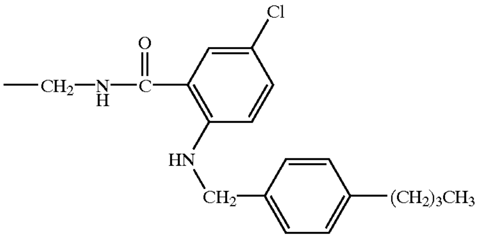 |
| 1656 | 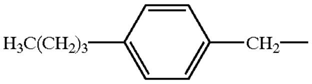 | 2 | 2 | 1 | — | H | 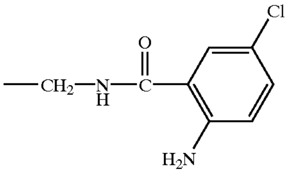 |
| 1657 | 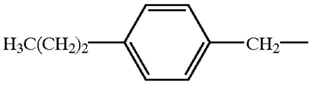 | 2 | 2 | 1 | — | H | 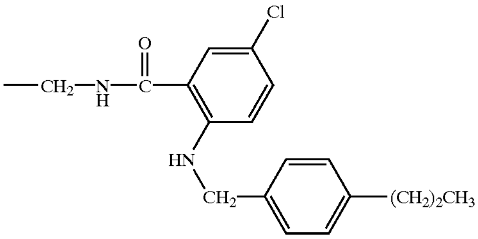 |
| 1658 | 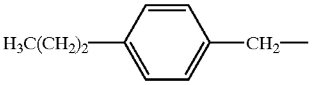 | 2 | 2 | 1 | — | H | 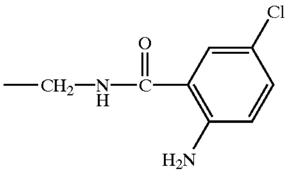 |
| 1659 | 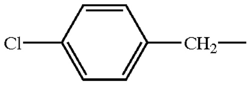 | 2 | 2 | 1 | — | H | 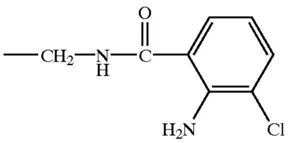 |
| 1660 | 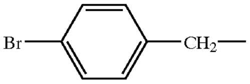 | 1 | 2 | 0 | R | H | 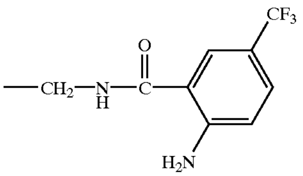 |

TABLE 1.151-continued
| Compd. No. | 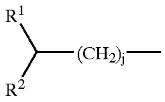 | k | m | n | chirality | $R^3$ | 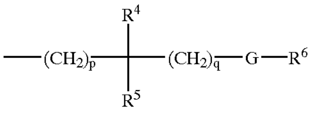 |
|---|---|---|---|---|---|---|---|
| 1661 | 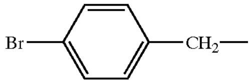 | 1 | 2 | 0 | R | H | 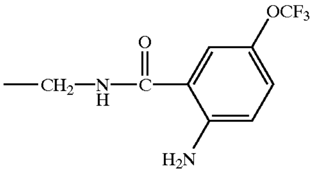 |
TABLE 1.152
| Compd. No. | 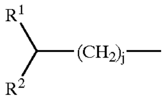 | k | m | n | chirality | $R^3$ | 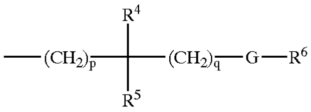 |
|---|---|---|---|---|---|---|---|
| 1662 | 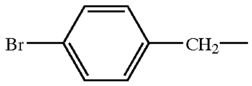 | 1 | 2 | 0 | R | H | 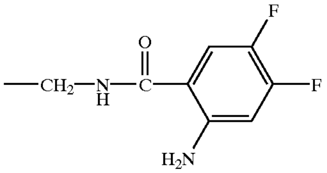 |
| 1663 | 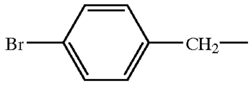 | 1 | 2 | 0 | R | H | 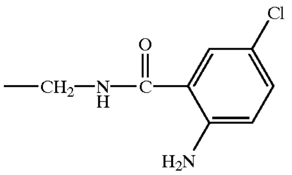 |
| 1664 | 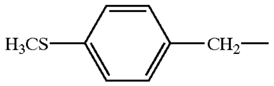 | 2 | 2 | 1 | — | H | 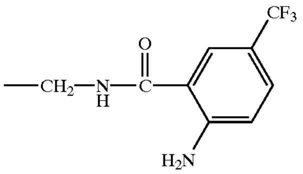 |
| 1665 | 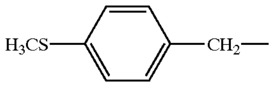 | 2 | 2 | 1 | — | H | 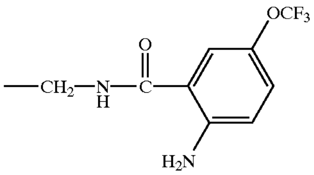 |
| 1666 | 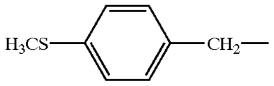 | 2 | 2 | 1 | — | H | 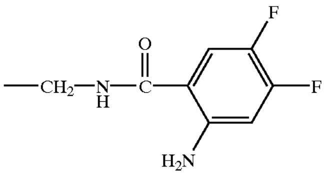 |

TABLE 1.152-continued
| Compd. No. | 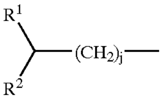 | k | m | n | chirality | $R^3$ | 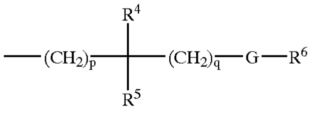 |
|---|---|---|---|---|---|---|---|
| 1667 | 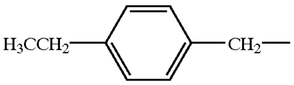 | 2 | 2 | 1 | — | H | 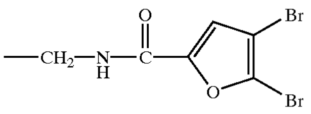 |
| 1668 | 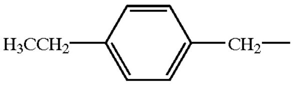 | 2 | 2 | 1 | — | H | 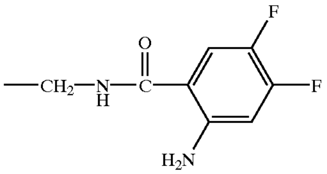 |
| 1669 | 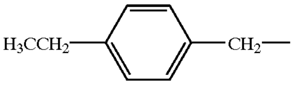 | 2 | 2 | 1 | — | H | 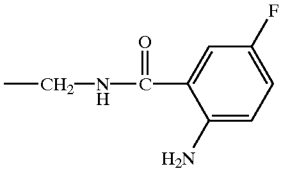 |
| 1670 | 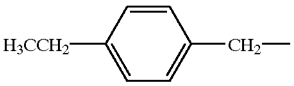 | 2 | 2 | 1 | — | H | 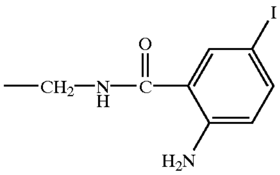 |
| 1671 | 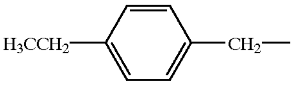 | 2 | 2 | 1 | — | H | 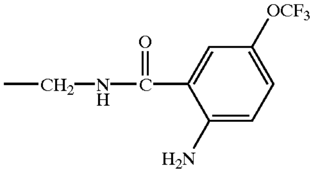 |
| 1672 | 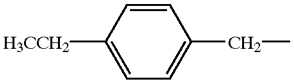 | 2 | 2 | 1 | — | H | 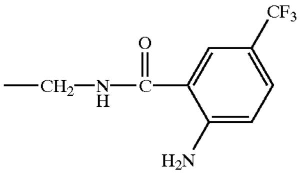 |
TABLE 1.153
| Compd. No. | 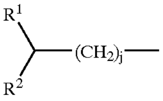 | k | m | n | chirality | $R^3$ | 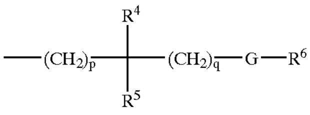 |
|---|---|---|---|---|---|---|---|
| 1673 | 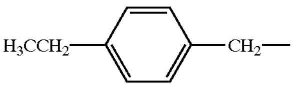 | 2 | 2 | 1 | — | H | 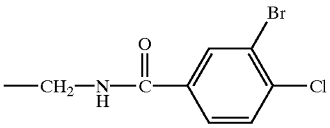 |

TABLE 1.153-continued
| Compd. No. | 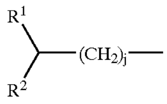 | k | m | n | chirality | $R^3$ | 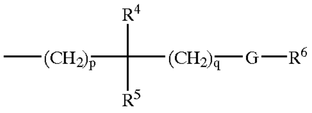 |
|---|---|---|---|---|---|---|---|
| 1674 | 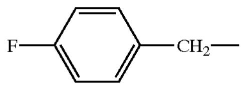 | 2 | 2 | 1 | — | H | 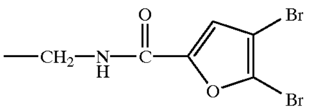 |
| 1675 | 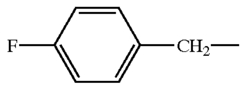 | 2 | 2 | 1 | — | H | 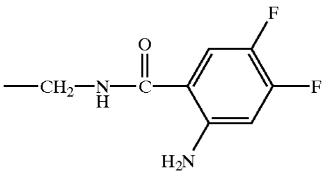 |
| 1676 | 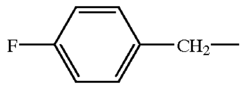 | 2 | 2 | 1 | — | H | 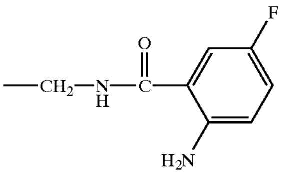 |
| 1677 | 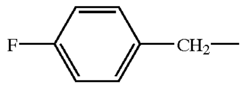 | 2 | 2 | 1 | — | H | 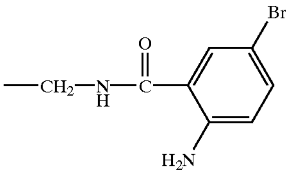 |
| 1678 | 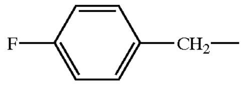 | 2 | 2 | 1 | — | H | 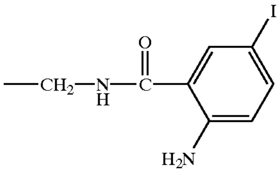 |
| 1679 | 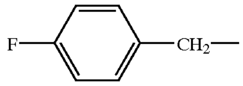 | 2 | 2 | 1 | — | H | 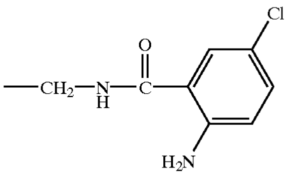 |
| 1680 | 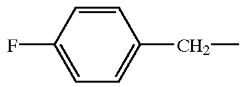 | 2 | 2 | 1 | — | H | 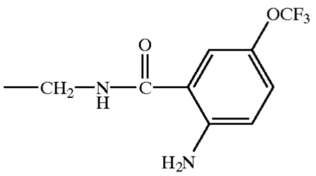 |
| 1681 | 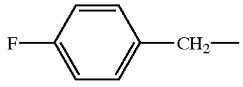 | 2 | 2 | 1 | — | H | 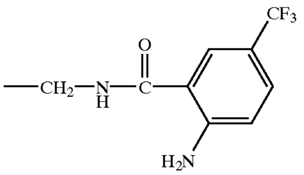 |

TABLE 1.153-continued
| Compd. No. | 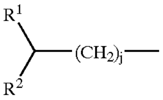 | k | m | n | chirality | $R^3$ | 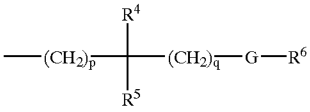 |
|---|---|---|---|---|---|---|---|
| 1682 | 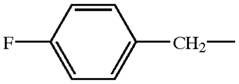 | 2 | 2 | 1 | — | H | 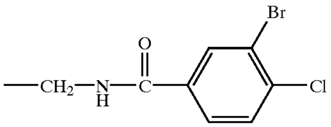 |
| 1683 | 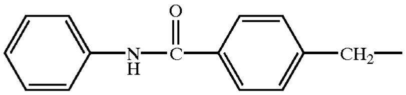 | 2 | 2 | 1 | — | H | 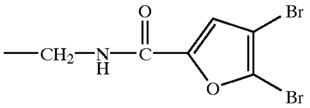 |
TABLE 1.154
| Compd. No. | 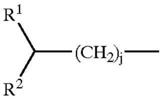 | k | m | n | chirality | $R^3$ | 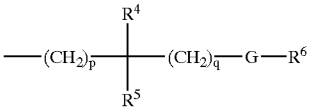 |
|---|---|---|---|---|---|---|---|
| 1684 | 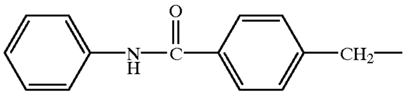 | 2 | 2 | 1 | — | H | 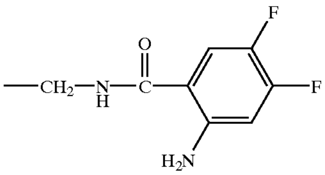 |
| 1685 | 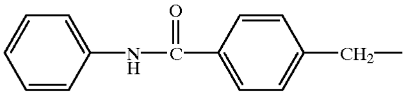 | 2 | 2 | 1 | — | H | 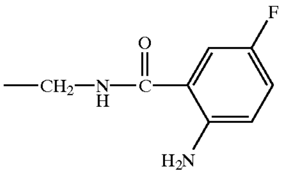 |
| 1686 | 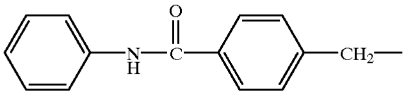 | 2 | 2 | 1 | — | H | 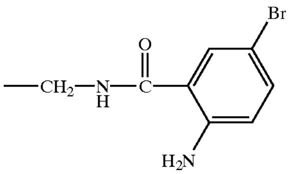 |
| 1687 | 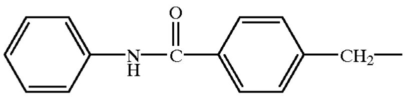 | 2 | 2 | 1 | — | H | 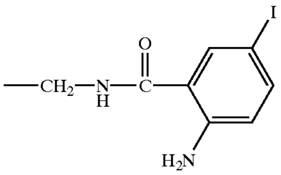 |
| 1688 | 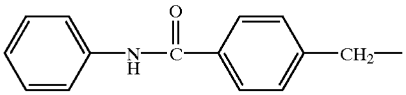 | 2 | 2 | 1 | — | H | 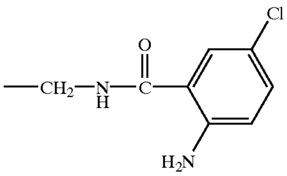 |

TABLE 1.154-continued
| Compd. No. | 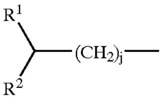 | k | m | n | chirality | $R^3$ | 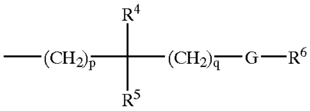 |
|---|---|---|---|---|---|---|---|
| 1689 | 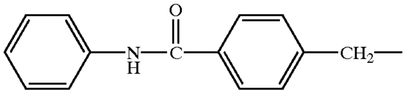 | 2 | 2 | 1 | — | H | 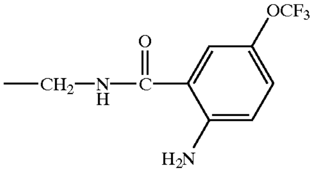 |
| 1690 | 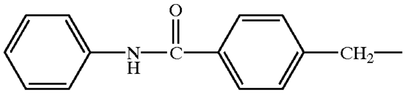 | 2 | 2 | 1 | — | H | 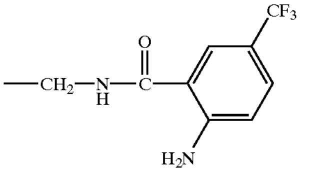 |
| 1691 | 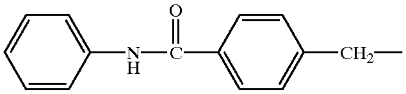 | 2 | 2 | 1 | — | H | 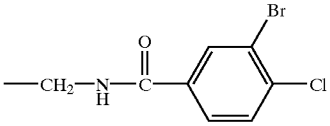 |
| 1692 | 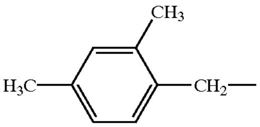 | 1 | 2 | 0 | R | H | 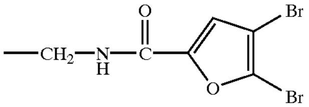 |
| 1693 | 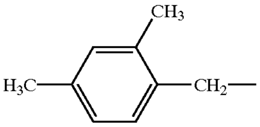 | 1 | 2 | 0 | R | H | 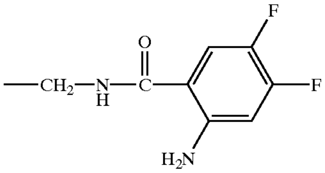 |
| 1694 | 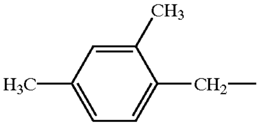 | 1 | 2 | 0 | R | H | 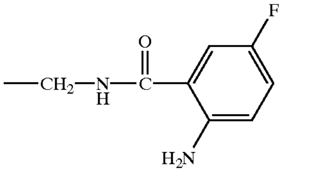 |
TABLE 1.155
| Compd. No. | 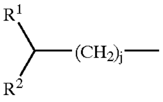 | k | m | n | chirality | $R^3$ | 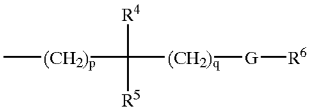 |
|---|---|---|---|---|---|---|---|
| 1695 | 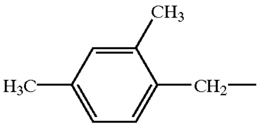 | 1 | 2 | 0 | R | H | 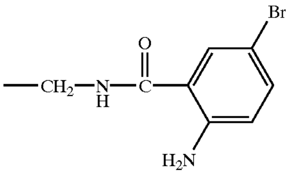 |

TABLE 1.155-continued
| Compd. No. | 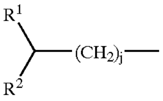 | k | m | n | chirality | $R^3$ | 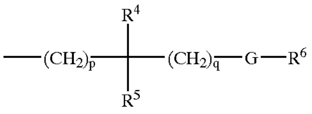 |
|---|---|---|---|---|---|---|---|
| 1696 | 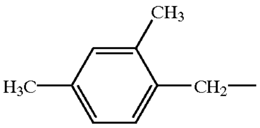 | 1 | 2 | 0 | R | H | 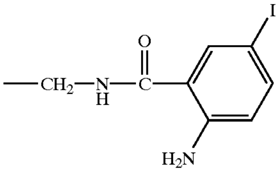 |
| 1697 | 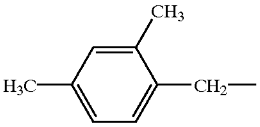 | 1 | 2 | 0 | R | H | 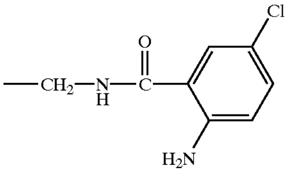 |
| 1698 | 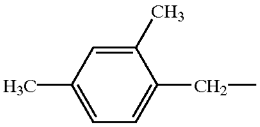 | 1 | 2 | 0 | R | H | 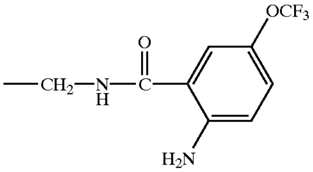 |
| 1699 | 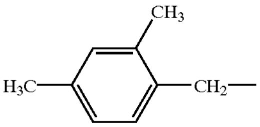 | 1 | 2 | 0 | R | H | 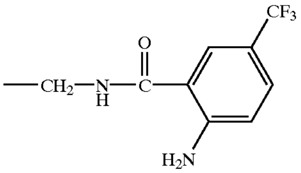 |
| 1700 | 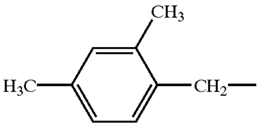 | 1 | 2 | 0 | R | H | 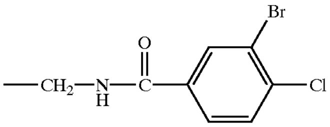 |
| 1701 | 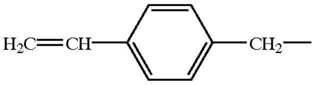 | 1 | 2 | 0 | R | H | 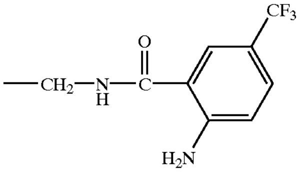 |
| 1702 | 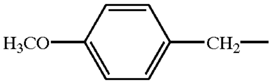 | 1 | 2 | 0 | R | H | 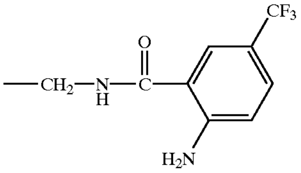 |
| 1703 | 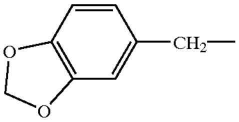 | 1 | 2 | 0 | R | H | 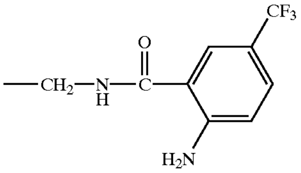 |

TABLE 1.155-continued
| Compd. No. | 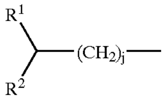 | k | m | n | chirality | $R^3$ | 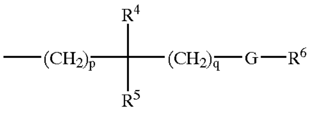 |
|---|---|---|---|---|---|---|---|
| 1704 | 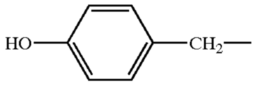 | 1 | 2 | 0 | R | H | 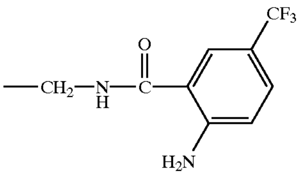 |
| 1705 | 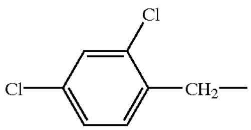 | 1 | 2 | 0 | R | H | 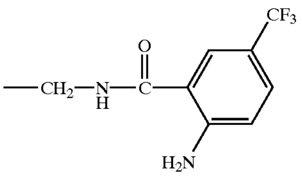 |
TABLE 1.156
| Compd. No. | 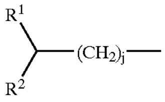 | k | m | n | chirality | $R^3$ | 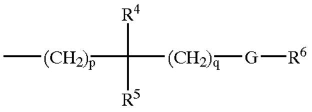 |
|---|---|---|---|---|---|---|---|
| 1706 | 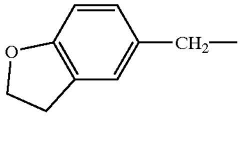 | 1 | 2 | 0 | R | H | 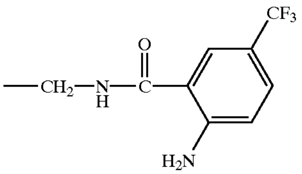 |
| 1707 | 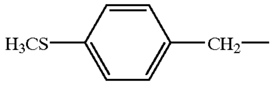 | 1 | 2 | 0 | R | H | 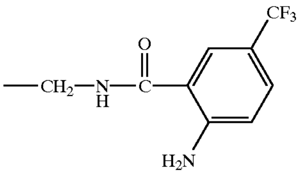 |
| 1708 | 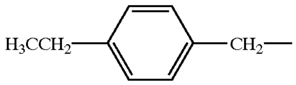 | 1 | 2 | 0 | R | H | 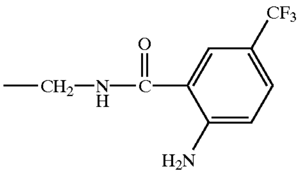 |
| 1709 | 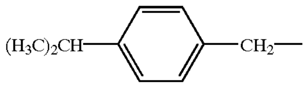 | 1 | 2 | 0 | R | H | 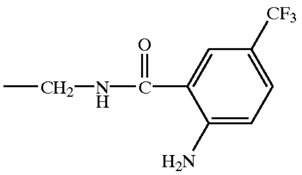 |

TABLE 1.156-continued
| Compd. No. 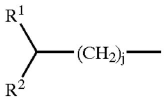 | | k | m | n | chirality | $R^3$ | 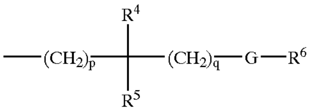 |
|---|---|---|---|---|---|---|---|
| 1710 | 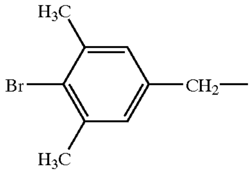 | 1 | 2 | 0 | R | H | 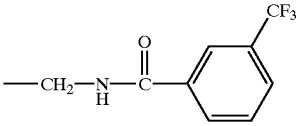 |
| 1711 | 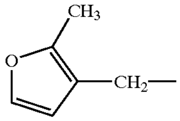 | 1 | 2 | 0 | R | H | 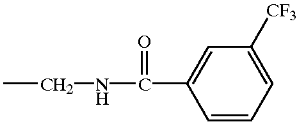 |
| 1712 | 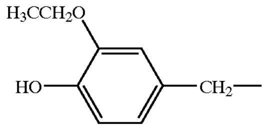 | 1 | 2 | 0 | R | H | 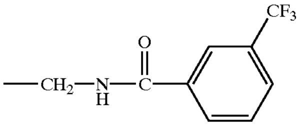 |
| 1713 | 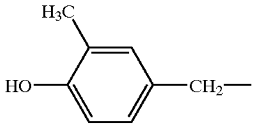 | 1 | 2 | 0 | R | H | 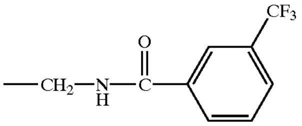 |
| 1714 | 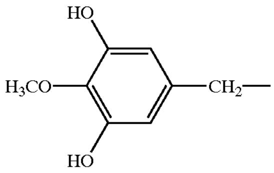 | 1 | 2 | 0 | R | H | 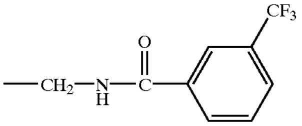 |
| 1715 | 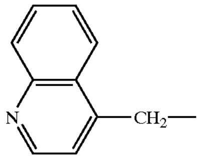 | 1 | 2 | 0 | R | H | 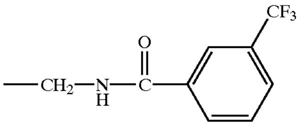 |
| 1716 | 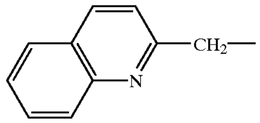 | 1 | 2 | 0 | R | H | 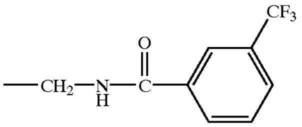 |

TABLE 1.157
| Compd. No. 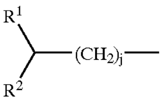 | k | m | n | chirality | $R^3$ | 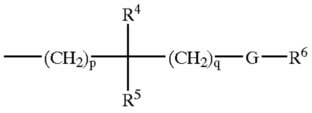 |
|---|---|---|---|---|---|---|
| 1717 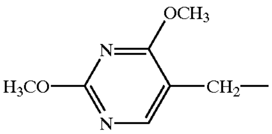 | 1 | 2 | 0 | R | H | 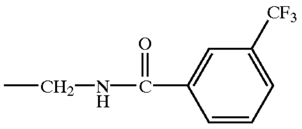 |
| 1718 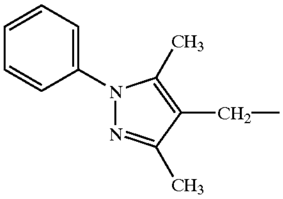 | 1 | 2 | 0 | R | H | 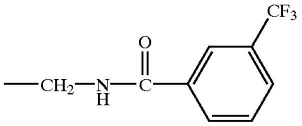 |
| 1719 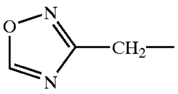 | 1 | 2 | 0 | R | H | 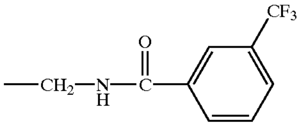 |
| 1720 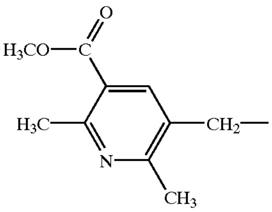 | 1 | 2 | 0 | R | H | 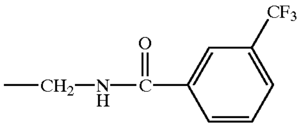 |
| 1721 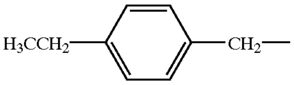 | 1 | 2 | 0 | R | H | 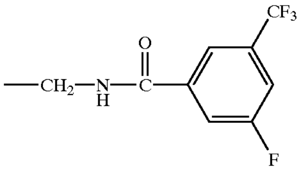 |
| 1722 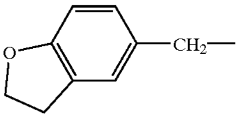 | 1 | 2 | 0 | R | H | 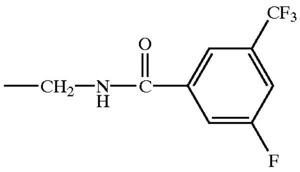 |
| 1723 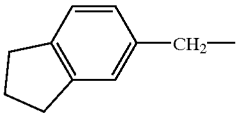 | 1 | 2 | 0 | R | H | 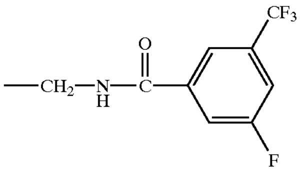 |
| 1724 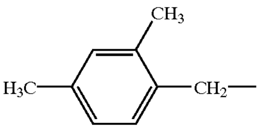 | 1 | 2 | 0 | R | H | 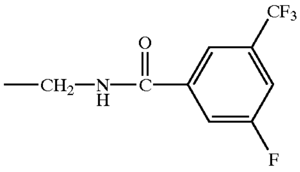 |

TABLE 1.157-continued
| Compd. No. 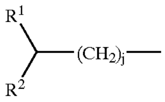 | k | m | n | chirality | $R^3$ | 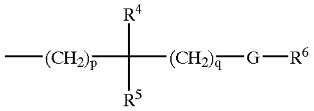 |
|---|---|---|---|---|---|---|
| 1725 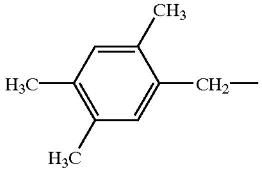 | 1 | 2 | 0 | R | H | 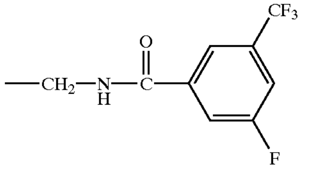 |
| 1726 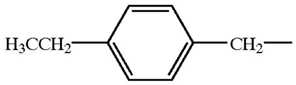 | 1 | 2 | 0 | R | H | 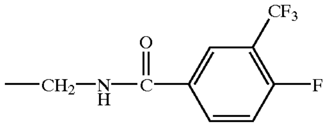 |
| 1727 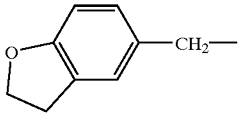 | 1 | 2 | 0 | R | H | 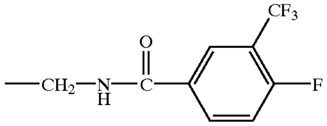 |
TABLE 1.158
| Compd. No. 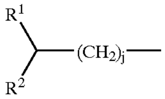 | k | m | n | chirality | $R^3$ | 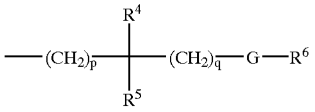 |
|---|---|---|---|---|---|---|
| 1728 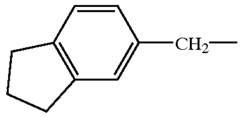 | 1 | 2 | 0 | R | H | 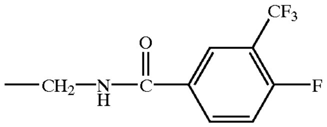 |
| 1729 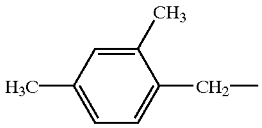 | 1 | 2 | 0 | R | H | 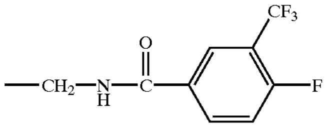 |
| 1730 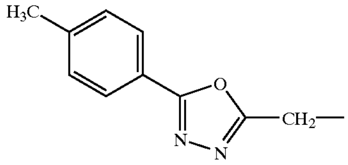 | 1 | 2 | 0 | R | H | 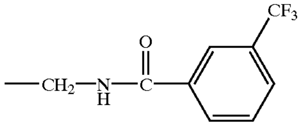 |
| 1731 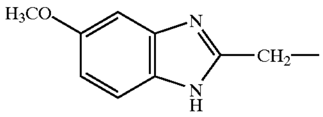 | 1 | 2 | 0 | R | H | 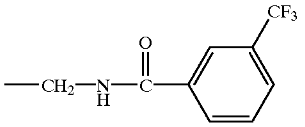 |
| 1732 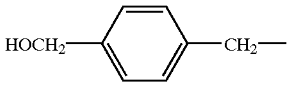 | 1 | 2 | 0 | R | H | 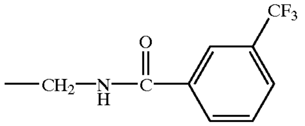 |

TABLE 1.158-continued
| Compd. No. 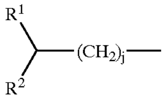 | k | m | n | chirality | $R^3$ | 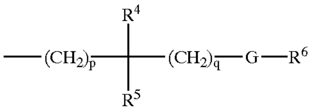 |
|---|---|---|---|---|---|---|
| 1733 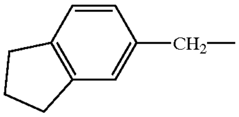 | 1 | 2 | 0 | R | H | 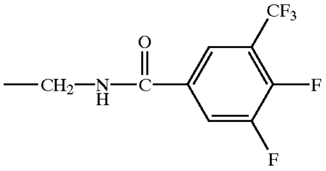 |
| 1734 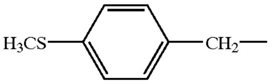 | 1 | 2 | 0 | R | H | 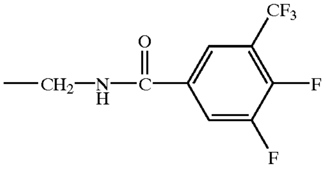 |
| 1735 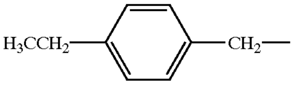 | 1 | 2 | 0 | R | H | 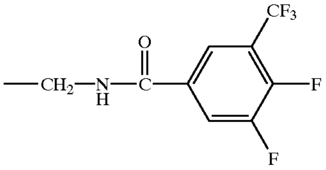 |
| 1736 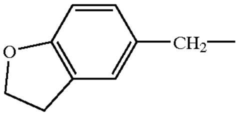 | 1 | 2 | 0 | R | H | 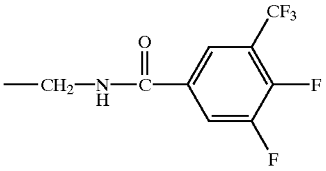 |
| 1737 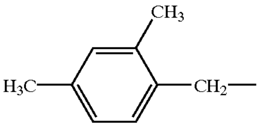 | 1 | 2 | 0 | R | H | 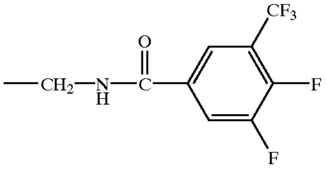 |
| 1738 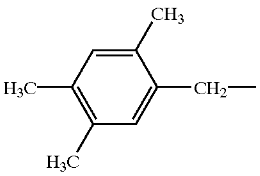 | 1 | 2 | 0 | R | H | 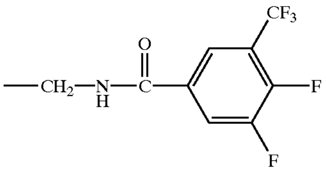 |

TABLE 1.159
| Compd. No. | 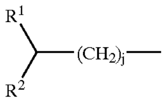 | k | m | n | chirality | $R^3$ | 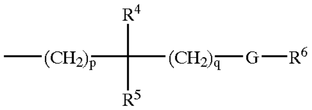 |
|---|---|---|---|---|---|---|---|
| 1739 | 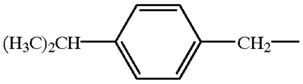 | 1 | 2 | 0 | R | H | 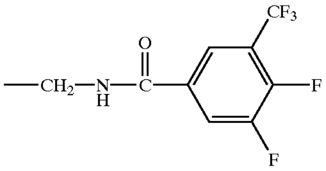 |
| 1740 | 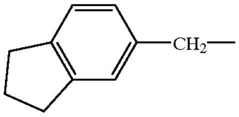 | 1 | 2 | 0 | R | H | 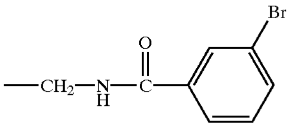 |
| 1741 | 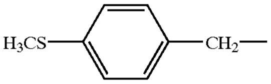 | 1 | 2 | 0 | R | H | 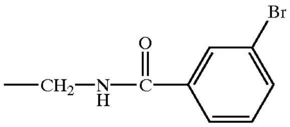 |
| 1742 | 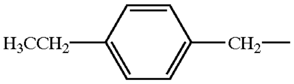 | 1 | 2 | 0 | R | H | 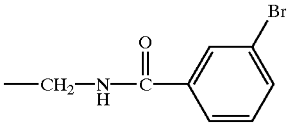 |
| 1743 | 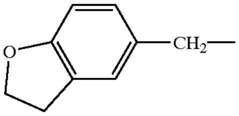 | 1 | 2 | 0 | R | H | 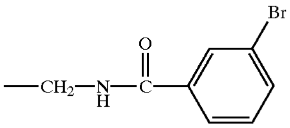 |
| 1744 | 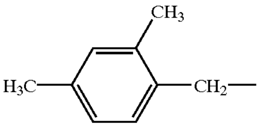 | 1 | 2 | 0 | R | H | 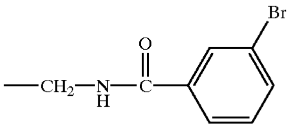 |
| 1745 | 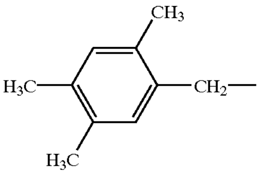 | 1 | 2 | 0 | R | H | 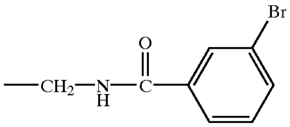 |
| 1746 | 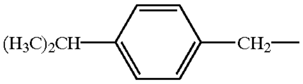 | 1 | 2 | 0 | R | H | 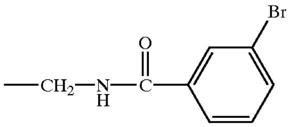 |
| 1747 | 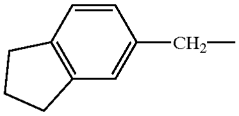 | 1 | 2 | 0 | R | H | 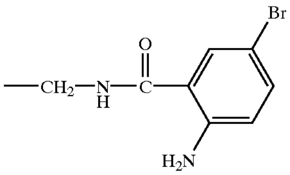 |

TABLE 1.159-continued
| Compd. No. | 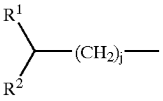 | k | m | n | chirality | $R^3$ | 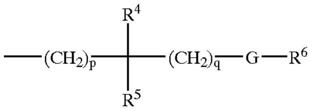 |
|---|---|---|---|---|---|---|---|
| 1748 | 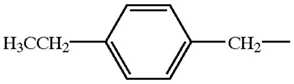 | 1 | 2 | 0 | R | H | 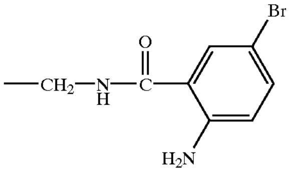 |
| 1749 | 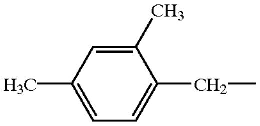 | 1 | 2 | 0 | R | H | 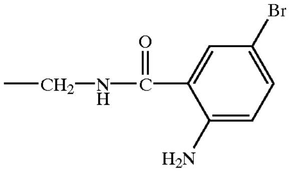 |
TABLE 1.160
| Compd No. | 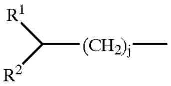 | k | m | n | chirality | $R^3$ | 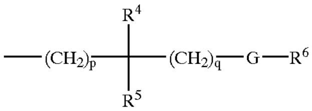 |
|---|---|---|---|---|---|---|---|
| 1750 | 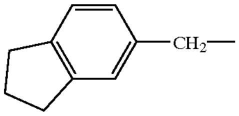 | 1 | 2 | 0 | R | H | 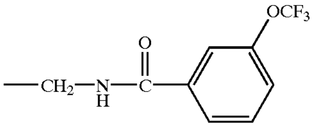 |
| 1751 | 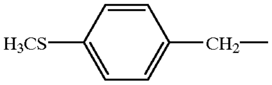 | 1 | 2 | 0 | R | H | 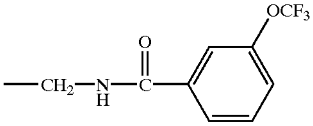 |
| 1752 | 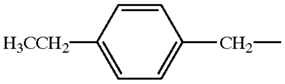 | 1 | 2 | 0 | R | H | 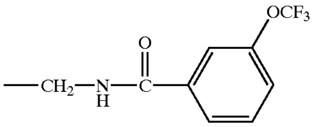 |
| 1753 | 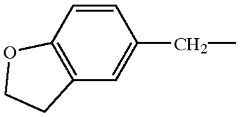 | 1 | 2 | 0 | R | H | 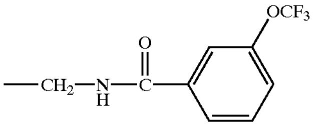 |
| 1754 | 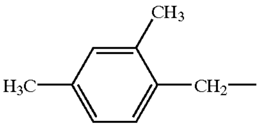 | 1 | 2 | 0 | R | H | 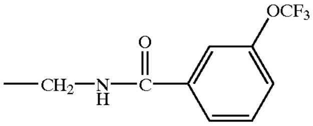 |

TABLE 1.160-continued
| Compd No. | 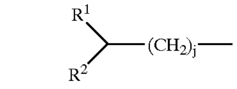 | k | m | n | chirality | $R^3$ | 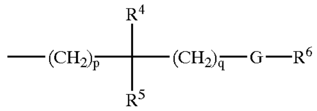 |
|---|---|---|---|---|---|---|---|
| 1755 | 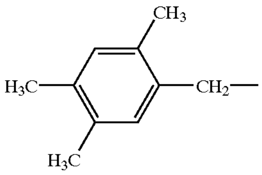 | 1 | 2 | 0 | R | H | 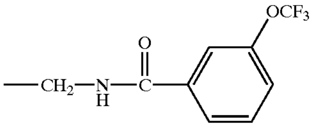 |
| 1756 | 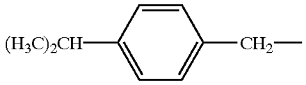 | 1 | 2 | 0 | R | H | 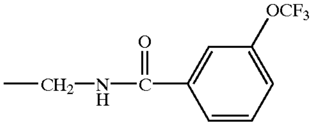 |
| 1757 | 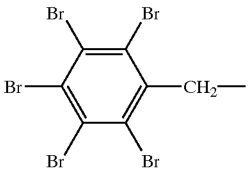 | 1 | 2 | 0 | R | H | 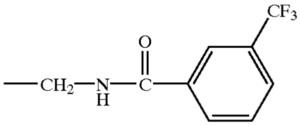 |
| 1758 | 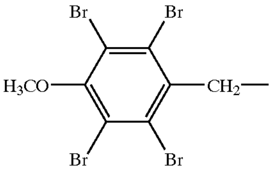 | 1 | 2 | 0 | R | H | 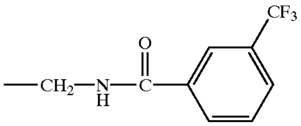 |
| 1759 | 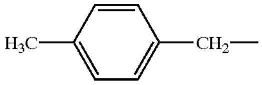 | 1 | 2 | 0 | R | H | 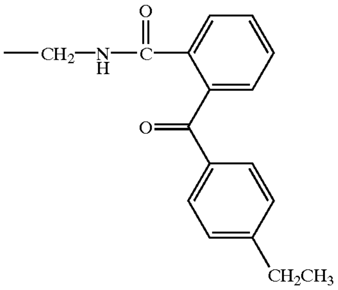 |
| 1760 | 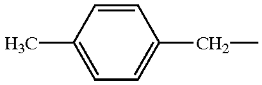 | 1 | 2 | 0 | R | H | 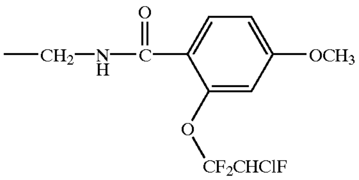 |

TABLE 1.161
| Compd No. | 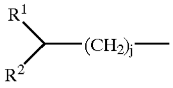 | k | m | n | chirality | $R^3$ | 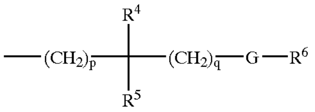 |
|---|---|---|---|---|---|---|---|
| 1761 | 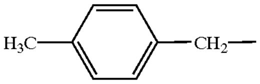 | 1 | 2 | 0 | R | H | 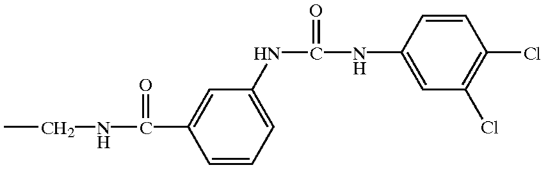 |
| 1762 | 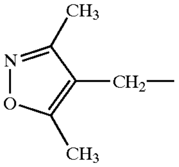 | 1 | 2 | 0 | R | H | 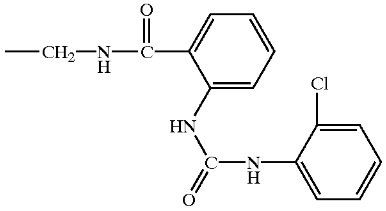 |
| 1763 | 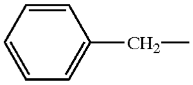 | 2 | 2 | 0 | — | H | 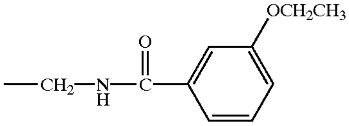 |
| 1764 | 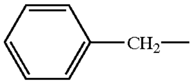 | 2 | 2 | 0 | — | H | 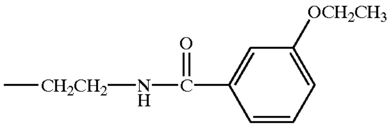 |
| 1765 | 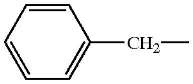 | 2 | 2 | 0 | — | H | 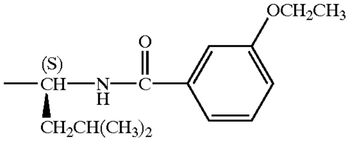 |
| 1766 | 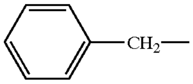 | 2 | 2 | 0 | — | H | 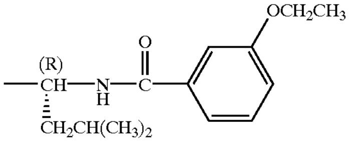 |
| 1767 | 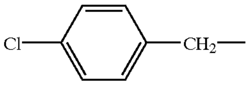 | 1 | 3 | 1 | — | H | 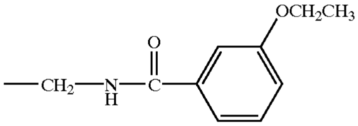 |
| 1768 | 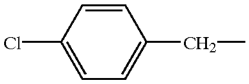 | 1 | 3 | 1 | — | H | 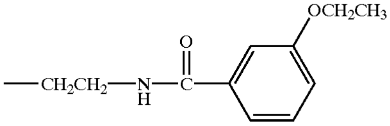 |
| 1769 | 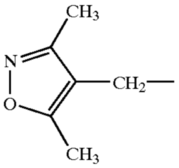 | 1 | 2 | 0 | R | H | 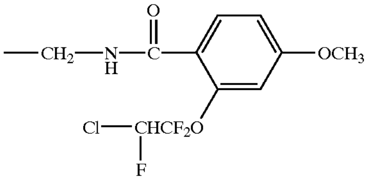 |

TABLE 1.161-continued
| Compd No. | 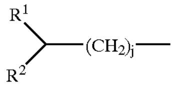 | k | m | n | chirality | $R^3$ | 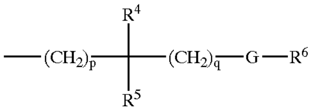 |
|---|---|---|---|---|---|---|---|
| 1770 | 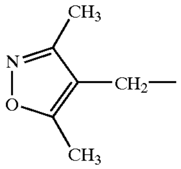 | 1 | 2 | 0 | R | H | 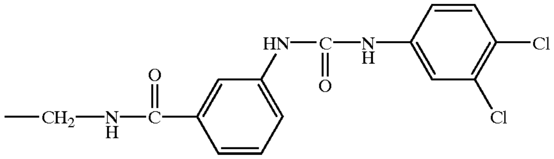 |
| 1771 | 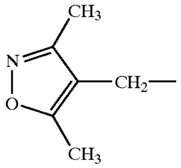 | 1 | 2 | 0 | R | H | 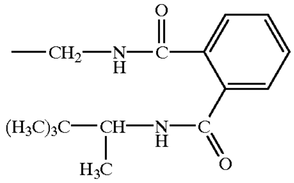 |
TABLE 1.162
| Compd No. | 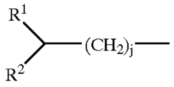 | k | m | n | chira-lity | $R^3$ | 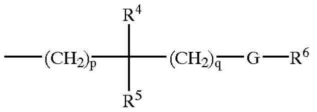 |
|---|---|---|---|---|---|---|---|
| 1772 | 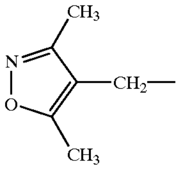 | 1 | 2 | 0 | R | H | 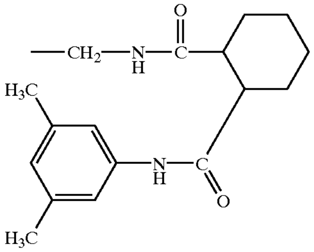 |
| 1773 | 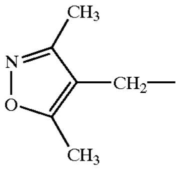 | 1 | 2 | 0 | R | H | 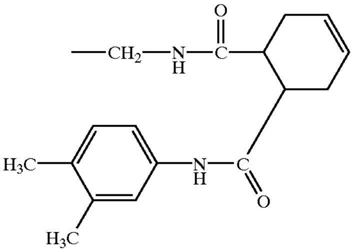 |
| 1774 | 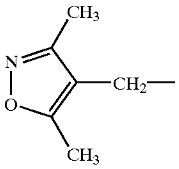 | 1 | 2 | 0 | R | H | 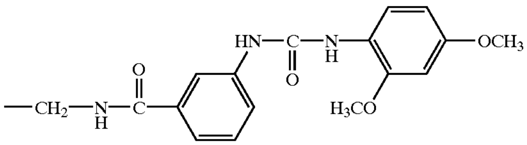 |

TABLE 1.162-continued
| Compd No. | 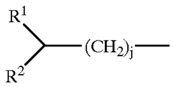 | k | m | n | chira-lity | $R^3$ | 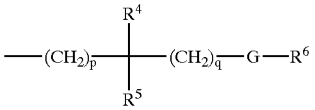 |
|---|---|---|---|---|---|---|---|
| 1775 | 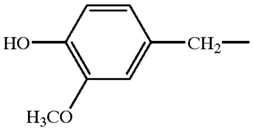 | 1 | 2 | 0 | R | H | 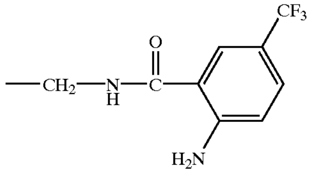 |
| 1776 | 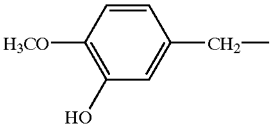 | 1 | 2 | 0 | R | H | 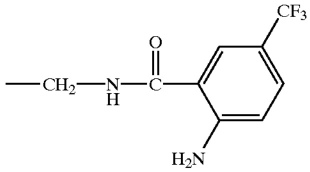 |
| 1777 | 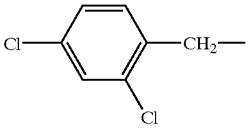 | 2 | 2 | 1 | — | H | 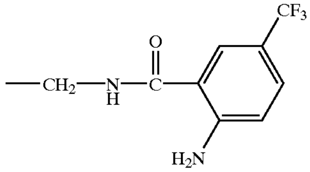 |
| 1778 | 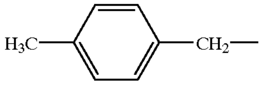 | 2 | 2 | 1 | — | H | 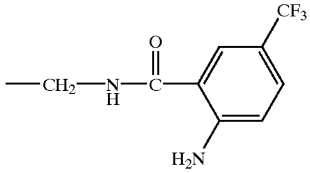 |
| 1779 | 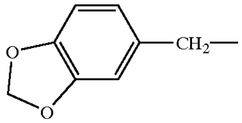 | 2 | 2 | 1 | — | H | 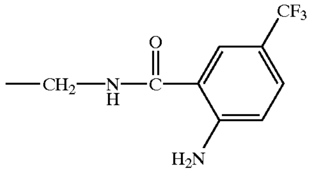 |
| 1780 | 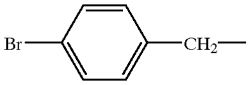 | 2 | 2 | 1 | — | H | 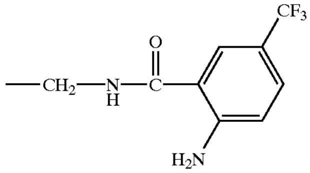 |
| 1781 | 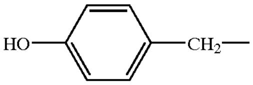 | 2 | 2 | 1 | — | H | 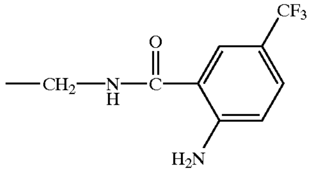 |

TABLE 1.162-continued
| Compd No. | 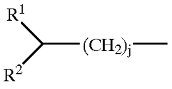 | k | m | n | chira-lity | $R^3$ | 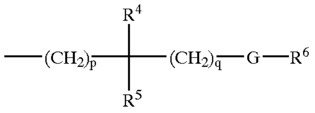 |
|---|---|---|---|---|---|---|---|
| 1782 | 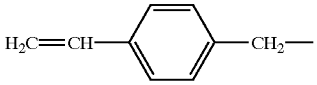 | 2 | 2 | 1 | — | H | 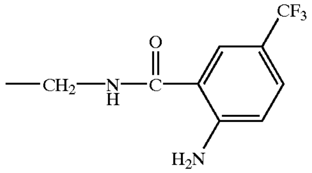 |
TABLE 1.163
| Compd No. | 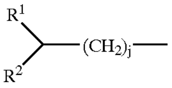 | k | m | n | chirality | $R^3$ | 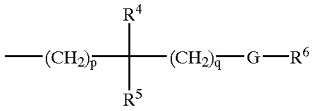 |
|---|---|---|---|---|---|---|---|
| 1783 | 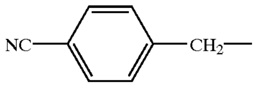 | 2 | 2 | 1 | — | H | 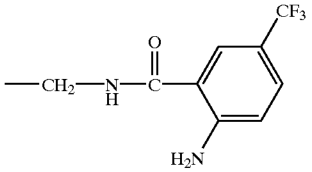 |
| 1784 | 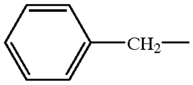 | 2 | 2 | 1 | — | H | 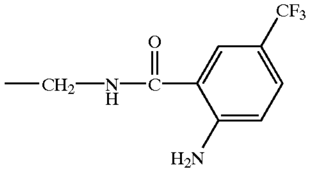 |
| 1785 | 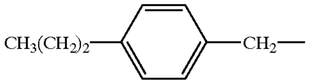 | 2 | 2 | 1 | — | H | 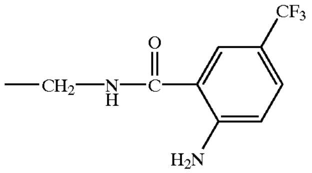 |
| 1786 | 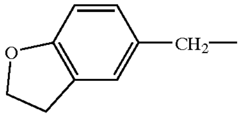 | 2 | 2 | 1 | — | H | 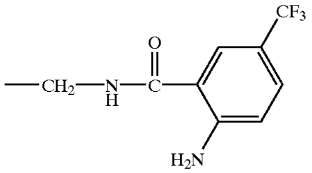 |
| 1787 | 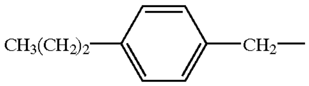 | 1 | 2 | 0 | R | H | 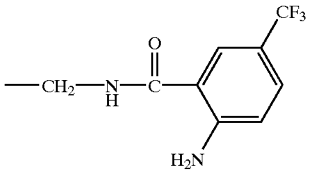 |

TABLE 1.163-continued
| Compd No. | 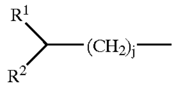 | k | m | n | chirality | $R^3$ | 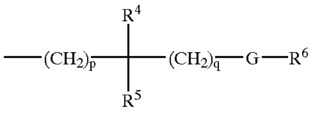 |
|---|---|---|---|---|---|---|---|
| 1788 | 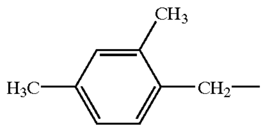 | 2 | 2 | 1 | — | H | 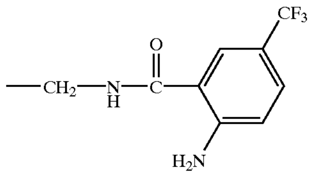 |
| 1789 | 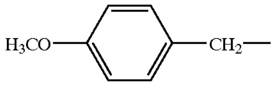 | 2 | 2 | 1 | — | H | 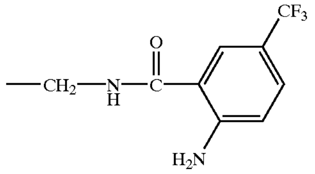 |
| 1790 | 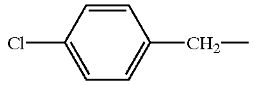 | 1 | 2 | 0 | S | H | 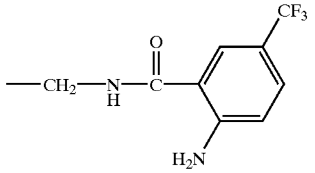 |
| 1791 | 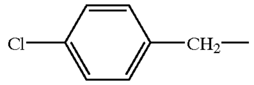 | 1 | 2 | 0 | S | H | 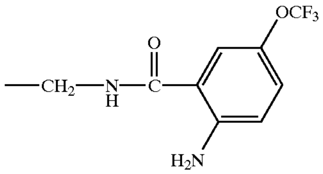 |
| 1792 | 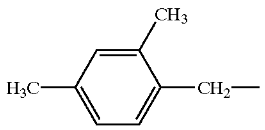 | 2 | 2 | 1 | — | H | 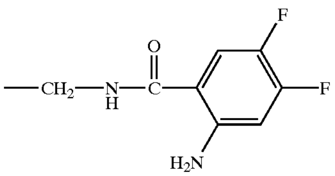 |
| 1793 | 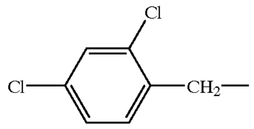 | 2 | 2 | 1 | — | H | 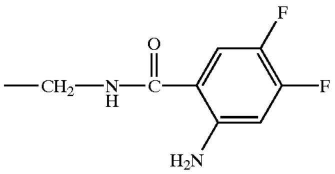 |

TABLE 1.164
| Compd No. | 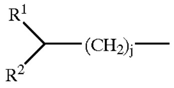 | k | m | n | chirality | $R^3$ | 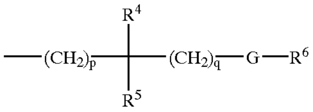 |
|---|---|---|---|---|---|---|---|
| 1794 | 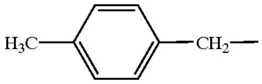 | 2 | 2 | 1 | — | H | 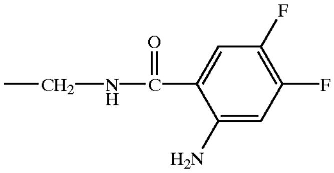 |
| 1795 | 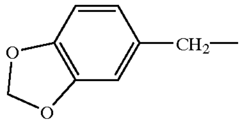 | 2 | 2 | 1 | — | H | 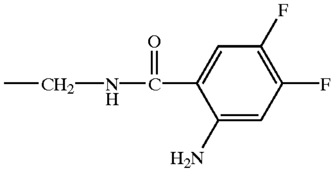 |
| 1796 | 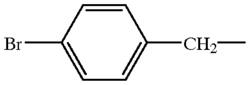 | 2 | 2 | 1 | — | H | 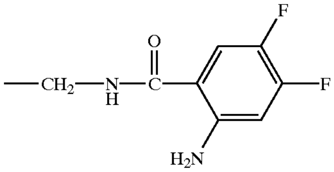 |
| 1797 | 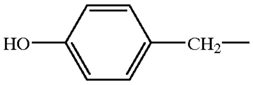 | 2 | 2 | 1 | — | H | 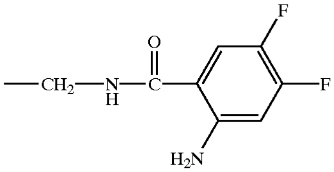 |
| 1798 | 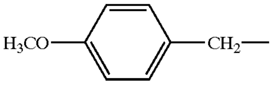 | 2 | 2 | 1 | — | H | 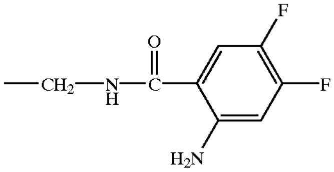 |
| 1799 | 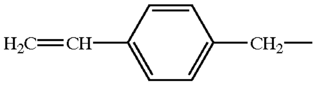 | 2 | 2 | 1 | — | H | 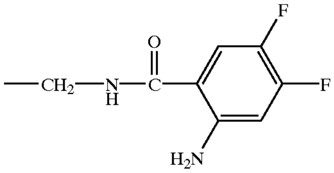 |
| 1800 | 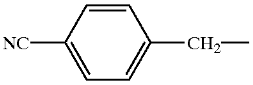 | 2 | 2 | 1 | — | H | 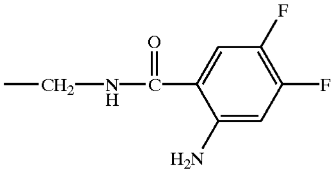 |
| 1801 | 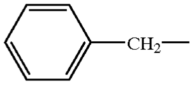 | 2 | 2 | 1 | — | H | 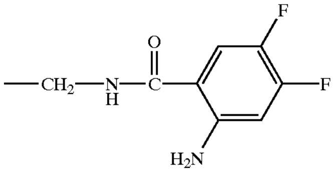 |

TABLE 1.164-continued
| Compd No. | 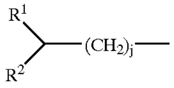 | k | m | n | chirality | $R^3$ | 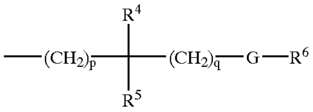 |
|---|---|---|---|---|---|---|---|
| 1802 | 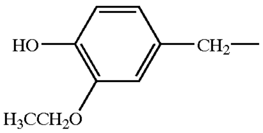 | 1 | 2 | 0 | R | H | 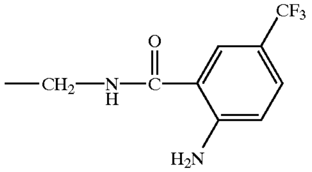 |
| 1803 | 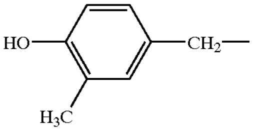 | 1 | 2 | 0 | R | H | 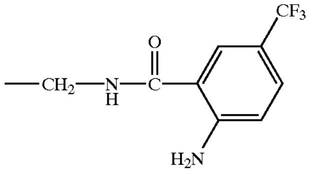 |
| 1804 | 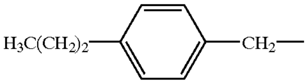 | 2 | 2 | 1 | — | H | 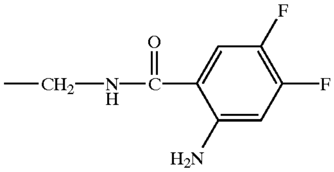 |
TABLE 1.165
| Compd No. | 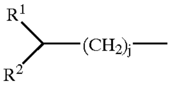 | k | m | n | chirality | $R^3$ | 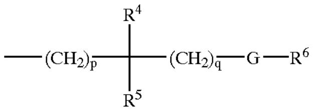 |
|---|---|---|---|---|---|---|---|
| 1805 | 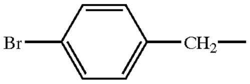 | 1 | 2 | 0 | R | H | 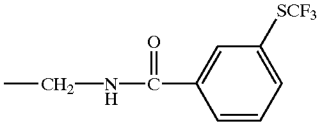 |
| 1806 | 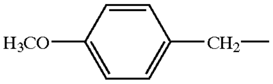 | 1 | 2 | 0 | R | H | 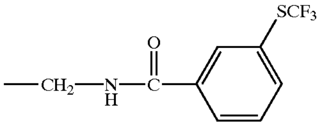 |
| 1807 | 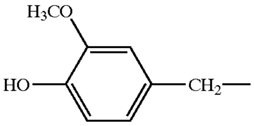 | 1 | 2 | 0 | R | H | 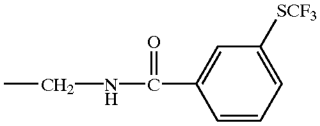 |
| 1808 | 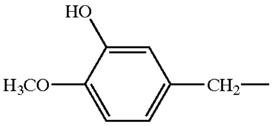 | 1 | 2 | 0 | R | H | 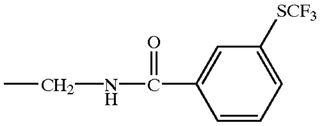 |

TABLE 1.165-continued
| Compd No. | 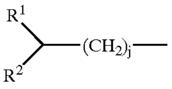 | k | m | n | chirality | $R^3$ | 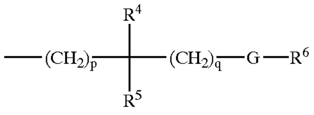 |
|---|---|---|---|---|---|---|---|
| 1809 | 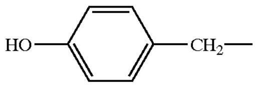 | 1 | 2 | 0 | R | H | 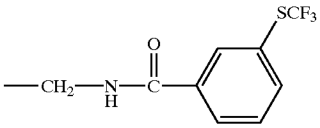 |
| 1810 | 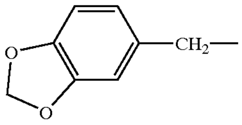 | 1 | 2 | 0 | R | H | 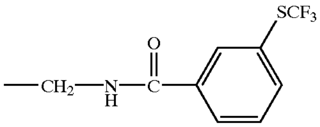 |
| 1811 | 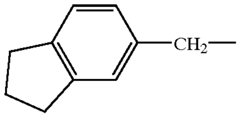 | 1 | 2 | 0 | R | H | 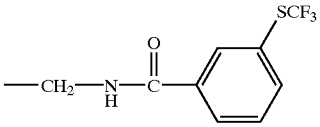 |
| 1812 | 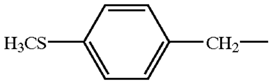 | 1 | 2 | 0 | R | H | 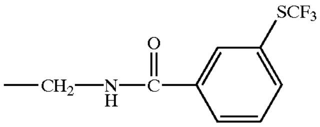 |
| 1813 | 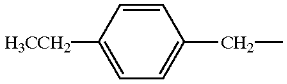 | 1 | 2 | 0 | R | H | 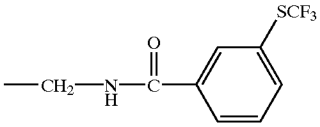 |
| 1814 | 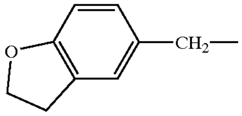 | 1 | 2 | 0 | R | H | 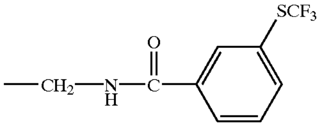 |
| 1815 | 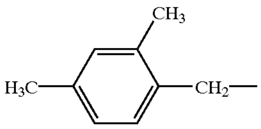 | 1 | 2 | 0 | R | H | 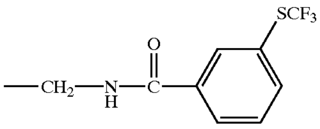 |
TABLE 1.166
| Compd No. | 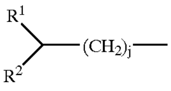 | k | m | n | chirality | $R^3$ | 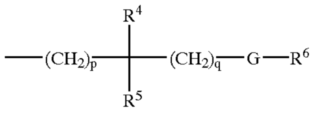 |
|---|---|---|---|---|---|---|---|
| 1816 | 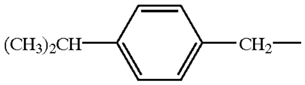 | 1 | 2 | 0 | R | H | 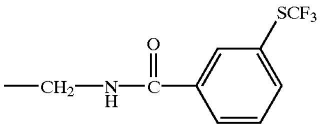 |

TABLE 1.166-continued
| Compd No. | 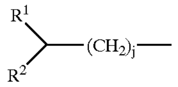 | k | m | n | chirality | $R^3$ | 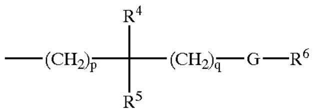 |
|---|---|---|---|---|---|---|---|
| 1817 | 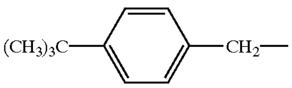 | 1 | 2 | 0 | R | H | 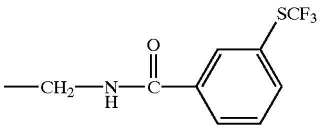 |
| 1818 | 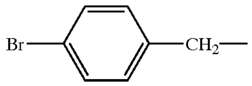 | 1 | 2 | 0 | R | H | 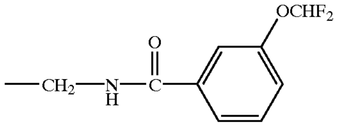 |
| 1819 | 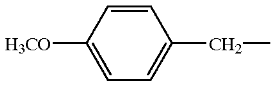 | 1 | 2 | 0 | R | H | 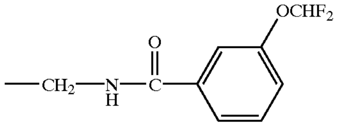 |
| 1820 | 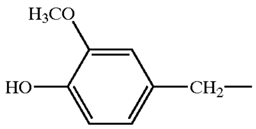 | 1 | 2 | 0 | R | H | 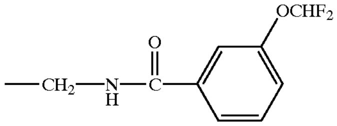 |
| 1821 | 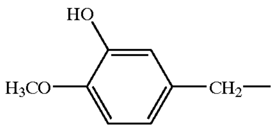 | 1 | 2 | 0 | R | H | 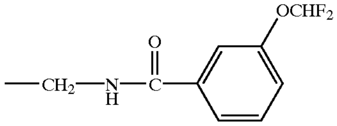 |
| 1822 | 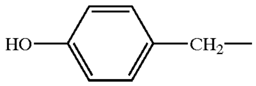 | 1 | 2 | 0 | R | H | 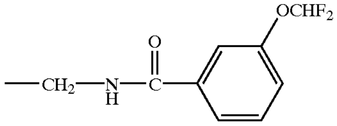 |
| 1823 | 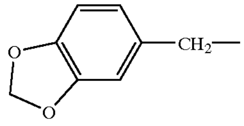 | 1 | 2 | 0 | R | H | 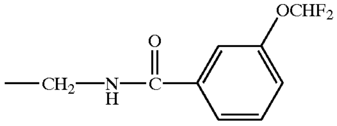 |
| 1824 | 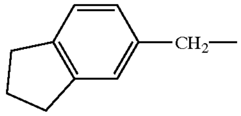 | 1 | 2 | 0 | R | H | 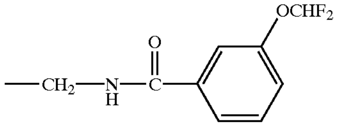 |
| 1825 | 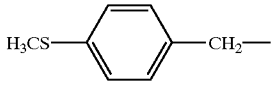 | 1 | 2 | 0 | R | H | 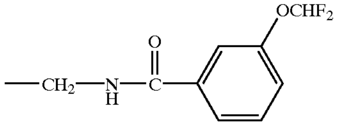 |
| 1826 | 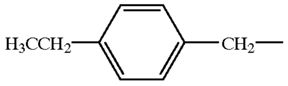 | 1 | 2 | 0 | R | H | 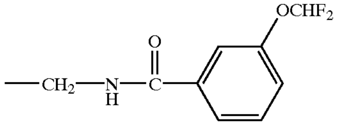 |

TABLE 1.167
| Compd No. | 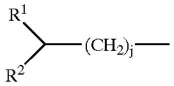 | k | m | n | chirality | $R^3$ | 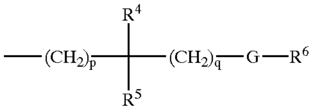 |
|---|---|---|---|---|---|---|---|
| 1827 | 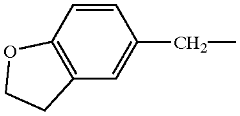 | 1 | 2 | 0 | R | H | 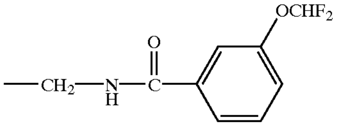 |
| 1828 | 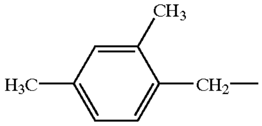 | 1 | 2 | 0 | R | H | 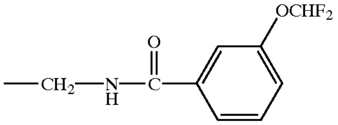 |
| 1829 | 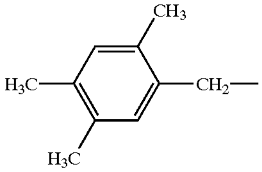 | 1 | 2 | 0 | R | H | 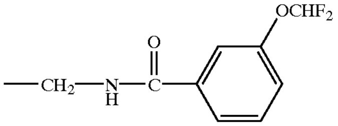 |
| 1830 | 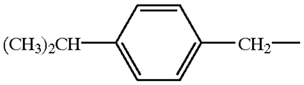 | 1 | 2 | 0 | R | H | 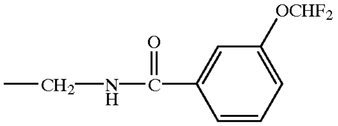 |
| 1831 | 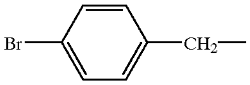 | 1 | 2 | 0 | R | H | 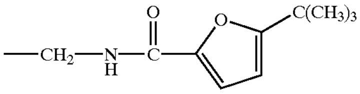 |
| 1832 | 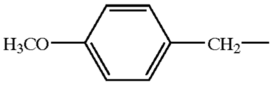 | 1 | 2 | 0 | R | H | 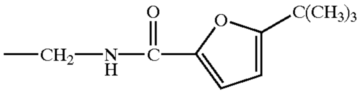 |
| 1833 | 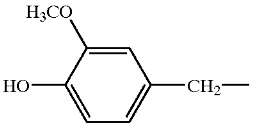 | 1 | 2 | 0 | R | H | 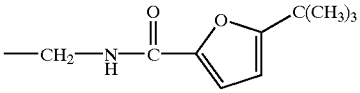 |
| 1834 | 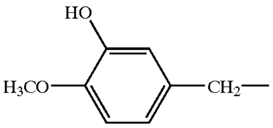 | 1 | 2 | 0 | R | H | 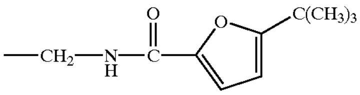 |
| 1835 | 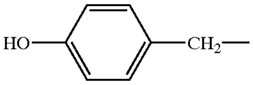 | 1 | 2 | 0 | R | H | 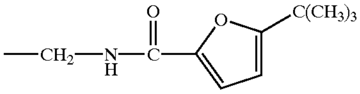 |
| 1836 | 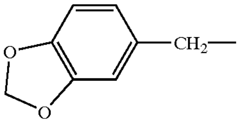 | 1 | 2 | 0 | R | H | 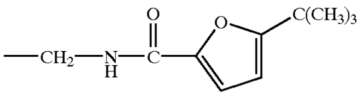 |

TABLE 1.167-continued
| Compd No. | 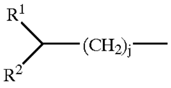 | k | m | n | chirality | $R^3$ | 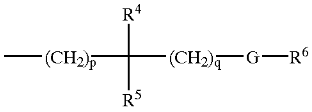 |
|---|---|---|---|---|---|---|---|
| 1837 | 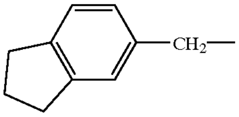 | 1 | 2 | 0 | R | H | 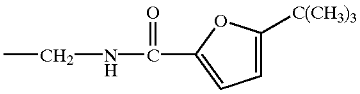 |
TABLE 1.168
| Compd No. | 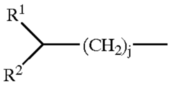 | k | m | n | chirality | $R^3$ | 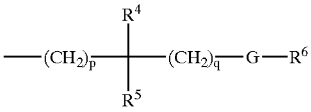 |
|---|---|---|---|---|---|---|---|
| 1838 | 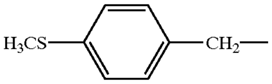 | 1 | 2 | 0 | R | H | 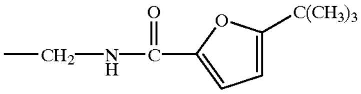 |
| 1839 | 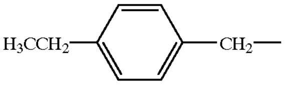 | 1 | 2 | 0 | R | H | 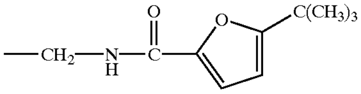 |
| 1840 | 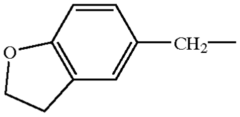 | 1 | 2 | 0 | R | H | 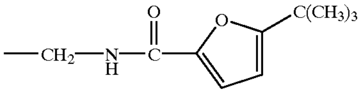 |
| 1841 | 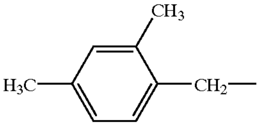 | 1 | 2 | 0 | R | H | 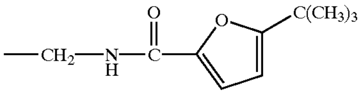 |
| 1842 | 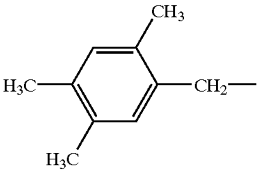 | 1 | 2 | 0 | R | H | 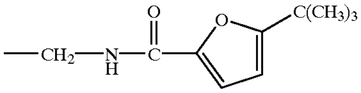 |
| 1843 | 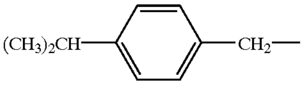 | 1 | 2 | 0 | R | H | 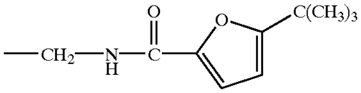 |
| 1844 | 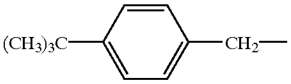 | 1 | 2 | 0 | R | H | 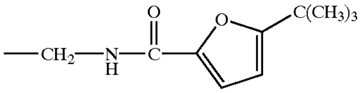 |

TABLE 1.168-continued
| Compd No. | 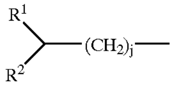 | k | m | n | chirality | $R^3$ | 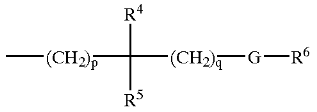 |
|---|---|---|---|---|---|---|---|
| 1845 | 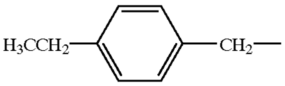 | 1 | 2 | 0 | R | H | 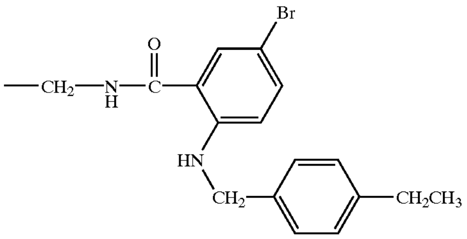 |
| 1846 | 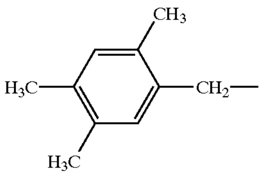 | 1 | 2 | 0 | R | H | 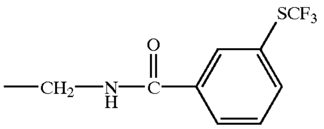 |
| 1847 | 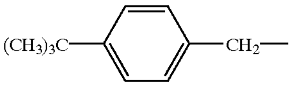 | 1 | 2 | 0 | R | H | 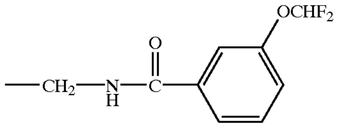 |
| 1848 | 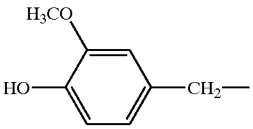 | 1 | 2 | 0 | R | H | 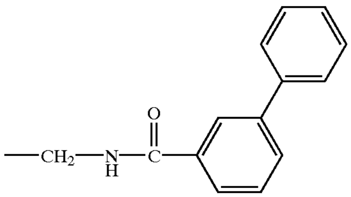 |
TABLE 1.169
| Compd No. | 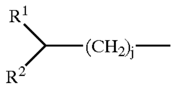 | k | m | n | chirality | $R^3$ | 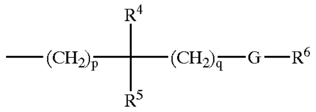 |
|---|---|---|---|---|---|---|---|
| 1849 | 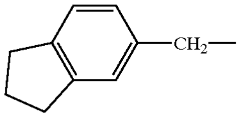 | 1 | 2 | 0 | R | H | 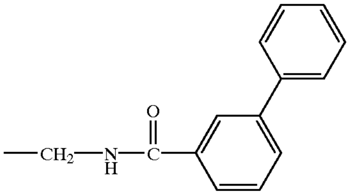 |
| 1850 | 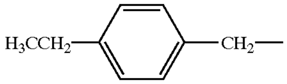 | 1 | 2 | 0 | R | H | 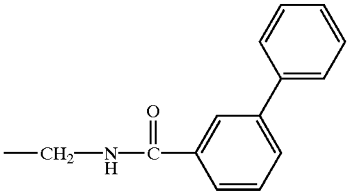 |

TABLE 1.169-continued
| Compd No. | 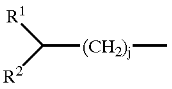 | k | m | n | chirality | $R^3$ | 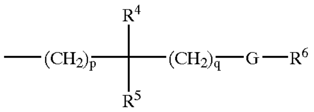 |
|---|---|---|---|---|---|---|---|
| 1851 | 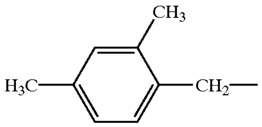 | 1 | 2 | 0 | R | H | 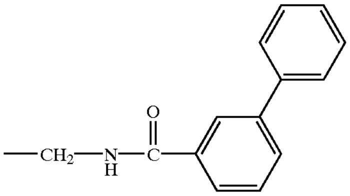 |
| 1852 | 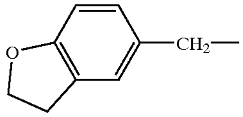 | 1 | 2 | 0 | R | H | 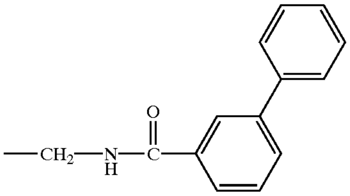 |
| 1853 | 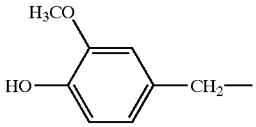 | 1 | 2 | 0 | R | H | 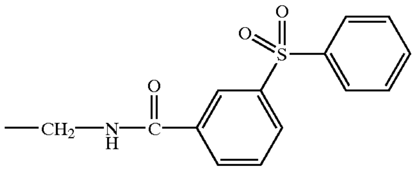 |
| 1854 | 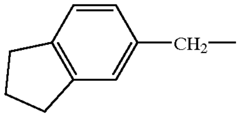 | 1 | 2 | 0 | R | H | 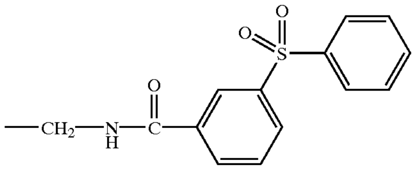 |
| 1855 | 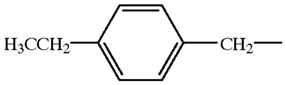 | 1 | 2 | 0 | R | H | 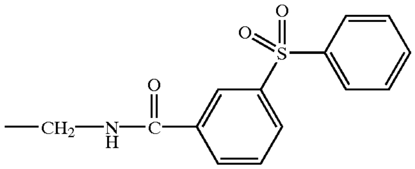 |
| 1856 | 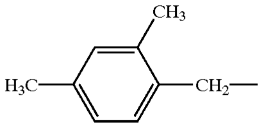 | 1 | 2 | 0 | R | H | 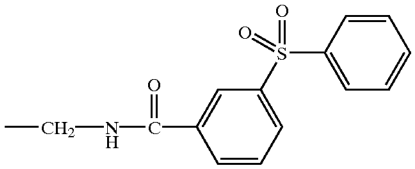 |
| 1857 | 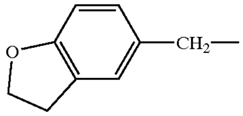 | 1 | 2 | 0 | R | H | 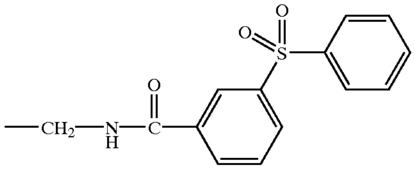 |

TABLE 1.169-continued
| Compd No. | 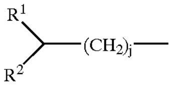 | k | m | n | chirality | $R^3$ | 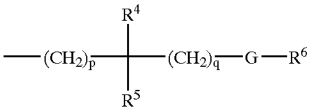 |
|---|---|---|---|---|---|---|---|
| 1858 | 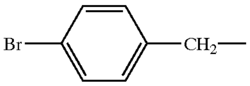 | 1 | 2 | 0 | R | H | 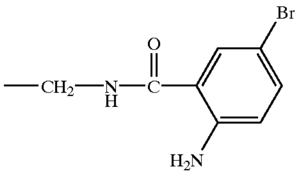 |
| 1859 | 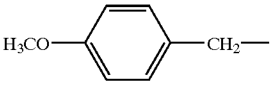 | 1 | 2 | 0 | R | H | 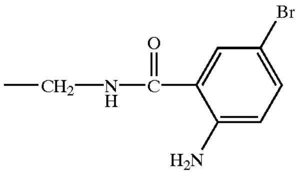 |
TABLE 1.170
| Compd. No. | 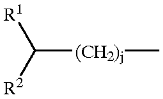 | k | m | n | chirality | $R^3$ | 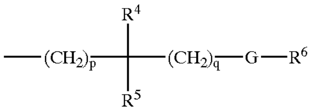 |
|---|---|---|---|---|---|---|---|
| 1860 | 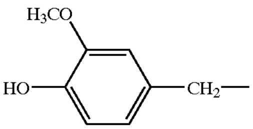 | 1 | 2 | 0 | R | H | 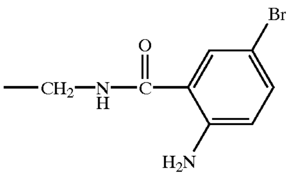 |
| 1861 | 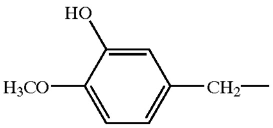 | 1 | 2 | 0 | R | H | 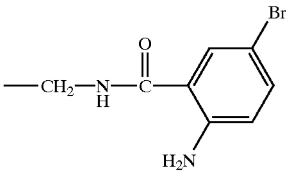 |
| 1862 | 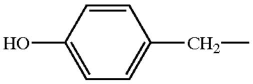 | 1 | 2 | 0 | R | H | 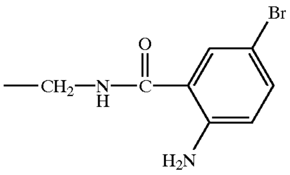 |
| 1863 | 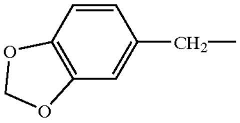 | 1 | 2 | 0 | R | H | 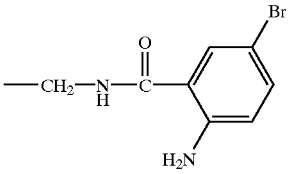 |

TABLE 1.170-continued
| Compd. No. | 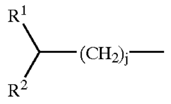 | k | m | n | chirality | $R^3$ | 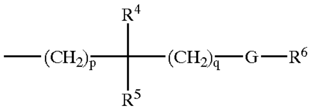 |
|---|---|---|---|---|---|---|---|
| 1864 | 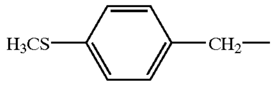 | 1 | 2 | 0 | R | H | 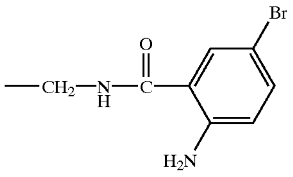 |
| 1865 | 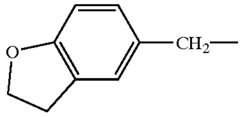 | 1 | 2 | 0 | R | H | 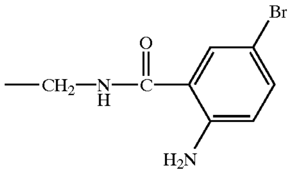 |
| 1866 | 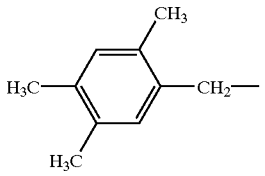 | 1 | 2 | 0 | R | H | 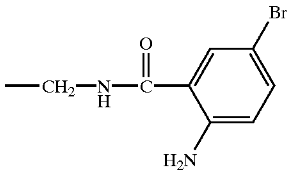 |
| 1867 | 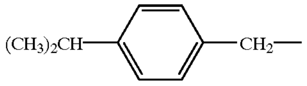 | 1 | 2 | 0 | R | H | 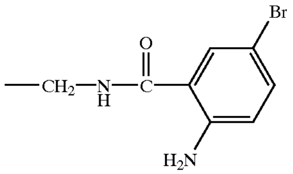 |
| 1868 | 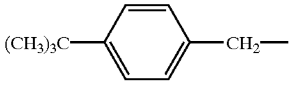 | 1 | 2 | 0 | R | H | 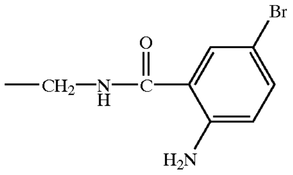 |
| 1869 | 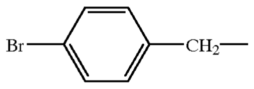 | 1 | 2 | 0 | R | H | 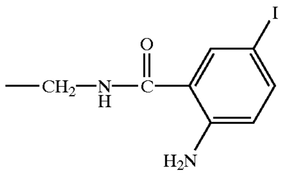 |
| 1870 | 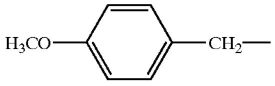 | 1 | 2 | 0 | R | H | 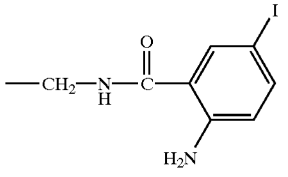 |

TABLE 1.171
| Compd. No. | 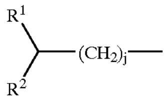 | k | m | n | chirality | $R^3$ | 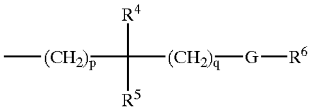 |
|---|---|---|---|---|---|---|---|
| 1871 | 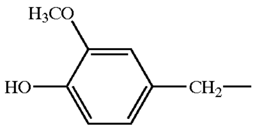 | 1 | 2 | 0 | R | H | 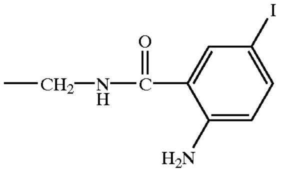 |
| 1872 | 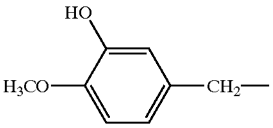 | 1 | 2 | 0 | R | H | 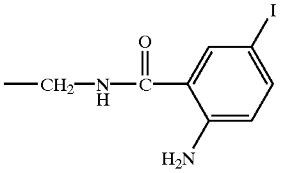 |
| 1873 | 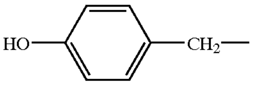 | 1 | 2 | 0 | R | H | 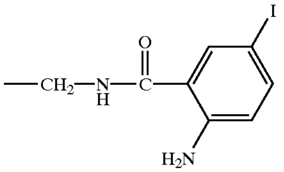 |
| 1874 | 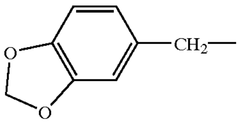 | 1 | 2 | 0 | R | H | 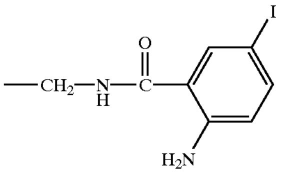 |
| 1875 | 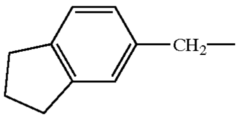 | 1 | 2 | 0 | R | H | 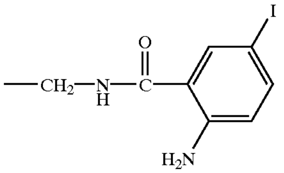 |
| 1876 | 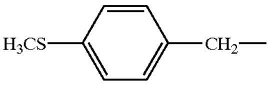 | 1 | 2 | 0 | R | H | 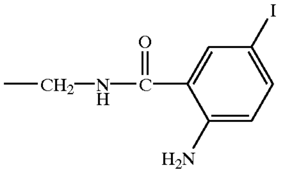 |
| 1877 | 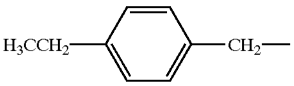 | 1 | 2 | 0 | R | H | 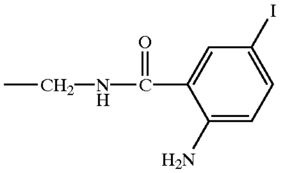 |
| 1878 | 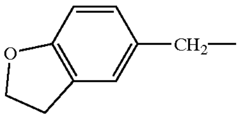 | 1 | 2 | 0 | R | H | 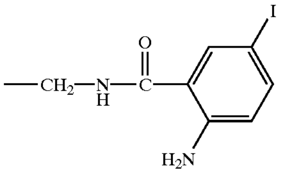 |

TABLE 1.171-continued
| Compd. No. | 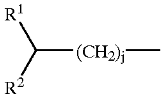 | k | m | n | chirality | $R^3$ | 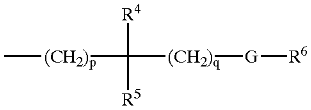 |
| --- | --- | --- | --- | --- | --- | --- | --- |
| 1879 | 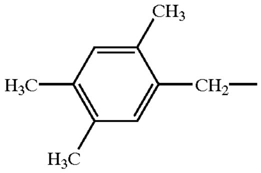 | 1 | 2 | 0 | R | H | 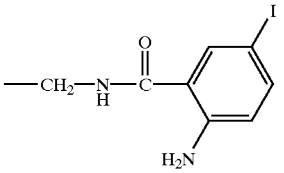 |
| 1880 | 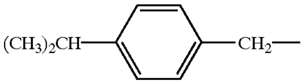 | 1 | 2 | 0 | R | H | 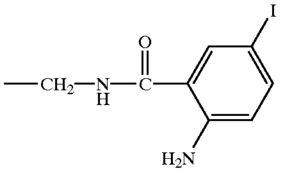 |
| 1881 | 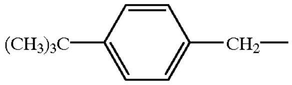 | 1 | 2 | 0 | R | H | 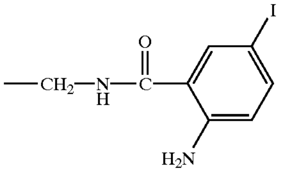 |
TABLE 1.172
| Compd. No. | 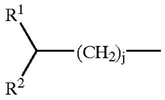 | k | m | n | chirality | $R^3$ | 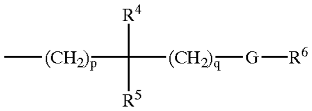 |
| --- | --- | --- | --- | --- | --- | --- | --- |
| 1882 | 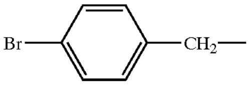 | 1 | 2 | 0 | R | H | 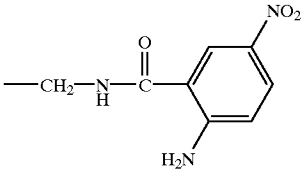 |
| 1883 | 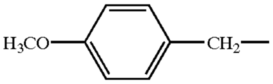 | 1 | 2 | 0 | R | H | 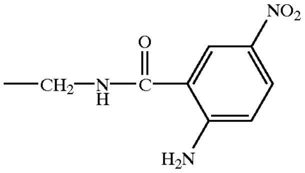 |
| 1884 | 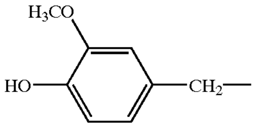 | 1 | 2 | 0 | R | H | 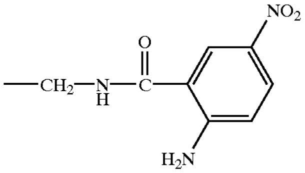 |

TABLE 1.172-continued
| Compd. No. | 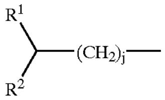 | k | m | n | chirality | $R^3$ | 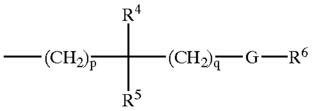 |
|---|---|---|---|---|---|---|---|
| 1885 | 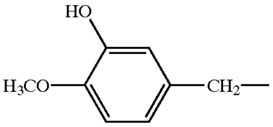 | 1 | 2 | 0 | R | H | 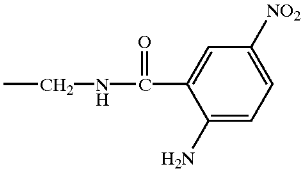 |
| 1886 | 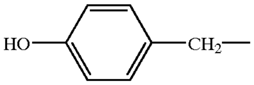 | 1 | 2 | 0 | R | H | 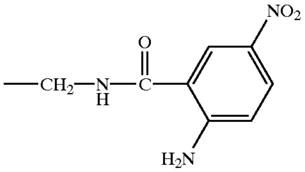 |
| 1887 | 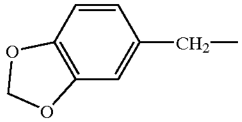 | 1 | 2 | 0 | R | H | 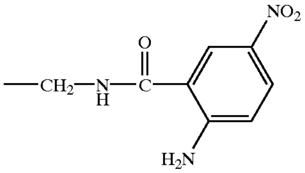 |
| 1888 | 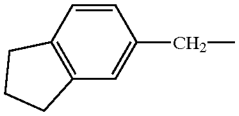 | 1 | 2 | 0 | R | H | 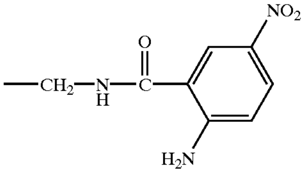 |
| 1889 | 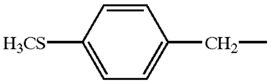 | 1 | 2 | 0 | R | H | 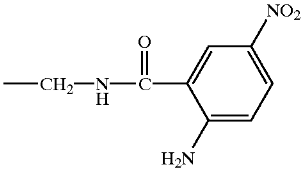 |
| 1890 | 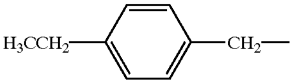 | 1 | 2 | 0 | R | H | 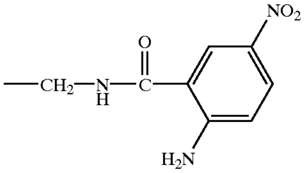 |
| 1891 | 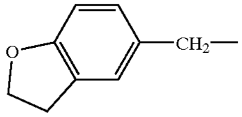 | 1 | 2 | 0 | R | H | 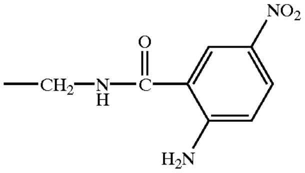 |

TABLE 1.172-continued
| Compd. No. | 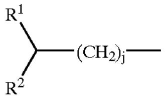 | k | m | n | chirality | $R^3$ | 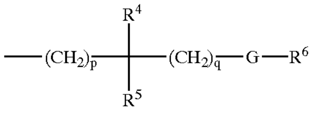 |
|---|---|---|---|---|---|---|---|
| 1892 | 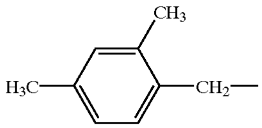 | 1 | 2 | 0 | R | H | 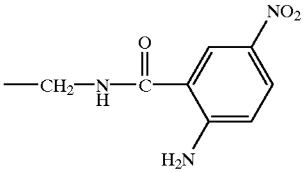 |
TABLE 1.173
| Compd. No. | 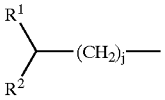 | k | m | n | chirality | $R^3$ | 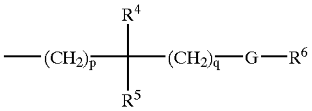 |
|---|---|---|---|---|---|---|---|
| 1893 | 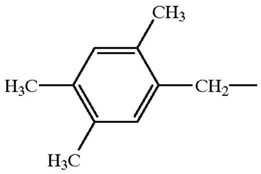 | 1 | 2 | 0 | R | H | 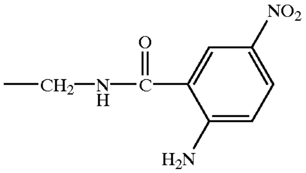 |
| 1894 | 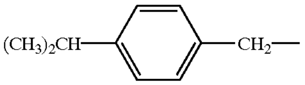 | 1 | 2 | 0 | R | H | 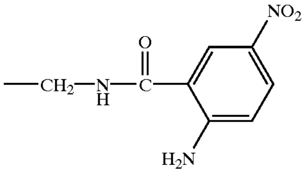 |
| 1895 | 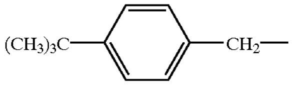 | 1 | 2 | 0 | R | H | 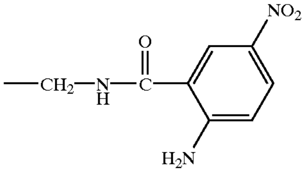 |
| 1896 | 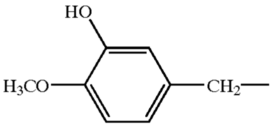 | 1 | 2 | 0 | R | H | 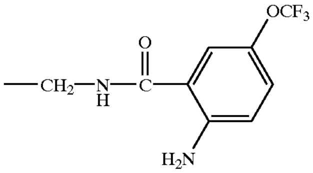 |
| 1897 | 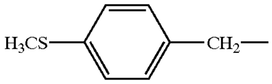 | 1 | 2 | 0 | R | H | 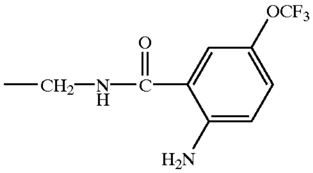 |

TABLE 1.173-continued
| Compd. No. | 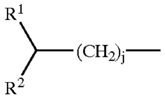 | k | m | n | chirality | $R^3$ | 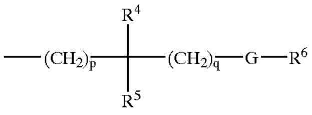 |
|---|---|---|---|---|---|---|---|
| 1898 | 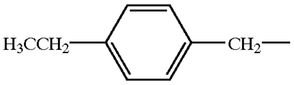 | 1 | 2 | 0 | R | H | 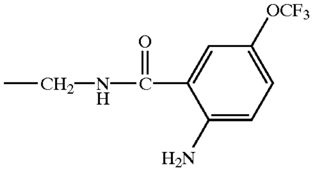 |
| 1899 | 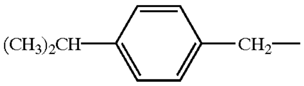 | 1 | 2 | 0 | R | H | 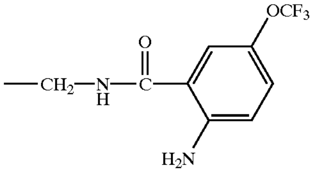 |
| 1900 | 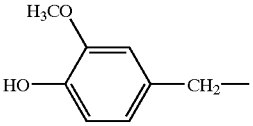 | 1 | 2 | 0 | R | H | 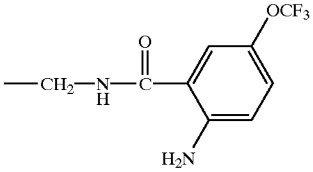 |
| 1901 | 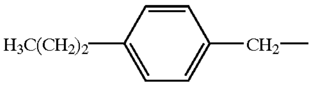 | 1 | 2 | 0 | R | H | 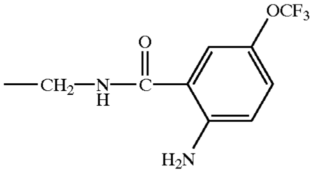 |
| 1902 | 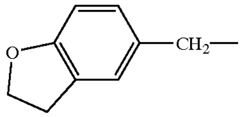 | 1 | 2 | 0 | R | H | 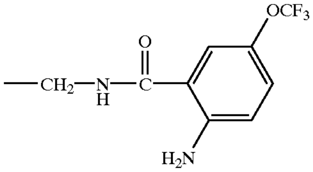 |
| 1903 | 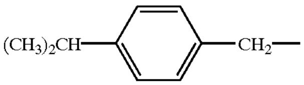 | 2 | 2 | 1 | — | H | 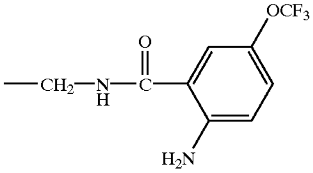 |

TABLE 1.174
| Compd. No. | 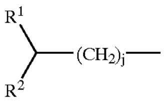 | k | m | n | chirality | $R^3$ | 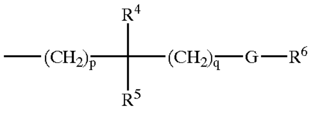 |
|---|---|---|---|---|---|---|---|
| 1904 | 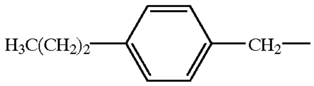 | 2 | 2 | 1 | — | H | 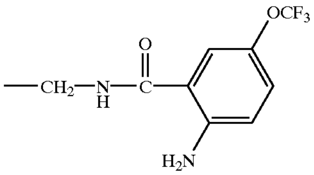 |
| 1905 | 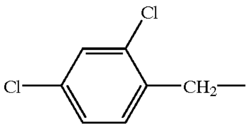 | 1 | 2 | 0 | R | H | 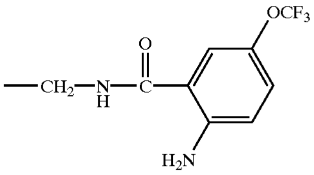 |
| 1906 | 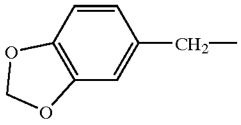 | 1 | 2 | 0 | R | H | 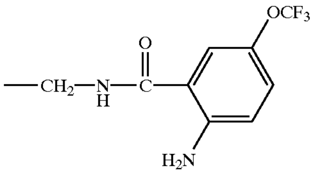 |
| 1907 | 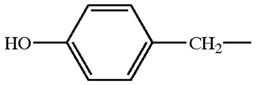 | 1 | 2 | 0 | R | H | 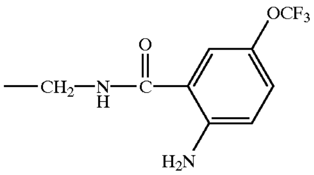 |
| 1908 | 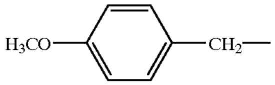 | 1 | 2 | 0 | R | H | 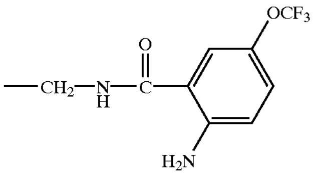 |
| 1909 | 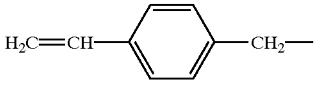 | 1 | 2 | 0 | R | H | 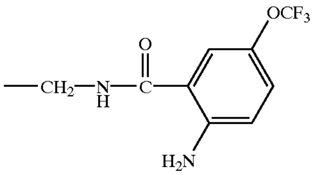 |
| 1910 | 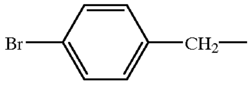 | 2 | 2 | 1 | — | H | 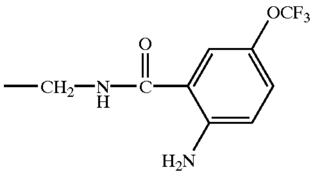 |

TABLE 1.174-continued
| Compd. No. | 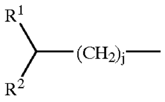 | k | m | n | chirality | $R^3$ | 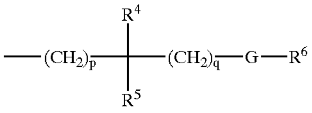 |
|---|---|---|---|---|---|---|---|
| 1911 | 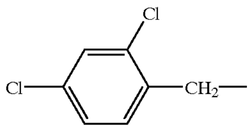 | 2 | 2 | 1 | — | H | 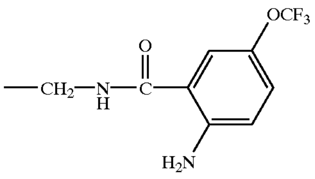 |
| 1912 | 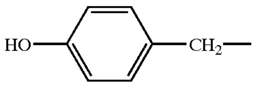 | 2 | 2 | 1 | — | H | 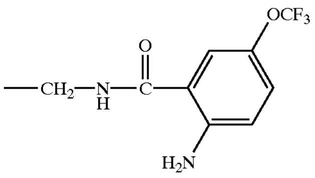 |
| 1913 | 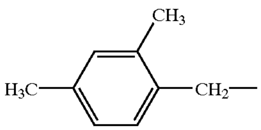 | 2 | 2 | 1 | — | H | 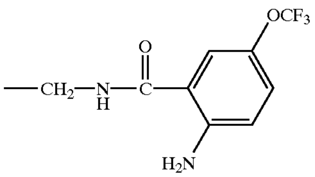 |
| 1914 | 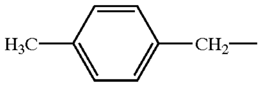 | 2 | 2 | 1 | — | H | 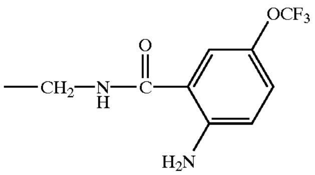 |
TABLE 1.175
| Compd. No. | 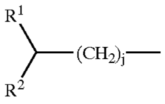 | k | m | n | chirality | $R^3$ | 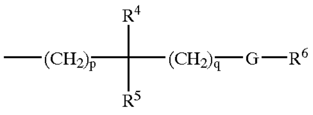 |
|---|---|---|---|---|---|---|---|
| 1915 | 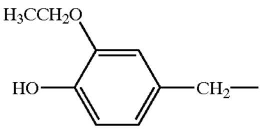 | 1 | 2 | 0 | R | H | 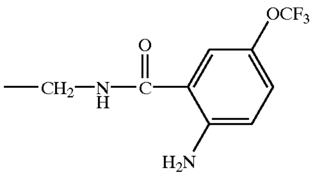 |
| 1916 | 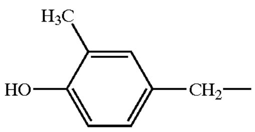 | 1 | 2 | 0 | R | H | 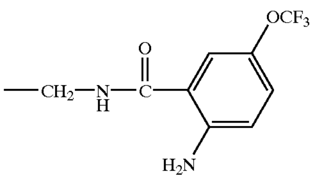 |

TABLE 1.175-continued
| Compd. No. | 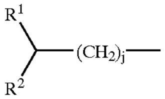 | k | m | n | chirality | $R^3$ | 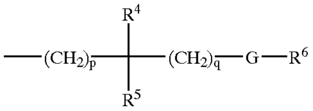 |
|---|---|---|---|---|---|---|---|
| 1917 | 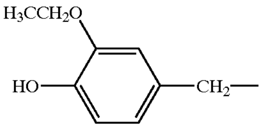 | 2 | 2 | 1 | — | H | 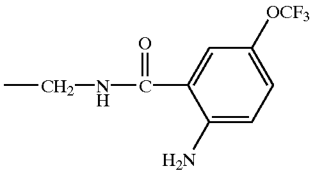 |
| 1918 | 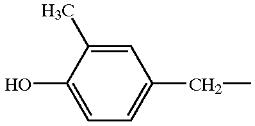 | 2 | 2 | 1 | — | H | 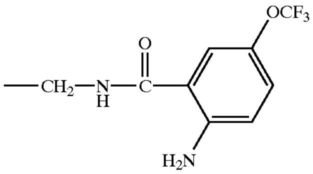 |
| 1919 | 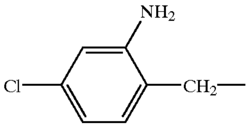 | 2 | 2 | 1 | — | H | 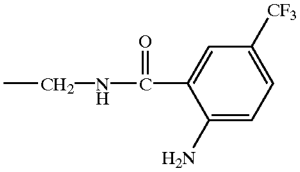 |
| 1920 | 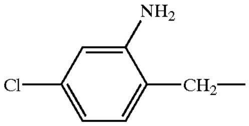 | 2 | 2 | 1 | — | H | 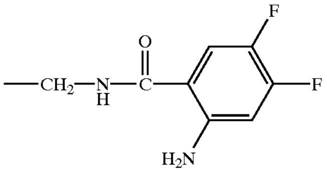 |
| 1921 | 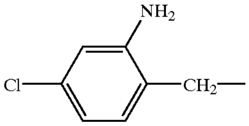 | 1 | 2 | 0 | R | H | 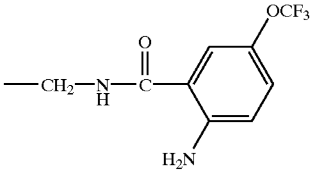 |
| 1922 | 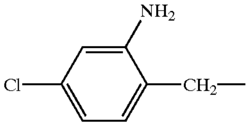 | 2 | 2 | 1 | — | H | 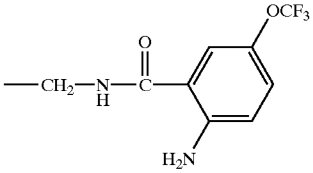 |
| 1923 | 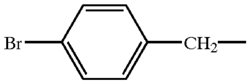 | 2 | 2 | 1 | — | H | 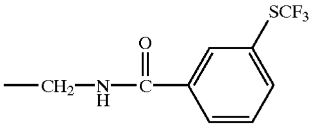 |
| 1924 | 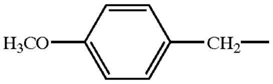 | 2 | 2 | 1 | — | H | 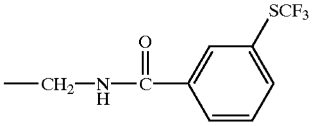 |

TABLE 1.175-continued
| Compd. No. | 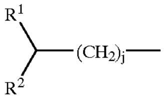 | k | m | n | chirality | $R^3$ | 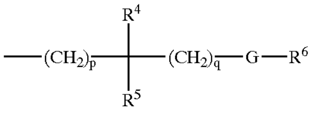 |
|---|---|---|---|---|---|---|---|
| 1925 | 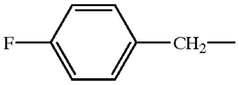 | 2 | 2 | 1 | — | H | 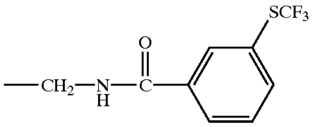 |
TABLE 1.176
| Compd. No. | 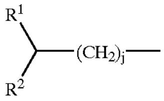 | k | m | n | chirality | $R^3$ | 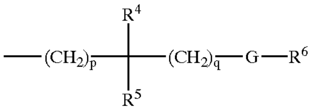 |
|---|---|---|---|---|---|---|---|
| 1926 | 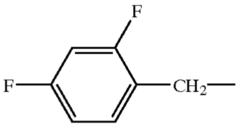 | 2 | 2 | 1 | — | H | 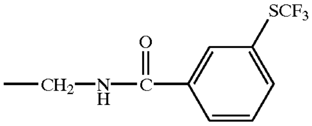 |
| 1927 | 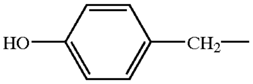 | 2 | 2 | 1 | — | H | 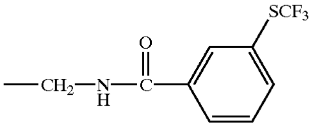 |
| 1928 | 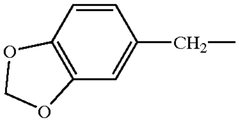 | 2 | 2 | 1 | — | H | 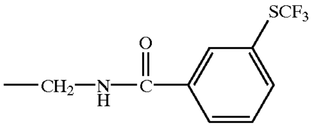 |
| 1929 | 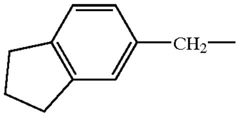 | 2 | 2 | 1 | — | H | 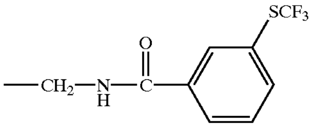 |
| 1930 | 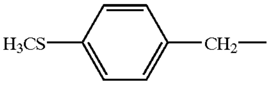 | 2 | 2 | 1 | — | H | 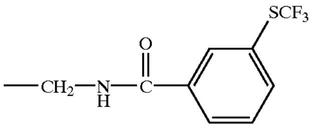 |
| 1931 | 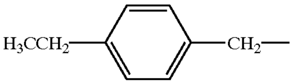 | 2 | 2 | 1 | — | H | 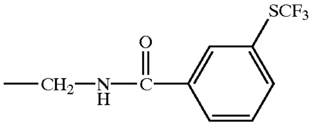 |
| 1932 | 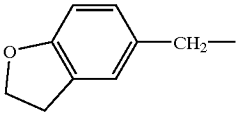 | 2 | 2 | 1 | — | H | 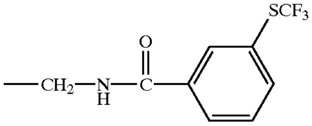 |

TABLE 1.176-continued
| Compd. No. | 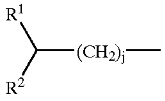 | k | m | n | chirality | $R^3$ | 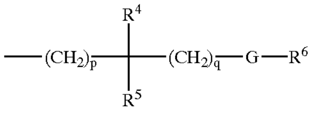 |
|---|---|---|---|---|---|---|---|
| 1933 | 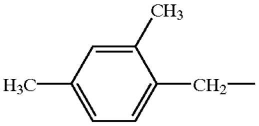 | 2 | 2 | 1 | — | H | 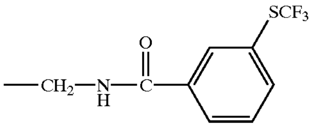 |
| 1934 | 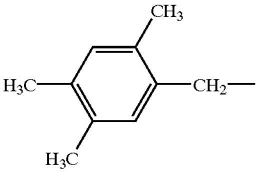 | 2 | 2 | 1 | — | H | 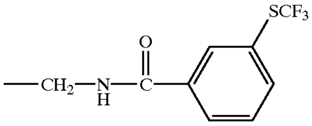 |
| 1935 | 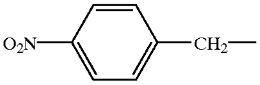 | 2 | 2 | 1 | — | H | 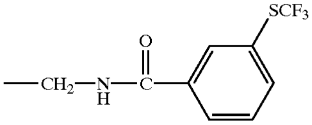 |
| 1936 | 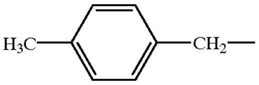 | 2 | 2 | 1 | — | H | 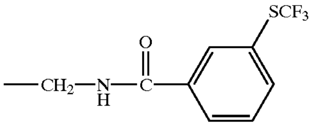 |
TABLE 1.177
| Compd. No. | 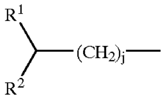 | k | m | n | chirality | $R^3$ | 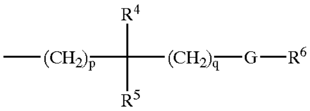 |
|---|---|---|---|---|---|---|---|
| 1937 | 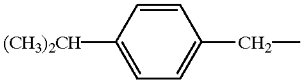 | 2 | 2 | 1 | — | H | 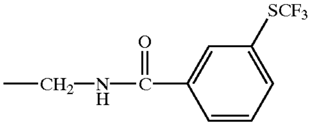 |
| 1938 | 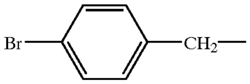 | 2 | 2 | 1 | — | H | 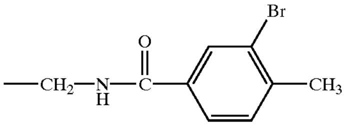 |
| 1939 | 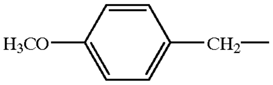 | 2 | 2 | 1 | — | H | 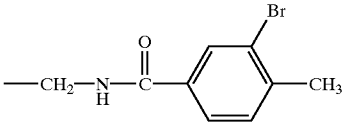 |
| 1940 | 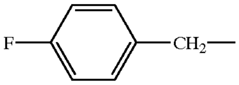 | 2 | 2 | 1 | — | H | 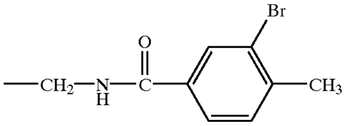 |

TABLE 1.177-continued
| Compd. No. | 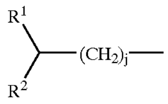 | k | m | n | chirality | $R^3$ | 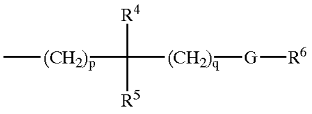 |
|---|---|---|---|---|---|---|---|
| 1941 | 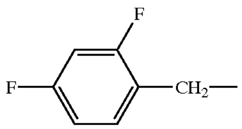 | 2 | 2 | 1 | — | H | 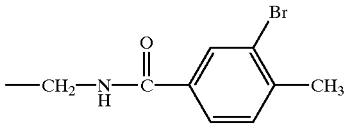 |
| 1942 | 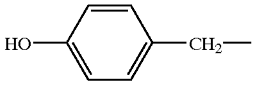 | 2 | 2 | 1 | — | H | 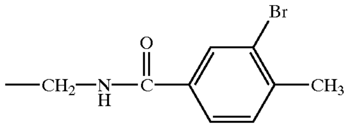 |
| 1943 | 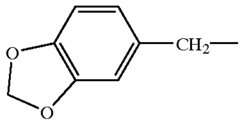 | 2 | 2 | 1 | — | H | 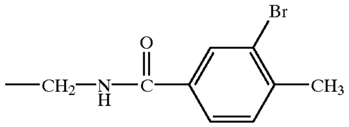 |
| 1944 | 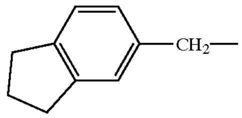 | 2 | 2 | 1 | — | H | 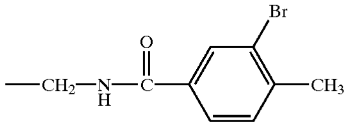 |
| 1945 | 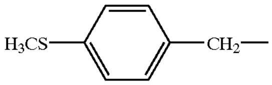 | 2 | 2 | 1 | — | H | 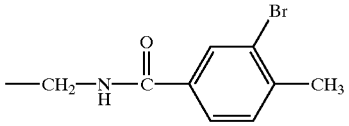 |
| 1946 | 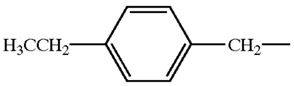 | 2 | 2 | 1 | — | H | 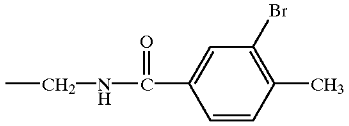 |
| 1947 | 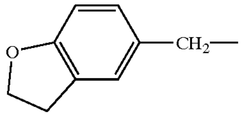 | 2 | 2 | 1 | — | H | 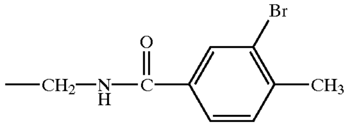 |
TABLE 1.178
| Compd. No. | 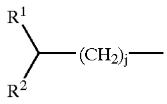 | k | m | n | chirality | $R^3$ | 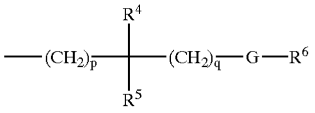 |
|---|---|---|---|---|---|---|---|
| 1948 | 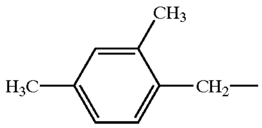 | 2 | 2 | 1 | — | H | 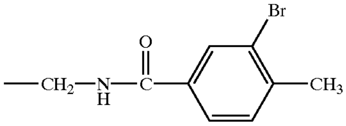 |

TABLE 1.178-continued
| Compd. No. | 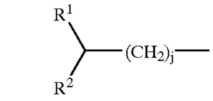 | k | m | n | chirality | $R^3$ | 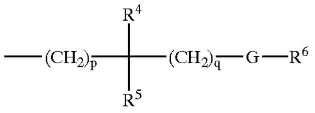 |
|---|---|---|---|---|---|---|---|
| 1949 | 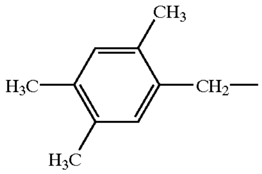 | 2 | 2 | 1 | — | H | 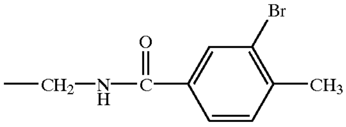 |
| 1950 | 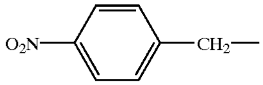 | 2 | 2 | 1 | — | H | 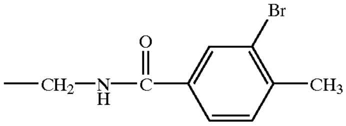 |
| 1951 | 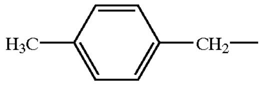 | 2 | 2 | 1 | — | H | 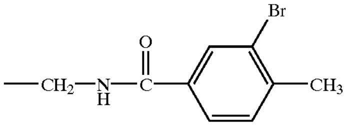 |
| 1952 | 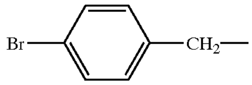 | 2 | 2 | 1 | — | H | 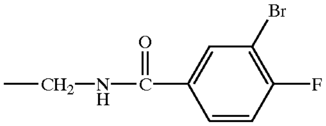 |
| 1953 | 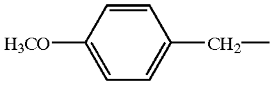 | 2 | 2 | 1 | — | H | 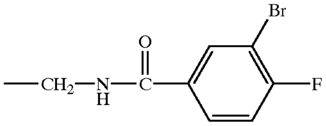 |
| 1954 | 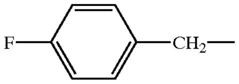 | 2 | 2 | 1 | — | H | 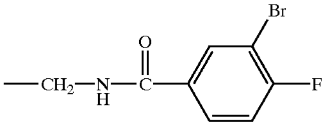 |
| 1955 | 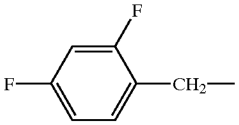 | 2 | 2 | 1 | — | H | 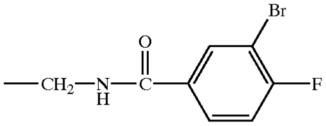 |
| 1956 | 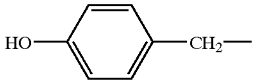 | 2 | 2 | 1 | — | H | 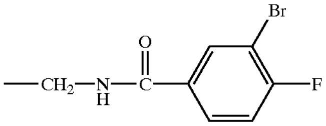 |
| 1957 | 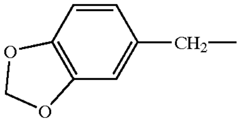 | 2 | 2 | 1 | — | H | 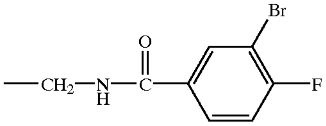 |
| 1958 | 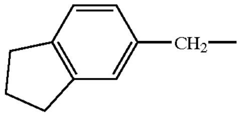 | 2 | 2 | 1 | — | H | 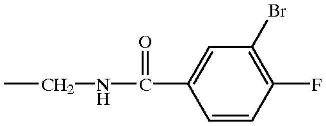 |

TABLE 1.179
| Compd. No. | 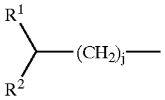 | k | m | n | chirality | $R^3$ | 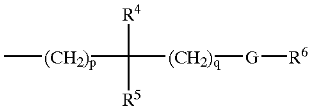 |
|---|---|---|---|---|---|---|---|
| 1959 | 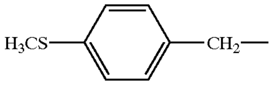 | 2 | 2 | 1 | — | H | 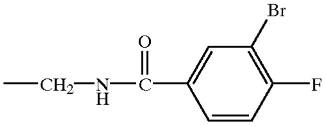 |
| 1960 | 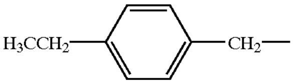 | 2 | 2 | 1 | — | H | 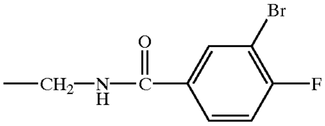 |
| 1961 | 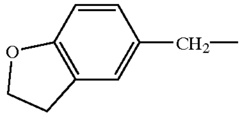 | 2 | 2 | 1 | — | H | 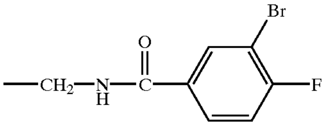 |
| 1962 | 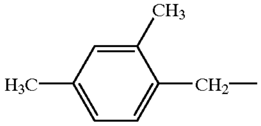 | 2 | 2 | 1 | — | H | 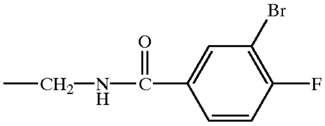 |
| 1963 | 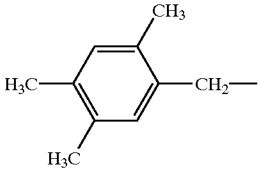 | 2 | 2 | 1 | — | H | 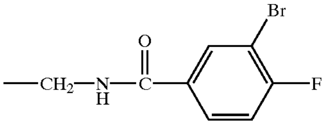 |
| 1964 | 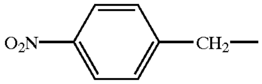 | 2 | 2 | 1 | — | H | 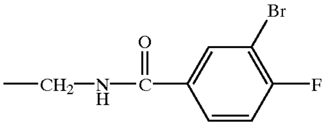 |
| 1965 | 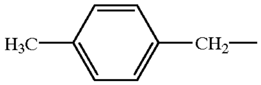 | 2 | 2 | 1 | — | H | 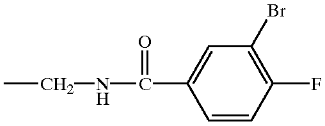 |
| 1966 | 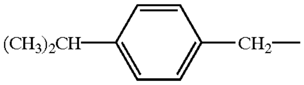 | 2 | 2 | 1 | — | H | 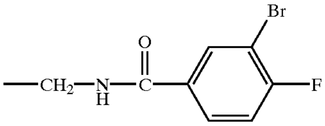 |
| 1967 | 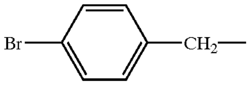 | 2 | 2 | 1 | — | H | 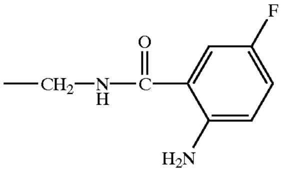 |

TABLE 1.179-continued
| Compd. No. | 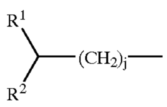 | k | m | n | chirality | $R^3$ | 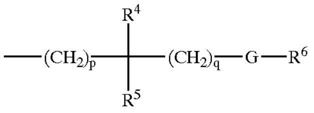 |
|---|---|---|---|---|---|---|---|
| 1968 | 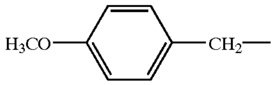 | 2 | 2 | 1 | — | H | 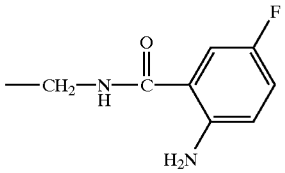 |
| 1969 | 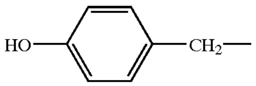 | 2 | 2 | 1 | — | H | 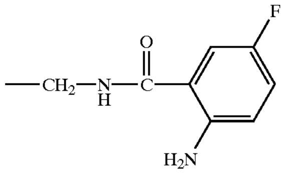 |
TABLE 1.180
| Compd. No. | 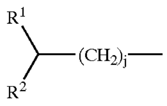 | k | m | n | chirality | $R^3$ | 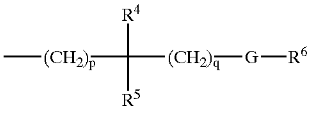 |
|---|---|---|---|---|---|---|---|
| 1970 | 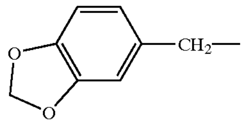 | 2 | 2 | 1 | — | H | 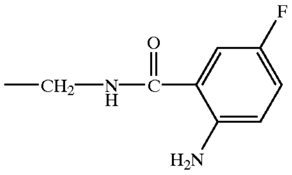 |
| 1971 | 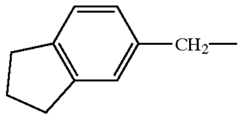 | 2 | 2 | 1 | — | H | 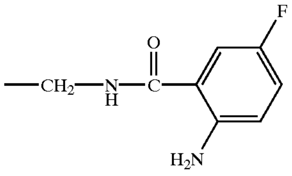 |
| 1972 | 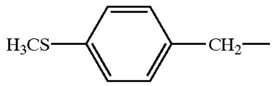 | 2 | 2 | 1 | — | H | 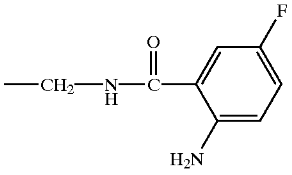 |
| 1973 | 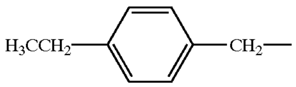 | 2 | 2 | 1 | — | H | 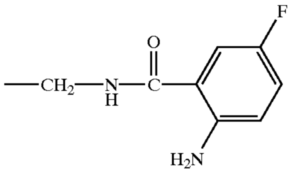 |

TABLE 1.180-continued
| Compd. No. | 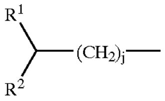 | k | m | n | chirality | $R^3$ | 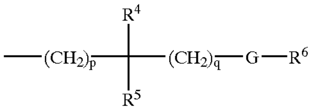 |
|---|---|---|---|---|---|---|---|
| 1974 | 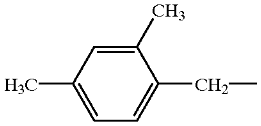 | 2 | 2 | 1 | — | H | 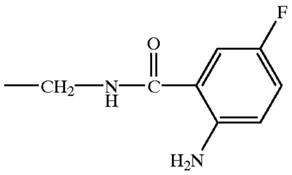 |
| 1975 | 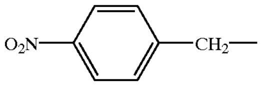 | 2 | 2 | 1 | — | H | 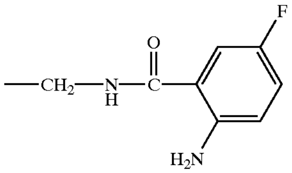 |
| 1976 | 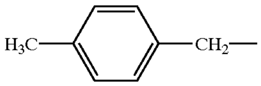 | 2 | 2 | 1 | — | H | 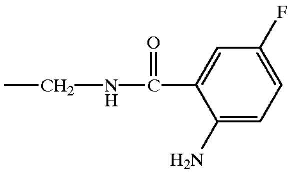 |
| 1977 | 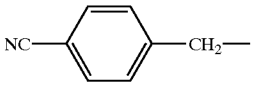 | 2 | 2 | 1 | — | H | 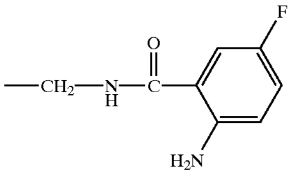 |
| 1978 | 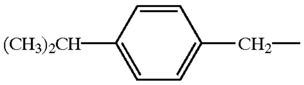 | 2 | 2 | 1 | — | H | 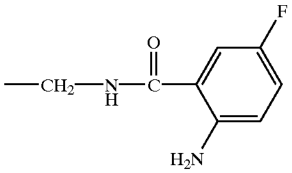 |
| 1979 | 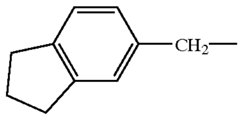 | 2 | 2 | 1 | — | H | 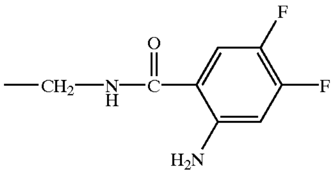 |
| 1980 | 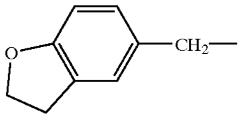 | 2 | 2 | 1 | — | H | 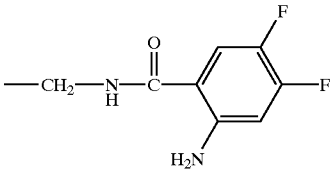 |

TABLE 1.181
| Compd. No. | 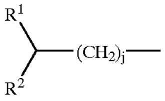 | k | m | n | chirality | $R^3$ | 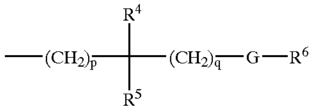 |
|---|---|---|---|---|---|---|---|
| 1981 | 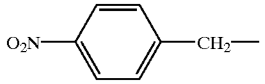 | 2 | 2 | 1 | — | H | 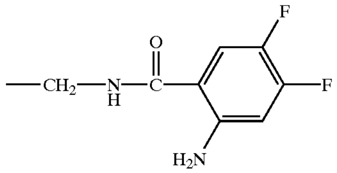 |
| 1982 | 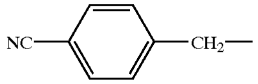 | 2 | 2 | 1 | — | H | 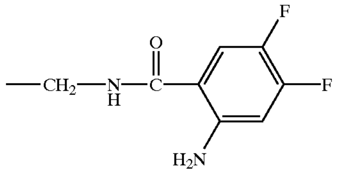 |
| 1983 | 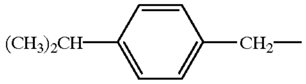 | 2 | 2 | 1 | — | H | 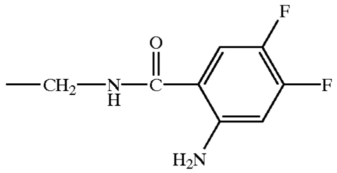 |
| 1984 | 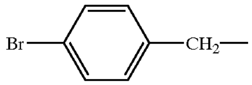 | 2 | 2 | 1 | — | H | 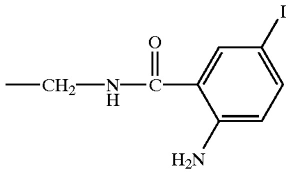 |
| 1985 | 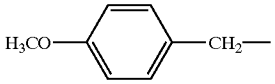 | 2 | 2 | 1 | — | H | 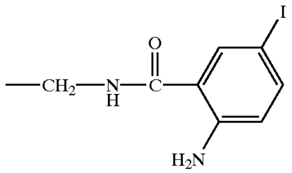 |
| 1986 | 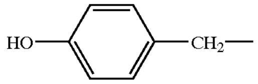 | 2 | 2 | 1 | — | H | 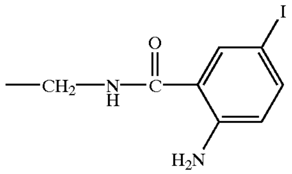 |
| 1987 | 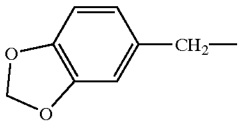 | 2 | 2 | 1 | — | H | 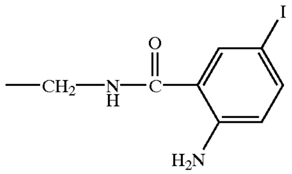 |
| 1988 | 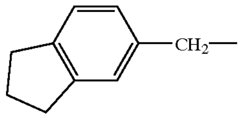 | 2 | 2 | 1 | — | H | 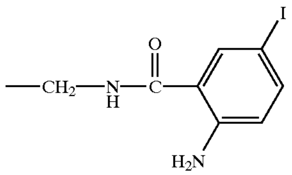 |

TABLE 1.181-continued
| Compd. No. | 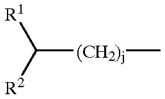 | k | m | n | chirality | $R^3$ | 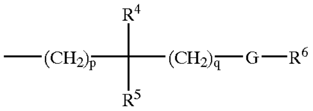 |
|---|---|---|---|---|---|---|---|
| 1989 | 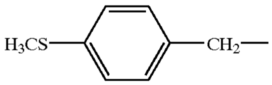 | 2 | 2 | 1 | — | H | 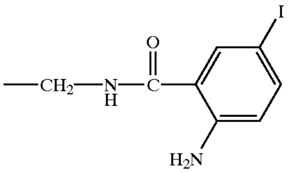 |
| 1990 | 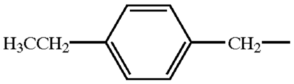 | 2 | 2 | 1 | — | H | 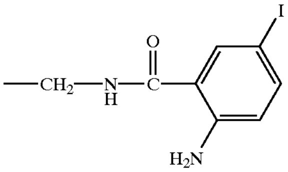 |
| 1991 | 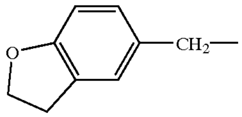 | 2 | 2 | 1 | — | H | 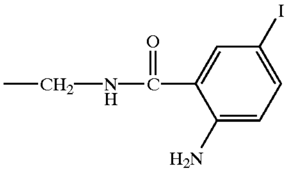 |
TABLE 1.182
| Compd. No. | 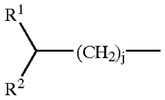 | k | m | n | chirality | $R^3$ | 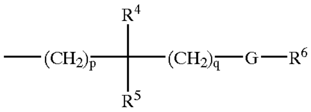 |
|---|---|---|---|---|---|---|---|
| 1992 | 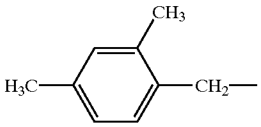 | 2 | 2 | 1 | — | H | 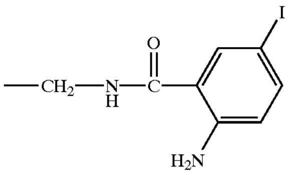 |
| 1993 | 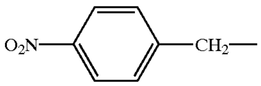 | 2 | 2 | 1 | — | H | 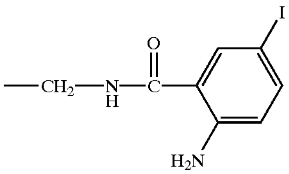 |
| 1994 | 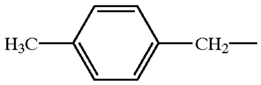 | 2 | 2 | 1 | — | H | 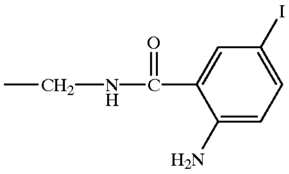 |

TABLE 1.182-continued
| Compd. No. | 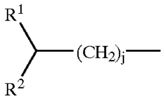 | k | m | n | chirality | $R^3$ | 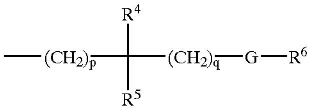 |
|---|---|---|---|---|---|---|---|
| 1995 | 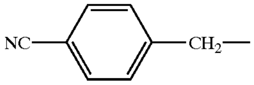 | 2 | 2 | 1 | — | H | 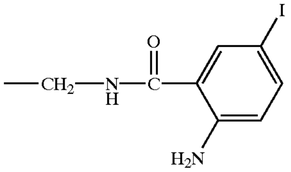 |
| 1996 | 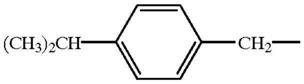 | 2 | 2 | 1 | — | H | 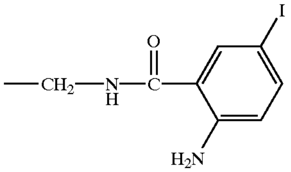 |
| 1997 | 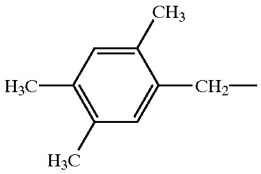 | 2 | 2 | 1 | — | H | 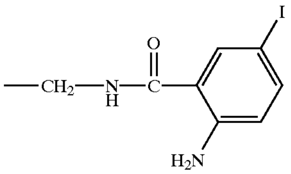 |
| 1998 | 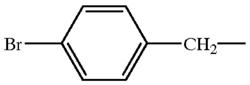 | 2 | 2 | 1 | — | H | 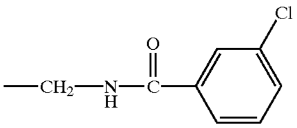 |
| 1999 | 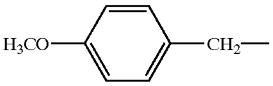 | 2 | 2 | 1 | — | H | 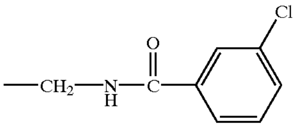 |
| 2000 | 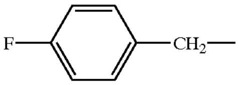 | 2 | 2 | 1 | — | H | 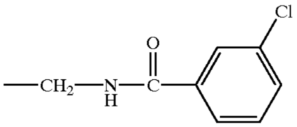 |
| 2001 | 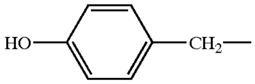 | 2 | 2 | 1 | — | H | 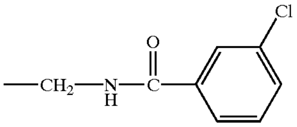 |
| 2002 | 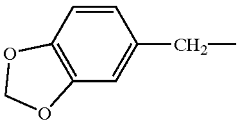 | 2 | 2 | 1 | — | H | 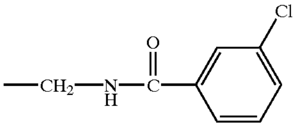 |

TABLE 1.183
| Compd. No. | 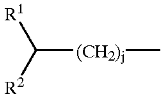 | k | m | n | chirality | $R^3$ | 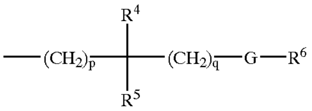 |
|---|---|---|---|---|---|---|---|
| 2003 | 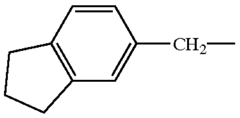 | 2 | 2 | 1 | — | H | 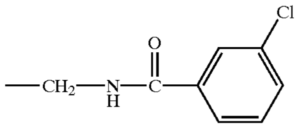 |
| 2004 | 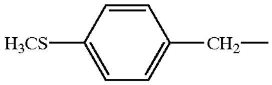 | 2 | 2 | 1 | — | H | 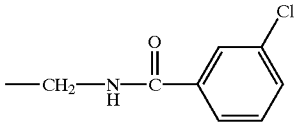 |
| 2005 | 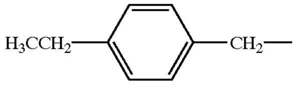 | 2 | 2 | 1 | — | H | 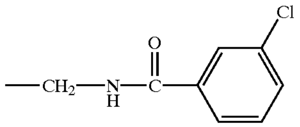 |
| 2006 | 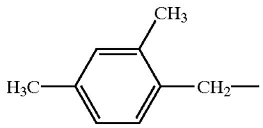 | 2 | 2 | 1 | — | H | 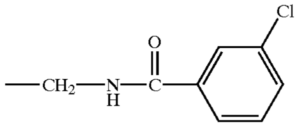 |
| 2007 | 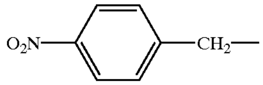 | 2 | 2 | 1 | — | H | 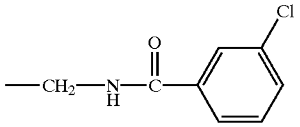 |
| 2008 | 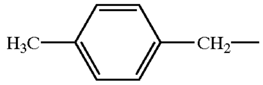 | 2 | 2 | 1 | — | H | 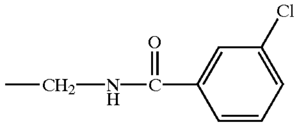 |
| 2009 | 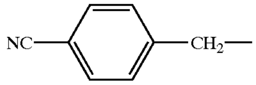 | 2 | 2 | 1 | — | H | 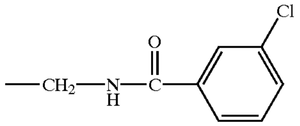 |
| 2010 | 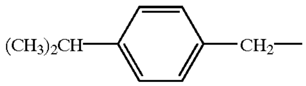 | 2 | 2 | 1 | — | H | 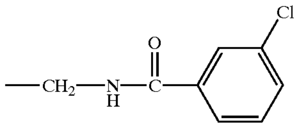 |
| 2011 | 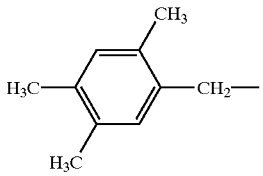 | 2 | 2 | 1 | — | H | 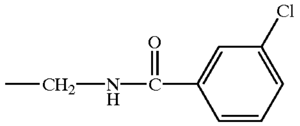 |
| 2012 | 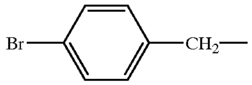 | 2 | 2 | 1 | — | H | 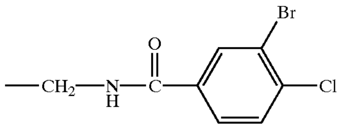 |

TABLE 1.183-continued
| Compd. No. | 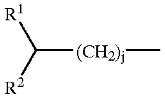 | k | m | n | chirality | $R^3$ | 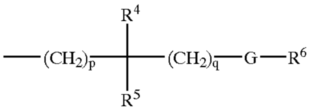 |
|---|---|---|---|---|---|---|---|
| 2013 | 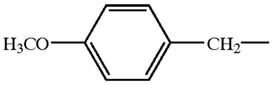 | 2 | 2 | 1 | — | H | 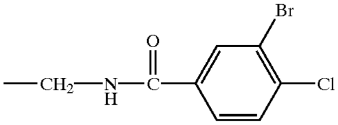 |
TABLE 1.184
| Compd. No. | 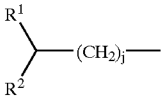 | k | m | n | chirality | $R^3$ | 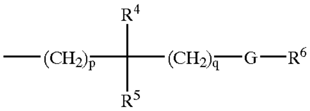 |
|---|---|---|---|---|---|---|---|
| 2014 | 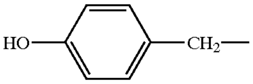 | 2 | 2 | 1 | — | H | 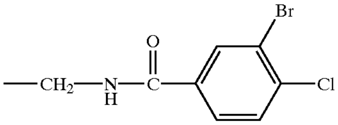 |
| 2015 | 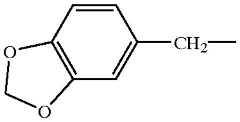 | 2 | 2 | 1 | — | H | 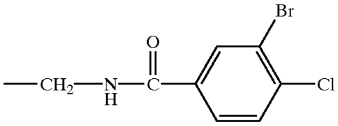 |
| 2016 | 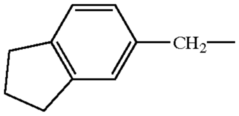 | 2 | 2 | 1 | — | H | 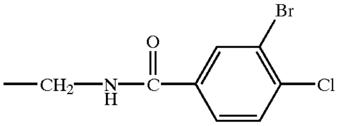 |
| 2017 | 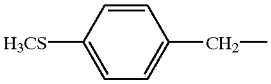 | 2 | 2 | 1 | — | H | 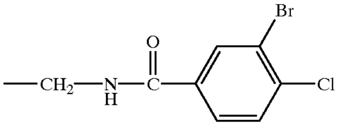 |
| 2018 | 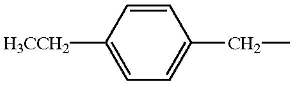 | 2 | 2 | 1 | — | H | 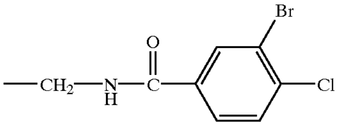 |
| 2019 | 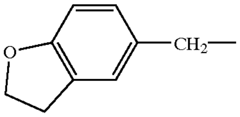 | 2 | 2 | 1 | — | H | 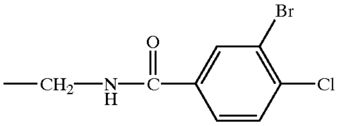 |
| 2020 | 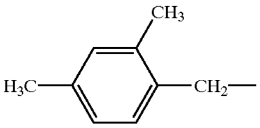 | 2 | 2 | 1 | — | H | 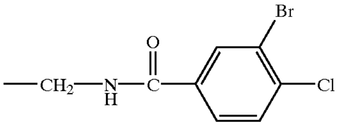 |

TABLE 1.184-continued
| Compd. No. | 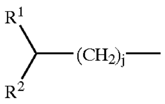 | k | m | n | chirality | $R^3$ | 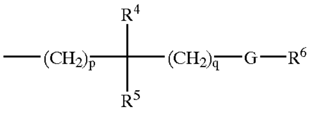 |
|---|---|---|---|---|---|---|---|
| 2021 | 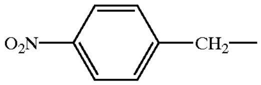 | 2 | 2 | 1 | — | H | 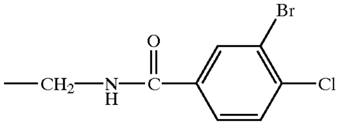 |
| 2022 | 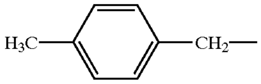 | 2 | 2 | 1 | — | H | 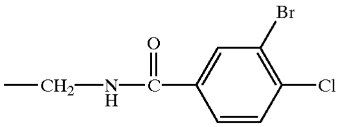 |
| 2023 | 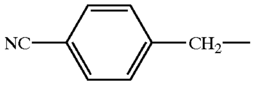 | 2 | 2 | 1 | — | H | 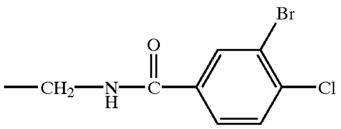 |
| 2024 | 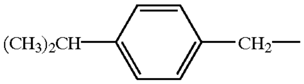 | 2 | 2 | 1 | — | H | 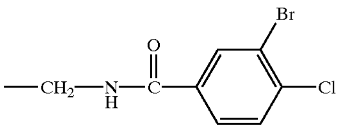 |
TABLE 1.185
| Compd. No. | 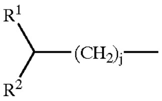 | k | m | n | chirality | $R^3$ | 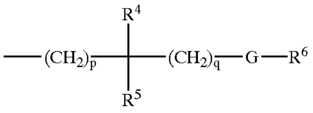 |
|---|---|---|---|---|---|---|---|
| 2025 | 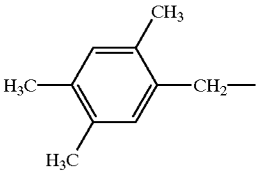 | 2 | 2 | 1 | — | H | 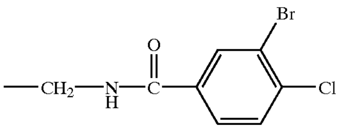 |
| 2026 | 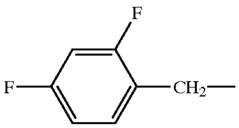 | 2 | 2 | 1 | — | H | 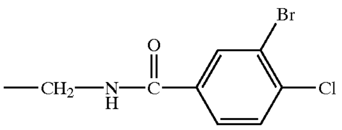 |
| 2027 | 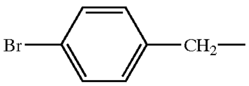 | 2 | 2 | 1 | — | H | 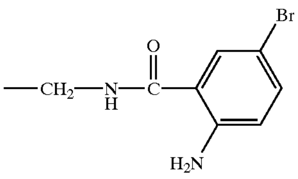 |

TABLE 1.185-continued
| Compd. No. | 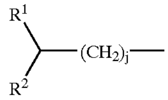 | k | m | n | chirality | $R^3$ | 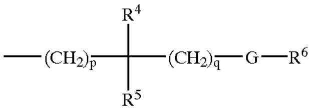 |
|---|---|---|---|---|---|---|---|
| 2028 | 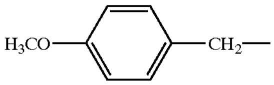 | 2 | 2 | 1 | — | H | 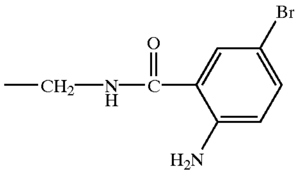 |
| 2029 | 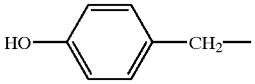 | 2 | 2 | 1 | — | H | 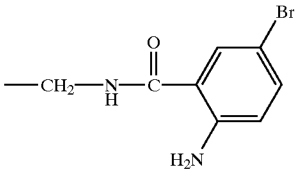 |
| 2030 | 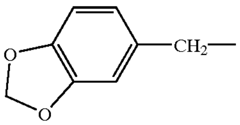 | 2 | 2 | 1 | — | H | 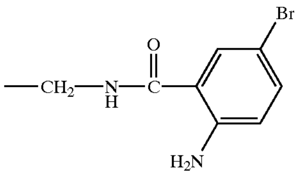 |
| 2031 | 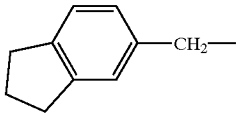 | 2 | 2 | 1 | — | H | 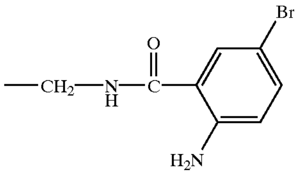 |
| 2032 | 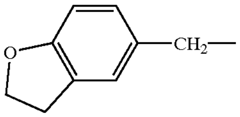 | 2 | 2 | 1 | — | H | 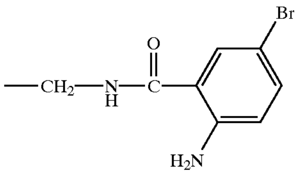 |
| 2033 | 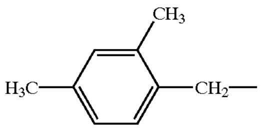 | 2 | 2 | 1 | — | H | 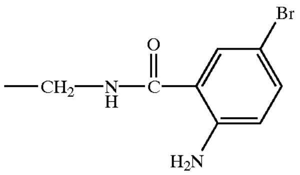 |
| 2034 | 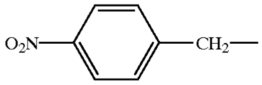 | 2 | 2 | 1 | — | H | 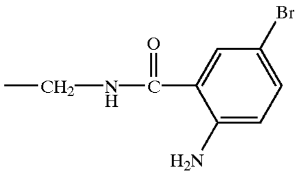 |

TABLE 1.185-continued
| Compd. No. | 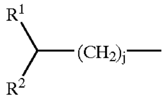 | k | m | n | chirality | $R^3$ | 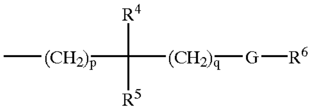 |
|---|---|---|---|---|---|---|---|
| 2035 | 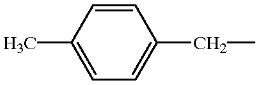 | 2 | 2 | 1 | — | H | 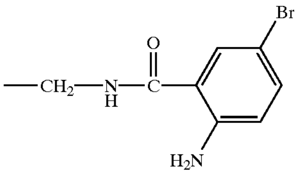 |
TABLE 1.186
| Compd. No. | 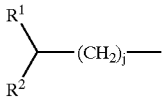 | k | m | n | chirality | $R^3$ | 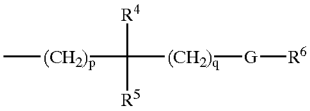 |
|---|---|---|---|---|---|---|---|
| 2036 | 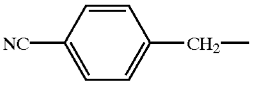 | 2 | 2 | 1 | — | H | 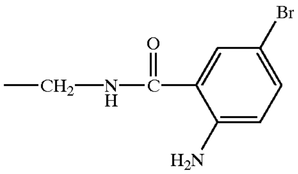 |
| 2037 | 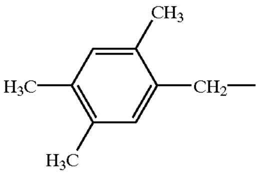 | 2 | 2 | 1 | — | H | 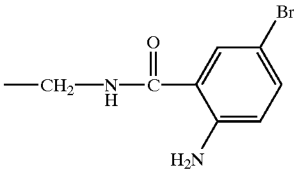 |
| 2038 | 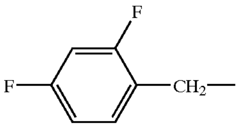 | 2 | 2 | 1 | — | H | 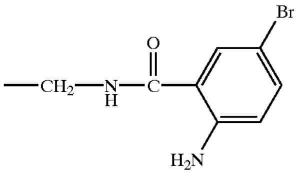 |
| 2039 | 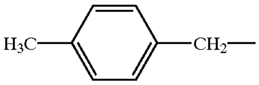 | 2 | 2 | 1 | — | H | 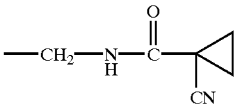 |
| 2040 | 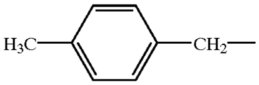 | 1 | 2 | 0 | R | H | 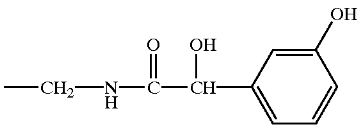 |
| 2041 | 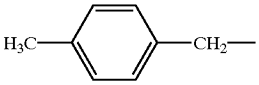 | 1 | 2 | 0 | R | H | 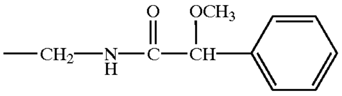 |

TABLE 1.186-continued
| Compd. No. | 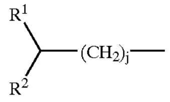 | k | m | n | chirality | $R^3$ | 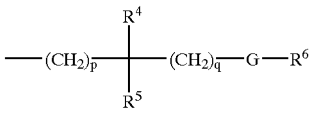 |
|---|---|---|---|---|---|---|---|
| 2042 | 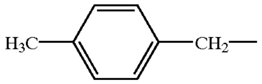 | 1 | 2 | 0 | R | H | 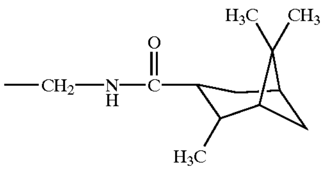 |
| 2043 | 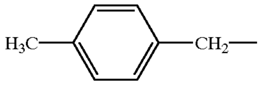 | 1 | 2 | 0 | R | H | 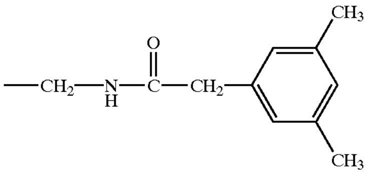 |
| 2044 | 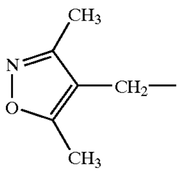 | 1 | 2 | 0 | R | H | 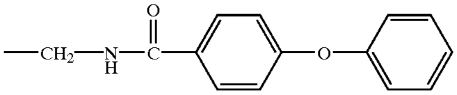 |
| 2045 | 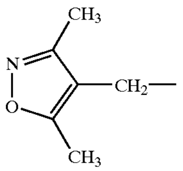 | 1 | 2 | 0 | R | H | 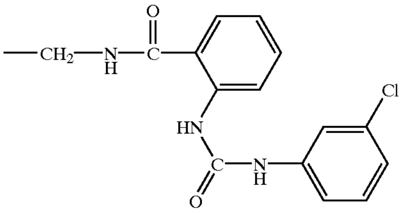 |
| 2046 | 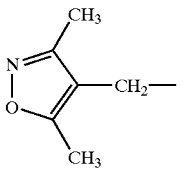 | 1 | 2 | 0 | R | H | 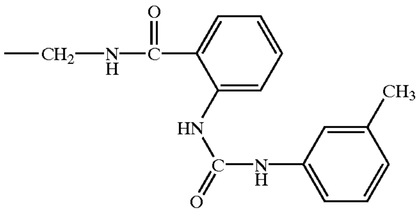 |

TABLE 1.187
| Compd. No. | 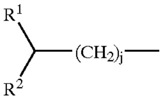 | k | m | n | chirality | $R^3$ | 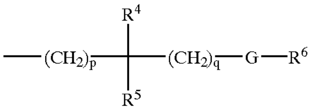 |
|---|---|---|---|---|---|---|---|
| 2047 | 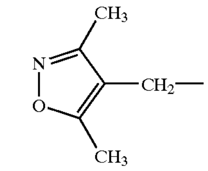 | 1 | 2 | 0 | R | H | 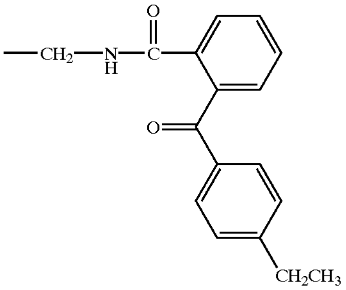 |
| 2048 | 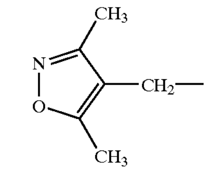 | 1 | 2 | 0 | R | H | 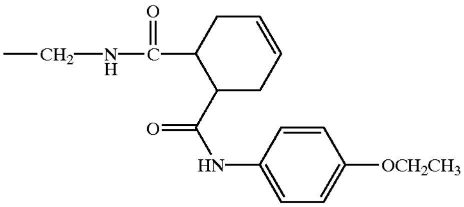 |
| 2049 | 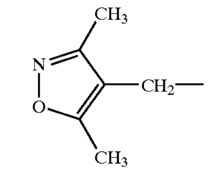 | 1 | 2 | 0 | R | H | 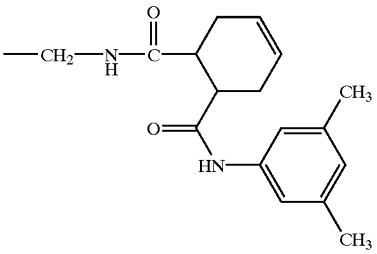 |
| 2050 | 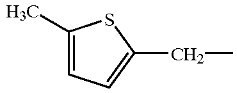 | 1 | 2 | 0 | R | H | 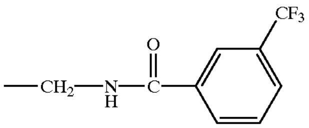 |
| 2051 | 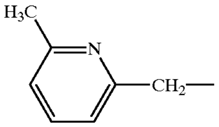 | 1 | 2 | 0 | R | H | 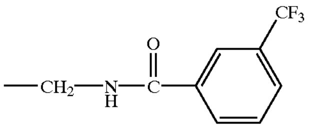 |
| 2052 | 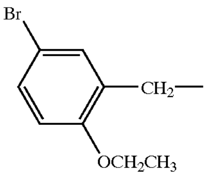 | 2 | 2 | 1 | — | H | 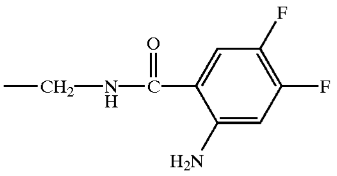 |
| 2053 | 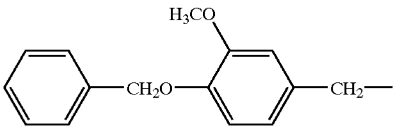 | 2 | 2 | 1 | — | H | 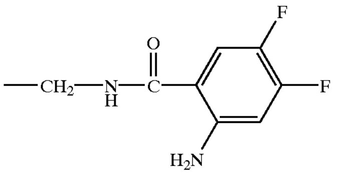 |

TABLE 1.187-continued
| Compd. No. | 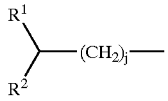 | k | m | n | chirality | $R^3$ | 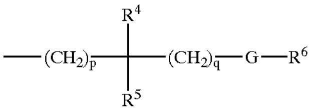 |
|---|---|---|---|---|---|---|---|
| 2054 | 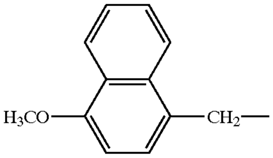 | 2 | 2 | 1 | — | H | 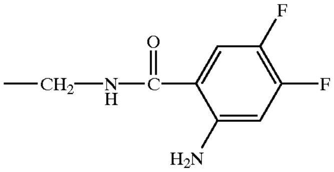 |
| 2055 | 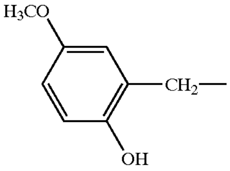 | 2 | 2 | 1 | — | H | 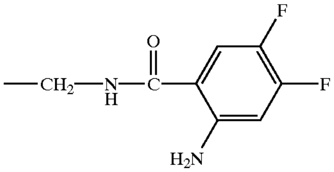 |
| 2056 | 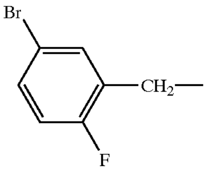 | 2 | 2 | 1 | — | H | 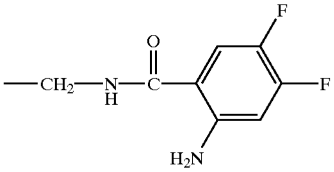 |
| 2057 | 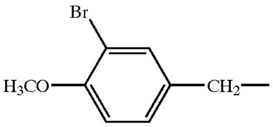 | 2 | 2 | 1 | — | H | 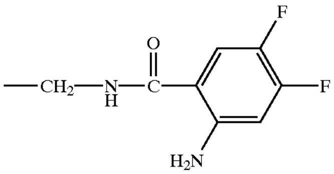 |
TABLE 1.188
| Compd. No. | 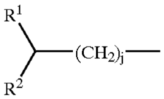 | k | m | n | chirality | $R^3$ | 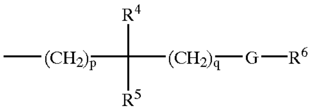 |
|---|---|---|---|---|---|---|---|
| 2058 | 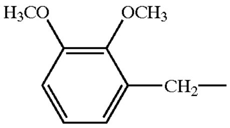 | 2 | 2 | 1 | — | H | 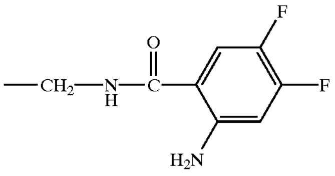 |
| 2059 | 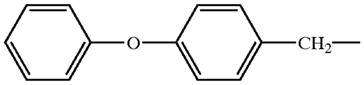 | 2 | 2 | 1 | — | H | 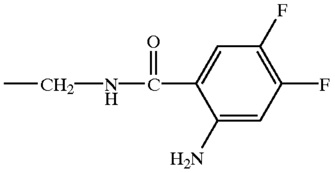 |

TABLE 1.188-continued
| Compd. No. | 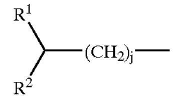 | k | m | n | chirality | $R^3$ | 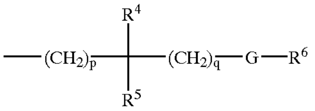 |
|---|---|---|---|---|---|---|---|
| 2060 | 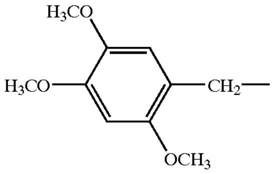 | 2 | 2 | 1 | — | H | 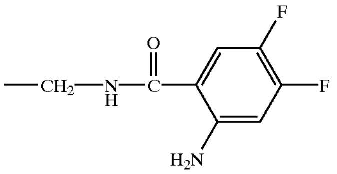 |
| 2061 | 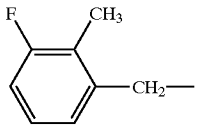 | 2 | 2 | 1 | — | H | 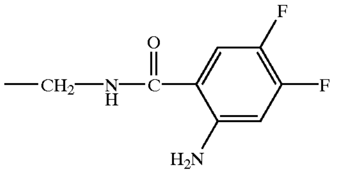 |
| 2062 | 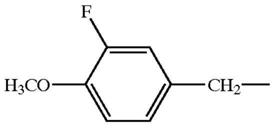 | 2 | 2 | 1 | — | H | 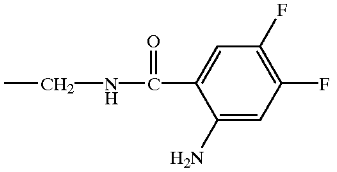 |
| 2063 | 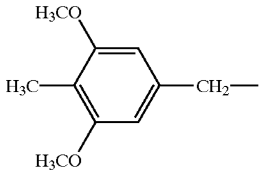 | 2 | 2 | 1 | — | H | 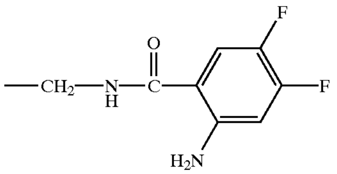 |
| 2064 | 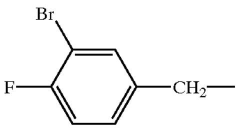 | 2 | 2 | 1 | — | H | 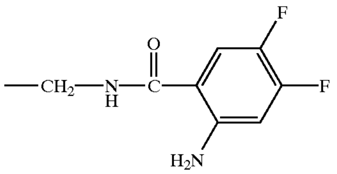 |
| 2065 | 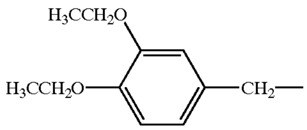 | 2 | 2 | 1 | — | H | 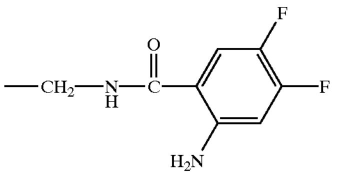 |
| 2066 | 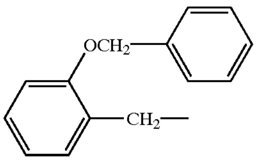 | 2 | 2 | 1 | — | H | 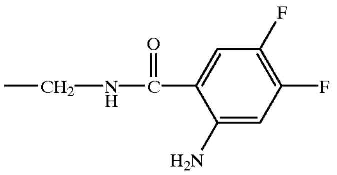 |
| 2067 | 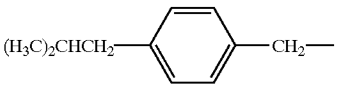 | 2 | 2 | 1 | — | H | 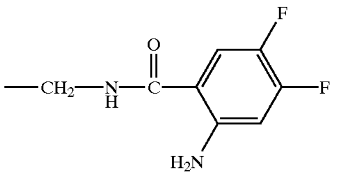 |

TABLE 1.188-continued
| Compd. No. | 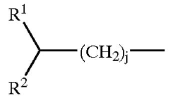 | k | m | n | chirality | $R^3$ | 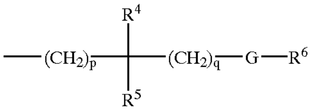 |
|---|---|---|---|---|---|---|---|
| 2068 | 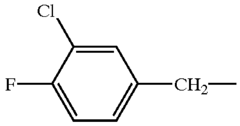 | 2 | 2 | 1 | — | H | 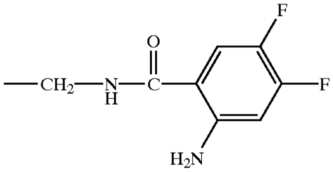 |
TABLE 1.189
| Compd. No. | 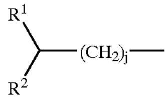 | k | m | n | chirality | $R^3$ | 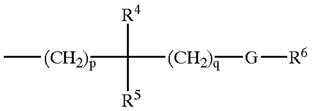 |
|---|---|---|---|---|---|---|---|
| 2069 | 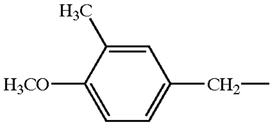 | 2 | 2 | 1 | — | H | 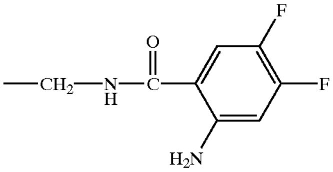 |
| 2070 | 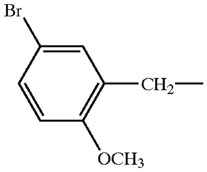 | 2 | 2 | 1 | — | H | 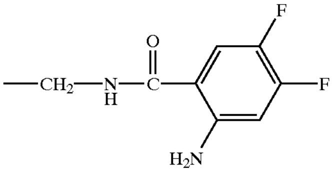 |
| 2071 | 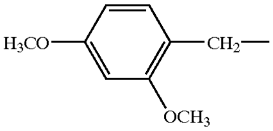 | 2 | 2 | 1 | — | H | 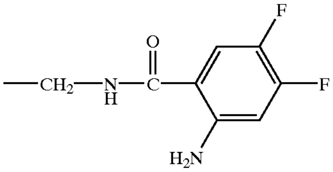 |
| 2072 | 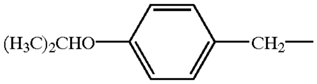 | 2 | 2 | 1 | — | H | 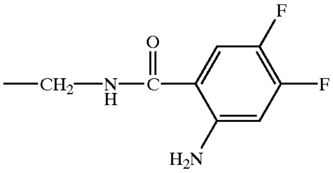 |
| 2073 | 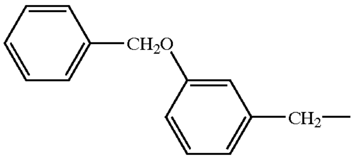 | 2 | 2 | 1 | — | H | 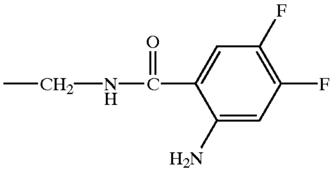 |

TABLE 1.189-continued
| Compd. No. | 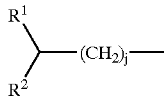 | k | m | n | chirality | $R^3$ | 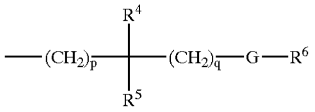 |
|---|---|---|---|---|---|---|---|
| 2074 | 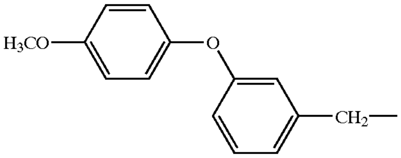 | 2 | 2 | 1 | — | H | 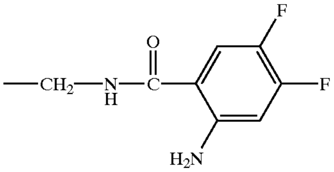 |
| 2075 | 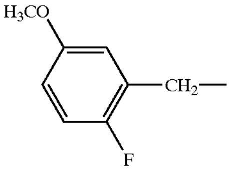 | 2 | 2 | 1 | — | H | 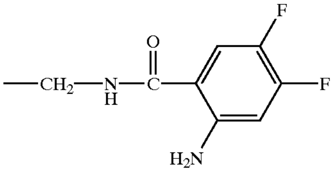 |
| 2076 | 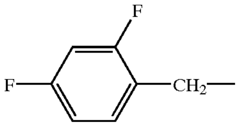 | 2 | 2 | 1 | — | H | 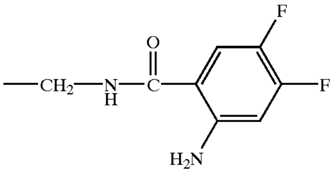 |
| 2077 | 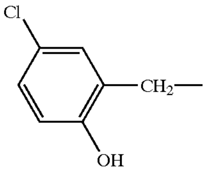 | 2 | 2 | 1 | — | H | 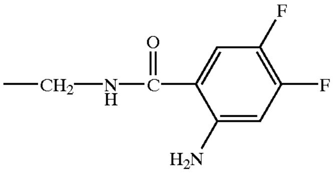 |
| 2078 | 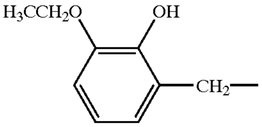 | 2 | 2 | 1 | — | H | 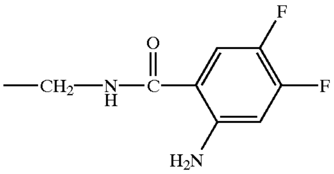 |
| 2079 | 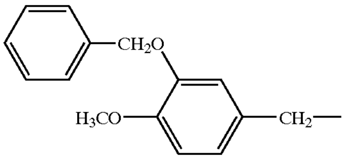 | 2 | 2 | 1 | — | H | 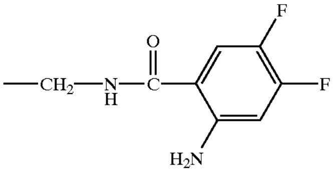 |

TABLE 1.190
| Compd. No. | 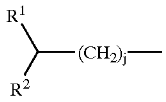 | k | m | n | chirality | $R^3$ | 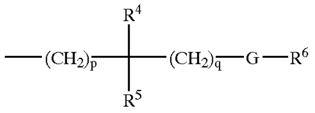 |
|---|---|---|---|---|---|---|---|
| 2080 | 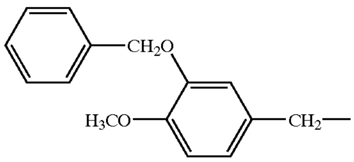 | 2 | 2 | 1 | — | H | 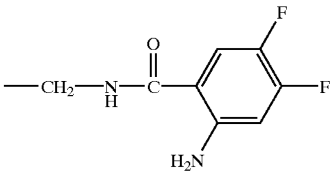 |
| 2081 | 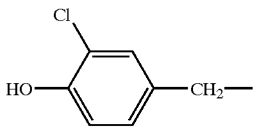 | 2 | 2 | 1 | — | H | 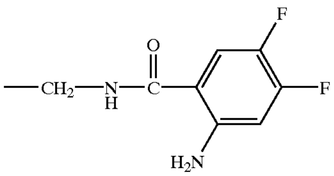 |
| 2082 | 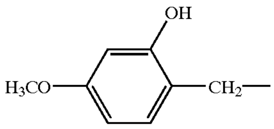 | 2 | 2 | 1 | — | H | 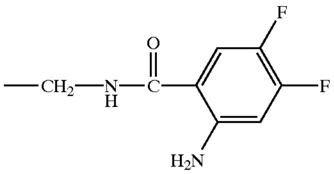 |
| 2083 | 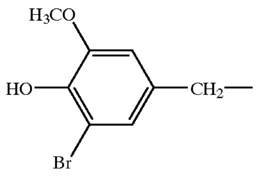 | 1 | 2 | 0 | R | H | 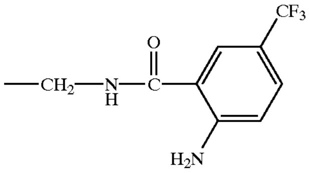 |
| 2084 | 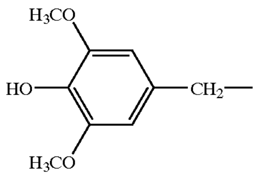 | 1 | 2 | 0 | R | H | 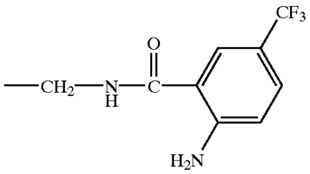 |
| 2085 | 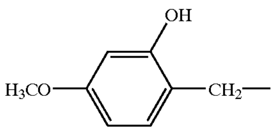 | 1 | 2 | 0 | R | H | 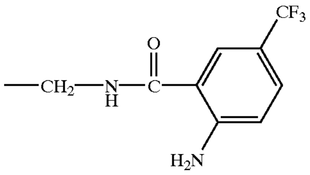 |
| 2086 | 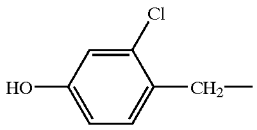 | 1 | 2 | 0 | R | H | 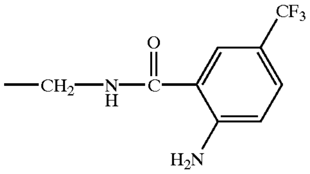 |
| 2087 | 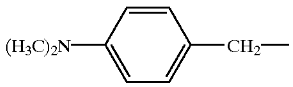 | 1 | 2 | 0 | R | H | 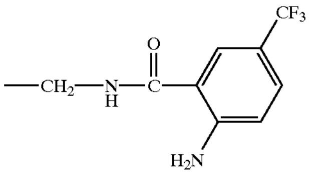 |

TABLE 1.190-continued
| Compd. No. | 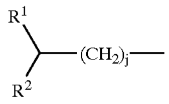 | k | m | n | chirality | $R^3$ | 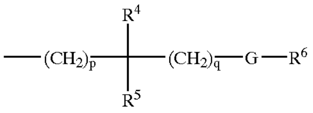 |
|---|---|---|---|---|---|---|---|
| 2088 | 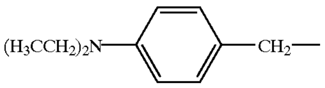 | 1 | 2 | 0 | R | H | 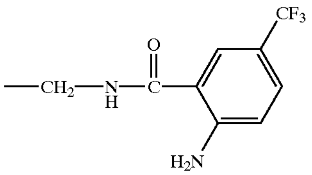 |
| 2089 | 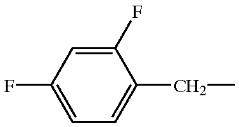 | 1 | 2 | 0 | R | H | 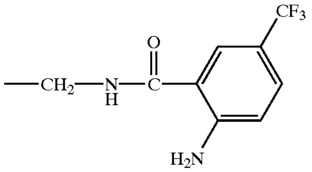 |
| 2090 | 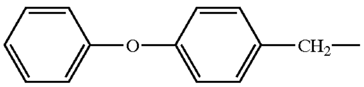 | 1 | 2 | 0 | R | H | 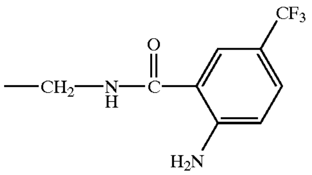 |
TABLE 1.191
| Compd. No. | 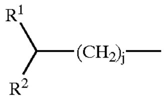 | k | m | n | chirality | $R^3$ | 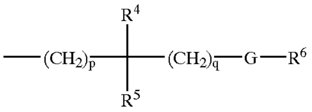 |
|---|---|---|---|---|---|---|---|
| 2091 | 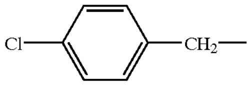 | 2 | 2 | 1 | — | H | 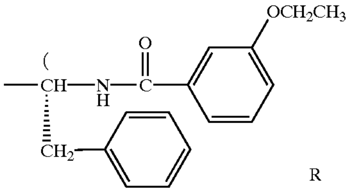 |
| 2092 | 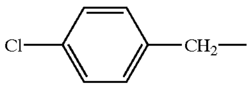 | 2 | 2 | 1 | — | H | 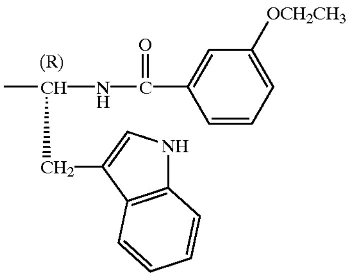 |

TABLE 1.191-continued
| Compd. No. | 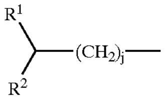 | k | m | n | chirality | $R^3$ | 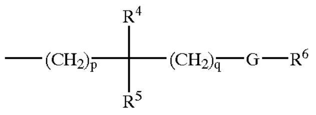 |
|---|---|---|---|---|---|---|---|
| 2093 | 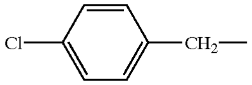 | 2 | 2 | 1 | — | H | 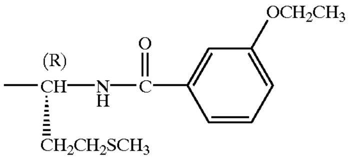 |
| 2094 | 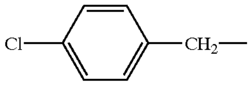 | 2 | 2 | 1 | — | H | 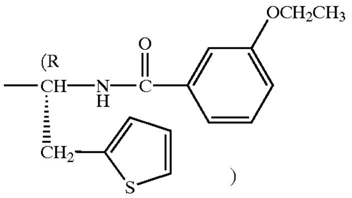 |
| 2095 | 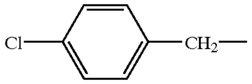 | 2 | 2 | 1 | — | H | 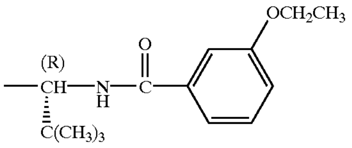 |
| 2096 | 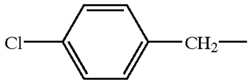 | 2 | 2 | 1 | — | H | 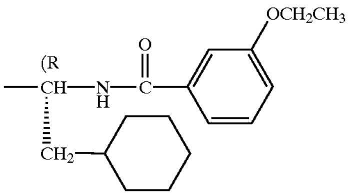 |
| 2097 | 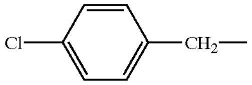 | 2 | 2 | 1 | — | H | 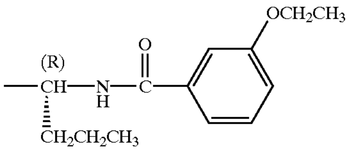 |
| 2098 | 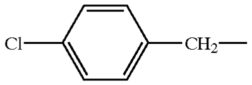 | 2 | 2 | 1 | — | H | 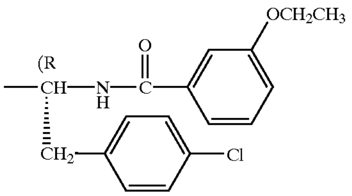 |
| 2099 | 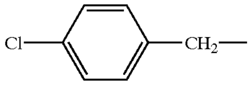 | 2 | 2 | 1 | — | H | 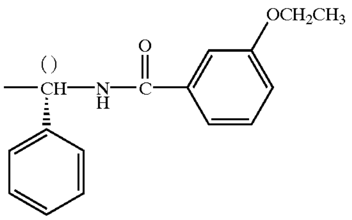 |

TABLE 1.191-continued
| Compd. No. | 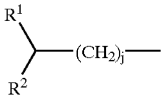 | k | m | n | chirality | $R^3$ | 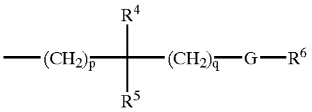 |
|---|---|---|---|---|---|---|---|
| 2100 | 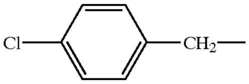 | 2 | 2 | 1 | — | H | 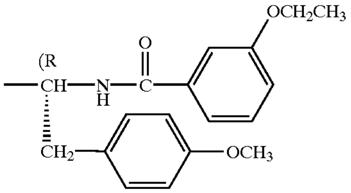 |
| 2101 | 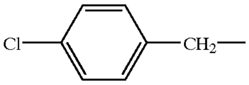 | 2 | 2 | 1 | — | H | 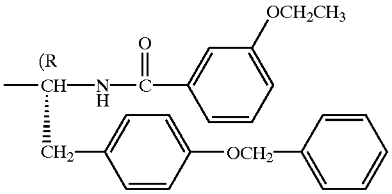 |
TABLE 1.192
| Compd. No. | 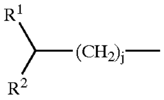 | k | m | n | chirality | $R^3$ | 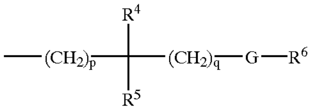 |
|---|---|---|---|---|---|---|---|
| 2102 | 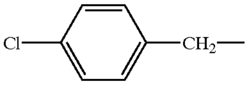 | 2 | 2 | 1 | — | H | 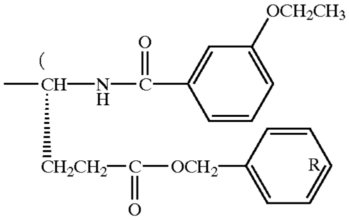 |
| 2103 | 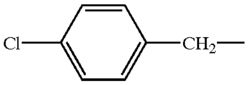 | 2 | 2 | 1 | — | H | 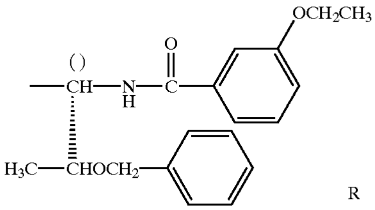 |
| 2104 | 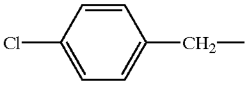 | 2 | 2 | 1 | — | H | 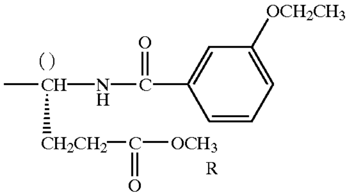 |

TABLE 1.192-continued
| Compd. No. | 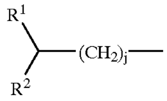 | k | m | n | chirality | $R^3$ | 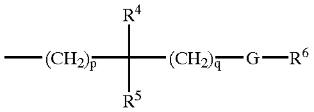 |
|---|---|---|---|---|---|---|---|
| 2105 | 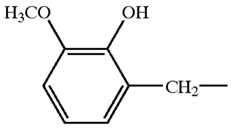 | 2 | 2 | 1 | — | H | 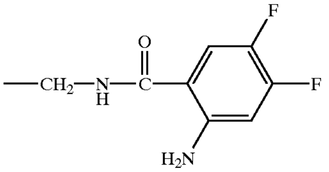 |
| 2106 | 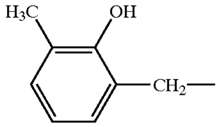 | 2 | 2 | 1 | — | H | 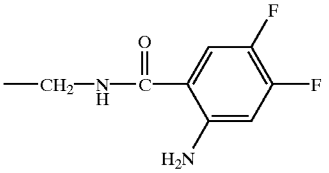 |
| 2107 | 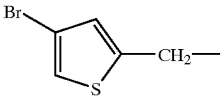 | 2 | 2 | 1 | — | H | 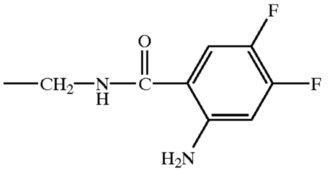 |
| 2108 | 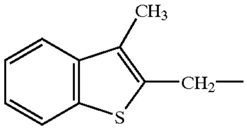 | 2 | 2 | 1 | — | H | 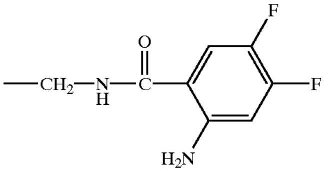 |
| 2109 | 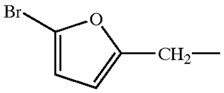 | 2 | 2 | 1 | — | H | 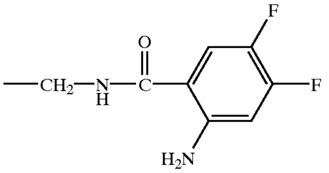 |
| 2110 | 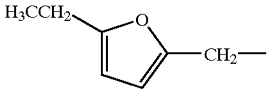 | 2 | 2 | 1 | — | H | 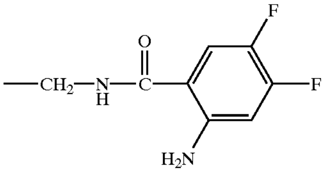 |
| 2111 | 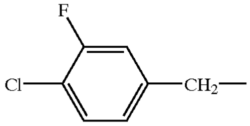 | 2 | 2 | 1 | — | H | 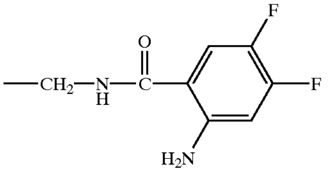 |

TABLE 1.192-continued
| Compd. No. | 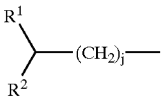 | k | m | n | chirality | $R^3$ | 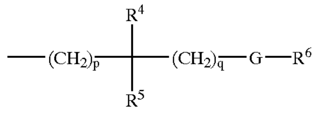 |
| --- | --- | --- | --- | --- | --- | --- | --- |
| 2112 | 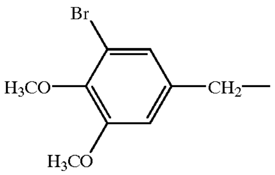 | 2 | 2 | 1 | — | H | 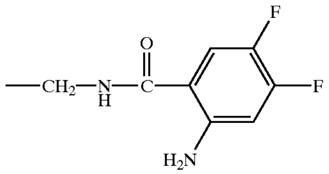 |
TABLE 1.193
| Compd. No. | 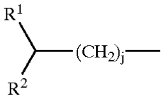 | k | m | n | chirality | $R^3$ | 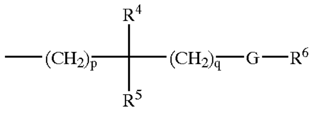 |
| --- | --- | --- | --- | --- | --- | --- | --- |
| 2113 | 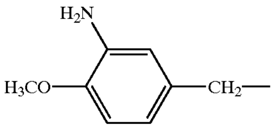 | 2 | 2 | 1 | — | H | 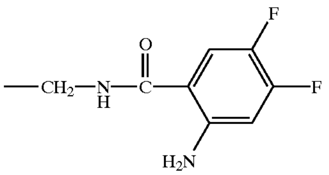 |
| 2114 | 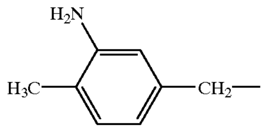 | 2 | 2 | 1 | — | H | 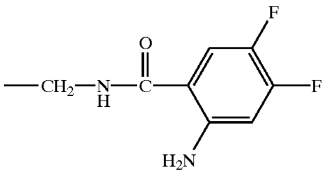 |
| 2115 | 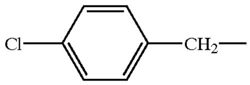 | 2 | 2 | 1 | — | H | 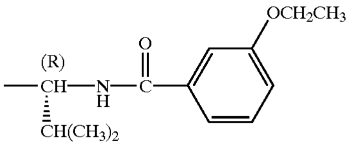 |
| 2116 | 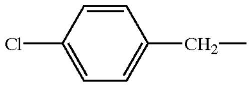 | 2 | 2 | 1 | — | H | 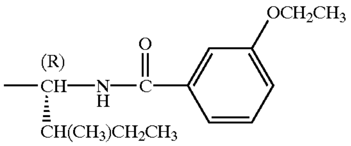 |
| 2117 | 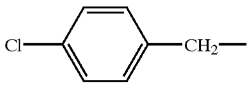 | 2 | 2 | 1 | — | H | 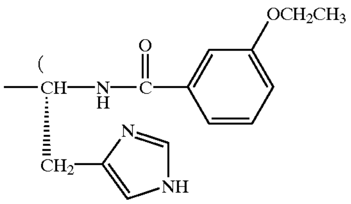 |

TABLE 1.193-continued
| Compd. No. | 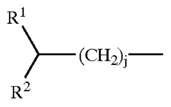 | k | m | n | chirality | $R^3$ | 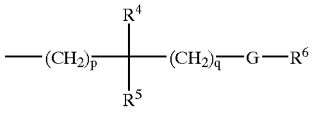 |
|---|---|---|---|---|---|---|---|
| 2118 | 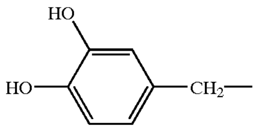 | 1 | 2 | 0 | R | H | 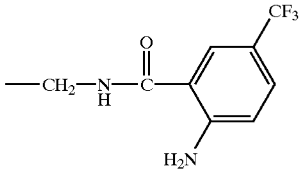 |
| 2119 | 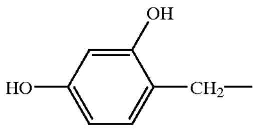 | 1 | 2 | 0 | R | H | 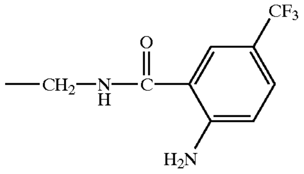 |
| 2120 | 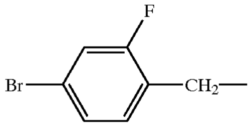 | 1 | 2 | 0 | R | H | 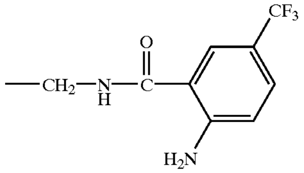 |
| 2121 | 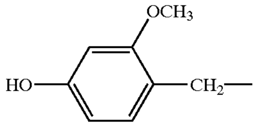 | 1 | 2 | 0 | R | H | 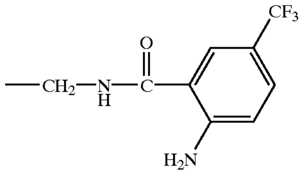 |
| 2122 | 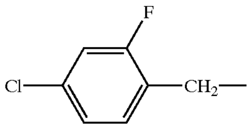 | 1 | 2 | 0 | R | H | 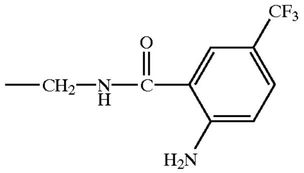 |
| 2123 | 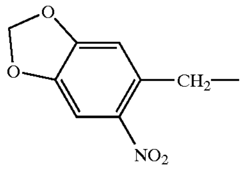 | 1 | 2 | 0 | R | H | 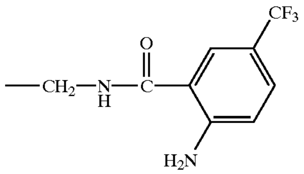 |

TABLE 1.194
| Compd. No. | 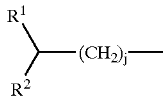 | k | m | n | chirality | $R^3$ | 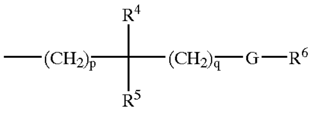 |
|---|---|---|---|---|---|---|---|
| 2124 | 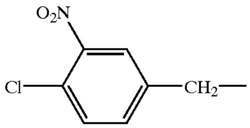 | 1 | 2 | 0 | R | H | 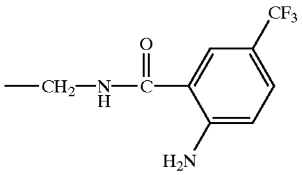 |
| 2125 | 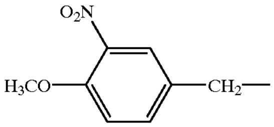 | 1 | 2 | 0 | R | H | 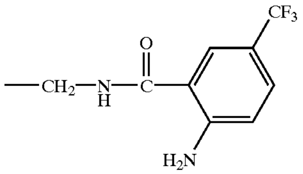 |
| 2126 | 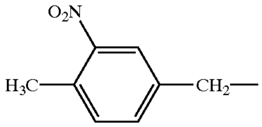 | 1 | 2 | 0 | R | H | 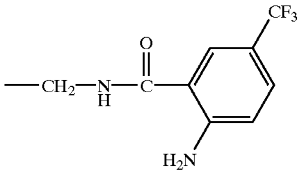 |
| 2127 | 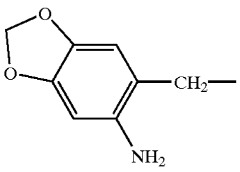 | 1 | 2 | 0 | R | H | 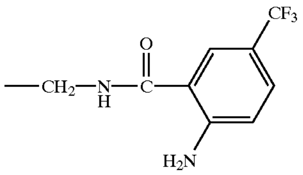 |
| 2128 | 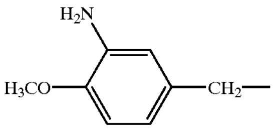 | 1 | 2 | 0 | R | H | 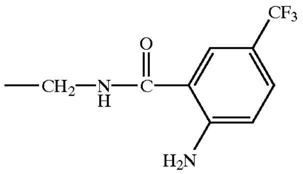 |
| 2129 | 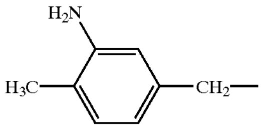 | 1 | 2 | 0 | R | H | 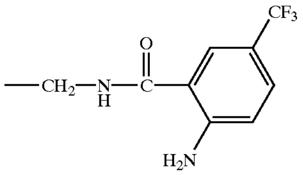 |
| 2130 | 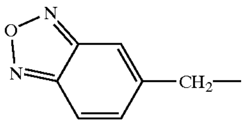 | 2 | 2 | 1 | — | H | 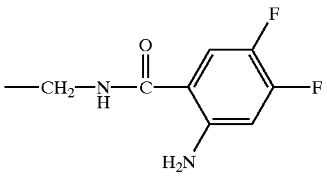 |
| 2131 | 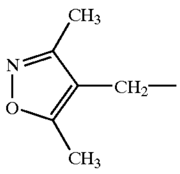 | 2 | 2 | 1 | — | H | 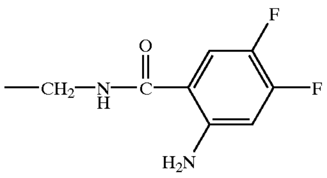 |

TABLE 1.194-continued
| Compd. No. | 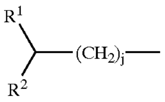 | k | m | n | chirality | $R^3$ | 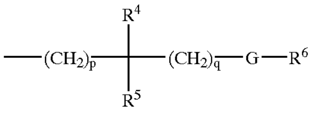 |
|---|---|---|---|---|---|---|---|
| 2132 | 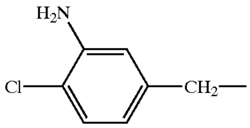 | 1 | 2 | 0 | R | H | 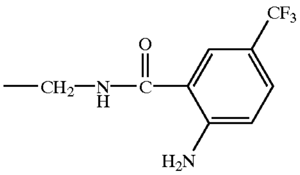 |
| 2133 | 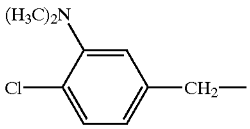 | 1 | 2 | 0 | R | H | 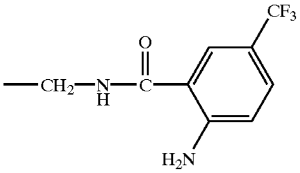 |
| 2134 | 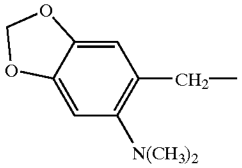 | 1 | 2 | 0 | R | H | 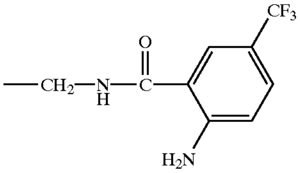 |
TABLE 1.195
| Compd. No. | 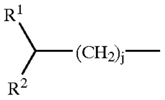 | k | m | n | chirality | $R^3$ | 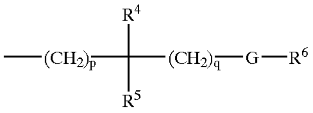 |
|---|---|---|---|---|---|---|---|
| 2135 | 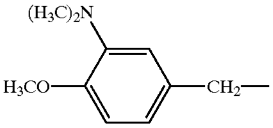 | 1 | 2 | 0 | R | H | 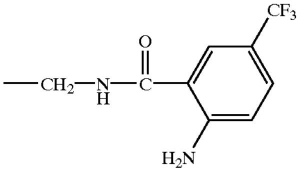 |
| 2136 | 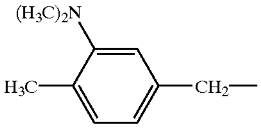 | 1 | 2 | 0 | R | H | 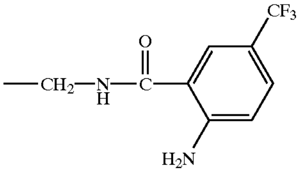 |
| 2137 | 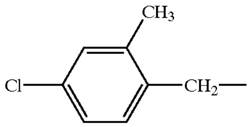 | 1 | 2 | 0 | R | H | 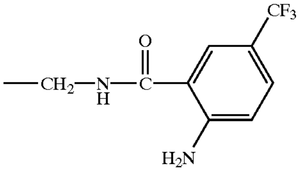 |

TABLE 1.195-continued
| Compd. No. | 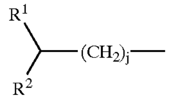 | k | m | n | chirality | $R^3$ | 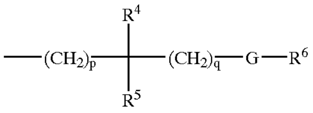 |
|---|---|---|---|---|---|---|---|
| 2138 | 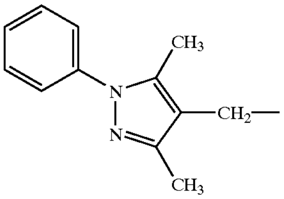 | 1 | 2 | 0 | R | H | 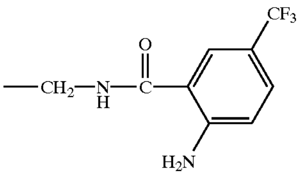 |
| 2139 | 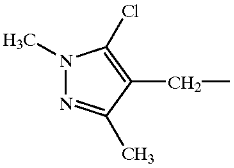 | 1 | 2 | 0 | R | H | 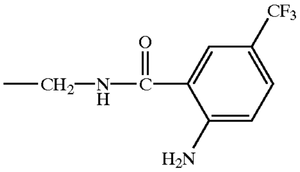 |
| 2140 | 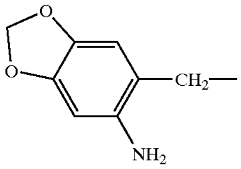 | 2 | 2 | 1 | — | H | 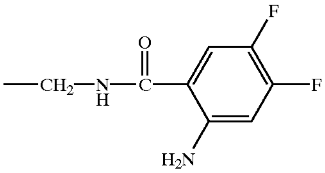 |
| 2141 | 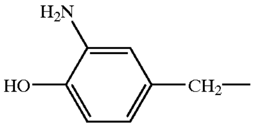 | 2 | 2 | 1 | — | H | 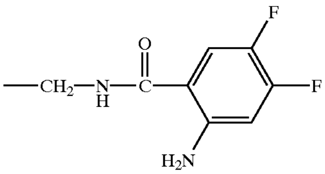 |
| 2142 | 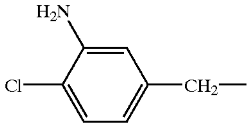 | 2 | 2 | 1 | — | H | 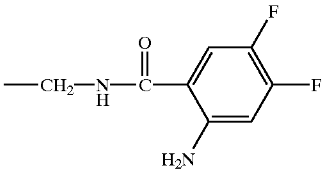 |
| 2143 | 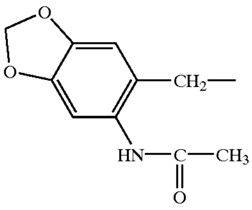 | 2 | 2 | 1 | — | H | 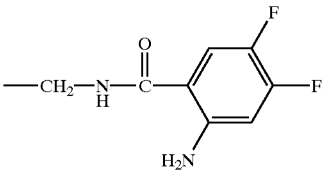 |
| 2144 | 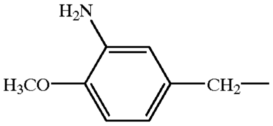 | 2 | 2 | 1 | — | H | 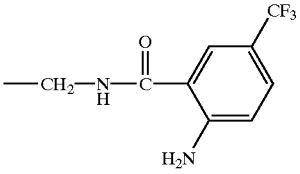 |

TABLE 1.195-continued
| Compd. No. | 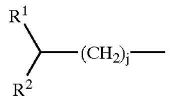 | k | m | n | chirality | $R^3$ | 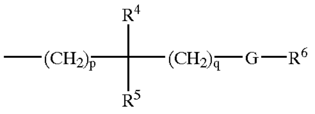 |
|---|---|---|---|---|---|---|---|
| 2145 | 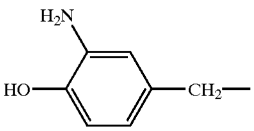 | 2 | 2 | 1 | — | H | 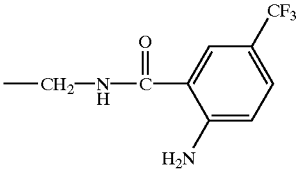 |
TABLE 1.196
| Compd. No. | 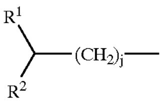 | k | m | n | chirality | $R^3$ | 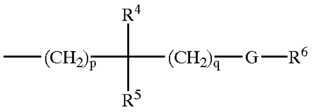 |
|---|---|---|---|---|---|---|---|
| 2146 | 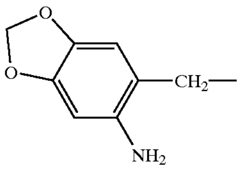 | 2 | 2 | 1 | — | H | 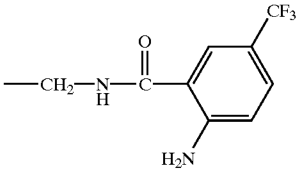 |
| 2147 | 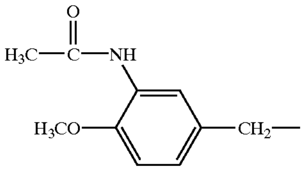 | 2 | 2 | 1 | — | H | 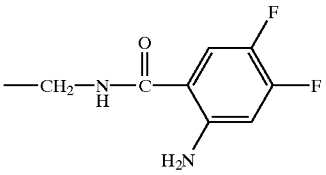 |
| 2148 | 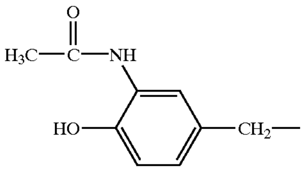 | 2 | 2 | 1 | — | H | 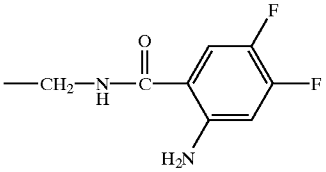 |
| 2149 | 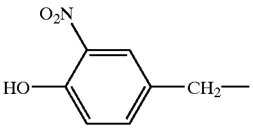 | 1 | 2 | 0 | R | H | 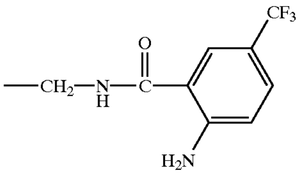 |
| 2150 | 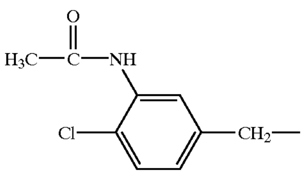 | 1 | 2 | 0 | R | H | 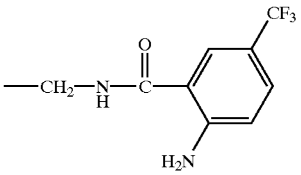 |

TABLE 1.196-continued
| Compd. No. | 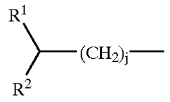 | k | m | n | chirality | $R^3$ | 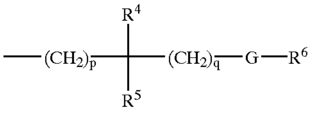 |
|---|---|---|---|---|---|---|---|
| 2151 | 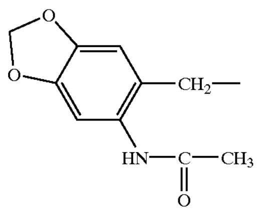 | 1 | 2 | 0 | R | H | 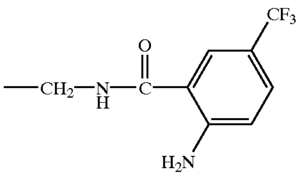 |
| 2152 | 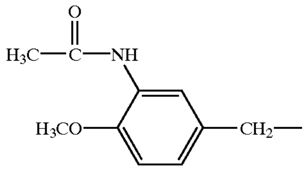 | 1 | 2 | 0 | R | H | 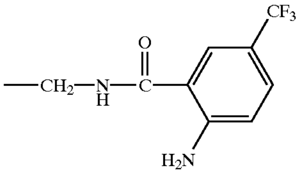 |
| 2153 | 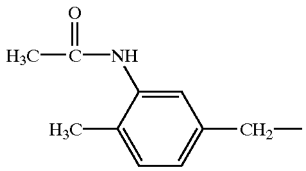 | 1 | 2 | 0 | R | H | 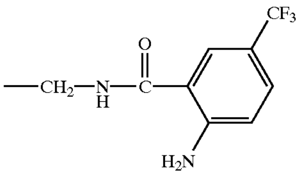 |
| 2154 | 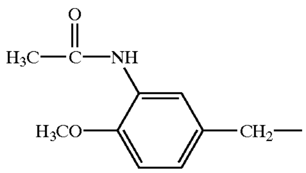 | 2 | 2 | 1 | — | H | 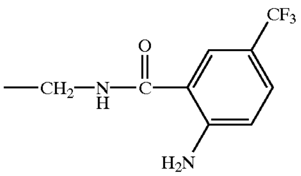 |
| 2155 | 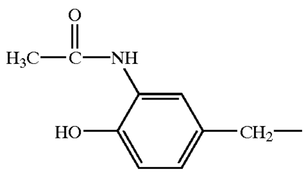 | 2 | 2 | 1 | — | H | 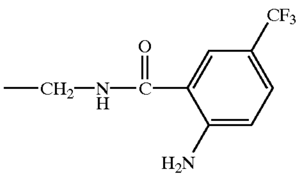 |
| 2156 | 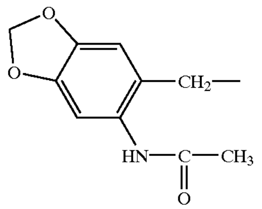 | 2 | 2 | 1 | — | H | 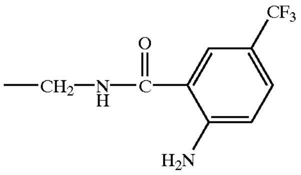 |

TABLE 1.197
| Compd. No. | 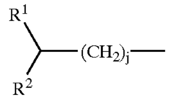 | k | m | n | chirality | $R^3$ | 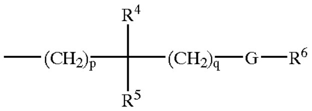 |
|---|---|---|---|---|---|---|---|
| 2157 | 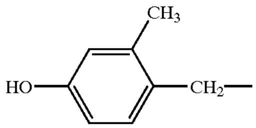 | 1 | 2 | 0 | R | H | 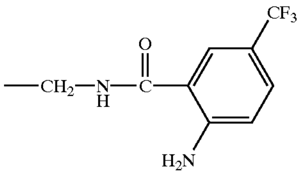 |
| 2158 | 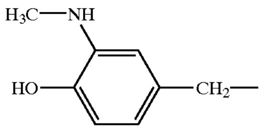 | 1 | 2 | 0 | R | H | 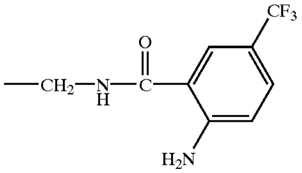 |
| 2159 | 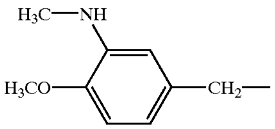 | 2 | 2 | 1 | — | H | 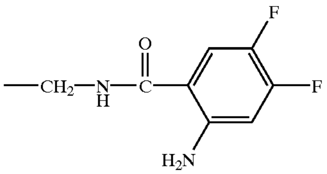 |
| 2160 | 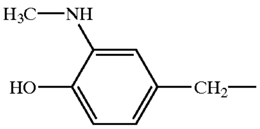 | 2 | 2 | 1 | — | H | 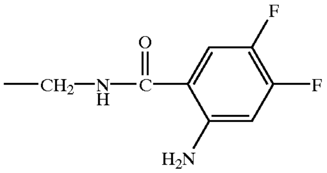 |
| 2161 | 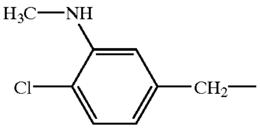 | 2 | 2 | 1 | — | H | 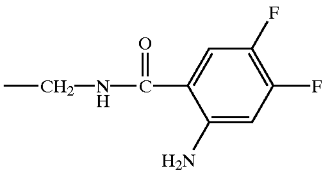 |
| 2162 | 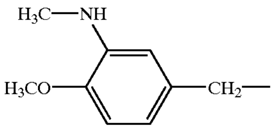 | 2 | 2 | 1 | — | H | 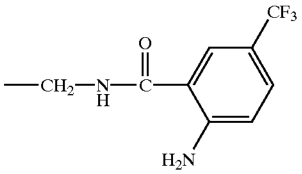 |
| 2163 | 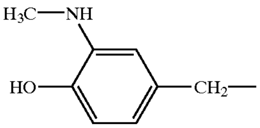 | 2 | 2 | 1 | — | H | 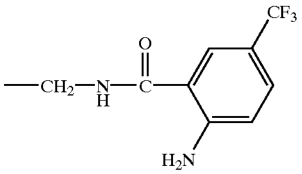 |
| 2164 | 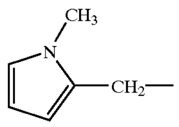 | 1 | 2 | 0 | R | H | 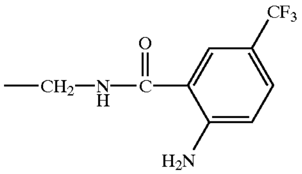 |

TABLE 1.197-continued
| Compd. No. | 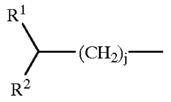 | k | m | n | chirality | $R^3$ | 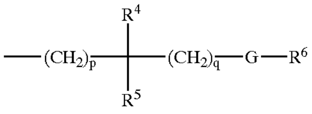 |
|---|---|---|---|---|---|---|---|
| 2165 | 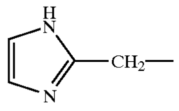 | 1 | 2 | 0 | R | H | 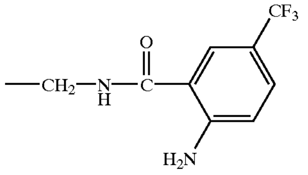 |
| 2166 | 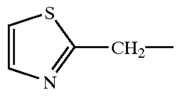 | 1 | 2 | 0 | R | H | 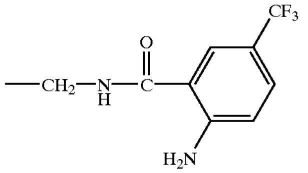 |
| 2167 | 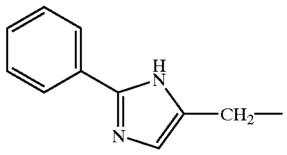 | 1 | 2 | 0 | R | H | 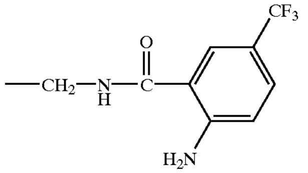 |
TABLE 1.198
| Compd. No. | 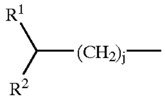 | k | m | n | chirality | $R^3$ | 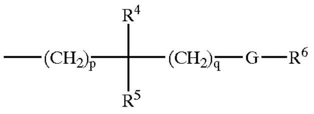 |
|---|---|---|---|---|---|---|---|
| 2168 | 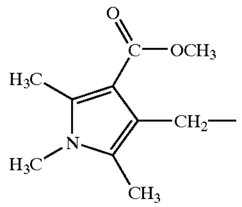 | 1 | 2 | 0 | R | H | 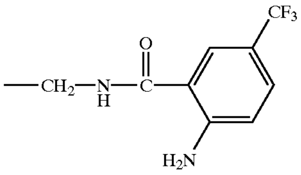 |
| 2169 | 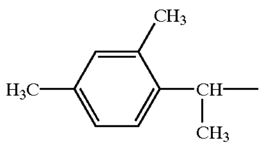 | 1 | 2 | 0 | R | H | 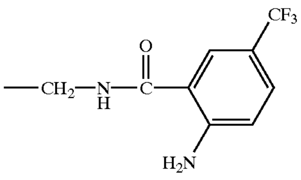 |

TABLE 1.198-continued
| Compd. No. | 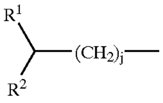 | k | m | n | chirality | $R^3$ | 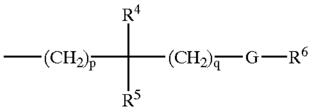 |
|---|---|---|---|---|---|---|---|
| 2170 | 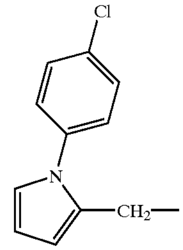 | 1 | 2 | 0 | R | H | 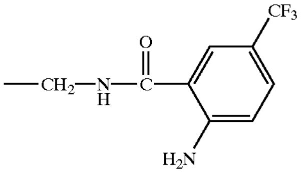 |
| 2171 | 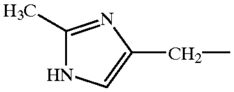 | 1 | 2 | 0 | R | H | 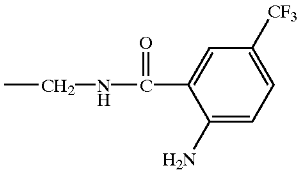 |
| 2172 | 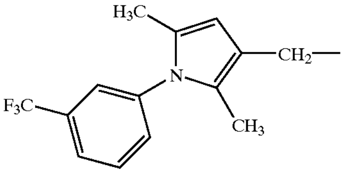 | 1 | 2 | 0 | R | H | 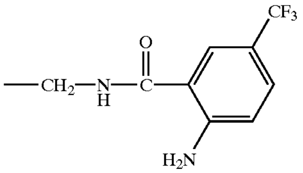 |
| 2173 | 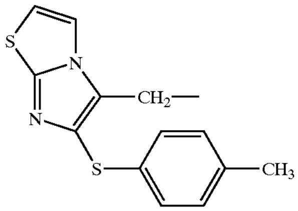 | 1 | 2 | 0 | R | H | 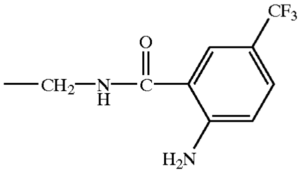 |
| 2174 | 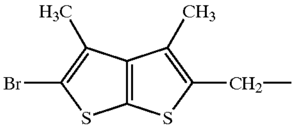 | 1 | 2 | 0 | R | H | 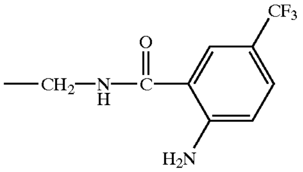 |
| 2175 | 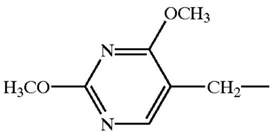 | 1 | 2 | 0 | R | H | 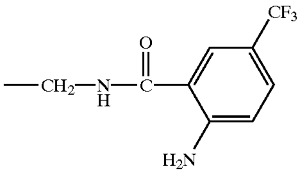 |
| 2176 | 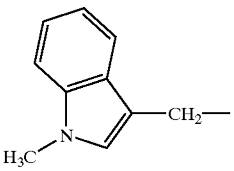 | 1 | 2 | 0 | R | H | 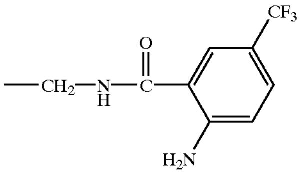 |

TABLE 1.198-continued
| Compd. No. | 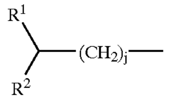 | k | m | n | chirality | $R^3$ | 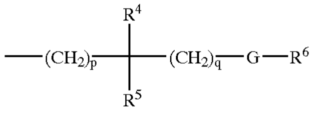 |
|---|---|---|---|---|---|---|---|
| 2177 | 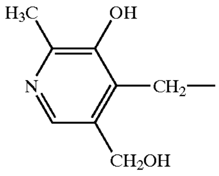 | 1 | 2 | 0 | R | H | 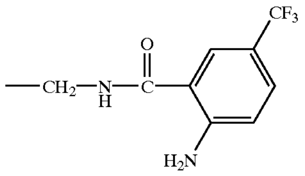 |
| 2178 | 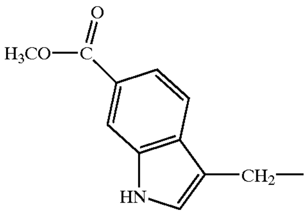 | 1 | 2 | 0 | R | H | 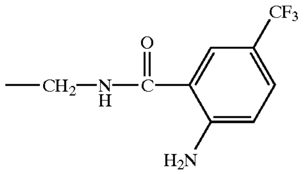 |
TABLE 1.199
| Compd. No. | 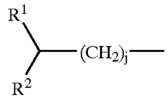 | k | m | n | chirality | $R^3$ | 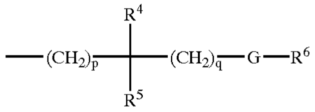 |
|---|---|---|---|---|---|---|---|
| 2179 | 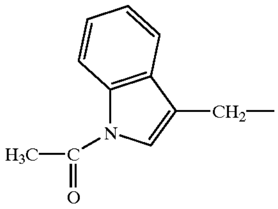 | 1 | 2 | 0 | R | H | 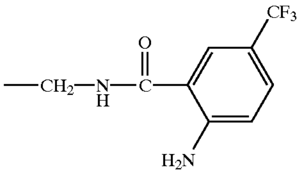 |
| 2180 | 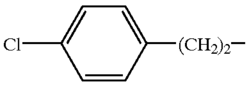 | 1 | 2 | 0 | R | H | 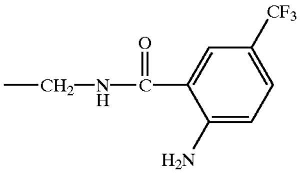 |
| 2181 | 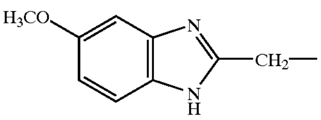 | 1 | 2 | 0 | R | H | 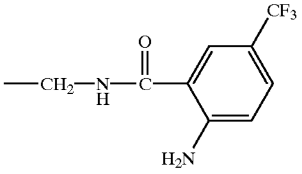 |
| 2182 | 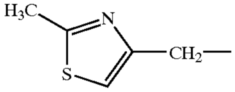 | 1 | 2 | 0 | R | H | 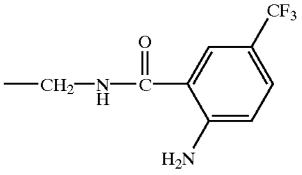 |

TABLE 1.199-continued
| Compd. No. | 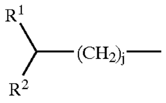 | k | m | n | chirality | $R^3$ | 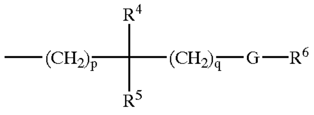 |
|---|---|---|---|---|---|---|---|
| 2183 | 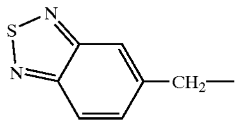 | 1 | 2 | 0 | R | H | 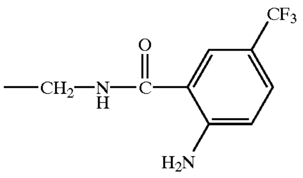 |
| 2184 | 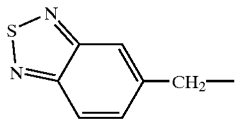 | 2 | 2 | 1 | — | H | 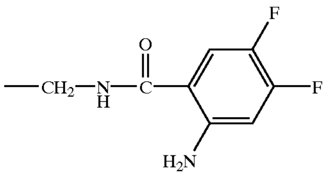 |
| 2185 | 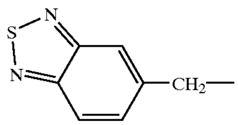 | 2 | 2 | 1 | — | H | 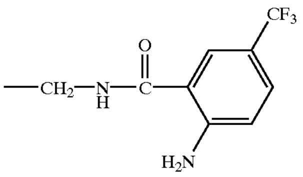 |
| 2186 | 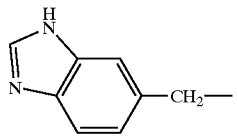 | 2 | 2 | 1 | — | H | 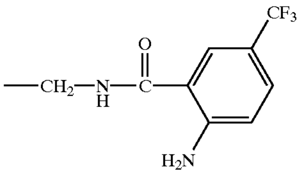 |
| 2187 | 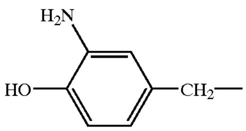 | 1 | 2 | 0 | R | H | 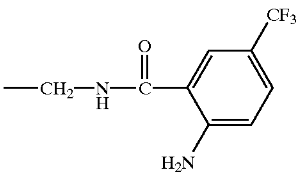 |
| 2188 | 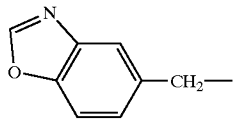 | 2 | 2 | 1 | — | H | 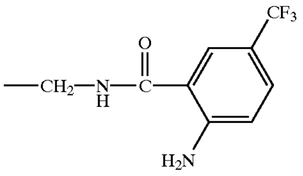 |
| 2189 | 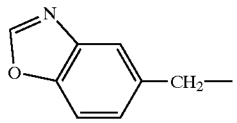 | 1 | 2 | 0 | R | H | 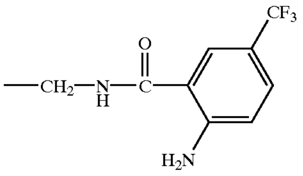 |

TABLE 1.200
| Compd. No. | 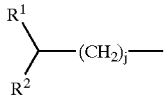 | k | m | n | chirality | $R^3$ | 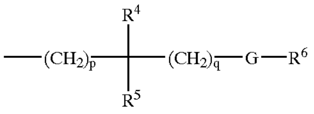 |
|---|---|---|---|---|---|---|---|
| 2190 | 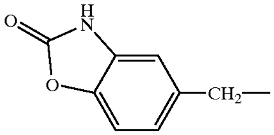 | 2 | 2 | 1 | — | H | 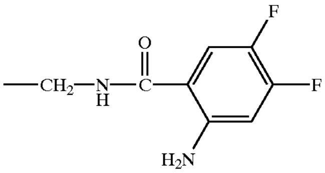 |
| 2191 | 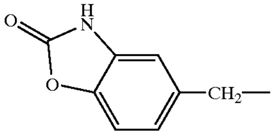 | 2 | 2 | 1 | — | H | 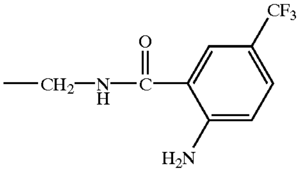 |
| 2192 | 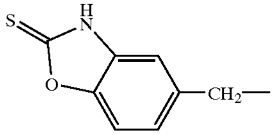 | 2 | 2 | 1 | — | H | 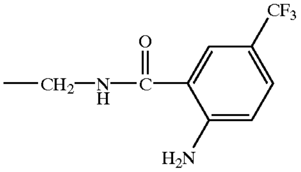 |
| 2193 | 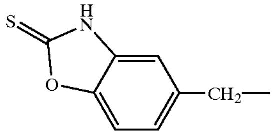 | 2 | 2 | 1 | — | H | 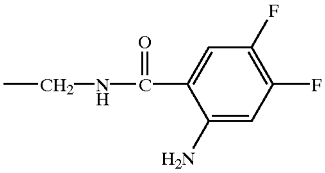 |
| 2194 | 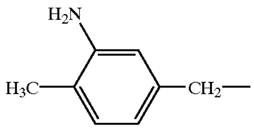 | 2 | 2 | 1 | — | H | 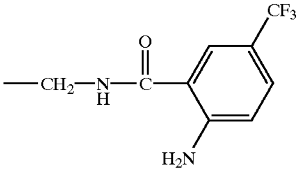 |
| 2195 | 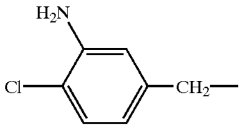 | 2 | 2 | 1 | — | H | 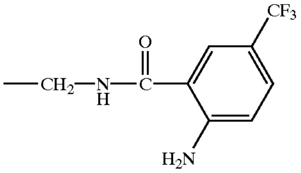 |
| 2196 | 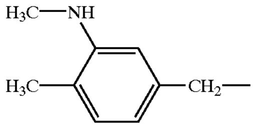 | 1 | 2 | 0 | R | H | 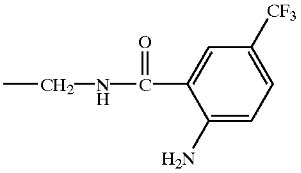 |
| 2197 | 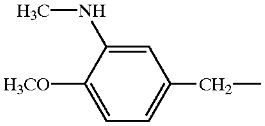 | 1 | 2 | 0 | R | H | 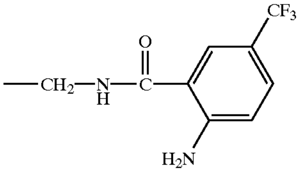 |

TABLE 1.200-continued
| Compd. No. | 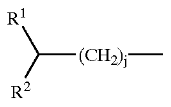 | k | m | n | chirality | $R^3$ | 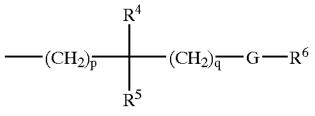 |
|---|---|---|---|---|---|---|---|
| 2198 | 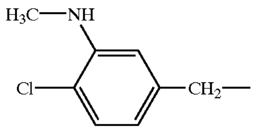 | 1 | 2 | 0 | R | H | 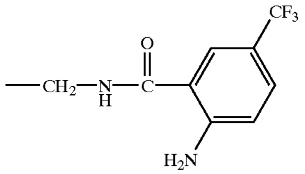 |
| 2199 | 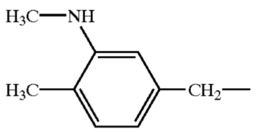 | 2 | 2 | 1 | — | H | 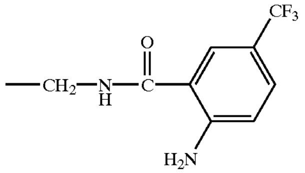 |
| 2200 | 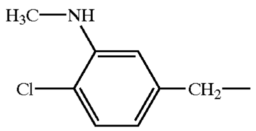 | 2 | 2 | 1 | — | H | 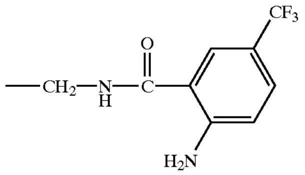 |
TABLE 1.201
| Compd. No. | 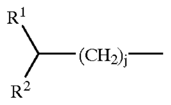 | k | m | n | chirality | $R^3$ | 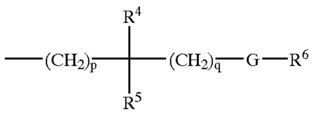 |
|---|---|---|---|---|---|---|---|
| 2201 | 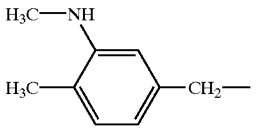 | 2 | 2 | 1 | — | H | 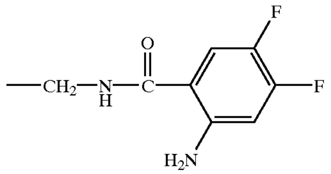 |
| 2202 | 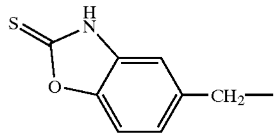 | 1 | 2 | 0 | R | H | 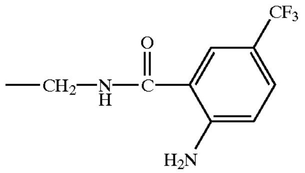 |
| 2203 | 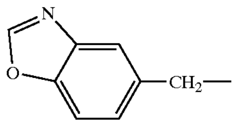 | 2 | 2 | 1 | — | H | 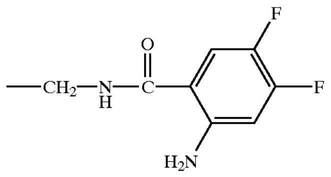 |

TABLE 1.201-continued

| Compd. No. | 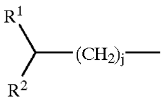 | k | m | n | chirality | $R^3$ | 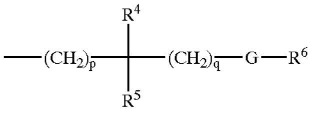 |
|---|---|---|---|---|---|---|---|
| 2204 | 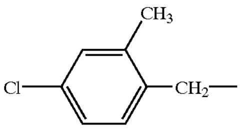 | 2 | 2 | 1 | — | H | 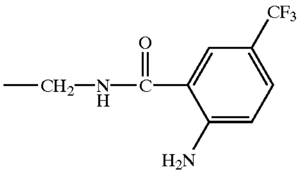 |
| 2205 | 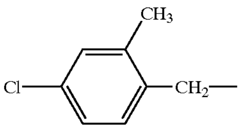 | 2 | 2 | 1 | — | H | 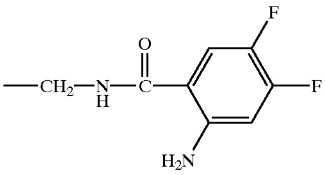 |
| 2206 | 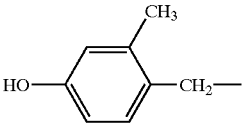 | 2 | 2 | 1 | — | H | 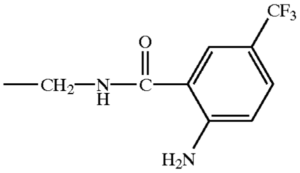 |
| 2207 | 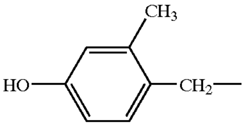 | 2 | 2 | 1 | — | H | 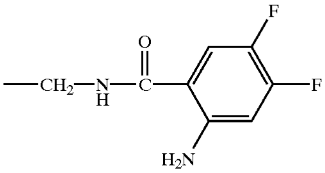 |
| 2208 | 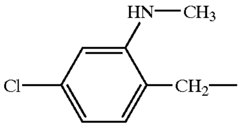 | 2 | 2 | 1 | — | H | 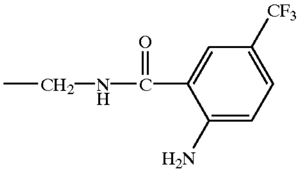 |
| 2209 | 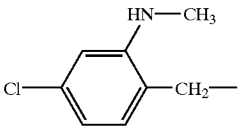 | 2 | 2 | 1 | — | H | 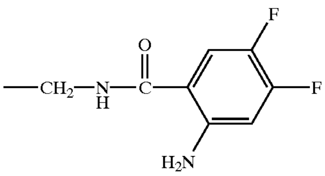 |

The present invention can also use acid addition salt of the cyclic amine compound where such acids include, for example, mineral acids such as hydrochloric acid, hydrobromic acid, sulfuric acid, phosphoric acid, carbonic acid, and the like, as well as organic acids such as maleic acid, citric acid, malic acid, tartaric acid, fumaric acid, methanesulfonic acid, trifluoroacetic acid, formic acid, and the like.

Furthermore, the present invention can also use a $C_1$–$C_6$ alkyl addition salt of the cyclic amine compound, such as 1-(4-chlorobenzyl)-1-methyl-4-[{N-(3-trifluoromethylbenzoyl)glycyl}aminomethyl]piperidinium iodide, where such alkyl include, for example, a methyl, ethyl, n-propyl, n-butyl, n-pentyl, n-hexyl, n-heptyl, n-octyl, isopropyl, isobutyl, sec-butyl, tert-butyl, isopentyl, neopentyl, tert-pentyl, 2-methylpentyl, 1-ethylbutyl, and the like, suitably specifically including, amethyl and ethyl group. As preferred specific examples for counter anion of the ammonium cation, a halide anion such as fluoride, chloride, bromide or iodide can be listed.

The present invention may use racemates and all possible optically active forms of the compound represented by the above formula (I).

Compound represented by the above general formula (I) can be synthesized by any of the general preparations given below.

(Preparation 1)

A preparation which call for treating one equivalent of a compound represented by the formula (II) below:

(II)

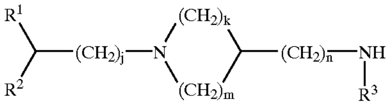

{where $R^1$, $R^2$, $R^3$, j, k, m, and n are the same as defined respectively in the above formula (I)} with 0.1–10 equivalents of a carboxylic acid represented by the formula (III) below:

(III)

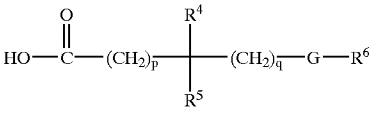

{where $R^4$, $R^5$, $R^6$, G, p, and q are the same as defined respectively in the above formula (I)}, or its reactive derivative, either in the absence or presence of solvent.

The reactive derivative for the carboxylic acid in the above formula (III) include highly reactive carboxylic acid derivatives, which are usually used in synthetic organic chemistry, such as acid halides, acid anhydrides, mixed acid anhydrides.

Such reactions can be more smoothly run by using suitable amounts of a dehydrating agent such as molecular sieve, coupling reagent such as dicyclohexylcarbodiimide (DCC), N-ethyl-N'-(3-dimethylaminopropyl)carbodiimide (EDCI or WSC), carbonyldiimidazole (CDI), N-hydroxysuccinimide (HOSu), N-hydroxybenzotriazole (HOBt), benzotriazol-1-yloxytris(pyrrolidino)phosphonium hexafluorophosphate (PyBOP®), 2-(1H -benzotriazol-1-yl)-1,1,3,3-tetramethyluronium hexafluorophosphate (HBTU), 2-(1H-benzotriazol-1-yl)-1,1,3,3-tetramethyluronium tetrafluoroborate (TBTU), 2- (5-norbornene-2,3-dicarboxyimido)-1,1,3,3-tetramethyluronium tetrafluoroborate (TNTU), O-(N-succinimidyl)-1,1,3,3-tetramethyluronium tetrafluoroborate (TSTU), bromotris(pyrrolidino)phosphonium hexafluorophosphate (PyBroP®), and the like, or base including inorganic salts such as potassium carbonate, sodium carbonate, sodium hydrogencarbonate, and the like, amines such as triethylamine, diisopropylethylamine, and pyridine, and the like, or polymer supported bases such as (piperidinomethyl) polystyrene, (morpholinomethyl)polystyrene, (diethylaminomethyl)polystyrene, poly(4-vinylpyridine), and the like.

(Preparation 2)

A preparation which calls for treating 1 equivalent of an alkylating reagent given by the formula (IV) below:

(IV)

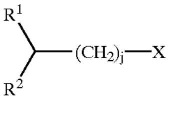

{where $R^1$, $R^2$, and j are the same as defined respectively in the above formula (I)}; X represents a halogen atom, alkylsulfonyloxy group, or arylsulfonyloxy group), with 0.1–10 equivalents of a compound represented by the formula (V) below:

(V)

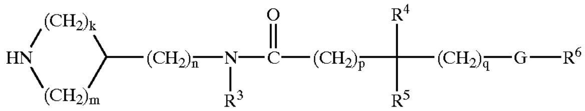

{where $R^3$, $R^4$, $R^5$, $R^6$, G, k, m, n, p, and q are the same as defined respectively in the above formula (I)} either in the absence or presence of solvent.

Such reactions can be more smoothly run if a base similar to that used in the above preparation 1 is present. In addition, the reactions in these preparations can also be promoted by iodide such as potassium iodide, sodium iodide, and the like.

In the above formulas (IV), X represents a halogen atom, alkylsulfonyloxy group, arylsulfonyloxy group. Such halogen atoms include preferably chlorine, bromine, and iodine atoms. Suitable specific examples for the alkylsulfonyloxy groups include methylsulfonyloxy, trifluoromethylsulfonyloxy group, and the like. A preferred specific example for the arylsulfonyloxy group includes a tosyloxy group.

(Preparation 3)

A preparation which calls for treating 1 equivalent of an aldehyde represented by the formula (VI) below:

(VI)

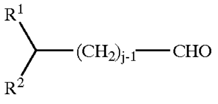

{where $R^1$ and $R^2$ are the same as defined respectively in the above formula (I); j represents 1 or 2} or the formula (VII) below:

$R^1$—CHO (VII)

{where $R^1$ is the same as defined in the above formula (I); j represents 0}, with 0.1–10 equivalents of a compound represented by the formula (V) either in the absence or presence of solvent under reductive conditions.

Such reactions are in general called reductive amination reactions and such reductive conditions may be generated by catalytic hydrogenation using a catalyst containing a metal such as palladium, platinum, nickel, rhodium, or the like, using complex hydrides, such as lithium aluminum hydride, sodium borohydride, sodium cyanoborohydride, sodium triacetoxyborohydride, and the like, boranes, or electrolytic reduction, and the like.

(Preparation 4)

A preparation which call for treating one equivalent of a compound represented by the formula (VIII) below:

(VIII)

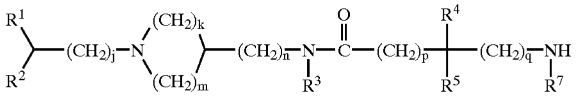

{where $R^1$, $R^2$, $R^3$, $R^4$, $R^5$, $R^7$, j, k, m, n, p and q are the same as defined respectively in the above formula (I)} with 0.1–10 equivalents of a carboxylic acid or sulfonic acid represented by the formula (IX) below:

HO—A—$R^6$ (IX)

{where $R^6$ is the same as defined in the above formulas (I); "A" represents a carbonyl group or sulfonyl group}, or its reactive derivative, either in the absence or presence of solvent.

The reactive derivative for the carboxylic acid or sulfonic acid in the above formula (IX) include highly reactive carboxylic acid or sulfonic acid derivative, which are usually used in synthetic organic chemistry, such as acid halides, acid anhydrides, mixed acid anhydrides.

Such reactions can be more smoothly run by using suitable amounts of a dehydrating agent, coupling reagent, or base which are similar to those used in the above preparation 1.

(Preparation 5)

A preparation which calls for treating 1 equivalent of a compound represented by the above formula (VIII) with 0.1–10 equivalents of a isocyanate or isothiocyanate represented by the formula (X) below:

$$Z{=}C{=}N{-}R^6 \qquad (X)$$

{where $R^6$ is the same as defined in the above formulas (I)); Z represents a oxygen atom or sulfur atom}, either in the absence or presence of solvent.

(Preparation 6)

A preparation which calls for treating 1 equivalent of a compound represented by the formula (XI) below:

(XI)

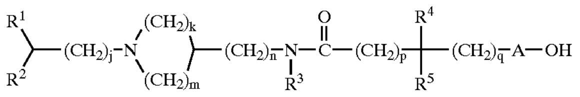

{where $R^1$, $R^2$, $R^3$, $R^4$, $R^5$, j, k, m, n, p and q are the same as defined respectively in the above formula (I)}; "A" represents a carbonyl group or sulfonyl group) with 0.1–10 equivalents of an amine represented by the formula (XII) below:

$$R^6{-}NH_2 \qquad (XII)$$

{where $R^6$ is the same as defined in the above formula (I)}, either in the absence or the presence of solvent.

Such reactions can be more smoothly run by using suitable amounts of a dehydrating agent, coupling reagent, or base which are similar to those used in the above preparation 1.

If the substrates submitted to each of the above preparations contains a substituent which reacts under each reaction condition or is thought to adversely affect the reaction in general in synthetic organic chemistry, that functional group can be protected by a known suitable protecting group followed by the reaction of the above preparations and deprotection using a known procedure to obtain the desired compound.

Furthermore, a compound of the present invention can be prepared by the further conversion of the substituent(s) of the compound, prepared with the above preparations 1–6, using known reactions which are usually used in synthetic organic chemistry, such as alkylation, acylation, reduction, and so on.

Each of the above preparations may use solvents for the reaction such as halogenated hydrocarbons such as dichloromethane, chloroform, and the like, aromatic hydrocarbons such as benzene, toluene, and the like, ethers such as diethyl ether, tetrahydrofuran, and the like, esters such as ethyl acetate, aprotic polar solvents such as dimethylformamide, dimethyl sulfoxide, acetonitrile, and the like, alcohols such as methanol, ethanol, isopropyl alcohol, and the like.

The reaction temperature in either of the preparations should be in the range of −78° C.–+150° C., preferably 0° C.–100° C. After completion of the reaction, the usual isolation and purification operations such as concentration, filtration, extraction, solid-phase extraction, recrystallization, chromatography, and the like may be used, to isolate the desired cyclic amine compound represented by the above formula (I). These can be converted into pharmaceutically acceptable acid addition salt or $C_1$–$C_6$ alkyl addition salt by the usual method.

Potential Industrial Utilities

The chemokine receptor antagonist, which contain the cyclic amine compound, its pharmaceutically acceptable acid addition salt or a pharmaceutically acceptable $C_1$–$C_6$ alkyl addition salt of this invention, which inhibits chemokines such as MIP-1α and/or MCP-1 and the like from action on target cells, are useful as therapeutic agents and/or preventive preparation for diseases such as atherosclerosis, rheumatoid arthritis, psoriasis, asthma, ulcerative colitis, nephritis (nephropathy), multiple sclerosis, pulmonary fibrosis, myocarditis, hepatitis, pancreatitis, sarcoidosis, Crohn's disease, endometriosis, congestive heart failure, viral meningitis, cerebral infarction, neuropathy, Kawasaki disease, sepsis, and the like, in which tissue infiltration of blood monocytes, lymphocytes, and the like plays a major role in the initiation, progression, and maintenance of the disease.

EXAMPLES

The present invention is now specifically described by the following examples. However, the present invention is not limited to these compounds described in these examples. Compound numbers in these examples represent numbers attached to these compounds listed as suitable specific examples in Tables 1.1–1.201.

Reference Example 1

Preparation of 3-Amino-1-(4-chlorobenzyl) pyrrolidine Dihydrochloride

4-Chlorobenzyl chloride (4.15 g, 25.8 mmol) and $Pr_2NEt$ (6.67 g, 51.6 mmol) were added to a solution of 3-{(tert-butoxycarbonyl)amino}pyrrolidine (4.81 g, 25.8 mmol) in DMF (50 mL). The reaction mixture was stirred at 70° C. for 15 h and the solvent was removed under reduced pressure. Recrystallization ($CH_3CN$, 50 mL) provided the desired material, 3-(tert-butoxycarbonyl)amino-1-(4-chlorobenzyl) pyrrolidine as a pale yellow solid (6.43 g, 80.2%): $^1H$ NMR ($CDCl_3$, 300 MHz) δ1.37 (s, 9 H), 1.5–1.7 (br, 1 H), 2.1–2.4 (m, 2 H), 2.5–2.7 (m, 2 H), 2.83 (br, 1 H), 3.57 (s, 2 H), 4.1–4.3 (br, 1 H), 4.9–5.1 (br, 1 H), 7.15–7.35 (br, 4 H); The purity was determined by RPLC/MS (98%); ESI/MS m/e 311.0 ($M^+$+H, $C_{16}H_{24}ClN_2O_2$).

A solution of 3-(tert-butoxycarbonyl)amino-1-(4-chlorobenzyl)pyrrolidine (6.38 g, 20.5 mmol) in $CH_3OH$ (80 mL) was treated with 1 N HCl-$Et_2O$ (100 mL) and was stirred at 25° C. for 15 h. The solvent was removed under reduced pressure to afford a solid which was purified by recrystallization (1:2 $CH_3OH$—$CH_3CN$, 150 mL) to give 3-amino-1-(4-chlorobenzyl)pyrrolidine dihydrochloride as a white powder (4.939 g, 84.9%): $^1H$ NMR ($d_6$-DMSO, 300 MHz) δ3.15 (br, 1 H), 3.3–3.75 (br-m, 4 H), 3.9 (br, 1 H), 4.05 (br, 1 H), 4.44 (br, 1 H), 4.54 (br, 1 H), 7.5–7.7 (m, 4 H), 8.45 (br, 1 H), 8.60 (br, 1 H); The purity was determined by RPLC/MS (>99%); ESI/MS m/e 211.0 ($M^+$+H, $C_{11}H_{16}ClN_2$).

Optically active (R)-3-amino-1-(4-chlorobenzyl) pyrrolidine dihydrochloride and (S)-3-amino-1-(4- chlorobenzyl)pyrrolidine dihydrochloride were also prepared pursuant to the above method using the corresponding reactant respectively. The products showed the same $^1$H NMR with that of the racemate.

Example 1

Preparation of 3-(N-Benzoylglycyl)amino-1-(4-chlorobenzyl)pyrrolidine (Compound No. 1)

N-Benzoylglycine (9.9 mg, 0.055 mmol), 3-ethyl-1-(3-(dimethylaminopropyl)carbodiimide hydrochloride (EDCI) (10.5 mg) and 1-hydroxybenzotriazole hydrate (HOBt) (7.4 mg) were added to a solution of 3-amino-1-(4-chlorobenzyl)pyrrolidine dihydrochloride (14.2 mg, 0.050 mmol) and Et$_3$N (15.2 mg) in CHCl$_3$ (2.5 mL). The reaction mixture was stirred at 25° C. for 16 h, washed with 2 N aqueous NaOH (2 mL×2) and brine (1 mL). After filtration through a PTFE membrane filter, the solvent was removed under reduced pressure to afford 3-(N-benzoylglycyl)amino-1-(4-chlorobenzyl)pyrrolidine (compound No. 1) as a pale yellow oil (17.7 mg, 95%): The purity was determined by RPLC/MS (95%); ESI/MS m/e 372.0 (M$^+$+H, C$_{20}$H$_{22}$ClN$_3$O$_2$).

Examples 2–32

The compounds of this invention were synthesized pursuant to methods of Example 1 using the corresponding reactant respectively. The ESI/MS data and yields are summarized in Table 2.

TABLE 2

| | Compound No. | Molecular Formula | ESI/MS m/e | Yield (mg) | Yield (%) |
|---|---|---|---|---|---|
| Example 2 | 2 | C21 H24 Cl N3 O2 | 386 | 16.4 | 85 |
| Example 3 | 3 | C19 H21 Cl N4 O2 | 373 | 18.7 | 100 |
| Example 4 | 4 | C21 H21 Cl F3 N3 O2 | 440 | 57.2 | 69 |
| Example 5 | 82 | C22 H23 Cl F3 N3 O2 | 454 | 5.6 | 11 |
| Example 6 | 85 | C21 H24 Cl N3 O2 | 386 | 22.6 | 59 |
| Example 7 | 86 | C21 H23 Cl N4 O4 | 431 | 21.2 | 98 |
| Example 8 | 214 | C22 H25 Cl N2 O2 | 385 | 23.9 | 62 |
| Example 9 | 215 | C23 H27 Cl N2 O3 | 415 | 17.4 | 84 |
| Example 10 | 216 | C20 H23 Cl N2 O2 S | 391 | 21.6 | quant |
| Example 11 | 217 | C23 H27 Cl N2 O4 | 431 | 15.3 | 66 |
| Example 12 | 218 | C23 H27 Cl N2 O2 | 399 | 12.8 | 64 |
| Example 13 | 219 | C22 H24 Cl F N2 O3 | 419 | 18.1 | 86 |
| Example 14 | 220 | C22 H25 Cl N2 O2 | 385 | 16.4 | 85 |
| Example 15 | 221 | C21 H23 Cl N2 O2 | 371 | 14.9 | 80 |
| Example 16 | 222 | C21 H22 Cl2 N2 O2 | 405 | 13.3 | 65 |
| Example 17 | 223 | C25 H31 Cl N2 O3 | 443 | 18.4* | 63 |
| Example 18 | 224 | C20 H23 Cl N2 O3 S | 407 | 11.2 | 28 |
| Example 19 | 225 | C22 H26 Cl N3 O2 | 400 | 22.7 | quant |
| Example 20 | 226 | C23 H28 Cl N3 O3 | 430 | 21.0 | 98 |
| Example 21 | 227 | C22 H25 Cl2 N3 O2 | 434 | 21.9 | 100 |
| Example 22 | 228 | C23 H28 Cl N3 O3 | 430 | 20.8 | 97 |
| Example 23 | 229 | C25 H32 Cl N3 O2 | 462 | 25.4 | quant |
| Example 24 | 230 | C26 H31 Cl F N3 O2 | 472 | 26.0 | quant |
| Example 25 | 231 | C24 H28 Cl N3 O3 | 442 | 30.3* | quant |
| Example 26 | 232 | C22 H32 Cl N3 O2 | 406 | 3.9 | 19 |
| Example 27 | 233 | C23 H28 Cl N3 O2 | 414 | 8.5 | 41 |
| Example 28 | 234 | C22 H27 Cl N4 O2 | 415 | 7.3 | 35 |
| Example 29 | 235 | C24 H29 Cl2 N3 O2 | 462 | 9.0 | 39 |
| Example 30 | 236 | C25 H29 Cl N4 O3 S | 501 | 17.4 | 69 |
| Example 31 | 237 | C21 H24 Cl N3 O3 | 402 | 14.2 | 71 |
| Example 32 | 238 | C21 H23 Cl2 N3 O3 | 436 | 23.4 | quant |

*Yield of TFA salt.

Reference Example 2

Preparation of (R)-3-{N-(tert-Butoxycarbonyl)glycyl}amino-1-(4-chlorobenzyl)pyrrolidine A mixture of (R)-3-amino-1-(4-chlorobenzyl)pyrrolidine dihydrochloride (4.54 g, 16.0 mmol), 2 N NaOH solution (80 mL), and ethyl acetate (80 mL) was shaken, the organic layer was separated, and the aqueous layer was extracted with ethyl acetate (80 mL×2). The combined organic layers were dried over anhydrous sodium sulfate, filtered, and evaporated to give free (R)-3-amino-1-(4-chlorobenzyl)pyrrolidine (3.35 g, 99%).

A solution of (R)-3-amino-1-(4-chlorobenzyl)pyrrolidine (3.35 g, 16 mmol) in CH$_2$Cl$_2$ (80 mL) was treated with Et$_2$N (2.5 mL, 17.6 mmol), N-tert-butoxycarbonylglycine (2.79 g, 16.0 mmol), EDCI (3.07 g, 16.0 mmol) and HOBt (2.16 g, 16 mmol). After the reaction mixture was stirred at 25° C. for 16 h, 2 N NaOH solution (80 mL) was added. The organic layer was separated, and the aqueous layer was extracted with dichloromethane (100 mL×3). The combined organic layer was washed with water (100 mL×2) and brine (100 mL), dried over anhydrous sodium sulfate, filtered, and concentrated. Column chromatography (SiO$_2$, ethyl acetate) afforded the desired (R)-3-{N-(tert-butoxycarbonyl)glycyl}amino 1-(4-chlorobenzyl)pyrrolidine (5.40 g, 92%).

Reference Example 3

Preparation of (R)-1-(4-Chlorobenzyl)-3-(glycylamino)pyrrolidine

To a solution of (R)-3-{N-(tert-butoxycarbonyl)glycyl}amino-1-(4-chlorobenzyl)pyrrolidine (5.39 g, 14.7 mmol) in methanol (60 mL) was added 4 N HCl in dioxane (38 mL). The solution was stirred at room temperature for 2 h. The reaction mixture was concentrated and 2 N NaOH solution (80 mL) was added. The mixture was extracted with dichloromethane (80 mL×3), and the combined extracts were dried over sodium sulfate and concentrated. Column chromatography (SiO$_2$, AcOEt/EtOH/Et$_3$N=90/5/5) gave (R)-3-(glycyl)amino-1-(4-chlorobenzyl)pyrrolidine (3.374 g, 86%): $^1$H NMR (CDCl$_3$, 270 MHz) δ1.77 (dd, J=1.3 and 6.9 Hz, 1 H), 2.20–3.39 (m, 2 H), 2.53 (dd, J=3.3 and 9.6 Hz, 1 H), 2.62 (dd, J=6.6 and 9.6 Hz, 1 H), 2.78–2.87 (m, 1 H), 3.31 (s, 2 H), 3.57 (s, 2 H), 4.38–4.53 (br, 1 H), 7.18–7.32 (m, 4 H), 7.39 (br. s, 1 H).

Other 3-acylamino-1-(4-chlorobenzyl)pyrrolidines were also synthesized pursuant to methods of Reference Example 2 and 3 using the corresponding reactants respectively.

(S)-1-(4-Chlorobenzyl)-3-(glycylamino)pyrrolidine: 3.45 g, 79% (2 steps).

(R)-3-(β-Alanylamino)-1-(4-chlorobenzyl)pyrrolidine: 3.79 g, 85% (2 steps).

(S)-3-(β-Alanylamino-)1-(4-chlorobenzyl)pyrrolidine: 3.72 g, 86% (2 steps).

(R)-3-{(S)-Alanylamino}-1-(4-chlorobenzyl)pyrrolidine: 368 mg, 65% (2 steps).

(R)-3-{(R)-Alanylamino}-1-(4-chlorobenzyl)pyrrolidine: 425 mg, 75% (2 steps).

(R)-3-{(2S)-2-Amino-3-thienylpropanoyl}amino-1-(4-chlorobenzyl)pyrrolidine: 566 mg, 78% (2 steps).

(R)-3-{(2R)-2-Amino-3-thienylpropanoyl}amino-1-(4-chlorobenzyl)pyrrolidine: 585 mg, 81% (2 steps).

(R)-3-(2-Amino-2-methylpropanoyl)amino-1-(4-chlorobenzyl)pyrrolidine: 404 mg, 66% (2 steps).

(R)-3-{(2S)-2-Amino-4-(methylsulfonyl)butanoyl}amino-1-(4-chlorobenzyl)pyrrolidine: 535 mg, 72% (2 steps).

Furthermore (R)-3-(glycylamino)-1-(4-methylbenzyl)pyrrolidine, (R)-1-(4-bromobenzyl)-3-(glycylamino)pyrrolidine, (R)-1-(2,4-dimethylbenzyl)-3-(glycylamino)pyrrolidine, and (R)-1-(3,5-dimethylisoxazol-4-ylmethyl)-3-(glycylamino)pyrrolidine were also synthesized pursuant to methods of Reference Example 1, 2 and 3 using the corresponding reactants respectively.

(R)-3-(Glycylamino)-1-(4-methylbenzyl)pyrrolidine: 4.65 g, 62% yield from 3-{(tert-butoxycarbonyl) amino}pyrrolidine.

(R)-1-(4-Bromobenzyl)-3-(glycylamino)pyrrolidine: 2.55 g, 68% yield from (R)-3-amino-1-(4-bromobenzyl) pyrrolidine; $^1H$ NMR ($CDCl_3$, 270 MHz) δ1.37–1.78 (m, 3 H), 2.23–2.39 (m, 2 H), 2.50–2.67(m, 2 H), 2.80–2.89 (m, 1 H 3.32 (s, 2 H), 3.58 (s, 2 H), 4.39–4.55 (m, 1 H), 7.21 (d, J=6.5 Hz, 2 H), 7.45 (d, J=6.5 Hz, 2 H).

(R)-1-(2,4-Dimethylbenzyl)-3-(glycylamino)pyrrolidine: 1.56 g, 58% yield from 3-{tert-butoxycarbonyl) amino}pyrrolidine; $^1H$ NMR ($CDCl_3$, 270 MHz) δ1.55–1.78 (m, 3 H), 2.30(s, 3 H), 2.23–2.31 (m, 2 H), 2.33(s, 3 H), 2.51–2.63 (m, 2 H), 2.78–2.87 (m, 1 H), 3.30 (s, 2 H), 3.55 (s, 2 H), 4.38–4.60 (m, 1 H), 6.95 (d, J=7.6 Hz, 1 H), 6.97 (s, 1 H), 7.13 (d, J=7.6 Hz, 1 H), 7.43 (br-s, 1 H).

(R)-1-(3,5-Dimethylisoxazol-4-ylmethyl)-3-(glycylamino) pyrrolidine: 3.14 g, 45% yield from 3-{(tert-butoxycarbonyl)amino}pyrrolidine.

Example 33

Preparation of (S)-3-[N-{3,5-Bis(trifluoromethyl) benzoyl}glycyl]amino-1-(4-chlorobenzyl)pyrrolidine (Compound No. 5)

A solution of 3,5-bis(trifluoromethyl)benzoyl chloride (0.060 mmol) in chloroform (0.4 mL) was added to a solution of (S)-1-(4-chlorobenzyl)-3-(glycylamino) pyrrolidine (0.050 mmol) and triethylamine (0.070 mmol) in chloroform (1.0 mL). After the reaction mixture was agitated at room temperature for 2.5 h, (aminomethyl)polystyrene resin (1.04 mmol/g, 50 mg, 50 mmol) was added and the mixture was agitated at room temperature for 12 h. The reaction mixture was filtered and the resin was washed with dichloromethane (0.5 mL). The filtrate and washing were combined, dichloromethane (4 mL) was added, and the solution was washed with 2 N aqueous NaOH solution (0.5 mL) to give (S)-3-[N-{3,5-bis(trifluoromethyl) benzoyl}glycyl]amino-1-(4-chlorobenzyl)pyrrolidine (compound No. 5) (14.4 mg, 57%): The purity was determined by RPLC/MS (97%); ESI/MS m/e 508.0 ($M^++H$, $C_{22}H_{20}ClF_6N_3O_2$).

Examples 34–239

The compounds of this invention were synthesized pursuant to methods of Example 33 using the corresponding reactant respectively. The ESI/MS data and yields are summarized in Table 3.

TABLE 3

| | Compound No. | Molecular Formula | ESI/MS m/e | Yield (mg) | Yield (%) |
|---|---|---|---|---|---|
| Example 34 | 5 | $C_{22}H_{21}ClF_6N_3O_2$ | 508.0 | 14.4 | 57 |
| Example 35 | 6 | $C_{21}H_{21}ClF_3N_3O_2$ | 440.0 | 17.0 | 77 |
| Example 36 | 7 | $C_{20}H_{21}BrClN_3O_2$ | 450.0 | 17.7 | 79 |
| Example 37 | 8 | $C_{20}H_{21}ClFN_3O_2$ | 390.0 | 12.7 | 65 |
| Example 38 | 9 | $C_{20}H_{20}Cl_3N_3O_2$ | 440.0 | 39.0 | quant |
| Example 39 | 10 | $C_{21}H_{24}ClN_3O_3$ | 402.5 | 23.5 | quant |
| Example 40 | 11 | $C_{22}H_{26}ClN_3O_4$ | 432.5 | 22.4 | quant |
| Example 41 | 12 | $C_{22}H_{26}ClN_3O_4$ | 432.5 | 15.9 | 74 |

TABLE 3-continued

| | Compound No. | Molecular Formula | ESI/MS m/e | Yield (mg) | Yield (%) |
|---|---|---|---|---|---|
| Example 42 | 13 | $C_{21}H_{21}ClF_3N_3O_2$ | 440.0 | 13.1 | 60 |
| Example 43 | 14 | $C_{21}H_{24}ClN_3O_2$ | 386.0 | 16.4 | 85 |
| Example 44 | 15 | $C_{20}H_{21}Cl_2N_3O_2$ | 406.0 | 15.7 | 77 |
| Example 45 | 16 | $C_{21}H_{24}ClN_3O_2$ | 402.0 | 28.2 | quant |
| Example 46 | 17 | $C_{20}H_{20}Cl_3N_3O_2$ | 442.0 | 35.6 | quant |
| Example 47 | 18 | $C_{21}H_{21}ClN_4O_2$ | 397.5 | 22.8 | quant |
| Example 48 | 19 | $C_{21}H_{22}ClN_3O_4$ | 416.0 | 16.3 | 78 |
| Example 49 | 20 | $C_{21}H_{20}ClF_4N_3O_2$ | 458.0 | 24.9 | quant |
| Example 50 | 21 | $C_{21}H_{20}ClF_4N_3O_2$ | 458.0 | 17.9 | 78 |
| Example 51 | 22 | $C_{21}H_{20}ClF_4N_3O_2$ | 458.0 | 9.4 | 41 |
| Example 52 | 23 | $C_{21}H_{20}ClF_4N_3O_2$ | 458.0 | 15.4 | 67 |
| Example 53 | 24 | $C_{21}H_{21}ClF_3N_3O_3$ | 456.0 | 20.7 | 91 |
| Example 54 | 25 | $C_{21}H_{20}ClF_4N_3O_2$ | 458.0 | 18.5 | 81 |
| Example 55 | 26 | $C_{20}H_{21}ClN_4O_4$ | 417.0 | 21.9 | quant |
| Example 56 | 27 | $C_{20}H_{21}ClN_4O_4$ | 417.0 | 16.8 | 81 |
| Example 57 | 28 | $C_{20}H_{21}ClN_4O_4$ | 417.0 | 6.8 | 33 |
| Example 58 | 29 | $C_{22}H_{20}ClF_6N_3O_2$ | 508.0 | 20.8 | 82 |
| Example 59 | 30 | $C_{21}H_{21}ClF_3N_3O_2$ | 440.0 | 15.2 | 69 |
| Example 60 | 31 | $C_{20}H_{21}BrClN_3O$ | 450.0 | 15.6 | 69 |
| Example 61 | 32 | $C_{20}H_{23}ClFN_3O_2$ | 390.0 | 11.8 | 61 |
| Example 62 | 33 | $C_{20}H_{20}Cl_3N_3O_2$ | 440.0 | 15.8 | 72 |
| Example 63 | 34 | $C_{21}H_{24}ClN_3O_3$ | 402.5 | 33.8 | quant |
| Example 64 | 35 | $C_{22}H_{26}ClN_3O_4$ | 432.5 | 56.1 | quant |
| Example 65 | 36 | $C_{22}H_{26}ClN_3O_4$ | 432.5 | 37.6 | quant |
| Example 66 | 37 | $C_{21}H_{21}ClF_3N_3O_2$ | 440.0 | 12.6 | 57 |
| Example 67 | 38 | $C_{21}H_{24}ClN_3O_2$ | 386.0 | 12.3 | 64 |
| Example 68 | 39 | $C_{20}H_{21}Cl_2N_3O_2$ | 406.0 | 15.9 | 78 |
| Example 69 | 40 | $C_{21}H_{24}ClN_3O_2$ | 402.0 | 11.6 | 58 |
| Example 70 | 41 | $C_{20}H_{20}Cl_3N_3O_2$ | 442.0 | 17.8 | 81 |
| Example 71 | 42 | $C_{21}H_{23}ClN_4O_2$ | 397.5 | 22.4 | quant |
| Example 72 | 43 | $C_{21}H_{22}ClN_3O_4$ | 416.0 | 30.1 | quant |
| Example 73 | 44 | $C_{21}H_{26}ClF_4N_3O_2$ | 458.0 | 13.4 | 59 |
| Example 74 | 45 | $C_{21}H_{20}ClF_4N_3O_2$ | 458.0 | 13.2 | 58 |
| Example 75 | 46 | $C_{21}H_{20}ClF_4N_3O_2$ | 458.0 | 14.4 | 63 |
| Example 76 | 47 | $C_{21}H_{21}ClF_3N_3O_3$ | 456.0 | 16.4 | 72 |
| Example 77 | 48 | $C_{21}H_{26}ClF_4N_3O_2$ | 458 | 16.5 | 72 |
| Example 78 | 49 | $C_{20}H_{21}ClN_4O_4$ | 417.0 | 12.5 | 60 |
| Example 79 | 50 | $C_{21}H_{20}ClF_4N_3O_2$ | 458.0 | 26.3 | quant |
| Example 80 | 51 | $C_{20}H_{21}BrClN_3O_2$ | 450.0 | 8.6 | 38 |
| Example 81 | 52 | $C_{20}H_{23}ClFN_3O_2$ | 390.5 | 4.1 | 21 |
| Example 82 | 53 | $C_{20}H_{21}Cl_2N_3O_2$ | 406.0 | 5.4 | 27 |
| Example 83 | 54 | $C_{26}H_{20}Cl_3N_3O_2$ | 440.0 | 8.8 | 40 |
| Example 84 | 55 | $C_{20}H_{20}BrCl_4N_3O_2$ | 440.0 | 7.7 | 35 |
| Example 85 | 56 | $C_{21}H_{24}ClN_3O_2$ | 386.0 | 4.8 | 25 |
| Example 86 | 57 | $C_{22}H_{26}ClN_3O_4$ | 429.5 | 4.9 | 23 |
| Example 87 | 58 | $C_{20}H_{21}Cl_2N_3O_2$ | 406.0 | 4.1 | 20 |
| Example 88 | 59 | $C_{20}H_{21}BrClN_3O_2$ | 452.0 | 3.5 | 16 |
| Example 89 | 60 | $C_{26}H_{26}ClN_3O_2$ | 448.5 | 7.3 | 33 |
| Example 90 | 61 | $C_{21}H_{21}ClF_3N_3O_2$ | 440.0 | 7.1 | 32 |
| Example 91 | 62 | $C_{21}H_{24}ClN_3O_2$ | 386.0 | 10.4 | 54 |
| Example 92 | 63 | $C_{22}H_{26}ClN_3O_2$ | 400.5 | 6.0 | 30 |
| Example 93 | 64 | $C_{21}H_{21}ClN_4O_2$ | 397.0 | 7.0 | 35 |
| Example 94 | 65 | $C_{24}H_{24}ClN_3O_2$ | 422.0 | 7.7 | 36 |
| Example 95 | 66 | $C_{24}H_{24}ClN_3O_2$ | 422.0 | 6.3 | 30 |
| Example 96 | 67 | $C_{20}H_{20}ClF_2N_3O_2$ | 408.0 | 4.7 | 23 |
| Example 97 | 68 | $C_{20}H_{20}ClF_2N_3O_2$ | 408.0 | 7.8 | 38 |
| Example 98 | 69 | $C_{20}H_{20}ClF_2N_3O_2$ | 408.0 | 7.3 | 36 |
| Example 99 | 70 | $C_{20}H_{20}ClF_2N_3O_2$ | 408.0 | 9.1 | 45 |
| Example 100 | 71 | $C_{22}H_{26}ClN_3O_4$ | 429.0 | 5.6 | 26 |
| Example 101 | 72 | $C_{21}H_{21}ClF_3N_3O_2$ | 456.0 | 6.2 | 27 |
| Example 102 | 73 | $C_{21}H_{21}ClF_3N_3O_2$ | 456.5 | 16.8 | 74 |
| Example 103 | 74 | $C_{22}H_{24}ClN_3O_4$ | 430.0 | 16.4 | 76 |
| Example 104 | 75 | $C_{20}H_{20}ClF_4N_3O_2$ | 458.0 | 16.1 | 70 |
| Example 105 | 76 | $C_{21}H_{20}ClF_4N_3O_2$ | 458.0 | 17.0 | 74 |
| Example 106 | 77 | $C_{20}H_{19}ClF_3N_3O_2$ | 426.0 | 16.2 | 76 |
| Example 107 | 78 | $C_{20}H_{19}ClF_3N_3O_2$ | 426.0 | 18.0 | 85 |
| Example 108 | 79 | $C_{22}H_{20}ClF_6N_3O_2$ | 508.0 | 18.8 | 74 |
| Example 109 | 80 | $C_{22}H_{20}ClF_6N_3O_2$ | 508.0 | 16.4 | 65 |
| Example 110 | 81 | $C_{22}H_{26}ClN_3O_2$ | 400.0 | 13.9 | 70 |
| Example 111 | 82 | $C_{20}H_{21}ClN_4O_4$ | 417.0 | 16.0 | 77 |
| Example 112 | 83 | $C_{20}H_{21}ClN_4O_4$ | 417.0 | 21.6 | quant |
| Example 113 | 84 | $C_{23}H_{22}ClF_6N_3O_2$ | 522.0 | 17.5 | 67 |
| Example 114 | 85 | $C_{22}H_{22}ClF_3N_3O_2$ | 454.0 | 13.9 | 61 |
| Example 115 | 89 | $C_{21}H_{23}BrClN_3O_2$ | 466.0 | 15.4 | 66 |
| Example 116 | 90 | $C_{21}H_{23}ClFN_3O_2$ | 404.0 | 10.7 | 53 |

TABLE 3-continued

| | Compound No. | Molecular Formula | ESI/MS m/e | Yield (mg) | Yield (%) |
|---|---|---|---|---|---|
| Example 117 | 91 | $C_{21}H_{22}Cl_3N_3O_2$ | 456.0 | 13.7 | 60 |
| Example 118 | 92 | $C_{22}H_{26}ClN_3O_3$ | 416.0 | 38.4 | quant |
| Example 119 | 93 | $C_{23}H_{28}ClN_3O_4$ | 446.0 | 25.2 | quant |
| Example 120 | 94 | $C_{23}H_{22}ClN_3O_4$ | 446.0 | 16.5 | 74 |
| Example 121 | 95 | $C_{22}H_{23}ClF_3N_3O_2$ | 454.0 | 16.3 | 72 |
| Example 122 | 96 | $C_{22}H_{26}ClN_3O_2$ | 400.5 | 16.7 | 84 |
| Example 123 | 97 | $C_{21}H_{26}Cl_2N_3O_2$ | 420.0 | 11.2 | 53 |
| Example 124 | 98 | $C_{22}H_{26}ClN_3O_2$ | 416.5 | 11.8 | 57 |
| Example 125 | 99 | $C_{21}H_{22}Cl_3N_3O_2$ | 454.0 | 14.8 | 65 |
| Example 126 | 100 | $C_{22}H_{23}ClN_4O_2$ | 411.0 | 9.5 | 46 |
| Example 127 | 101 | $C_{22}H_{24}ClN_3O_4$ | 430.5 | 13.2 | 61 |
| Example 128 | 102 | $C_{22}H_{23}ClF_4N_3O_2$ | 472.0 | 13.1 | 56 |
| Example 129 | 103 | $C_{22}H_{22}ClF_4N_3O_2$ | 472.0 | 36.5 | quant |
| Example 130 | 104 | $C_{22}H_{22}ClF_4N_3O_2$ | 472.0 | 22.8 | 97 |
| Example 131 | 105 | $C_{22}H_{22}ClF_4N_3O_2$ | 472.0 | 20.1 | 85 |
| Example 132 | 106 | $C_{22}H_{23}ClF_3N_3O_3$ | 470.0 | 27.4 | quant |
| Example 133 | 107 | $C_{22}H_{22}ClF_4N_3O_2$ | 472.0 | 18.5 | 78 |
| Example 134 | 108 | $C_{21}H_{23}ClN_4O_4$ | 431.0 | 11.9 | 55 |
| Example 135 | 109 | $C_{21}H_{23}ClN_4O_4$ | 431.0 | 23.9 | quant |
| Example 136 | 110 | $C_{21}H_{23}ClN_4O_4$ | 431.0 | 24.4 | quant |
| Example 137 | 111 | $C_{23}H_{22}ClF_6N_3O_2$ | 522.0 | 9.5 | 36 |
| Example 138 | 112 | $C_{22}H_{23}ClF_3N_3O_2$ | 454.0 | 3.9 | 17 |
| Example 139 | 113 | $C_{21}H_{23}BrClN_3O_2$ | 466.0 | 7.5 | 32 |
| Example 140 | 114 | $C_{21}H_{23}ClFN_3O_2$ | 404.0 | 6.1 | 30 |
| Example 141 | 115 | $C_{21}H_{22}Cl_3N_3O_2$ | 456.0 | 6.6 | 29 |
| Example 142 | 116 | $C_{22}H_{26}ClN_3O_2$ | 416.0 | 4.8 | 23 |
| Example 143 | 117 | $C_{23}H_{28}ClN_3O_4$ | 446.0 | 6.4 | 29 |
| Example 144 | 118 | $C_{23}H_{28}ClN_3O_4$ | 446.0 | 24.6 | quant |
| Example 145 | 119 | $C_{22}H_{23}ClF_3N_3O_2$ | 454.0 | 5.2 | 23 |
| Example 146 | 120 | $C_{22}H_{26}ClN_3O_2$ | 400.5 | 4.4 | 22 |
| Example 147 | 121 | $C_{21}H_{23}Cl_2N_3O_2$ | 420.0 | 7.8 | 37 |
| Example 148 | 122 | $C_{22}H_{26}ClN_3O_2$ | 416.5 | 14.1 | 68 |
| Example 149 | 123 | $C_{21}H_{23}Cl_3N_3O_2$ | 454.0 | 5.4 | 24 |
| Example 150 | 124 | $C_{22}H_{23}ClN_4O_2$ | 411.0 | 34.0 | quant |
| Example 151 | 125 | $C_{22}H_{24}ClN_3O_4$ | 430.5 | 32.0 | quant |
| Example 152 | 126 | $C_{22}H_{22}ClF_4N_3O_2$ | 472.0 | 4.6 | 19 |
| Example 153 | 127 | $C_{22}H_{22}ClF_4O_3O_2$ | 472.0 | 10.4 | 44 |
| Example 154 | 128 | $C_{22}H_{22}ClF_4O_3O_2$ | 472.0 | 7.3 | 31 |
| Example 155 | 129 | $C_{22}H_{22}ClF_4N_3O_2$ | 472.0 | 13.5 | 57 |
| Example 156 | 130 | $C_{22}H_{23}ClF_3N_3O_3$ | 470.0 | 15.1 | 64 |
| Example 157 | 131 | $C_{22}H_{22}ClF_4N_3O_2$ | 472.0 | 8.6 | 36 |
| Example 158 | 132 | $C_{21}H_{23}ClN_4O_4$ | 431.0 | 4.4 | 20 |
| Example 159 | 133 | $C_{21}H_{23}ClN_4O_4$ | 431.0 | 32.0 | quant |
| Example 160 | 134 | $C_{21}H_{23}ClN_4O_4$ | 431.0 | 6.9 | 32 |
| Example 161 | 135 | $C_{21}H_{23}BrClN_3O_2$ | 466.0 | 7.8 | 34 |
| Example 162 | 136 | $C_{21}H_{23}ClFN_3O_2$ | 404.0 | 13.7 | 68 |
| Example 163 | 137 | $C_{21}H_{23}Cl_2N_3O_2$ | 420.5 | 14.6 | 69 |
| Example 164 | 138 | $C_{21}H_{22}Cl_3N_3O_2$ | 454.0 | 17.7 | 78 |
| Example 165 | 139 | $C_{21}H_{22}BrCl_4N_3O_2$ | 454.0 | 17.2 | 76 |
| Example 166 | 140 | $C_{22}H_{26}ClN_3O_2$ | 400.0 | 15.0 | 75 |
| Example 167 | 141 | $C_{23}H_{28}ClN_3O_4$ | 443.5 | 13.9 | 62 |
| Example 168 | 142 | $C_{21}H_{23}Cl_2N_3O_2$ | 420.0 | 13.7 | 65 |
| Example 169 | 143 | $C_{21}H_{23}BrClN_3O_2$ | 464.0 | 16.1 | 69 |
| Example 170 | 144 | $C_{27}H_{29}ClN_3O_2$ | 462.0 | 17.6 | 76 |
| Example 171 | 145 | $C_{22}H_{23}ClF_3N_3O_2$ | 454.0 | 16.0 | 71 |
| Example 172 | 146 | $C_{22}H_{26}ClN_3O_2$ | 400.0 | 14.9 | 75 |
| Example 173 | 147 | $C_{23}H_{28}ClN_3O_2$ | 414.0 | 16.2 | 78 |
| Example 174 | 148 | $C_{22}H_{28}ClN_4O_2$ | 411.0 | 14.9 | 73 |
| Example 175 | 149 | $C_{25}H_{24}ClN_3O_2$ | 436.0 | 17.1 | 78 |
| Example 176 | 150 | $C_{25}H_{26}ClN_3O_2$ | 436.0 | 13.1 | 60 |
| Example 177 | 151 | $C_{21}H_{22}ClF_2N_3O_2$ | 422.0 | 14.8 | 70 |
| Example 178 | 152 | $C_{21}H_{22}ClF_2N_3O_2$ | 422.0 | 15.3 | 73 |
| Example 179 | 153 | $C_{21}H_{22}ClF_2N_3O_2$ | 422.0 | 15.3 | 73 |
| Example 180 | 154 | $C_{21}H_{22}ClF_2N_3O_2$ | 422.0 | 16.4 | 78 |
| Example 181 | 155 | $C_{23}H_{28}ClN_3O_4$ | 443.0 | 16.9 | 76 |
| Example 182 | 156 | $C_{22}H_{23}ClF_3N_3O_2$ | 470.5 | 12.6 | 54 |
| Example 183 | 157 | $C_{22}H_{23}ClF_3N_3O_2$ | 470.0 | 20.0 | 85 |
| Example 184 | 158 | $C_{23}H_{26}ClN_3O_4$ | 444.0 | 17.4 | 78 |
| Example 185 | 159 | $C_{22}H_{22}ClF_4N_3O_2$ | 472.0 | 18.4 | 78 |
| Example 186 | 160 | $C_{22}H_{22}ClF_4N_5O_2$ | 472.0 | 19.6 | 83 |
| Example 187 | 161 | $C_{21}H_{23}ClF_3N_3O_2$ | 440.0 | 17.0 | 77 |
| Example 188 | 162 | $C_{21}H_{23}ClF_3N_3O_2$ | 440.0 | 17.1 | 78 |
| Example 189 | 163 | $C_{23}H_{22}ClF_6N_3O_2$ | 522.0 | 20.8 | 80 |
| Example 190 | 164 | $C_{23}H_{22}ClF_6N_3O_2$ | 522.0 | 2.7 | 10 |
| Example 191 | 165 | $C_{23}H_{25}ClN_3O_2$ | 414.0 | 16.4 | 79 |
| Example 192 | 166 | $C_{22}H_{23}ClF_3N_3O_2$ | 454.0 | 8.6 | 38 |
| Example 193 | 167 | $C_{21}H_{23}BrClN_3O_2$ | 464.0 | 11.6 | 50 |
| Example 194 | 168 | $C_{21}H_{23}Cl_2N_3O_2$ | 420.0 | 11.5 | 55 |
| Example 195 | 169 | $C_{21}H_{22}Cl_3N_3O_2$ | 454.0 | 10.0 | 44 |
| Example 196 | 170 | $C_{22}H_{22}ClF_4N_3O_2$ | 472.0 | 10.4 | 44 |
| Example 197 | 171 | $C_{21}H_{23}Cl_2N_3O_2$ | 420.0 | 8.9 | 42 |
| Example 198 | 172 | $C_{21}H_{24}ClN_3O_2$ | 386.0 | 10.3 | 53 |
| Example 199 | 173 | $C_{21}H_{23}ClN_4O_4$ | 431.0 | 14.6 | 68 |
| Example 200 | 174 | $C_{22}H_{23}ClF_3N_3O_2$ | 454.0 | 10.4 | 46 |
| Example 201 | 175 | $C_{21}H_{23}BrClN_3O_2$ | 464.0 | 13.4 | 58 |
| Example 202 | 176 | $C_{21}H_{23}Cl_2N_3O_2$ | 420.0 | 12.7 | 60 |
| Example 203 | 177 | $C_{21}H_{22}Cl_3N_3O_2$ | 454.0 | 13.2 | 58 |
| Example 204 | 178 | $C_{22}H_{22}ClF_4N_3O_2$ | 472.0 | 12.9 | 55 |
| Example 205 | 179 | $C_{21}H_{23}Cl_2N_3O_2$ | 420.0 | 13.3 | 63 |
| Example 206 | 180 | $C_{21}H_{24}ClN_3O_2$ | 386.0 | 24.2 | quant |
| Example 207 | 181 | $C_{21}H_{23}ClN_4O_4$ | 431.0 | 1.0 | 1 |
| Example 208 | 182 | $C_{23}H_{25}ClF_3N_3O_2$ | 468.0 | 15.1 | 65 |
| Example 209 | 183 | $C_{22}H_{25}BrClN_3O_2$ | 478.0 | 18.0 | 75 |
| Example 210 | 184 | $C_{22}H_{25}Cl_2N_3O_2$ | 434.0 | 16.3 | 75 |
| Example 211 | 185 | $C_{22}H_{24}Cl_3N_3O_2$ | 468.0 | 18.6 | 79 |
| Example 212 | 186 | $C_{23}H_{24}ClF_4N_3O_2$ | 486.0 | 16.5 | 68 |
| Example 213 | 187 | $C_{22}H_{25}Cl_2N_3O_2$ | 434.0 | 14.4 | 66 |
| Example 214 | 188 | $C_{22}H_{26}ClN_3O_3$ | 400.0 | 14.0 | 70 |
| Example 215 | 189 | $C_{22}H_{25}ClN_4O_4$ | 445.0 | 16.8 | 76 |
| Example 216 | 190 | $C_{26}H_{25}ClF_3N_3O_2S$ | 536.0 | 17.7 | 66 |
| Example 217 | 191 | $C_{25}H_{25}BrClN_3O_2S$ | 546.0 | 20.4 | 75 |
| Example 218 | 192 | $C_{25}H_{25}Cl_2N_3O_2S$ | 502.0 | 16.9 | 67 |
| Example 219 | 193 | $C_{25}H_{24}Cl_3N_3O_2S$ | 536.0 | 18.3 | 68 |
| Example 220 | 194 | $C_{26}H_{24}ClF_4N_3O_2S$ | 554.0 | 19.4 | 70 |
| Example 221 | 195 | $C_{25}H_{25}Cl_2N_3O_2S$ | 502.0 | 19.1 | 76 |
| Example 222 | 196 | $C_{25}H_{26}ClN_3O_2S$ | 468.0 | 16.0 | 68 |
| Example 223 | 197 | $C_{25}H_{25}ClN_4O_4S$ | 513.0 | 18.4 | 72 |
| Example 224 | 198 | $C_{26}H_{25}ClF_3N_3O_2S$ | 536.0 | 13.9 | 52 |
| Example 225 | 199 | $C_{25}H_{25}BrClN_3O_2S$ | 546.0 | 12.9 | 47 |
| Example 226 | 200 | $C_{25}H_{25}Cl_2N_3O_2S$ | 502.0 | 15.6 | 62 |
| Example 227 | 201 | $C_{25}H_{24}Cl_3N_3O_2S$ | 536.0 | 17.3 | 64 |
| Example 228 | 202 | $C_{26}H_{24}ClF_4N_3O_2S$ | 554.0 | 15.4 | 56 |
| Example 229 | 203 | $C_{25}H_{25}Cl_2N_3O_2S$ | 502.0 | 13.5 | 54 |
| Example 230 | 204 | $C_{25}H_{26}ClN_3O_2S$ | 468.0 | 13.7 | 59 |
| Example 231 | 205 | $C_{25}H_{25}ClN_4O_4S$ | 513.0 | 13.9 | 54 |
| Example 232 | 206 | $C_{24}H_{27}ClF_3N_3O_4S$ | 546.0 | 10.0 | 37 |
| Example 233 | 207 | $C_{23}H_{27}BrClN_3O_4S$ | 558.0 | 17.1 | 61 |
| Example 234 | 208 | $C_{23}H_{27}Cl_2N_3O_4S$ | 512.0 | 17.0 | 66 |
| Example 235 | 209 | $C_{23}H_{26}Cl_3N_3O_4S$ | 546.0 | 7.3 | 27 |
| Example 236 | 210 | $C_{24}H_{26}ClF_4N_3O_4S$ | 564.0 | 19.2 | 68 |
| Example 237 | 211 | $C_{23}H_{27}Cl_2N_3O_4S$ | 512.0 | 7.9 | 31 |
| Example 238 | 212 | $C_{23}H_{28}ClN_3O_4S$ | 478.0 | 13.7 | 57 |
| Example 239 | 213 | $C_{23}H_{27}ClN_4O_4S$ | 523.0 | 5.5 | 21 |

Example 240

Preparation of (R)-3-[N-{3-Fluoro-5-(trifluoromethyl)benzoyl}glycyl]amino-1-(3,5-dimethylisoxazol-4-ylmethyl)pyrrolidine (Compound No. 1191)

A solution of3-fluoro-5-(trifluoromethyl)benzoyl chloride (0.058 mmol) in dichloromethane (1 mL) was added to a mixture of (R)-1-(3,5-dimethylisoxazol-4-ylmethyl)-3-(glycylamino)pyrrolidine (0.050 mmol) and piperidinomethylpolystyrene (58 mg) in chloroform (0.2 mL) and dichloromethane (0.75 mL). After the reaction mixture was stirred at room temperature for 2 h, methanol (1.0 mL) was added and the mixture was stirred at room temperature for 30 min. The reaction mixture was loaded onto Varian™ SCX column, and washed with $CH_3OH$ (16 mL). Product was eluted off using 2 N $NH_3$ in $CH_3OH$ (6 mL) and concentrated to afford (R)-3-[N-{3-fluoro-5-(trifluoromethyl)benzoyl}glycyl]amino-1-(3,5-dimethylisoxazol-4-ylmethyl)pyrrolidine (Compound No. 1191) (19.5 mg, 88%): The purity was determined by RPLC/MS (100%); ESI/MS m/e 443.2 ($M^+$+H, $C_{20}H_{22}F_4N_4O_3$).

Examples 241–265

The compounds of this invention were synthesized pursuant to methods of Example 240 using the corresponding reactant respectively. The ESI/MS data and yields are summarized in Table 4.

TABLE 4

| | Compound No. | Molecular Formula | ESI/MS m/e | Yield (mg) | Yield (%) |
|---|---|---|---|---|---|
| Example 241 | 1192 | C20 H22 F4 N4 O3 | 443.2 | 19.2 | 87 |
| Example 242 | 1193 | C20 H23 F3 N4 O4 | 441.0 | 17.5 | 79 |
| Example 243 | 1194 | C21 H22 F6 N4 O3 | 493.0 | 20.4 | 83 |
| Example 244 | 1195 | C19 H23 Br N4 O3 | 435.1 | 16.8 | 77 |
| Example 245 | 1196 | C19 H23 N5 O5 | 402.2 | 16.2 | 81 |
| Example 246 | 1197 | C20 H22 F4 N4 O3 | 443.2 | 17.6 | 80 |
| Example 247 | 1198 | C19 H23 Cl N4 O3 | 391.0 | 16.5 | 84 |
| Example 248 | 1199 | C20 H26 N4 O3 | 371.0 | 16.1 | 87 |
| Example 249 | 1200 | C19 H22 Cl2 N4 O3 | 425.0 | 18.0 | 85 |
| Example 250 | 1201 | C19 H22 F2 N4 O3 | 393.0 | 16.6 | 85 |
| Example 251 | 1202 | C20 H22 F4 N4 O3 | 443.2 | 16.8 | 76 |
| Example 252 | 1203 | C22 H24 F3 N3 O3 | 436.2 | 17.1 | 79 |
| Example 253 | 1204 | C23 H23 F6 N3 O2 | 488.2 | 18.1 | 74 |
| Example 254 | 1205 | C21 H24 Br N3 O2 | 430.0 | 17.5 | 81 |
| Example 255 | 1206 | C21 H24 N4 O4 | 397.0 | 16.2 | 82 |
| Example 256 | 1207 | C22 H23 F4 N3 O2 | 438.2 | 17.5 | 80 |
| Example 257 | 1208 | C21 H24 Cl N3 O2 | 386.0 | 15.8 | 82 |
| Example 258 | 1209 | C22 H27 N3 O2 | 366.0 | 15.7 | 86 |
| Example 259 | 1210 | C21 H23 Cl2 N3 O2 | 420.0 | 17.8 | 85 |
| Example 260 | 1211 | C21 H23 F2 N3 O2 | 388.0 | 16.3 | 84 |
| Example 261 | 1212 | C22 H23 F4 N3 O2 | 438.2 | 17.4 | 80 |
| Example 262 | 1213 | C24 H24 Cl F6 N3 O2 | 536.2 | 24.0 | 90 |
| Example 263 | 1214 | C23 H24 Cl F4 N3 O3 | 486.2 | 22.2 | 91 |
| Example 264 | 1215 | C22 H24 Cl3 N3 O2 | 467.9 | 20.9 | 89 |
| Example 265 | 1216 | C22 H24 Cl F2 N3 O2 | 436.0 | 19.3 | 89 |

Example 266

Preparation of (R)-1-(4-Chlorobenzyl)-3-[{N-{4-(dimethylamino)benzoyl)glycyl}amino]pyrrolidine (Compound No. 952)

A solution of (R)-1-(4-chlorobenzyl)-3-(glycylamino) pyrrolidine (13.8 mg, 0.052 mmol) in $CHCl_3$ (2 mL) was treated with $Et_3N$ (0.021 mL, 0.15 mmol), 4-(dimethylamino)benzoic acid (10 mg, 0.061 mmol), EDCI (10.2 mg, 0.053 mmol) and HOBt (7.5 mg, 0.055 mmol). The reaction mixture was stirred at room temperature for 16 h. The solution was washed with 2 N aqueous NaOH solution (2 mL×2) and brine (2 mL), and dried by filtration through a PTFE membrane using $CH_2Cl_2$ (3 mL). Concentration afforded the desired material (compound No. 952) (24.9 mg, quant): The purity was determined by RPLC/MS (91%); ESI/MS m/e 415.0 ($M_+$+H, $C_{22}H_{27}ClN_4O_2$).

Examples 267–347

The compounds of this invention were synthesized pursuant to methods of Example 266 using the corresponding reactant respectively. Solid-phase extraction (Varian™ SCX column) or chromatography (HPLC-$C_{18}$), if needed, afforded the desired material. The ESI/MS data and yields are summarized in Table 5.

TABLE 5

| | Compound No. | Molecular Formula | ESI/MS m/e | Yield (mg) | Yield (%) |
|---|---|---|---|---|---|
| Example 267 | 951 | C22 H24 Cl N3 O4 | 430.0 | 26.3 | quant |
| Example 268 | 953 | C23 H29 Cl N402 | 429.0 | 28.8 | quant |
| Example 269 | 954 | C21 H25 Cl N4 O2 | 401.0 | 27.9 | quant |
| Example 270 | 955 | C22 H27 Cl N4 O2 | 415.0 | 26.8 | quant |
| Example 271 | 956 | C21 H24 Cl N3 O3 | 402.0 | 10.3 | 51 |
| Example 272 | 957 | C20 H22 Cl N3 O3 | 388.0 | 1.4 | 7 |
| Example 273 | 958 | C21 H24 Cl N3 O3 | 402.5 | 1.2 | 6 |
| Example 274 | 959 | C22 H25 Cl N4 O3 | 429.5 | 4.7 | 22 |
| Example 275 | 960 | C23 H27 Cl N4 O3 | 443.0 | 10.9 | 49 |
| Example 276 | 961 | C21 H25 Cl N4 O2 | 401.0 | 28.4 | quant |
| Example 277 | 962 | C22 H27 Cl N4 O2 | 415.0 | 24.9 | quant |
| Example 278 | 963 | C21 H24 Cl N3 O3 | 402.0 | 4.4 | 22 |
| Example 279 | 964 | C22 H24 Cl N3 O4 | 430.0 | 29.5 | quant |
| Example 280 | 965 | C23 H26 Cl N3 O4 | 444.0 | 27.2 | quant |
| Example 281 | 966 | C22 H24 Cl N3 O3 | 414.0 | 27.0 | quant |
| Example 282 | 967 | C23 H26 Cl N3 O3 | 428.0 | 27.0 | quant |
| Example 283 | 968 | C22 H23 Cl N4 O2 | 411.0 | 21.4 | quant |
| Example 284 | 969 | C23 H25 Cl N4 O2 | 425.0 | 27.6 | quant |
| Example 285 | 970 | C22 H27 Cl N4 O2 | 415.0 | 28.6 | quant |
| Example 286 | 971 | C23 H29 Cl N4 O2 | 429.0 | 27.9 | quant |
| Example 287 | 972 | C20 H23 Cl N4 O2 | 387.0 | 26.2 | quant |
| Example 288 | 973 | C21 H25 Cl N4 O2 | 401.0 | 26.8 | quant |
| Example 289 | 974 | C20 H23 Cl N4 O2 | 387.0 | 26.6 | quant |
| Example 290 | 975 | C21 H25 Cl N4 O2 | 401.0 | 28.2 | quant |
| Example 291 | 976 | C22 H23 Cl N4 O2 | 411.0 | 29.2 | quant |
| Example 292 | 977 | C23 H25 Cl N4 O2 | 425.0 | 29.5 | quant |
| Example 293 | 978 | C20 H21 Cl N6 O2 | 413.0 | 2.2 | 11 |
| Example 294 | 979 | C21 H23 Cl N6 O2 | 427.0 | 10.2 | 48 |
| Example 295 | 980 | C22 H25 Cl N4 O3 | 429.0 | 28.8 | quant |
| Example 296 | 981 | C23 H27 Cl N4 O3 | 443.0 | 11.9 | 54 |
| Example 297 | 982 | C22 H27 Cl N4 O2 | 415.0 | 27.4 | quant |
| Example 298 | 983 | C23 H29 Cl N4 O2 | 429.5 | 28.1 | quant |
| Example 299 | 984 | C21 H24 Cl N3 O3 | 402.0 | 27.7 | quant |
| Example 300 | 985 | C22 H26 Cl N3 O3 | 416.0 | 28.6 | quant |
| Example 301 | 1149 | C21 H28 N4 O4 | 401 | 15.5* | 38 |
| Example 302 | 1150 | C21 H28 N4 O3 | 385 | 10.9* | 28 |
| Example 303 | 1151 | C21 H25 F3 N4 O3 | 439 | 17.3* | 39 |
| Example 304 | 1152 | C21 H24 F N5 O3 | 415 | 12.7* | 30 |
| Example 305 | 1153 | C21 H24 Cl N5 O3 | 430 | 17.5* | 41 |
| Example 306 | 1154 | C22 H27 N5 O3 | 410 | 20.6* | 50 |
| Example 307 | 1155 | C19 H23 F3 N4 O4 | 429 | 13.8* | 32 |
| Example 308 | 1156 | C21 H30 N4 O4 | 403 | 17.7* | 43 |
| Example 309 | 1157 | C18 H24 N4 O3 S2 | 409 | 12.6* | 30 |
| Example 310 | 1158 | C19 H23 Cl2 N5 O3 | 440 | 16.9* | 38 |
| Example 311 | 1159 | C22 H31 N5 O6 | 462 | 38.6* | 85 |
| Example 312 | 1160 | C20 H26 Br N5 O3 | 464 | 20.4 | 45 |
| Example 313 | 1289 | C20 H27 N5 O4 | 403 | 5.8* | 14 |
| Example 314 | 1290 | C21 H29 N5 O3 | 400 | 6.9* | 17 |
| Example 315 | 1291 | C24 H28 N4 O2 | 405 | 22.4 | 68 |
| Example 316 | 1292 | C22 H27 Br N4 O2 | 461 | 23.8 | 15 |
| Example 317 | 1293 | C22 H23 F4 N3 O2 | 438 | 20.9 | 59 |
| Example 318 | 1294 | C22 H23 F4 N3 O2 | 438 | 20.8 | 59 |
| Example 319 | 1295 | C23 H31 N3 O3 | 398 | 17.5 | 54 |
| Example 320 | 1296 | C20 H25 N3 O2 S2 | 404 | 18.8 | 58 |
| Example 321 | 1297 | C21 H24 F3 N3 O3 | 424 | 18.1 | 53 |
| Example 322 | 1388 | C21 H32 N6 O3 | 417 | 7.4* | 24 |
| Example 323 | 1389 | C19 H22 N6 O4 | 399 | 15.2 | 48 |
| Example 324 | 1401 | C23 H25 Cl N4 O2 | 425 | 8.3* | 16 |
| Example 325 | 1402 | C24 H32 N4 O5 | 457 | 8.3* | 15 |
| Example 326 | 1403 | C20 H24 N4 O2 | 353 | 14.8 | 52 |
| Example 327 | 1404 | C20 H24 N4 O2 | 353 | 17.0 | 60 |
| Example 328 | 1405 | C21 H26 N4 O2 S | 399 | 17.3 | 54 |
| Example 329 | 1407 | C22 H28 N4 O2 S | 413 | 19.1 | 57 |
| Example 330 | 1410 | C19 H24 N4 O3 | 357 | 9.7* | 59 |
| Example 331 | 1769 | C22 H26 Cl F3 N4 O5 | 519 | 11.6* | 20 |
| Example 332 | 1770 | C26 H28 Cl2 N6 O4 | 559 | 13.1* | 21 |
| Example 333 | 1771 | C26 H37 N5 O4 | 484 | 12.7* | 23 |
| Example 334 | 1772 | C28 H39 N5 O4 | 510 | 5.5* | 9 |
| Example 335 | 1773 | C28 H37 N5 O4 | 509 | 6.2* | 11 |
| Example 336 | 1774 | C28 H34 N6 06 | 551 | 13.6* | 22 |
| Example 337 | 2039 | C19 H24 N4 O2 | 341 | 5.2* | 14 |
| Example 338 | 2040 | C22 H27 N3 O4 | 398 | 2.0* | 5 |
| Example 339 | 2041 | C23 H29 N3 O3 | 396 | 6.2* | 15 |
| Example 340 | 2042 | C25 H37 N3 O2 | 413 | 2.6* | 6 |
| Example 341 | 2043 | C24 H31 N3 O2 | 394 | 6.8* | 17 |

TABLE 5-continued

| | Compound No. | Molecular Formula | ESI/MS m/e | Yield (mg) | Yield (%) |
|---|---|---|---|---|---|
| Example 342 | 2044 | C25 H28 N4 O4 | 449 | 8.7* | 16 |
| Example 343 | 2045 | C26 H29 Cl N6 O4 | 525 | 11.4* | 19 |
| Example 344 | 2046 | C27 H32 N6 O4 | 505 | 7.7* | 13 |
| Example 345 | 2047 | C28 H32 N4 O4 | 489 | 10.0* | 18 |
| Example 346 | 2048 | C28 H37 N5 05 | 524 | 3.7* | 6 |
| Example 347 | 2049 | C28 H37 N5 O4 | 509 | 5.3* | 9 |

*Yield of TFA salt.

Example 348

Preparation of (R)-1-(4-Chlorobenzyl)-3-[{N-(2-amino-5-chlorobenzoyl)glycyl}amino]pyrrolidine (Compound No. 1084)

A solution of (R)-1-(4-chlorobenzyl)-3-(glycylamino) pyrrolidine (0.050 mmol) in $CHCl_3$ (2 mL) was treated with 2-amino-5-chlorobenzoic acid (0.060 mmol) and diisopropylcarbodiimide (0.060 mmol). The reaction mixture was stirred at room temperature for 15 h. The mixture was loaded onto Varian™ SCX column, and washed with $CH_3OH$ (15 mL). Product was eluted off using 2 N $NH_3$ in $CH_3OH$ (5 mL) and concentrated to afford (R)-1-(4-chlorobenzyl)-3-{N-(2-amino-5-chlorobenzoyl)glycyl}amino]pyrrolidine (Compound No. 1084) (12.7 mg, 60%): The purity was determined by RPLC/MS (87%); ESI/MS m/e 421.0 ($M^++H$, $C_{20}H_{22}Cl_2N_4O_2$).

Examples 349–361

The compounds of this invention were synthesized pursuant to methods of Example 348 using the corresponding reactant respectively. If the starting amine remained, treatment with isocyanatomethylated polystyrene (50 mg) in $CHCl_3$ (1 mL) at room temperature, filtration and concentration afforded the desired material. The ESI/MS data and yields are summarized in Table 6.

TABLE 6

| | Compound No. | Molecular Formula | ESI/MS m/e | Yield (mg) | Yield (%) |
|---|---|---|---|---|---|
| Example 349 | 1085 | $C_{20}H_{22}ClN_5O_4$ | 432.0 | 4.1 | 19 |
| Example 350 | 1086 | $C_{20}H_{23}ClN_4O_2$ | 387.0 | 7.9 | 41 |
| Example 351 | 1087 | $C_{22}H_{23}ClN_4O_2$ | 411.0 | 15.0 | 73 |
| Example 352 | 1088 | $C_{18}H_{20}ClN_3O_3$ | 362.0 | 12.9 | 71 |

TABLE 6-continued

| | Compound No. | Molecular Formula | ESI/MS m/e | Yield (mg) | Yield (%) |
|---|---|---|---|---|---|
| Example 353 | 1089 | $C_{22}H_{22}ClFN_4O_2$ | 429.0 | 16.0 | 75 |
| Example 354 | 1090 | $C_{22}H_{26}ClN_3O_3$ | 416.0 | 15.8 | 76 |
| Example 355 | 1091 | $C_{21}H_{24}Cl_2N_4O_2$ | 435.0 | 10.9 | 50 |
| Example 356 | 1092 | $C_{21}H_{24}ClN_5O_4$ | 446.0 | 7.9 | 35 |
| Example 357 | 1093 | $C_{21}H_{25}ClN_4O_2$ | 401.0 | 9.5 | 47 |
| Example 358 | 1094 | $C_{23}H_{25}ClN_4O_2$ | 425.0 | 15.8 | 74 |
| Example 359 | 1095 | $C_{19}H_{22}ClN_3O_3$ | 376.0 | 13.5 | 72 |
| Example 360 | 1096 | $C_{23}H_{24}ClFN_4O_2$ | 443.0 | 11.8 | 53 |
| Example 361 | 1097 | $C_{23}H_{28}ClN_3O_3$ | 430.0 | 15.1 | 70 |

Example 362

Preparation of (R)-1-(4-Chlorobenzyl)-3-[{N-(3-bromo-4-methylbenzoyl)glycyl}amino]pyrrolidine (Compound No. 1098)

A solution of (R)-1-(4-chlorobenzyl)-3-(glycylamino) pyrrolidine (0.050 mmol) in $CHCl_3$ (1.35 mL) and tert-butanol (0.15 mL) was treated with 3-bromo-4-methylbenzoic acid (0.060mmol), diisopropylcarbodiimide (0.060mmol), and HOBt (0.060 mmol). The reaction mixture was stirred at room temperature for 15 h. The mixture was loaded onto Varian™ SCX column, and washed with $CH_3OH/CHCl_3$ 1:1 (12 mL) and $CH_3OH$ (12 mL). Product was eluted off using 2 N $NH_3$ in $CH_3OH$ (5 mL) and concentrated to afford (R)-1-(4-chlorobenzyl)-3-[{N-(3-bromo-4-methylbenzoyl)glycyl}amino]pyrrolidine (Compound No. 1098) (11.6 mg, 50%): The purity was determined by RPLC/MS (94%); ESI/MS m/e 466.0 ($C_{21}H_{23}BrClN_3O_2$).

Examples 363–572

The compounds of this invention were synthesized pursuant to methods of Example 362 using the corresponding reactant respectively. Preparative TLC, if needed, afforded the desired material. The ESI/MS data and yields are summarized in Table 7.

The following 3 compounds were obtained as byproduct of Compound Nos. 1415, 1416, and 1417, respectively.

1419: 7.9 mg, 38% yield; ESI/MS m/e 419.0 ($C_{20}H_{23}ClN_4O_2S$).

1420: 7.1 mg, 36% yield; ESI/MS m/e 399.2 ($C_{21}H_{26}N_4O_2S$).

1421: 7.4 mg, 37% yield; ESI/MS m/e 404.2 ($C_{19}H_{25}$N5O3S).

TABLE 7

| | Compound No. | Molecular Formula | ESI/MS m/e | Yield (mg) | Yield (%) |
|---|---|---|---|---|---|
| Example 363 | 1099 | $C_{20}H_{20}BrClFN_3O_2$ | 470.0 | 3.1 | 13 |
| Example 364 | 1100 | $C_{20}H_{20}Cl_2FN_3O_2$ | 424.0 | 3.1 | 15 |
| Example 365 | 1101 | $C_{21}H_{23}ClIN_3O_2$ | 512.0 | 12.5 | 49 |
| Example 366 | 1102 | $C_{21}H_{23}ClN_4O_4$ | 431.2 | 7.7 | 36 |
| Example 367 | 1103 | $C_{22}H_{26}BrN_3O_2$ | 446.0 | 13.8 | 62 |
| Example 368 | 1104 | $C_{21}H_{24}BrFN_3O_2$ | 450.0 | 16.5 | 74 |
| Example 369 | 1105 | $C_{21}H_{23}ClFN_3O_2$ | 404.2 | 14.7 | 73 |
| Example 370 | 1106 | $C_{22}H_{26}IN_3O_2$ | 492.0 | 18.5 | 75 |
| Example 371 | 1107 | $C_{22}H_{26}N_4O_4$ | 411.2 | 15.2 | 74 |
| Example 372 | 1108 | $C_{20}H_{25}BrN_4O_3$ | 449.0 | 12.8 | 57 |
| Example 373 | 1109 | $C_{19}H_{22}BrFN_4O_3$ | 455.0 | 16.2 | 71 |

TABLE 7-continued

| | Compound No. | Molecular Formula | ESI/MS m/e | Yield (mg) | Yield (%) |
|---|---|---|---|---|---|
| Example 374 | 1110 | $C_{19}H_{22}ClFN_4O_3$ | 409.2 | 14.4 | 70 |
| Example 375 | 1111 | $C_{20}H_{25}ON_4O_3$ | 497.0 | 17.9 | 72 |
| Example 376 | 1112 | $C_{20}H_{26}N5O_5$ | 416.2 | 14.9 | 72 |
| Example 377 | 1113 | $C_{23}H_{27}BrClN_3O_2$ | 494.0 | 16.1 | 65 |
| Example 378 | 1114 | $C_{22}H_{24}BrClFN_3O_2$ | 498.0 | 20.2 | 81 |
| Example 379 | 1115 | $C_{22}H_{24}Cl_2FN_3O_2$ | 452.2 | 18.6 | 82 |
| Example 380 | 1116 | $C_{23}H_{27}ClIN_3O_2$ | 539.1 | 21.9 | 81 |
| Example 381 | 1117 | $C_{23}H_{27}ClN_4O_4$ | 459.2 | 18.7 | 81 |
| Example 382 | 1171 | $C_{21}H_{23}BrClN_3O_2$ | 466.0 | 4.9 | 21 |
| Example 383 | 1172 | $C_{22}H_{23}ClN_4O_3$ | 427.2 | 16.1 | 75 |
| Example 384 | 1173 | $C_{23}H_{25}ClN_4O_3$ | 441.2 | 22.8 | quant |
| Example 385 | 1174 | $C_{20}H_{22}ClFN_4O_2$ | 405.2 | 21.4 | quant |
| Example 386 | 1175 | $C_{22}H_{26}BrN_3O_2$ | 446.0 | 15.8 | 71 |
| Example 387 | 1176 | $C_{23}H_{26}N_4O_3$ | 407.2 | 17.6 | 87 |
| Example 388 | 1177 | $C_{24}H_{28}N_4O_3$ | 421.2 | 20.2 | 96 |
| Example 389 | 1178 | $C_{21}H_{25}FN_4O_2$ | 385.0 | 16.2 | 84 |
| Example 390 | 1179 | $C_{21}H_{25}N_5O_4$ | 412.2 | 2.3 | 11 |
| Example 391 | 1180 | $C_{23}H_{26}N_4O_2$ | 391.0 | 21.6 | quant |
| Example 392 | 1181 | $C_{20}H_{25}BrN_4O_3$ | 451.0 | 20.1 | 89 |
| Example 393 | 1182 | $C_{21}H_{25}N_5O_4$ | 412.2 | 13.3 | 65 |
| Example 394 | 1183 | $C_{22}H_{27}N_5O_4$ | 426.2 | 20.9 | 98 |
| Example 395 | 1184 | $C_{19}H_{24}FN_5O_3$ | 390.0 | 20.0 | quant |
| Example 396 | 1185 | $C_{19}H_{24}N_6O_5$ | 417.2 | 18.2 | 87 |
| Example 397 | 1186 | $C_{21}H_{25}N_5O_3$ | 396.2 | 17.6 | 89 |
| Example 398 | 1187 | $C_{23}H_{28}BrClN_3O_2$ | 494.0 | 22.1 | 90 |
| Example 399 | 1188 | $C_{24}H_{28}ClN_4O_3$ | 455.2 | 17.2 | 76 |
| Example 400 | 1189 | $C_{25}H_{26}ClN_4O_3$ | 469.2 | 21.1 | 90 |
| Example 401 | 1190 | $C_{22}H_{26}ClFN_4O_2$ | 433.2 | 20.4 | 94 |
| Example 402 | 1217 | $C_{21}H_{20}Cl_2F_3N_3O_2$ | 474.0 | 38.5 | 81 |
| Example 403 | 1218 | $C_{21}H_{23}Cl_2N_4O_2$ | 404.2 | 35.6 | 88 |
| Example 404 | 1219 | $C_{21}H_{23}Cl_2N_3O_2$ | 420.0 | 3.7 | 9 |
| Example 405 | 1220 | $C_{20}H_{22}ClIN_4O_2$ | 513.0 | 53.0 | quant |
| Example 406 | 1221 | $C_{20}H_{21}ClF_2N_4O_2$ | 423.0 | 38.7 | 92 |
| Example 407 | 1222 | $C_{19}H_{23}ClN_4O_2$ | 375.2 | 33.6 | 90 |
| Example 408 | 1223 | $C_{26}H_{26}ClN_3O_2S$ | 496.0 | 43.7 | 88 |
| Example 409 | 1224 | $C_{20}H_{21}ClN_4O_5$ | 433.0 | 40.6 | 94 |
| Example 410 | 1225 | $C_{32}H_{26}ClF_3N_3O_2$ | 454.2 | 18.4 | 41 |
| Example 411 | 1226 | $C_{32}H_{26}FN_3O_2$ | 384.0 | 17.1 | 45 |
| Example 412 | 1227 | $C_{22}H_{26}ClN_3O_2$ | 400.2 | 17.5 | 44 |
| Example 413 | 1228 | $C_{21}H_{25}IN_4O_2$ | 493.0 | 23.3 | 47 |
| Example 414 | 1229 | $C_{21}H_{24}F_2N_4O_2$ | 403.2 | 18.4 | 46 |
| Example 415 | 1230 | $C_{20}H_{26}N_4O_2$ | 355.2 | 15.7 | 44 |
| Example 416 | 1231 | $C_{27}H_{26}N_3O_2S$ | 476.0 | 20.9 | 88 |
| Example 417 | 1232 | $C_{21}H_{24}N_4O_5$ | 413.0 | 19.9 | 96 |
| Example 418 | 1233 | $C_{20}H_{22}ClF_3N_4O_3$ | 459.0 | 19.4 | 85 |
| Example 419 | 1234 | $C_{20}H_{25}FN_4O_3$ | 389.0 | 17.8 | 92 |
| Example 420 | 1235 | $C_{20}H_{25}ClN_4O_3$ | 405.2 | 18.7 | 92 |
| Example 421 | 1236 | $C_{19}H_{24}IN_5O_3$ | 498.0 | 23.9 | 96 |
| Example 422 | 1237 | $C_{19}H_{23}F_2N_5O_3$ | 408.2 | 19.0 | 93 |
| Example 423 | 1238 | $C_{18}H_{25}N_5O_3$ | 360.0 | 16.3 | 91 |
| Example 424 | 1239 | $C_{25}H_{28}N_4O_3S$ | 481.2 | 21.4 | 89 |
| Example 425 | 1240 | $C_{19}H_{23}N_5O_6$ | 418.0 | 19.9 | 95 |
| Example 426 | 1241 | $C_{23}H_{24}Cl_2F_3N_3O_2$ | 502.0 | 22.5 | 90 |
| Example 427 | 1242 | $C_{23}H_{27}ClFN_3O_2$ | 432.2 | 21.2 | 98 |
| Example 428 | 1243 | $C_{23}H_{27}Cl_2N_3O_2$ | 448.0 | 21.6 | 96 |
| Example 429 | 1244 | $C_{22}H_{26}ClN_4O_2$ | 541.0 | 26.4 | 98 |
| Example 430 | 1245 | $C_{22}H_{25}ClF_2N_4O_2$ | 451.0 | 21.3 | 94 |
| Example 431 | 1246 | $C_{21}H_{27}ClN_4O_3$ | 403.2 | 19.4 | 96 |
| Example 432 | 1247 | $C_{28}H_{30}ClN_3O_2S$ | 524.0 | 24.7 | 94 |
| Example 433 | 1248 | $C_{22}H_{25}ClN_4O_5$ | 461.0 | 20.7 | 90 |
| Example 434 | 1249 | C20 H20 Cl2 N4 O4 | 451.0 | 7.4 | 33 |
| Example 435 | 1250 | C21 H23 Cl N4 O4 | 431.2 | 15.5 | 72 |
| Example 436 | 1251 | C19 H22 Cl N5 O5 | 436.0 | 22.9 | quant |
| Example 437 | 1252 | C23 H28 Cl N3 O2 | 414.2 | 17.9 | 86 |
| Example 438 | 1253 | C24 H31 N3 O2 | 394.2 | 15.8 | 80 |
| Example 439 | 1254 | C22 H30 N4 O3 | 399.2 | 17.3 | 87 |
| Example 440 | 1255 | C20 H22 Br Cl N4 O2 | 467.0 | 21.3 | 91 |
| Example 441 | 1256 | C21 H25 Br N4 O2 | 445.0 | 20.7 | 93 |
| Example 442 | 1257 | C19 H24 Br N5 O3 | 450.0 | 21.8 | 97 |
| Example 443 | 1258 | C21 H25 Cl N5 O3 | 401.2 | 18.1 | 90 |
| Example 444 | 1259 | C19 H24 Cl N5 O3 | 406.0 | 20.1 | 99 |
| Example 445 | 1260 | C23 H29 N3 O3 | 396.2 | 16.8 | 85 |
| Example 446 | 1261 | C23 H30 Cl N3 O3 | 432.2 | 19.8 | 92 |
| Example 447 | 1262 | C24 H33 N3 O3 | 412.2 | 17.4 | 85 |
| Example 448 | 1263 | C22 H32 N4 O4 | 417.2 | 18.7 | 90 |
| Example 449 | 1264 | C25 H26 Cl N3 O3 | 452.2 | 29.1 | quant |

TABLE 7-continued

| | Compound No. | Molecular Formula | ESI/MS m/e | Yield (mg) | Yield (%) |
|---|---|---|---|---|---|
| Example 450 | 1265 | C26 H29 N3 O3 | 432.2 | 18.1 | 84 |
| Example 451 | 1266 | C24 H28 N4 O4 | 437.2 | 19.3 | 88 |
| Example 452 | 1267 | $C_{23}H_{22}ClF_3N_4O_3$ | 495.2 | 20.6 | 83 |
| Example 453 | 1268 | $C_{21}H_{23}Cl_2N_3O_3$ | 436.0 | 17.5 | 80 |
| Example 454 | 1269 | $C_{20}H_{21}BrClN_3O_3$ | 468.0 | 19.2 | 82 |
| Example 455 | 1270 | $C_{20}H_{21}Cl_2N_3O_3$ | 422.2 | 17.3 | 82 |
| Example 456 | 1271 | $C_{20}H_{20}ClFN_4O_4$ | 435.0 | 17.1 | 79 |
| Example 457 | 1272 | $C_{24}H_{25}F_3N_4O_3$ | 475.2 | 21.7 | 91 |
| Example 458 | 1273 | $C_{22}H_{26}ClN_3O_3$ | 416.2 | 17.8 | 86 |
| Example 459 | 1274 | $C_{21}H_{24}BrN_3O_3$ | 448.0 | 19.5 | 87 |
| Example 460 | 1275 | $C_{21}H_{24}ClN_3O_3$ | 402.2 | 16.7 | 83 |
| Example 461 | 1276 | $C_{21}H_{23}FN_4O_4$ | 415.2 | 18.1 | 87 |
| Example 462 | 1277 | $C_{22}H_{24}F_3N_5O_4$ | 480.2 | 20.3 | 85 |
| Example 463 | 1278 | $C_{20}H_{25}ClN_4O_4$ | 421.2 | 18.6 | 88 |
| Example 464 | 1279 | $C_{19}H_{23}BrN_4O_4$ | 451.0 | 21.3 | 94 |
| Example 465 | 1280 | $C_{19}H_{23}ClN_4O_4$ | 407.2 | 19.1 | 94 |
| Example 466 | 1281 | $C_{19}H_{22}FN_5O_5$ | 420.2 | 19.1 | 91 |
| Example 467 | 1282 | $C_{25}H_{26}ClF_3N_4O_3$ | 523.2 | 25.0 | 96 |
| Example 468 | 1283 | $C_{23}H_{27}Cl_2N_3O_3$ | 464.2 | 12.2 | 53 |
| Example 469 | 1284 | $C_{22}H_{25}BrClN_3O_3$ | 496.0 | 24.1 | 97 |
| Example 470 | 1285 | $C_{22}H_{25}Cl_2N_3O_3$ | 450.2 | 21.8 | 97 |
| Example 471 | 1321 | $C_{20}H_{20}BrCl_2N_3O_2$ | 486.0 | 5.1 | 21 |
| Example 472 | 1322 | $C_{21}H_{23}Cl_2N_3O_2$ | 420.0 | 10.5 | 50 |
| Example 473 | 1323 | $C_{20}H_{20}Cl_2IN_3O_2$ | 532.0 | 7.1 | 27 |
| Example 474 | 1324 | $C_{21}H_{24ClN3}O_3$ | 402.2 | 22.2 | quant |
| Example 475 | 1325 | $C_{27}H_{26}ClN_3O_3$ | 476.0 | 22.2 | 93 |
| Example 476 | 1326 | $C_{20}H_{21}ClIN_3O_3$ | 514.0 | 26.9 | quant |
| Example 477 | 1327 | $C_{21}H_{25}ClN_4O_2$ | 401.2 | 24.2 | quant |
| Example 478 | 1328 | $C_{21}H_{23}BrClN_3O_2$ | 466.0 | 23.1 | 99 |
| Example 479 | 1329 | $C_{22}H_{26}ClN_3O_2$ | 400.2 | 16.4 | 82 |
| Example 480 | 1330 | $C_{21}H_{23}ClIN_3O_2$ | 512.2 | 20.8 | 81 |
| Example 481 | 1331 | $C_{21}H_{24}N_3O_3$ | 382.2 | 19.6 | quant |
| Example 482 | 1332 | $C_{28}H_{29}N_4O_2$ | 456.2 | 21.1 | 93 |
| Example 483 | 1333 | $C_{21}H_{24}IN_3O_3$ | 494.0 | 25.3 | quant |
| Example 484 | 1334 | $C_{22}H_{28}N_4O_2$ | 381.2 | 19.0 | quant |
| Example 485 | 1335 | $C_{19}H_{22}BrClN_4O_3$ | 471.0 | 25.8 | quant |
| Example 486 | 1336 | $C_{20}H_{25}ClIN_4O_3$ | 405.2 | 18.5 | 91 |
| Example 487 | 1337 | $C_{19}H_{22}ClIN_4O_3$ | 517.0 | 23.1 | 89 |
| Example 488 | 1338 | $C_{20}H_{26}N_4O4$ | 387.2 | 20.6 | quant |
| Example 489 | 1339 | $C_{26}H_{28}N_4O_4$ | 461.2 | 23.7 | quant |
| Example 490 | 1340 | $C_{19}H_{23}IN_4O_4$ | 499.0 | 28.2 | quant |
| Example 491 | 1341 | $C_{20}H_{26}N_4O_4$ | 386.0 | 20.5 | quant |
| Example 492 | 1342 | $C_{22}H_{24}BrCl_2N_3O_2$ | 514.0 | 27.2 | quant |
| Example 493 | 1343 | $C_{23}H_{27}Cl_2N_3O_2$ | 448.0 | 21.4 | 95 |
| Example 494 | 1344 | $C_{22}H_{24}Cl_2IN_3O_2$ | 560.0 | 27.0 | 96 |
| Example 495 | 1345 | $C_{23}H_{28}ClN_3O_3$ | 430.2 | 23.8 | quant |
| Example 496 | 1346 | $C_{22}H_{25}ClIN_3O_3$ | 542.0 | 29.4 | quant |
| Example 497 | 1347 | $C_{19}H_{22}ClN_3O_2S$ | 392.0 | 16.9 | 43 |
| Example 498 | 1348 | $C_{20}H_{25}N_3O_2S$ | 372.2 | 6.9 | 19 |
| Example 499 | 1349 | $C_{18}H_{24}N_4O_3S$ | 377.2 | 8.1 | 43 |
| Example 500 | 1350 | $C_{21}H_{26}ClN_3O_2$ | 420.0 | 13.0 | 62 |
| Example 501 | 1351 | $C_{22}H_{24}BrClN_4O_3$ | 509.2 | 5.0 | 10 |
| Example 502 | 1352 | $C_{23}H_{27}BrN_4O_3$ | 489.2 | 3.6 | 15 |
| Example 503 | 1353 | $C_{21}H_{26}BrN_5O_4$ | 494.0 | 2.8 | 11 |
| Example 504 | 1354 | $C_{24}H_{28}BrClN_4O_3$ | 537.2 | 5.2 | 19 |
| Example 505 | 1355 | C21 H22 Cl N5 O2 | 412.0 | 25.5 | quant |
| Example 506 | 1356 | C22 H25 N5 O2 | 392.0 | 16.5 | 84 |
| Example 507 | 1357 | C20 H24 N6 O3 | 397.2 | 19.9 | quant |
| Example 508 | 1358 | C23 H26 Cl N5 O2 | 440.2 | 21.8 | 99 |
| Example 509 | 1368 | $C_{21}H_{20}Cl_2F_3N_3O_2$ | 474.0 | 18.4 | 78 |
| Example 510 | 1369 | $C_{24}H_{24}ClF_6IN_3O_4$ | 568.0 | 24.1 | 85 |
| Example 511 | 1370 | $C_{18}H_{19}BrClN_3O_2S$ | 458.0 | 19.4 | 85 |
| Example 512 | 1371 | $C_{26}H_{26}ClN_3O_4S$ | 512.2 | 22.1 | 86 |
| Example 513 | 1372 | $C_{26}H_{26}ClN_3O_2$ | 448.0 | 19.1 | 85 |
| Example 514 | 1373 | $C_{22}H_{23}ClF_3N_3O_2$ | 454.2 | 16.2 | 71 |
| Example 515 | 1374 | $C_{25}H_{27}F_6IN_3O_4$ | 548.2 | 22.1 | 81 |
| Example 516 | 1375 | $C_{19}H_{22}BrN_3O_2S$ | 436.0 | 17.1 | 78 |
| Example 517 | 1376 | $C_{27}H_{29}N_3O_4S$ | 492.0 | 19.4 | 79 |
| Example 518 | 1377 | $C_{27}H_{29}N_3O_2$ | 428.2 | 18.1 | 85 |
| Example 519 | 1378 | $C_{20}H_{22}ClF_3N_4O_5$ | 459.0 | 17.3 | 75 |
| Example 520 | 1379 | $C_{23}H_{26}F_6IN_4O_5$ | 553.2 | 21.0 | 76 |
| Example 521 | 1380 | $C_{17}H_{21}BrN_4O_3S$ | 443.0 | 16.4 | 74 |
| Example 522 | 1381 | $C_{25}H_{28}N_4O_5S$ | 497.0 | 18.4 | 74 |
| Example 523 | 1382 | $C_{25}H_{28}N_4O_3$ | 433.2 | 17.3 | 80 |
| Example 524 | 1383 | $C_{23}H_{24}Cl_2F_3N_3O_2$ | 502.0 | 20.0 | 80 |
| Example 525 | 1384 | $C_{20}H_{23}BrClN_3O_2S$ | 486.0 | 21.0 | 87 |

TABLE 7-continued

| | Compound No. | Molecular Formula | ESI/MS m/e | Yield (mg) | Yield (%) |
|---|---|---|---|---|---|
| Example 526 | 1385 | $C_{28}H_{30}ClN_3O_4S$ | 540.2 | 23.8 | 88 |
| Example 527 | 1386 | $C_{28}H_{30}ClN_3O_2$ | 476.0 | 20.0 | 84 |
| Example 528 | 1411 | $C_{22}H_{24}Cl_2N_4O_3$ | 463.0 | 0.4 | 2 |
| Example 529 | 1412 | $C_{23}H_{27}ClN_4O_2$ | 443.0 | 1.3 | 6 |
| Example 530 | 1413 | $C_{21}H_{26}ClN_5O_4$ | 448.0 | 1.1 | 5 |
| Example 531 | 1414 | $C_{24}H_{23}Cl_2N_4O_3$ | 491.0 | 0.8 | 3 |
| Example 532 | 1415 | $C_{21}H_{22}ClN_5O_2S$ | 444.0 | 6.8 | 31 |
| Example 533 | 1416 | $C_{22}H_{25}N_5O_2S$ | 424.0 | 4.8 | 23 |
| Example 534 | 1417 | $C_{20}H_{24}N_6O_3S$ | 429.2 | 4.5 | 21 |
| Example 535 | 1418 | $C_{23}H_{26}ClN_5O_3S$ | 472.0 | 10.4 | 44 |
| Example 536 | 1423 | C27 H26 Cl N3 O3 | 476.0 | 23.9 | quant |
| Example 537 | 1424 | C27 H29 N3 O4 S | 456.2 | 28.0 | quant |
| Example 538 | 1425 | C26 H28 N4 O4 | 461.2 | 22.3 | 97 |
| Example 539 | 1426 | C29 H30 Cl N3 O3 | 504.2 | 26.8 | quant |
| Example 540 | 1583 | C21 H22 Cl F3 N4 O2 | 455.0 | 14.6 | 64 |
| Example 541 | 1584 | C21 H22 Cl F3 N4 O3 | 471.0 | 17.4 | 74 |
| Example 542 | 1585 | C19 H20 Br Cl N4 O2 | 453.0 | 15.6 | 69 |
| Example 543 | 1586 | C19 H20 Cl2 N4 O2 | 407.2 | 2.3 | 11 |
| Example 544 | 1587 | C26 H26 Cl N3 O3 | 464.0 | 15.4 | 66 |
| Example 545 | 1588 | C20 H23 Cl N4 O2 | 387.0 | 14.8 | 77 |
| Example 546 | 1589 | C22 H25 F3 N4 O2 | 435.2 | 11.1 | 51 |
| Example 547 | 1590 | C20 H25 F3 N4 O3 | 451.2 | 16.3 | 72 |
| Example 548 | 1591 | C20 H23 Br N4 O2 | 433.0 | 15.4 | 71 |
| Example 549 | 1592 | C20 H23 Cl N4 O2 | 387.0 | 15.6 | 81 |
| Example 550 | 1593 | C27 H29 N3 O3 | 444.2 | 14.8 | 67 |
| Example 551 | 1594 | C20 H24 F3 N5 O3 | 440.2 | 16.2 | 74 |
| Example 552 | 1595 | C20 H24 F3 N5 O4 | 456.2 | 15.4 | 68 |
| Example 553 | 1596 | C18 H22 Br N5 O3 | 436.0 | 15.6 | 72 |
| Example 554 | 1597 | C18 H22 Cl N5 O3 | 391.8 | 14.4 | 73 |
| Example 555 | 1598 | C25 H28 N4 O4 | 449.2 | 15.9 | 71 |
| Example 556 | 1599 | C19 H25 N5 O3 | 372.2 | 15.8 | 85 |
| Example 557 | 1606 | C21 H21 Cl F3 N3 O2 S | 472.0 | 17.0 | 72 |
| Example 558 | 1607 | C21 H21 Cl F3 N3 O2 S | 452.2 | 15.3 | 68 |
| Example 559 | 1608 | C20 H23 F3 N4 O3 S | 457.2 | 15.9 | 70 |
| Example 560 | 1660 | C21 H22 Br F3 N4 O2 | 501.0 | 19.0 | 76 |
| Example 561 | 1661 | C21 H22 Br F3 N4 O3 | 517.0 | 16.2 | 63 |
| Example 562 | 1662 | C20 H21 Br F2 N4 O2 | 469.0 | 15.1 | 65 |
| Example 563 | 1663 | C20 H22 Br Cl N4 O2 | 467.0 | 14.5 | 62 |
| Example 564 | 1692 | C20 H23 Br2 N3 O3 | 514 | 7.3 | 28 |
| Example 565 | 1693 | C22 H26 F2 N4 O2 | 417 | 16.2 | 78 |
| Example 566 | 1694 | C22 H27 F N4 O2 | 399 | 21.8 | quant |
| Example 567 | 1695 | C22 H27 Br N4 O2 | 459 | 24.5 | quant |
| Example 568 | 1696 | C22 H27 I N4 O2 | 507 | 27.4 | quant |
| Example 569 | 1697 | C22 H27 Cl N4 O2 | 415 | 22.1 | quant |
| Example 570 | 1698 | C23 H27 F3 N4 O3 | 465 | 24.3 | quant |
| Example 571 | 1699 | C23 H27 F3 N4 O2 | 449 | 25.3 | quant |
| Example 572 | 1700 | C22 H25 Br Cl N3 O2 | 480 | 17.8 | 74 |

For example, Compound No. 1583 showed the following NMR spectra: $^1$H NMR (400 MHZ, $CD_3OD$) δ1.64–1.72 (m, 1 H), 2.20–2.30 (m, 1 H), 2.41–2.51 (m, 2 H), 2.71–2.78 (m, 2 H), 3.59 (dd, J=15.4, 12.9 Hz, 2 H), 3.94 (s, 2 H), 4.35–4.41 (m, 1 H), 6.82 (d, J=8.6 Hz, 1 H), 7.29 (s, 4 H), 7.40 (dd, J=8.6, 1.7 Hz, 1 H), 7.85 (d, J=0.96 HZ, 1 H).

Reference Example 4

Preparation of (S)-3-[N-{3-(trifluoromethyl) benzoyl}glycyl]aminopyrrolidine

A suspension of (S)-1-(4-chlorobenzyl)-3-[N-{3-(trifluoromethyl)benzoyl}glycyl]aminopyrrolidine (2.93 g, 6.66 mmol) and $Pd(OH)_2$ in 5% $HCO_2H$/methanol (70 mL) was stirred at 60° C. for 3 h. The Pd catalyst was filtered off through Celite, and the filtrate was concentrated. To the residue was added 2N aqueous NaOH solution (100 mL) and the mixture was extracted with ethyl acetate (100 mL×3). The combined extracts were washed with brine, dried over anhydrous sodium sulfate, filtered, and concentrated. Column chromatography ($SiO_2$, AcOEt/MeOH/$Et_3N$=85/10/5–60/30/5) gave (S)-3-[N-{3-(trifluoromethyl) benzoyl}glycyl]aminopyrrolidine (1.70 g, 81%) as an oil: $^1$H NMR ($CDCl_3$, 270 MHz) δ1.76 (d, J=7.3 Hz, 1 H), 2.07–2.25 (m, 1 H), 2.81–2.98 (m, 2 H), 3.02–3.11 (m, 2 H), 4.12 (s, 2 H), 4.41 (br, 1 H), 6.90 (br, 1 H), 7.45 (br, 1 H), 7.58 (dd, J=7.3 and 7.3 Hz, 1 H), 7.77 (d, J=7.3 Hz, 1 H), 8.02 (d, J=7.3 Hz, 1 H), 8.11 (s, 1H); ESI/MS n/e 316.0 ($M^+$+H, $C_{14}H_{16}F_3N_3O_2$).

(R)-3-[N-{3-(Trifluoromethyl)benzoyl}glycyl] aminopyrrolidine was also prepared pursuant to the above method using the corresponding reactant: 1.49 g, 68%; The product showed the same $^1$H NMR and ESI/MS with those of (S)-isomer.

(R)-3-[N-{2-Amino-5-(trifluoromethyl)benzoyl}glycyl] aminopyrrolidine was also prepared pursuant to the above method using the corresponding reactant: 316 mg, 93%; ESI/MS m/e 331.2 ($M^+$+H, $C_{14}H_{17}F_3N_4O_2$)

(R)-3-[N-{2-(tert-Butoxycarbonylamino)-5-(trifluoromethoxy)benzoyl}glycyl]aminopyrrolidine was also prepared pursuant to the above method using the corresponding reactant: quant; $^1$H NMR ($CDCl_3$, 400 MHz) δ1.51 (s, 9 H), 1.60–1.70 (m, 2 H), 2.10–2.25 (m, 1H), 2.80–2.88 (m, 1 H), 2.89–2.98 (m, 1 H), 3.04–3.18 (m, 2 H), 4.05 (d, J=4.9 Hz, 2 H), 4.43 (br, 1 H), 6.15 (br, 1 H), 7.03 (br, 1 H), 7.32 (d, J=9.3 Hz, 1 H), 7.38 (s, 1 H), 8.42 (d, J=9.3 Hz, 1 H).

Example 573

Preparation of (R)-3-[{N-(2-(tert-Butoxycarbonylamino)-5-trifluoromethylbenzoyl) glycyl}amino]-1-(4-chlorobenzyl)pyrrolidine A solution of (R)-1-(4-chlorobenzyl)-3-(glycylamino) pyrrolidine (5.0 g, 18.7 mmol) in dichloromethane (100 mL) was treated with $Et_3N$ (2.9 mL, 20.5 mmol), 2-(tert-butoxycarbonylamino)-5-(trifluoromethyl)benzoic acid (6.27 g, 20.5 mmol), EDCI (3.9 g, 20.5 mmol) and HOBt (2.8 g, 20.5 mmol). The reaction mixture was stirred at room temperature overnight. To the reaction mixture was added 2 N aqueous NaOH solution (80 mL) and the mixture was extracted with di-chloromethane. The extract was dried over anhydrous $Na_2SO_4$, filtered, and evaporated. Column chromatography ($SiO_2$, hexane/ethyl acetate=1/1–1/4) afforded (R)-3-[{N-(2-(tert-butoxycarbonylamino)-5-trifluoromethylbenzoyl}glycyl]amino)-1-(4-chlorobenzyl) pyrrolidine (9.41 g, 91%) as a white amorphous solid: ESI/MS m/e 555.2 ($M^+$+H, $C_{26}H_{30}ClF_3N_4O_4$).

Reference Example 5

Preparation of (R)-3-[{N-(2-(tert-butoxycarbonylamino)-5-trifluoromethylbenzoyl) glycyl}amino]pyrrolidine A mixture of (R)-3-[{N-(2-(tert-butoxycarbonylamino)-5-trifluoromethylbenzoyl}glycyl)amino]-1-(4-chlorobenzyl)pyrrolidine (6.3 g, 11.4 mmol), $Pd(OH)_2$ (1.68 g), $HCO_2H$ (3.7 mL), and methanol (80 mL) was stirred at 50° C. overnight. After the mixture was cooled to room temperature, the Pd catalyst was filtered off through Celite and the filtrate was concentrated. Column chromatography ($SiO_2$, AcOEt, AcOEt/MeOH=5/1–4/1) gave (R)-3-[{N-2-(tert-butoxycarbonylamino)-5-trifluoromethylbenzoyl}glycyl]aminolpyrrolidine (4.42 g, 90%) as a white solid: $^1H$ NMR ($CDCl_3$, 400 MHz) δ1.48 (s, 9 H), 2.0–2.4 (m, 2 H), 3.42–3.71 (m, 5 H), 4.00–4.22 (m, 2 H), 4.56 (br, 1 H), 7.48 (d, J=9.0 Hz, 1 H), 7.93 (s, 1 H), 8.17 (br, 1 H), 8.33 (d, J=9.0 Hz, 1 H), 8.45 (br, 1 H).

Example 574

Preparation of (S)-1-Benzyl-3-[N-{3-(trifluoromethyl)benzoyl}glycyl]aminopyrrolidine (Compound No. 239)

A solution of (S)-3-[N-{3-(trifluoromethyl) benzoyl}glycyl]aminopyrrolidine (0.060 mmol) in $CH_3CN$ (1.1 mL) and (piperidinomethyl)polystyrene (2.6–2.8 mmol/g, 30 mg) were added to a solution of benzyl bromide (0.050 mmol) in $CH_3CN$ (0.4 mL). The reaction mixture was stirred at 45° C. for 5 h. After the mixture was cooled to room temperature, the resin was removed by filtration and the filtrate was concentrated. The residue was resolved in $CH_3CN$ (1.0 mL) and phenyl isocyanate (0.008 mL, 0.05 mmol) was added. The mixture was stirred at room temperature for 1 h, loaded onto Varian™ SCX column, and washed with $CH_3OH$ (15 mL). Product was eluted off using 2 N $NH_3$ in $CH_3OH$ (6 mL) and concentrated to afford (S)-1-benzyl-3-[N-{3- (trifluoromethyl)benzoyl}glycyl] aminopyrrolidine (compound No. 239) (9.0 mg, 44%): The purity was determined by RPLC/MS (99%); ESI/MS m/e 406.0 ($M^+$+H, $C_{21}H_{22}F_3N_3O_2$).

Example 575

Preparation of (R)-1-(4-Butylbenzyl)-3-[{N-(3-trifluoromethylbenzoyl)glycyl}amino]pyrrolidine (Compound No. 1648)

To a mixture of (R)-3-[N-(3-(trifluoromethyl)benzoyl) glycyl]aminopyrrolidine (0.050 mmol), 4-butylbenzaldehyde (0.18 mmol), $NaBH_3CN$ (0.23 mmol), and methanol (1.85 mL) was added acetic acid (0.060 mL). The reaction mixture was stirred at 60° C. for 12 h. The mixture was cooled to room temperature, loaded onto Varian™ SCX column, and washed with $CH_3OH$ (15 mL) . Product was eluted off using 2 N $NH_3$ in $CH_3OH$ (5 mL) and concentrated to afford (R)-1-(4-butylbenzyl)-3-[{N-(3-trifluoromethylbenzoyl)glycyl}amino]pyrrolidine (Compound No. 1648) (20.6 mg, 89%): The purity was determined by RPLC/MS (9%); ESI/MS m/e 462.2 ($M^+$+H, $C_{25}H_{30}F_3N_3O_2$)

Examples 576–738

The compounds of this invention were synthesized pursuant to methods of Examples 574 or 575 using the corresponding reactant respectively. Preparative TLC or chromatography (HPLC-$C_{18}$), if needed, afforded the desired material. The ESI/MS data and yields are summarized in Table 8.

TABLE 8

| | Compound No. | Molecular Formula | ESI/MS m/e | Yield (mg) | Yield (%) |
|---|---|---|---|---|---|
| Example 576 | 240 | $C_{21}H_{21}F_4N_3O_2$ | 424.0 | 10.2 | 48 |
| Example 577 | 241 | $C_{21}H_{21}ClF_3N_3O_2$ | 440.0 | 12.1 | 55 |
| Example 578 | 242 | $C_{21}H_{21}Cl_2F_3N_3O_2$ | 474.0 | 13.9 | 59 |
| Example 579 | 243 | $C_{21}H_{26}Cl_2F_3N_3O_2$ | 474.0 | 13.8 | 58 |
| Example 580 | 244 | $C_{22}H_{24}F_3N_3O_2$ | 420.0 | 13.1 | 62 |
| Example 581 | 245 | $C_{21}H_{21}F_4N_3O_2$ | 424.0 | 11.9 | 56 |
| Example 582 | 246 | $C_{21}H_{21}ClF_3N_3O_2$ | 440.0 | 8.5 | 39 |
| Example 583 | 247 | $C_{21}H_{26}Cl_2F_2N_3O_2$ | 474.0 | 10.5 | 44 |
| Example 584 | 248 | $C_{22}H_{24}CF_3N_3O_2$ | 436.0 | 11.0 | 51 |
| Example 585 | 249 | $C_{22}H_{21}ClF_6N_3O_2$ | 474.0 | 12.8 | 54 |
| Example 586 | 250 | $C_{22}H_{24}F_3N_3O_2$ | 420.0 | 11.0 | 52 |
| Example 587 | 251 | $C_{21}H_{21}F_4N_3O_2$ | 424.0 | 13.5 | 64 |
| Example 588 | 252 | $C_{22}H_{24}F_3N_3O_3$ | 436.0 | 11.8 | 54 |
| Example 589 | 253 | $C_{22}H_{24}F_3N_3O_2$ | 420.0 | 11.1 | 53 |
| Example 590 | 254 | $C_{21}H_{20}ClF_3N_4O_4$ | 485.0 | 2.4 | 10 |
| Example 591 | 255 | $C_{21}H_{21}F_3N_4O_4$ | 451.0 | 12.2 | 54 |
| Example 592 | 256 | $C_{21}H_{21}F_3N_4O_4$ | 451.0 | 11.4 | 51 |
| Example 593 | 257 | $C_{22}H_{21}F_6N_3O_2$ | 474.0 | 11.1 | 47 |
| Example 594 | 258 | $C_{24}H_{26}F_3N_3O_4$ | 478.0 | 15.3 | 64 |

TABLE 8-continued

| | Compound No. | Molecular Formula | ESI/MS m/e | Yield (mg) | Yield (%) |
|---|---|---|---|---|---|
| Example 595 | 259 | $C_{22}H_{23}ClF_3N_3O_2$ | 420.0 | 6.4 | 31 |
| Example 596 | 260 | $C_{21}H_{20}Cl_2F_3N_3O_2$ | 474.0 | 12.1 | 51 |
| Example 597 | 261 | $C_{22}H_{21}ClF_6N_3O_2$ | 474.0 | 13.6 | 57 |
| Example 598 | 262 | $C_{21}H_{21}BrF_3N_3O_2$ | 484.0 | 15.2 | 63 |
| Example 599 | 263 | $C_{21}H_{21}BrF_3N_3O_2$ | 484.0 | 14.5 | 60 |
| Example 600 | 264 | $C_{27}H_{26}F_3N_3O_3$ | 498.0 | 9.3 | 37 |
| Example 601 | 265 | $C_{21}H_{21}BrF_3N_3O_2$ | 484.0 | 11.6 | 48 |
| Example 602 | 266 | $C_{22}H_{22}F_3N_3O_4$ | 450.0 | 8.9 | 40 |
| Example 603 | 267 | $C_{22}H_{24}F_3N_3O_3$ | 436.0 | 10.3 | 47 |
| Example 604 | 268 | $C_{23}H_{25}F_3N_4O_3$ | 463.0 | 6.3 | 27 |
| Example 605 | 269 | $C_{22}H_{24}F_3N_3O_4S$ | 484.0 | 8.0 | 33 |
| Example 606 | 270 | $C_{23}H_{24}F_3N_3O_4$ | 464.0 | 8.9 | 38 |
| Example 607 | 271 | $C_{21}H_{20}F_5N_3O_2$ | 442.0 | 6.1 | 28 |
| Example 608 | 272 | $C_{21}H_{22}F_3N_3O_3$ | 422.0 | 13.6 | 59 |
| Example 609 | 273 | $C_{22}H_{21}F_3N_4O_2$ | 431.0 | 12.6 | 59 |
| Example 610 | 274 | $C_{22}H_{21}F_3N_4O_2$ | 431.0 | 7.7 | 36 |
| Example 611 | 275 | $C_{22}H_{21}F_3N_4O_2$ | 431.0 | 12.7 | 59 |
| Example 612 | 276 | $C_{21}H_{20}F_5N_3O_2$ | 442.0 | 11.7 | 53 |
| Example 613 | 277 | $C_{27}H_{26}F_3N_3O_2$ | 482.0 | 9.5 | 39 |
| Example 614 | 278 | $C_{23}H_{24}F_3N_3O_4$ | 464.0 | 13.0 | 56 |
| Example 615 | 279 | $C_{22}H_{21}F_6N_3O_3$ | 490.0 | 10.4 | 42 |
| Example 616 | 280 | $C_{22}H_{21}F_6N_3O_3$ | 490.0 | 12.0 | 49 |
| Example 617 | 281 | $C_{22}H_{22}F_3N_3O_4$ | 450.0 | 4.9 | 22 |
| Example 618 | 282 | $C_{25}H_{30}F_3N_3O_2$ | 462.0 | 12.0 | 52 |
| Example 619 | 283 | $C_{20}H_{23}F_3N_4O_3$ | 425.0 | 8.1 | 38 |
| Example 620 | 284 | $C_{27}H_{25}ClF_3N_3O_2$ | 516.0 | 4.8 | 19 |
| Example 621 | 285 | $C_{21}H_{22}F_3N_3O_2$ | 406.0 | 4.8 | 24 |
| Example 622 | 286 | $C_{21}H_{21}F_4N_3O_2$ | 424.0 | 4.5 | 21 |
| Example 623 | 287 | $C_{21}H_{21}ClF_3N_3O_2$ | 440.0 | 5.8 | 26 |
| Example 624 | 288 | $C_{21}H_{24}Cl_2F_3N_3O_2$ | 474.0 | 8.1 | 34 |
| Example 625 | 289 | $C_{21}H_{26}Cl_2F_3N_3O_2$ | 474.0 | 8.0 | 34 |
| Example 626 | 290 | $C_{22}H_{24}F_3N_3O_2$ | 420.0 | 6.0 | 29 |
| Example 627 | 291 | $C_{21}H_{21}F_4N_3O_2$ | 424.0 | 6.2 | 29 |
| Example 628 | 292 | $C_{21}H_{21}ClF_3N_3O_2$ | 440.0 | 4.5 | 20 |
| Example 629 | 293 | $C_{21}H_{20}Cl_2F_3N_3O_2$ | 474.0 | 5.1 | 22 |
| Example 630 | 294 | $C_{22}H_{24}CF_3N_3O_3$ | 436.0 | 4.2 | 19 |
| Example 631 | 295 | $C_{22}H_{21}ClF_6N_3O_2$ | 474.0 | 6.0 | 25 |
| Example 632 | 296 | $C_{22}H_{24}F_3N_3O_2$ | 420.0 | 4.3 | 21 |
| Example 633 | 297 | $C_{21}H_{21}F_4N_3O_2$ | 424.0 | 8.2 | 39 |
| Example 634 | 298 | $C_{22}H_{24}F_3N_3O_3$ | 436.0 | 12.2 | 56 |
| Example 635 | 299 | $C_{22}H_{24}F_3N_3O_2$ | 420.0 | 8.1 | 39 |
| Example 636 | 300 | $C_{21}H_{20}ClF_3N_4O_4$ | 485.0 | 13.7 | 57 |
| Example 637 | 301 | $C_{21}H_{21}F_3N_4O_4$ | 451.0 | 15.1 | 67 |
| Example 638 | 302 | $C_{21}H_{21}F_3N_4O_4$ | 451.0 | 16.6 | 74 |
| Example 639 | 303 | $C_{22}H_{21}F_6N_3O_2$ | 474.0 | 12.6 | 53 |
| Example 640 | 304 | $C_{24}H_{26}F_3N_3O_4$ | 478.0 | 14.5 | 61 |
| Example 641 | 305 | $C_{22}H_{23}ClF_3N_3O_2$ | 420.0 | 8.4 | 37 |
| Example 642 | 306 | $C_{21}H_{20}Cl_2F_3N_3O_2$ | 474.0 | 13.5 | 57 |
| Example 643 | 307 | $C_{22}H_{21}ClF_6N_3O_2$ | 474.0 | 3.7 | 16 |
| Example 644 | 308 | $C_{21}H_{21}BrF_3N_3O_2$ | 484.0 | 7.2 | 30 |
| Example 645 | 309 | $C_{21}H_{21}BrF_3N_3O_2$ | 484.0 | 6.7 | 28 |
| Example 646 | 310 | $C_{27}H_{26}F_3N_3O_3$ | 498.0 | 4.2 | 17 |
| Example 647 | 311 | $C_{21}H_{21}BrF_3N_3O_2$ | 484.0 | 6.3 | 26 |
| Example 648 | 312 | $C_{22}H_{23}F_3N_3O_4$ | 450.0 | 2.4 | 11 |
| Example 649 | 313 | $C_{22}H_{24}F_3N_3O_3$ | 436.0 | 1.9 | 9 |
| Example 650 | 314 | $C_{23}H_{25}F_3N_4O_3$ | 463.0 | 5.0 | 22 |
| Example 651 | 315 | $C_{22}H_{24}F_3N_3O_4S$ | 484.0 | 2.5 | 10 |
| Example 652 | 316 | $C_{23}H_{24}F_3N_3O_4$ | 464.0 | 3.3 | 14 |
| Example 653 | 317 | $C_{21}H_{20}F_5N_3O_2$ | 442.0 | 4.5 | 20 |
| Example 654 | 318 | $C_{21}H_{22}F_3N_3O_3$ | 422.0 | 7.9 | 34 |
| Example 655 | 319 | $C_{22}H_{21}F_3N_4O_2$ | 431.0 | 6.5 | 30 |
| Example 656 | 320 | $C_{22}H_{21}F_3N_4O_2$ | 431.0 | 14.2 | 66 |
| Example 657 | 321 | $C_{22}H_{21}F_3N_4O_2$ | 431.0 | 14.9 | 69 |
| Example 658 | 322 | $C_{21}H_{24}F_5N_3O_2$ | 442.0 | 13.6 | 62 |
| Example 659 | 323 | $C_{27}H_{26}F_3N_3O_2$ | 482.0 | 3.9 | 16 |
| Example 660 | 324 | $C_{23}H_{24}F_3N_3O_4$ | 464.0 | 15.2 | 66 |
| Example 661 | 325 | $C_{22}H_{21}F_6N_3O_3$ | 490.0 | 16.1 | 66 |
| Example 662 | 326 | $C_{22}H_{21}F_6N_3O_3$ | 490.0 | 13.6 | 56 |
| Example 663 | 327 | $C_{22}H_{21}F_3N_3O_4$ | 450.0 | 5.4 | 24 |
| Example 664 | 328 | $C_{25}H_{31}F_3N_3O_2$ | 462.0 | 10.9 | 47 |
| Example 665 | 329 | $C_{26}H_{23}F_3N_4O_3$ | 425.0 | 12.0 | 57 |
| Example 666 | 986 | C27 H25 Cl F3 N3 O2 | 516.0 | 1.5 | 6 |
| Example 667 | 1118 | C28 H27 F3 N4 O3 | 525 | 21.5 | 62 |
| Example 668 | 1119 | C22 R24 F3 N3 O2 S | 452 | 16.9 | 57 |
| Example 669 | 1120 | C23 H26 F3 N3 O4 | 466 | 20.5 | 67 |
| Example 670 | 1121 | C22 H23 F3 N4 O4 | 465 | 16.8 | 55 |

TABLE 8-continued

| | Compound No. | Molecular Formula | ESI/MS m/e | Yield (mg) | Yield (%) |
|---|---|---|---|---|---|
| Example 671 | 1122 | C28 H36 F3 N3 O2 | 504 | 21.0 | 63 |
| Example 672 | 1123 | C25 H23 Br F3 N3 O2 | 534 | 26.6 | 75 |
| Example 673 | 1124 | C19 H19 F3 N4 O5 | 441 | 21.3 | 73 |
| Example 674 | 1133 | C23 H26 F3 N3 O4 | 467 | 33.6 | 84 |
| Example 675 | 1134 | C24 H28 F3 N3 O5 | 496 | 34.8 | 82 |
| Example 676 | 1135 | C22 H21 F3 N4 O6 | 495 | 32.6 | 77 |
| Example 677 | 1136 | C23 H24 F3 N3 O5 | 480 | 36.6 | 89 |
| Example 678 | 1137 | C22 H21 Br F3 N3 O4 | 529 | 30.8 | 69 |
| Example 679 | 1138 | C24 H26 F3 N3 O2 | 446 | 32.7 | 86 |
| Example 680 | 1139 | C22 H24 F3 N3 O2 | 420 | 18.6 | 51 |
| Example 681 | 1140 | C21 H20 F3 N5 O6 | 496 | 20.5 | 49 |
| Example 682 | 1141 | C25 H24 F3 N3 O2 | 456 | 22.5 | 58 |
| Example 683 | 1142 | C25 H24 F3 N3 O2 | 456 | 21.6 | 55 |
| Example 684 | 1143 | C35 H34 F3 N3 O4 | 618 | 27.3 | 53 |
| Example 685 | 1144 | C23 H26 F3 N3 O4 | 466 | 25.5 | 64 |
| Example 686 | 1145 | C23 H25 F3 N4 O6 | 511 | 38.0 | 88 |
| Example 687 | 1146 | C28 H28 F3 N3 O3 | 512 | 38.3 | 89 |
| Example 688 | 1147 | C23 H25 F3 N4 O3 | 463 | 27.1 | 62 |
| Example 689 | 1148 | C27 H26 F3 N3 O2 | 482 | 22.4 | 57 |
| Example 690 | 1161 | C22 H24 F3 N3 O4 | 452 | 13.5 | 58 |
| Example 691 | 1162 | C24 H28 F3 N3 O3 | 464 | 16.7 | 70 |
| Example 692 | 1163 | C22 H23 F4 N3 O3 | 454 | 15.8 | 68 |
| Example 693 | 1164 | C23 H26 F3 N3 O3 | 450 | 15.7 | 68 |
| Example 694 | 1165 | C23 H24 F3 N3 O4 | 464 | 16.3 | 68 |
| Example 695 | 1166 | C22 H23 Br F3 N3 O3 | 513 | 15.0 | 57 |
| Example 696 | 1168 | C17 H17 Cl F3 N5 O2 S | 448 | 6.9* | 23 |
| Example 697 | 1169 | C20 H22 F3 N5 O3 S | 470 | 1.7* | 6 |
| Example 698 | 1170 | C22 H22 F3 N5 O2 | 446 | 2.3* | 8 |
| Example 699 | 1286 | C26 H33 F3 N4 O3 | 507 | 25.3* | 51 |
| Example 700 | 1287 | C21 H20 F3 N5 O6 | 496 | 4.0* | 8 |
| Example 701 | 1288 | C22 H24 F3 N3 O4 | 452 | 3.6* | 13 |
| Example 702 | 1298 | C23 H25 Br F3 N3 O4 | 544 | 28.4 | quant |
| Example 703 | 1299 | C24 H28 F3 N3 O5 | 496 | 1.4 | 6 |
| Example 704 | 1300 | C23 H26 F3 N3 O4 | 466 | 7.3 | 33 |
| Example 705 | 1301 | C24 H28 F3 N3 O5 | 496 | 12.6 | 53 |
| Example 706 | 1302 | C24 H28 F3 N3 O3 | 464 | 24.5 | quant |
| Example 707 | 1303 | C23 H25 Br F3 N3 O4 | 544 | 22.2 | 86 |
| Example 708 | 1304 | C29 H30 F3 N3 O4 | 542 | 28.6 | quant |
| Example 709 | 1305 | C26 H26 F3 N3 O3 | 486 | 35.4 | quant |
| Example 710 | 1306 | C24 H28 F3 N3 O4 | 480 | 8.1 | 35 |
| Example 711 | 1307 | C23 H26 F3 N3 O5 | 482 | 27.9 | quant |
| Example 712 | 1308 | C23 H24 F3 N3 O3 | 448 | 5.9 | 28 |
| Example 713 | 1309 | C23 H25 F3 I N3 O4 | 592 | 24.0 | 85 |
| Example 714 | 1310 | C22 H24 F3 N3 O4 | 452 | 3.4 | 16 |
| Example 715 | 1311 | C22 H22 F3 N3 O4 | 450 | 3.4 | 16 |
| Example 716 | 1312 | C21 H21 F3 I N3 O2 | 532 | 18.1 | 72 |
| Example 717 | 1313 | C21 H21 Br F3 N3 O2 | 484 | i7.4 | 76 |
| Example 718 | 1314 | C19 H19 F3 N4 O4 S | 457 | 16.8 | 77 |
| Example 719 | 1315 | C20 H22 F3 N3 O3 | 410 | 13.6 | 70 |
| Example 720 | 1316 | C22 H20 Cl F6 N3 O2 | 508 | 18.6 | 77 |
| Example 721 | 1317 | C21 H20 Cl F3 N4 O4 | 485 | 17.0 | 74 |
| Example 722 | 1318 | C21 H20 Cl F4 N3 O2 | 458 | 17.0 | 78 |
| Example 723 | 1319 | C21 H20 Cl F4 N3 O2 | 458 | 17.6 | 81 |
| Example 724 | 1320 | C21 H20 Br F4 N3 O2 | 502 | i8.5 | 77 |
| Example 725 | 1390 | C26 H32 F3 N3 O2 | 476 | 16.1 | 51 |
| Example 726 | 1391 | C23 H26 F3 N3 O2 | 434 | 20.0 | 76 |
| Example 727 | 1392 | C22 H23 Cl F3 N3 O2 | 454 | 20.0 | 67 |
| Example 728 | 1393 | C23 H26 F3 N3 O2 | 434 | 20.1 | 70 |
| Example 729 | 1394 | C22 H23 F3 N4 O4 | 465 | 18.4 | 60 |
| Example 730 | 1395 | C23 H24 F3 N3 O2 | 432 | 21.4 | 75 |
| Example 731 | 1396 | C26 H26 F3 N3 O2 | 470 | 20.4 | 66 |
| Example 732 | 1397 | C21 H20 Br2 F3 N3 O2 | 562 | 14.5 | 54 |
| Example 733 | 1398 | C22 H22 Cl2 F3 N3 O2 | 488 | 10.8 | 47 |
| Example 734 | 1399 | C22 H22 Cl2 F3 N3 O2 | 488 | 9.4 | 40 |
| Example 735 | 1400 | C22 H23 Cl F3 N3 O2 | 454 | 19.1 | 88 |
| Example 736 | 1614 | C22 H21 F6 N3 S | 506.0 | 24.2 | 96 |
| Example 737 | 2050 | C20 H22 F3 N3 O2 S | 426 | 6.0 | 30 |
| Example 738 | 2051 | C21 H23 F3 N4 O2 | 421 | 6.5 | 32 |

*Yield of TFA salt.

Examples 739–748

The compounds of this invention were synthesized pursuant to methods of Example 738 using the corresponding reactant respectively. Preparative TLC, if needed, afforded the desired material. The ESI/MS data and yields are summarized in Table 9.

TABLE 9

| | Compound No. | Molecular Formula | ESI/MS m/e | Yield (mg) | Yield (%) |
|---|---|---|---|---|---|
| Example 739 | 1650 | C24 H28 F3 N3 O2 | 448.0 | 20.4 | 91 |
| Example 740 | 1706 | C23 H25 F3 N4 O3 | 463.2 | 3.7 | 11 |
| Example 741 | 1707 | C22 H25 F3 N4 O2 S | 467.0 | 10.3 | 29 |
| Example 742 | 1708 | C23 H27 F3 N4 O2 | 449.2 | 11.4 | 34 |
| Example 743 | 1709 | C24 H29 F3 N4 O2 | 463.2 | 15.2 | 44 |
| Example 744 | 1775 | C22 H25 F3 N4 O4 | 467.2 | 9.2 | 26.3 |
| Example 745 | 1776 | C22 H25 F3 N4 O4 | 467.2 | 8.9 | 25.4 |
| Example 746 | 1787 | C24 H29 F3 N4 O2 | 463.2 | 5.6 | 16.1 |
| Example 747 | 1802 | C23 H27 F3 N4 O4 | 481.2 | 11.7 | 32.5 |
| Example 748 | 1803 | C22 H25 F3 N4 O3 | 451.2 | 9.6 | 28.4 |

Example 749

Preparation of (R)-3-[{N-(2-Amino-5-trifluoromethoxybenzoyl)glycyl}amino]-1-(3-hydroxy-4-methoxybenzyl)pyrrolidine (Compound No. 1896)

To a mixture of (R)-3-[N-{2-(tert-butoxycarbonylamino)-5-(trifluoromethoxy)benzoyl}glycyl]aminopyrrolidine (0.050 mmol), 3-hydroxy-4-methoxybenzaldehyde (0.060 mmol), $NaBH_3CN$ (0.15 mmol), and methanol (1.3 mL) was added acetic acid (0.050 mL). The reaction mixture was stirred at 60° C. for 8 h. The mixture was cooled to room temperature, loaded onto Varian™ SCX column, and washed with $CH_3OH$ (10 mL). Product was eluted off using 2 N $NH_3$ in $CH_3OH$ (5 mL) and concentrated. To the resulting material was added 4 N HCl in 1,4-dioxane and the solution was stirred overnight at room temperature. Concentration and preparative TLC gave (R)-3-[{N-(2-amino-5-trifluoromethoxybenzoyl)glycyl}amino]-1-(3-hydroxy-4-methoxybenzyl)pyrrolidine (Compound No. 1896) (9.1 mg, 38%): The purity was determined by RPLC/MS (93%); ESI/MS m/e 483 ($M^+$+H, $C_{22}H_{25}F_3N_4O_5$).

Examples 750–757

The compounds of this invention were synthesized pursuant to methods of Example 749 using the corresponding reactant respectively. The ESI/MS data and yields are summarized in Table 10.

TABLE 10

| | Compound No. | Molecular Formula | ESI/MS m/e | Yield (mg) | Yield (%) |
|---|---|---|---|---|---|
| Example 750 | 1897 | C22 H25 F3 N4 O3 S | 483 | 22.7 | 94.1 |
| Example 751 | 1898 | C23 H27 F3 N4 O3 | 465 | 12.2 | 52.5 |
| Example 752 | 1899 | C24 H29 F3 N4 O3 | 479 | 14.4 | 60.2 |
| Example 753 | 1900 | C22 H25 F3 N4 O5 | 483 | 2.6 | 10.8 |
| Example 754 | 1901 | C24 H29 F3 N4 O3 | 479 | 14.5 | 60.6 |
| Example 755 | 1902 | C23 H25 F3 N4 O4 | 479 | 12.0 | 50.2 |
| Example 756 | 1915 | C23 H27 F3 N4 O5 | 467.2 | 2.5 | 6.7 |
| Example 757 | 1916 | C22 H25 F3 N4 O4 | 467.2 | 3.1 | 8.9 |

Example 758

Preparation of (R)-3-[{N-(2-Amino-5-(trifluoromethyl)benzoyl)glycyl}amino]-1-(4-vinylbenzyl)pyrrolidine (Compound No. 1701)

A mixture of (R)-3-[{N-(2-amino-5-(trifluoromethyl)benzoyl)glycyl}amino]pyrrolidine (0.050 mmol), 4-vinylbenzyl chloride (9.9 mg, 0.065 mmol), peperidinomethylpolystyrene (60 mg), acetonitrile (1.0 mL) and chloroform (0.30 mL) was stirred at 50° C. for 12 h. The reaction mixture was cooled, loaded onto Varian™ SCX column and washed with $CH_3OH$ (15 mL). Product was eluted using 2 N $NH_3$ in $CH_3OH$ (5 mL) and concentrated to afford (R)-3-[{N-(2-amino-5-(trifluoromethyl)benzoyl)glycyl}amino-]-(4-vinylbenzyl)pyrrolidine (compound No. 1701) (19.6 mg, 88%): The purity was determined by RPLC/MS (92%); ESI/MS m/e 547.2 ($M^+$+H, $C_{23}H_{25}ClF_3N_4O_2$).

Examples 759–762

The compounds of this invention were synthesized pursuant to methods of Example 758 using the corresponding reactant respectively. Preparative TLC, if needed, afforded the desired material. The ESI/MS data and yields are summarized in Table 11.

TABLE 11

| | Compound No. | Molecular Formula | ESI/MS m/e | Yield (mg) | Yield (%) |
|---|---|---|---|---|---|
| Example 759 | 1702 | C22 H25 F3 N4 O3 | 451.2 | 5.3 | 24 |
| Example 760 | 1703 | C22 H23 F3 N4 O4 | 465.2 | 5.0 | 22 |
| Example 761 | 1704 | C21 H23 F3 N4 O3 | 437.2 | 20.9 | 96 |
| Example 762 | 1705 | C21 H21 Cl2 F3 N4 O2 | 489.2 | 9.3 | 38 |

Example 763

Preparation of (R)-3-[{N-(2-Amino-5-(trifluoromethoxy)benzoyl)glycyl}amino]-1-(2,4-dichlorobenzyl)pyrrolidine (Compound No. 1905)

A mixture of (R)-3-[{N-(2-amino-5-(trifluoromethoxy)benzoyl)glycyl}amino]pyrrolidine (0.050 mmol), 2,4-dichlorobenzyl chloride (0.060 mmol), peperidinomethylpolystyrene (60 mg), acetonitrile (0.8 mL) and chloroform (0.5 mL) was stirred at 60° C. for 12 h. The reaction mixture was cooled, loaded onto Varian™ SCX column and washed with 50% $CHCl_3/CH_3OH$ (10 mL) and $CH_3OH$ (10 mL). Product was eluted using 2 N $NH_3$ in $CH_3OH$ (5 mL) and concentrated. To the resulting material was added 4 N HCl in 1,4-dioxane (2 mL), and the solution was stirred overnight at room temperature. Concentration and preparative TLC afforded (R)-3-[{N-(2-amino-5-(trifluoromethoxy)benzoyl)glycyl}amino]-1-(2,4-dichlorobenzyl)pyrrolidine (Compound No. 1905) (17.6 mg, 70%): The purity was determined by RPLC/MS (93%); ESI/MS m/e 505 ($M^++H$, $C_{21}H_{21}Cl_2F_3N_4O_3$).

Examples 764–770

The compounds of this invention were synthesized pursuant to methods of Example 763 using the corresponding reactant respectively. The ESI/MS data and yields are summarized in Table 12.

TABLE 12

| | Compound No. | Molecular Formula | ESI/MS m/e | Yield (mg) | Yield (%) |
|---|---|---|---|---|---|
| Example 764 | 1906 | C22 H23 F3 N4 O5 | 481 | 9.4 | 39.1 |
| Example 765 | 1907 | C21 H23 F3 N4 O4 | 453 | 7.5 | 33.2 |
| Example 766 | 1908 | C22 H25 F3 N4 O4 | 467 | 7.7 | 33.0 |
| Example 767 | 2180 | C22 H24 Cl F3 N4 O2 | 469 | 1.3 | 26 |
| Example 768 | 2181 | C23 H25 F3 N6 O3 | 491 | 4.3 | 52 |
| Example 769 | 2182 | C19 H22 F3 N5 O2 S | 442 | 7.0 | 51 |
| Example 770 | 1909 | C23 H25 F3 N4 O3 | 463 | 8.7 | 37.6 |

Example 771

Preparation of (R)-3-[{N-(2-Amino-5-trifluoromethoxybenzoyl)glycyl}amino]-1-(2-amino-4-chlorobenzyl)pyrrolidine (Compound No. 1921)

A mixture of (R)-3-[{N-(2-amino-5-trifluoromethoxybenzoyl)glycyl}amino]pyrrolidine (0.050 mmol), 4-chloro-2-nitrobenzyl chloride (0.050 mmol), peperidinomethylpolystyrene (60 mg), acetonitrile (1.0 mL) and chloroform (0.7 mL) was stirred overnight at 50° C. The reaction mixture was cooled, loaded onto Varian™ SCX column and washed with 50% $CHCl_3/CH_3OH$ (10 mL) and $CH_3OH$ (10 mL). Product was eluted using 2 N $NH_3$ in $CH_3OH$ (5 mL) and concentrated. To the resulting material was added ethanol (3 mL) and 10% Pd-C (15 mg), and the mixture was stirred under $H_2$ at room temperature for 1.5 h. Filtration, concentration, and preparative TLC afforded (R)-3-[{N-(2-amino-5-trifluoromethoxybenzoyl)glycyl}amino]-1-(2-amino-4-chlorobenzyl)pyrrolidine (Compound No. 1921) (2.2 mg, 6%): The purity was determined by RPLC/MS (81%); ESI/MS m/e 486.2 ($M^++H$, $C_{21}H_{23}ClF_3N_5O_3$).

Example 772

Preparation of (R)-3-[{N-(2-Amino-5-trifluoromethylbenzoyl)glycyl}amino]-1-(4-bromo-2-fluorobenzyl)pyrrolidine (Compound No. 2120)

To a mixture of (R)-3-[{N-(2-(tert-butoxycarbonylamino)-5-trifluoromethylbenzoyl)glycyl}amino]pyrrolidine (0.050 mmol), 4-bromo-2-fluorobenzaldehyde (0.15 mmol), methanol (1.5 mL), and acetic acid (0.016 mL) was added $NaBH_3CN$ (0.25 mmol) in methanol (0.50 mL). The reaction mixture was stirred at 50° C. overnight. The mixture was cooled to room temperature, loaded onto Varian™ SCX column, and washed with $CH_3OH$ (5 mL×2). Product was eluted off using 2 N $NH_3$ in $CH_3OH$ (5 mL) and concentrated. The residue was dissolved in methanol (0.25 mL) and 4 N HCl in dioxane (0.50 mL) was added. The solution was stirred at room temperature for 5 h and concentrated. The residue was dissolved in methanol, loaded onto Varian™ SCX column, and washed with $CH_3OH$ (5 mL×2). Product was eluted off using 2 N $NH_3$ in $CH_3OH$ (5 mL) and concentrated. The resulting material was dissolved into ethyl acetate (0.5 mL), loaded onto Varian™ Si column, eluted off using ethyl acetate/methanol=5:1 (6 mL), and concentrated to afford (R)-3-[{N-(2-amino-5-trifluoromethylbenzoyl)glycyl}amino]-1-(4-bromo-2-fluorobenzyl)pyrrolidine (Compound No. 2120) (16.0 mg, 31%): The purity was determined by RPLC/MS (99%); ESI/MS m/e 517.0 ($M^++H$, $C_{21}H_{21}BrF_4N_4O_2$).

Examples 773–793

The compounds of this invention were synthesized pursuant to methods of Example 772 using the corresponding reactant respectively. The ESI/MS data and yields are summarized in Table 13.

TABLE 13

| | Compound No. | Molecular Formula | ESI/MS m/e | Yield (mg) | Yield (%) |
|---|---|---|---|---|---|
| Example 773 | 2083 | C22 H24 Br F3 N4 O4 | 545.2 | 2.9 | 11 |
| Example 774 | 2084 | C23 H27 F3 N4 O5 | 497.2 | 5.1 | 21 |
| Example 775 | 2085 | C22 H25 F3 N4 O4 | 467.2 | 3.1 | 13 |
| Example 776 | 2086 | C21 H22 Cl F3 N4 O3 | 471.0 | 4.6 | 20 |
| Example 777 | 2087 | C23 H28 F3 N5 O2 | 464.2 | 5.6 | 24 |
| Example 778 | 2088 | C25 H32 F3 N5 O2 | 492.2 | 5.9 | 24 |
| Example 779 | 2089 | C21 H21 F5 N4 O2 | 457.2 | 4.5 | 20 |
| Example 780 | 2090 | C27 H27 F3 N4 O3 | 513.2 | 8.0 | 31 |
| Example 781 | 2118 | C21 H23 F3 N4 O4 | 453.1 | 2.7 | 12 |
| Example 782 | 2119 | C21 H23 F3 N4 O4 | 453.1 | 4.3 | 19 |
| Example 783 | 2121 | C22 H25 F3 N4 O4 | 467.0 | 1.2 | 2 |
| Example 784 | 2122 | C21 H21 Cl F4 N4 O2 | 472.9 | 13.1 | 28 |
| Example 785 | 2123 | C22 H22 F3 N5 O6 | 510.1 | 13.1 | 51 |
| Example 786 | 2124 | C21 H21 Cl F3 N5 O4 | 500.1 | 15.6 | 62 |
| Example 787 | 2125 | C22 H24 F3 N5 O5 | 496.0 | 16.0 | 65 |
| Example 788 | 2126 | C22 H24 F3 N5 O4 | 480.1 | 15.6 | 65 |
| Example 789 | 2137 | C22 H24 Cl F3 N4 O2 | 469.2 | 2.6 | 11 |
| Example 790 | 2138 | C26 H29 F3 N6 O2 | 515.3 | 25.1 | 98 |
| Example 791 | 2139 | C20 H24 Cl F3 N6 O2 | 473.2 | 25.0 | 98 |
| Example 792 | 2149 | C21 H22 F3 N5 O5 | 482.3 | 4.9 | 34 |
| Example 793 | 2157 | C22 H25 F3 N4 O3 | 451.2 | 15.5 | 70 |

Example 794

Preparation of (R)-3-[{N-(2-Amino-5-trifluoromethylbenzoyl)glycyl}amino]-1-(2,4-dimethoxypyrimidin-5-ylmethyl)pyrrolidine (Compound No. 2175)

(R)-3-[{N-(2-Amino-5-trifluoromethylbenzoyl)glycyl}amino]pyrrolidine (17.2 mg, 0.04 mmol) was dissolved in THF (1 mL) and 2,4-dimethoxy-5-pyrimidine carboxaldehyde (6.7 mg, 0.04 mmol) was added followed by sodium triacetoxyborohydride (12.7 mg, 0.06 mmol) and glacial acetic acid (2.4 mg, 0.04 mmol). The mixture was stirred at room temperature for 24 h and evaporated. The residue was then dissolved in dichloromethane (1 mL) and washed with 1 N NaOH solution (1 mL). The organic phase was recovered and evaporated then treated with 25% trifluoroacetic acid in dichloromethane (1 mL) for 1 h at room temperature and evaporated. The residue was purified using LC/MS to afford (R)-3-[{N-(2-amino-5-trifluoromethylbenzoyl)glycyl}amino]-1-(2,4-dimethoxypyrimidin-5-ylmethyl)pyrolidine (Compound No. 2175) (18.6 mg, 78%): The purity was determined by RPLC/MS (98%); ESI/MS m/e 483 ($M^+$+H, $C_{21}H_{25}F_3N_6O_4$).

Examples 795–803

The compounds of this invention were synthesized pursuant to methods of Example 794 using the corresponding reactant respectively. The ESI/MS data and yields are summarized in Table 14.

TABLE 14

| | Compound No. | Molecular Formula | ESI/MS m/e | Yield (mg) | Yield (%) |
|---|---|---|---|---|---|
| Example 795 | 2165 | C18 H21 F3 N6 O2 | 411 | 2.0 | 27 |
| Example 796 | 2166 | C18 H20 F3 N5 O2 S | 428 | 9.9 | 66 |

TABLE 14-continued

| | Compound No. | Molecular Formula | ESI/MS m/e | Yield (mg) | Yield (%) |
|---|---|---|---|---|---|
| Example 797 | 2167 | C24 H25 F3 N6 O2 | 487 | 15.1 | 73 |
| Example 798 | 2169 | C24 H29 F3 N4 O2 | 463 | 1.2 | 24 |
| Example 799 | 2170 | C26 H25 Cl F3 N5 O2 | 520 | 6.0 | 40 |
| Example 800 | 2171 | C19 H23 F3 N6 O2 | 425 | 16.8 | 88 |
| Example 801 | 2174 | C23 H24 Br F3 N4 O2 S2 | 591 | 5.3 | 53 |
| Example 802 | 2178 | C25 H28 F3 N5 O4 | 518 | 5.4 | 62 |
| Example 803 | 2179 | C25 H28 F3 N5 O3 | 502 | 6.3 | 60 |

Example 804

Preparation of (R)-1-(2-Amino-4,5-methylenedioxybenzyl)-3-[{N-(2-amino-5-trifluoromethylbenzoyl)glycyl}amino]pyrrolidine (Compound No. 2127)

A mixture of (R)-3-[{N-(2-amino-5-trifluoromethylbenzoyl)glycyl}amino]-1-(4,5-methylenedioxy-2-nitrobenzyl)pyrrolidine (30.5 mg), 10% Pd-activated carbone (6 mg), and methanol (3 mL) was stirred under a hydrogen atmosphere at room temperature for 10 h. The Pd catalyst was filtered off through Celite, and the filtrate was concentrated. Solid phase extraction (Bond Elut™ SI, 20% methanol/AcOEt) afforded (R)-1-(2-amino-4,5-methylenedioxybenzyl)-3-[{N-(2-amino-5-trifluoromethylbenzoyl)glycyl}amino]pyrrolidine (Compound No. 2127) (21.9 mg, 76%): The purity was determined by RPLC/MS (95%); ESI/MS m/e 480.1 ($M^+$+H, $C_{22}H_{24}F_3N_5O_4$).

Examples 805 and 806

The compounds of this invention were synthesized pursuant to methods of Example 804 using the corresponding reactant respectively. The ESI/MS data and yields are summarized in Table 15.

TABLE 15

| | Compound No. | Molecular Formula | ESI/MS m/e | Yield (mg) | Yield (%) |
|---|---|---|---|---|---|
| Example 805 | 2128 | C22 H26 F3 N5 O3 | 466.0 | 8.6 | 30 |
| Example 806 | 2129 | C22 H26 F3 N5 O2 | 450.1 | 13.1 | 37 |

Example 807

Preparation of (R)-1-(3-Amino-4-chlorobenzyl)-3-[{N-(2-amino-5-trifluoromethylbenzoyl)glycyl}amino]pyrrolidine (Compound No. 2132)

A mixture of (R)-3-[{N-(2-amino-5-trifluoromethylbenzoyl)glycyl}amino]-1-(4-chloro-3-nitrobenzyl)pyrrolidine (32.6 mg), 10% Pd-activated carbone (8 mg), ethyl acetate (2.7 mL) and methanol (0.3 mL) was stirred under a hydrogen atmosphere at room temperature for 15 h. The Pd catalyst was filtered off, and the filtrate was concentrated. Solid phase extraction (Bond Elut™ SI, 20% methanol/AcOEt) afforded (R)-1-(3-amino-4-chlorobenzyl)-3-[{N-(2-amino-5-trifluoromethylbenzoyl)glycyl}amino]pyrrolidine (Compound No. 2132) (10.5 mg, 34%): The purity was determined by RPLC/MS (84%); ESI/MS m/e 470.2 ($M^+$+H, $C_{21}H_{23}ClF_3N_5O_2$).

Example 808

Preparation of (R)-1-(2-Amino-4,5-methylenedioxybenzyl)-3-[{N-(2-(tert-butoxycarbonylamino)-5-trifluoromethylbenzoyl) glycyl}amino]pyrrolidine To a mixture of (R)-3-[{N-(2-(tert-butoxycarbonylamino)-5-trifluoromethylbenzoyl) glycyl}amino]pyrrolidine (0.150 mmol), 4,5-methylenedioxy-2-nitrobenzaldehyde (0.45 mmol), methanol (4.5 mL), and acetic acid (0.048 mL) was added $NaBH_3CN$ (0.75 mmol) in methanol (1.50 mL). The reaction mixture was stirred at 50° C. overnight. The mixture was cooled to room temperature, loaded onto Varian™ SCX column, and washed with $CH_3OH$. Product was eluted off using 2 N $NH_3$ in $CH_3OH$ and concentrated to afford (R)-3-[{N-(2-(tert-butoxycarbonylamino)-5-trifluoromethylbenzoyl)glycyl}amino]-1-(4,5-methylenedioxy-2-nitrobenzyl)pyrrolidine.

A mixture of (R)-3-[{N-(2-(tert-butoxycarbonylamino)-5-trifluoromethylbenzoyl)glycyl}amino]-1-(4,5-methylenedioxy-2-nitrobenzyl)pyrrolidine prepared above, 10% Pd-activated carbone (22 mg), and methanol (3.0 mL) was stirred under a hydrogen atmosphere at room temperature overnight. The Pd catalyst was filtered off, and the filtrate was concentrated to afford (R)-1-(2-amino-4,5-methylenedioxybenzyl)-3-[{N-(2-(tert-butoxycarbonylamino)-5-trifluoromethylbenzoyl) glycyl}amino]pyrrolidine (87.1 mg, quant.): Any remarkable by-products were not detected in TLC.

(R)-1-(3-Amino-4-methoxybenzyl)-3-[{N-(2-(tert-butoxycarbonylamino)-5-trifluoromethylbenzoyl) glycyl}amino]pyrrolidine and (R)-1-(3-amino-4-methylbenzyl)-3-[{N-(2-(tert-butoxycarbonylamino)-5-trifluoromethylbenzoyl)glycyl}amino]pyrrolidine were also synthesized pursuant to methods of Example 808 using the corresponding reactant respectively.

(R)-1-(3-Amino-4-methoxybenzyl)-3-[{N-(2-(tert-butoxycarbonylamino)-5-trifluoromethylbenzoyl) glycyl}amino]pyrrolidine: 101 mg, quant.; Any remarkable by-products were not detected in TLC.

(R)-1-(3-amino-4-methylbenzyl)-3-[{N-(2-(tert-butoxycarbonylamino)-5-trifluoromethylbenzoyl) glycyl}amino]pyrrolidine: 97.2 mg, quant.; Any remarkable by-products were not detected in TLC.

Example 809

Preparation of (R)-1-(3-Amino-4-chlorobenzyl)-3-[{N-(2-(tert-butoxycarbonylamino)-5-trifluoromethylbenzoyl)glycyl}amino]pyrrolidine To a mixture of (R)-3-[{N-(2-(tert-butoxycarbonylamino)-5-trifluoromethylbenzoyl) glycyl}amino]pyrrolidine (0.150 mmol), 4-chloro-3-nitrobenzaldehyde (0.45 mmol), methanol (4.5 mL), and acetic acid (0.048 mL) was added $NaBH_3CN$ (0.75 mmol) in methanol (1.50 mL). The reaction mixture was stirred at 50° C. overnight. The mixture was cooled to room temperature, loaded onto Varian™ SCX column, and washed with $CH_3OH$. Product was eluted off using 2 N $NH_3$ in $CH_3OH$ and concentrated to afford (R)-3-[{N-(2-(tert-butoxycarbonylamino)-5-trifluoromethylbenzoyl) glycyl}amino]-1-(4-chloro-3-nitrobenzyl)pyrrolidine.

A mixture of (R)-3-[{N-(2-(tert-butoxycarbonylamino)-5-trifluoromethylbenzoyl)glycyl}amino]-1-(4-chloro-3-nitrobenzyl)pyrrolidine prepared above, 10% Pd-activated carbone (22 mg), ethyl acetate (2.7 mL) and methanol (0.3 mL) was stirred under a hydrogen atmosphere at room temperature for 15 h. The Pd catalyst was filtered off, and the filtrate was concentrated to afford (R)-1-(3-amino-4-chlorobenzyl)-3-[{N-(2-(tert-butoxycarbonylamino)-5-trifluoromethylbenzoyl)glycyl}amino]pyrrolidine (89.7 mg, quant.): Any remarkable by-products were not detected in TLC.

Example 810

Preparation of (R)-1-(3-Amino-4-hydroxybenzyl)3-[{N-(2-Amino-5-trifluoromethylbenzoyl) glycyl}amino]pyrrolidine (Compound No. 2187)

A solution of (R)-1-(3-amino-4-hydroxybenzyl)-3-[{N-(2-(tert-butoxycarbonylamino)-5-trifluoromethylbenzoyl) glycyl}amino]pyrrolidine (20 mg), prepared pursuant to methods of Example 808, in 4 N HCl in dioxane (2.0 mL) was stirred at room temperature overnight. After the solution was concentrated, the residue was dissolved in methanol, loaded onto Varian™ SCX column, washed with $CH_3OH$, and eluted off using 2 N $NH_3$ in $CH_3OH$. Concentration and preparative TLC ($SiO_2$, AcOEt/MeOH=4:1) afforded (R)-1-(3-amino-4-hydroxybenzyl)3-[{N-(2-Amino-5-trifluoromethylbenzoyl)glycyl}amino]pyrrolidine (Compound No. 2187) (9.6 mg, 59%): The purity was determined by RPLC/MS (86%); ESI/MS m/e 452.3 ($M^+$+H, $C_{21}H_{24}F_3N_5O_3$).

Example 811

Preparation of (R)-3-[{N-(2-Amino-5-trifluoromethylbenzoyl)glycyl}amino]-1-{4-chloro-3-(dimethylamino)benzyl}pyrrolidine (Compound No. 2133)

To a mixture of (R)-1-(3-amino-4-chlorobenzyl)-3-[{N-(2-(tert-butoxycarbonylamino)-5-trifluoromethylbenzoyl) glycyl}amino]pyrrolidine (44.9 mg), methanol (0.95 mL), acetic acid (0.05 mL), and 37% aqueous HCHO solution (0.15 mL) was added $NaBH_3CN$ (38 mg). The reaction mixture was stirred at 50° C. overnight. The mixture was cooled to room temperature and evaporated. To the residue was added 2 N aqueous NaOH solution and ethyl acetate, the organic layer was separated, and the aqueous layer was extracted with ethyl acetate. The combined organic layers were dried and concentrated, and the residue was loaded onto Varian™ SCX column and washed with $CH_3OH$. Product was eluted off using 2 N $NH_3$ in $CH_3OH$ and concentrated. The residue was dissolved in 50% conc. HCl/dioxane and the solution was stirred at room temperature for 1 h. The reaction mixture was adjusted to pH 10 with 5 N aqueous NaOH solution and extracted with ethyl acetate (2 times). The combined extracts were dried over $Na_2SO_4$, filtered, and evaporated. Preparative TLC ($SiO_2$, 20% MeOH/AcOEt) gave (R)-3-[{N-(2-amino-5-trifluoromethylbenzoyl)glycyl}amino]-1-{4-chloro-3-(dimethylamino)benzyl}pyrrolidine (Compound No. 2133). (10.9 mg, 28%): The purity was determined by RPLC/MS (95%); ESI/MS m/e 498.3 ($M^+$+H, $C_{23}H_{27}ClF_3N_5O_2$).

Examples 812–814

The compounds of this invention were synthesized pursuant to methods of Example 811 using the corresponding reactant respectively. The ESI/MS data and yields are summarized in Table 16.

TABLE 16

| | Compound No. | Molecular Formula | ESI/MS m/e | Yield (mg) | Yield (%) |
|---|---|---|---|---|---|
| Example 812 | 2134 | $C_{24}H_{28}F_3N_5O_4$ | 508.4 | 19.0 | 50 |
| Example 813 | 2135 | $C_{24}H_{30}F_3N_5O_3$ | 494.4 | 21.8 | 50 |
| Example 814 | 2136 | $C_{24}H_{30}F_3N_5O_2$ | 478.4 | 29.2 | 69 |

Example 815

Preparation of (R)-3-[{N-(2-Amino-5-trifluoromethylbenzoyl)glycyl}amino]-1-(3-methylamino-4-hydroxybenzyl)pyrrolidine (Compound No. 2158)

To a mixture of (R)-1-(3-amino-4-hydroxybenzyl)-3-[{N-(2-(tert-butoxycarbonylamino)-5-trifluoromethylbenzoyl) glycyl}amino]pyrrolidine (27.3 mg, 0.049 mmol), 37% HCHO solution (4.0 mg, 0.049 mmol), acetic acid (0.10 mL) and methanol (1.3 mL) was added $NaBH_3CN$ (9.2 mg) in methanol (0.2 mL). The reaction mixture was stirred at 60° C. overnight. The mixture was cooled to room temperature, loaded onto Varian™ SCX column, and washed with $CH_3OH$ (5 mL×2). Product was eluted off using 2 N $NH_3$ in $CH_3OH$ (8 mL) and concentrated.

The resulting material was dissolved in methanol (1 mL) and 4 N HCl in dioxane (1.0 mL) was added. The solution was stirred at room temperature for 3 h. After the solution was concentrated, the residue was dissolved in methanol (1 mL), loaded onto Varian™ SCX column, washed with $CH_3OH$ (5 mL×2), and eluted off using 2 N $NH_3$ in $CH_3OH$ (8 mL). Concentration and preparative TLC ($SiO_2$) afforded (R)-3-[{N-(2-amino-5-trifluoromethylbenzoyl) glycyl}amino]-1-(3-methylamino-4-hydroxybenzyl) pyrrolidine (Compound No. 2158) (4.3 mg, 19%): The purity was determined by RPLC/MS (71%); ESI/MS m/e 480.3 ($M^+$+H, $C_{22}H_{26}F_3N_5O_3$).

Example 816

Preparation of (R)-1-(3-Acetylamino-4-methoxybenzyl)-3-[{N-(2-amino-5-trifluoromethylbenzoyl)glycyl}amino]pyrrolidine (Compound No. 2152)

To a solution of (R)-1-(3-amino-4-methoxybenzyl)-3-[{N-(2-(tert-butoxycarbonylamino)-5-trifluoromethylbenzoyl)glycyl}amino]pyrrolidine (50.5 mg) in pyridine (1 mL) was added acetic anhydride (1 mL). The reaction mixture was stirred at room temperature overnight and methanol was added. The mixture was evaporated, and 1 N NaOH solution was added. The mixture was extracted with ethyl acetate and the organic layer was concentrated. Preparative TLC gave (R)-1-(3-acetylamino-4-methoxybenzyl)-3-[{N-(2-(tert-butoxycarbonylamino)-5-trifluoromethylbenzoyl)glycyl}amino]pyrrolidine.

The resulting (R)-1-(3-acetylamino-4-methoxybenzyl)-3-[{N-(2-(tert-butoxycarbonylamino)-5-trifluoromethylbenzyl)glycyl}amino]pyrrolidine was dissolved in 50% 6 N hydrochloric acid in dioxane and the solution was stirred at room temperature for 2 h. The mixture was adjusted to pH 10 with 5 M NaOH solution, and extracted with ethyl acetate. The organic layer was evaporated and preparative TLC ($SiO_2$, AcOEt/MeOH=4:1) afforded (R)-1-(3-acetylamino-4-methoxybenzyl)-3-[{N-(2-amino-5-trifluoromethylbenzoyl)glycyl}amino]pyrrolidine (Compound No. 2152) (3.7 mg, 8%): The purity was determined by RPLC/MS (100%); ESI/MS m/e 508.3 ($M^+$+H, $C_{24}H_{28}F_3N_5O_4$).

Examples 817–819

The compounds of this invention were synthesized pursuant to methods of Example 816 using the corresponding reactants respectively. The ESI/MS data and yields are summarized in Table 17.

TABLE 17

| | Compound No. | Molecular Formula | ESI/MS m/e | Yield (mg) | Yield (%) |
|---|---|---|---|---|---|
| Example 817 | 2150 | C23H25ClF3N5O3 | 512.3 | 3.8 | 9 |
| Example 818 | 2151 | C24H26F3N5O5 | 522.2 | 3.1 | 8 |
| Example 819 | 2153 | C24H28F3N5O3 | 492.3 | 4.3 | 10 |

Example 820

Preparation of (R)-3-[{N-(2-Amino-5-trifluoromethylbenzoyl)glycyl}amino]-1-(benz[d]oxazol-5-yl)pyrrolidine (Compound No. 2189)

A solution of (R)-1-(3-amino-4-hydroxybenzyl)-3-[{N-(2-(tert-butoxycarbonylamino)-5-trifluoromethylbenzoyl) glycyl}amino]pyrrolidine (20 mg), prepared pursuant to methods of Example 808, in THF (2 mL) was treated with triethyl orthoformate (0.020 mL, 3.3 eq) and pyridinium p-toluenesulphonate (1.2 mg, 0.4 eq). The reaction mixture was stirred overnight under reflux. After cooling to room temperature, the mixture was concentrated. The residue was dissolved in AcOEt, loaded onto BondElut™ Si column, eluted off using ethyl acetate/methanol=4/1, and concentrated.

The resulting material was dissolved into AcOEt (1.5 mL), and 4 N HCl in dioxane (0.5 mL) was added. The solution was stirred at room temperature overnight, adjusted to pH 10 with 5 M NaOH aqueous solution, and extracted with AcOEt. The extract was concentrated and purified by PTLC ($SiO_2$, AcOEt/MeOH=4:1) to afford (R)-3-[{N-(2-amino-5-trifluoromethylbenzoyl)glycyl}amino]-1-(benz[d]oxazol-5-yl)pyrrolidine (Compound No. 2189) (0.5 mg, 3%): The purity was determined by RPLC/MS (97%); ESI/MS m/e 462.3 ($M^+$+H, $C_{22}H_{22}F_3N_5O_3$).

Example 821

Preparation of (R)-3-[{N-(2-Amino-5-trifluoromethylbenzoyl)glycyl}amino]-1-(benzo[c]thiadiazol-5-yl)pyrrolidine (Compound No. 2183)

To a mixture of 5-(hydroxymethyl)benzo[c]thiadiazole (8.3 mg, 0.050 mmol), (piperidinomethyl)polystyrene (86 mg), and chloroform (1 mL) was added methanesulfonyl chloride (0.0042 mL) and the mixture was stirred at room temperature for 1.5 h. Acetonitrile (1 mL) and (R)-3-[{N-(2-(tert-butoxycarbonylamino)-5-trifluoromethylbenzoyl) glycyl}amino]pyrrolidine (0.060 mmol) was added and the reaction mixture was stirred at 50° C. for 3 h. After cooling to room temperature, phenyl isocyanate (30 mg) was added, and the mixture was stirred at room temperature for 1 h, loaded onto Varian™ SCX column and washed with $CH_3OH$ (5 mL) and $CHCl_3$ (5 mL). Product was eluted using 2 N $NH_3$ in $CH_3OH$ (3 mL) and concentrated.

The resulting material was dissolved into dichloromethane (1 mL), and 1 M chlorotrimethylsilane and 1 M phenol in dichloromethane (1 mL) was added. The solution was stirred at room temperature for 5 h, loaded onto Varian™ SCX column and washed with $CH_3OH$ and dichloromethane. Product was eluted using 2 N $NH_3$ in $CH_3OH$ and concentrated. Preparative TLC ($SiO_2$, AcOEt/MeOH=3:1) afforded (R)-3-[{N-(2-amino-5-trifluoromethylbenzoyl)glycyl}amino]-1-(benzo[c]thiadiazol-5-yl)pyrrolidine (Compound No. 2183) (11.5 mg, 48%): The purity was determined by RPLC/MS (86%); ESI/MS m/e 479.2 ($M^+$+H, $C_{21}H_{21}F_3N_6O_2S$).

Reference Example 6

Preparation of 4-[{N-(1-(9-fuluorenylmethoxycarbonyl)pyrrolidin-3-yl)carbamoylmethyl}aminomethyl]-3-methoxyphenyloxymethyl-polystyrene To a solution of (R)-1-(9-fuluorenylmethoxycarbonyl)-3-glycylaminopyrrolidine hydrochloride (4.38 g, 10 mmol) in DMF (65 mL) were added acetic acid (0.3 mL), sodium triacetoxyborohydride (1.92 g), and 4-formyl-3-(methoxyphenyloxymethyl)-polystyrene (1 mmol/g, 200 g). The mixture was shaken for 2 h and filtered. The resin was washed with MeOH, DMF, $CH_2Cl_2$, and methanol, and dried to afford the desired material (2.73 g).

Examples 822–912

General Procedure for Solid-Phase Synthesis of 3-Aminopyrrolidines.

To a mixture of the corresponding acid (1.6 mmol), HBTU (1.6 mmol), and DMF (6 mL) was added diisopropylethylamine (3.6 mmol), and the mixture was shaken for 2 min. 4-[{N-(1-(9-fuluorenylmethoxycarbonyl)pyrrolidin-3-yl)carbamoylmethyl}aminomethyl]-3-methoxyphenyloxymethyl-polystyrene (400 mg, 0.4 mmol) was added and the mixture was shaken for 1 h and filtered. The resin was rinsed with DMF and $CH_2Cl_2$, and dried.

A mixture of the resulting resin, piperidine (3.2 mL), and DMF (12.8 mL) was shaken for 10 min and filtered. The resin was washed with DMF and $CH_2Cl_2$, and dried.

To the dry resin (0.05 mmol) was added a mixture of NaBH$(OAc)_3$ (0.25 mmol), AcOH (0.025 mL) and DMF (1 mL). The corresponding aldehyde (2.5 mmol) was added, and the mixture was shaken for 2 h, then filtered and washed with $CH_3OH$, 10% diisopropylethylamine in DMF, DMF, $CH_2Cl_2$, and $CH_3OH$. A mixture of the resin, water (0.050 mL), and trifluoroacetic acid (0.95 mL) was shaken for 1 h and filtered. The resin was washed with $CH_2Cl_2$ and $CH_3OH$. The filtrate and washings were combined and concentrated. The crude material was loaded onto Varian™ SCX column and washed with $CH_3OH$ (15 mL). Product was eluted using 2 N $NH_3$ in $CH_3OH$ (5 mL) and concentrated. Preparative TLC or HPLC, if needed, afforded the desired material. The ESI/MS data and yields are summarized in Table 18.

TABLE 18

| | Compound No. | Molecular Formula | ESI/MS m/e | Yield (mg) | Yield (%) |
|---|---|---|---|---|---|
| Example 822 | 1805 | C21 H21 Br F3 N3 O2 S | 516 | 13.3 | 76 |
| Example 823 | 1806 | C22 H24 F3 N3 O3 S | 468 | 12.8 | 81 |
| Example 824 | 1807 | C22 H24 F3 N3 O4 S | 484 | 13.7 | 83 |
| Example 825 | 1808 | C22 H24 F3 N3 O4 S | 484 | 14.9 | 91 |
| Example 826 | 1809 | C21 H22 F3 N3 O3 S | 454 | 12.9 | 84 |
| Example 827 | 1810 | C22 H22 F3 N3 O4 3 | 482 | 12.9 | 79 |
| Example 828 | 1811 | C24 H26 F3 N3 O2 S | 478 | 12.9 | 79 |
| Example 829 | 1812 | C22 H24 F3 N3 O2 S2 | 484 | 5.3 | 32 |
| Example 830 | 1813 | C23 H26 F3 N3 O2 S | 466 | 12.8 | 81 |
| Example 831 | 1814 | C23 H24 F3 N3 O3 S | 480 | 9.7 | 59 |
| Example 832 | 1815 | C23 H26 F3 N3 O2 S | 466 | 12.7 | 80 |
| Example 833 | 1816 | C24 H28 F3 N3 O2 S | 480 | 14.4 | 88 |
| Example 834 | 1817 | C25 H30 F3 N3 O2 S | 494 | 14.1 | 84 |
| Example 835 | 1818 | C21 H22 Br F2 N3 O3 | 482 | 13.4 | 82 |
| Example 836 | 1819 | C22 H25 F2 N3 O4 | 434 | 11.7 | 79 |
| Example 837 | 1820 | C22 H25 F2 N3 O5 | 450 | 11.8 | 77 |
| Example 838 | 1821 | C22 H25 F2 N3 O5 | 450 | 13.3 | 87 |
| Example 839 | 1822 | C21 H23 F2 N3 O4 | 420 | 11.9 | 83 |
| Example 840 | 1823 | C22 H23 F2 N3 O5 | 448 | 11.9 | 78 |
| Example 841 | 1824 | C24 H27 F2 N3 O3 | 444 | 9.1 | 60 |
| Example 842 | 1825 | C22 H25 F2 N3 O3 S | 450 | 11.3 | 74 |
| Example 843 | 1826 | C23 H27 F2 N3 O3 | 432 | 10.8 | 74 |
| Example 844 | 1827 | C23 H25 F2 N3 O4 | 446 | 12.7 | 84 |
| Example 845 | 1828 | C23 H27 F2 N3 O3 | 432 | 11.7 | 80 |
| Example 846 | 1829 | C24 H29 F2 N3 O3 | 446 | 14.3 | 94 |
| Example 847 | 1830 | C24 H29 F2 N3 O3 | 446 | 10.0 | 66 |
| Example 848 | 1831 | C22 H28 Br N3 O3 | 462 | 4.8 | 31 |
| Example 849 | 1832 | C23 H31 N3 O4 | 414 | 10.4 | 74 |
| Example 850 | 1833 | C23 H31 N3 O5 | 430 | 12.1 | 83 |
| Example 851 | 1834 | C23 H31 N3 O5 | 430 | 12.0 | 82 |
| Example 852 | 1835 | C22 H29 N3 O4 | 400 | 7.9 | 58 |
| Example 853 | 1836 | C23 H29 N3 O5 | 428 | 11.1 | 76 |
| Example 854 | 1837 | C25 H33 N3 O3 | 424 | 13.3 | 92 |
| Example 855 | 1838 | C23 H31 N3 O3 S | 430 | 8.7 | 60 |
| Example 856 | 1839 | C24 H33 N3 O3 | 412 | 11.3 | 81 |
| Example 857 | 1840 | C24 H31 N3 O4 | 426 | 12.9 | 89 |
| Example 858 | 1841 | C24 H33 N3 O3 | 413 | 12.8 | 91 |
| Example 859 | 1842 | C25 H35 N3 O3 | 426 | 8.7 | 60 |
| Example 860 | 1843 | C25 H35 N3 O3 | 426 | 12.2 | 84 |
| Example 861 | 1844 | C26 H37 N3 O3 | 440 | 11.3 | 76 |
| Example 862 | 1845 | C31 H37 Br N4 O2 | 577 | 6.4 | 30 |
| Example 863 | 1846 | C23 H28 F3 N3 O2 S | 480 | 12.8 | 81 |
| Example 864 | 1847 | C25 H31 F2 N3 O3 | 460 | 12.2 | 78 |
| Example 865 | 1848 | C27 H29 N3 O4 | 460 | 6.1 | 39 |
| Example 866 | 1849 | C29 H31 N3 O2 | 454 | 15.1 | 98 |
| Example 867 | 1850 | C28 H31 N3 O2 | 442 | 12.7 | 85 |
| Example 868 | 1851 | C28 H31 N3 O2 | 442 | 14.3 | 95 |
| Example 869 | 1852 | C28 H29 N3 O3 | 456 | 3.4 | 22 |
| Example 870 | 1853 | C27 H29 N3 O6 S | 524 | 15.4 | 87 |
| Example 871 | 1854 | C29 H31 N3 O4 S | 518 | 15.8 | 90 |
| Example 872 | 1855 | C28 H31 N3 O4 S | 506 | 17.0 | 99 |
| Example 873 | 1856 | C28 H31 N3 O4 S | 506 | 3.0 | 17 |
| Example 874 | 1857 | C28 H29 N3 O5 S | 520 | 10.0 | 57 |
| Example 875 | 1858 | C20 H22 Br2 N4 O2 | 511 | 9.3* | 37 |
| Example 876 | 1859 | C21 H25 Br N4 O3 | 461 | 6.7* | 29 |
| Example 877 | 1860 | C21 H25 Br N4 O4 | 477 | 9.5* | 40 |
| Example 878 | 1861 | C21 H25 Br N4 O4 | 477 | 10.0* | 42 |
| Example 879 | 1862 | C20 H23 Br N4 O3 | 447 | 7.8* | 34 |
| Example 880 | 1863 | C21 H23 Br N4 O4 | 475 | 3.4* | 14 |
| Example 881 | 1864 | C21 H25 Br N4 O2 S | 477 | 3.9* | 16 |
| Example 882 | 1865 | C22 H25 Br N4 O3 | 473 | 6.4* | 27 |
| Example 883 | 1866 | C23 H29 Br N4 O2 | 472 | 7.0* | 29 |
| Example 884 | 1867 | C23 H29 Br N4 O2 | 473 | 7.6* | 32 |
| Example 885 | 1868 | C24 H31 Br N4 O2 | 487 | 9.1* | 37 |
| Example 886 | 1869 | C20 H22 Br I N4 O2 | 557 | 8.9* | 33 |
| Example 887 | 1870 | C21 H25 I N4 O3 | 509 | 9.2* | 37 |
| Example 888 | 1871 | C21 H25 I N4 O4 | 525 | 6.3* | 25 |
| Example 889 | 1872 | C21 H25 I N4 O4 | 525 | 5.9* | 23 |
| Example 890 | 1873 | C20 H23 I N4 O3 | 495 | 7.7* | 31 |
| Example 891 | 1874 | C21 H23 I N4 O4 | 523 | 8.2* | 32 |
| Example 892 | 1875 | C23 H27 I N4 O2 | 519 | 6.7* | 26 |
| Example 893 | 1876 | C21 H25 I N4 O2 | 525 | 4.3* | 17 |
| Example 894 | 1877 | C22 H27 I N4 O2 | 507 | 7.9* | 32 |
| Example 895 | 1878 | C22 H25 I N4 O3 | 521 | 8.4* | 33 |
| Example 896 | 1879 | C23 H29 I N4 O2 | 521 | 8.2* | 32 |
| Example 897 | 1880 | C23 H29 I N4 O2 | 521 | 8.1* | 32 |

TABLE 18-continued

| | Compound No. | Molecular Formula | ESI/MS m/e | Yield (mg) | Yield (%) |
|---|---|---|---|---|---|
| Example 898 | 1881 | C24 H31 I N4 O2 | 535 | 8.6* | 33 |
| Example 899 | 1882 | C20 H22 Br N5 O4 | 476 | 5.3* | 22 |
| Example 900 | 1883 | C21 H25 N5 O5 | 428 | 5.7* | 26 |
| Example 901 | 1884 | C21 H25 N5 O6 | 444 | 8.2* | 36 |
| Example 902 | 1885 | C21 H25 N5 O6 | 444 | 5.0* | 22 |
| Example 903 | 1886 | C20 H23 N5 O5 | 414 | 8.7* | 40 |
| Example 904 | 1887 | C21 H23 N5 O6 | 442 | 7.8* | 34 |
| Example 905 | 1888 | C23 H27 N5 O4 | 438 | 5.6* | 25 |
| Example 906 | 1889 | C21 H25 N5 O4 S | 444 | 13.2* | 58 |
| Example 907 | 1890 | C22 H27 N5 O4 | 426 | 11.3* | 51 |
| Example 908 | 1891 | C22 H25 N5 O5 | 440 | 7.4* | 33 |
| Example 909 | 1892 | C22 H27 N5 O4 | 426 | 5.5* | 25 |
| Example 910 | 1893 | C23 H29 N5 O4 | 440 | 5.7* | 25 |
| Example 911 | 1894 | C23 H29 N5 O4 | 440 | 9.4* | 41 |
| Example 912 | 1895 | C24 H31 N5 O4 | 455 | 8.5* | 37 |

*Yield of TFA salt.

Reference Example 7

Preparation of 2-Carbamoyl-1-(4-chlorobenzyl)pyrrolidine

A solution of dl-prolinamide hydrochloride (2.5 g, 21.8 mmol) in $CH_3CN$ (35 mL) was treated with $Et_3N$ (7.45 mL) and 4-chlorobenzyl chloride (3.88 g, 24.1 mmol). The reaction mixture was stirred at 70° C. for 4 h and then at 25° C. for 16 h. The resulting mixture was diluted with $CH_2Cl_2$ (20 mL) and was washed with water (3×30 mL). The organic phase was dried ($MgSO_4$) and concentrated. Chromatography ($SiO_2$, 1% $CH_3OH$—$CH_2Cl_2$) afforded 2-carbamoyl-1-(4-chlorobenzyl)pyrrolidine (5.21 g, 81%).

Reference Example 8

Preparation of 2-(Aminomethyl)-1-(4-chlorobenzyl)pyrrolidine 2-carbamoyl-1-(4-chlorobenzyl)pyrrolidine was dissolved in 1M $BH_3$-THF (9.4 mL) and heated to 70° C. After 16 h and 25 h, additional 0.5 equiv. of 1M $BH_3$-THF were added. After 40 h, 1 N aqueous HCl solution (14 mL) was added and the reaction was heated to reflux for 3 h, 3 N aqueous HCl solution (6 mL) was added and the reaction was heated for an additional 3 h. The reaction mixture was cooled to 25° C., basicified with 4 N aqueous NaOH solution and extracted with $CH_2Cl_2$ (4×15 mL). Chromatography ($SiO_2$, 8:1:1 $^-$PrOH—$H_2O$—$NH_4OH$) afforded 2-(aminomethyl)-1-(4-chlorobenzyl)pyrrolidine (1.21 g, 86%).

Optically active (S)-2-(aminomethyl)-1-(4-chlorobenzyl)pyrrolidine and (R)-2-(aminomethyl)-1-(4-chlorobenzyl)pyrrolidine were also prepared pursuant to the above method using the corresponding reactant respectively.

(S)-2-(aminomethyl)-1-(4-chlorobenzyl)pyrrolidine: $^1$H NMR ($CDCl_3$, 400 MHz) δ1.40–1.80 (m, 5 H), 1.80–1.95 (m, 1 H), 2.12–2.21 (m, 1 H), 2.48–2.65 (m, 1 H), 2.66–2.78 (m, 2 H), 2.85–2.95 (m, 1 H), 3.26 (d, J=13.2 Hz, 1 H), 3.93 (d, J=13.2 Hz, 1 H), 7.20–7.40 (m, 4 H).

(R)-2-(aminomethyl)-1-(4-chlorobenzyl)pyrrolidine showed the same $^1$H NMR with that of (S)-isomer.

Example 913

Preparation of 2-{(N-benzoylleucyl)aminomethyl}-1-(4-chlorobenzyl)pyrrolidine (Compound No. 344)

A solution of 2-(aminomethyl)-1-(4-chlorobenzyl)pyrrolidine (22.5 mg, 0.10 mmol) and dl-benzoylleucine (0.12 mmol) in $CHCl_3$ (1 mL) was treated with EDCI (23 mg), HOBt (16.2 mg) and $Et_3N$ (15.2 μL), and stirred at 25° C. for 16 h. The reaction mixture was diluted with $CH_2Cl_2$ (0.5 mL), washed with 2 N aqueous NaOH solution (2×0.75 mL), dried by filtration through a PTFE membrane and concentrated to afford 2-{(N-benzoylleucyl)aminomethyl}-1-(4-chlorobenzyl)pyrrolidine (compound No. 344) (74 mg, quant): The purity was determined by RPLC/MS (85%); ESI/MS m/e 442 ($M^+$+H, $C_{25}H_{32}ClN_3O_2$).

Examples 914–935

The compounds of this invention were synthesized pursuant to methods of Example 913 using the corresponding reactant respectively. Chromatography, if needed, (HPLC-$C_{18}$, $CH_3CN/H_2O/TFA$) afforded the desired material as the TFA salt. The ESI/MS data and yields are summarized in Table 19 and compound No. 339 and 340 showed the following $^1$H NMR spectra respectively.

TABLE 19

| | Compound No. | Molecular Formula | ESI/MS m/e | Yield (mg) | Yield (%) |
|---|---|---|---|---|---|
| Example 914 | 330 | C21 H24 Cl N3 O2 | 386 | 75* | quant |
| Example 915 | 331 | C22 H26 Cl N3 O2 | 400 | 44* | 70 |
| Example 916 | 332 | C24 H30 Cl N3 O5 | 476 | 57 | quant |
| Example 917 | 333 | C20 H23 Cl N4 O2 | 387 | 40 | quant |
| Example 918 | 334 | C22 H26 Cl N3 O2 | 400 | 68 | quant |
| Example 919 | 335 | C21 H23 Cl N4 O4 | 431 | 73 | quant |
| Example 920 | 336 | C22 H23 Cl F3 N3 O2 | 454 | 75 | quant |
| Example 921 | 337 | C22 H26 Cl N3 O2 | 400 | 68 | quant |
| Example 922 | 338 | C22 H26 Cl N3 O2 | 400 | 70 | quant |
| Example 923 | 341 | C22 H26 Cl N3 O2 | 400 | 80* | quant |
| Example 924 | 342 | C22 H26 Cl N3 O2 | 400 | 68 | quant |
| Example 925 | 343 | C24 H30 Cl N3 O2 | 428 | 63 | quant |
| Example 926 | 345 | C23 H27 Cl N2 O2 | 399 | 68* | quant |
| Example 927 | 346 | C23 H26 Cl F N2 O3 | 433 | 51 | quant |
| Example 928 | 347 | C24 H29 Cl N2 O2 | 413 | 47 | quant |
| Example 929 | 348 | C23 H27 Cl N2 O2 | 399 | 26 | quant |
| Example 930 | 349 | C21 H25 Cl N2 O3 S | 421 | 42 | quant |
| Example 931 | 350 | C26 H33 Cl N2 O3 | 457 | 12.4 | 54 |
| Example 932 | 351 | C22 H26 Cl N3 O3 | 416 | 34 | 81 |
| Example 933 | 352 | C22 H25 Cl2 N3 O3 | 450 | 51 | quant |

*Yield of TFA salt.

Example 934

Compound No. 339: 82%; $^1$H NMR ($CDCl_3$) δ1.52–1.75 (m, 4 H), 1.84–1.95 (m, 1 H), 2.10–2.20 (m, 1 H), 2.67–2.78 (m, 1 H), 2.80–2.90 (m, 1 H), 3.10–3.20 (m, 1 H), 3.25 (d, J=13.1 Hz, 1 H), 3.50–3.60 (m, 1 H), 3.89 (d, J=13.1 Hz, 1 H), 4.28–4.20 (m, 2 H), 7.00–7.05 (m, 1 H), 7.12–7.29 (m, 4 H), 7.51 (t, J=7.8 Hz, 1 H), 7.74 (d, J=7.8 Hz, 1 H), 7.99 (d, J=7.8 Hz, 1 H), 8.10–8.27 (m, 2 H).

Example 935

Compound No. 340: 68%; $^1$H NMR ($CDCl_3$) δ1.55–1.73 (m, 4 H), 1.86–1.97 (m, 1 H), 2.12–2.21 (m, 1 H), 2.67–2.76 (m, 1 H), 2.86–2.93 (m, 1 H), 3.14–3.21 (m, 1 H), 3.27 (d, J=13.1 Hz, 1 H), 3.52–3.59 (m, 1 H), 3.89 (d, J=13.1 Hz, 1 H), 4.09–4.21 (m, 2 H), 7.00–7.07 (m, 1 H), 7.12–7.30 (m, 4 H), 7.50 (t, J=7.8 Hz, 1 H), 7.73 (d, J=7.8 Hz, 1 H), 8.01 (d, J=7.8 Hz, 1 H), 8.10–8.25 (m, 2 H).

Reference Example 9

Preparation of 3-(Aminomethyl)-1-(4-chlorobenzyl)pyrrolidine

To a mixture of 4-carboxy-1-(4-chlorobenzyl)pyrrolidin-2-one (5.05 g, 20 mmol), EDCI (2.85 g, 22 mmol), HOBt (2.97 g, 22 mmol) and dichloromethane (100 mL) was added 0.5 M ammonia indioxane (60 mL, 30 mmol). The reaction mixture was stirred at room temperature for 15 h and washed with 2N HCl (3 times) and 2 N NaOH aqueous solution (100 mL×4). The organic layer was dried over anhydrous magnesium sulfate, filtered, and concentrated to afford 3-carbamoyl-1-(4-chlorobenzyl)pyrrolidin-2-one (1.49 g) as a colorless solid.

To a solution of 3-carbamoyl-1-(4-chlorobenzyl) pyrrolidin-2-one (1.45 g) in THF (15 mL) was added 1.0 N $BH_3$ in THF (25 mL). The reaction mixture was stirred at 65° C. for 15 h. After cooling to room temperature, the solvent was removed under reduced pressure. Water (30 mL) and conc. HCl (10 mL) were added and the mixture was stirred at 100° C. for 2 h and room temperature for 1 h. 2 N NaOH aqueous solution (100 mL) was added and the mixture was extracted with AcOEt (50 mL×3). The combined organic layers were dried over $K_2C_3$, filtered and concentrated. Column chromatography ($SiO_2$, 15% $CH_3OH$-5% $Et_3N$ in $CH_2Cl_2$) afforded 3-(aminomethyl)-1-(4-chlorobenzyl)pyrrolidine (860 mg, 19%) as a colorless oil.

Reference Example 10

Preparation of 1-(4-Chlorobenzyl)-3-{(glycylamino) methyl}pyrrolidine

A mixture of 3-(aminomethyl)-1-(4-chlorobenzyl) pyrrolidine (860 mg, 3.8 mmol), $Et_3N$ (5.7 mmol), N-tert-butoxycarbonylglycine (704 mg), EDCI (594 mg), HOBt (673 mg), and dichloromethane (20 mL) was stirred at room temperature for 15 h. Dichloromethane (50 mL) was added and the solution was washed with 2 N NaOH solution (50 mL×2), dried over anhydrous sodium sulfate, filtered, and concentrated to afford 3-[{N-(tert-butoxycarbonyl) glycyl}aminomethyl]-1(4chlorobenzyl)pyrrolidine (1.31 g, 90%).

To a solution of 3-[{N-(tert-butoxycarbonyl) glycyl}aminomethyl]-1-(4-chlorobenzyl)pyrrolidine (804 mg, 2.11 mmol) in methanol (10 mL) was added 4 N HCl in dioxane (5 mL). The solution was stirred at room temperature for 3.5 h. The reaction mixture was concentrated and 1 N NaOH solution (20 mL) was added. The mixture was extracted with dichloromethane (20 mL×3), and the combined extracts were dried over sodium sulfate and concentrated to give desired 1-(4-chlorobenzyl)-3-{(glycylamino) methyl}pyrrolidine (599 mg, 100%): The purity was determined by RPLC/MS (100%); ESI/MS m/e 282.2 ($M^+$+H, $C_{14}H_{20}ClN_3O$).

Example 936

Preparation of 3-[{N-(3-Trifluoromethylbenzoyl) glycyl}aminomethyl]-1-(4-chlorobenzyl)pyrrolidine (Compound No. 1463)

A solution of 3-(trifluoromethyl)benzoyl chloride (0.058 mmol) in dichloromethane (0.2 mL) was added to a mixture of 1-(4-chlorobenzyl)-3-{(glycylamino)methyl}pyrrolidine (0.050 mmol) and peperidinomethylpolystyrene (60 mg) in chloroform (0.2 mL) and dichloromethane (1 mL). After the reaction mixture was stirred at room temperature for 2.5 h, methanol (0.30 mL) was added and the mixture was stirred at room temperature for 1 h. The reaction mixture was loaded onto Varian™ SCX column, and washed with $CH_3OH$ (15 mL). Product was eluted off using 2 N $NH_3$ in $CH_3OH$ (5 mL) and concentrated to afford (3-[{N-(3-trifluoromethylbenzoyl)glycyl}aminomethyl]-1-(4-chlorobenzyl)pyrrolidine (Compound No. 1463) (22.4 mg, 99%): The purity was determined by RPLC/MS (97%); ESIJMS m/e 454.2 ($M^+$+H, $C_{22}H_{23}ClF_3N_3O_2$).

Examples 937–944

The compounds of this invention were synthesized pursuant to methods of Example 936 using the corresponding reactant respectively. The ESI/MS data and yields are summarized in Table 20.

TABLE 20

| | Compound No. | Molecular Formula | ESI/MS m/e | Yield (mg) | Yield (%) |
|---|---|---|---|---|---|
| Example 937 | 1464 | C22 H23 Cl F3 N3 O3 | 470.0 | 21.0 | 89 |
| Example 938 | 1465 | C23 H22 Cl F6 N3 O2 | 522.0 | 24.5 | 94 |
| Example 939 | 1466 | C21 H23 Br Cl N3 O2 | 466.0 | 20.8 | 90 |
| Example 940 | 1467 | C21 H23 Cl2 N3 O2 | 420.0 | 19.6 | 93 |
| Example 941 | 1468 | C21 H23 Cl N4 O4 | 431.2 | 19.5 | 91 |
| Example 942 | 1469 | C22 H22 Cl F4 N3 O2 | 472.0 | 21.8 | 92 |
| Example 943 | 1470 | C21 H22 Cl3 N3 O2 | 456.0 | 22.1 | 97 |
| Example 944 | 1471 | C21 H22 Cl F2 N3 O2 | 422.0 | 20.9 | 99 |

Example 945

Preparation of 3-[{N-(2-Amino-4,5-difluorobenzoyl)glycyl}aminomethyl]-1-(4-chlorobenzyl)pyrrolidine (Compound No. 1506)

A solution of 1-(4-chlorobenzyl)-3-{(glycylamino) methyl}pyrrolidine (0.050 mmol) in $CHCl_3$ (1.35 mL) and tert-butanol (0.05 mL) was treated with 2-amino-4,5-difluorobenzoic acid (0.060 mmol), diisopropylcarbodiimide (0.060 mmol), and HOBt (0.060 mmol). The reaction mixture was stirred at room temperature for 19 h. The mixture was loaded onto Varian™ SCX column, and washed with $CH_3OH/CHCl_3$ 1:1 (10 mL) and $CH_3OH$ (10 mL). Product was eluted off using 2 N $NH_3$ in $CH_3OH$ (5 mL) and concentrated to afford 3-[{N-(2-amino-4,5-difluorobenzoyl) glycyl}aminomethyl]-1-(4-chlorobenzyl)pyrrolidine (Compound No. 1506) (22.0 mg, quant): The purity was determined by RPLC/MS (92%); ESI/MS m/e 437 ($C_{21}H_{23}ClF_2N_4O_2$).

Examples 946–952

The compounds of this invention were synthesized pursuant to methods of Example 945 using the corresponding reactant respectively. The ESI/MS data and yields are summarized in Table 21.

TABLE 21

| | Compound No. | Molecular Formula | ESI/MS m/e | Yield (mg) | Yield (%) |
|---|---|---|---|---|---|
| Example 946 | 1506 | C21 24 Br Cl N4 O2 | 481 | 20.6 | 86 |
| Example 947 | 1507 | C21 H24 F Cl N4 O2 | 419 | 21.7 | quant |
| Example 948 | 1509 | C27 H28 Cl N3 O2 | 462 | 26.5 | quant |
| Example 949 | 1510 | C21 H24 Cl I N4 O2 | 527 | 22.0 | 84 |
| Example 950 | 1511 | C19 H21 Br Cl N3 O2 S | 472 | 23.7 | quant |
| Example 951 | 1512 | C21 H24 Cl2 N4 O2 | 435 | 22.3 | quant |
| Example 952 | 1513 | C27 H28 Cl N3 O4 S | 526 | 24.6 | 94 |

Reference Example 11

Preparation of 1-(4-Chlorobenzyl)nipecotic acid

4-Chlorobenzyl chloride (6.42 g, 39.9 mmol) and $^iPr_2NEt$ (7.74 g, 40.0 mmol) were added to a solution of ethyl nipecotate (6.29 g, 40.0 mmol) in $CH_3CN$ (15 mL). The reaction mixture was stirred at 70° C. for 1.5 h. The solvent was removed under reduced pressure. Saturated aqueous $NaHCO_3$ (50 mL) was added to the residue and the mixture was extracted with EtOAc (100 mL). The organic phase was washed with saturated aqueous $NaHCO_3$ and brine, and dried over $Na_2SO_4$. The solvent was removed under reduced pressure to afford ethyl 1-(4-chlorobenzyl)nipecotate as a red yellow oil (11.025 g, 97.8%) used without further purification. The purity was determined by RPLC/MS (97%); ESI/MS m/e 382.2 ($M^+$+H, $C_{15}H_{21}ClNO_2$).

A solution of LiOH (1.66 g) in $H_2O$ (25 mL) was added to the solution of ethyl 1-(4-chlorobenzyl)nipecotate in THF (60 mL) and $CH_3OH$ (20 mL). The reaction mixture was stirred at room temperature for 15 h. The solvent was removed under reduced pressure to afford an amorphous solid which was purified by column chromatography ($SiO_2$, 50% $CH_3OH$—$CH_2Cl_2$) to yield 1-(4-chlorobenzyl) nipecotic acid (9.75 g, 98.2%) as a pale yellow amorphous solid. The purity was determined by RPLC/MS (>95%); ESI/MS m/e 254.0 ($M^+$+H, $C_{13}H_{17}ClNO_2$).

Reference Example 12

Preparation of 1-(4-Chlorobenzyl)-3-{(tert-butoxycarbonyl)amino}piperidine

A solution of 1-(4-chlorobenzyl)nipecotic acid (7.06 g, 27.8 mmol) in $^t$BuOH (500 mL) was treated with $Et_3N$ (3.38 g) and activated 3 A molecular sieves (30 g). Diphenylphosphoryl azide (8.58 g) was added, and the reaction mixture was warmed at reflux for 18 h. The mixture was cooled and the solvent was ref for 18 h. The mixture was cooled and the solvent was remove under vacuum. Tie residue was dissolved in EtOAc (500 mL), and the organic phase was washed with saturated aqueous $NaHCO_3$ (2×100 mL) and brine (50 mL), dried ($Na_2SO_4$), and concentrated in vacuo. Chromatography ($SiO_2$, 25% EtOAc-hexane) afforded 1-(4-chlorobenzyl)-3-{(tert-butoxycarbonyl)amino}piperidine (2.95 g, 32.6%) as a white crystalline solid: $^1$H NMR ($CDCl_3$, 300 MHz) δ1.4–1.75 (br, 4 H), 2.2–2.7 (br, 4 H), 3.5 (br, 2 H), 3.8 (br, 1 H), 7.3 (br, 4 H); The purity was determined by RPLC/MS (>99%); ESI/MS m/e 269.2 ($M^+$+H–56, $C_{17}H_{26}ClN_2O_2$).

Reference Example 13

Preparation of 3-Amino-1-(4-chlorobenzyl) piperidine

A solution of 1-(4-chlorobenzyl)-3-{(tert-butoxycarbonyl)amino}piperidine (2.55 g, 7.85 mmol) in $CH_3OH$ (25 mL) was treated with 1 N HCl-$Et_2O$ (50 mL). The reaction mixture was stirred at 25° C. for 15 h. The solvent was removed under reduced pressure to afford 3-amino-1-(4-chlorobenzyl)piperidine dihydrochloride as an amorphous solid (2.49 g, quant). The purity was determined by RPLC/MS (>95%),; ESI/MS m/e 225.2 ($M^+$+H, $C_{12}H_{18}ClN_2$).

Example 953

Preparation of 1-(4-Chlorobenzyl)-3-[{N-(3-methylbenzoyl)glycyl}amino]piperidine (Compound No. 355)

N-(3-Methylbenzoyl)glycine (10.6 mg, 0.055 mmol), EDCI (10.5 mg) and 1-hydroxybenzotriazole hydrate (7.4 mg) were added to a solution of 1-(4-chlorobenzyl)-3-aminopiperidine dihydrochloride (14.9 mg, 0.050 mmol) and $Et_3N$ (15.2 mg) in $CHCl_3$ (2.5 mL). The reaction mixture was stirred at 25° C. for 16 h, washed with 2 N aqueous NaOH (2 mL×2) and brine (1 mL). After filtration through PTFE membrane filter, the solvent was removed under reduced pressure to afford 1-(4-chlorobenzyl)-3-[{N-(3-methylbenzoyl)glycyl}amino]piperidine (compound No. 355) as a pale yellow oil (17.4 mg, 87%): The purity was determined by RPLC/MS (97%); ESI/MS m/e 400.0 ($M^+$+H, $C_{22}H_{26}ClN_3O_2$).

Examples 954–982

The compounds of this invention were synthesized pursuant to methods of Example 953 using the corresponding reactant respectively. The ESI/MS data and yields are summarized in Table 22 and compound No. 358 showed the following $^1$H NMR spectra.

TABLE 22

| | Compound No. | Molecular Formula | ESI/MS m/e | Yield (mg) | Yield (%) |
|---|---|---|---|---|---|
| Example 954 | 354 | C21 H24 Cl N3 O2 | 386 | 16.1 | 83 |
| Example 955 | 356 | C20 H23 Cl N4 O2 | 387 | 19.4 | 100 |
| Example 956 | 357 | C22 H26 Cl N3 O2 | 400 | 16.8 | 84 |
| Example 957 | 359 | C22 H26 Cl N3 O2 | 400 | 8.9 | 17 |
| Example 958 | 360 | C22 H25 Cl N4 O4 | 445 | 25.6 | quant |
| Example 959 | 361 | C23 H27 Cl N2 O2 | 399 | 15.5 | 29 |
| Example 960 | 362 | C24 H29 Cl N2 O3 | 429 | 12.4 | 58 |
| Example 961 | 363 | C21 H25 Cl N2 O2 S | 405 | 22.2 | quant |
| Example 962 | 364 | C24 H29 Cl N2 O4 | 445 | 20.7 | 93 |
| Example 963 | 365 | C24 H29 Cl N2 O2 | 413 | 15.6 | 75 |
| Example 964 | 366 | C23 H26 Cl F N2 O3 | 433 | 21.6 | 100 |
| Example 965 | 367 | C23 H27 Cl N2 O2 | 399 | 11.9 | 60 |
| Example 966 | 368 | C22 H25 Cl N2 O2 | 385 | 16.0 | 83 |
| Example 967 | 369 | C22 H24 Cl2 N2 O2 | 419 | 13.9 | 60 |
| Example 968 | 370 | C26 H33 Cl N2 O3 | 457 | 15.9 | 54 |
| Example 969 | 371 | C25 H31 Cl N2 O3 | 443 | 19.6 | 84 |
| Example 970 | 372 | C21 H25 Cl N2 O3 S | 421 | 23.0 | quant |
| Example 971 | 373 | C23 H28 Cl N3 O2 | 414 | 19.1 | 92 |
| Example 972 | 374 | C24 H30 Cl N3 O3 | 444 | 18.6 | 84 |
| Example 973 | 375 | C23 H27 Cl2 N3 O2 | 448 | 18.0 | 80 |
| Example 974 | 376 | C24 H30 Cl N3 O3 | 444 | 19.6 | 88 |
| Example 975 | 377 | C25 H31 Cl2 N3 O2 | 476 | 20.7 | 87 |
| Example 976 | 378 | C27 H33 Cl F N3 O2 | 486 | 23.9 | 98 |
| Example 977 | 379 | C25 H30 Cl N3 O3 | 456 | 33.3 | quant |
| Example 978 | 380 | C24 H30 Cl N3 O2 | 428 | 9.8 | 46 |
| Example 979 | 381 | C21 H26 Cl N3 O3 S | 436 | 10.3 | 47 |
| Example 980 | 382 | C22 H26 Cl N3 O3 | 416 | 24.4 | quant |
| Example 981 | 383 | C22 H25 Cl2 N3 O3 | 450 | 27.5 | quant |

Example 982

Compound No. 358: 88%; $^1$H NMR ($CDCl_3$) δ1.53–1.75 (m, 4 H), 2.12–2.20 (m, 1 H), 2.37–2.50 (m, 2 H), 2.53–2.61 (m, 1 H), 3.38–3.50 (m, 2 H), 2.53–2.61 (m, 1 H), 3.38–3.50 (m, 2 H), 4.06–4.20 (m, 3 H), 7.10–7.13 (m, 1 H), 7.18–7.30 (m, 4 H), 7.59 (t, J=7.8 Hz, 1 H), 7.79 (d, J=7.8 Hz, 1 H), 8.01 (d, J=7.8 Hz, 1 H), 8.11 (s, 1 H).

Reference Example 14

Preparation of 1-benzyl-4-[{N-(tert-butoxycarbonyl) glycyl}amino]piperidine

A solution of 4-amino-1-benzylpiperidine (3.80 g, 20 mmol) in $CH_2Cl_2$ (40 mL) was treated with N-(tert-butoxycarbonyl)glycine (3.48 g, 20 mmol), EDCI (4.02 g, 21 mmol) and HOBt (2.83 g, 21 mmol). After the reaction mixture was stirred at room temperature for 12 h, 2 N NaOH solution (20 mL) was added. The organic layer was separated, and the aqueous layer was extracted with dichloromethane (20 mL×2). The combined organic layers were washed with water (20 mL) and brine (20 mL), dried over anhydrous sodium sulfate, filtered, and concentrated. Column chromatography ($SiO_2$, ethyl acetate/MeOH/$Et_3N$=85/12/3) afforded 1-benzyl-4-{N-(tert-butoxycarbonyl) glycyl}aminopiperidine (6.59 g, 95.1).

Reference Example 15

Preparation of 1-(4-Chlorobenzyl)-4-(glycylamino) piperidine

To a solution of 1-benzyl-4-{N-(tert-butoxycarbonyl) glycyl}aminopiperidine (6.59 g) in methanol (80 mL) was added 4 N HCl in dioxane (19 mL). The solution was stirred at room temperature for 2 h. The reaction mixture was concentrated and 2 N aqueous NaOH solution (20 mL) was added. The mixture was extracted with dichloromethane (40 mL×3), and the combined extracts were dried over anhydrous sodium sulfate and concentrated. Column chromatography ($SiO_2$, AcOEt/MeOH/$Et_3N$=85/12/3) gave 1-(4-chlorobenzyl)-4-(glycylamino)piperidine (3.91 g, 83%): $^1H$ NMR ($CDCl_3$, 400 MHz) d 1.47–1.59 (m, 2 H), 1.59 (br, 2 H), 1.76–1.96 (m, 2 H), 2.10–2.19 (m, 2 H), 2.75–2.87 (m, 2 H), 3.29 (s, 2 H), 3.50 (s, 2 H), 3.65–3.89 (m, 1 H), 7.15–7.23 (m, 1 H), 7.23–7.33 (mn, 5 H).

Other 4-acylamino-1-benzylpiperidines were also synthesized pursuant to methods of Reference Example 13 and 14 using the corresponding reactant respectively.

4-(β-alanylamino)-1-benzylpiperidine: 2.46 g, 51% (2 steps).
1-benzyl-4-((S)-leucylamino)piperidine: 1.78 g, 74% (2 steps).
1-benzyl-4-((R)-leucylamino)piperidine: 1.48 g, 61% (2 steps).

Example 983

Preparation of 4-(N-benzoylglycyl)amino-1-benzylpiperidine (Compound No. 386)

A solution of benzoyl chloride (0.060 mmol) in chloroform (0.4 mL) was added to a solution of 1-(4-chlorobenzyl)-4-(glycylamino)piperidine (0.050 mmol) and triethylamine (0.070 mmol) in chloroform (1.0 mL). After the reaction mixture was agitated at room temperature for 2.5 h, (aminomethyl)polystyrene resin (1.04 mmol/g, 50 mg, 50 mmol) was added and the mixture was agitated at room temperature for 12 h. The reaction mixture was filtered and the resin was washed with dichloromethane (0.5 mL). The filtrate and washing were combined, dichloromethane (4 mL) was added, and the solution was washed with 2 N aqueous NaOH solution (0.5 mL) to give 4-(N-benzoylglycyl)amino-1-benzylpiperidine (compound No. 386) (11.3 mg, 64%): The purity was determined by RPLC/MS (94%); ESI/MS m/e 352.0 ($M^+$+H, $C_{21}H_{25}N_3O_2$).

Examples 984–1034

The compounds of this invention were synthesized pursuant to methods of Example 983 using the corresponding reactant respectively. The ESI/MS data and yields are summarized in Table 23.

TABLE 23

| | Compound No. | Molecular Formula | ESI/MS m/e | Yield (mg) | Yield (%) |
|---|---|---|---|---|---|
| Example 984 | 384 | C22 H26 Cl N3 O2 | 400 | 60.0 | quant |
| Example 985 | 385 | C21 H23 Cl N4 O4 | 431 | 58.7 | 91 |
| Example 986 | 387 | C25 H27 N3 O2 | 402.5 | 15.5 | 77 |
| Example 987 | 388 | C21 H24 N4 O4 | 397.0 | 16.2 | 82 |
| Example 988 | 389 | C23 H27 N3 O4 | 410.0 | 16.2 | 79 |
| Example 989 | 390 | C22 H24 F3 N3 O2 | 420.0 | 17.4 | 83 |
| Example 990 | 391 | C22 H23 F4 N3 O2 | 438.0 | 18.4 | 84 |
| Example 991 | 392 | C22 H24 F3 N3 O3 | 436.0 | 17.1 | 79 |
| Example 992 | 393 | C21 H24 Br N3 O2 | 430.0 | 18.0 | 84 |
| Example 993 | 394 | C21 H24 Cl N3 O2 | 386.0 | 16.4 | 85 |
| Example 994 | 395 | C21 H24 Br N3 O2 | 430.0 | 17.2 | 80 |
| Example 995 | 396 | C21 H23 F2 N3 O2 | 388.0 | 15.1 | 78 |
| Example 996 | 397 | C21 H23 Cl2 N3 O2 | 420.0 | 11.7 | 56 |
| Example 997 | 398 | C22 H27 N3 O2 | 366.0 | 13.1 | 72 |
| Example 998 | 399 | C26 H29 N3 O2 | 416.0 | 15.8 | 76 |
| Example 999 | 400 | C22 H26 N4 O4 | 411.0 | 17.4 | 85 |
| Example 1000 | 401 | C24 H29 N3 O4 | 424.0 | 16.9 | 80 |
| Example 1001 | 402 | C23 H26 F3 N3 O2 | 434.0 | 17.7 | 82 |
| Example 1002 | 403 | C23 H25 F4 N3 O2 | 452.0 | 18.6 | 82 |
| Example 1003 | 404 | C23 H26 F3 N3 O3 | 450.0 | 17.8 | 79 |
| Example 1004 | 405 | C22 H26 Br N3 O2 | 444.0 | 17.9 | 81 |
| Example 1005 | 406 | C22 H26 Cl N3 O2 | 400.0 | 15.5 | 78 |
| Example 1006 | 407 | C22 H26 Br N3 O2 | 444.0 | 17.8 | 80 |
| Example 1007 | 408 | C22 H25 F2 N3 O2 | 402.0 | 15.6 | 78 |
| Example 1008 | 409 | C22 H25 Cl2 N3 O2 | 434.0 | 17.6 | 81 |
| Example 1009 | 410 | C25 H33 N3 O2 | 408.0 | 16.2 | 79 |
| Example 1010 | 411 | C29 H35 N3 O2 | 458.5 | 18.8 | 82 |
| Example 1011 | 412 | C25 H32 N4 O4 | 453.0 | 19.4 | 86 |
| Example 1012 | 413 | C27 H35 N3 O4 | 466.0 | 19.8 | 85 |
| Example 1013 | 414 | C26 H32 F3 N3 O2 | 476.0 | 20.2 | 85 |
| Example 1014 | 415 | C26 H31 F4 N3 O2 | 494.0 | 20.5 | 83 |
| Example 1015 | 416 | C26 H32 F3 N3 O3 | 492.0 | 19.5 | 79 |
| Example 1016 | 417 | C25 H32 Br N3 O2 | 486.0 | 19.1 | 79 |
| Example 1017 | 418 | C25 H32 Cl N3 O2 | 442.0 | 17.7 | 80 |
| Example 1018 | 419 | C25 H32 Br N3 O2 | 486.0 | 20.3 | 83 |
| Example 1019 | 420 | C25 H31 F2 N3 O2 | 444.0 | 18.6 | 84 |
| Example 1020 | 421 | C25 H31 Cl2 N3 O2 | 476.0 | 19.4 | 81 |
| Example 1021 | 422 | C25 H33 N3 O2 | 408.0 | 14.4 | 71 |
| Example 1022 | 423 | C29 H35 N3 O2 | 458.0 | 16.4 | 72 |
| Example 1023 | 424 | C25 H32 N4 O4 | 453.0 | 18.1 | 80 |
| Example 1024 | 425 | C27 H35 N3 O4 | 466.0 | 16.4 | 70 |
| Example 1025 | 426 | C26 H32 F3 N3 O2 | 476.0 | 17.3 | 73 |
| Example 1026 | 427 | C26 H31 F4 N3 O2 | 494.0 | 18.8 | 76 |
| Example 1027 | 428 | C26 H32 F3 N3 O3 | 492.0 | 18.4 | 75 |
| Example 1028 | 429 | C25 H32 Br N3 O2 | 486.0 | 17.9 | 74 |
| Example 1029 | 430 | C25 H32 Cl N3 O2 | 442.0 | 15.7 | 71 |
| Example 1030 | 431 | C25 H32 Br N3 O2 | 486.0 | 17.7 | 73 |
| Example 1031 | 432 | C25 H31 F2 N3 O2 | 444.0 | 16.6 | 75 |
| Example 1032 | 433 | C25 H31 Cl2 N3 O2 | 476.0 | 18.7 | 78 |
| Example 1033 | 1016 | C22 H23 Cl F3 N3 O2 | 454 | 32.5* | 53 |
| Example 1034 | 1017 | C21 H24 Cl N3 O2 | 386 | 55.2* | quant |

*Yield of TFA salt.

Reference Example 16

Preparation of 3-Carbamoyl-1-(4-chlorobenzyl) piperidine

A solution of nipecotamide (6.40 g, 50 mmol) in $CH_3CN$ (150 mL) and ethanol (20 mL) was treated with $Et_3N$ (7.0 mL, 50 mmol) and 4-chlorobenzyl chloride (8.05 g, 50 mmol). The reaction mixture was stirred at 50° C. for 16 h. After cooling to room temperature, saturated aqueous $NaHCO_3$ (50 mL) and water (150 mL) was added to the reaction mixture. The mixture was extracted with ethyl acetate (150 mL×3) and the combined organic layers were washed with brine, dried ($Na_2SO_4$) and concentrated to give a pale red solid. The crude solid was washed with ether (100 mL) to afford 3-carbamoyl-1-(4-chlorobenzyl)piperidine (6.98 g, 54%).

Reference Example 17

Preparation of 3-(Aminomethyl)-1-(4-chlorobenzyl) piperidine

3-Carbamoyl-1-(4-chlorobenzyl)piperidine (3.80 g, 15 mmol) was dissolved in THF (30 mL) and 1 M $BH_3$-THF (9.4 mL) was added to the solution. The reaction mixture was stirred at 70° C. for 15 h. After the mixture was cooled to 0° C., 2 N aqueous HCl solution (50 mL) was added and the mixture was stirred at room temperature for additional 3 h, basicified with 4 N aqueous NaOH solution, and extracted with ethyl acetate (100 mL×3). The combined extracts were washed with brine, dried over anhydrous $Na_2SO_4$, filtered and concentrated. Column chromatography ($SiO_2$, ethyl acetate/EtOH/$Et_3N$=80/15/5) afforded 3-(aminomethyl)-1-(4-chlorobenzyl)piperidine (2.05 g, 55%): $^1H$ NMR ($CDCl_3$, 400 MHz) δ1.00–1.09 (m, 1 H), 1.50–1.87 (m, 7 H), 1.97–2.06 (m, 1 H), 2.65–2.77 (m, 2 H), 3.16–3.26 (m, 2 H), 3.32 (s, 2 H), 3.40. (d, J=13.3 Hz, 1 H), 3.49 (d, J=13.3 Hz, 1 H), 7.22–7.33 (m, 5 H).

Example 1035

Preparation of 3-{(N-Benzoylglycyl)amino}methyl-1-(4-chlorobenzyl)piperidine (Compound No. 434)

A solution of benzoyl chloride (0.060 mmol) in chloroform (0.4 mL) was added to a solution of 3-(aminomethyl)-1-(4-chlorobenzyl)piperidine (0.050 mmol) and triethylamine (0.070 mmol) in chloroform (1.0 mL). After the reaction mixture was agitated at room temperature for 2.5 h, (aminomethyl)polystyrene resin (1.04 mmol/g, 50 mg, 50 mmol) was added and the mixture was agitated at room temperature for 12 h. The reaction mixture was filtered and the resin was washed with dichloromethane (0.5 mL). The filtrate and washing were combined, dichloromethane (4 mL) was added, and the solution was washed with 2 N aqueous NaOH solution (0.5 mL) to give 3-{(N-benzoylglycyl)amino}methyl-1-(4-chlorobenzyl)piperidine (compound No. 434) (14.7 mg, 74%): The purity was determined by RPLC/MS (91%); ESI/MS m/e 400 ($M^+$+H, $C_{22}H_{26}ClN_3O_2$).

Examples 1036–1058

The compounds of this invention were synthesized pursuant to methods of Example 1035 using the corresponding reactant respectively. The ESI/MS data and yields are summarized in Table 24.

TABLE 24

| | Compound No. | Molecular Formula | ESI/MS m/e | Yield (mg) | Yield (%) |
|---|---|---|---|---|---|
| Example 1036 | 435 | C26 H28 Cl N3 O2 | 450 | 16.0 | 71 |
| Example 1037 | 436 | C22 H25 Cl N4 O4 | 445 | 18.9 | 85 |
| Example 1038 | 437 | C24 H28 Cl N3 O4 | 458 | 18.2 | 79 |
| Example 1039 | 438 | C23 H25 Cl F3 N3 O2 | 468 | 19.0 | 81 |
| Example 1040 | 439 | C23 H24 Cl F4 N3 O2 | 486 | 20.2 | 83 |
| Example 1041 | 440 | C23 H25 Cl F3 N3 O3 | 484 | 18.9 | 78 |
| Example 1042 | 441 | C22 H25 Br Cl N3 O2 | 478 | 19.2 | 80 |
| Example 1043 | 442 | C22 H25 Cl2 N3 O2 | 434 | 17.3 | 80 |
| Example 1044 | 443 | C22 H25 Br Cl N3 O2 | 478 | 18.8 | 79 |
| Example 1045 | 444 | C22 H24 Cl F2 N3 O2 | 436 | 16.7 | 77 |
| Example 1046 | 445 | C22 H24 Cl3 N3 O2 | 468 | 17.9 | 76 |
| Example 1047 | 446 | C23 H28 Cl N3 O2 | 414 | 14.6 | 71 |
| Example 1048 | 447 | C27 H30 Cl N3 O2 | 464 | 17.0 | 73 |
| Example 1049 | 448 | C23 H27 Cl N4 O4 | 459 | 19.5 | 85 |

TABLE 24-continued

| | Compound No. | Molecular Formula | ESI/MS m/e | Yield (mg) | Yield (%) |
|---|---|---|---|---|---|
| Example 1050 | 449 | C25 H30 Cl N3 O4 | 472 | 17.1 | 72 |
| Example 1051 | 450 | C24 H27 Cl F3 N3 O2 | 482 | 19.4 | 81 |
| Example 1052 | 451 | C24 H26 Cl F4 N3 O2 | 500 | 18.2 | 73 |
| Example 1053 | 452 | C24 H27 Cl F3 N3 O3 | 498 | 18.8 | 76 |
| Example 1054 | 453 | C23 H27 Br Cl N3 O2 | 492 | 19.4 | 79 |
| Example 1055 | 454 | C23 H27 Cl2 N3 O2 | 448 | 16.5 | 74 |
| Example 1056 | 455 | C23 H27 Br Cl N3 O2 | 492 | 19.3 | 78 |
| Example 1057 | 456 | C23 H26 Cl F2 N3 O2 | 450 | 17.1 | 76 |
| Example 1058 | 457 | C23 H26 Cl3 N3 O2 | 482 | 16.9 | 70 |

Reference Example 18

Preparation of 4-(Aminomethyl)-1-(4-chlorobenzyl) piperidine

A solution of 4-(aminomethyl)piperidine (7.00 g, 61.3 mmol) in $CH_3CN$ (100 mL) was treated sequentially with $K_2CO_3$ (3.02 g) and 4-chlorobenzyl chloride (3.52 g, 21.8 mmol). The reaction mixture was heated to 60° C. for 16 h, cooled to 25° C. and concentrated. The residue was partitioned between $CH_2Cl_2$ (75 mL) and water (50 mL), and was washed with water (2×50 mL) and brine (1×50 mL). The organic phase was dried ($MgSO_4$) and concentrated. Chromatography ($SiO_2$, 4% $H_2O$-$^i$PrOH) afforded 4-(aminomethyl)-1-(4-chlorobenzyl)piperidine (3.58 g, 69%).

Example 1059

Preparation of 4-{(N-Benzoylglycyl)amino}methyl-1-(4-chlorobenzyl)piperidine (Compound No. 458)

A solution of 4-(aminomethyl)-1-(4-chlorobenzyl) piperidine (50 mg, 0.21 mmol) in $CH_2Cl_3$ (1 mL) was treated with hippuric acid (38 mg, 0.21 mmol), EDCI (48 mg, 0.24 mmol), HOBt (31 mg, 0.23 mmol) and $Et_3N$ (38 μL, 0.27 mmol). The reaction mixture was stirred for 16 h at 25° C., diluted with 1 mL of $CH_2Cl_2$, washed with 2 N aqueous NaOH solution (2×0.75 mL), dried ($MgSO_4$) and concentrated. Chromatography ($SiO_2$, 6 to 8% $CH_3OH$/$CH_3Cl_2$ gradient elution) afforded 4-{(N-benzoylglycyl) amino}methyl-1-(4-chlorobenzyl)piperidine (compound No. 458) which was treated with TFA to give a TFA salt (105 mg, 97%): The purity was determined by RPLC/MS (85%); ESI/MS m/e 400 ($M^+$+H, $C_{22}H_{26}ClN_3O_2$).

Examples 1060–1086

The compounds of this invention were synthesized pursuant to methods of Example 1059 using the corresponding reactant respectively. The ESI/MS data and yields are summarized in Table 25.

TABLE 25

| | Compound No. | Molecular Formula | ESI/MS m/e | Yield (mg) | Yield (%) |
|---|---|---|---|---|---|
| Example 1060 | 459 | C23 H28 Cl N3 O2 | 414 | 86* | 78 |
| Example 1061 | 460 | C23 H28 Cl N3 O2 | 414 | 55 | quant |
| Example 1062 | 461 | C23 H25 Cl F3 N3 O2 | 468 | 65 | quant |

TABLE 25-continued

| | Compound No. | Molecular Formula | ESI/MS m/e | Yield (mg) | Yield (%) |
|---|---|---|---|---|---|
| Example 1063 | 462 | C23 H28 Cl N3 O2 | 414 | 61 | quant |
| Example 1064 | 463 | C23 H28 Cl N3 O2 | 414 | 54 | quant |
| Example 1065 | 464 | C25 H32 Cl N3 O5 | 490 | 56 | quant |
| Example 1066 | 465 | C21 H 25 Cl N4 O2 | 401 | 38 | 96 |
| Example 1067 | 466 | C22 H25 Cl N4 O4 | 445 | 15 | 34 |
| Example 1068 | 557 | C23 H28 Cl N3 O2 | 414 | 58* | 66 |
| Example 1069 | 558 | C23 H 28 Cl N3 O2 | 414 | 55 | quant |
| Example 1070 | 618 | C25 H32 Cl N3 O2 | 442 | 58 | quant |
| Example 1071 | 686 | C26 H34 Cl N3 O2 | 456 | 62 | quant |
| Example 1072 | 749 | C34 H37 Cl N4 O2 | 569 | 7.2* | 18 |
| Example 1073 | 750 | C24 H30 Cl N3 O3 | 444 | 4.7* | 14 |
| Example 1074 | 840 | C24 H29 Cl N2 O2 | 413 | 52* | 58 |
| Example 1075 | 841 | C23 H27 Cl N2 O2 | 399 | 52 | quant |
| Example 1076 | 842 | C23 H26 Cl2 N2 O2 | 433 | 55 | quant |
| Example 1077 | 843 | C25 H31 Cl N2 O2 | 427 | 58 | quant |
| Example 1078 | 844 | C24 H29 Cl N2 O2 | 413 | 56 | quant |
| Example 1079 | 845 | C24 H29 Cl N2 O4 S | 477 | 62 | quant |
| Example 1080 | 846 | C29 H31 Cl N2 O3 | 491 | 43 | 88 |
| Example 1081 | 847 | C24 H28 Cl F N2 O3 | 447 | 54 | quant |
| Example 1082 | 848 | C25 H31 Cl N2 O2 | 427 | 47 | quant |
| Example 1083 | 849 | C25 H31 Cl N2 O4 | 459 | 55 | quant |
| Example 1084 | 850 | C22 H27 Cl N2 O3 S | 435 | 46 | quant |
| Example 1085 | 873 | C20 H28 Cl N3 O2 | 378 | 44.8 | quant |
| Example 1086 | 874 | C23 H27 Cl2 N3 O3 | 464 | 51 | quant |

*Yield of TFA salt.

Reference Example 19

Preparation of 1-(4-Chlorobenzyl)-4-{N-(3,3-diphenylpropyl)aminomethyl}piperidine 4-(Aminomethyl)-1-(4-chlorobenzyl)piperidine (120 mg) was alkylated with 3,3-diphenylpropyl methanesulfonate (1.0 equiv.) in the presence of NaI (2.6 equiv.) in $CH_3CN$ at 70° C. for 16 h. General workup and column chromatography ($SiO_2$) afforded 1-(4-chlorobenzyl)-4-{N-(3,3-diphenylpropyl)aminomethyl}piperidine (118 mg, 54%): The purity was determined by RPLC (98%).

Reference Example 20

Preparation of 1-(4-Chlorobenzyl)-4-{N-(2,2-diphenylethyl)aminomethyl}piperidine Reductive amination of 4-(aminomethyl)-1-(4-chlorobenzyl)piperidine (120 mg) with 2,2-diphenylacetaldehyde (0.66 equiv.) and polymer-supported borohydride in methanol at 25° C. for 16 h, followed by general workup and column chromatography ($SiO_2$) afforded 1-(4-chlorobenzyl)-4-{N-(2,2-diphenylethyl) aminomethyl}piperidine (70 mg, 49%): The purity was determined by RPLC (98%).

Example 1087

Preparation of 4-{N-(N-Benzoylglycyl)-N-(2,2-diphenylethyl)aminomethyl}-1-(4-chlorobenzyl) piperidine (Compound No. 524)

A solution of 1-(4-chlorobenzyl)-4-{N-(2,2-diphenylethyl)aminomethyl}piperidine (0.084 mmol) in $CH_2Cl_2$ was treated with hippuric acid (1.1 equiv.), HBTU (1.1 equiv.), HOBt (1.1 equiv.). The reaction mixture was stirred at 40° C. for 24 h. General workup and preparative TLC ($SiO_2$) afforded 4-{N-(N-benzoylglycyl)-N-(2,2-diphenylethyl)aminomethyl)}-1-(4-chlorobenzyl)piperidine (Compound No. 524) (8.5 mg, 17%): The purity was determined by RPLC/MS (98%); ESI/MS m/e 580 ($M^+$+H, $C_{36}H_{38}ClN_3O_2$).

Examples 1088–1090

The compounds of this invention were synthesized pursuant to methods of Example 1087 using the corresponding reactant respectively. The ESI/MS data and yields are summarized in Table 26.

TABLE 26

| | Compound No. | Molecular Formula | ESI/MS m/e | Yield (mg) | Yield (%) |
|---|---|---|---|---|---|
| Example 1088 | 521 | C38 H39 Cl F3 N3 O2 | 662 | 5.5 | 10 |
| Example 1089 | 522 | C37 H37 Cl F3 N3 O2 | 648 | 8.6 | 16 |
| Example 1090 | 523 | C37 H40 Cl N3 O2 | 594 | 4.8 | 10 |

Reference Example 21

Preparation of 1-(4-Chlorobenzyl)-4-{(valylamino) methyl}piperidine

A solution of 4-(aminomethyl)-1-(4-chlorobenzyl) piperidine (1.0 g, 4.2 mmol) in $CH_2Cl_2$ (21 mL) was treated with $Et_3N$ (0.76 mL, 5.44 mmol), dl-N-(tert-butoxycarbonyl)valine (1.09 g, 5.03 mmol), EDCI (883 mg, 4.61 mmol) and HOBt (623 mg, 4.61 mmol). The reaction mixture was stirred at 25° C. for 16 h. The resulting solution was diluted with $CH_2Cl_2$ (20 mL), and washed with 2 N NaOH solution (2x20 mL), brine (1x20 mL) and dried ($MgSO_4$). Concentration and chromatography ($SiO_2$, 3% $CH_3OH/CH_2Cl_2$) afforded 1-(4-chlorobenzyl)-4-[{(N-Boc-valyl)amino}methyl]piperidine (1.1 g, 60%) as a pale amber oil: ESI/MS m/e 438 ($M^+$+H).

1-(4-Chlorobenzyl)-4-[{(N-Boc-valyl)amino}methyl] piperidine (1.1 g, 2.51 mmol) was dissolved in 3 M HCl-$CH_3OH$ solution (25 mL) and stirred at 25° C. for 1 h. The reaction mixture was concentrated and the resulting salt was dissolved in 3:1 $^t$BuOH-$H_2O$ (25 mL). Anion ($OH^-$) exchange resin was added until the solution was slightly basic. Filtration and concentration afforded 1-(4-chlorobenzyl)-4-{(valylamino)methyl}piperidine (819 mg, 97%) which required no further purification: RPLC (97%); ESI/MS 338.1 ($M^+$+H, $C_{18}H_{28}ClN_3O$).

Other 4-{(acylamino)methyl)-1-(4-chlorobenzyl}piperidines were also synthesized pursuant to methods of Reference Example 20 using the corresponding reactant respectively.

1-(4-chlorobenzyl)-4-{(glycylamino)methyl}piperidine: 0.830 g, 67% (2 steps); ESI/MS 269 ($M^+$+H).

1-(4-chlorobenzyl)-4-{(serylamino)methyl}piperidine: 0.286 g, 20% (2 steps); ESI/MS 326 ($M^+$+H).

4-{(alanylamino)methyl}-1-(4-chlorobenzyl)piperidine: 1.20 g, 65% (2 steps); ESI/MS 310 ($M^+$+H).

1-(4-chlorobenzyl)-4-{(prolylamino)methyl}piperidine: 1.48 g, 86% (2 steps); ESI/MS 336 ($M^+$+H).

1-(4-chlorobenzyl)-4-{(glutaminylamino)methyl}piperidine: 0.830 g, 27% (2 steps); ESI/MS 367 ($M^+$+H).

1-(4-chlorobenzyl)-4-{((2-methylalanyl)amino)methyl}piperidine: 2.24 g, 62% (2 steps); ESI/MS 324 ($M^+$+H).

1-(4-chlorobenzyl)-4-{((O-methylseryl)amino)methyl}piperidine: 0.686 g, 38% (2 steps); ESI/MS 340 ($M^+$+H).

1-(4-chlorobenzyl)-4-{((1-aminocyclopropylcarbonyl)amino)methyl}piperidine: 2.03 g, 82% (2 steps); ESI/MS 322 ($M^+$+H).

1-(4-chlorobenzyl)-4-{(leucylamino)methyl}piperidine: 1.30 g, 58% (2 steps); ESI/MS 352 ($M^+$+H).

1-(4-chlorobenzyl)-4-{((O-benzylseryl)amino)methyl}piperidine: 1.34 g, 56% (2 steps); ESI/MS 416 ($M^+$+H).

Reference Example 22

Preparation of 1-(tert-Butoxycarbonyl)-4-[{N-(9-fluorenylmethyloxycarbonyl)glycyl}aminomethyl]piperidine A solution of 4-(aminomethyl)-1-(tert-butoxycarbonyl)piperidine (5.72 g) in $CH_2Cl_2$ (150 mL) was treated with $Et_3N$ (3.51 g), N-(9-fluorenylmethyloxycarbonyl)glycine (7.93 g, 26.7 mmol), EDCI (3.80 g) and HOBt (4.33 g). After the reaction mixture was stirred at room temperature for 5 h, the mixture was washed with water (100 mL×3) and brine (100 mL×2), dried over anhydrous sodium sulfate, filtered, and concentrated. Recrystallization from $CH_3CN/CH_3OH$ (150 mL/1 mL) at 0° C. afforded 1-(tert-Butoxycarbonyl)-4-[{N-(9-fluorenylmethyloxycarbonyl)glycyl}aminomethyl]piperidine (5.75 g, 44%) as pale yellow crystals.

Reference Example 23

Preparation of 4-[{N-(9-Fluorenylmethyloxycarbonyl)glycyl}aminomethyl]piperidine To 1-(tert-Butoxycarbonyl)-4-[{N-(9-fluorenylmethyloxycarbonyl)glycyl}aminomethyl]piperidine (3.17 g, 6.42 mmol) was added 4 N HCl in dioxane (50 mL). The solution was stirred at room temperature for 5 h. The reaction mixture was concentrated to give 4-[{N-(9-fluorenylmethyloxycarbonyl)glycyl}aminomethyl]piperidine (3.85 g) as a white solid. The product was used without further purification.

Reference Example 24

Preparation of 4-[{N-(9-Fluorenylmethyloxycarbonyl)glycyl}aminomethyl]-1-(4-methylthiobenzyl)piperidine To A solution of 4-[{N-(9-fluorenylmethyloxycarbonyl)glycyl}aminomethyl]piperidine (1.00 g, 2.33 mmol) in 1% AcOH/DMF (15 mL) were added 4-methylthiobenzaldehyde (1.24 g) and NaBH (OAc): (2.56 g). The reaction mixture was stirred at 60° C. for 1 h, cooled to room temperature, and concentrated. Saturated aqueous $NaHCO_3$ solution (50 mL) was added and the mixture was extracted with AcOEt (50 mL×2). The combined extracts were dried over anhydrous sodium sulfate, filtered, and concentrated. Column chromatography (SiO2, 5%–10% $CH_3OH/CH_2Cl_2$) afforded 4-[{N-(9-fluorenylmethyloxycarbonyl)glycyl}aminomethyl]-1-(4-methylthiobenzyl)piperidine (602 mg) as a colorless oil.

Reference Example 25

Preparation of 1-(4-Ethylbenzyl)-4-[{N-(9-fluorenylmethyloxycarbonyl)glycyl}aminomethyl]piperidine To A solution of 4-[{N-(9-fluorenylmethyloxycarbonyl)glycyl}aminomethyl]piperidine (1.00 g, 2.33 mmol) in 2.5% $AcOH/CH_3OH$ (80 mL) were added 4-ethylbenzaldehyde (1.09 g, 8.16 mmol) and $NaBH_3CN$ (6.59 g, 10.5 mmol). The reaction mixture was stirred at 60° C. for 13 h. After the mixture was cooled to room temperature, 1 N aqueous NaOH solution (50 mL) and dichloromethane (50 mL) were added. The organic layer was separated and the aqueous layer was extracted with dichloromethane (50 mL×3). The combined organic layers were washed with brine, dried over anhydrous sodium sulfate, filtered, and concentrated. Column chromatography (SiO2, $CH_3OH$/AcOEt 2:8) afforded 1-(4-ethylbenzyl)-4-[{N-(9-fluorenylmethyloxycarbonyl)glycyl}aminomethyl]piperidine (740 mg, 62%).

Reference Example 26

Preparation of 4-{(Glycylamino)methyl}-1-(4-methylthiobenzyl)piperidine

A solution of 4-[{N-(9-fluorenylmethyloxycarbonyl)glycyl}aminomethyl]-1-(4-methylthiobenzyl)piperidine (590 mg) and piperidine (1 mL) in DMF (4 mL) was stirred at room temperature for 2 h. Concentration and column chromatography ($SiO_2$, $Et_3N:CH_3OH:CH_2Cl_2$=1:1:9) afforded 4-{(glycylamino)methyl}-1-(4-methylthiobenzyl)piperidine (365 mg) as a white solid: $^1H$ NMR ($CDCl_3$, 270 MHz) δ1.25(dd, J=12 Hz, 4.1 Hz, 2 H), 1.34(dd, J=12 Hz, 4.1 Hz, 2 H), 1.51 (br-s, 2 H), 1.66 (d, J=12 Hz, 2 H), 1.77 (d, J=7.3 Hz, 1 H), 1.94 (t, J=9.5 Hz, 2 H), 2.48 (s, 3 H), 2.80 (d, J=12 Hz, 2 H), 3.18 (t, J=6.2 Hz, 2 H), 3.35 (s, 2 H), 3.45 (s, 2 H), 7.18–7.29 (m, 4 H), 7.35 (br-s, 1 H).

1-(4-Ethylbenzyl)-4-{(glycylamino)methyl}piperidine was also synthesized pursuant to methods of Reference Example 25 using the corresponding reactant: 333 mg, 79%.

Reference Example 27

Preparation of 4-{(glycylamino)methyl}-1-(4-fluorobenzyl)piperidine

A solution of 4-[{N-(9-fluorenylmethyloxycarbonyl)glycyl}aminomethyl]piperidine (1.50 g, 3.49 mmol), 4-fluorobenzyl bromide (0.478 mL, 3.84 mmol), and $Et_3N$ (1.47 mL, 10.5 mmol) in $CH_3CN$ (200 mL) was stirred at room temperature for 13 h and concentrated. Column chromatography (SiO2, 10% $CH_3OH/CH_2Cl_2$) afforded 4-[{N-(9fluorenylmethyloxycarbonyl)glycyl}aminomethyl]-1(4-fluorobenzyl)piperidine A solution of the 4-[{N-(9-fluorenylmethyloxycarbonyl)glycyl}aminomethyl]-1-(4-fluorobenzyl)piperidine and piperidine (5 mL) in DMF (5 mL) was stirred at room temperature for 17 h. Concentration and column chromatography ($SiO_2$, $Et_3N:CH_3OH:CH_2Cl_2$=0.5:2:8) afforded 4-{(glycylamino)methyl}-1-(4-fluorobenzyl) piperidine (453 mg, 46%).

Reference Example 28

Preparation of 4-{(glycylamino)methyl}-1-{4-(N-phenylcarbamoyl)benzyl}piperidine To a mixture of 4-[{N-(9-fluorenylmethyloxycarbonyl) glycyl}aminomethyl]piperidine (1.27 g, 2.96 mmol), $Et_3N$ (1.25 mL, 8.88 mmol), KI (50 mg, 0.30 mmol) and $CH_3CN$ (200 mL) was added dropwise a solution of 4-(N-phenylcarbamoyl)benzyl chloride (800 mg, 3.26 mmol) in $CH_3CN$ (100 mL). The mixture was stirred at room temperature for 19 h and at 60° C. for 5 h. Concentration and column chromatography ($SiO_2$, 5% $CH_3OH/CH_2Cl_2$-$Et_3N:CH_3OH:CH_2C_2$=2:2:96) afforded 4-{(glycylamino) methyl}-1-{4-(N-phenylcarbamoyl)benzyl}piperidine (340 mg, 30%).

Example 1091

Preparation of 1-(4-Chlorobenzyl)-4-[{N-(3-cyanobenzoyl)valyl}aminomethyl]piperidine (Compound No. 619)

A solution of 1-(4-chlorobenzyl)-4-{(valylamino) methyl}piperidine (20 mg, 0.059 mmol) in $CH_2Cl_2$ (0.60 mL) was treated with $Et_3N$ (0.011 mL, 0.077 mmol), m-cyanobenzoic acid (28 mg, 0.071 mmol), EDCI (13 mg, 0.065 mmol) and HOBt (9 mg, 0.065 mmol). The reaction mixture was stirred at 25° C. for 16 h. The resulting solution was diluted with $CH_2Cl_2$ (0.75 mL), washed with 2 N aqueous NaOH solution (2×0.75 mL) and dried by filtration through a PTFE membrane. Concentration afforded the 1-(4-chlorobenzyl)-4-[{N-(3-cyanobenzoyl) valyl}aminomethyl]piperidine (compound No. 619) (24.2 mg, 88%) which required no further purification: The purity was determined by RPLC/MS (85%); ESI/MS m/e 467 ($M^+$+H, $C_{26}H_{31}ClN_4O_2$).

Examples 1092–1543

The compounds of this invention were synthesized pursuant to methods of Example 1091 using the corresponding reactant respectively. The ESI/MS data and yields are summarized in Table 27.

TABLE 27

| | Compound No. | Molecular Formula | ESI/MS m/e | Yield (mg) | Yield (%) |
|---|---|---|---|---|---|
| Example 1092 | 467 | C22 H25 Br Cl N3 O2 | 478 | 11 | 46 |
| Example 1093 | 468 | C24 H31 Cl N4 O2 | 443 | 9 | 41 |
| Example 1094 | 469 | C23 H28 Cl N3 O3 | 430 | 7* | 27 |
| Example 1095 | 470 | C23 H25 Cl N4 O2 | 425 | 21 | quant |
| Example 1096 | 471 | C24 H28 Cl N3 O4 | 458 | 7 | 29 |
| Example 1097 | 472 | C29 H31 N3 O3 | 504 | 5* | 21 |
| Example 1098 | 473 | C24 H28 Cl N3 O3 | 442 | 16 | 71 |
| Example 1099 | 474 | C23 H25 Cl F3 N3 O2 | 468 | 14 | 60 |
| Example 1100 | 475 | C25 H32 Cl N3 O2 | 442 | 5 | 22 |
| Example 1101 | 476 | C22 H25 Cl N4 O4 | 445 | 4 | 17 |
| Example 1102 | 477 | C25 H32 Cl N3 O3 | 458 | 10* | 36 |
| Example 1103 | 478 | C21 H27 Cl N4 O2 | 403 | 9 | 47 |
| Example 1104 | 479 | C20 H24 Cl N3 O3 | 390 | 17 | 87 |
| Example 1105 | 480 | C20 H23 Br Cl N3 O3 | 470 | 23 | quant |
| Example 1106 | 481 | C20 H24 Cl N3 O2 S | 406 | 7 | 33 |
| Example 1107 | 482 | C21 H26 Cl N3 O2 S | 420 | 9 | 45 |
| Example 1108 | 483 | C21 H26 Cl N3 O2 S | 420 | 8 | 40 |
| Example 1109 | 484 | C24 H27 Cl N4 O2 | 439 | 9* | 34 |
| Example 1110 | 485 | C24 H24 Cl F6 N3 O2 | 536 | 13 | 49 |
| Example 1111 | 486 | C23 H25 Cl N4 O2 | 425 | 16 | 74 |
| Example 1112 | 487 | C22 H25 Cl2 N3 O2 | 434 | 5 | 24 |
| Example 1113 | 488 | C22 H27 Cl N4 O2 | 415 | 7 | 32 |
| Example 1114 | 489 | C24 H24 Cl F6 N3 O2 | 536 | 21 | 78 |
| Example 1115 | 490 | C24 H30 Cl N3 O3 | 444 | 8 | 35 |
| Example 1116 | 491 | C23 H24 Cl F4 N3 O2 | 486 | 19 | 79 |
| Example 1117 | 492 | C23 H25 Cl F3 N3 O3 | 484 | 18 | 76 |
| Example 1118 | 493 | C23 H24 Cl2 F3 N3 O2 | 502 | 23 | 92 |
| Example 1119 | 494 | C23 H24 Cl F4 N3 O2 | 486 | 19 | 79 |
| Example 1120 | 495 | C23 H24 Cl F4 N3 O2 | 486 | 20 | 83 |
| Example 1121 | 496 | C23 H24 Cl F4 N3 O2 | 486 | 12 | 48 |
| Example 1122 | 497 | C25 H32 Cl N3 O3 | 458 | 4 | 16 |
| Example 1123 | 498 | C23 H26 Cl F3 N4 O2 | 483 | 13 | 52 |
| Example 1124 | 499 | C24 H31 Cl N4 O2 | 443 | 8 | 36 |
| Example 1125 | 500 | C23 H28 Cl N3 O3 | 430 | 10 | 48 |
| Example 1126 | 501 | C22 H24 Br Cl N4 O4 | 523 | 10 | 39 |
| Example 1127 | 502 | C22 H24 Cl F N4 O4 | 463 | 4 | 17 |
| Example 1128 | 503 | C22 H24 Cl2 N4 O4 | 479 | 12 | 52 |
| Example 1129 | 504 | C24 H30 Cl N3 O4 | 460 | 11 | 43 |
| Example 1130 | 505 | C22 H24 Br Cl N4 O4 | 523 | 2 | 8 |
| Example 1131 | 506 | C20 H23 Cl N4 O5 | 435 | 2 | 10 |
| Example 1132 | 507 | C21 H26 Cl N3 O3 | 404 | 9 | 44 |
| Example 1133 | 508 | C24 H26 Cl N3 O2 S | 456 | 1 | 5 |
| Example 1134 | 509 | C20 H23 Br Cl N3 O2 S | 484 | 12 | 48 |
| Example 1135 | 510 | C22 H28 Cl N3 O3 | 418 | 9 | 44 |
| Example 1136 | 511 | C24 H32 Cl N3 O3 | 446 | 9 | 40 |
| Example 1137 | 512 | C25 H29 Cl N4 O2 | 453 | 10 | 45 |
| Example 1138 | 513 | C24 H28 Cl N3 O3 | 442 | 9 | 41 |
| Example 1139 | 514 | C26 H34 Cl N3 O2 | 456 | 11 | 49 |

TABLE 27-continued

| | Compound No. | Molecular Formula | ESI/MS m/e | Yield (mg) | Yield (%) |
|---|---|---|---|---|---|
| Example 1140 | 515 | C23 H28 Cl N3 O3 | 430 | 5 | 24 |
| Example 1141 | 525 | C23 H28 Cl N3 O4 S | 478 | 20 | 85 |
| Example 1142 | 526 | C20 H24 Cl N3 O3 | 390 | 6 | 31 |
| Example 1143 | 527 | C20 H24 Cl N3 O2 S | 406 | 8 | 39 |
| Example 1144 | 528 | C25 H30 Cl F3 N4 O4 | 543 | 28.2 | 95 |
| Example 1145 | 529 | C20 H23 Cl N4 O4 S | 451 | 9 | 39 |
| Example 1146 | 530 | C31 H33 Cl N4 O2 | 529 | 5 | 17 |
| Example 1147 | 531 | C21 H26 Cl N3 O3 S | 436 | 8 | 37 |
| Example 1148 | 532 | C22 H28 Cl N3 O3 | 418 | 8 | 40 |
| Example 1149 | 533 | C21 H26 Cl N3 O3 | 404 | 6 | 32 |
| Example 1150 | 534 | C21 H25 Cl N4 O5 | 449 | 5 | 20 |
| Example 1151 | 535 | C22 H26 Cl N3 O3 S | 448 | 8 | 37 |
| Example 1152 | 536 | C23 H31 Cl N4 O2 | 431 | 6 | 28 |
| Example 1153 | 537 | C25 H34 Cl N3 O3 | 460 | 8 | 34 |
| Example 1154 | 538 | C27 H30 Cl N3 O3 | 480 | 9 | 36 |
| Example 1155 | 539 | C22 H25 Cl F3 N3 O3 | 472 | 18 | 75 |
| Example 1156 | 540 | C25 H29 Cl N4 O2 | 453 | 8 | 36 |
| Example 1157 | 541 | C22 H26 Cl N5 O4 | 460 | 2.4 | 10 |
| Example 1158 | 542 | C24 H30 Cl N3 O2 | 428 | 4.6* | 51 |
| Example 1159 | 543 | C24 H30 Cl N3 O2 | 428 | 20.6* | 71 |
| Example 1160 | 544 | C22 H25 Cl F N3 O2 | 418 | 15.8* | 56 |
| Example 1161 | 545 | C22 H24 Cl3 N3 O2 | 468 | 7.3* | 23 |
| Example 1162 | 546 | C22 H24 Cl3 N3 O2 | 468 | 17.4* | 55 |
| Example 1163 | 547 | C22 H24 Cl3 N3 O2 | 468 | 14.1* | 44 |
| Example 1164 | 548 | C22 H24 Cl3 N3 O2 | 468 | 6.8* | 22 |
| Example 1165 | 549 | C22 H24 Cl2 N4 O4 | 479 | 5.7* | 18 |
| Example 1166 | 550 | C22 H24 Cl2 N4 O4 | 479 | 18.9* | 58 |
| Example 1167 | 551 | C24 H30 Cl N3 O2 | 428 | 14.2* | 49 |
| Example 1168 | 552 | C24 H27 Cl F3 N3 O2 | 482 | 30.6* | 94 |
| Example 1169 | 553 | C25 H26 Cl F6 N3 O2 | 550 | 38.0* | quant |
| Example 1170 | 554 | C24 H26 Cl F N4 O2 | 457 | 0.9* | 3 |
| Example 1171 | 555 | C24 H26 Cl2 N4 O2 | 473 | 11.1* | 35 |
| Example 1172 | 556 | C25 H29 Cl N4 O2 | 453 | 12.5* | 41 |
| Example 1173 | 559 | C25 H26 Cl F6 N3 O2 | 550 | 15 | 72 |
| Example 1174 | 560 | C24 H27 Cl N4 O2 | 439 | 12 | 68 |
| Example 1175 | 561 | C23 H27 Br Cl N3 O2 | 494 | 14 | 73 |
| Example 1176 | 562 | C23 H27 Cl2 N3 O2 | 448 | 13 | 75 |
| Example 1177 | 563 | C25 H26 Cl F6 N3 O2 | 550 | 14 | 66 |
| Example 1178 | 564 | C25 H32 Cl N3 O3 | 458 | 5 | 28 |
| Example 1179 | 565 | C24 H26 Cl F4 N3 O2 | 500 | 12 | 61 |
| Example 1180 | 566 | C24 H27 Cl F3 N3 O3 | 498 | 12 | 62 |
| Example 1181 | 567 | C24 H26 Cl2 F3 N3 O2 | 516 | 12 | 61 |
| Example 1182 | 568 | C24 H26 Cl F4 N3 O2 | 500 | 15 | 77 |
| Example 1183 | 569 | C24 H26 Cl F4 N3 O2 | 500 | 11 | 59 |
| Example 1184 | 570 | C24 H26 Cl F4 N3 O2 | 500 | 16 | 84 |
| Example 1185 | 571 | C26 H34 Cl N3 O3 | 472 | 14 | 77 |
| Example 1186 | 572 | C24 H28 Cl F3 N4 O2 | 497 | 11 | 55 |
| Example 1187 | 573 | C21 H25 Br Cl N3 O2 S | 500 | 12 | 64 |
| Example 1188 | 574 | C21 H25 Br Cl N3 O2 S | 500 | 15 | 75 |
| Example 1189 | 575 | C25 H34 Cl N3 O3 | 460 | 16 | 87 |
| Example 1190 | 576 | C22 H28 Cl N3 O2 S2 | 466 | 13 | 71 |
| Example 1191 | 577 | C22 H28 Cl N3 O3 | 418 | 12 | 72 |
| Example 1192 | 578 | C25 H28 Cl N3 O2 S | 470 | 15 | 81 |
| Example 1193 | 579 | C25 H29 Cl N4 O2 | 453 | 17 | 94 |
| Example 1194 | 580 | C22 H28 Cl N3 O2 S | 434 | 15 | 91 |
| Example 1195 | 581 | C21 H26 Cl N3 O2 S | 420 | 13 | 80 |
| Example 1196 | 582 | C22 H28 Cl N3 O2 S | 434 | 10 | 59 |
| Example 1197 | 583 | C26 H31 Cl N4 O2 | 467 | 6 | 31 |
| Example 1198 | 584 | C30 H32 Cl N3 O3 | 518 | 18 | 92 |
| Example 1199 | 585 | C24 H27 Cl N4 O2 | 439 | 14 | 85 |
| Example 1200 | 586 | C23 H27 Cl2 N3 O2 | 448 | 17 | 97 |
| Example 1201 | 587 | C24 H27 Cl F3 N3 O2 | 482 | 17 | 91 |
| Example 1202 | 588 | C23 H29 Cl N4 O2 | 429 | 5 | 29 |
| Example 1203 | 589 | C27 H36 Cl N3 O2 | 470 | 4 | 24 |
| Example 1204 | 590 | C26 H34 Cl N3 O2 | 456 | 6 | 36 |
| Example 1205 | 591 | C25 H33 Cl N4 O2 | 457 | 7 | 38 |
| Example 1206 | 592 | C24 H30 Cl N3 O3 | 444 | 4 | 20 |
| Example 1207 | 593 | C24 H30 Cl N3 O3 | 444 | 2 | 14 |
| Example 1208 | 594 | C23 H28 Cl N3 O3 | 430 | 4 | 25 |
| Example 1209 | 595 | C25 H30 Cl N3 O4 | 472 | 7 | 38 |
| Example 1210 | 596 | C25 H30 Cl N3 O3 | 456 | 7 | 40 |
| Example 1211 | 597 | C25 H30 Cl N3 O3 | 456 | 15 | 85 |
| Example 1212 | 598 | C21 H26 Cl N3 O3 | 404 | 15 | 94 |
| Example 1213 | 599 | C22 H29 Cl N4 O2 | 417 | 5 | 30 |
| Example 1214 | 600 | C21 H25 Br Cl N3 O3 | 484 | 6 | 34 |
| Example 1215 | 601 | C24 H30 Cl N3 O3 | 444 | 5 | 28 |

TABLE 27-continued

| | Compound No. | Molecular Formula | ESI/MS m/e | Yield (mg) | Yield (%) |
|---|---|---|---|---|---|
| Example 1216 | 602 | C25 H33 Cl N4 O2 | 457 | 5 | 28 |
| Example 1217 | 603 | C23 H29 Cl N4 O2 | 429 | 4 | 22 |
| Example 1218 | 604 | C21 H27 Cl N4 O2 | 403 | 9 | 58 |
| Example 1219 | 605 | C21 H26 Cl N3 O3 | 404 | 17 | 87 |
| Example 1220 | 606 | C21 H26 Cl N3 O2 S | 420 | 15 | 74 |
| Example 1221 | 607 | C22 H28 Cl N3 O3 S | 450 | 31 | quant |
| Example 1222 | 608 | C23 H30 Cl N3 O3 | 432 | 17 | 80 |
| Example 1223 | 609 | C22 H28 Cl N3 O3 | 418 | 18 | 89 |
| Example 1224 | 610 | C23 H28 Cl N3 O3 S | 462 | 20 | 86 |
| Example 1225 | 611 | C26 H36 Cl N3 O3 | 474 | 21 | 90 |
| Example 1226 | 612 | C28 H32 Cl N3 O3 | 494 | 20 | 84 |
| Example 1227 | 613 | C23 H27 Cl F3 N3 O3 | 486 | 19 | 81 |
| Example 1228 | 614 | C24 H33 Cl N4 O2 | 445 | 23 | quant |
| Example 1229 | 615 | C25 H29 Cl N4 O2 | 453 | 4 | 20 |
| Example 1230 | 616 | C32 H35 Cl N4 O2 | 543 | 11 | 40 |
| Example 1231 | 617 | C25 H27 Cl F3 N3 O2 | 482 | 6.7 | 37 |
| Example 1232 | 620 | C25 H31 Br Cl N3 O2 | 520 | 15 | 49 |
| Example 1233 | 621 | C25 H31 Cl2 N3 O2 | 476 | 18 | 64 |
| Example 1234 | 622 | C27 H37 Cl N4 O2 | 485 | 14 | 50 |
| Example 1235 | 623 | C26 H34 Cl N3 O3 | 472 | 19 | 69 |
| Example 1236 | 624 | C25 H31 Cl N4 O4 | 487 | 21 | 73 |
| Example 1237 | 625 | C25 H33 Cl N4 O2 | 457 | 19 | 69 |
| Example 1238 | 626 | C27 H30 Cl F6 N3 O2 | 578 | 8 | 25 |
| Example 1239 | 627 | C27 H36 Cl N3 O3 | 486 | 16 | 55 |
| Example 1240 | 628 | C27 H34 Cl N3 O4 | 500 | 24 | 80 |
| Example 1241 | 629 | C26 H30 Cl F4 N3 O2 | 528 | 18 | 56 |
| Example 1242 | 630 | C26 H31 Cl F3 N3 O3 | 526 | 21 | 68 |
| Example 1243 | 631 | C26 H30 Cl2 F3 N3 O2 | 544 | 15 | 48 |
| Example 1244 | 632 | C26 H30 Cl F4 N3 O2 | 528 | 13 | 41 |
| Example 1245 | 633 | C26 H30 Cl F4 N3 O2 | 528 | 20 | 63 |
| Example 1246 | 634 | C26 H30 Cl F4 N3 O2 | 528 | 19 | 62 |
| Example 1247 | 635 | C28 H38 Cl N3 O3 | 500 | 11 | 36 |
| Example 1248 | 636 | C26 H34 Cl N3 O2 | 456 | 21 | 89 |
| Example 1249 | 637 | C26 H31 Cl F3 N3 O2 | 510 | 20 | 95 |
| Example 1250 | 638 | C26 H31 Cl N4 O2 | 467 | 15 | 54 |
| Example 1251 | 639 | C27 H37 Cl N4 O2 | 485 | 19 | 66 |
| Example 1252 | 640 | C26 H34 Cl N3 O3 | 472 | 16 | 56 |
| Example 1253 | 641 | C27 H34 Cl N3 O4 | 500 | 18 | 59 |
| Example 1254 | 642 | C32 H36 Cl N3 O3 | 546 | 24 | 73 |
| Example 1255 | 643 | C26 H31 Cl F3 N3 O2 | 510 | 16 | 54 |
| Example 1256 | 644 | C29 H40 Cl N3 O2 | 498 | 18 | 61 |
| Example 1257 | 645 | C25 H33 Cl N4 O2 | 457 | 22 | 78 |
| Example 1258 | 646 | C26 H34 Cl N3 O3 | 472 | 13 | 47 |
| Example 1259 | 647 | C27 H34 Cl N3 O3 | 500 | 13 | 46 |
| Example 1260 | 648 | C28 H38 Cl N3 O2 | 484 | 17 | 60 |
| Example 1261 | 649 | C28 H38 Cl N3 O3 | 500 | 12.5 | 42 |
| Example 1262 | 650 | C32 H36 Cl N3 O3 | 546 | 1* | 2 |
| Example 1263 | 651 | C28 H35 Cl N4 O2 | 495 | 4* | 12 |
| Example 1264 | 652 | C25 H31 Cl N4 O4 | 487 | 5* | 14 |
| Example 1265 | 653 | C30 H42 Cl N3 O3 | 528 | 1* | 3 |
| Example 1266 | 654 | C27 H34 Cl N3 O3 | 484 | 7* | 21 |
| Example 1267 | 655 | C26 H32 Cl F3 N4 O2 | 525 | 6* | 16 |
| Example 1268 | 656 | C23 H30 Cl N3 O3 | 432 | 6* | 18 |
| Example 1269 | 657 | C23 H30 Cl N3 O2 S | 448 | 4* | 13 |
| Example 1270 | 658 | C27 H33 Cl N4 O2 | 48 | 1* | 4 |
| Example 1271 | 659 | C23 H29 Cl N4 O4 S | 493 | 4* | 10 |
| Example 1272 | 660 | C34 H39 Cl N4 O2 | 571 | 3* | 7 |
| Example 1273 | 661 | C24 H32 Cl N3 O3 S | 478 | 3* | 7 |
| Example 1274 | 662 | C25 H34 Cl N3 O3 | 460 | 2* | 6 |
| Example 1275 | 663 | C24 H32 Cl N3 O3 | 446 | 2* | 5 |
| Example 1276 | 664 | C24 H31 Cl N4 O5 | 491 | 2* | 5 |
| Example 1277 | 665 | C25 H32 Cl N3 O3 S | 490 | 1* | 3 |
| Example 1278 | 666 | C26 H37 Cl N4 O2 | 473 | 3* | 7 |
| Example 1279 | 667 | C30 H36 Cl N3 O3 | 522 | 3* | 7 |
| Example 1280 | 668 | C25 H31 Cl F3 N3 O3 | 514 | 2* | 6 |
| Example 1281 | 669 | C24 H33 Cl N4 O2 | 445 | 15* | 45 |
| Example 1282 | 670 | C23 H29 Br Cl N3 O3 | 510 | 3* | 7 |
| Example 1283 | 671 | C23 H29 Cl N4 O5 | 477 | 2* | 5 |
| Example 1284 | 672 | C23 H31 Cl N4 O2 | 431 | 2* | 7 |
| Example 1285 | 673 | C23 H30 Cl N3 O2 S | 448 | 2* | 6 |
| Example 1286 | 674 | C24 H32 Cl N3 O2 S | 462 | 3* | 9 |
| Example 1287 | 675 | C24 H32 Cl N3 O2 S | 462 | 1* | 4 |
| Example 1288 | 676 | C27 H33 Cl N4 O2 | 482 | 2* | 6 |
| Example 1289 | 677 | C28 H35 Cl N4 O2 | 495 | 2* | 6 |
| Example 1290 | 678 | C24 H32 Cl N3 O3 | 446 | 3* | 9 |
| Example 1291 | 679 | C27 H32 Cl N3 O2 S | 498 | 1* | 3 |

TABLE 27-continued

| | Compound No. | Molecular Formula | ESI/MS m/e | Yield (mg) | Yield (%) |
|---|---|---|---|---|---|
| Example 1292 | 680 | C23 H29 Br Cl N3 O2 S | 526 | 2* | 6 |
| Example 1293 | 681 | C25 H34 Cl N3 O3 | 460 | 2* | 5 |
| Example 1294 | 682 | C27 H38 Cl N3 O3 | 488 | 2* | 4 |
| Example 1295 | 683 | C24 H32 Cl N3 O2 S2 | 494 | 1* | 4 |
| Example 1296 | 684 | C26 H36 Cl N3 O4 S2 | 554 | 2* | 5 |
| Example 1297 | 685 | C24 H32 Cl N3 O4 S2 | 526 | 3* | 7 |
| Example 1298 | 687 | C25 H30 Cl N3 O2 | 440 | 24 | quant |
| Example 1299 | 688 | C27 H28 Cl F6 N3 O2 | 576 | 28 | 98 |
| Example 1300 | 689 | C26 H29 Cl N4 O2 | 465 | 23 | 99 |
| Example 1301 | 690 | C25 H29 Br Cl N3 O2 | 518 | 26 | 99 |
| Example 1302 | 691 | C27 H35 Cl N4 O2 | 483 | 24 | 97 |
| Example 1303 | 692 | C26 H32 Cl N3 O3 | 470 | 24 | quant |
| Example 1304 | 693 | C27 H28 Cl F6 N3 O2 | 576 | 16 | 55 |
| Example 1305 | 694 | C27 H34 Cl N3 O3 | 484 | 25 | quant |
| Example 1306 | 695 | C27 H32 Cl N3 O4 | 498 | 12 | 47 |
| Example 1307 | 696 | C26 H29 Cl F3 N3 O3 | 524 | 25 | 95 |
| Example 1308 | 697 | C26 H29 Cl N4 O2 | 465 | 15 | 64 |
| Example 1309 | 698 | C27 H35 Cl N4 O2 | 483 | 24 | quant |
| Example 1310 | 699 | C26 H32 Cl N3 O3 | 470 | 26 | quant |
| Example 1311 | 700 | C27 H32 Cl N3 O4 | 498 | 15 | 62 |
| Example 1312 | 701 | C27 H32 Cl N3 O3 | 482 | 11 | 44 |
| Example 1313 | 702 | C26 H29 Cl F3 N3 O2 | 508 | 23 | 94 |
| Example 1314 | 703 | C28 H36 Cl N3 O2 | 482 | 26 | quant |
| Example 1315 | 704 | C25 H29 Cl N4 O4 | 485 | 11 | 43 |
| Example 1316 | 705 | C24 H30 Cl N3 O2 S | 460 | 25 | quant |
| Example 1317 | 706 | C24 H30 Cl N3 O2 S | 460 | 25 | quant |
| Example 1318 | 707 | C26 H29 Cl F3 N3 O2 | 508 | 15 | 55 |
| Example 1319 | 708 | C23 H27 Br Cl N3 O2 S | 526 | 25 | 92 |
| Example 1320 | 709 | C24 H30 Cl N3 O2 S2 | 492 | 26 | quant |
| Example 1321 | 710 | C23 H27 Br Cl N3 O2 S | 526 | 25 | 94 |
| Example 1322 | 711 | C25 H32 Cl N3 O3 | 458 | 26 | quant |
| Example 1323 | 712 | C27 H30 Cl N3 O2 S | 496 | 26 | quant |
| Example 1324 | 713 | C24 H30 Cl N3 O3 | 444 | 26 | quant |
| Example 1325 | 714 | C28 H33 Cl N4 O2 | 493 | 12 | 50 |
| Example 1326 | 715 | C23 H28 Cl N3 O2 S | 446 | 24 | quant |
| Example 1327 | 716 | C27 H31 Cl N4 O2 | 479 | 32 | quant |
| Example 1328 | 717 | C23 H27 Cl N4 O5 | 475 | 23 | 95 |
| Example 1329 | 718 | C23 H29 Cl N4 O2 | 429 | 24 | quant |
| Example 1330 | 719 | C23 H28 Cl N3 O3 | 430 | 24 | quant |
| Example 1331 | 720 | C23 H27 Br Cl N3 O3 | 510 | 24 | 95 |
| Example 1332 | 721 | C24 H31 Cl N4 O2 | 443 | 22 | 98 |
| Example 1333 | 722 | C26 H32 Cl N3 O3 | 470 | 9 | 37 |
| Example 1334 | 723 | C25 H31 Cl N4 O2 | 455 | 10 | 44 |
| Example 1335 | 724 | C29 H38 Cl N3 O2 | 496 | 28 | quant |
| Example 1336 | 725 | C32 H34 Cl N3 O3 | 544 | 26 | 95 |
| Example 1337 | 726 | C27 H33 Cl N4 O3 | 497 | 3 | 11 |
| Example 1338 | 727 | C25 H29 Cl2 N3 O2 | 474 | 25 | quant |
| Example 1339 | 728 | C25 H31 Cl N4 O2 | 455 | 21 | 92 |
| Example 1340 | 729 | C25 H29 Cl N4 O4 | 485 | 26 | quant |
| Example 1341 | 730 | C25 H29 Cl2 N3 O2 | 474 | 21 | 90 |
| Example 1342 | 731 | C27 H32 Cl N3 O3 | 482 | 10 | 41 |
| Example 1343 | 732 | C26 H28 Cl F4 N3 O2 | 526 | 27 | quant |
| Example 1344 | 733 | C28 H36 Cl N3 O3 | 498 | 22 | 89 |
| Example 1345 | 734 | C26 H28 Cl F4 N3 O2 | 526 | 25 | 94 |
| Example 1346 | 735 | C26 H28 Cl F4 N3 O2 | 526 | 23 | 87 |
| Example 1347 | 736 | C26 H30 Cl F3 N4 O2 | 523 | 24 | 78 |
| Example 1348 | 737 | C26 H28 Cl F4 N3 O2 | 526 | 21 | 66 |
| Example 1349 | 738 | C25 H32 Cl N3 O3 | 458 | 23 | 84 |
| Example 1350 | 739 | C27 H31 Cl N4 O2 | 479 | 19 | 66 |
| Example 1351 | 740 | C24 H31 Cl N4 O5 | 489 | 23 | 77 |
| Example 1352 | 741 | C23 H27 Cl N4 O4 S | 491 | 26 | 88 |
| Example 1353 | 742 | C24 H30 Cl N3 O3 S | 476 | 23 | 82 |
| Example 1354 | 743 | C23 H28 Cl N3 O3 | 430 | 21 | 81 |
| Example 1355 | 744 | C26 H32 Cl N3 O2 | 454 | 25 | 91 |
| Example 1356 | 745 | C27 H36 Cl N3 O3 | 486 | 23 | 80 |
| Example 1357 | 746 | C26 H35 Cl N4 O2 | 471 | 27 | 96 |
| Example 1358 | 747 | C25 H29 Cl F3 N3 O3 | 512 | 23 | 74 |
| Example 1359 | 748 | C23 H28 Cl N3 O2 S | 446 | 22 | 82 |
| Example 1360 | 751 | C24 H30 Cl N3 O3 | 444 | 3 | 11 |
| Example 1361 | 752 | C25 H26 Cl F6 N3 O3 | 566 | 7 | 20 |
| Example 1362 | 753 | C24 H27 Cl N4 O3 | 455 | 6 | 22 |
| Example 1363 | 754 | C23 H27 Cl2 N3 O3 | 464 | 8 | 29 |
| Example 1364 | 755 | C24 H30 Cl N3 O4 | 460 | 6 | 22 |
| Example 1365 | 756 | C23 H27 Cl N4 O5 | 475 | 5 | 18 |
| Example 1366 | 757 | C25 H32 Cl N3 O4 | 474 | 5 | 18 |
| Example 1367 | 758 | C25 H30 Cl N3 O5 | 488 | 5 | 18 |

TABLE 27-continued

| | Compound No. | Molecular Formula | ESI/MS m/e | Yield (mg) | Yield (%) |
|---|---|---|---|---|---|
| Example 1368 | 759 | C24 H27 Cl F3 N3 O4 | 514 | 6 | 20 |
| Example 1369 | 760 | C24 H26 Cl F4 N3 O3 | 516 | 6 | 18 |
| Example 1370 | 761 | C24 H26 Cl F4 N3 O3 | 516 | 3 | 10 |
| Example 1371 | 762 | C24 H27 Cl F3 N3 O3 | 498 | 2 | 95 |
| Example 1372 | 763 | C23 H28 Cl N3 O3 | 430 | 4 | 95 |
| Example 1373 | 764 | C24 H30 Cl N3 O2 | 428 | 9 | 42 |
| Example 1374 | 765 | C25 H32 Cl N3 O2 | 442 | 10 | 47 |
| Example 1375 | 766 | C25 H29 Cl F3 N3 O2 | 496 | 10 | 42 |
| Example 1376 | 767 | C25 H32 Cl N3 O4 S | 506 | 8 | 32 |
| Example 1377 | 768 | C24 H29 Br Cl N3 O2 | 506 | 9 | 35 |
| Example 1378 | 769 | C25 H29 Cl F3 N3 O3 | 512 | 6 | 22 |
| Example 1379 | 770 | C25 H28 Cl F4 N3 O2 | 514 | 3 | 10 |
| Example 1380 | 771 | C25 H28 Cl F4 N3 O2 | 514 | 10 | 37 |
| Example 1381 | 772 | C25 H29 Cl F3 N3 O2 | 496 | 8 | 33 |
| Example 1382 | 773 | C26 H36 Cl N3 O3 | 474 | 10 | 41 |
| Example 1383 | 774 | C23 H30 Cl N3 O2 S2 | 480 | 12 | 50 |
| Example 1384 | 775 | C27 H38 Cl N3 O3 | 488 | 14 | 57 |
| Example 1385 | 776 | C29 H34 Cl N3 O3 | 508 | 12 | 49 |
| Example 1386 | 777 | C24 H29 Cl F3 N3 O3 | 500 | 22 | 87 |
| Example 1387 | 778 | C24 H28 Cl2 N4 O4 | 507 | 6 | 22 |
| Example 1388 | 779 | C24 H29 Cl2 N3 O2 | 462 | 10 | 46 |
| Example 1389 | 780 | C24 H29 Cl N4 O4 | 473 | 15 | 65 |
| Example 1390 | 781 | C26 H31 Cl N4 O2 | 467 | 7* | 20 |
| Example 1391 | 782 | C25 H32 Cl N3 O3 | 458 | 8* | 23 |
| Example 1392 | 783 | C26 H34 Cl N3 O3 | 472 | 7* | 19 |
| Example 1393 | 784 | C26 H31 Cl F3 N3 O2 | 510 | 7* | 17 |
| Example 1394 | 785 | C26 H34 Cl N3 O4 | 488 | 6* | 17 |
| Example 1395 | 786 | C24 H28 Cl N3 O2 | 426 | 22 | 9 |
| Example 1396 | 787 | C25 H30 Cl N3 O2 | 440 | 21 | 94 |
| Example 1397 | 788 | C25 H27 Cl F3 N3 O2 | 494 | 4* | 14 |
| Example 1398 | 789 | C25 H30 Cl N3 O4 S | 504 | 9 | 35 |
| Example 1399 | 790 | C24 H27 Cl2 N3 O2 | 460 | 5* | 16 |
| Example 1400 | 791 | C24 H27 Cl N4 O4 | 471 | 3* | 10 |
| Example 1401 | 792 | C25 H27 Cl F3 N3 O3 | 510 | 5* | 16 |
| Example 1402 | 793 | C25 H26 Cl F4 N3 O2 | 511 | 5* | 16 |
| Example 1403 | 794 | C25 H26 Cl F4 N3 O2 | 512 | 5* | 16 |
| Example 1404 | 795 | C25 H27 Cl F3 N3 O2 | 494 | 6* | 21 |
| Example 1405 | 796 | C23 H28 Cl N3 O2 S2 | 478 | 4* | 14 |
| Example 1406 | 797 | C27 H36 Cl N3 O3 | 486 | 7* | 29 |
| Example 1407 | 798 | C29 H32 Cl N3 O3 | 506 | 3 | 13 |
| Example 1408 | 799 | C24 H27 Cl F3 N3 O3 | 498 | 3* | 11 |
| Example 1409 | 800 | C24 H26 Cl2 N4 O4 | 505 | 5* | 15 |
| Example 1410 | 801 | C26 H29 Cl N4 O2 | 465 | 12 | 41 |
| Example 1411 | 802 | C25 H30 Cl N3 O3 | 456 | 5* | 15 |
| Example 1412 | 803 | C26 H32 Cl N3 O3 | 470 | 6* | 16 |
| Example 1413 | 804 | C26 H29 Cl F3 N3 O2 | 508 | 8* | 20 |
| Example 1414 | 805 | C26 H32 Cl N3 O4 | 486 | 6* | 15 |
| Example 1415 | 806 | C24 H27 Br Cl N3 O2 | 506 | 5* | 14 |
| Example 1416 | 807 | C27 H32 Cl N5 O3 | 510 | 29.7 | quant |
| Example 1417 | 808 | C26 H33 Cl N4 O3 | 485 | 29.9 | quant |
| Example 1418 | 809 | C25 H30 Cl2 N4 O3 | 505 | 30.2 | quant |
| Example 1419 | 810 | C30 H35 Cl N4 O4 | 551 | 31.0 | quant |
| Example 1420 | 811 | C25 H29 Cl2 N5 O5 | 550 | 30.4 | quant |
| Example 1421 | 812 | C24 H31 Cl N4 O3 S2 | 523 | 25.0 | 88 |
| Example 1422 | 813 | C26 H30 Cl F3 N4 O3 | 539 | 20.5 | 70 |
| Example 1423 | 814 | C26 H30 Cl F3 N4 O4 | 555 | 22.7 | 75 |
| Example 1424 | 815 | C26 H29 Cl F4 N4 O3 | 557 | 25.8 | 85 |
| Example 1425 | 816 | C26 H30 Cl F3 N4 O3 | 539 | 25.3 | 86 |
| Example 1426 | 817 | C26 H29 Cl F4 N4 O3 | 557 | 26.8 | 88 |
| Example 1427 | 818 | C25 H30 Br Cl N4 O3 | 551 | 27.1 | 90 |
| Example 1428 | 819 | C27 H29 Cl F6 N4 O3 | 607 | 13.9 | 42 |
| Example 1429 | 820 | C25 H30 Cl N5 O5 | 516 | 14.1 | 51 |
| Example 1430 | 821 | C24 H28 Cl2 N4 O5 | 523 | 40 | 86 |
| Example 1431 | 822 | C23 H30 Cl N3 O3 S2 | 496 | 41 | 93 |
| Example 1432 | 823 | C26 H31 Cl N4 O3 | 483 | 43 | quant |
| Example 1433 | 824 | C27 H38 Cl N3 O4 | 503 | 37 | 83 |
| Example 1434 | 825 | C29 H34 Cl N3 O4 | 524 | 28 | 61 |
| Example 1435 | 826 | C24 H29 Cl F3 N3 O4 | 516 | 40 | 87 |
| Example 1436 | 827 | C26 H31 Cl N4 O3 | 483 | 31 | 72 |
| Example 1437 | 828 | C25 H29 Cl F3 N3 O4 | 528 | 40 | 86 |
| Example 1438 | 829 | C25 H28 Cl F4 N3 O3 | 530 | 45 | 97 |
| Example 1439 | 830 | C25 H28 Cl F4 N3 O3 | 530 | 35 | 74 |
| Example 1440 | 831 | C24 H29 Br Cl N3 O3 | 523 | 45 | 98 |
| Example 1441 | 832 | C24 H29 Cl2 N3 O3 | 478 | 38 | 91 |
| Example 1442 | 833 | C24 H29 Cl N4 O5 | 488 | 38 | 87 |
| Example 1443 | 834 | C25 H29 Cl F3 N3 O3 | 512 | 42 | 93 |

TABLE 27-continued

| | Compound No. | Molecular Formula | ESI/MS m/e | Yield (mg) | Yield (%) |
|---|---|---|---|---|---|
| Example 1444 | 835 | C24 H30 Cl N3 O3 | 444 | 43 | quant |
| Example 1445 | 836 | C25 H32 Cl N3 O3 | 458 | 37 | 91 |
| Example 1446 | 837 | C25 H29 Cl F3 N3 O3 | 512 | 41 | 91 |
| Example 1447 | 838 | C26 H34 Cl N3 O4 | 488 | 34 | 78 |
| Example 1448 | 839 | C27 H36 Cl N3 O6 | 534 | 37 | 71 |
| Example 1449 | 942 | C27 H30 Cl F6 N3 O2 | 578 | 17 | 48 |
| Example 1450 | 997 | C26 H34 Cl N3 O2 | 456 | 7.6* | 23 |
| Example 1451 | 998 | C27 H33 Cl F3 N3 O2 | 524 | 6 | 15 |
| Example 1452 | 999 | C27 H36 Cl N3 O2 | 470 | 8 | 24 |
| Example 1453 | 1000 | C27 H36 Cl N3 O3 | 486 | 9 | 24 |
| Example 1454 | 1001 | C28 H38 Cl N3 O3 | 500 | 4 | 10 |
| Example 1455 | 1002 | C27 H33 Cl F3 N3 O3 | 540 | 9 | 23 |
| Example 1456 | 1003 | C28 H38 Cl N3 O2 | 484 | 7 | 21 |
| Example 1457 | 1004 | C28 H38 Cl N3 O4 | 516 | 11 | 30 |
| Example 1458 | 1005 | C29 H40 Cl N3 O5 | 547 | 9 | 23 |
| Example 1459 | 1006 | C30 H42 Cl N3 O4 | 544 | 8 | 21 |
| Example 1460 | 1007 | C32 H46 Cl N3 O5 | 589 | 7 | 17 |
| Example 1461 | 1008 | C25 H31 Cl N4 O3 | 471 | 25 | 79 |
| Example 1462 | 1009 | C26 H33 Cl N4 O4 | 501 | 35 | 97 |
| Example 1463 | 1010 | C27 H35 Cl N4 O4 | 515 | 35 | 9 |
| Example 1464 | 1011 | C27 H35 Cl N4 O3 | 499 | 32 | 54 |
| Example 1465 | 1012 | C27 H35 Cl N4 O5 | 531 | 27 | 77 |
| Example 1466 | 1013 | C28 H37 Cl N4 O6 | 561 | 14 | 37 |
| Example 1467 | 1014 | C29 H39 Cl N4 O5 | 559 | 24 | 66 |
| Example 1468 | 1015 | C31 H43 Cl N4 O6 | 603 | 25 | 65 |
| Example 1469 | 1018 | C26 H34 Cl N3 O4 | 488 | 13.0* | 39 |
| Example 1470 | 1019 | C28 H38 Cl N3 O5 | 532 | 13.4* | 37 |
| Example 1471 | 1020 | C25 H32 Cl N3 O4 | 474 | 12.7* | 40 |
| Example 1472 | 1021 | C26 H28 Cl F6 N3 O4 | 596 | 13.8* | 34 |
| Example 1473 | 1022 | C25 H32 Cl N3 O4 | 474 | 14.2* | 37 |
| Example 1474 | 1023 | C25 H32 Cl N3 O2 | 442 | 11.5* | 32 |
| Example 1475 | 1024 | C26 H34 Cl N3 O5 | 504 | 12.0* | 30 |
| Example 1476 | 1025 | C27 H36 Cl N3 O4 | 502 | 14.7* | 37 |
| Example 1477 | 1026 | C29 H40 Cl N3 O5 | 546 | 13.5* | 32 |
| Example 1478 | 1027 | C26 H34 Cl N3 O4 | 488 | 11.9* | 31 |
| Example 1479 | 1028 | C27 H30 Cl F6 N3 O4 | 610 | 14.6* | 31 |
| Example 1480 | 1029 | C25 H32 Cl N3 O3 | 458 | 14.0* | 38 |
| Example 1481 | 1030 | C24 H27 Cl F3 N3 O3 | 498 | 14.0* | 35 |
| Example 1482 | 1031 | C24 H30 Cl N3 O3 | 444 | 10.4* | 29 |
| Example 1483 | 1032 | C25 H32 Cl N3 O4 | 474 | 14.9* | 39 |
| Example 1484 | 1033 | C25 H32 Cl N3 O2 | 442 | 13.3* | 37 |
| Example 1485 | 1034 | C26 H34 Cl N3 O5 | 504 | 13.7* | 34 |
| Example 1486 | 1035 | C27 H36 Cl N3 O4 | 502 | 16.7* | 42 |
| Example 1487 | 1036 | C29 H40 Cl N3 O5 | 547 | 15.5* | 36 |
| Example 1488 | 1037 | C26 H34 Cl N3 O4 | 488 | 14.1* | 36 |
| Example 1489 | 1038 | C27 H30 Cl F6 N3 O4 | 610 | 17.5* | 37 |
| Example 1490 | 1039 | C25 H32 Cl N3 O3 | 458 | 15.1* | 41 |
| Example 1491 | 1040 | C24 H27 Cl F3 N3 O3 | 498 | 15.4* | 39 |
| Example 1492 | 1041 | C24 H30 Cl N3 O3 | 444 | 12.7* | 35 |
| Example 1493 | 1042 | C22 H26 Br Cl N4 O2 | 495 | 10.4* | 25 |
| Example 1494 | 1043 | C22 H26 Cl2 N4 O2 | 449 | 11.1* | 29 |
| Example 1495 | 1044 | C23 H29 Cl N4 O2 | 429 | 5.2* | 14 |
| Example 1496 | 1045 | C23 H29 Cl N4 O3 | 445 | 12.4* | 33 |
| Example 1497 | 1046 | C22 H25 Cl3 N4 O2 | 483 | 10.0* | 25 |
| Example 1498 | 1047 | C24 H31 Cl N4 O2 | 443 | 12.1* | 32 |
| Example 1499 | 1048 | C25 H33 Cl N4 O5 | 505 | 16.1* | 39 |
| Example 1500 | 1049 | C23 H28 Br Cl N4 O2 | 507 | 12.0* | 29 |
| Example 1501 | 1050 | C28 H38 Cl N3 O4 | 516 | 39.2* | quant |
| Example 1502 | 1051 | C28 H38 Cl N3 O2 | 484 | 34.0* | quant |
| Example 1503 | 1052 | C29 H40 Cl N3 O5 | 546 | 14.5* | 39 |
| Example 1504 | 1053 | C30 H42 Cl N3 O4 | 544 | 11.8* | 32 |
| Example 1505 | 1054 | C32 H46 Cl N3 O5 | 588 | 12.2* | 31 |
| Example 1506 | 1055 | C29 H40 Cl N3 O4 | 530 | 44.5* | quant |
| Example 1507 | 1056 | C30 H36 Cl F6 N3 O4 | 652 | 46.0* | quant |
| Example 1508 | 1057 | C28 H38 Cl N3 O3 | 500 | 11.2* | 32 |
| Example 1509 | 1058 | C27 H36 Cl N3 O3 | 486 | 35.5* | quant |
| Example 1510 | 1059 | C27 H33 Cl F3 N3 O3 | 540 | 41.4* | quant |
| Example 1511 | 1060 | C29 H40 Cl N3 O4 | 530 | 13.6* | 37 |
| Example 1512 | 1061 | C30 H36 Cl F6 N3 O4 | 652 | 44.2* | quant |
| Example 1513 | 1062 | C28 H38 Cl N3 O3 | 500 | 39.9* | quant |
| Example 1514 | 1063 | C27 H36 Cl N3 O3 | 486 | 12.0* | 35 |
| Example 1515 | 1064 | C27 H33 Cl F3 N3 O3 | 540 | 37.8* | quant |
| Example 1516 | 1065 | C28 H38 Cl N3 O4 | 516 | 12.3* | 34 |
| Example 1517 | 1066 | C28 H38 Cl N3 O2 | 484 | 30.7* | 90 |
| Example 1518 | 1067 | C29 H40 Cl N3 O5 | 546 | 13.8* | 37 |
| Example 1519 | 1068 | C30 H42 Cl N3 O4 | 544 | 13.1* | 35 |

TABLE 27-continued

| | Compound No. | Molecular Formula | ESI/MS m/e | Yield (mg) | Yield (%) |
|---|---|---|---|---|---|
| Example 1520 | 1069 | C32 H46 Cl N3 O5 | 589 | 14.1* | 35 |
| Example 1521 | 1070 | C29 H34 Cl N3 O3 S2 | 572 | 38.3 | 93 |
| Example 1522 | 1071 | C32 H35 Cl N4 O3 | 559 | 39.6 | 98 |
| Example 1523 | 1072 | C33 H42 Cl N3 O4 | 580 | 40.9 | 98 |
| Example 1524 | 1073 | C35 H38 Cl N3 O4 | 600 | 40.5 | 94 |
| Example 1525 | 1074 | C30 H33 Cl F3 N3 O4 | 592 | 38.7 | 91 |
| Example 1526 | 1075 | C31 H33 Cl F3 N3 O4 | 604 | 38 | 87 |
| Example 1527 | 1076 | C30 H33 Cl N4 O5 | 565 | 38.5 | 94 |
| Example 1528 | 1077 | C31 H33 Cl F3 N3 O3 | 588 | 35.8 | 84 |
| Example 1529 | 1078 | C30 H34 Cl N3 O3 | 520 | 34.7 | 93 |
| Example 1530 | 1079 | C31 H36 Cl N3 O3 | 534 | 38.4 | quant |
| Example 1531 | 1080 | C32 H38 Cl N3 O4 | 564 | 39.3 | 97 |
| Example 1532 | 1081 | C33 H40 Cl N3 O6 | 610 | 45.5 | quant |
| Example 1533 | 1082 | C28 H36 Cl N3 O3 | 498 | 4.1* | 10 |
| Example 1534 | 1083 | C28 H36 Cl N3 O3 | 498 | 6.4* | 16 |
| Example 1535 | 1125 | C30 H32 Cl2 N4 O5 | 599 | 3.4* | 8 |
| Example 1536 | 1126 | C30 H32 Br Cl N4 O5 | 644 | 3.4* | 7 |
| Example 1537 | 1127 | C32 H35 Cl N4 O3 | 559 | 1.6* | 4 |
| Example 1538 | 1128 | C31 H32 Cl F4 N3 O3 | 606 | 4.3* | 10 |
| Example 1539 | 1129 | C31 H32 Cl F4 N3 O3 | 606 | 5.9* | 14 |
| Example 1540 | 1130 | C30 H33 Br Cl N3 O3 | 599 | 5.7* | 13 |
| Example 1541 | 1131 | C30 H33 Cl2 N3 O3 | 554 | 6.4* | 16 |
| Example 1542 | 1132 | C31 H33 Cl F3 N3 O3 | 588 | 6.3* | 15 |
| Example 1543 | 1167 | C27 H34 Cl N3 O3 | 484 | 1.8* | 4 |

*Yield of TFA salt.

Example 1544

Preparation of 1-(4-Chlorobenzyl)-4-[{N-(3,5-bis(trifluoromethyl)benzoyl)glycyl}aminomethyl]piperidine (Compound No. 1213)

A solution of 3,5-bis(trifluoromethyl)benzoyl chloride (0.058 mmol) in dichloromethane (1 mL) was added to a mixture of 1-(4-chlorobenzyl)-4-{(glycylamino)methyl}piperidine (0.050 mmol) and piperidinomethylpolystyrene (58 mg) in chloroform (0.2 mL) and dichloromethane (0.75 mL). After the reaction mixture was stirred at room temperature for 2 h, methanol (1.0 mL) was added and the mixture was stirred at room temperature for 30 min. The reaction mixture was loaded onto Varian™ SCX column, and washed with $CH_3OH$ (16 mL). Product was eluted off using 2 N $NH_3$ in $CH_3OH$ (6 mL) and concentrated to afford 1-(4-chlorobenzyl)-4-[{N-(3,5-bis(trifluoromethyl)benzoyl)glycyl}aminomethyl]piperidine (Compound No. 1213) (24.0 mg, 90%): The purity was determined by RPLC/MS (100%); ESI/MS m/e 536.2 ($M^+$+H, $C_{24}H_{24}ClF_6N_3O_2$).

Examples 1545–1547

The compounds of this invention were synthesized pursuant to methods of Example 1544 using the corresponding reactant respectively. The ESI/MS data and yields are summarized in Table 28.

TABLE 28

| | Compound No. | Molecular Formula | ESI/MS m/e | Yield (mg) | Yield (%) |
|---|---|---|---|---|---|
| Example 1545 | 1214 | C23 H24 Cl F4 N3 O3 | 486.2 | 22.2 | 91 |
| Example 1546 | 1215 | C22 H24 Cl3 N3 O2 | 467.9 | 20.9 | 89 |
| Example 1547 | 1216 | C22 H24 Cl F2 N3 O2 | 436.0 | 19.3 | 89 |

Example 1548

Preparation of 4-[{N-(3-Bromo-4-methylbenzoyl)glycyl}aminomethyl]-1-(4-chlorobenzyl)piperidine (Compound No. 1113).

A solution of 1-(4-chlorobenzyl)-4-{(glycylamino)methyl)piperidine (0.050 mmol) in $CHCl_3$ (1.35 mL) and tert-butanol (0.15 mL) was treated with 3-bromo-4-methylbenzoic acid (0.060 mmol), diisopropylcarbodiimide (0.060 mmol), and HOBt (0.060 mmol). The reaction mixture was stirred at room temperature for 15 h. The mixture was loaded onto Varian™ SCX column, and washed with $CH_3OH/CHCl_3$ 1:1 (12 mL) and $CH_3OH$ (12 mL). Product was eluted off using 2 N $NH_3$ in $CH_3OH$ (5 mL) and concentrated to afford 4-[{N-(3-bromo-4-methylbenzoyl)glycyl}aminomethyl]-1-(4-chlorobenzyl)piperidine (Compound No. 1113) (16.1 mg, 65%): The purity was determined by RPLC/MS (95%); ESI/MS m/e 494.0 ($C_{23}H_{27}BrClN_3O_2$).

Examples 1549–1619

The compounds of this invention were synthesized pursuant to methods of Example 1548 using the corresponding reactant respectively. Preparative TLC, if needed, afforded the desired material. The ESI/MS data and yields are summarized in Table 29.

Compound No. 1422 was obtained as byproduct of Compound No. 1418: 5.6 mg, 25% yield; ESI/MS m/e 447.2 ($C_{22}H_{27}ClN_4O_2S$).

TABLE 29

| | Compound No. | Molecular Formula | ESI/MS m/e | Yield (mg) | Yield (%) |
|---|---|---|---|---|---|
| Example 1549 | 1114 | $C_{22}H_{24}BrClFN_3O_2$ | 498.0 | 20.2 | 81 |
| Example 1550 | 1115 | $C_{22}H_{24}Cl_2FN_3O_2$ | 452.2 | 18.6 | 82 |

TABLE 29-continued

| | Compound No. | Molecular Formula | ESI/MS m/e | Yield (mg) | Yield (%) |
|---|---|---|---|---|---|
| Example 1551 | 1116 | $C_{23}H_{27}ClIN_3O_2$ | 539.1 | 21.9 | 81 |
| Example 1552 | 1117 | $C_{23}H_{27}ClN_4O_4$ | 459.2 | 18.7 | 81 |
| Example 1553 | 1187 | $C_{23}H_{27}BrClN_3O_2$ | 494.0 | 22.1 | 90 |
| Example 1554 | 1188 | $C_{24}H_{27}ClN_4O_3$ | 455.2 | 17.2 | 76 |
| Example 1555 | 1189 | $C_{25}H_{29}ClN_4O_3$ | 469.2 | 21.1 | 90 |
| Example 1556 | 1190 | $C_{22}H_{26}ClFN_4O_2$ | 433.2 | 20.4 | 94 |
| Example 1557 | 1241 | $C_{23}H_{24}Cl_2F_3N_3O_2$ | 502.0 | 22.5 | 90 |
| Example 1558 | 1242 | $C_{23}H_{27}ClFN_3O_2$ | 432.2 | 21.2 | 98 |
| Example 1559 | 1243 | $C_{23}H_{27}Cl_2N_3O_2$ | 448.0 | 21.6 | 96 |
| Example 1560 | 1244 | $C_{22}H_{26}ClIN_4O_2$ | 541.0 | 26.4 | 98 |
| Example 1561 | 1245 | $C_{22}H_{25}ClF_2N_4O_2$ | 451.0 | 21.3 | 94 |
| Example 1562 | 1246 | $C_{21}H_{27}ClN_4O_2$ | 403.2 | 19.4 | 96 |
| Example 1563 | 1247 | $C_{28}H_{30}ClN_3O_2S$ | 524.0 | 24.7 | 94 |
| Example 1564 | 1248 | $C_{22}H_{25}ClN_4O_5$ | 461.0 | 20.7 | 90 |
| Example 1565 | 1282 | $C_{25}H_{26}ClF_3N_4O_3$ | 523.2 | 25.0 | 96 |
| Example 1566 | 1283 | $C_{23}H_{27}Cl_2N_3O_3$ | 464.2 | 12.2 | 53 |
| Example 1567 | 1284 | $C_{22}H_{25}BrClN_3O_3$ | 496.0 | 24.1 | 97 |
| Example 1568 | 1285 | $C_{22}H_{25}Cl_2N_3O_3$ | 450.2 | 21.8 | 97 |
| Example 1569 | 1342 | $C_{22}H_{24}BrCl_2N_3O_2$ | 514.0 | 27.2 | quant |
| Example 1570 | 1343 | $C_{23}H_{27}Cl_2N_3O_2$ | 448.0 | 21.4 | 95 |
| Example 1571 | 1344 | $C_{22}H_{24}Cl_2IN_3O_2$ | 560.0 | 27.0 | 96 |
| Example 1572 | 1345 | $C_{23}H_{28}ClN_3O_2$ | 430.2 | 23.8 | quant |
| Example 1573 | 1346 | $C_{22}H_{25}ClIN_3O_3$ | 542.0 | 29.4 | quant |
| Example 1574 | 1350 | $C_{23}H_{26}ClN_3O_2S$ | 420.0 | 13.0 | 62 |
| Example 1575 | 1354 | $C_{24}H_{28}BrClN_4O_3$ | 537.2 | 5.2 | 19 |
| Example 1576 | 1358 | $C_{23}H_{26}ClN_5O_2$ | 440.2 | 21.8 | 99 |
| Example 1577 | 1383 | $C_{23}H_{24}Cl_2F_3N_3O_2$ | 502.0 | 20.0 | 80 |
| Example 1578 | 1384 | $C_{20}J_{23}BrClN_3O_2S$ | 486.0 | 21.0 | 87 |
| Example 1579 | 1385 | $C_{28}H_{30}ClN_3O_4S$ | 540.2 | 23.8 | 88 |
| Example 1580 | 1386 | $C_{28}H_{30}ClN_3O_2$ | 476.0 | 20.0 | 84 |
| Example 1581 | 1414 | $C_{24}H_{28}Cl_2N_4O_3$ | 491.0 | 0.8 | 3 |
| Example 1582 | 1418 | $C_{23}H_{26}ClN_5O_2S$ | 472.0 | 10.4 | 44 |
| Example 1583 | 1436 | C29 H30 Cl N3 O3 | 504.2 | 26.8 | quant |
| Example 1584 | 1600 | C23 H26 Cl F3 N4 O2 | 483.2 | 16.5 | 68 |
| Example 1585 | 1601 | C23 H26 Cl F3 N4 O3 | 499.0 | 20.0 | 80 |
| Example 1586 | 1602 | C21 H24 Br Cl N4 O2 | 481.0 | 18.1 | 75 |
| Example 1587 | 1603 | C21 H24 Cl2 N4 O2 | 435.0 | 5.5 | 25 |
| Example 1588 | 1604 | C27 H30 Cl N3 O3 | 492.0 | 18.6 | 76 |
| Example 1589 | 1605 | C21 H27 Cl N4 O2 | 415.2 | 18.1 | 87 |
| Example 1590 | 1609 | C23 H25 N3 O2 S | 500.0 | 18.3 | 73 |
| Example 1591 | 1659 | C22 H26 Cl2 N4 O2 | 449.0 | 366.0 | 83 |
| Example 1592 | 1664 | C24 H29 F3 N4 O2 S | 495.2 | 13.7 | 55 |
| Example 1593 | 1665 | C24 H29 F3 N4 O3 S | 511.2 | 14.9 | 58 |
| Example 1594 | 1666 | C23 H28 F2 N4 O2 S | 463.2 | 12.9 | 56 |
| Example 1595 | 1667 | C22 H27 Br2 N3 O3 | 542 | 26.1 | 96 |
| Example 1596 | 1668 | C24 H30 F2 N4 O2 | 445 | 22.9 | quant |
| Example 1597 | 1669 | C24 H31 F N4 O2 | 427 | 24.0 | quant |
| Example 1598 | 1670 | C24 H31 I N4 O2 | 535 | 28.1 | quant |
| Example 1599 | 1671 | C25 H31 F3 N4 O3 | 493 | 26.8 | quant |
| Example 1600 | 1672 | C25 H31 F3 N4 O2 | 478 | 24.7 | quant |
| Example 1601 | 1673 | C24 H29 Br Cl N3 O2 | 508 | 24.9 | 98 |
| Example 1602 | 1674 | C20 H22 Br2 F N3 O3 | 532 | 25.6 | 96 |
| Example 1603 | 1675 | C22 H25 F3 N4 O2 | 435 | 21.5 | 99 |
| Example 1604 | 1676 | C22 H26 F2 N4 O2 | 417 | 21.4 | quant |
| Example 1605 | 1677 | C22 H26 Br F N4 O2 | 479 | 23.4 | 98 |
| Example 1606 | 1678 | C22 H26 F I N4 O2 | 525 | 27.4 | quant |
| Example 1607 | 1679 | C22 H26 Cl F N4 O2 | 433 | 22.4 | quant |
| Example 1608 | 1680 | C23 H26 F4 N4 O3 | 483 | 25.5 | quant |
| Example 1609 | 1681 | C23 H26 F4 N4 O2 | 467 | 23.2 | 99 |
| Example 1610 | 1682 | C23 H26 Br Cl F N3 O | 498 | 24.2 | 98 |
| Example 1611 | 1683 | C27 H28 Br2 N4 O4 | 633 | 31.8 | quant |
| Example 1612 | 1684 | C29 H31 F2 N5 O3 | 536 | 28.3 | quant |
| Example 1613 | 1685 | C29 H32 F N5 O3 | 518 | 31.1 | quant |
| Example 1614 | 1686 | C29 H32 Br N5 O3 | 578 | 29.6 | quant |
| Example 1615 | 1687 | C29 H32 I N5 O3 | 626 | 32.4 | quant |
| Example 1616 | 1688 | C29 H32 Cl N5 O3 | 534 | 28.2 | quant |
| Example 1617 | 1689 | C30 H32 F3 N5 O4 | 584 | 31.7 | quant |
| Example 1618 | 1690 | C30 H32 F3 N5 O3 | 568 | 30.6 | quant |
| Example 1619 | 1691 | C29 H30 Br Cl N4 O3 | 599 | 31.4 | quant |

For example, Compound 1245 and 1600 showed the following NMR spectra.

Compound No. 1245: $^1$H NMR (270 MHz, $CDCl_3$) δ1.20–1.97 (m, 7 H), 2.80–2.86 (m, 2 H), 3.19 (t, J=6.5 Hz, 2 H), 3.43 (s, 2 H), 4.02 (d, J=5.3 Hz, 2 H), 5.52 (br s, 2 H), 6.44 (d, J=11.9, 6.6 Hz, 1 H), 7.02 (br s, 1 H), 7.21–7.32 (m, 5 H).

Compound No. 1600: $^1$H NMR (270 MHz, $CDCl_3$) δ1.25–1.97 (m, 9 H), 2.82–2.87 (m, 2 H), 3.21 (t, J=6.5 Hz, 2 H), 3.44 (s, 2 H), 4.06 (d, J=5.1 Hz, 2 H), 5.98 (br s, 1 H), 6.71 (d, J=8.3 Hz, 1 H), 6.87 (br s, 1 H), 7.26 (s, 4 H), 7.43 (dd, J=5.9 Hz, 1 H), 7.64 (s, 1 H).

Example 1620

Preparation of 1-(4-Chlorobenzyl)-4-[{N-(4-isopropylphenylsulfonyl)glycyl}aminomethyl]piperidine (Compound No. 869)

A solution of 1-(4-chlorobenzyl)-4-{(glycylamino)methyl}piperidine (14.8 mg, 0.05 mmol) in $CHC_3$ (2 mL) was treated with (piperidinomethyl)polystyrene resin (28 mg, 2.8 mmol/g), 4-isopropylbenzenesulfonyl chloride (1.5 equiv.) and stirred at 25° C. for 16 h. (Aminomethyl)polystyrene was added to scavenge the residual sulfonyl chloride and the reaction mixture was stirred at 25° C. for 16 h. Filtration and concentration afforded 1-(4-chlorobenzyl)-4-[{(4-isopropylphenylsulfonyl)glycyl}aminomethyl]piperidine (compound No. 869) (22.1 mg, 92%): The purity was determined, by RPLC/MS (86%); ESI/MS m/e 478 ($M^+$+H, $C_{24}H_{32}ClN_3O_3S$).

Examples 1621–1627

The compounds of this invention were synthesized pursuant to methods of Example 1620 using the corresponding reactant respectively. The ESI/MS data and yields are summarized in Table 30.

TABLE 30

| | Compound No. | Molecular Formula | ESI/MS m/e | Yield (mg) | Yield (%) |
|---|---|---|---|---|---|
| Example 1621 | 865 | C22 H28 Cl N3 O3 S | 450 | 16.2 | 72 |
| Example 1622 | 866 | C22 H25 Cl F3 N3 O3 S | 504 | 8.8 | 35 |
| Example 1623 | 867 | C23 H24 Cl F6 N3 O3 S | 572 | 8.0 | 28 |
| Example 1624 | 868 | C23 H30 Cl N3 O3 S | 464 | 9.6 | 41 |
| Example 1625 | 870 | C22 H28 Cl N3 O3 S | 450 | 8.8 | 39 |
| Example 1626 | 871 | C25 H34 Cl N3 O3 S | 492 | 11.1 | 45 |
| Example 1627 | 872 | C21 H26 Cl N3 O3 S | 436 | 9.6 | 44 |

Example 1628

Preparation of 1-(4-Chlorobenzyl)-4-[{2-(3-(4-trifluoromethylphenyl)ureido)acetylamino}methyl]piperidine (Compound No. 852)

A solution of 1-(4-chlorobenzyl)-4-{(glycylamino)methyl}piperidine (14.8 mg, 0.05 mmol) in $CHCl_3$ (2 mL) was treated with (piperidinomethyl)polystyrene resin (28 mg, 2.8 mmol/g), 3-(trifluoromethyl)phenyl isocyanate (1.3 equiv.) and stirred at 25° C. for 16 h. (Aminomethyl)polystyrene was added to scavenge the residual isocyanate and the reaction mixture was stirred at 25° C. for 16 h. Filtration and concentration afforded 1-(4-chlorobenzyl)-4-[{2-(3-(4-trifluoromethylphenyl)ureido)acetylamino}methyl]piperidine (19 mg, 78%) (compound No. 852): The purity was determined by RPLC/MS (92%); ESI/MS m/e 483 ($M^+$+H, $C_{23}H_{26}ClF_3N_4O_2$)

Examples 1629–1641

The compounds of this invention were synthesized pursuant to methods of Example 1628 using the corresponding reactant respectively. The ESI/MS data and yields are summarized in Table 31.

TABLE 31

| | Compound No. | Molecular Formula | ESI/MS m/e | Yield (mg) | Yield (%) |
|---|---|---|---|---|---|
| Example 1629 | 851 | C23 H26 Cl F3 N4 O2 | 483 | 13.2 | 55 |
| Example 1630 | 853 | C22 H27 Cl N4 O2 | 416 | 8.5* | 32 |
| Example 1631 | 854 | C23 H29 Cl N4 O2 | 429 | 11.4* | 42 |
| Example 1632 | 855 | C23 H29 Cl N4 O2 | 429 | 10.1* | 37 |
| Example 1633 | 856 | C24 H29 Cl N4 O3 | 457 | 10.3* | 36 |
| Example 1634 | 857 | C23 H29 Cl N4 O3 | 445 | 10.9* | 39 |
| Example 1635 | 858 | C23 H29 Cl N4 O3 | 445 | 8.6* | 31 |
| Example 1636 | 859 | C22 H26 Cl2 N4 O2 | 449 | 11.0* | 39 |
| Example 1637 | 860 | C23 H26 Cl N5 O2 | 440 | 9.2* | 33 |
| Example 1638 | 861 | C22 H27 Cl N4 O S | 431 | 13.3 | 62 |
| Example 1639 | 862 | C23 H29 Cl N4 O S | 445 | 15.3 | 69 |
| Example 1640 | 863 | C23 H29 Cl N4 O2 S | 461 | 14.7 | 64 |
| Example 1641 | 864 | C23 H29 Cl N4 O2 S | 461 | 13.1 | 57 |

*Yield of TFA salt.

Example 1642

Preparation of 1-(4-Chlorobenzyl)-4-[{N-(3-ethoxybenzoyl)-D-phenylalanyl}aminomethyl]piperidine (Compound No. 2091)

A solution of 1-(4-chlorobenzyl)-4-(aminomethyl)piperidine (100 mg) in $CHCl_3$ (3 mL) was treated with $Et_3N$ (0.090 mL), N-(tert-butoxycarbonyl)-D-phenylalanine (122 mg), EDCI (89 mg) and HOBt (62 mg). The reaction mixture was stirred at room temperature for 17 h. The reaction mixture was washed with 1 N aqueous NaOH solution (2 mL×2) and brine (2 mL). The organic layer was dried and concentrated to afford 1-(4-chlorobenzyl)-4-[{N-(tert-butoxycarbonyl)-D-phenylalanyl}aminomethyl]piperidine.

The resulting 1-(4-chlorobenzyl)-4-[{N-(tert-butoxycarbonyl)-D-phenylalanyl}aminomethyl]piperidine was dissolved in methanol. (5 mL) and 4 N HCl in dioxane (1.5 mL) was added. The solution was stirred at room temperature for 19 h and concentrated.

A solution of the resulting material and 3-ethoxybenzoic acid (80 mg, 0.48 mmol) in $CHCl_3$ (1 mL)was treated with $Et_3N$ (0.090 mL), EDCI (90 mg) and HOBt (68 mg). The reaction mixture was stirred at room temperature for 11 h. The reaction mixture was washed with 1 N aqueous NaOH solution (1.5 mL×2) and brine (1.5 mL). The organic layer was dried and concentrated. Column chromatography ($SiO_2$, $CH_2Cl_2$/MeOH=95:5) afforded 1-(4-chlorobenzyl)-4-[{N-(3-ethoxybenzoyl)-D-phenylalanyl}aminomethyl]piperidine (Compound No. 2091) (183.5 mg, 82%): The purity was determined by RPLC/MS (99%); ESI/MS m/e 534.0 ($M^+$+H, $C_{31}H_{36}ClN_3O_3$).

Examples 1643–1657

The compounds of this invention were synthesized pursuant to methods of Example 1642 using the corresponding reactant respectively. The ESI/MS data and yields are summarized in Table 32.

TABLE 32

| | Compound No. | Molecular Formula | ESI/MS m/e | Yield (mg) | Yield (%) |
|---|---|---|---|---|---|
| Example 1643 | 2092 | C33 H37 Cl N4 O3 | 572.8 | 152.9 | 64 |
| Example 1644 | 2093 | C27 H36 Cl N3 O3 S | 518.0 | 177.4 | 82 |
| Example 1645 | 2094 | C29 H34 Cl N3 O3 S | 539.9 | 164.4 | 73 |
| Example 1646 | 2095 | C28 H38 Cl N3 O3 | 500.0 | 139.1 | 66 |
| Example 1647 | 2096 | C31 H42 Cl N3 O3 | 540.0 | 161.7 | 71 |
| Example 1648 | 2097 | C27 H36 Cl N3 O3 | 485.8 | 157.8 | 78 |
| Example 1649 | 2098 | C31 H35 Cl2 N3 O3 | 567.9 | 172.2 | 72 |
| Example 1650 | 2099 | C30 H34 Cl N3 O3 | 519.8 | 144.7 | 66 |
| Example 1651 | 2100 | C32 H38 Cl N3 O4 | 564.0 | 181.5 | 77 |
| Example 1652 | 2101 | C38 H42 Cl N3 O4 | 639.9 | 192.3 | 72 |
| Example 1653 | 2103 | C33 H40 Cl N3 O4 | 577.8 | 159.9 | 66 |
| Example 1654 | 2104 | C28 H36 Cl N3 O5 | 530.1 | 99.7 | 45 |
| Example 1655 | 2115 | C27 H36 Cl N3 O3 | 486.2 | 122.9 | 60 |
| Example 1656 | 2116 | C28 H38 Cl N3 O3 | 500.1 | 118.3 | 57 |
| Example 1657 | 2117 | C28 H34 Cl N5 O3 | 524.1 | 98.3 | 45 |

Reference Example 29

Preparation of 1-(tert-Butoxycarbonyl)-4-[{N-(3-(trifluoromethyl)benzoyl)glycyl}aminomethyl]piperidine N-{3-(Trifluoromethyl)benzoyl}glycine (4.22 g, 17.0 mmol), EDCI (4.25 g, 22.1 mmol), 1-hydroxybenzotriazole hydrate (2.99 g, 22.1 mmol) and $Et_3N$ (1.72 g) were added to a solution of 1-(tert-butoxycarbonyl)-4-(aminomethyl)piperidine (4.03 g) in dry $CH_2Cl_2$ (200 mL). The reaction mixture was stirred at 25° C. for 20 h. $H_2O$ (100 mL) was added to the reaction mixture and the mixture was extracted with $CH_2Cl_2$(2×50 mL). The combined extracts were washed with $H_2O$ (2×50 mL), brine (50 mL) and dried ($MgSO_4$). The solvent was removed under reduced pressure to afford an yellow oil which was purified by column chromatography ($SiO_2$, 70% EtOAc-hexane) to give 1-(tert-butoxycarbonyl)-4-[{N-(3-(trifluoromethyl)benzoyl)glycyl}aminomethyl]piperidine as a white solid (6.39 g, 85%): $^1$H-NMR ($CDCl_3$, 300 MHz) δ1.4 (s, 9 H), 1.0–1.8 (m, 5 H), 2.6–2.8 (m, 2 H), 3.15–3.3 (m, 2 H), 4.0–4.3 (m, 4 H), 6.6–6.7 (m, 1H), 7.64 (s, 1 H), 7.60 (dd, 1 H, J=7.2, 7,2 Hz), 7.79 (d, 1 H, J=7,2 Hz), 8.0 (d, 1 H, J=7.2 Hz), 8.11 (s, 1 H); The purity was determined by RPLC/MS (97%); ESI/MS m/e 444.3 ($M^+$+H, $C_{21}H_{28}F_3N_3O_4$).

Reference Example 30

Preparation of 4-[{N-(3-(Trifluoromethyl)benzoyl)glycyl}aminomethyl]piperidine A solution of 1-(tert-butoxycarbonyl)-4-[{N-(3-(trifluoromethyl)benzoyl)glycyl}aminomethyl]piperidine (2.29 9, 5.16 mmol) in $CH_3OH$ (40 mL) was treated with 1 N HCl-$Et_2O$ (55 mL). The reaction mixture was stirred at 25° C. for 15 h and the solvent was removed under reduced pressure. 2 N aqueous NaOH solution (100 mL) was added to the reaction mixture and the mixture was extracted with EtOAc (3×100 mL). The combined extracts were washed with brine and dried ($K_2CO_3$). The solvent was removed under reduced pressure to afford a white solid which was purified by column chromatography ($SiO_2$, $CH_3OH$/$CH_2Cl_2$/$Et_3N$=7/6/1)) to give 4-[{N-(3-(trifluoromethyl)benzoyl)glycyl}aminomethyl]piperidine as a white solid (1.27 g, 72%): The purity was determined by RPLC/MS (98%); ESI/MS m/e 344.1 ($M^+$+H, $Cl_{16}H_{20}F_3O_2$)

Example 1658

Preparation of 1-{3-(Trifluoromethoxy)benzyl}-4-[{N-(3-(trifluoromethyl)benzoyl) glycyl}aminomethyl]piperidine (Compound No. 927)

A solution of 4-[{N-(3(trifluoromethyl)benzoyl) glycyl}aminomethyl]piperidine (19.9 mg, 0.058 mmol) in $CH_3CN$ (1.0 mL) and (piperidinomethyl)polystyrene (55 mg, 2.7 mmol base/g resin) were added to a solution of 3-(trifluoromethoxy)benzyl bromide (12.3 mg, 0.048 mmol) in $CH_3CN$ (1.0 mL). The reaction mixture was stirred at 60° C. for 2.5 h. Phenyl isocyanate (6.9 mg, 0.048 mmol) was added to the cooled reaction mixture and the mixture was stirred at 25° C. for 1 h. The reaction mixture was loaded onto Varian™ SCX column and washed with $CH_3OH$ (20 mL). Product was eluted off using 2 N $NH_3$ in $CH_3OH$ (6 mL) and concentrated to afford 1-{3-(trifluoromethoxy) benzyl}-4-[{N-(3-(trifluoromethyl)benzoyl) glycyl}aminomethyl]piperidine (compound No. 927) (22.8 mg, 91%) as a pale yellow oil: The purity was determined by RPLC/MS (99%); ESI/MS m/e 518.1 ($M^+$+H, $C_{24}H_{26}F_6N_3O_3$)

Examples 1659–1710

The compounds of this invention were synthesized pursuant to methods of Example 1658 using the corresponding reactant respectively. The ESI/MS data and yields are summarized in Table 33.

TABLE 33

| | Compound No. | Molecular Formula | ESI/MS m/e | Yield (mg) | Yield (%) |
|---|---|---|---|---|---|
| Example 1659 | 875 | C23 H26 F3 N3 O2 | 434 | 6.3 | 40 |
| Example 1660 | 876 | C23 H25 Br F3 N3 O2 | 512 | 4.3 | 23 |
| Example 1661 | 877 | C24 H25 F3 N4 O2 | 459 | 11.3 | 68 |
| Example 1662 | 878 | C23 H25 F3 N4 O4 | 479 | 8.3 | 48 |
| Example 1663 | 884 | C25 H29 F3 N4 O3 | 491 | 10.8 | 61 |
| Example 1664 | 885 | C24 H28 F3 N3 O4 S | 512 | 9.0 | 49 |
| Example 1665 | 886 | C23 H25 F4 N3 O2 | 452 | 12.7 | 78 |
| Example 1666 | 887 | C24 H25 F6 N3 O2 | 502 | 13.9 | 77 |
| Example 1667 | 888 | C23 H26 F3 N3 O3 | 450 | 11.5 | 71 |
| Example 1668 | 889 | C29 H30 F3 N3 O2 | 510 | 12.4 | 68 |
| Example 1669 | 890 | C27 H28 F3 N3 O2 | 484 | 12.0 | 69 |
| Example 1670 | 891 | C23 H24 Cl2 F3 N3 O2 | 502 | 11.4 | 63 |
| Example 1671 | 892 | C24 H28 F3 N3 O3 | 464 | 11.7 | 70 |
| Example 1672 | 893 | C24 H26 F3 N5 O5 | 522 | 13.9 | 74 |
| Example 1673 | 894 | C26 H32 F3 N3 O3 | 492 | 11.3 | 64 |
| Example 1674 | 895 | C24 H28 F3 N3 O2 | 448 | 4.8 | 30 |
| Example 1675 | 896 | C24 H25 F3 N4 O2 | 459 | 17.5 | quant |
| Example 1676 | 897 | C24 H26 F3 N3 O4 | 478 | 9.2 | 57 |
| Example 1677 | 898 | C24 H26 F3 N3 O4 | 478 | 8.9 | 55 |
| Example 1678 | 899 | C24 H28 F3 N3 O3 | 464 | 13.7 | 82 |
| Example 1679 | 900 | C25 H28 F3 N3 O4 | 492 | 18.6 | quant |
| Example 1680 | 901 | C29 H30 F3 N3 O2 | 510 | 13.7 | 75 |
| Example 1681 | 902 | C23 H24 F3 N5 06 | 524 | 12.6 | 67 |
| Example 1682 | 903 | C25 H30 F3 N3 O4 | 494 | 14.0 | 79 |
| Example 1683 | 906 | C25 H30 F3 N3 O2 | 462 | 11.2 | 67 |
| Example 1684 | 907 | C31 H34 F3 N3 O2 | 538 | 19.6 | 75 |
| Example 1685 | 908 | C30 H31 F3 N4 O3 | 553 | 30.4 | 76 |
| Example 1686 | 909 | C30 H31 F3 N4 O3 | 553 | 12.6 | 63 |
| Example 1687 | 910 | C23 H24 Cl2 F3 N3 O2 | 502 | 11.0 | 61 |
| Example 1688 | 911 | C23 H25 Cl F3 N3 O2 | 468 | 20.2 | 89 |
| Example 1689 | 912 | C23 H24 Br2 F3 N3 O2 | 590 | 20.2 | 95 |
| Example 1690 | 913 | C24 H28 F3 N3 O3 | 464 | 12.6 | 76 |
| Example 1691 | 914 | C30 H32 F3 N3 O3 | 540 | 13.9 | 72 |
| Example 1692 | 915 | C24 H28 F3 N3 O3 | 464 | 8.3 | 25 |
| Example 1693 | 916 | C22 H25 F3 N4 O2 | 435 | 2.5 | 8 |
| Example 1694 | 917 | C22 H25 F3 N4 O2 | 435 | 2.7 | 9 |
| Example 1695 | 918 | C26 H30 F3 N3 O4 | 506 | 3.9 | 22 |

TABLE 33-continued

| | Compound No. | Molecular Formula | ESI/MS m/e | Yield (mg) | Yield (%) |
|---|---|---|---|---|---|
| Example 1696 | 919 | C24 H28 F3 N3 O2 | 448 | 15.9 | 99 |
| Example 1697 | 920 | C24 H25 F6 N3 O3 | 518 | 20.3 | 81 |
| Example 1698 | 921 | C27 H28 F3 N3 O2 | 484 | 15.5 | 89 |
| Example 1699 | 922 | C20 H26 F3 N3 O2 | 398 | 7.3 | 51 |
| Example 1700 | 923 | C29 H29 Cl F3 N3 O2 | 544 | 12.5 | 48 |
| Example 1701 | 928 | C24 H25 F6 N3 O3 | 518 | 21.4 | 86 |
| Example 1702 | 929 | C24 H28 F3 N3 O2 S | 480 | 23.7 | quant |
| Example 1703 | 930 | C24 H28 F3 N3 O2 | 448 | 21.3 | 99 |
| Example 1704 | 931 | C24 H25 F3 N4 O2 | 459 | 21.4 | 97 |
| Example 1705 | 932 | C23 H24 Cl F3 N4 O4 | 513 | 15.6 | 63 |
| Example 1706 | 933 | C24 H28 F3 N3 O2 | 448 | 16.6 | 77 |
| Example 1707 | 934 | C22 H25 F3 N4 O2 | 435 | 18.0 | 43 |
| Example 1708 | 935 | C23 H25 F3 N4 O4 | 479 | 15.1 | 65 |
| Example 1709 | 936 | C23 H25 F3 N4 O4 | 479 | 15.4 | 67 |
| Example 1710 | 1615 | C24 H25 F6 N3 O2 S | 534.2 | 26.3 | 99 |

Example 1711

Preparation of 1-{4-(Dimethylamino)benzyl}-4-[{N-(3-(trifluoromethyl)benzoyl) glycyl}aminomethyl]piperidine (Compound No. 937)

A solution of 4-[{-(3-(trifluoromethyl)benzoyl) glycyl}aminomethyl]piperidine (20.0 mg, 0.058 mmol) in $CH_3OH$ (1.0 mL) and $NaBH_3CN$ (16.5 mg) were added to a solution of 4-(dimethylamino)benzaldehyde (30.4 mg, 0.204 mmol) in 5% $CH_3COOH/CH_3OH$ (1.0 mL). The reaction mixture was stirred at 60° C. for 19 h. The solvent was evaporated to afford a solid. $CH_3CN$ (2.0 mL) and phenyl isocyanate (6.9 mg, 0.048 mmol) were added to the solid and the mixture was stirred at 25° C. for 1 h. The reaction mixture was loaded onto Varian™ SCX column and washed with $CH_3OH$ (20 mL). Product was eluted using 2 N $NH_3$—$CH_3OH$ (6 mL) and the eluant was concentrated to afford 1-(4-(dimethylamino)benzyl)-4-[{N-(3-(trifluoromethyl)benzoyl)glycyl}aminomethyl]piperidine (compound No. 937) as a pale yellow oil (13.5 mg, 49%): The purity was determined by RPLC/MS (87%); ESI/MS m/e 477.3 ($M^+$+H, $C_{25}H_{31}F_3N_4O_2$).

Examples 1712–1729

The compounds of this invention were synthesized pursuant to methods of Example 1711 using the corresponding reactant respectively. Preparative TLC ($SiO_2$), if needed, afforded the desired material. The ESI/MS data and yields are summarized in Table 34.

TABLE 34

| | Compound No. | Molecular Formula | ESI/MS m/e | Yield (mg) | Yield (%) |
|---|---|---|---|---|---|
| Example 1712 | 879 | C24 H26 F3 N3 O4 | 478 | 13.0 | 62 |
| Example 1713 | 880 | C24 H26 F3 N3 O4 | 478 | 16.3 | 78 |
| Example 1714 | 881 | C23 H25 Br F3 N3 O2 | 512 | 11.4 | 51 |
| Example 1715 | 882 | C29 H30 F3 N3 O3 | 526 | 13.4 | 58 |
| Example 1716 | 883 | C23 H25 Cl F3 N3 O2 | 468 | 7.9 | 39 |
| Example 1717 | 904 | C23 H26 F3 N3 O3 | 450 | 3.3 | 17 |
| Example 1718 | 905 | C21 H23 F3 N4 O4 S | 485 | 27.7 | 98 |
| Example 1719 | 938 | C23 H24 Cl F4 N3 O2 | 486 | 8.6 | 30 |
| Example 1720 | 939 | C23 H24 Cl F3 N4 O4 | 513 | 11.0 | 37 |
| Example 1721 | 940 | C23 H26 F3 N3 O3 | 450 | 5.5 | 21 |

TABLE 34-continued

| | Compound No. | Molecular Formula | ESI/MS m/e | Yield (mg) | Yield (%) |
|---|---|---|---|---|---|
| Example 1722 | 941 | C24 H24 Cl F6 N3 O2 | 536 | 11.2 | 36 |
| Example 1723 | 987 | C30 H32 F3 N3 O2 | 524 | 17.5 | 76 |
| Example 1724 | 1449 | C25 H30 F3 N3 O2 | 462 | 21.6 | 80 |
| Example 1725 | 1450 | C26 H32 F3 N3 O2 | 476 | 23.5 | 85 |
| Example 1726 | 1452 | C27 H35 F3 N4 O2 | 505 | 5.1 | 17 |
| Example 1727 | 1453 | C26 H32 F3 N3 O3 | 492 | 22.0 | 77 |
| Example 1728 | 1454 | C25 H30 F3 N3 O3 | 478 | 21.4 | 77 |
| Example 1729 | 1456 | C25 H28 F3 N3 O4 | 492 | 23.8 | 83 |

Example 1730

Preparation of 1-{3-Hydroxy-4-methoxybenzyl}-4-[{N-(3-(trifluoromethyl)benzoyl) glycyl}aminomethyl]piperidine (Compound No. 1452)

To a solution of 4-[{N-(3-(trifluoromethyl)benzoyl) glycyl}aminomethyl]piperidine (20.0 mg, 0.058 mmol) and 3-hydroxy-4-methoxybenzaldehyde (33 mg)in 5% $CH_3COOH/CH_3OH$ (1.0 mL) was added $NaBH_3CN$ (16.5 mg) in 5% $CH_3COOH/CH_3OH$ (1.0 mL). The reaction mixture was stirred at 60° C. for 15 h. The reaction mixture was loaded onto Varian™ SCX column and washed with $CH_3OH$ (15 mL). Product was eluted using 2 N $NH_3$—$CH_3OH$ (5 mL) and the eluant was concentrated to afford 1-(3-hydroxy-4-methoxybenzyl)-4-[{N-(3-(trifluoromethyl) benzoyl)glycyl}aminomethyl]piperidine (Compound No. 1452) (25.8 mg, 92%): The purity was determined by RPLC/MS (91%); ESI/MS m/e 480 ($M^+$+H, $C_{24}H_{28}F_3N_3O_4$).

Examples 1731–1733

The compounds of this invention were synthesized pursuant to methods of Example 1730 using the corresponding reactant respectively. The ESI/MS data and yields are summarized in Table 35.

TABLE 35

| | Compound No. | Molecular Formula | ESI/MS m/e | Yield (mg) | Yield (%) |
|---|---|---|---|---|---|
| Example 1731 | 1455 | C24 H28 F3 N3 O4 | 480 | 24.0 | 86 |
| Example 1732 | 1647 | C27 H34 F3 N3 O2 | 490.2 | 23.6 | 96 |
| Example 1733 | 1649 | C26 H32 F3 N3 O2 | 476.2 | 23.1 | 97 |

Example 1734

Preparation of 1-(4-Benzylbenzyl)-4-[{N-(3-(trifluoromethyl)benzoyl)glycyl}aminomethyl] piperidine (Compound No. 926)

A solution of methanesulfonyl chloride (4.2 mg, 0.037 mmol) in $CHCl_3$ (1.0 mL) and (piperidinomethyl) polystyrene (54 mg, 2.7 mmol base/g resin) were added to a solution of 4-(benzyl)benzyl alcohol (8.7 mg, 0.044 mmol) in $CHCl_3$ (1.0 mL). The reaction mixture was stirred at 25° C. for 15 h. A solution of 4-[{N-(3-(trifluoromethyl) benzoyl)glycyl}aminomethyl]piperidine (15.1 mg, 0.044 mmol) in $CH_3CN$ (1.0 mL) and KI (2 mg) were added to the reaction mixture and the mixture was stirred at 65° C. for 5 h. Phenyl isocyanate (5.2 mg) was added to the cooled reaction mixture and the mixture was stirred at 25° C. for 1 h. The reaction mixture was loaded onto Varian™ SCX column and washed with $CH_3OH$ (20 mL). Product was eluted off using 2 N $NH_3$ in $CH_3OH$ (6 mL) and concentrated to afford 1-(4-benzylbenzyl)-4-[{N-(3-(trifluoromethyl)benzoyl)glycyl}aminomethyl]piperidine (compound No. 926) as a pale yellow oil (5.6 mg, 29%): The purity was determined by RPLC/MS (94%); ESI/MS m/e 524.1 ($M^+$+H, $C_{30}H_{32}F_3N_3O_2$).

Reference Example 31

Preparation of 4-[{N-(Benzyloxycarbonyl)glycyl) amino}methyl]-1-(tert-butoxycarbonyl)piperidine A solution of 4-(aminomethyl)-1-(tert-butoxycarbonyl) piperidine (3.54 g, 16.5 mmol) in $CH_2Cl_2$ (80 mL) was treated with $Et_3N$ (2.8 mL, 20 mmol), N-(benzyloxycarbonyl)glycine (3.77 g, 18 mmol), EDCI (3.45 g, 18 mmol) and HOBt (2.43 g, 18 mmol). After the reaction mixture was stirred at room temperature for 15 h, 2 N aqueous NaOH solution (100 mL) was added. The organic layer was separated, and the aqueous layer was extracted with dichloromethane (100 mL×3). The combined organic layers were dried over anhydrous sodium sulfate, filtered, and concentrated. Column chromatography ($SiO_2$, ethyl acetate) afforded the desired 4-[{(N-(Benzyloxycarbonyl) glycyl)amino}methyl]-1-(tert-butoxycarbonyl)piperidine (6.27 g, 94%) as an amorphous solid.

Reference Example 32

Preparation of 4-{(Glycylamino}methyl}-1-(tert-butoxycarbonyl)piperidine

A solution of 4-[{(N-(benzyloxycarbonyl)glycyl) amino}methyl]1-(tert-butoxycarbonyl)piperidine (6.26 g, 15.4 mmol) in methanol (100 mL) was hydrogenated at 1 atm in the presence of 5% palladium on charcoal (620 mg) at room temperature for 7 h. The catalyst was removed by filtration through Celite and the combined filtrate was concentrated to afford 4-{(glycylamino}methyl}-1-(tert-butoxycarbonyl)piperidine (3.84 g, 92%) as a solid.

Reference Example 33

Preparation of 4-[{(N-(2-Amino-5-chlorobenzoyl) glycyl)amino}methyl]-1-(tert-butoxycarbonyl) piperidine A solution of 4-{(glycylamino}methyl)-1-(tert-butoxycarbonyl)piperidine (1.33 g, 4.90 mmol) in $CH_2Cl_2$ (25 mL) was treated with $Et_3N$ (0.75 mL, 5.4 mmol), 2-amino-5-chlorobenzoic acid (840 mg, 4.9 mmol), EDCI (940 mg, 4.9 mmol) and HOBt (660 mg, 4.9 mmol). After the reaction mixture was stirred at room temperature for 3 h, 2 N aqueous NaOH solution (20 mL) was added. The organic layer was separated, and the aqueous layer was extracted with dichloromethane (20 mL×3). The combined organic layers were dried over anhydrous sodium sulfate, filtered, and concentrated. Column chromatography ($SiO_2$, ethyl acetate) afforded the desired 4-[{(N-(2-amino-5-chlorobenzoyl)glycyl)amino}methyl]-1-(tert-butoxycarbonyl)piperidine (1.63 g, 78%) as a solid.

Reference Example 34

Preparation of 4-[{(N-(2-Amino-5-chlorobenzoyl) glycyl)amino}methyl]piperidine To a solution of 4-[{(N-(2-amino-5-chlorobenzoyl) glycyl)amino}methyl]-1-(tert-butoxycarbonyl)piperidine (1.63 g, 3.84 mmol) in methanol (20 mL) was added 4 N HCl in dioxane (9.5 mL). The solution was stirred at room temperature for 6 h. The reaction mixture was concentrated and 2 N aqueous NaOH solution (20 mL) was added. The mixture was extracted with dichloromethane (20 mL×3), and the combined extracts were dried over sodium sulfate, filtered and concentrated to give 4-[{N-(2-amino-5-chlorobenzoyl)glycyl)amino}methyl]piperidine (1.19 g, 95%): $^1$H NMR ($CDCl_3$, 270 MHz) δ1.10–1.76 (m, 4 H), 2.55 (td, J=2.4 and 12.2 Hz, 2 H), 3.00–3.10 (m, 2 H), 3.17 (t, J=6.2 Hz, 2 H), 3.48 (s, 2 H), 4.03 (d, J=4.9 Hz, 2 H), 5.50 (br. s, 2 H), 6.11–6.23 (m, 1 H), 6.60 (d, J=8.8 Hz, 1 H), 6.85–7.02 (m, 1 H), 7.15 (dd, J=2.7 and 8.8 Hz, 1 H), 7.38 (d, J=2.4 Hz, 1 H); ESI/MS m/e 325.2 ($C_{15}H_{21}ClN_4O_2$).

4-[{(N-(2-Amino-5-bromobenzoyl)glycyl) amino}methyl]piperidine was also synthesized pursuant to methods of Reference Examples 32 and 33 using the corresponding reactant: 951 mg, 64% (2 steps).ESI/MS m/e 369.2 ($C_{15}H_{21}BN_4O_2$).

Example 1735

Preparation of 4-[{(N-(2-(tert-Butoxycarbonylamino)-4,5-difluorobenzoyl)glycyl) amino}methyl]-1-(4-chlorobenzyl)piperidine A solution of 1-(4-chlorobenzyl)-4-{(glycylamino) methyl}piperidine dihydrochloride (738 mg, 2 mmol) in $CH_2Cl_2$ (20 mL) was treated with $Et_3N$ (1.1 mL, 8 mmol), 2-(tert-butoxycarbonylamino)-4,5-difluorobenzoic acid (607 mg, 2.2 mmol), EDCI (422 mg, 2.2 mmol) and HOBt (337 mg, 2.2 mmol). After the reaction mixture was stirred at room temperature for 14 h, 0.6 N aqueous NaOH solution (50 mL) was added, and the mixture was extracted with dichloromethane (3 times) The combined organic layers were dried over anhydrous sodium sulfate, filtered, and concentrated. Column chromatography ($SiO_2$, ethyl acetate then ethyl acetate/methanol=92/8) afforded the desired 4-[{(N-(2-(tert-butoxycarbonylamino)-4,5-difluorobenzoyl) glycyl)amino}methyl]-1-(4-chlorobenzyl)piperidine (1.01 g, 92%): ESI/MS m/e 551.3 ($M^+$+H, $C_{27}H_{33}ClF_2N_4O_4$).

4-[{(N-(2-(tert-butoxycarbonylamino)-5-trifluoromethylbenzoyl)glycyl)amino}methyl]-1-(4-chlorobenzyl)piperidine was also prepared pursuant to the above method using the corresponding reactant: 3.03 g, 82%; ESI/MS m/e 583.2 ($M^+$+H, $C_{28}H_{34}ClF_3N_4O_4$).

Reference Example 35

Preparation of 4-[{(N-(2-Amino-5-trifluoromethylbenzoyl)glycyl)amino}methyl] piperidine A suspension of 1-(4-chlorobenzyl)-4-[{(N-(2-amino-5-trifluoromethylbenzoyl)glycyl)amino}methyl]piperidine (447 mg, 0.93 mmol) and $Pd(OH)_2$ (60 mg, 0.23 mmol) in 5% $HCO_2H$/methanol (10 mL) was stirred at 50° C. for 14 h. The Pd catalyst was filtered off through Celite, and the filtrate was concentrated. To the residue was added 1N aqueous NaOH solution (15 mL) and the mixture was extracted with ethyl acetate (30 mL×3). The combined extracts were dried over anhydrous sodium sulfate, filtered, and concentrated. Column chromatography ($SiO_2$, AcOEt/MeOH/$Et_3N$=70/25/5) gave 4- [{N-(2-amino-5-trifluoromethylbenzoyl)glycyl)amino}methyl]piperidine (284 mg, 86%): ESI/MS m/e 359.0 ($M^+$+H, $C_{16}H_{21}F_3N_4O_2$).

4-[{(N-(2-Amino-4,5-difluorobenzoyl)glycyl) amino}methyl]piperidine, 4-[{N-(2-(tert-Butoxycarbonylamino)-5-trifluoromethoxybenzoyl) glycyl}aminomethyl]piperidine, 4-[{N-(2-(tert-butoxycarbonylamino)-4,5-difluorobenzoyl)glycyl) amino}methyl]piperidine, and 4-[{(N-(2-(tert-butoxycarbonylamino)-5-trifluoromethylbenzoyl)glycyl) amino}methyl]piperidine were also prepared pursuant to the above method using the corresponding reactant, respectively.

4-[{(N-(2-amino-4,5-difluorobenzoyl)glycyl) amino}methyl]piperidine: 564 mg, 89%; ESI/MS m/e 327.2 ($M^+$+H, $C_{15}H_{20}F_2N_4O_2$).

4-[{N-(2-(tert-Butoxycarbonylamino)-5-trifluoromethoxybenzoyl)glycyl)amino}methyl]piperidine: quant; $^1$H NMR ($CDCl_3$, 400 MHz) δ1.10–1.25 (m, 2 H), 1.45–1.73 (m, 3 H), 1.51 (s, 9 H), 2.53–2.64 (m, 2 H), 3.04–3.13 (m, 2 H), 3.22 (t, J=6.3 Hz, 2 H), 4.09 (d, J=4.6 Hz, 2 H), 5.91 (br. s, 1 H), 7.08 (br. s., 1 H), 7.32 (d, J=9.0 Hz, 1 H), 7.38 (s, 1 H), 8.43 (d, J=9.0 Hz, 1 H).

4-[{(N-(2-(tert-butoxycarbonylamino)-4,5-difluorobenzoyl)glycyl)amino}methyl]piperidine: 310 mg, 40%; ESI/MS m/e 427.3 ($M^+$+H, $C_{20}H_{23}F_2N_4O_4$).

4-[{(N-(2-(tert-butoxycarbonylamino)-5-trifluoromethylbenzoyl)glycyl)amino}methyl]piperidine: 1.35 g, 57%; ESI/MS m/e 459.3 ($M^+$+H, $C_{21}H_{29}F_3N_4O_4$)

Example 1736

Preparation of 4-[{N-(2-Amino-5-chlorobenzoyl) glycyl}aminomethyl]-1-(4-ethoxybenzyl)piperidine (Compound No. 1429) and 1-(4-Ethoxybenzyl)-4-[{N-(2-(4-ethoxybenzyl)amino-5-chlorobenzoyl) glycyl}aminomethyl]piperidine (Compound No. 1433)

Sodium cyanoborohydride (140 mmol) in methanol (0.4 mL) was added to a mixture of 4-[{N -(2-amino-5-chlorobenzoyl)glycyl}aminomethyl]piperidine (0.10 mmol), 4-ethoxybenzaldehyde (0.10 mmol), acetic acid (0.050 mL), and methanol (1.6 mL). The reaction mixture was stirred at 60° C. for 14 h. The reaction mixture was loaded onto Varian™ SCX column and washed with $CH_3OH$ (20 mL). Product was eluted using 2 N $NH_3$ in $CH_3OH$ (6 mL) and concentrated. Preparative TLC (SiO2, AcOEt/CH3OH 5:1) afforded 4-[{N-(2-amino-5-chlorobenzoyl) glycyl}aminomethyl]-1-(4-ethoxybenzyl)piperidine (Compound No. 1429) and 1-(4-ethoxybenzyl)-4-[{N-(2-(4-ethoxybenzyl)amino-5-chlorobenzoyl) glycyl}aminomethyl]piperidine (Compound No. 1433).

Compound No. 1429: 4.5 mg, 20%: The purity was determined by RPLC/MS (95%); ESI/MS m/e 459.2 ($M^+$+H, $C_{24}H_{31}ClN_4O_3$).

Compound No. 1433: 8.4 mg, 28%: The purity was determined by RPLC/MS (98%); ESI/MS m/e 593.2 ($M^+$+H, $Ca_{33}H_{41}ClN_4O_4$).

Examples 1737–1779

The compounds of this invention were synthesized pursuant to methods of Example 1736 using the corresponding reactant respectively. The ESI/MS data and yields are summarized in Table 36.

TABLE 36

| | Compound No. | Molecular Formula | ESI/MS m/e | Yield (mg) | Yield (%) |
|---|---|---|---|---|---|
| Example 1737 | 1430 | C24 H29 Cl N4 O4 | 473.0 | 3.1 | 13 |
| Example 1738 | 1431 | C24 H31 Br N4 O3 | 505.2 | 5.8 | 23 |
| Example 1739 | 1432 | C24 H29 Br N4 O4 | 517.0 | 4.1 | 16 |
| Example 1740 | 1434 | C33 H41 Br N4 O6 | 637.2 | 9.7 | 30 |
| Example 1741 | 1435 | C24 H31 Cl N4 O2 | 443.2 | 9.7 | 44 |
| Example 1742 | 1436 | C25 H33 Cl N4 O2 | 457.2 | 12.5 | 55 |
| Example 1743 | 1437 | C25 H33 Cl N4 O3 | 473.2 | 9.4 | 40 |
| Example 1744 | 1438 | C24 H31 Br N4 O2 | 489.2 | 5.9 | 24 |
| Example 1745 | 1439 | C25 H33 Br N4 O2 | 503.2 | 15.2 | 61 |
| Example 1746 | 1440 | C25 H33 Br N4 O3 | 519.2 | 11.0 | 43 |
| Example 1747 | 1441 | C23 H29 Br N4 O2 S | 507.2 | 9.3 | 37 |
| Example 1748 | 1442 | C33 H41 Cl N4 O2 | 561.4 | 6.8 | 24 |
| Example 1749 | 1443 | C35 H45 Cl N4 O2 | 589.4 | 9.8 | 33 |
| Example 1750 | 1444 | C35 H45 Cl N4 O4 | 621.4 | 9.4 | 30 |
| Example 1751 | 1445 | C33 H41 Br N4 O2 | 605.2 | 6.5 | 21 |
| Example 1752 | 1446 | C35 H45 Br N4 O2 | 635.2 | 10.7 | 34 |
| Example 1753 | 1447 | C35 H45 Br N4 O4 | 665.4 | 12.4 | 37 |
| Example 1754 | 1448 | C31 H37 Br N4 O2 S2 | 643.2 | 7.6 | 24 |
| Example 1755 | 1457 | C24 H32 Cl N5 O2 | 458.2 | 4.5 | 20 |
| Example 1756 | 1458 | C23 H29 Cl N4 O4 | 461.2 | 6.0 | 26 |
| Example 1757 | 1459 | C24 H32 Br N5 O2 | 504.0 | 6.8 | 27 |
| Example 1758 | 1460 | C23 H29 Br N4 O4 | 505.0 | 8.0 | 32 |
| Example 1759 | 1461 | C31 H37 Cl N4 O6 | 597.2 | 5.9 | 20 |
| Example 1760 | 1462 | C31 H37 Br N4 O6 | 643.2 | 6.0 | 19 |
| Example 1761 | 1514 | C26 H36 Cl N5 O2 | 486.2 | 5.5 | 23 |
| Example 1762 | 1515 | C23 H29 Cl N4 O4 | 463.0 | 5.8 | 25 |
| Example 1763 | 1516 | C26 H36 Br N5 O2 | 530.2 | 4.2 | 16 |
| Example 1764 | 1517 | C23 H29 Br N4 O4 | 505.0 | 6.5 | 26 |
| Example 1765 | 1518 | C31 H37 Cl N4 O6 | 597.2 | 4.3 | 14 |
| Example 1766 | 1519 | C31 H37 Br N4 O6 | 641.2 | 5.3 | 17 |
| Example 1767 | 1570 | C23 H29 Cl N4 O2 S | 461.0 | 2.7 | 12 |
| Example 1768 | 1571 | C31 H37 Cl N4 O2 S2 | 597.2 | 4.9 | 16 |
| Example 1769 | 1651 | C37 H49 Br N4 O2 | 663.2 | 5.5 | 17 |
| Example 1770 | 1652 | C26 H35 Br N4 O2 | 515.2 | 6.0 | 23 |
| Example 1771 | 1653 | C35 H45 Br N4 O2 | 633.2 | 5.0 | 16 |
| Example 1772 | 1654 | C25 H33 Br N4 O2 | 501.0 | 6.2 | 25 |
| Example 1773 | 1655 | C37 H49 Cl N4 O2 | 617.4 | 5.6 | 18 |
| Example 1774 | 1656 | C26 H35 Cl N4 O2 | 471.2 | 5.9 | 25 |
| Example 1775 | 1657 | C35 H45 Cl N4 O2 | 589.2 | 4.6 | 16 |
| Example 1776 | 1658 | C25 H33 Cl N4 O2 | 457.2 | 5.3 | 23 |
| Example 1777 | 1785 | C26 H33 F3 N4 O2 | 491.2 | 4.7 | 12.8 |
| Example 1778 | 1786 | C25 H29 F3 N4 O3 | 491.2 | 3.7 | 10.1 |
| Example 1779 | 1804 | C25 H32 F2 N4 O2 | 459.2 | 3.3 | 9.6 |

Example 1780

Preparation of 4-[{N-(2-Amino-5-trifluoromethoxybenzoyl)glycyl}aminomethyl]-1-(4-isopropylbenzyl)piperidine (Compound No. 1903)

To a mixture of 4-[{N-(2-(tert-butoxycarbonylamino)-5-trifluoromethoxy)benzoylglycyl}aminomethyl]piperidine (0.050 mmol), 4-isopropylbenzaldehyde (0.060 mmol), $NaBH_3CN$ (0.15 mmol), and methanol (1.3 mL) was added acetic acid (0.050 mL). The reaction mixture was stirred at 60° C. for 8 h. The mixture was cooled to room temperature, loaded onto Varian™ SCX column, and washed with $CH_3OH$ (10 mL). Product was eluted off using 2 N $NH_3$ in $CH_3OH$ (5 mL) and concentrated. To the resulting material was added 4 N HCl in 1,4-dioxane (2 mL) and the solution was stirred overnight at room temperature. Concentration and preparative TLC gave 4-[{N-(2-amino-5-trifluoromethoxybenzoyl)glycyl}aminomethyl]-1-(4-isopropylbenzyl)piperidine (Compound No. 1903) (6.6 mg, 26%): The purity was determined by RPLC/MS (93%); ESI/MS m/e 507 ($M^+$+H, $C_{26}H_{33}F_3N_4O_3$).

Examples 1781–1783

The compounds of this invention were synthesized pursuant to methods of Example 1780 using the corresponding reactant respectively. The ESI/MS data and yields are summarized in Table 37.

TABLE 37

| | Compound No. | Molecular Formula | ESI/MS m/e | Yield (mg) | Yield (%) |
|---|---|---|---|---|---|
| Example 1781 | 1904 | C26 H33 F3 N4 O3 | 507 | 9.6 | 37.9 |
| Example 1782 | 1917 | C25 H31 F3 N4 O5 | 525.2 | 1.2 | 3.1 |
| Example 1783 | 1918 | C24 H29 F3 N4 O4 | 495.2 | 2.8 | 7.5 |

Example 1784

Preparation of 4-[{N-(2-Amino-4,5-difluorobenzoyl)glycyl}aminomethyl]-1-(5-bromo-2-ethoxybenzyl)piperidine (Compound No. 2052)

To a mixture of 4-[{N-(2-(tert-butoxycarbonylamino)-4,5-difluorobenzoyl)glycyl}aminomethyl]piperidine (0.050 mmol), 5-bromo-2-ethoxybenzaldehyde (0.15 mmol), methanol (1.2 mL), and acetic acid (0.030 mL) was added $NaBH_3CN$ (0.25 mmol) in methanol (0.50 mL). The reaction mixture was stirred at 50° C. for 13 h. The mixture was cooled to room temperature, loaded onto Varian™ SCX column, and washed with $CH_3OH$ (5 mL×3). Product was eluted off using 2 N $NH_3$ in $CH_3OH$ (5 mL) and concentrated. To the resulting material were added dichloromethane (1 mL) and trifluoroacetic acid (TFA) (0.50 mL) and the solution was stirred at room temperature for 10 min. The reaction mixture was concentrated, and the residue was dissolved in methanol, loaded onto Varian™ SCX column, and washed with $CH_3OH$ (5 mL×2). Product was eluted off using 2 N $NH_3$ in $CH_3OH$ (5 mL) and concentrated. Preparative TLC (SiO2, ethyl acetate/methanol=10/1) gave 4-[{N-(2-amino-4,5-difluorobenzoyl)glycyl)amino}methyl]-1-(5-bromo-2-ethoxybenzyl)piperidine (Compound No. 2052) (10.2 mg, 38%): The purity was determined by RPLC/MS (96%); ESI/MS m/e 539.2 ($M^+$+H, $C_{24}H_{29}BrF_2N_4O_3$).

Examples 1785–1792

The compounds of this invention were synthesized pursuant to methods of Example 1784 using the corresponding reactant respectively. The ESI/MS data and yields are summarized in Table 38.

TABLE 38

| | Compound No. | Molecular Formula | ESI/MS m/e | Yield (mg) | Yield (%) |
|---|---|---|---|---|---|
| Example 1785 | 2053 | C30 H34 F2 N4 O4 | 553.4 | 12.7 | 46 |
| Example 1786 | 2054 | C27 H30 F2 N4 O3 | 497.2 | 13.7 | 55 |
| Example 1787 | 2055 | C23 H28 F2 N4 O4 | 463.2 | 10.1 | 44 |
| Example 1788 | 2056 | C22 H24 Br F3 N4 O2 | 515.2 | 7.7 | 30 |
| Example 1789 | 2057 | C23 H27 Br F2 N4 O3 | 527.0 | 8.6 | 33 |
| Example 1790 | 2058 | C24 H30 F2 N4 O4 | 477.2 | 6.4 | 27 |
| Example 1791 | 2059 | C28 H30 F2 N4 O3 | 509.4 | 6.7 | 26 |
| Example 1792 | 2060 | C25 H32 F2 N4 O5 | 507.2 | 7.2 | 28 |

Example 1793

Preparation of 4-[{N-(2-Amino-4,5-difluorobenzoyl)glycyl}aminomethyl]-1-(3,4-diethoxybenzyl)piperidine (Compound No. 2065)

To a mixture of 4-[{N-(2-(tert-butoxycarbonylamino-4,5-difluorobenzoyl)glycyl}aminomethyl]piperidine (0.050 mmol), 3,4-diethoxybenzaldehyde (0.15 mmol), methanol (1.2 mL), and acetic acid (0.050 mL) was added $NaBH_3CN$ (0.25 mmol) in methanol (0.50 mL). The reaction mixture was stirred at 50° C. overnight. The mixture was cooled to room temperature, loaded onto Varian™ SCX column, and washed with $CH_3OH$ (5 mL×2). Product was eluted off using 2 N $NH_3$ in $CH_3OH$ (5 mL) and concentrated. To the resulting material ere added dichloromethane (2 mL) and phenyl isocyanate (0.10 mL) and the solution as stirred at room temperature for 1 h, loaded onto Varian™ SCX column, and washed with $CH_3OH$ (5 mL×2). Product was eluted off using 2 N $NH_3$ in $CH_3OH$ (5 mL) and concentrated. The residue was dissolved in methanol (0.25 mL) and 4 N HCl in dioxane (0.125 mL) was added. The solution was stirred at room temperature overnight and concentrated. The residue was dissolved in methanol, loaded onto Varian™ SCX column, and washed with $CH_3OH$ (5 mL×2). Product was eluted off using 2 N NH, in $CH_3OH$ (5 mL) and concentrated to afford 4-[{N-(2-amino-4,5-difluorobenzoyl) glycyl}aminomethyl]-1-(3,4-diethoxybenzyl)piperidine (Compound No. 2065) (21.2 mg, 84%): The purity was determined by RPLC/MS (97%); ESI/MS m/e 505.2 ($M^+$+H, $C_{26}H_{34}F_2N_4O_4$).

Examples 1794–1808

The compounds of this invention were synthesized pursuant to methods of Example 1793 using the corresponding reactant respectively. The ESI/MS data and yields are summarized in Table 39.

TABLE 39

| | Compound No. | Molecular Formula | ESI/MS m/e | Yield (mg) | Yield (%) |
|---|---|---|---|---|---|
| Example 1794 | 2061 | C23 H27 F3 N4 O2 | 449.2 | 12.6 | 56 |
| Example 1795 | 2062 | C23 H27 F3 N4 O3 | 465.2 | 19.7 | 85 |
| Example 1796 | 2063 | C25 H32 F2 N4 O4 | 491.2 | 19.8 | 81 |
| Example 1797 | 2064 | C22 H24 Br F3 N4 O2 | 515.2 | 17.5 | 68 |
| Example 1798 | 2066 | C29 H32 F2 N4 O3 | 523.2 | 18.0 | 69 |
| Example 1799 | 2067 | C26 H34 F2 N4 O2 | 473.2 | 21.9 | 93 |
| Example 1800 | 2068 | C22 H24 Cl F3 N4 O2 | 469.2 | 11.2 | 48 |
| Example 1801 | 2069 | C24 H30 F2 N4 O3 | 461.4 | 20.2 | 88 |
| Example 1802 | 2070 | C23 H27 Br F2 N4 O3 | 527.2 | 17.7 | 67 |
| Example 1803 | 2071 | C24 H30 F2 N4 O4 | 477.2 | 10.9 | 46 |
| Example 1804 | 2072 | C25 H32 F2 N4 O3 | 475.2 | 19.3 | 81 |
| Example 1805 | 2073 | C29 H32 F2 N4 O3 | 523.2 | 22.8 | 87 |
| Example 1806 | 2074 | C29 H32 F2 N4 O4 | 539.2 | 22.5 | 84 |
| Example 1807 | 2075 | C23 H27 F3 N4 O3 | 465.2 | 14.9 | 64 |
| Example 1808 | 2076 | C22 H24 F4 N4 O2 | 453.2 | 21.9 | 97 |

Example 1809

Preparation of 4-[{N-(2-Amino-4,5-difluorobenzoyl) glycyl}aminomethyl]-1-(2-hydroxy-3-methylbenzyl) piperidine (Compound No. 2106)

To a mixture of 4-[{N-(2-(tert-butoxycarbonylamino-4,5-difluorobenzoyl)glycyl}aminomethyl]piperidine (0.050 mmol), 2-hydroxy-3-methylbenzaldehyde (0.25 mmol), methanol (1.0 mL), and acetic acid (0.040 mL) was added $NaBH_3CN$ (0.40 mmol) in methanol (0.50 mL). The reaction mixture was stirred at 50° C. overnight. The mixture was cooled to room temperature, loaded onto Varian™ SCX column, and washed with $CH_3OH$ (5 mL×2). Product was eluted off using 2 N $NH_3$ in $CH_3OH$ (5 mL) and concentrated. The resulting material was dissolved into ethyl acetate/methanol=5:1 (1 mL), loaded onto Varian™ Si column, eluted off using ethyl acetate/methanol=5:1 (5 mL), and concentrated. The residue was dissolved in methanol (2 mL) and 4 N HCl in dioxane (0.50 mL) was added. The solution was stirred at room temperature overnight and concentrated. The residue was dissolved in methanol, loaded onto Varian™ SCX column, and washed with $CH_3OH$ (5 mL×2). Product was eluted off using 2 N $NH_a$ in $CH_3OH$ (5 mL) and concentrated. Preparative TLC afforded 4-[{N-(2-amino-4,5-difluorobenzoyl)glycyl}aminomethyl]-1-(2-hydroxy-3-methylbenzyl)piperidine (Compound No. 2106) The purity was determined by RPLC/MS (97%); ESI/MS m/e 447.0 ($M^+$+H, $C_{23}H_{28}F_2N_4O_4$).

Examples 1810–1823

The compounds of this invention were synthesized pursuant to methods of Example 1809 using the corresponding reactant respectively. The ESI/MS data and yields are summarized in Table 40.

TABLE 40

| | Compound No. | Molecular Formula | ESI/MS m/e | Yield (mg) | Yield (%) |
|---|---|---|---|---|---|
| Example 1810 | 2077 | C22 H25 Cl F2 N4 O3 | 467.2 | 3.7 | 16 |
| Example 1811 | 2078 | C24 H30 F2 N4 O4 | 477.2 | 1.9 | 8 |
| Example 1812 | 2079 | C30 H34 F2 N4 O4 | 553.4 | 4.8 | 17 |
| Example 1813 | 2080 | C22 H25 Cl F2 N4 O3 | 467.2 | 13.5 | 58 |
| Example 1814 | 2081 | C22 H25 Cl F2 N4 O3 | 467.2 | 13.8 | 59 |
| Example 1815 | 2082 | C23 H28 F2 N4 O4 | 463.2 | 9.6 | 42 |
| Example 1816 | 2105 | C23 H28 F2 N4 O4 | 463.2 | ND | ND |
| Example 1817 | 2106 | C23 H28 F2 N4 O3 | 447.0 | ND | ND |
| Example 1818 | 2107 | C20 H23 Br F2 N4 O2 S | 503.1 | ND | ND |
| Example 1819 | 2108 | C25 H28 F2 N4 O2 S | 487.2 | ND | ND |
| Example 1820 | 2109 | C20 H23 Br F2 N4 O3 | 487.0 | ND | ND |
| Example 1821 | 2110 | C22 H28 F2 N4 O3 | 435.1 | ND | ND |
| Example 1822 | 2111 | C22 H24 Cl F3 N4 O2 | 469.0 | ND | ND |
| Example 1823 | 2112 | C24 H29 Br F2 N4 O4 | 557.0 | ND | ND |

ND: Not determined.

Example 1824

Preparation of 4-[{N-(2-Amino-4,5-difluorobenzoyl)glycyl}aminomethyl]-1-(3-amino-4-methylbenzyl)piperidine (Compound No. 2114)

To a mixture of 4-[{N-(2-(tert-butoxycarbonylamino)-4,5-difluorobenzoyl)glycyl}aminomethyl]piperidine (0.050 mmol), 4-methyl-3-nitrobenzaldehyde (0.25 mmol), methanol (1.2 mL), and acetic acid (0.050 mL) was added $NaBH_3CN$ (0.50 mmol) in methanol (1.0 mL). The reaction mixture was stirred at 50° C. overnight. The mixture was cooled to room temperature, loaded onto Varian™ SCX column, and washed with $CH_3OH$ (5 mL×2). Product was eluted off using 2 N $NH_3$ in $CH_3OH$ (5 mL) and concentrated. The resulting material was dissolved into ethyl acetate/methanol=2/1 (2 mL), loaded onto Varian™ Si column, eluted off using ethyl acetate/methanol=2/1 (6 mL), and concentrated. The residue was dissolved in methanol (1 mL) and 4 N HCl in dioxane (0.50 mL) was added. The solution was stirred at room temperature overnight and concentrated. The residue was dissolved in methanol, loaded onto Varian™ SCX column, washed with $CH_3OH$ (5 mL×2), and eluted off using 2 N $NH_3$ in $CH_3OH$ (5 mL). Concentration afforded 4-[{N-(2-amino-4,5-difluorobenzoyl) glycyl}aminomethyl]-1-(4-methyl-3-nitrobenzyl) piperidine.

A mixture of 4-[{N-(2-amino-4,5-difluorobenzoyl) glycyl}aminomethyl]-1-(4-methyl-3-nitrobenzyl)piperidine prepared above, 5% palladium-activated carbon (15 mg), and methanol (2 mL) was stirred under a hydrogen atmosphere at room temperature for 4 h. The Pd catalyst was filtered off through Celite and the filtrate was concentrated. Preparative TLC ($SiO_2$, ethyl acetate/MeOH=3/1) gave 4-[{N-(2-amino-4,5-difluorobenzoyl)glycyl}aminomethyl]-1-(3-amino-4-methylbenzyl)piperidine (Compound No. 2114) (2.9 mg, 13%): The purity was determined by RPLC/MS (100%.); ESI/MS m/e 446.1 ($M^+$+H, $C_{23}H_{29}F_2N_5O_2$).

Example 1825

Preparation of 4-[{N-(2-Amino-4,5-difluorobenzoyl)glycyl}aminomethyl]-1-(3-amino-4-methoxybenzyl)piperidine (Compound No. 2113)

The titled compound, 4-[{N-(2-amino-4,5-difluorobenzoyl)glycyl}aminomethyl]-1- (3-amino-4-methoxybenzyl)piperidine (Compound No. 2113), was synthesized pursuant to methods of Example 1824 using the corresponding reactant: 4.6 mg, 20% yield; ESI/MS m/e 462.2 ($M^+$+H, $C_{23}H_{29}F_2N_5O_3$).

Example 1826

Preparation of 1-(3-Amino-4-hydroxybenzyl)-4-[{N-(2-(tert-butoxycarbonylamino)-4,5-difluorobenzoyl)glycyl)amino}methyl]piperidine To a mixture of 4-[{N-(2-(tert-butoxycarbonylamino-4,5-difluorobenzoyl)glycyl}aminomethyl]piperidine (0.35 mmol), 4-hydroxy-3-nitrobenzaldehyde (1.22 mmol), methanol (3.8 mL), and acetic acid (0.175 mL) was added $NaBH_3CN$ (1.58 mmol) in methanol (3.2 mL). The reaction mixture was stirred at 50° C. overnight. The mixture was cooled to room temperature, loaded onto Varian™ SCM column, and washed with $CH_3OH$ . Product was eluted off using 2 N $NH_3$ in $CH_3OH$ and concentrated. The resulting material was dissolved into ethyl acetate/methanol=5/1, loaded onto Varian™ Si column, eluted off using ethyl acetate/methanol=5/1 (10 mL), and concentrated to give 4-[{N-(2-(tert-butoxycarbonylamino)-4,5-difluorobenzoyl)glycyl}aminomethyl]-1-(4-hydroxy-3-nitrobenzyl)piperidine (175 mg, 87%).

A mixture of 4-[{N-(2-(tert-butoxycarbonylamino)-4,5-difluorobenzoyl)glycyl}aminomethyl]-1-(4-hydroxy-3-nitrobenzyl)piperidine prepared above, 10% palladium-activated carbon (45 mg), and methanol (5 mL) was stirred under a hydrogen atmosphere at room temperature for 2 h. The Pd catalyst was filtered off and the filtrate was concentrated to afford 1-(3-amino-4-hydroxybenzyl)-4-[{N-(2-(tert-butoxycarbonylamino)-4,5-difluorobenzoyl)glycyl}aminomethyl]piperidine (100 mg, 60%).

Example 1827

Preparation of 4-[{N-(2-Amino-4,5-difluorobenzoyl)glycyl}aminomethyl]-1-(3-amino-4-hydroxybenzyl)piperidine (Compound No. 2141)

To a solution of 1-(3-amino-4-hydroxybenzyl)-4-[{N-(2-(tert-butoxycarbonylamino)-4,5-difluorobenzoyl)glycyl{aminomethyl]piperidine (20.0 mg, 0.035 mmol) in methanol (1 mL) was added 4 N HCl in dioxane (0.50 mL) and the solution was stirred at room temperature overnight. After the solution was concentrated, the residue was dissolved in methanol, loaded onto Varian™ SCX column, washed with $CH_3OH$ (5 mL×2), and eluted off using 2 N $NH_3$ in $CH_3OH$ (5 mL). Concentration afforded 4-[{N-(2-amino-4,5-difluorobenzoyl)glycyl}aminomethyl]-1-(3-amino-4-hydroxybenzyl)piperidine (Compound No. 2141) (17.6 mg, quant.): The purity was determined by RPLC/MS (85%); ESI/MS m/e 448.3 ($M^+$+H, $C_{22}H_{27}F_2N_5O_3$).

Examples 1828–1831

The compounds of this invention were synthesized pursuant to methods of Examples 1826 and 1827 using the corresponding reactants respectively. Preparative TLC ($SiO_2$), if needed, afforded the desired material. The ESI/MS data and yields of last step are summarized in Table 41.

TABLE 41

| | Compound No. | Molecular Formula | ESI/MS m/e | Yield (mg) | Yield (%) |
|---|---|---|---|---|---|
| Example 1828 | 2140 | C23 H27 F2 N5 O4 | 476.3 | 6.7 | 28.4 |
| Example 1829 | 2144 | C24 H30 F3 N5 O3 | 494.2 | 18.7 | 82.0 |
| Example 1830 | 2145 | C23 H28 F3 N5 O3 | 480.3 | 19.8 | 63.7 |
| Example 1831 | 2146 | C24 H28 F3 NS O4 | 508.3 | 13.5 | 81.7 |

Example 1832

Preparation of 1-(3-Amino-4-chlorobenzyl) -4-[{N-(2-(tertbutoxycarbonylamino)-4,5-difluorobenzoyl)glycyl}aminomethyl]piperidine To a mixture of 4-[{N-(2-(tert-butoxycarbonylamino-4,5-difluorobenzoyl)glycyl}aminomethyl]piperidine (0.14 mmol), 4-chloro-3-nitrobenzaldehyde (0.50 mmol), methanol (1.5 mL), and acetic acid (0.070 mL) was added $NaBH_3CN$ (0.63 mmol) in methanol (1.3 mL). The reaction mixture was stirred at 50° C. overnight. The mixture was cooled to room temperature, loaded onto Varian™ SCX column, and washed with $CH_3OH$. Product was eluted off using 2 N $NH_3$ in $CH_3OH$ and concentrated. The resulting material was dissolved into ethyl acetate/methanol=5/1, loaded onto Varian™ Si column, eluted off using ethyl acetate/methanol=5/1 (6 mL), and concentrated to give 4-[{N-(2-(tert-butoxycarbonylamino)-4,5-difluorobenzoyl)glycyl}aminomethyl]-1-(4-chloro-3-nitrobenzyl)piperidine (44 mg, 53%): ESI/MS m/e 596.3 ($M^+$+H).

A mixture of 4-[{N-(2-(tert-butoxycarbonylamino)-4,5-difluorobenzoyl)glycyl}aminomethyl]-1-(4-chloro-3-nitrobenzyl)piperidine (121 mg, 0.20 mmol), 10% palladium-activated carbon (85 mg), ethyl acetate (10 mL), and methanol (1 mL) was stirred under a hydrogen atmosphere at room temperature for 19 h. The Pd catalyst was filtered off and the filtrate was concentrated to afford 1-(3-amino-4-chlorobenzyl)-4-[{N-(2-(tert-butoxycarbonylamino)-4,5-difluorobenzoyl)glycyl}aminomethyl]piperidine (78 mg, 68%).

Example 1833

Preparation of 1-(3-Amino-4-chlorobenzyl)-4-[{N-(2-amino-4,5-difluorobenzoyl)glycyl}aminomethyl]piperidine (Compound No. 2142)

The titled compound, 1-(3-amino-4-chlorobenzyl)-4-[{N-(2-amino-4,5-difluorobenzoyl)glycyl}aminomethyl]piperidine (Compound No. 2142) was synthesized pursuant to method of Example 1832 using the corresponding reactant: 13.7 mg, 98%); The purity was determined by RPLC/MS (83%); ESI/MS m/e 466.2 ($M^+$+H, $C_{22}H_{26}ClF_2N_5O_2$).

Example 1834

Preparation of 1-(3-Acetylamino-4-hydroxybenzyl)-4-[{N-(2-amino-4,5-difluorobenzoyl)glycyl}aminomethyl]piperidine (Compound No. 2148)

To a mixture of 1-(3-amino-4-hydroxybenzyl)-4-[{N-(2-(tert-butoxycarbonylamino)-4,5-difluorobenzoyl)

glycyl}aminomethyl]piperidine (27 mg, 0.049 mmol), (piperidinomethyl)polystyrene (2.7 mmol/g, 60 mg, 0.15 mmol) and dichloromethane (2 mL) was added acetic anhydride (0.12 mmol) in dichloromethane (0.12 mL). The reaction mixture was stirred at room temperature for 3 h. The mixture was loaded onto Varian™ SCX column, and washed with $CH_3OH$. Product was eluted off using 2 N $NH_3$ in $CH_3OH$ and concentrated to give 1-(3-acetylamino)-4-hydroxybenzyl)-4-[{N-(2-(tert-butoxycarbonylamino)-4,5-difluorobenzoyl)glycyl}aminomethyl]piperidine (30 mg, quant.): ESI/MS m/e 590.4 ($M^++H$, $C_{29}H_{37}F_2N_5O_6$).

To a solution of 1-(3-acetylamino-4-hydroxybenzyl)-4-[{N-(2-(tert-butoxycarbonylamino-4,5-difluorobenzoyl) glycyl}aminomethyl]piperidine obtained above in methanol (1 mL) was added 4 N HCl in dioxane (0.50 mL) and the solution was stirred at room temperature overnight. After the solution was concentrated, the residue was dissolved in methanol, loaded onto Varian™ SCX column, washed with $CH_3OH$ (5 mL×2), and eluted off using 2 N $NH_3$ in $CH_3OH$ (5 mL). Concentration and preparative TLC ($SiO_2$, AcOEt/MeOH=3:2) afforded 1-(3-acetylamino-4-hydroxybenzyl)-4-[{N-(2-amino-4,5-difluorobenzoyl)glycyl}aminomethyl]piperidine (Compound No. 2148) (2.3 mg, 9.2%): The purity was determined by RPLC/MS (98%); ESI/MS m/e 490.3 ($M^++H$, $C_{24}H_{29}F_2N_5O_4$).

Examples 1835–1839

The compounds of this invention were synthesized pursuant to methods of Examples 1826 and 1834 using the corresponding reactants respectively. The ESI/MS data and yields are summarized in Table 42.

TABLE 42

| | Compound No. | Molecular Formula | ESI/MS m/e | Yield (mg) | Yield (%) |
|---|---|---|---|---|---|
| Example 1835 | 2143 | C25 H29 F2 N5 O5 | 518.3 | 4.8 | 45 |
| Example 1836 | 2147 | C25 H31 F2 N5 O4 | 504.3 | 3.0 | 23 |
| Example 1837 | 2154 | C26 H32 F3 N5 O4 | 536.4 | 4.1 | 66 |
| Example 1838 | 2155 | C25 H30 F3 N5 O4 | 522.3 | 5.5 | 71 |
| Example 1839 | 2156 | C26 H30 F3 N5 O5 | 550.3 | 7.0 | 78 |

Example 1840

Preparation of 4-[{N-(2-Amino-4,5-difluorobenzoyl)glycyl}aminomethyl]-1-(3-methylamino-4-hydroxybenzyl)piperidine (Compound No. 2160)

To a mixture of 4-[{N-(2-(tert-butoxycarbonylamino-4,5-difluorobenzoyl) glycyl}aminomethyl]-1-(3-amino-4-hydroxybenzyl)piperidine (20.4 mg, 0.037 mmol), 37% HCHO solution (3.0 mg, 0.037 mmol) , acetic acid (0.10 mL) and methanol (1.3 mL) was added $NaBH_3CN$ (7.0 mg) in methanol (0.2 mL). The reaction mixture was stirred at 60° C. overnight. The mixture was cooled to room temperature, loaded onto Varian™ SCX column, and washed with $CH_3OH$ (5 mL×2). Product was eluted off using 2 N $NH_3$ in $CH_3OH$ (8 mL) and concentrated to give 4-[{N-(2-(tert-butoxycarbonylamino)-4,5-difluorobenzoyl) glycyl}aminomethyl]-1-(3-methylamino-4-hydroxybenzyl) piperidine.

To a solution of 4-[{N-(2-(tert-butoxycarbonylamino)-4,5-difluorobenzoyl)glycyl}aminomethyl]-1-(3-methylamino-4-hydroxybenzyl)piperidine obtained above in methanol (1.0 mL) was added 4 N HCl in dioxane (1.0 mL) and the solution was stirred at room temperature for 3 h. After the solution was concentrated, the residue was dissolved in methanol (1 mL), loaded onto Varian™ SCX column, washed with $CH_3OH$ (5 mL×2), and eluted off using 2 N $NH_3$ in $CH_3OH$ (8 mL). Concentration and preparative TLC ($SiO_2$) afforded 4-[{N-(2-amino-4,5-difluorobenzoyl)glycyl}aminomethyl]-1-(3-methylamino-4-hydroxybenzyl)piperidine (Compound No. 2160) (3.4 mg, 20%): The purity was determined by RPLC/MS (96%); ESI/MS m/e 462.4 ($M^++H$, $C_{23}H_{29}F_2N_5O_3$).

Examples 1841–1844

The compounds of this invention were synthesized pursuant to methods of Examples 1826 and 1840 using the corresponding reactants respectively. The ESI/MS data and yields are summarized in Table 43.

TABLE 43

| | Compound No. | Molecular Formula | ESI/MS m/e | Yield (mg) | Yield (%) |
|---|---|---|---|---|---|
| Example 1841 | 2159 | C24 H31 F2 N5 O3 | 476.3 | 7.6 | 48 |
| Example 1842 | 2161 | C23 H28 Cl F2 N5 O2 | 480.3 | 7.3 | 45 |
| Example 1843 | 2162 | C25 H32 F3 N5 O3 | 508.4 | 6.0 | 24 |
| Example 1844 | 2163 | C24 H30 F3 N5 O3 | 494.3 | 4.3 | 15 |

Example 1845

Preparation of 4-[{N-(2-Amino-4,5-difluorobenzoyl)glycyl}aminomethyl]-1-(benzo[c]furazan-5-yl)piperidine (Compound No. 2130)

A mixture of 4-[{N-(2-(tert-butoxycarbonylamino)-4,5-difluorobenzoyl)glycyl}aminomethyl]piperidine (0.050 mmol), 5-(bromomethyl)benzo[c]furazan (0.75 mmol), (piperidinomethyl)polystyrene (2.6–2.8 mmol/g, 60 mg, 0.15 mmol), methanol (0.2 mL), acetonitrile (1.0 mL), and chloroform (0.50 mL) was stirred at 50° C. overnight. The mixture was cooled to room temperature, loaded onto Varian™ SCX column, and washed with $CH_3OH$ (5 mL×2). Product was eluted off using 2 N $NH_3$ in $CH_3OH$ (5 mL) and concentrated. To the resulting material were added chloroform (1.5 mL) and phenyl isocyanate (0.075 mL) and the solution was stirred at room temperature for 1 h, loaded onto Varian™ SCX column, and washed with $CH_3OH$ (5 mL×2). Product was eluted off using 2 N $NH_3$ in $CH_3OH$ (5 mL) and concentrated. The residue was dissolved in methanol (1 mL) and 4 N HCl in dioxane (0.50 mL) was added. The solution was stirred at room temperature overnight and concentrated. The residue was dissolved in methanol, loaded onto Varian™ SCX column, washed with $CH_3OH$ (5 mL×2), and eluted off using 2 N $NH_3$ in $CH_3OH$ (5 mL). Concentration and preparative TLC ($SiO_2$, ethyl acetate/MeOH=5/1) afforded 4-[{N-(2-amino-4,5-difluorobenzoyl) glycyl}aminomethyl]-1-(benzo[c]furazan-5-yl)piperidine (Compound No. 2130) (3.6 mg, 16%): The purity was determined by RPLC/MS (87%); ESI/MS m/e 459.3 ($M^++H$, $C_{22}H_{24}F_2N_6O_3$).

Example 1846

Preparation of 4-[{N-(2-Amino-4,5-difluorobenzoyl)glycyl}aminomethyl]-1-(3,5-dimethylisoxazol-4-yl)piperidine (Compound No. 2131)

The titled compound, 4-[{N-(2-amino-4,5-difluorobenzoyl)glycyl}aminomethyl]-1-(3,5- dimethylisoxazol-4-yl)piperidine (Compound No. 2131), was synthesized pursuant to methods of Example 1845 using the corresponding reactant: 3.8 mg, 18% yield; ESI/MS m/e 436.2 ($M^{+}$+H, $C_{21}H_{27}F_{2}N_{5}O_{3}$).

Example 1847

Preparation of 4-[{N-(2-Amino-5-chlorobenzoyl) glycyl}aminomethyl]-1-{4-(trifluoromethylthio) benzyl}piperidine (Compound No. 1616)

A mixture of 4-[{N-(2-amino-5-chlorobenzoyl) glycyl}aminomethyl]piperidine (16.2 mg, 0.050 mmol), 4-(trifluoromethylthio)benzyl bromide (20.3 mg, 0.075 mmol), piperidinomethyl-polystyrene (60 mg), acetonitrile (1.0 mL) and chloroform (0.50 mL) was stirred at 60° C. for 15 h. The reaction mixture was cooled, loaded onto Varian™ SCX column and washed with $CH_3OH$ (15 mL). Product was eluted using 2 N $NH_3$ in $CH_3OH$ (5 mL) and concentrated to afford 4-[{N-(2-amino-5-chlorobenzoyl) glycyl}aminomethyl]-1-[4-(trifluoromethylthio)benzyl] piperidine (Compound No.1616) (21.9 mg, 85%): The purity was determined by RPLC/MS (96%); ESI/MS m/e 545.2 ($M^{+}$+H, $C_{23}H_{26}ClF_{3}N_{4}O_{2}S$).

Example 1848–1868

The compound of this invention was synthesized pursuant to methods of Example 1847 using the corresponding reactant. Preparative TLC, if needed, afforded the desired material. The ESI/MS data and yields are summarized in Table 44.

TABLE 44

| | Compound No. | Molecular Formula | ESI/MS m/e | Yield (mg) | Yield (%) |
|---|---|---|---|---|---|
| Example 1848 | 1617 | C23 H26 Br F3 N4 O2 S | 559.0 | 21.0 | 75 |
| Example 1849 | 1777 | C23 H25 Cl2 F3 N4 O2 | 517.0 | 16.3 | 63.0 |
| Example 1850 | 1778 | C24 H29 F3 N4 O2 | 463.2 | 9.5 | 41.1 |
| Example 1851 | 1779 | C24 H27 F3 N4 O4 | 493.2 | 12.7 | 51.6 |
| Example 1852 | 1780 | C23 H26 Br F3 N4 O2 | 527.0 | 16.4 | 62.2 |
| Example 1853 | 1781 | C23 H27 F3 N4 O3 | 465.2 | 10.0 | 28.7 |
| Example 1854 | 1782 | C25 H29 F3 N4 O2 | 475.2 | 12.2 | 34.3 |
| Example 1855 | 1783 | C24 H26 F3 N5 O2 | 474.2 | 17.2 | 48.4 |
| Example 1856 | 1784 | C23 H27 F3 N4 O2 | 449.2 | 11.3 | 33.6 |
| Example 1857 | 1788 | C25 H31 F3 N4 O2 | 477.2 | 10.0 | 42.0 |
| Example 1858 | 1789 | C24 H29 F3 N4 O3 | 479.2 | 10.0 | 27.9 |
| Example 1859 | 1792 | C24 H30 F2 N4 O2 | 445.2 | 5.9 | 26.5 |
| Example 1860 | 1793 | C22 H24 Cl2 F2 N4 O2 | 485.2 | 9.2 | 37.9 |
| Example 1861 | 1794 | C23 H28 F2 N4 O2 | 431.2 | 5.7 | 26.5 |
| Example 1862 | 1795 | C23 H26 F2 N4 O4 | 461.2 | 6.0 | 26.1 |
| Example 1863 | 1796 | C22 H25 Br F2 N4 O2 | 497.0 | 10.5 | 42.4 |
| Example 1864 | 1797 | C22 H26 F2 N4 O3 | 433.2 | 3.5 | 16.2 |
| Example 1865 | 1798 | C23 H28 F2 N4 O3 | 447.2 | 5.6 | 25.1 |
| Example 1866 | 1799 | C24 H28 F2 N4 O2 | 443.2 | 5.5 | 24.9 |
| Example 1867 | 1800 | C23 H25 F2 N5 O2 | 442.2 | 9.4 | 42.6 |
| Example 1868 | 1801 | C22 H26 F2 N4 O2 | 417.2 | 6.5 | 31.2 |

Example 1869

Preparation of 4-[{N-(2-Amino-5-trifluoromethoxybenzoyl)glycyl}aminomethyl]-1-(4-bromobenzyl)piperidine (Compound No. 1910)

A mixture of 4-[{N-(2-(tert-butoxycarbonylamino-5-trifluoromethoxybenzoyl)glycyl}aminomethyl]piperidine (0.050 mmol), 4-bromobenzyl bromide (0.060 mmol), piperidinomethylpolystyrene (60 mg), acetonitrile (0.8 mL) and chloroform (0.5 mL) was stirred at 60° C. for 12 h. The reaction mixture was cooled, loaded onto Varian™ SCX column and washed with 50% $CHCl_3/CH_3OH$ (10 mL) and $CH_3OH$ (10 mL). Product was eluted using 2 N $NH_3$ in $CH_3OH$ (5 mL) and concentrated. To the resulting material was added 4 N HCl in 1,4-dioxane (2 mL), and the solution was stirred overnight at room temperature.

Concentration and preparative TLC afforded 4-[{N-(2-amino-5-trifluoromethoxybenzoyl)glycyl}aminomethyl]-1-(4-bromobenzyl)piperidine (Compound No. 1910) (6.5 mg, 24%): The purity was determined by RPLC/MS (96%); ESI/MS m/e 545 ($M^{+}$+H, $C_{23}H_{26}BrF_{3}N_{4}O_{3}$ ).

Examples 1870–1873

The compounds of this invention were synthesized pursuant to methods of Example 1869 using the corresponding reactant respectively. The ESI/MS data and yields are summarized in Table 45.

TABLE 45

| | Compound No. | Molecular Formula | ESI/MS m/e | Yield (mg) | Yield (%) |
|---|---|---|---|---|---|
| Example 1870 | 1911 | C23 H25 Cl2 F3 N4 O3 | 533 | 10.6 | 39.7 |
| Example 1871 | 1912 | C23 H27 F3 N4 O4 | 481 | 12.5 | 52.0 |
| Example 1872 | 1913 | C25 H31 F3 N4 O3 | 493 | 7.5 | 30.5 |
| Example 1873 | 1914 | C24 H29 F3 N4 O3 | 479 | 11.0 | 46.0 |

Example 1874

Preparation of 4-[{N-(2-Amino-5-trifluoromethylbenzoyl)glycyl}aminomethyl]-1-(benzo[d]imidazol-5-yl)piperidine (Compound No. 2186)

A mixture of 4-[{N-(2-(tert-butoxycarbonylamino-5-trifluoromethylbenzoyl)glycyl}aminomethyl]piperidine (0.060 mmol), 1-(tert-butoxycarbonyl)-6-(bromomethyl) benzo[d]imidazole (15.6 mg, 0.050 mmol), (piperidinomethyl)polystyrene (86 mg), and acetonitrile (2 mL) was stirred at 50° C. for 3 h. After cooling to room temperature, phenyl isocyanate (30 mg) was added and the mixture was stirred at room temperature for 1 h, loaded onto Varian™ SCX column and washed with $CH_3OH$ (5 mL) and $CHCl_3$ (5 mL). Product was eluted using 2 N $NH_3$ in $CH_3OH$ (3 mL) and concentrated.

The resulting material was dissolved into methanol (1 mL), and 4 N HCl in dioxane (1 mL) was added. The solution was stirred at room temperature overnight, loaded onto Varian™ SCX column and washed with $CH_3OH$ and dichloromethane. Product was eluted using 2 N $NH_3$ in $CH_3OH$ and concentrated. Preparative TLC ($SiO_2$, AcOEt/MeOH=3:1) afforded 4-[{N-(2-amino-5-trifluorobenzoyl) glycyl}aminomethyl]-1-(benzo[d]imidazol-5-yl)piperidine (Compound No. 2186) (1.9 mg, 7.8%): The purity was determined by RPLC/MS (100%); ESI/MS m/e 489.4 ($M^{+}$+H, $C_{24}H_{27}F_{3}N_{6}O_{2}$).

Example 1875

Preparation of 4-[{N-(2-Amino-4,5-difluorobenzoyl)glycyl}aminomethyl]-1-(benzo[c]thiadiazol-5-yl)piperidine (Compound No. 2184)

To a mixture of 5-(hydroxymethyl)benzo[c]thiadiazole (8.3 mg, 0.050 mmol), (piperidinomethyl)polystyrene (86 mg), and chloroform (1 mL) was added methanesulfonyl chloride (0.0042 mL) and the mixture was stirred at room temperature for 1.5 h. Acetonitrile (1 mL) and 4-[{N-(2-(tert-butoxycarbonylamino)-4,5-difluorobenzoyl)glycyl}aminomethyl]piperidine (0.060 mmol) was added and the reaction mixture was stirred at 50° C. for 3 h. After cooling to room temperature, phenyl isocyanate (30 mg) was added, and the mixture was stirred at room temperature for 1 h, loaded onto Varian™ SCX column and washed with $CH_3OH$ (5 mL) and $CHCl_3$ (5 mL). Product was eluted using 2 N $NH_3$ in $CH_3OH$ (3 mL) and concentrated.

The resulting material was dissolved into dichloromethane (1 mL), and 1 M chlorotrimethylsilane and 1 M phenol in dichloromethane (1 mL) was added. The solution was stirred at room temperature for 5 h, loaded onto Varian™ SCX column and washed with $CH_3OH$ and dichloromethane. Product was eluted using 2 N $NH_3$ in $CH_3OH$ and concentrated. Preparative TLC ($SiO_2$, AcOEt/MeOH=3:1) afforded 4-[{N-(2-amino-4,5-difluorobenzoyl)glycyl}aminomethyl]-1-(benzo[c]thiadiazol-5-yl)piperidine (Compound No. 2184) (1.3 mg, 5.5%): The purity was determined by RPLC/MS (100%); ESI/MS m/e 475.2 ($M^+$+H, $C_{22}H_{24}F_2N_6O_2S$).

Example 1876

Preparation of 4-[{N-(2-Amino-5-trifluoromethylbenzoyl)glycyl}aminomethyl]-1-(benzo[c]thiadiazol-5-yl)piperidine (Compound No. 2185)

The titled compound, 4-[{N-(2-amino-5-trifluoromethylbenzoyl)glycyl}aminomethyl]-1-(benzo[c]thiadiazol-5-yl)piperidine (Compound No. 2185) was synthesized pursuant to methods of Example 1875 using the corresponding reactant: 7.2 mg, 28% yield; ESI/MS m/e 507.4 ($M^+$+H, $C_{23}H_{26}F_3N_6O_2S$).

Example 1877

Preparation of 4-[{N-(2-Amino-5-trifluoromethylbenzoyl)glycyl}aminomethyl]-1-(2-amino-4-chlorobenzyl)piperidine (Compound No. 1919)

A mixture of 4-[{N-(2-amino-5-trifluoromethylbenzoyl)glycyl}aminomethyl]piperidine (0.050 mmol), 4-chloro-2-nitrobenzyl chloride (0.050 mmol), piperidinomethylpolystyrene (60 mg), acetonitrile (1.0 mL) and chloroform (0.7 mL) was stirred overnight at 50° C. The reaction mixture was cooled, loaded onto Varian™ SCX column and washed with 50% $CHCl_3/CH_3OH$ (10 mL) and $CH_3OH$ (10 mL). Product was eluted using 2 N $NH_3$ in $CH_3OH$ (5 mL) and concentrated. To the resulting material was added ethanol (3 mL) and 10% Pd—C (15 mg), and the mixture was stirred under $H_2$ at room temperature for 1.5 h. Filtration, concentration, and preparative TLC afforded 4-[{N-(2-amino-5-trifluoromethylbenzoyl)glycyl}aminomethyl]-1-(2-amino-4-chlorobenzyl)piperidine (Compound No. 1919) (5.1 mg, 14%): The purity was determined by RPLC/MS (90%); $^1$H NMR (400 MHz, $CDCl_3$) δ1.09–1.32 (m, 4H), 1.41–1.59 (m, 1 H), 1.66 (d, J=12.5 Hz, 2 H), 1.88 (t, J=11.5 Hz, 2 H), 2.82 (d, J=11.5 Hz, 2 H), 3.17 (t, J=6.5 Hz, 2 H), 3.42 (s, 2 H), 4.05 (d, J=5.5 Hz, 2 H), 4.85 (br s, 1 H), 5.92 (br s, 2 H), 6.25–6.36 (m, 1 H), 6.55–6.66 (m, 1 H), 6.70 (d, J=8.5 Hz, 1 H), 6.85 (d, J=8.5 Hz, 1 H), 7.26 (s, 1 H), 7.42 (d, J=8.5 Hz, 1 H), 7.68 (s, 1 H); ESI/MS m/e 498.2 ($M^+$+H, $C_{23}H_{27}ClF_3N_5O_2$).

Examples 1878 and 1879

The compounds of this invention were synthesized pursuant to methods of Example 1877 using the corresponding reactant respectively. The ESI/MS data and yields are summarized in Table 46.

TABLE 46

| | Compound No. | Molecular Formula | ESI/MS m/e | Yield (mg) | Yield (%) |
|---|---|---|---|---|---|
| Example 1878 | 1920 | C22 H26 Cl F2 N5 O2 | 466.2 | 3.5 | 10.0 |
| Example 1879 | 1922 | C23 H27 Cl F3 N5 O3 | 514.2 | 1.2 | 3.1 |

Example 1880

Preparation of 4-[{N-(2-Amino-5-trifluoromethylbenzoyl)glycyl}aminomethyl]-1-(benzo[d]oxazol-5-yl)piperidine (Compound No. 2188)

A solution of 1-(3-amino-4-hydroxybenzyl)-4-[{N-(2-(tert-butoxycarbonylamino)-5-trifluoromethylbenzoyl)glycyl}aminomethyl]piperidine (34.8 mg, 0.060 mmol), prepared pursuant to methods of Example 1826, in THF (2 mL) was treated with triethyl orthoformate (0.033 mL, 3.3 eq) and pyridinium p-toluenesulphonate (2 mg, 0.4 eq). The reaction mixture was stirred overnight under reflux. After cooling to room temperature, the mixture was concentrated. The residue was dissolved in AcOEt, loaded onto Bond-Elut™ Si column, eluted off using ethyl acetate/methanol=4/1, and concentrated.

The resulting material was dissolved into AcOEt (1.5 mL), and 4 N HCl in dioxane (0.5 mL) was added. The solution was stirred at room temperature overnight, adjusted to pH 10 with 5 M NaOH aqueous solution, and extracted with AcOEt. The extract was concentrated and purified by PTLC ($SiO_2$, AcOEt/MeOH=4:1) to afford 4-[{N-(2-amino-5-trifluoromethylbenzoyl)glycyl}aminomethyl]-1-(benz[d]oxazol-5-yl)piperidine (Compound No. 2188) (1.6 mg, 5%): The purity was determined by RPLC/MS (94%); ESI/MS m/e 490.3 ($M^+$+H, $C_{24}H_{26}F_3N_5O_3$).

Example 1881

Preparation of 4-[{N-(2-Amino-4,5-difluorobenzoyl)glycyl}aminomethyl]-1-(2-oxo-2,3-dihydro-1,3-benzoxazol-5-yl)piperidine (Compound No. 2190)

To a mixture of 1-(3-amino-4-hydroxy)-4-[{N-(2-(tert-butoxycarbonylamino)-4,5-difluorobenzoyl)glycyl}aminomethyl]piperidine (22 mg, 0.040 mmol), $NaHCO_3$ (0.040 mmol), water (0.7 mL), and methanol (1.5 mL) was added phenyl chloroformate (0.046 mmol) and the mixture was stirred at room temperature for 3 h. A 1 N NaOH solution (0.040 mL) was added, and the reaction mixture was stirred for additional 1.5 h. The mixture was extracted with ethyl acetate and evaporated. The residue was dissolved in methanol, loaded onto Varian™ SCX column and washed with $CH_3OH$ (5 mL×2). Product was eluted using 2 N $NH_3$ in $CH_3OH$ (5 mL) and concentrated.

To the resulting material was added 1 M chlorotrimethylsilane and 1 M phenol in dichloromethane (2 mL). The solution was stirred at room temperature for 2 h and evaporated. The residue was dissolved in methanol, loaded onto Varian™ SCX column and washed with CHOH (5 mL×2). Product was eluted using 2 N $NH_3$ in $CH_3OH$ (5 mL) and concentrated. Preparative TLC.($SiO_2$, AcOEt/MeOH=5:2) afforded 4-[{N-(2-amino-4,5-difluorobenzoyl)

glycyl}aminomethyl]-1-(2-oxo-2,3-dihydro-1,3-benzoxazol-5-yl)piperidine (Compound No. 2190) (4.1 mg, 22%): The purity was determined by RPLC/MS (100%); ESI/MS m/e 474.2 ($M^+$+H, $C_{23}H_{25}F_2N_5O_4$).

Example 1882–1884

The compounds of this invention were synthesized pursuant to methods of Example 1881 using the corresponding reactant respectively (phenyl chlorothionoformate was used instead of phenyl chloroformate for preparation of Compounds 2192 and 2193). The ESI/MS data and yields are summarized in Table 47.

TABLE 47

| | Compound No. | Molecular Formula | ESI/MS m/e | Yield (mg) | Yield (%) |
|---|---|---|---|---|---|
| Example 1882 | 2191 | C24 H26 F3 N5 O4 | 506.3 | 3.1 | 10 |
| Example 1883 | 2192 | C23 H25 F2 N5 O3 S | 490.2 | 6.9 | 35 |
| Example 1884 | 2193 | C24 H26 F3 N5 O3 S | 522.2 | 3.6 | 11 |

Reference Example 36

Preparation of 4-[{N-(1-(9-Fuluorenylmethoxycarbonyl)piperidine-4-ylmethyl)carbamoylmethyl}aminomethyl]-3-methoxyphenyloxymethyl-polystyrene To a solution of 1-(9-fuluorenylmethoxycarbonyl)-4-(glycylaminomethyl)piperidine hydrochloride (10 mmol) in DMF (65 mL) were added acetic acid (0.3 mL), sodium triacetoxyborohydride (1.92 g), and 4-formyl-3-(methoxyphenyloxymethyl)-polystyrene (1 mmol/g, 200 g). The mixture was shaken for 2 h and filtered. The resin was washed with MeOH, DMF, $CH_2Cl_2$, and methanol, and dried to afford the desired material.

Example 1885–2000

General Procedure for Solid-Phase Synthesis of 4-Aminomethylpiperidines

To a mixture of the corresponding acid (1.6 mmol), HBTU (1.6 mmol), and DMF (6 mL) was added diisopropylethylamine (3.6 mmol), and the mixture was shaken for 2 min. 4-[{N-(1-(9-fuluorenylmethoxycarbonyl)piperidine4-ylmethyl)carbamoylmethyl}aminomethyl]-3-methoxyphenyloxymethyl-polystyrene (0.4 mmol) was added and the mixture was shaken for 1 h and filtered. The resin was rinsed with DMF and $CH_2Cl_2$, and dried.

A mixture of the resulting resin, piperidine (3.2 mL), and DMF (12.8 mL) was shaken for 10 min and filtered. The resin was washed with DMF and $CH_2Cl_2$, and dried.

To the dry resin (0.05 mmol) was added a mixture of $NaBH(OAc)_3$ (0.25 mmol), AcOH (0.025 mL) and DMF (1 mL). The corresponding aldehyde (2.5 mmol) was added, and the mixture was shaken for 2 h, then filtered and washed with $CH_3OH$, 10% diisopropylethylamine in DMF, DMF, $CH_2Cl_2$, and $CH_3OH$. A mixture of the resin, water (0.050 mL), and trifluoroacetic acid (0.95 mL) was shaken for 1 h and filtered. The resin was washed with $CH_2Cl_2$ and $CH_3OH$. The filtrate and washings were combined and concentrated. The crude material was loaded onto Varian™ SCX column and washed with $CH_3OH$ (15 mL). Product was eluted using 2 N $NH_3$ in $CH_3OH$ (5 mL) and concentrated. Preparative TLC or HPLC, if needed, afforded the desired material. The ESI/MS data and yields are summarized in Table 48.

TABLE 48

| | Compound No. | Molecular Formula | ESI/MS m/e | Yield (mg) | Yield (%) |
|---|---|---|---|---|---|
| Example 1885 | 1923 | C23 H25 Br F3 N3 O2 S | 544 | 15.7 | 87 |
| Example 1886 | 1924 | C24 H28 F3 N3 O3 S | 496 | 14.6 | 89 |
| Example 1887 | 1925 | C23 H25 F4 N3 O2 S | 484 | 11.7 | 73 |
| Example 1888 | 1926 | C23 H24 F5 N3 O2 S | 502 | 13.9 | 84 |
| Example 1889 | 1927 | C23 H26 F3 N3 O3 S | 482 | 10.7 | 67 |
| Example 1890 | 1928 | C24 H26 F3 N3 O4 S | 510 | 14.3 | 85 |
| Example 1891 | 1929 | C26 H30 F3 N3 O2 S | 506 | 14.7 | 88 |
| Example 1892 | 1930 | C24 H28 F3 N3 O2 S2 | 512 | 14.4 | 85 |
| Example 1893 | 1931 | C25 H30 F3 N3 O2 S | 494 | 14.3 | 88 |
| Example 1894 | 1932 | C25 H28 F3 N3 O3 S | 509 | 7.1* | 35 |
| Example 1895 | 1933 | C25 H30 F3 N3 O2 S | 494 | 14.3 | 88 |
| Example 1896 | 1934 | C26 H32 F3 N3 O2 S | 509 | 14.4 | 86 |
| Example 1897 | 1935 | C23 H25 F3 N4 O4 S | 511 | 14.9 | 88 |
| Example 1898 | 1936 | C24 H28 F3 N3 O2 S | 480 | 13.3 | 84 |
| Example 1899 | 1937 | C26 H32 F3 N3 O2 S | 509 | 11.1 | 66 |
| Example 1900 | 1938 | C23 H27 Br2 N3 O2 | 538 | 5.3* | 25 |
| Example 1901 | 1939 | C24 H30 Br N3 O3 | 488 | 5.0* | 25 |
| Example 1902 | 1940 | C23 H27 Br F N3 O2 | 476 | 4.9* | 25 |
| Example 1903 | 1941 | C23 H26 Br F2 N3 O2 | 494 | 6.1* | 30 |
| Example 1904 | 1942 | C23 H28 Br N3 O3 | 474 | 1.7* | 9 |
| Example 1905 | 1943 | C24 H28 Br N3 O4 | 502 | 6.6* | 32 |
| Example 1906 | 1944 | C26 H32 Br N3 O2 | 498 | 7.0* | 35 |
| Example 1907 | 1945 | C24 H30 Br N3 O2 S | 504 | 11.1 | 67 |
| Example 1908 | 1946 | C25 H32 Br N3 O2 | 488 | 3.2* | 16 |
| Example 1909 | 1947 | C25 H30 Br N3 O3 | 500 | 5.7 | 35 |
| Example 1910 | 1948 | C25 H32 Br N3 O2 | 486 | 4.9* | 25 |
| Example 1911 | 1949 | C26 H34 Br N3 O2 | 500 | 6.7* | 33 |
| Example 1912 | 1950 | C23 H27 Br N4 O4 | 503 | 5.0* | 25 |
| Example 1913 | 1951 | C24 H30 Br N3 O2 | 472 | 5.1* | 26 |
| Example 1914 | 1952 | C22 H24 Br2 F N3 O2 | 542 | 14.9 | 83 |
| Example 1915 | 1953 | C23 H27 Br F N3 O3 | 492 | 13.9 | 86 |
| Example 1916 | 1954 | C22 H24 Br F2 N3 O2 | 480 | 12.5 | 79 |
| Example 1917 | 1955 | C22 H23 Br F3 N3 O2 | 498 | 13.2 | 80 |
| Example 1918 | 1956 | C22 H25 Br F N3 O3 | 478 | 7.0 | 44 |
| Example 1919 | 1957 | C23 H25 Br F N3 O4 | 506 | 4.0* | 20 |
| Example 1920 | 1958 | C25 H29 Br F N3 O2 | 502 | 14.6 | 88 |

TABLE 48-continued

| | Compound No. | Molecular Formula | ESI/MS m/e | Yield (mg) | Yield (%) |
|---|---|---|---|---|---|
| Example 1921 | 1959 | C23 H27 Br F N3 O2 S | 508 | 13.1 | 78 |
| Example 1922 | 1960 | C24 H29 Br F N3 O2 | 490 | 13.8 | 85 |
| Example 1923 | 1961 | C24 H27 Br F N3 O3 | 504 | 2.7* | 13 |
| Example 1924 | 1962 | C24 H29 Br F N3 O2 | 490 | 12.7 | 78 |
| Example 1925 | 1963 | C25 H31 Br F N3 O2 | 504 | 13.5 | 81 |
| Example 1926 | 1964 | C22 H24 Br F N4 O4 | 507 | 14.8 | 88 |
| Example 1927 | 1965 | C23 H27 Br F N3 O2 | 476 | 12.1 | 77 |
| Example 1928 | 1966 | C25 H31 Br F N3 O2 | 504 | 13.4 | 80 |
| Example 1929 | 1967 | C22 H26 Br F N4 O2 | 477 | 4.7* | 20 |
| Example 1930 | 1968 | C23 H29 F N4 O3 | 429 | 6.9* | 32 |
| Example 1931 | 1969 | C22 H27 F N4 O3 | 415 | 3.7* | 17 |
| Example 1932 | 1970 | C23 H27 F N4 O4 | 443 | 5.4* | 24 |
| Example 1933 | 1971 | C25 H31 F N4 O2 | 439 | 4.3* | 20 |
| Example 1934 | 1972 | C23 H29 F N4 O2 S | 445 | 6.2* | 28 |
| Example 1935 | 1973 | C24 H31 F N4 O2 | 427 | 6.3* | 29 |
| Example 1936 | 1974 | C24 H31 F N4 O2 | 427 | 4.9* | 23 |
| Example 1937 | 1975 | C22 H26 F N5 O4 | 444 | 5.9* | 27 |
| Example 1938 | 1976 | C23 H29 F N4 O2 | 413 | 6.7* | 32 |
| Example 1939 | 1977 | C23 H26 F N5 O2 | 424 | 5.1* | 24 |
| Example 1940 | 1978 | C25 H33 F N4 O2 | 441 | 6.3* | 29 |
| Example 1941 | 1979 | C25 H30 F2 N4 O2 | 457 | 8.0* | 35 |
| Example 1942 | 1980 | C24 H28 F2 N4 O3 | 459 | 6.0* | 26 |
| Example 1943 | 1981 | C22 H25 F2 N5 O4 | 462 | 9.3* | 41 |
| Example 1944 | 1982 | C23 H25 F2 N5 O2 | 442 | 6.0* | 27 |
| Example 1945 | 1983 | C25 H32 F2 N4 O2 | 459 | 8.3* | 37 |
| Example 1946 | 1984 | C22 H26 Br I N4 O2 | 585 | 9.7* | 36 |
| Example 1947 | 1985 | C23 H29 I N4 O3 | 537 | 9.2* | 36 |
| Example 1948 | 1986 | C22 H27 I N4 O3 | 523 | 5.8* | 23 |
| Example 1949 | 1987 | C23 H27 I N4 O4 | 551 | 8.2* | 32 |
| Example 1950 | 1988 | C25 H31 I N4 O2 | 547 | 6.7* | 26 |
| Example 1951 | 1989 | C23 H29 I N4 O2 3 | 553 | 6.4* | 25 |
| Example 1952 | 1990 | C24 H31 I N4 O2 | 535 | 7.2* | 29 |
| Example 1953 | 1991 | C24 H29 I N4 O3 | 549 | 5.6* | 22 |
| Example 1954 | 1992 | C24 H31 I N4 O2 | 535 | 6.2* | 25 |
| Example 1955 | 1993 | C22 H26 I N5 O4 | 552 | 10.2* | 40 |
| Example 1956 | 1994 | C23 H29 I N4 O2 | 521 | 7.5* | 30 |
| Example 1957 | 1995 | C23 H26 I N5 O2 | 532 | 6.8* | 27 |

TABLE 48-continued

| | Compound No. | Molecular Formula | ESI/MS m/e | Yield (mg) | Yield (%) |
|---|---|---|---|---|---|
| Example 1958 | 1996 | C25 H33 I N4 O2 | 549 | 7.1* | 28 |
| Example 1959 | 1997 | C25 H33 I N4 O2 | 549 | 3.0* | 12 |
| Example 1960 | 1998 | C22 H25 Br Cl N3 O2 | 478 | 7.6* | 39 |
| Example 1961 | 1999 | C23 H28 Cl N3 O3 | 430 | 7.0* | 39 |
| Example 1962 | 2000 | C22 H25 Cl F N3 O2 | 418 | 14.1 | 102 |
| Example 1963 | 2001 | C22 H26 Cl N3 O3 | 416 | 6.3* | 36 |
| Example 1964 | 2002 | C23 H26 Cl N3 O4 | 444 | 7.1* | 39 |
| Example 1965 | 2003 | C25 H30 Cl N3 O2 | 440 | 15.3 | 105 |
| Example 1966 | 2004 | C23 H28 Cl N3 O2 S | 446 | 8.4* | 45 |
| Example 1967 | 2005 | C24 H30 Cl N3 O2 | 428 | 7.4* | 41 |
| Example 1968 | 2006 | C24 H30 Cl N3 O2 | 428 | 13.8 | 98 |
| Example 1969 | 2007 | C22 H25 Cl N4 O4 | 445 | 16.0 | 109 |
| Example 1970 | 2008 | C23 H28 Cl N3 O2 | 414 | 14.1 | 103 |
| Example 1971 | 2009 | C23 H25 Cl N4 O2 | 425 | 14.8 | 106 |
| Example 1972 | 2010 | C25 H32 Cl N3 O2 | 442 | 14.5 | 99 |
| Example 1973 | 2011 | C25 H32 Cl N3 O2 | 442 | 14.5 | 99 |
| Example 1974 | 2012 | C22 H24 Br2 Cl N3 O2 | 558 | 12.8* | 58 |
| Example 1975 | 2013 | C23 H27 Br Cl N3 O3 | 508 | 8.6* | 42 |
| Example 1976 | 2014 | C22 H25 Br Cl N3 O3 | 494 | 6.0* | 30 |
| Example 1977 | 2015 | C23 H25 Br Cl N3 O4 | 522 | 8.4* | 40 |
| Example 1978 | 2016 | C25 H29 Br Cl N3 O2 | 518 | 17.6 | 103 |
| Example 1979 | 2017 | C23 H27 Br Cl N3 O2 S | 524 | 17.1 | 99 |
| Example 1980 | 2018 | C24 H29 Br Cl N3 O2 | 506 | 14.7 | 88 |
| Example 1981 | 2019 | C24 H27 Br Cl N3 O3 | 520 | 8.0* | 38 |
| Example 1982 | 2020 | C24 H29 Br Cl N3 O2 | 506 | 14.7 | 88 |
| Example 1983 | 2021 | C22 H24 Br Cl N4 O4 | 523 | 12.0* | 57 |
| Example 1984 | 2022 | C23 H27 Br Cl N3 O2 | 492 | 8.5* | 42 |
| Example 1985 | 2023 | C23 H24 Br Cl N4 O2 | 503 | 6.3* | 31 |
| Example 1986 | 2024 | C25 H31 Br Cl N3 O2 | 520 | 9.6* | 46 |
| Example 1987 | 2025 | C25 H31 Br Cl N3 O2 | 520 | 15.0 | 87 |
| Example 1988 | 2026 | C22 H23 Br Cl F2 N3 O2 | 514 | 15.8 | 93 |
| Example 1989 | 2027 | C22 H26 Br2 N4 O2 | 537 | 10.7* | 42 |
| Example 1990 | 2028 | C23 H29 Br N4 O3 | 489 | 8.5* | 36 |
| Example 1991 | 2029 | C22 H27 Br N4 O3 | 475 | 7.5* | 32 |
| Example 1992 | 2030 | C23 H27 Br N4 O4 | 503 | 6.8* | 28 |
| Example 1993 | 2031 | C25 H31 Br N4 O2 | 499 | 6.2* | 26 |
| Example 1994 | 2032 | C24 H29 Br N4 O3 | 501 | 8.9* | 37 |

TABLE 48-continued

| | Compound No. | Molecular Formula | ESI/MS m/e | Yield (mg) | Yield (%) |
|---|---|---|---|---|---|
| Example 1995 | 2033 | C24 H31 Br N4 O2 | 487 | 9.1* | 39 |
| Example 1996 | 2034 | C22 H26 Br N5 O4 | 504 | 6.4* | 26 |
| Example 1997 | 2035 | C23 H29 Br N4 O2 | 473 | 6.5* | 28 |
| Example 1998 | 2036 | C23 H26 Br N5 O2 | 484 | 6.3* | 27 |
| Example 1999 | 2037 | C25 H33 Br N4 O2 | 501 | 5.4* | 22 |
| Example 2000 | 2038 | C22 H25 Br F2 N4 O2 | 495 | 5.4* | 23 |

*Yield of TFA salt.

Example 2001

Preparation of 1-(3-Carbamoylbenzyl)-4-[{N-(3-(trifluoromethyl)benzoyl)glycyl}aminomethyl] piperidine (Compound No. 924).

EDCI (10.7 mg), 1-hydroxybenzotriazole hydrate (7.5 mg), $Et_3N$ (15.4 mg), 0.5 M $NH_3$ in dioxane (0.1 mL, 0.05 mmol) and DMF (0.5 mL) were added to a solution of 1-(3-carboxybenzyl)-4-[{N-(3-(trifluoromethyl)benzoyl) glycyl}aminomethyl]piperidine (19.4 mg, 0.041 mmol) in $CHCl_3$ (2.5 mL). The reaction mixture was stirred at 25° C. for 20 h, washed with 2 N aqueous NaOH (2×2 mL) and brine (1 mL). After filtration through PTFE membrane filter, the solvent was removed under reduced pressure to afford 1-(3-carbamoylbenzyl)-4-[{N-(3-(trifluoromethyl)benzoyl) glycyl}aminomethyl]piperidine (compound No. 924) as a pale yellow solid (17.9 mg, 92%): The purity was determined by RPLC/MS (89%); ESI/MS m/e 447.3 ($M^+$+H, $C_{24}H_{27}F_3N_4O_3$).

Example 2002

Preparation of 1-(4-Carbamoylbenzyl)-4-[{N-(3-(trifluoromethyl)benzoyl)glycyl}aminomethyl] piperidine (Compound No. 925)

Compound No. 925 was synthesized pursuant to methods of Example 2001 using the corresponding reactant: 14.2 mg, 72%; The purity was determined by RPLC/MS (86%); ESI/MS m/e 447 ($M^+$+H, $C_{24}H_{27}F_3N_4O_3$).

Example 2003

Preparation of 1-(4-Aminobenzyl)-4-[{N-(3-(trifluoromethyl)benzoyl)glycyl}aminomethyl] piperidine (Compound No. 516)

A solution of 1-(4-nitrobenzyl)-4-[{N-(3-(trifluoromethyl)benzoyl)glycyl}aminomethyl]piperidine (22.4 mg, 0.047 mmol) in EtOH (3 mL) was hydrogenated at 1 atm for 1 h in the presence of 5% palladium on charcoal (10 mg) at 25° C. The catalyst was removed by filtration and washed with EtOH (5 mL). The combined filtrate was evaporated to afford 1-(4-aminobenzyl)-4-[{N-(3-(trifluoromethyl)benzoyl)glycyl}aminomethyl]piperidine (compound No. 516) as a pale yellow solid (20.1 mg, 96%). The purity was determined by RPLC/MS (99%); ESI/MS m/e 449.1 ($M^+$+H, $C_{23}H_{27}F_3N_4O_2$).

Example 2004 and 2005

Compounds No. 517 and 518 were synthesized pursuant to methods of Example 2003 using the corresponding reactant respectively. The ESI/MS data and yields are summarized in Table 49.

TABLE 49

| | Compound No. | Molecular Formula | ESI/MS m/e | Yield (mg) | Yield (%) |
|---|---|---|---|---|---|
| Example 2004 | 517 | C23 H27 F3 N4 O2 | 449 | 26.5 | 78 |
| Example 2005 | 518 | C23 H27 F3 N4 O2 | 449 | 25.3 | 71 |

Example 2006

Preparation of 1-{4-(Benzoylamino)benzyl}-4-[{N-(3-(trifluoromethyl)benzoyl)glycyl}aminomethyl] piperidine (Compound No. 519)

EDCI (4.7 mg), 1-hydroxybenzotriazole hydrate (3.3 mg), $Et_3N$ (2.5 mg) and benzoic acid (3.0 mg) were added to a solution of 1-(4-aminobenzyl)-4-[{N-(3-(trifluoromethyl) benzoyl)glycyl}aminomethyl]piperidine (10.1 mg, 0.023 mmol) in $CH_2Cl_2$ (2.5 mL). The reaction mixture was stirred at 25° C. for 16 h, washed with 2 N aqueous NaOH (2×2 mL) and brine (1 mL). After filtration through PTFE membrane filter, the solvent was removed under reduced pressure to afford an yellow oil which was purified by preparative TLC ($SiO_3$, 10% $CH_3OH$—$CH_2Cl_2$) to give 1-(4-(benzoylamino)benzyl)-4-[{N-(3-(trifluoromethyl)benzoyl) glycyl}aminomethyl]piperidine (compound No. 519) as a colorless oil (4.6 mg, 36%): The purity was determined by RPLC/MS (99%); ESI/MS m/e 553.2 ($M^+$+H, $C_{30}H_{31}F_3N_4O_3$).

Example 2007

Preparation of 1-(4-(Piperidinocarbonyl)benzyl)-4-[{N-(3-(trifluoromethyl)benzoyl) glycyl}aminomethyl]piperidine (Compound No. 1572)

Piperidine (0.048 mmol), diisopropylcarbodiimide (0.45 mmol) in DMF (0.15 mL), 1-hydroxybenzotriazole hydrate (0.45 mmol) in DMF (0.15 mL) were added to a solution of 1-(4-carboxybenzyl)-4-[{N-(3-(trifluoromethyl)benzoyl) glycyl}aminomethyl]piperidine (0.040 mmol) in DMF (1.0 mL). The reaction mixture was stirred at room temperature for 17 h, loaded onto Varian™ SCX column, and washed with $CHCl_3/CH_3OH$ 1:1 (5 mL) and $CH_3OH$ (5 mL). Product was eluted off using 2 N $NH_3$ in $CH_3OH$ (5 mL) and concentrated to afford 1-{4-(piperidinocarbonyl)benzyl}-4-[{N-(3-(trifluoromethyl)benzoyl)glycyl}aminomethyl] piperidine (Compound No. 1572) (14.3 mg, 66%): The purity was determined by RPLC/MS (99%); ESI/MS m/e 545 ($M^+$+H, $C_{25}H_{35}F_3N_4O_3$).

Example 2008–2015

The compounds of this invention were synthesized pursuant to methods of Example 2007 using the corresponding reactant respectively. The ESI/MS data and yields are summarized in Table 50.

TABLE 50

| | Compound No. | Molecular Formula | ESI/MS m/e | Yield (mg) | Yield (%) |
|---|---|---|---|---|---|
| Example 2008 | 1573 | C31 H33 F3 N4 O4 | 583 | 17.6 | 76 |
| Example 2009 | 1574 | C31 H33 F3 N4 O3 | 567 | 18.8 | 83 |
| Example 2010 | 1575 | C30 H30 Cl F3 N4 O3 | 587 | 3.2 | 14 |
| Example 2011 | 1576 | C28 H33 F3 N4 O4 | 547 | 21.1 | 97 |
| Example 2012 | 1577 | C26 H31 F3 N4 O4 | 521 | 5.1 | 24 |
| Example 2013 | 1578 | C31 H33 F3 N4 O3 | 567 | 16.9 | 75 |
| Example 2014 | 1579 | C31 H33 F3 N4 O3 | 567 | 6.0 | 26 |
| Example 2015 | 1580 | C29 H35 F3 N4 O3 | 545 | 15.1 | 69 |

Example 2016

Preparation of 1-[4-(Chloroformyl)benzyl]-4-[{N-(3-(trifluoromethyl)benzoyl)glycyl}aminomethyl]piperidine A mixture of 1-(4-carboxybenzyl)-4-[{N-(3-(trifluoromethyl)benzoyl)glycyl}aminomethyl]piperidine (240 mg) and thionyl chloride (1 mL) was stirred at room temperature for 12 h and the excess thionyl chloride was removed under reduced pressure to give desired 1-[4-(chloroformyl)benzyl]-4-[{N-(3-(trifluoromethyl)benzoyl)glycyl}aminomethyl]piperidine. The acid chloride was used without further purification.

Example 2017

Preparation of 1-[4-{N-(2-Methoxyethyl)carbamoyl}benzyl]-4-[{N-(3-(trifluoromethyl)benzoyl)glycyl}aminomethyl]piperidine (Compound No. 1612)

A mixture of 1-[4-(chloroformyl)benzyl]-4-[{N-(3-(trifluoromethyl)benzoyl)glycyl}aminomethyl]piperidine (0.042 mmol), 2-methoxyethylamine (3.8 mg, 0.050 mmol), piperidinomethylpolystyrene (46 mg) and dichloromethane (1.5 mL) was stirred at room temperature for 17 h. Water (0.020 mL) was added and the mixture was stirred for 30 min. Methanol (1 mL) was added and the mixture was loaded onto Varian™ SCX column, and washed with $CH_3OH$ (10 mL). Product was eluted off using 2 N $NH_3$ in $CH_3OH$ (5 mL) and concentrated to afford 1-[4-{N-(2-methoxyethyl)carbamoyl}benzyl]-4-[{N-(3-(trifluoromethyl)benzoyl)glycyl}aminomethyl]piperidine (Compound No. 1612) (26.7 mg, 100%): The purity was determined by RPLC/MS (92%); ESI/MS m/e 535.2 ($M^-$+H, $C_{27}H_{33}F_3N_4O_4$).

Example 2018–2020

The compounds of this invention were synthesized pursuant to methods of Example 2017 using the corresponding reactant respectively. Preparative TLC, if needed, afforded the desired material. The ESI/MS data and yields are summarized in Table 51.

TABLE 51

| | Compound No. | Molecular Formula | ESI/MS m/e | Yield (mg) | Yield (%) |
|---|---|---|---|---|---|
| Example 2048 | 1610 | C31 H30 F6 N4 O3 | 621.2 | 4.4 | 14 |
| Example 2019 | 1611 | C30 H29 Cl2 F3 N4 O3 | 621.2 | 35.7 | quant |
| Example 2020 | 1613 | C32 H35 F3 N4 O3 | 581.2 | 29.9 | quant |

Example 2021

Preparation of 4-[N-{5-Bromo-2-(methylamino)benzoyl}glycyl]aminomethyl-1-(4-chlorohenzyl)piperidine (Compound No. 1427)

A solution of 4-{N-(2-amino-5-bromobenzoyl)glycyl}aminomethyl-1-(4-chlorobenzyl)piperidine (Compound No. 1042) (50 mg, 0.10 mmol) in triethyl orthoformate (6.5 mL) was stirred at 150° C. for 17 h. Concentration afforded a yellow solid. To a solution of the yellow solid in ethanol (3 mL) was added sodium borohydride (7.6 mg, 0.2 mmol) and the mixture was stirred at room temperature for 14 h. A resulting white precipitate was resolved in di-chloromethane and the solution was washed with 1 N aqueous NaOH (2 mL). The organic layer was separated, dried over $K_2CO_3$, filtered and evaporated. Column chromatography ($SiO_2$, 20% MeOH/$CHCl_3$) gave 4-[N-{5-bromo-2-(methylamino)benzoyl}glycyl]aminomethyl-1-(4-chlorobenzyl)piperidine (Compound No. 1427) (40 mg, 80%): The purity was determined by RPLC/MS (100%); ESI/MS m/e 505 ($C_{23}H_{28}BrClF_6N_4O_2$).

Example 2022

Preparation of 4-[N-{5-Bromo-2-(dimethylamino)benzoyl}glycyl]aminomethyl-1-(4-chlorobenzyl)piperidine (Compound No. 1428)

Sodium cyanoborohydride (26 mg, 0.42 mmol) and acetic acid (14 $\mu$L) was added successively to a mixture of 4-{N-(2-amino-5-bromobenzoyl)glycyl}aminomethyl-1-(4-chlorobenzyl)piperidine (Compound No. 1042) (67 mg, 0.14 mmol), 37% formaldehyde solution in water (0.112 mL, 1.4 mmol), acetonitrile (2 mL), and methanol (1.5 mL). After the solution was stirred at 50° C. for 30 h, 1 N aqueous NaOH and dichloromethane were added. The aqueous layer was separated and the organic layer was dried over $K_2CO_3$, filtered and evaporated. Column chromatography ($SiO_2$, 20% MeOH/AcOEt) gave 4-[N-{5-bromo-2-(dimethylamino)benzoyl)glycyl}aminomethyl-1-(4-chlorobenzyl)piperidine (Compound No. 1428) (60 mg, 82%): The purity was determined by RPLC/MS (100%); ESI/MS m/e 523 ($C_{24}H_{30}BrClF_6N_4O_2$).

Example 2023

Preparation of 4-[{N-(5-Bromo-2-(methylsulfonylamino)benzoyl)glycyl}aminomethyl]-1-(4-chlorobenzyl)piperidine (Compound No. 1581)

A mixture of 4-[{N-(2-amino-5-bromobenzoyl)glycyl}aminomethyl]-1-(4-chlorobenzyl)piperidine (25 mg, 0.05 mmol), methanesulfonyl chloride (0.0045 mL), triethylamine (0.026 mL) and dichloromethane (2 mL) was stirred at room temperature for 17 h. The reaction mixture was purified with column chromatography ($SiO_2$), loaded onto Varian™ SAX column, and washed with $CH_3OH$ (5 mL). Product was eluted off using 0.1 N HCl, in $CH_3OH$ (5 mL) and concentrated to afford 4-[{N-(5-bromo-2-(methylsulfonylamino)benzoyl)glycyl}aminomethyl]-1-(4-chlorobenzyl)piperidine (Compound No. 1581) (5.4 mg, 19%): ESI/MS m/e 573.0 ($M^+$+H, $C_{23}H_{28}BrClN_4O_4S$).

Example 2024

Preparation of 4-[{N-(5-Bromo-2-(bis(methylsulfonyl)amino)benzoyl)glycyl}aminomethyl]-1-(4-chlorobenzyl)piperidine (Compound No. 1582)

A mixture of 1-(4-chlorobenzyl)-4-[{N-(2-amino-5-bromobenzoyl)glycyl}aminomethyl]piperidine (57 mg, 0.10 mmol), methanesulfonyl chloride (0.018 mL, 0.24 mmol), triethylamine (0.068 mL) and dichloromethane (2 mL) was stirred at room temperature for 8 h. Aqueous 1 N NaOH solution (1 mL) was added and the mixture was extracted with dichloromethane (2 mL×3). The combined extracts were dried over K2CO3, filtered and evaporated. Column chromatography ($SiO_2$) gave 4-[{N-(5-bromo-2-(bis(methylsulfonyl)amino)benzoyl)glycyl}aminomethyl]-1-(4-chlorobenzyl)pipcridine (Compound No. 1582) (40 mg, 62%): ESI/MS m/e 651 ($M^+$+H, $C_{24}H_{30}BrClN_4O_6S_2$).

Example 2025

Preparation of 1-(4-Chlorobenzyl)-1-methyl-4-[{N-(3-(trifluoromethyl)benzoyl)glycyl}aminomethyl] piperidinium Iodide (Methylammnonium Iodide of Compound No. 461)

A solution of 4-[{N-(3-(trifluoromethyl)benzoyl)glycyl}aminomethyl]piperidine (30 mg, 0.087 mmol) in $CH_3CN$ (1.0 mL) and (piperidinomethyl)polystyrene (80 mg, 2.7 mmol base/g resin) were added to a solution of 4-chlorobenzyl chloride (11.7 mg, 0.073 mmol) in $CH_3CN$ (1.0 mL). The reaction mixture was stirred at 60° C. for 2 h. Phenyl isocyanate (10.4 mg, 0.087 mmol) was added to the cooled reaction mixture and the mixture was stirred at 25° C. for 1 h. The reaction mixture was loaded onto Varian™ SCX column and washed with $CH_3OH$ (20 mL). Product was eluted off using 2 N $NH_3$ in $CH_3OH$ (6 mL) and concentrated to afford 1-(4-chlorobenzyl)-4-[{N-(3-(trifluoromethyl)benzoyl)glycyl}aminomethyl]piperidine as a colorless oil used without purification. Iodomethane (28 mg, 0.20 mmol) was added to a solution of 1-(4-chlorobenzyl)-4-]{N-(3-(trifluoromethyl)benzoyl)glycyl}aminomethyl]piperidine in $CH_3CN$ (2.0 mL) and the reaction mixture was stirred at 70° C. for 4 h. The solvent was removed under reduced pressure to afford 1-(4-chlorobenzyl)-1-methyl-4-[{N-(3-(trifluoromethyl)benzoyl)glycyl}aminomethyl]piperidinium iodide as a pale yellow oil (31.7 mg, 71%): The purity was determined by RPLC/MS (99%); ESI/MS m/e 482.1 ($M^+$, $C_{24}H_{28}ClF_3N_3O_2$).

Example 2026

Preparation of 1-{4-Chlorobenzyl}-4-[N-methyl-N-{N-(3-(trifluoromethyl)benzoyl)glycyl}aminomethyl]piperidine (Compound No. 520)

Formaldehyde (108 mg, 1.33 mmol, 37% wt solution in $H_2O$) was added to a solution of 1-(4-chlorobenzyl)-4-(aminomethyl)piperidine (318 mg, 1.33 mmol) and $NaBH_3CN$ (668 mg) in 10% $CH_3COOH/CH_3OH$ (3 mL). The reaction mixture was stirred at 25° C. for 1 h. The reaction mixture was loaded on DOWEX™ 50W×2 column (10 mL) and washed with $CH_3OH$ (100 mL). Product was eluted off using 2 N $NH_3$ in $CH_3OH$ (100 mL) and concentrated to afford 173 mg of crude 1-(42chlorobenzyl)-4-{(methylamino)methyl}piperidine as a colorless oil used without purification.

EDCI (85 mg), 1-hydroxybenzotriazole hydrate (60 mg) were added to a solution of 1-(4-chlorobenzyl)-4-{(methylamino)methyl}piperidine (222 mg, 0.44 mmol) in $CH_2Cl_2$ (4 mL). The reaction mixture was stirred at 25° C. for 1 h and then washed with 2 N aqueous NaOH (2 mL×2) and brine (1 mL). After filtration through PTFE membrane filter, the solvent was removed under reduced pressure to afford an yellow oil which was purified by preparative TLC ($SiO_2$, 5% $CH_3OH/CH_2Cl_2$) to give 1-(4-chlorobenzyl)-4-[N-methyl-N-{N-(3-(trifluoromethyl)benzoyl)glycyl}aminomethyl]piperidine (compound No. 520) as a pale yellow oil (14.0 mg, 3.4%). The purity was determined by RPLC/MS (99%); ESI/MS m/e 482.1 ($M^+$+H, $C_{24}H_{27}ClF_3N_3O_2$).

Reference Example 37

Preparation of 3-Aminohomopiperidine

A solution of DL-α-amino-ε-caprolactam (2 g, 16 mmol) in THF (70 mL) was treated with 1 M $BH_3$-THF solution (80 mL) and heated to reflux for 3 h. 2 N aqueous HCl solution (50 mL) was added and the reaction was heated to reflux for an additional hour before cooling to 25° C. The reaction was basicified (pH 10) by the addition of 4 N NaOH solution and extracted with EtOAc (3×200 mL). The combined organic phases were washed with saturated aqueous $NaHCO_3$, dried ($MgSO_4$) and concentrated to yield the desired material (990 mg, 54%) which was used without any further purification.

Reference Example 38

Preparation of 3-Amino-1-(4-chlorobenzyl) homopiperidine

A solution of 3-aminohomopiperidine (1.71 g, 15 mmol) in $CH_3CN$ (45 mL) was treated with p-chlorobenzyl chloride (463 mg, 2.9 mmol) and $K_2CO$ (828 g, 6 mmol) and heated to 70° C. for 9 h. The reaction mixture was cooled to 25° C. and concentrated to afford a yellow solid. The residue was partitioned between $H_2O$ (5 mL) and EtOAc (50 mL), and extracted with EtOAc (2×50 mL). The combined organic extracts were washed with brine (20 mL), dried ($Na_2SO_4$) and concentrated. The resulting yellow oil was purified by chromatography ($SiO_2$, 5–20% $CH_3OH$—$CH_2Cl_2$ gradient elution) to afford the desired product as a yellow oil (639 mg, 93%).

Example 2027

Preparation of 1-(4-Chlorobenzyl)-3-{(4-benzoylbutyryl)amino}homopiperidine (Compound No. 994)

A solution of 3-amino-1-(4-chlorobenzyl)homopiperidine (24 mg, 0.10 mmol) and 4-benzoylbutyric acid (1.2 equiv.) in CHCl3 (1 mL) was treated with EDCI (23 mg), HOBt (16.2 mg) and $Et_3N$ (15.2 μL), and stirred at 25° C. for 16 h. The reaction mixture was diluted with $CH_2Cl_2$ (0.5 mL), washed with 2 N aqueous NaOH solution (2×0.75 mL), dried by filtration through a PTFE membrane and concentrated to afford 1-(4-chlorobenzyl)-3-{(4-benzoylbutyryl)amino}homopiperidine (compound No. 994) (43 mg, 99%): The purity was determined by RPLC/MS (98%); ESI/MS m/e 413 ($M^+$+H, $C_{24}H_{28}ClN_2O_2$).

Example 2028–2042

The compounds of this invention were synthesized pursuant to methods of Example 2027 using the corresponding reactant respectively. Chromatography (HPLC-C18), if needed, afforded the desired material as the TFA salt. The ESI/MS data and yields are summarized in Table 52.

TABLE 52

| | Compound No. | Molecular Formula | ESI/MS m/e | Yield (mg) | Yield (%) |
|---|---|---|---|---|---|
| Example 2028 | 943 | C23 H25 Cl F3 N3 O2 | 468 | 6 | 28 |
| Example 2029 | 944 | C23 H28 Cl N3 O2 | 414 | 5 | 29 |
| Example 2030 | 945 | C22 H25 Cl N4 O4 | 445 | 6 | 30 |
| Example 2031 | 946 | C23 H27 Cl N4 O4 | 459 | 5 | 24 |
| Example 2032 | 947 | C25 H31 Cl N2 O4 | 459 | 4 | 20 |
| Example 2033 | 948 | C24 H29 Cl2 N3 O2 | 462 | 6 | 32 |
| Example 2034 | 949 | C25 H32 Cl N3 O2 | 442 | 6 | 31 |
| Example 2035 | 988 | C23 H25 Cl F3 N3 O2 | 468 | 45 | 92 |
| Example 2036 | 989 | C23 H28 Cl N3 O3 | 430 | 44 | 97 |
| Example 2037 | 990 | C22 H26 Cl N3 O2 | 400 | 41 | 99 |
| Example 2038 | 991 | C23 H27 Cl N2 O2 | 399 | 41 | 97 |
| Example 2039 | 992 | C25 H31 Cl N2 O4 | 459 | 47 | 98 |
| Example 2040 | 993 | C25 H31 Cl N2 O2 | 427 | 44 | 98 |
| Example 2041 | 995 | C25 H31 Cl N2 O3 | 443 | 44 | 95 |
| Example 2042 | 996 | C24 H31 Cl N4 O2 | 443 | 5* | 11 |

*Yield of TFA salt.

Example 2043

Measurement of Inhibition of MIP-1α Binding to THP-1 Cells by Test Compounds Human monocytic leukemia cell line THP-1 was suspended in assay buffer (RPMI-1640 (Gibco-BRL Co.) containing 0.1% BSA and 25 mM HEPES adjusted to pH 7.4) to give a cell suspension of a concentration of $1\times10^{-}$ cells/mL. The test compound was diluted in the assay buffer and used as the test compound solution. Iodinated human MIP-1α (DuPont NEN Co.) was diluted in assay buffer to 250 nCi/mL and used as the labeled ligand solution. In a 96 well filter plate (Millipore Co.), 25 μL of test compound solution, 25 μL of labeled ligand solution and 50 μL of cell suspension were aliquoted into each well in this order, stirred (total reaction volume 100 μL), and incubated for one hour at 18° C.

After the reaction, the reaction solution was filtered, and the filter was washed twice with 200 μL of cold PBS (200 μL of cold PBS was added and then filtered). The filter was air-dried and 25 μL of liquid scintillator was added into each well. The radioactivity retained by the cells on the filter were measured using TopCount (Packard Instrument Co.).

To calculate the ability of test compounds to inhibit binding of human MIP-1α to THP-1 cells, non-specific binding determined by adding 100 ng of unlabeled human MIP-1α (Peprotech Co.) in place of the test compound was subtracted, while the counts with no test compound added was taken as 100%.

$$\text{Inhibition}(\%)=\{1-(A-B)/(C-B)\}\times100$$

(A, counts with test compound added; B, counts with 100 ng of unlabeled human MIP-1α added; C, counts with $[^{125}I]$-labeled human MIP-1α added).

When inhibition by the cyclic amine derivative of this invention was measured, for example, the following compounds demonstrated 20–50%, 50%–80% and >80% inhibitory activity at 2 μM or 10 μM, respectively. These compounds are 20%–50% inhibition at 10 μM: Compound Nos. 29, 37, 41, 45, 46, 47, 50, 82, 85, 107, 120, 134, 214, 217, 218, 220, 222, 225, 226, 227, 228, 229, 230, 231, 233, 234, 236, 237, 238, 333, 334, 335, 336, 338, 340, 342, 347, 348, 349, 350, 352, 357, 359, 361, 366, 372, 374, 375, 376, 380, 382, 383, 385, 470, 471, 472, 473, 474, 483, 484, 488, 489, 491, 497, 499, 500, 502, 506, 508, 510, 514, 515, 518, 524, 543, 553, 554, 555, 556, 563, 571, 575, 576, 578, 579, 580, 583, 586, 587, 588, 590, 591, 592, 595, 596, 598, 603, 610, 611, 612, 614, 624, 625, 626, 629, 635, 638, 639, 640, 641, 642, 643, 644, 646, 647, 648, 649, 652, 653, 658, 659, 660, 665, 666, 669, 671, 675, 677, 679, 681, 682, 684, 691, 695, 696, 700, 702, 704, 706, 711, 712, 714, 717, 721, 723, 724, 726, 727, 728, 729, 731, 737, 739, 740, 741, 742, 744, 746, 765, 767, 772, 773, 774, 775, 776, 780, 781, 785, 786, 787, 788, 790, 791, 792, 793, 795, 796, 797, 798, 805, 806, 807, 810, 813, 820, 821, 822, 824, 825, 827, 829, 830, 833, 834, 837, 838, 844, 853, 855, 873, 877, 878, 880, 882, 887, 888, 891, 894, 901, 903, 904, 905, 911, 929, 932, 933, 935, 938, 940, 948, 993, 996, 1006, 1018, 1026, 1028, 1035, 1048, 1053, 1054, 1055, 1056, 1068, 1070, 1071, 1072, 1073, 1075, 1076, 1081, 1763, 1764.

50%–80 inhibition at 10 μM: Compound Nos. 1, 2, 3, 4, 7, 13, 22, 23, 24, 25, 27, 31, 32, 38, 48, 83, 119, 121, 123, 131, 215, 216, 221, 235, 337, 351, 354, 358, 362, 363, 365, 367, 368, 369, 373, 378, 381, 384, 458, 459, 463, 465, 466, 467, 468, 478, 479, 480, 482, 485, 486, 487, 492, 493, 494, 495, 496, 498, 501, 503, 504, 507, 511, 512, 513, 520, 523, 527, 529, 530, 531, 532, 533, 534, 535, 536, 537, 538, 539, 540, 541, 542, 545, 546, 547, 548, 549, 550, 551, 552, 558, 559, 560, 561, 562, 565, 567, 568, 569, 570, 572, 573, 574, 577, 581, 582, 594, 597, 599, 600, 602, 604, 606, 607, 608, 609, 613, 615, 616, 618, 619, 620, 621, 628, 630, 631, 632, 633, 634, 636, 637, 645, 651, 654, 655, 657, 661, 662, 664, 673, 674, 676, 678, 680, 683, 685, 687, 688, 689, 693, 703, 705, 707, 708, 709, 710, 713, 716, 718, 719, 720, 725, 730, 732, 733, 734, 735, 736, 749, 750, 751, 752, 753, 754, 756, 758, 760, 762, 763, 764, 766, 768, 769, 770, 771, 777, 778, 779, 784, 794, 799, 800, 802, 804, 808, 809, 811, 812, 815, 816, 819, 828, 831, 832, 835, 836, 839, 840, 845, 846, 847, 848, 850, 851, 854, 857, 858, 859, 860, 861, 862, 863, 865, 866, 867, 868, 872, 874, 876, 886, 899, 910, 942, 998, 1604, 1005, 1007, 1013, 1015, 1016, 1017, 1019, 1020, 1021, 1022, 1024, 1030, 1037, 1042, 1043, 1044, 1045, 1046, 1047, 1049, 1050, 1052, 1059, 1060, 1061, 1067, 1069, 1074, 1078, 1079, 1080, 1766.

>80% inhibition at 10 μM: Compound Nos. 461, 464, 469, 481, 490, 505, 509, 521, 526, 528, 544, 564, 566, 601, 605, 617, 622, 623, 627, 650, 656, 663, 668, 672, 686, 690, 692, 694, 715, 743, 747, 748, 755, 757, 759, 761, 782, 783, 803, 814, 817, 818, 826, 849, 856, 864, 869, 870, 871, 999, 1000, 1001, 1002, 1003, 1008, 1009, 1010, 1011, 1012, 1023, 1029, 1031, 1032, 1033, 1034, 1036, 1038, 1039, 1040, 1041, 1051, 1057, 1058, 1062, 1063, 1064, 1065, 1066, 1082, 1083.

20%–50% inhibition at 2 μM: Compound Nos. 1042, 1043, 1244, 1245, 1416, 1435, 1436, 1438, 1441, 1480, 1570, 1583, 1584, 1589, 1590, 1594, 1595, 1601, 1660, 1672, 1687, 1724, 1779, 1780, 1787, 1795, 1796, 1798, 1799, 1802, 1893, 1894, 1898, 1900, 1915, 1919, 1920, 2092, 2096, 2098, 2100.

50%–80% inhibition at 2 μM: Compound Nos. 1190, 1414, 1600, 2091, 2094, 2095.

>80% inhibition at 2 μM: Compound Nos. 2093, 2097, 2099, 2103, 2104.

Example 2044

Measurement of Inhibition of MCP-1 Binding to THP-1 Cells

1. Construction of Recombinant Baculovirus Carrying the Human MCP-1 Gene

Based on the previously published human MCP-1 gene sequence (for example T. Yoshimura et al., FEBS Lett., 1989, 244, 487–493), two synthetic DNA primers (5'-CACTCTAGACTCCAGCATGA-3' and 5'-TAGCTGCAGATTCTTGGGTTG-3') flanked by restriction enzyme sites were used to amplify a DNA fragment from cDNA derived from human endothelial cells (purchased from Kurabow Co.); the amplified fragment was cut with the restriction enzymes (PstI and XbaI), ligated into a transfer vector pVL1393 (Invitrogen Co.), and the resulting vector was co-transfected along with infectious baculovirus into Sf-9 insect cells and the supernatant was plaque assayed to yield human MCP-1 gene baculovirus recombinant.

2. Synthesis of [$^{125}$I]-labeled Human MCP-1 Expressed in Baculovirus

Using the method of K. Ishii et al. (Biochem Biophys Research Communications, 1995, 206, 955–961), 5x$10^6$ Sf-6 insect cells was infected with 5x$10^7$ PFU (plaque forming units) of the above human MCP-1 recombinant baculovirus and cultured for 7 days in Ex-Cell 401 medium. The culture supernatant was affinity purified using a heparin Sepharose column (Pharmacia Co.) and then further purified using reverse phase HPLC (Vydac C18 column) to prepare purified human MCP-1. The purified human MCP-1 was protein labeled by Amersham Co. using the Bolton Hunter method to yield [$^{125}$I]-labeled baculovirus expressed human MCP-1 (specific activity 2000 Ci/mmol).

3-1. Measurement of Inhibition of Binding of [$^{125}$I]-labeled Baculovirus Expressed Human MCP-1 to THP-1 cells (Method 1)

Human monocytic leukemia cell line THP-1 was suspended in assay buffer (RPMI-1640 (Gibco-BRL Co.) containing 0.1% BSA and 25 mM HEPES adjusted to pH 7.4) to give a cell suspension of a concentration of 1x$10^7$ cells/mL. The test compound was diluted in the assay buffer and used as the test compound solution. ($^{125}$I)-1labeled human MCP-1 described above was diluted in assay buffer to 1 mCi/mL and used as the labeled ligand solution. In a 96 well filter plate (Millipore Co.), 25 $\mu$L of test compound solution, 25 $\mu$L of labeled ligand solution and 50 $\mu$L of cell suspension were aliquoted into each well in this order, stirred (total reaction volume 100 $\mu$L), and incubated for one hour at 18° C.

After the reaction, the reaction solution was filtered, and the filter was washed twice with 200 $\mu$L of cold PBS (200 $\mu$L of cold PBS was added and then filtered). The filter was air-dried and 25 $\mu$L of liquid scintillator was added into each well. The radioactivity retained by the cells on the filter were measured using TopCount (Packard Instrument Co.).

To calculate the ability of test compound to inhibit binding of human MCP-1 to THP-1 cells, non-specific binding, determined by adding 100 ng of unlabeled human MCP-1 in place of the test compound was subtracted, while the counts with no test compound added was taken as 100%.

$$\text{Inhibition }(\%)=1-(A-B)/(C-B))\times 100$$

(A, counts with test compound added; B, counts with 100 ng of unlabeled human MCP-1 added; C, counts with [$^{125}$I]-labeled human MCP-1 added).

When inhibition by the cyclic amine derivative of this invention was measured, for example, the following compounds demonstrated 20%–50%, 50%–80% and >80% inhibitory activity at 1 $\mu$M, 10 $\mu$L or 100 $\mu$L, respectively. These compounds are 20%–50 inhibition at 100 $\mu$M: Compound Nos. 3, 6, 11, 15, 16, 19, 28, 44, 88, 92, 94, 104, 111, 112, 124, 125, 133, 219, 220, 224, 228, 236, 338, 343, 346, 347, 348, 349, 362, 363, 367, 368, 371, 373, 381, 618, 847, 849, 850, 866, 867, 869, 870, 871, 872, 873.

50%–80% inhibition at 100 $\mu$M: Compound Nos. 1, 8, 10, 12, 18, 21, 26, 30, 33, 35, 39, 84, 89, 90, 91, 96, 97, 98, 99, 100, 101, 103, 106, 108, 109, 110, 116, 122, 126, 216, 218, 221, 225, 226, 231, 330, 332, 333, 334, 337, 341, 342, 350, 352, 354, 356, 359, 360, 361, 364, 366, 374, 375, 379, 382, 462, 463, 464, 557, 686, 840, 841, 842, 843, 844, 845, 846, 848, 862, 863, 864, 865, 868.

>80% inhibition at 100 PM: Compound Nos. 2, 4, 5, 7, 13, 14, 17, 20, 22, 23, 24, 25, 27, 29, 31, 32, 34, 36, 38, 40, 41, 42, 43, 45, 46, 47, 48, 49, 50, 83, 85, 86, 95, 102, 105, 107, 113, 114, 115, 119, 120, 121, 123, 127, 128, 129, 130, 131, 132, 134, 214, 215, 217, 227, 237, 238, 331, 335, 336, 339, 340, 345, 351, 355, 357, 358, 383, 458, 459, 460, 466, 558, 851, 852, 861, 874.

20%–50% inhibition at 10 $\mu$M: Compound Nos. 12, 18, 30, 34, 40, 42, 43, 51, 52, 53, 54, 55, 56, 57, 59, 60, 64, 66, 75, 76, 77, 78, 79, 82, 89, 90, 97, 98, 102, 103, 116, 127, 128, 129, 130, 132, 135, 136, 140, 141, 144, 156, 157, 159, 160, 161, 162, 163, 166, 167, 168, 169, 170, 171, 172, 173, 174, 175, 176, 178, 179, 190, 191, 192, 195, 197, 200, 202, 203, 204, 205, 208, 233, 234, 235, 239, 240, 241, 242, 243, 245, 247, 249, 250, 255, 263, 264, 269, 274, 278, 279, 282, 306, 316, 317, 323, 324, 380, 404, 409, 433, 446, 448, 449, 451, 470, 471, 473, 476, 479, 486, 488, 489, 497, 498, 499, 501, 504, 507, 508, 509, 510, 512, 514, 516, 519, 527, 530, 532, 542, 545, 560, 563, 564, 565, 566, 568, 569, 572, 573, 574, 575, 578, 583, 584, 586, 587, 589, 590, 599, 600, 601, 603, 606, 612, 613, 620, 621, 622, 624, 625, 627, 629, 630, 632, 634, 636, 637, 640, 641, 642, 643, 644, 645, 646, 647, 648, 649, 658, 678, 682, 687, 692, 694, 764, 775, 856, 857, 860, 881, 882, 883, 884, 890, 892, 899, 900, 903, 905, 907, 908, 911, 912, 916, 917, 921, 922, 923, 925, 927, 931, 932, 935, 939, 940, 968, 986, 1039, 1041, 1045, 1047, 1062, 1063, 1083.

50%–80% inhibition at 10 $\mu$M: Compound Nos. 7, 32, 36, 61, 62, 63, 65, 67, 69, 70, 71, 72, 73, 74, 81, 91, 105, 114, 121, 123, 134, 137, 138, 139, 146, 147, 148, 149, 151, 154, 165, 177, 232, 244, 248, 251, 252, 253, 256, 259, 261, 266, 267, 276, 286, 292, 293, 295, 301, 305, 307, 310, 314, 315, 320, 322, 328, 434, 435, 436, 437, 439, 440, 443, 447,.450, 452, 453, 454, 455, 456, 468, 469, 472, 474, 475, 477, 478, 480, 481, 482, 483, 485, 490, 493, 494, 500, 505, 511, 517, 520, 529, 534, 540, 543, 544, 548, 555, 556, 561, 562, 570, 576, 579, 611, 617, 853, 854, 855, 858, 859, 875, 877, 879, 880, 885, 886, 887, 888, 891, 894, 895, 904, 906, 909, 910, 913, 914, 918, 928, 930, 933, 937, 938, 945, 970, 1040, 1044, 1046.

>80% inhibition at 10 $\mu$M: Compound Nos. 31, 45, 46, 48, 58, 68, 80, 83, 113, 115, 142, 143, 145, 150, 152, 265, 268, 272, 275, 283, 285, 287, 288, 290, 291, 294, 296, 297, 302, 308, 309, 313, 321, 325, 326, 358, 438, 441, 442, 444, 445, 457, 466, 467, 484, 487, 491, 492, 495, 496, 503, 518, 537, 538, 547, 554, 876, 878, 919, 929, 943.

20%–50% inhibition at 1 $\mu$M: Compound Nos. 1118, 1121, 1136, 1143, 1146, 1158, 1159, 1167, 1170, 1359, 1361, 1362, 1363.

50%–80% inhibition at 1 $\mu$M: Compound Nos. 1133, 1134, 1137, 1141, 1156, 1161, 1162, 1163, 1164, 1166.

>80% inhibition at 1 $\mu$M: Compound No. 1147.

3-2. Measurement of Inhibition of Binding of [$^{125}$I]-labeled Baculovirus Expressed Human MCP-1 to THP-1 Cells (Method 2)

Human monocytic leukemia cell line THP-1 was suspended in assay buffer (50 mM HEPES, pH 7.4, 1.0 mM $CaCl_2$, 5.0 mM $MgCl_2$, 0.5% BSA) to give a cell suspension of a concentration of $1\times10^7$ cells/mL. The test compound was diluted in the assay buffer and used as the test compound solution. [$^{125}$I]-labeled human MCP-1 described above was diluted in assay buffer to 1 mCi/mL and used as the labeled ligand solution. Ina 96well filter plate (Millipore Co.), 25 $\mu$L of test compound solution, 25 $\mu$L of labeled ligand solution and 50 $\mu$L of cell suspension were aliquoted into each well in this order, stirred (total reaction volume 100 $\mu$L), and incubated for one hour at 18° C.

After the reaction, the reaction solution was filtered, and the filter was washed twice with 200 $\mu$L of cold PBS (200 $\mu$L of cold PBS was added and then filtered). The filter was air-dried and 25 $\mu$L of liquid scintillator was added into each well. The radioactivity retained by the cells on the filter were measured using TopCount (Packard Instrument Co.).

To calculate the ability of test compound to inhibit binding of human MCP-1 to THP-1 cells, non-specific binding determined by adding 100 ng of unlabeled human MCP-1 in place of the test compound was subtracted, while the counts with no test compound added was taken as 100%.

$$\text{Inhibition}(\%)=(1-(A-B)/(C-B))\times100$$

(A, counts with test compound added; B, counts with 100 ng of unlabeled human MCP-1 added; C, counts with [$^{125}$I]-labeled human MCP-1 added).

When inhibition by the cyclic amine derivative of this invention was measured, for example, the following compounds demonstrated 20%–50%, 50%–80% and >80% inhibitory activity at 0.2 $\mu$M, 1 $\mu$M or 10 $\mu$M, respectively. These compounds are 20%–50% inhibition at 10 $\mu$M: Compound No. 1560.

50%–80% inhibition at 10 $\mu$M: Compound No. 1550.

>80% inhibition at 10 $\mu$M: Compound Nos. 541, 1042, 1043, 1559.

20%–50% inhibition at 1 $\mu$M: Compound Nos. 1098, 1100, 1101, 1104, 1105, 1109, 1110, 1116, 1174, 1175, 1176, 1178, 1187, 1188, 1189, 1197, 1198, 1199, 1200, 1201, 1202, 1209, 1210, 1211, 1212, 1222, 1225, 1229, 1230, 1237, 1238, 1243, 1250, 1259, 1261, 1265, 1266, 1272, 1277, 1282, 1294, 1299, 1302, 1307, 1315, 1318, 1319, 1320, 1329, 1330, 1335, 1336, 1337, 1343, 1344, 1353, 1355, 1356, 1357, 1358, 1368, 1372, 1385, 1386, 1392, 1400, 1413, 1422, 1423, 1425, 1426, 1429, 1430, 1432, 1437, 1440, 1445, 1446, 1447, 1448, 1450, 1452, 1453, 1455, 1458, 1459, 1461, 1463, 1464, 1466, 1468, 1469, 1470, 1471, 1474, 1479, 1482, 1485, 1507, 1508, 1510, 1511, 1512, 1513, 1514, 1515, 1516, 1518, 1519, 1521, 1522, 1524, 1535, 1538, 1540, 1542, 1544, 1571, 1573, 1574, 1575, 1576, 1577, 1578, 1579, 1580, 1581, 1582, 1585, 1587, 1598, 1602, 1603, 1604, 1609, 1611, 1612, 1613, 1614, 1615, 1616, 1617, 1618, 1622, 1627, 1630, 1643, 1646, 1662, 1669, 1716, 1717, 1723, 1728, 1731, 1733, 1736, 1739, 1740, 1747, 1750, 1755, 1757, 1758, 1759, 1760, 1761, 1762, 1769, 1770, 1771, 1772, 1773, 1774, 1777, 1783, 1784, 1785, 1791, 1793, 1904, 1911, 1917, 2057, 2061, 2063, 2064, 2065, 2066, 2067, 2068, 2069, 2071, 2072, 2073, 2074, 2075, 2076, 2080, 2081, 2082, 2110, 2112, 2123, 2130, 2131, 2139.

50%–80% inhibition at 1 $\mu$M: Compound Nos. 37, 298, 318, 1084, 1091, 1103, 1106, 1108, 1111, 1113, 1114, 1115, 1138, 1142, 1165, 1179, 1190, 1192, 1193, 1195, 1196, 1204, 1205, 1206, 1207, 1208, 1245, 1246, 1255, 1257, 1258, 1262, 1263, 1293, 1300, 1342, 1351, 1352, 1354, 1370, 1371, 1373, 1375, 1377, 1378, 1380, 1381, 1383, 1384, 1391, 1411, 1412, 1414, 1417, 1418, 1419, 1421, 1424, 1431, 1436, 1439, 1449, 1454, 1456, 1457, 1460, 1462, 1472, 1473, 1487, 1502, 1504, 1506, 1517, 1525, 1526, 1527, 1529, 1530, 1531, 1532, 1533, 1534, 1536, 1537, 1539, 1541, 1545, 1593, 1600, 1601, 1606, 1608, 1619, 1620, 1621, 1623, 1624, 1625, 1626, 1628, 1629, 1645, 1650, 1654, 1658, 1663, 1664, 1665, 1670, 1671, 1672, 1673, 1675, 1678, 1679, 1681, 1684, 1687, 1688, 1689, 1690, 1711, 1712, 1714, 1718, 1722, 1725, 1726, 1727, 1729, 1730, 1732, 1734, 1735, 1737, 1741, 1742, 1743, 1744, 1745, 1746, 1748, 1751, 1753, 1754, 1756, 1779, 1781, 1782, 1786, 1788, 1789, 1790, 1792, 1795, 1797, 1798, 1800, 1801, 1804, 1848, 1862, 1883, 1885, 1886, 1887, 1889, 1893, 1894, 1903, 1905, 1910, 1912, 1913, 1914, 1918, 1922, 1976, 1985, 2027, 2035, 2062, 2083, 2084, 2088, 2089, 2090, 2111, 2124, 2125, 2126, 2135.

>80% inhibition at 1 $\mu$M: Compound Nos. 299, 311, 312, 329, 1042, 1043, 1085, 1119, 1191, 1203, 1220, 1228, 1236, 1244, 1256, 1288, 1295, 1308, 1310, 1376, 1382, 1393, 1395, 1415, 1416, 1420, 1435, 1438, 1441, 1480, 1481, 1570, 1583, 1584, 1589, 1590, 1594, 1595, 1607, 1634, 1660, 1661, 1666, 1668, 1695, 1696, 1697, 1698, 1699, 1701, 1702, 1703, 1704, 1705, 1706, 1707, 1708, 1709, 1713, 1724, 1749, 1752, 1775, 1776, 1778, 1780, 1787, 1794, 1796, 1799, 1802, 1803, 1841, 1869, 1870, 1871, 1872, 1876, 1877, 1892, 1896, 1897, 1898, 1899, 1900, 1901, 1902, 1906, 1907, 1908, 1909, 1915, 1916, 1919, 1920, 1921, 2085, 2086, 2087, 2113, 2114, 2118, 2119, 2120, 2121, 2122, 2127, 2128, 2129, 2132, 2133, 2136, 2137, 2138, 2159, 2161, 2162, 2187, 2189, 2193.

20%–50% inhibition at 0.2 $\mu$M: Compound Nos. 1680, 1682, 1686, 1691, 1694, 1700, 1805, 1810, 1811, 1812, 1813, 1815, 1816, 1817, 1818, 1819, 1820, 1824, 1825, 1826, 1827, 1828, 1832, 1833, 1834, 1835, 1836, 1839, 1840, 1842, 1843, 1851, 1852, 1853, 1854, 1855, 1856, 1858, 1859, 1860, 1863, 1864, 1865, 1866, 1868, 1874, 1878, 1879, 1880, 1888, 1890, 1891, 1895, 1926, 1927, 1928, 1929, 1930, 1934, 1935, 1937, 1945, 1946, 1951, 1952, 1953, 1954, 1959, 1960, 1961, 1962, 1966, 1969, 1970, 1971, 1972, 1973, 1977, 1978, 1979, 1980, 1981, 1985, 2014, 2027, 2028, 2033, 2035, 2039, 2040, 2041, 2042, 2044, 2045, 2046.

50%–80% inhibition at 0.2 $\mu$M: Compound Nos. 1677, 1678, 1679, 1681, 1687, 1688, 1689, 1690, 1695, 1697, 1808, 1809, 1841, 1848, 1861, 1862, 1869, 1870, 1871, 1872, 1873, 1876, 1877, 1883, 1884, 1885, 1886, 1887, 1889, 1893, 1894, 1976.

>80% inhibition at 0.2 $\mu$M: Compound No. 1696, 1892.

Example 2045

Measurement of Inhibition of Binding of [$^{125}$I]-Labeled Human MCP-1 to Cells Expressing the MCP-1 Receptor 1. Derivation of Cells Expressing the MCP-1 Receptor cDNA fragment containing the MCP-1 receptor reported by S. Yamagami et al., Biochemical Biophysical Research Communications 1994, 202, 1156–1162) was cloned into the expression plasmid pCEP4 (Invitrogen Co.) at the NotI site, and the plasmid obtained was transfected into the human kidney epithelial cell line 293-EBNA using the Lipofectamine reagent (Gibco-BRL Co.). The cells were cultured in the presence of the selective agent (Hygromycin), and a stably expressing transfectant line was obtained. The expression of the receptor was confirmed by binding of [$^{125}$I]-labeled human MCP-1.

2. Measurement of Inhibition of Binding of [$^{125}$I]-labeled Baculovirus Expressed Human MCP-1 to the MCP-1 Receptor Expressing Cells The MCP-1 receptor expressing cells on tissue culture dishes were scraped using a cell scraper and suspended in assay buffer (D-MEM(Gibco-BRL Co.) containing 0.1% BSA and 25 mM HEPES adjusted to pH 7.4) to give a cell suspension of a concentration of $6\times10^6$ cells/mL. The test compound was diluted in the assay buffer. The remainder of the procedure was as described in Example 2044.

When the inhibition by some typical compounds of the present invention was measured, the inhibitory activities were substantially the same as those in Example 2044, respectively.

Example 2046

Measurement of Inhibition of Cell Chemotaxis

In order to determine the inhibition of cell chemotaxis by the compounds of this invention, we measured cell chemotaxis caused by monocyte chemotactic factor MCP-1 using the human monocytic leukemia cell line THP-1 as the chemotactic cell according to the method of Fall et al. (J. Immunol.Methods, 190, 33, 239–247). $2\times10^6$ cells/mL of THP-1 cells (suspended in RPMI-1640 (Flow Laboratories Co.)+10% FCS) was placed in the upper chamber (200 $\mu$L) of a 96 well micro-chemotaxis chamber (Neuroprobe, registered tradename), and human recombinant MCP-1 in a same solution (Peprotech Co.) at a final concentration of 20 ng/mL was placed in the lower chamber, with a polycarbonate filter (PVP-free, Neuroprobe; registered tradename) placed between the two chambers. These were incubated at 37° C. for 2 hr in 5% $CO_2$.

The filter was removed, and the cells which had migrated to the underside of the filter was fixed, stained using Diff Quick (Kokusai Shiyaku Co.) and then quantitated using a plate reader (Molecular Device Co.) at a wavelength of 550 nm to determine the index of cell migration as a mean of 3 wells. In addition, test compounds were placed in the upper and lower chambers along with THP-1 and MCP-1, respectively, and the inhibition of cell migration (inhibition $IC_{50;}$ ($\mu$M) was determined. Inhibition was defined as {(cells migration induced MCP-1 with no test compound in the upper and lower chambers)–(cells migration with no MCP-1 added in the lower chamber)=100%}, and the concentration of the test compound which gave 50% inhibition was designated $IC_{50}$.

When inhibition by the cyclic amine derivative of this invention was measured, for example, the 50% inhibition concentration ($IC_{50}$) for the following compounds were $IC_{50}$<0.1 $\mu$M.

$IC_{50}$<0.1 $\mu$M: Compound Nos. 4, 37, 298, 299, 311, 312, 318, 329, 461, 886, 909, 1042, 1043, 1085, 1119, 1138, 1142, 1165, 1179, 1191, 1203, 1205, 1220, 1228, 1236, 1244, 1245, 1256, 1288, 1293, 1295, 1308, 1310, 1352, 1376, 1382, 1393, 1395, 1416, 1420, 1435, 1436, 1438, 1441, 1480, 1531, 1532, 1570, 1583, 1584, 1589, 1590, 1594, 1595, 1600, 1601, 1607, 1660, 1661, 1664, 1666, 1668, 1698, 1699, 1701, 1702, 1703, 1704, 1706, 1707, 1708, 1709, 1713, 1775, 1776, 1778, 1779, 1787, 1794, 1796, 1799, 1802, 1803, 1896, 1898, 1899, 1900, 1901, 1902, 1906, 1907, 1908, 1909, 1915, 1916, 1919, 1920, 1921, 2087, 2114, 2128, 2129, 2132, 2137, 2141, 2144, 2157, 2158, 2189.

What is claimed is:

1. A compound of the formula (I) below:

(I)

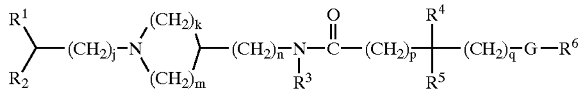

a pharmaceutically acceptable acid addition salt thereof or a pharmaceutically acceptable $C_1$–$C_6$ alkyl addition salt thereof, wherein $R^1$ is a phenyl group, a $C_3$–$C_8$ cycloalkyl group, or an aromatic heterocyclic group having 1–3 heteroatoms selected from the group consisting of an oxygen atom, a sulfur atom, a nitrogen atom, or a combination thereof, in which the phenyl or aromatic heterocyclic group may be condensed with a benzene ring or an aromatic heterocyclic group having 1–3 heteroatoms selected from the group consisting of an oxygen atom, a sulfur atom, a nitrogen atom, or a combination thereof, to form a condensed ring, and the phenyl group, $C_3$–$C_8$ cycloalkyl group, aromatic heterocyclic group, or condensed ring may be substituted with one or more of a halogen atom, a hydroxy group, a cyano group, a nitro group, a carboxy group, a carbamoyl group, a $C_1$–$C_6$ alkyl group, a $C_3$–$C_8$ cycloalkyl group, a $C_2$–$C_6$ alkenyl group, a $C_1$–$C_6$ alkoxy group, a $C_1$–$C_6$ alkylthio group, a $C_3$–$C_5$ alkylene group, a $C_2$–$C_4$ alkylenoxy group, a $C_1$–$C_3$ alkylenedioxy group, a phenyl group, a phenoxy group, a phenylthio group, a benzyl group, a benzyloxy group, a benzoylamino group, a $C_2$–$C_7$ alkanoyl group, a $C_2$–$C_7$ alkoxycarbonyl group, a $C_2$–$C_7$ alkanoyloxy group, a $C_2$–$C_7$ alkanoylamino group, a $C_2$–$C_7$ N-alkylcarbamoyl group, a $C_4$–$C_9$ N-cycloalkylcarbamoyl group, a $C_1$–$C_6$ alkylsulfonyl group, a $C_3$–$C_8$ (alkoxycarbonyl)methyl group, a N-phenylcarbamoyl group, a piperidinocarbonyl group, a morpholinocarbonyl group, a 1-pyrrolidinylcarbonyl group, a divalent group represented by the formula: —NH(C═O)O—, a divalent group represented by the formula: —NH(C═S)O—, an amino group, a mono($C_1$–$C_6$ alkyl)amino group, or a di($C_1$–$C_6$ alkyl)amino group, wherein the substituent for the phenyl group, $C_3$–$C_8$ cycloalkyl group, aromatic heterocyclic group, or condensed ring is optionally substituted with one or more of a halogen atom, a hydroxy group, an amino group, a trifluoromethyl group, a $C_1$–$C_6$ alkyl group, or a $C_1$–$C_6$ alkoxy group;

$R^2$ is a hydrogen atom, a $C_1$–$C_6$ alkyl group, a $C_2$–$C_7$ alkoxycarbonyl group, a hydroxy group, or a phenyl group, in which the $C_1$–$C_6$ alkyl or phenyl group may be substituted with one or more of a halogen atom, a hydroxy group, a $C_1$–$C_6$ alkyl group, or a $C_1$–$C_6$ alkoxy group, and when j=0, $R^2$ is not a hydroxy group;

j represents an integer of 0–2;

k represents an integer of 0–1; and m represents an integer of 2–3, with the proviso that the total sum of k and m is 3;

n represents 0 or 1;

$R^3$ is a hydrogen atom or a $C_1$–$C_6$ alkyl group optionally substituted with one or two phenyl groups each of which may be substituted with one or more of a halogen atom, a hydroxy group, a $C_1$–$C_6$ alkyl group, or a $C_1$–$C_6$ alkoxy group;

$R^4$ and $R^5$ are the same or different from each other and are a hydrogen atom, a hydroxy group, a phenyl group, or a $C_1$–$C_6$ alkyl group, in which the $C_1$–$C_6$ alkyl group is optionally substituted with one or more of a halogen atom, a hydroxy group, a cyano group, a nitro group, a carboxy group, a carbamoyl group, a mercapto group, a guanidino group, a $C_3$–$C_8$ cycloalkyl group, a $C_1$–$C_6$ alkoxy group, a $C_1$–$C_6$ alkylthio group, a phenyl group optionally substituted with one or more of a halogen atom, a hydroxy group, a $C_1$–$C_6$ alkyl group, a $C_1$–$C_6$ alkoxy group, or a benzyloxy group, a phenoxy group, a benzyloxy group, a benzyloxycarbonyl group, a $C_2$–$C_7$ alkanoyl group, a $C_2$–$C_7$, alkoxycarbonyl group, a $C_2$–$C_7$ alkanoyloxy group, a $C_2$–$C_7$ alkanoylamino group, a $C_2$–$C_7$, N-alkylcarbamoyl group, a $C_1$–$C_6$ alkylsulfonyl group, an amino group, a mono($C_1$–$C_6$ alkyi)amino group, a di($C_1$–$C_6$ alkyl)amino group, or an aromatic heterocyclic group having 1–3 of heteroatoms selected from the group consisting of an oxygen atom, a sulfur atom, a nitrogen atom, or a combination thereof and optionally condensed with benzene ring, with the proviso that when one of $R^4$ and $R^5$ is a hydrogen atom, the other is not an isobutyl group, or $R^4$ and $R^5$ taken together form a 3 to 6 membered cyclic hydrocarbon;

p represents 0 or 1;

q represents 0 or 1;

G is a group represented by —CO—, —$SO_2$—, —CO—O—, —$NR^7$—CO—, —CO—$NR^7$—, —NH—CO—NH—, —NH—CS—NH—, —$NR^7$—$SO_2$—, —$SO_2$—$NR^7$—, —NH—CO—O—, or —O—CO—NH—, wherein $R^7$ is a hydrogen atom or a $C_1$–$C_6$ alkyl group, or $R^7$ taken together with $R^5$ represents $C_2$–$C_5$ alkylene group;

$R^6$ is a phenyl group, a $C_3$–$C_8$ cycloalkyl group, a $C_3$–$C_8$ cycloalkenyl group, a benzyl group, or an aromatic heterocyclic group having 1–3 heteroatoms selected from the group consisting of an oxygen atom, a sulfur atom, a nitrogen atom, or a combination thereof, in which the phenyl, benzyl, or aromatic heterocyclic group may be condensed with a benzene ring or an aromatic heterocyclic group having 1–3 heteroatoms selected from the group consisting of an oxygen atom, a sulfur atom, a nitrogen atom, or a combination thereof, to form a condensed ring, and the phenyl group, $C_3$–$C_8$ cycloalkyl group, $C_3$–$C_8$ cycloalkenyl group, benzyl group, aromatic heterocyclic group, or condensed ring may be substituted with one or more of a halogen atom, a hydroxy group, a mercapto group, a cyano group, a nitro group, a thiocyanato group, a carboxy group, a carbamoyl group, a trifluoromethyl group, a $C_1$–$C_6$ alkyl group, a $C_3$–$C_6$ cycloalkyl group, a $C_2$–$C_6$ alkenyl group, a $C_1$–$C_6$ alkoxy group, a $C_3$–$C_8$ cycloalkyloxy group, a $C_1$–$C_6$ alkylthio group, a $C_1$–$C_3$ alkylenedioxy group, a phenyl group, a phenoxy group, a phenylamino group, a benzyl group, a benzoyl group, a phenylsulfinyl group, a phenylsufonyl group, a 3-phenylureido group, a $C_2$–$C_7$ alkanoyl group, a $C_2$–$C_7$ alkoxycarbonyl group, a $C_2$–$C_7$, alkanoyloxy group, a $C_2$–$C_7$ alkanoylamino group, a $C_2$–$C_7$ N-alkylcarbamoyl group, a $C_1$–$C_6$ alkylsulfonyl group, a phenylcarbamoyl group, a N, N-di($C_1$–$C_6$ alkyl) sulfamoyl group, an amino group, a mono ($C_1$–$C_6$ alkyl) amino group, a di($C_1$–$C_6$ alkyl) amino group, a benzylamino group, a $C_2$–$C_7$ (alkoxycarbonyl) amino group, a $C_1$–$C_6$ (alkylsulfonyl) amino group, or a bis($C_1$–$C_6$ alkylsulfonyl) amino group, wherein the substituent for the phenyl group, $C_3$–$C_8$ cycloalkyl group, $C_3$–$C_8$ cycloalkenyl group, benzyl group, aromatic heterocyclic group, or condensed ring is optionally substituted with one or more of a halogen atom, a cyano group, a hydroxy group, an amino group, a trifluoromethyl group, a $C_1$–$C_6$ alkyl group, a $C_1$–$C_6$ alkoxy group, a $C_1$–$C_6$ alkylthio group, a mono ($C_1$–$C_6$ alkyl) amino group, or a di($C_1$–$C_6$ alkyl) amino group.

2. A compound, its pharmaceutically acceptable acid addition salt or its pharmaceutically acceptable $C_1$–$C_6$ alkyl addition salt as set forth in claim 1, wherein k=1 and m=2 in the above formula (I).

3. A compound, its pharmaceutically acceptable acid addition salt or its pharmaceutically acceptable $C_1$–$C_6$ alkyl addition salt as set forth in claim 2, wherein n=0 in the above formula (I).

4. A compound, its pharmaceutically acceptable acid addition salt or its pharmaceutically acceptable $C_1$–$C_6$ alkyl addition salt as set forth in claim 1, wherein k=0, m=3 and n=1 in the above formula (I).

5. A compound, its pharmaceutically acceptable acid addition salt or its pharmaceutically acceptable $C_1$–$C_6$ alkyl addition salt as set forth in claim 1, wherein j=0 in the above formula(I).

6. A compound, its pharmaceutically acceptable acid addition salt or its pharmaceutically acceptable $C_1$–$C_6$ alkyl addition salt as set forth in claim 1, wherein p=0, q=0 and G is a group represented by —$NR^7$—CO— in the above formula (I).

7. A compound, its pharmaceutically acceptable acid addition salt or its pharmaceutically acceptable $C_1$–$C_6$ alkyl addition salt as set forth in claim 1, wherein $R^2$ is a hydrogen atom, $R^3$ is a hydrogen atom and $R^7$ is a hydrogen atom in the above formula (I).

8. A compound, its pharmaceutically acceptable acid addition salt or its pharmaceutically acceptable $C_1$–$C_6$ alkyl addition salt as set forth in claim 1, wherein the substituent for the phenyl group, $C_3$–$C_8$ cycloalkyl group, aromatic heterocyclic group, or condensed ring in $R^1$ is one or more of a halogen atom, a hydroxy group, a $C_1$–$C_6$ alkyl group, a $C_2$–$C_6$ alkenyl group, a $C_2$–$C_6$ alkoxy group, a $C_1$–$C_6$ alkylthio group, a $C_2$–$C_4$ alkylenoxy group, a methylenedioxy group, a N-phenylcarbamoyl group, an amino group, a mono($C_1$–$C_6$ alkyl)amino group, or a di($C_1$–$C_6$ alkyl) amino group in the above formula (I).

9. A compound, its pharmaceutically acceptable acid addition salt or its pharmaceutically acceptable $C_1$–$C_6$ alkyl addition salt as set forth in claim 1, wherein the substituent for the phenyl group, $C_3$–$C_8$ cycloalkyl group, $C_3$–$C_8$ cycloalkenyl group, benzyl group, aromatic heterocyclic group, or condensed ring in $R^6$ is one or more of a halogen atom, a nitro group, a trifluoromethyl group, a $C_1$–$C_6$ alkyl group, a $C_1$–$C_6$ alkoxy group, a phenylsulfonyl group, a $C_2$–$C_7$ alkanoylamino group, or an amino group in the above formula (I).

10. A compound, its pharmaceutically acceptable acid addition salt or its pharmaceutically acceptable $C_1$–$C_6$ alkyl addition salt as set forth in claim 1, wherein $R^1$ is a phenyl group or an isoxazolyl group in the above formula (I).

11. A compound, its pharmaceutically acceptable acid addition salt or its pharmaceutically acceptable $C_1$–$C_6$ alkyl addition salt as set forth in claim 1, wherein $R^6$ is a phenyl group, a furyl group, or a thienyl group in the above formula (I).

12. A method of inhibiting the binding of a chemokine to the receptor of a target cell and/or its action on a target cell using a pharmaceutical preparation containing a therapeutically effective amount of a compound represented by the formula (I) below:

(I)

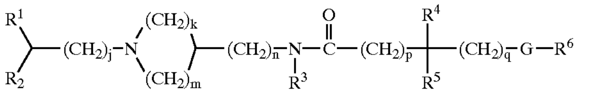

a pharmaceutically acceptable acid addition salt thereof or a pharmaceutically acceptable $C_1$–$C_6$ alkyl addition salt thereof, wherein $R^1$ is a phenyl group, a $C_3$–$C_8$ cycloalkyl group, or an aromatic heterocyclic group having 1–3 heteroatoms selected from the group consisting of an oxygen atom, a sulfur atom, a nitrogen atom, or a combination thereof, in which the phenyl or aromatic heterocyclic group may be condensed with a benzene ring or an aromatic heterocyclic group having 1–3 heteroatoms selected from the group consisting of an oxygen atom, a sulfur atom, a nitrogen atom, or a combination thereof, to form a condensed ring, and the phenyl group, $C_3$–$C_8$ cycloalkyl group, aromatic heterocyclic group, or condensed ring may be substituted with one or more of a halogen atom, a hydroxy group, a cyano group, a nitro group, a carboxy group, a carbamoyl group, a $C_1$–$C_6$ alkyl group, a $C_3$–$C_8$ cycloalkyl group, a $C_2$–$C_6$ alkenyl group, a $C_1$–$C_6$ alkoxy group, a $C_1$–$C_6$ alkylthio group, a $C_3$–$C_5$ alkylene group, a $C_2$–$C_4$ alkylenoxygroup, a $C_1$–$C_3$ alkylenedioxy group, a phenyl group, a phenoxy group, a phenylthio group, a benzyl group, a benzyloxy group, a benzoylamino group, a $C_2$–$C_7$ alkanoyl group, a $C_2$–$C_7$ alkoxycarbonyl group, a $C_2$–$C_7$ alkanoyloxy group, a $C_2$–$C_7$, alkanoylamino group, a $C_2$—C—, N-alkylcarbamoyl group, a $C_4$–$C_9$ N-cycloalkylcarbamoyl group, a $C_1$–$C_6$ alkylsulfonyl group, a $C_3$–$C_8$ (alkoxycarbonyl)methyl group, a N-phenylcarbamoyl group, a piperidinocarbonyl group, a morpholinocarbonyl group, a 1-pyrrolidinylcarbonyl group, an amino group, a mono ($C_1$–$C_6$ alkyl) amino group, or a di($C_1$–$C_6$ alkyl)amino group, wherein the substituent for the phenyl group, $C_3$–$C_8$ cycloalkyl group, aromatic heterocyclic group, or condensed ring is optionally substituted with one or more of a halogen atom, a hydroxy group, an amino group, a trifluoromethyl group, a $C_1$–$C_6$ alkyl group, or a $C_1$–$C_6$ alkoxy group;

$R^2$ is a hydrogen atom, a $C_1$–$C_6$ alkyl group, a $C_2$–$C_7$ alkoxycarbonyl group, a hydroxy group, or a phenyl group, in which the $C_1$–$C_6$ alkyl or phenyl group may be substituted with one or more of a halogen atom, a hydroxy group, a $C_1$–$C_6$ alkyl group, or a $C_1$–$C_6$ alkoxy group, and when j=0, $R^2$ is not a hydroxy group;

j represents an integer of 0–2;

k represents an integer of 0–1 and m represents an integer of 2–3, with the proviso that the total sum of k and m is 3 n represents 0 or 1;

$R^3$ is a hydrogen atom or a $C_1$–$C_6$ alkyl group optionally substituted with one or two phenyl groups each of which may be substituted with one or more of a halogen atom, a hydroxy group, a $C_1$–$C_6$ alkyl group, or a $C_1$–$C_6$ alkoxy group;

$R^4$ and $R^5$ are the same or different from each other and are a hydrogen atom, a hydroxy group, a phenyl group, or a $C_1$–$C_6$ alkyl group, in which the $C_1$–$C_6$ alkyl group is optionally substituted with one or more of a halogen atom, a hydroxy group, a cyano group, a nitro group, a carboxy group, a carbamoyl group, a mercapto group, a guanidino group, a $C_3$–$C_8$ cycloalkyl group, a $C_1$–$C_6$ alkoxy group, a $C_1$–$C_6$ alkylthio group, a phenyl group optionally substituted with one or more of a halogen atom, a hydroxy group, a $C_1$–$C_6$ alkyl group, a $C_1$–$C_6$ alkoxy group, or a benzyloxy group, a phenoxy group, a benzyloxy group, a benzyloxycarbonyl group, a $C_2$–$C_7$, alkanoyl group, a $C_2$–$C_7$ alkoxycarbonyl group, a $C_2$–$C_7$ alkanoyloxy group, a $C_2$–$C_7$ alkanoylamino group, a $C_2$–$C_7$ N-alkylcarbamoyl group, a $C_1$–$C_6$ alkylsulfonyl group, an amino group, a mono($C_1$–$C_6$ alkyl)amino group, a di($C_1$–$C_6$ alkyl)amino group, or an aromatic heterocyclic group having 1–3 of heteroatoms selected from the group consisting of an oxygen atom, a sulfur atom, a nitrogen atom, or a combination thereof and optionally condensed with benzene ring, or $R^4$ and $R^5$ taken together form a 3 to 6 membered cyclic hydrocarbon;

p represents 0 or 1;

q represents 0 or 1;

G is a group represented by —CO—, —$SO_2$—, —CO—O—, —$NR^7$—CO—, —CO—$NR^7$—, —NH—CO—NH—, —NH—CS—NH—, —$NR^7$—$SO_2$—, —$SO_2$—$NR^7$—, —NH—CO—O—, or —O—CO—NH—, wherein $R^7$ is a hydrogen atom or a $C_1$–$C_6$ alkyl group, or $R^7$ taken together with $R^5$ represents $C_2$–$C_5$ alkylene group;

$R^6$ is a phenyl group, a $C_3$–$C_8$ cycloalkyl group, a $C_3$–$C_8$ cycloalkenyl group, a benzyl group, or an aromatic heterocyclic group having 1–3 heteroatoms selected from the group consisting of an oxygen atom, a sulfur atom, a nitrogen atom, or a combination thereof, in which the phenyl, benzyl, or aromatic heterocyclic group may be condensed with a benzene ring or an aromatic heterocyclic group having 1–3 heteroatoms selected from the group consisting of an oxygen atom, a sulfur atom, a nitrogen atom, or a combination thereof, to form a condensed ring, and the phenyl group, $C_3$–$C_8$ cycloalkyl group, $C_3$–$C_8$ cycloalkenyl group, benzyl group, aromatic heterocyclic group, or condensed ring may be substituted with one or more of a halogen atom, a hydroxy group, a mercapto group, a cyano group, a nitro group, a thiocyanato group, a carboxy group, a carbamoyl group, a trifluoromethyl group, a $C_1$–$C_6$ alkyl group, a $C_3$–$C_6$ cycloalkyl group, a $C_2$–$C_6$ alkenyl group, a $C_1$–$C_6$ alkoxy group, a $C_3$–$C_8$ cycloalkyloxy group, a $C_1$–$C_6$ alkylthio group, a $C_1$–$C_3$ alkylenedioxy group, a phenyl group, a phenoxy group, a phenylamino group, a benzyl group, a benzoyl group, a phenylsulfinyl group, a phenylsufonyl group, a 3-phenylureido group, a $C_2$–$C_7$ alkanoyl group, a $C_2$–$C_7$ alkoxycarbonyl group, a $C_2$–$C_7$, alkanoyloxy group, a $C_2$–$C_7$ alkanoylamino group, a $C_2$–$C_7$ N-alkylcarbamoyl group, a $C_1$–$C_6$ alkylsulfonyl group, a phenylcarbamoyl group, a N, N-di($C_1$–$C_6$ alkyl) sulfamoyl group, an amino group, a mono ($C_1$–$C_6$ alkyl) amino group, a di($C_1$–$C_6$ alkyl) amino group, a benzylamino group, a $C_2$–$C_7$ (alkoxycarbonyl) amino group, a $C_1$–$C_6$ (alkylsulfonyl) amino group, or a bis($C_1$–$C_6$ alkylsulfonyl) amino group, wherein the substituent for the phenyl group, $C_3$–$C_8$ cycloalkyl group, $C_3$–$C_8$ cycloalkenyl group, benzyl group, aromatic heterocyclic group, or condensed ring is optionally substituted with one or more of a halogen atom, a cyano group, a hydroxy group, an amino group, a trifluoromethyl group, a $C_1$–$C_6$ alkyl group, a $C_1$–$C_6$ alkoxy group, a $C_1$–$C_6$ alkylthio group, a mono ($C_1$–$C_6$ alkyl) amino group, or a di($C_1$–$C_6$ alkyl) amino group.

13. A method of inhibiting the binding of a chemokine to the receptor of a target cell and/or its action on a target cell as set forth in claim 12, wherein k=1 and m=2 in the above formula (I).

14. A method of inhibiting the binding of a chemokine to the receptor of a target cell and/or its action on a target cell as set forth in claim 13, wherein n=0 in the above formula (I).

15. A method of inhibiting the binding of a chemokine to the receptor of a target cell and/or its action on a target cell as set forth in claim 12, wherein k=0, m=3 and n=1 in the above formula (I).

16. A method of inhibiting the binding of a chemokine to the receptor of a target cell and/or its action on a target cell as set forth in claim 12, wherein j=0 in the above formula (I).

17. A method of inhibiting the binding of a chemokine to the receptor of a target cell and/or its action on a target cell as set forth in claim 12, wherein p=0, q=0 and G is a group represented by —$NR^7$—CO— in the above formula (I).

18. A method of inhibiting the binding of a chemokine to the receptor of a target cell and/or its action on a target cell as set forth in claim 12, wherein $R^2$ is a hydrogen atom, $R^3$ is a hydrogen atom and $R^7$ is a hydrogen atom in the above formula (I).

19. A method of inhibiting the binding of a chemokine to the receptor of a target cell and/or its action on a target cell as set forth in claim 12, wherein the substituent for the phenyl group, $C_3$–$C_8$ cycloalkyl group, aromatic heterocyclic group, or condensed ring in $R^1$ is one or more of a halogen atom, a hydroxy group, a $C_1$–$C_6$ alkyl group, a $C_2$–$C_6$ alkenyl group, a $C_1$–$C_6$ alkoxy group, a $C_1$–$C_6$ alkylthio group, a $C_2$–$C_4$ alkylenoxy group, a methylenedioxy group, a N-phenylcarbamoyl group, an amino group, a mono($C_1$–$C_6$ alkyl)amino group, or a di($C_1$–$C_6$ alkyl) amino group in the above formula (I).

20. A method of inhibiting the binding of a chemokine to the receptor of a target cell and/or its action on a target cell as set forth in claim 12, wherein the substituent for the phenyl group, $C_3$–$C_8$ cycloalkyl group, $C_3$–$C_8$ cycloalkenyl group, benzyl group, aromatic heterocyclic group, or condensed ring in $R^6$ is one or more of a halogen atom, a nitro group, a trifluoromethyl group, a $C_1$–$C_6$ alkyl group, a $C_1$–$C_6$ alkoxy group, a phenylsulfonyl group, a $C_2$–$C_7$ alkanoylamino group, or an amino group in the above formula (I).

21. A method of inhibiting the binding of a chemokine to the receptor of a target cell and/or its action on a target cell as set forth in claim 12, wherein $R^1$ is a phenyl group or an isoxazolyl group in the above formula (I).

22. A method of inhibiting the binding of a chemokine to the receptor of a target cell and/or its action on a target cell as set forth in claim 12, wherein $R^6$ is a phenyl group, a furyl group, or a thienyl group in the above formula (I).

23. A method of inhibiting the binding of a chemokine to the receptor of a target cell and/or its action on a target cell as set forth in claim 12, wherein the chemokine is MIP-1α.

24. A method of inhibiting the binding of a chemokine to the receptor of a target cell and/or its action on a target cell as set forth in claim 12, wherein the chemokine is MCP-1.

25. A method of inhibiting the binding of a chemokine to the receptor of a target cell and/or its action on a target cell as set forth in claim 12, herein the chemokine receptor is CCRl.

26. A method of inhibiting the binding of a chemokine to the receptor of a target cell and/or its action on a target cell as set forth in claim 12, wherein the chemokine receptor is CCR2A or CCR2B.

27. A compound, its pharmaceutically acceptable acid addition salt or its pharmaceutically acceptable $C_1$–$C_6$ alkyl addition salt as set forth in claim 1, wherein the compound is 3-[{N-(2-amino-5-trifluoromethylbenzoyl)glycyl}amino]-1-(4-chlorobenzyl)pyrrolidine.

28. A compound, its pharmaceutically acceptable acid addition salt or its pharmaceutically acceptable $C_1$–$C_6$ alkyl addition salt as set forth in claim 1, wherein the compound is 3-[{N-(2-amino-5-trifluoromethylbenzoyl)glycyl}amino]-1-(4-methoxybenzyl)pyrrolidine.

29. A compound, its pharmaceutically acceptable acid addition salt or its pharmaceutically acceptable $C_1$–$C_6$ alkyl addition salt as set forth in claim 1, wherein the compound is 3-[{N-(2-amino-5-trifluoromethylbenzoyl)glycyl}amino]-1-(3,4-methylenedioxybenzyl)pyrrolidine.

30. A compound, its pharmaceutically acceptable acid addition salt or its pharmaceutically acceptable $C_1$–$C_6$ alkyl addition salt as set forth in claim 1, wherein the compound is 3-[{N-(2-amino-5-trifluoromethylbenzoyl)glycyl}amino]-1-(2,3-dihydro-1-benzofuran-5-ylmethyl)pyrrolidine.

31. A compound, its pharmaceutically acceptable acid addition salt or its pharmaceutically acceptable $C_1$–$C_6$ alkyl addition salt as set forth in claim 1, wherein the compound is 3-[{N-(2-amino-5-trifluoromethylbenzoyl)glycyl}amino]-1-(4-methylthiobenzyl)pyrrolidine.

32. A compound, its pharmaceutically acceptable acid addition salt or its pharmaceutically acceptable $C_1$–$C_6$ alkyl addition salt as set forth in claim 1, wherein the compound is 3-[{N-(2-amino-5-trifluoromethylbenzoyl)glycyl}amino]-1-(4-ethylbenzyl)pyrrolidine.

33. A compound, its pharmaceutically acceptable acid addition salt or its pharmaceutically acceptable $C_1$–$C_6$ alkyl addition salt as set forth in claim 1, wherein the compound is 3-[{N-(2-amino-5-trifluoromethoxybenzoyl)glycyl}amino]-1-(4-ethylbenzyl)pyrrolidine.

34. A compound, its pharmaceutically acceptable acid addition salt or its pharmaceutically acceptable $C_1$–$C_6$ alkyl addition salt as set forth in claim 1, wherein the compound is 1-(3-amino-4-methoxybenzyl)-3-[{N-(2-amino-5-trifluoromethylbenzoyl)glycyl}amino]pyrrolidine.

35. A compound, its pharmaceutically acceptable acid addition salt or its pharmaceutically acceptable $C_1$–$C_6$ alkyl addition salt as set forth in claim 1, wherein the compound is 3-[{N-(2-amino-5-trifluoromethylbenzoyl)glycyl}amino]-1-(4-chloro-3-methylbenzyl)pyrrolidine.

36. A compound, its pharmaceutically acceptable acid addition salt or its pharmaceutically acceptable $C_1$–$C_6$ alkyl addition salt as set forth in claim 1, wherein the compound is 3-[{N-(2-amino-5-trifluoromethylbenzoyl)glycyl}amino]-1-(4-hydroxy-3-(methylamino)benzyl)pyrrolidine.

37. A compound, its pharmaceutically acceptable acid addition salt or its pharmaceutically acceptable $C_1$–$C_6$ alkyl addition salt as set forth in claim 1, wherein the compound is 3-[{N-(2-amino-5-trifluoromethylbenzoyl)glycyl}amino]-1-(1,3-benzoxazol-5-ylmethyl)pyrrolidine.

* * * * *